United States Patent
Hoge et al.

(10) Patent No.: US 11,027,025 B2
(45) Date of Patent: Jun. 8, 2021

(54) COMPOSITIONS COMPRISING SYNTHETIC POLYNUCLEOTIDES ENCODING CRISPR RELATED PROTEINS AND SYNTHETIC SGRNAS AND METHODS OF USE

(71) Applicant: ModernaTX, Inc., Cambridge, MA (US)

(72) Inventors: Stephen G. Hoge, Cambridge, MA (US); Eric Yi-Chun Huang, Cambridge, MA (US); Tirtha Chakraborty, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 14/903,869

(22) PCT Filed: Jul. 11, 2014

(86) PCT No.: PCT/US2014/046434
§ 371 (c)(1),
(2) Date: Jan. 8, 2016

(87) PCT Pub. No.: WO2015/006747
PCT Pub. Date: Jan. 15, 2015

(65) Prior Publication Data
US 2016/0367702 A1 Dec. 22, 2016

Related U.S. Application Data

(60) Provisional application No. 61/886,545, filed on Oct. 3, 2013, provisional application No. 61/844,890, filed on Jul. 11, 2013.

(51) Int. Cl.
| | | |
|---|---|---|
| *A61K 48/00* | (2006.01) | |
| *C12N 15/90* | (2006.01) | |
| *C12N 9/16* | (2006.01) | |
| *C12N 15/11* | (2006.01) | |

(52) U.S. Cl.
CPC ............ *A61K 48/0066* (2013.01); *C12N 9/16* (2013.01); *C12N 15/111* (2013.01); *C12N 15/907* (2013.01); *A61K 48/00* (2013.01); *C12N 2310/10* (2013.01); *C12N 2310/141* (2013.01); *C12N 2310/20* (2017.05); *C12N 2310/315* (2013.01); *C12N 2310/346* (2013.01)

(58) Field of Classification Search
CPC ...... C12N 9/22; C12N 15/111; C12N 151/115
See application file for complete search history.

(56) References Cited

U.S. PATENT DOCUMENTS

| | | |
|---|---|---|
| 5,034,506 A | 7/1991 | Summerton et al. |
| 5,426,180 A | 6/1995 | Kool |
| 5,489,677 A | 2/1996 | Sanghvi et al. |
| 5,512,439 A | 4/1996 | Hornes et al. |
| 5,591,722 A | 1/1997 | Montgomery et al. |
| 5,637,459 A | 6/1997 | Burke et al. |
| 5,639,873 A | 6/1997 | Barascut et al. |
| 5,789,578 A | 8/1998 | Burton et al. |
| 5,808,039 A | 9/1998 | Reddy et al. |
| 5,989,911 A | 11/1999 | Fournier et al. |
| 6,022,715 A | 2/2000 | Merenkova et al. |
| 6,022,737 A | 2/2000 | Niven et al. |
| 6,248,268 B1 | 6/2001 | Cook |
| 6,303,378 B1 | 10/2001 | Bridenbaugh et al. |
| 6,423,492 B1 | 7/2002 | Harbron |
| 6,511,832 B1 | 1/2003 | Guarino et al. |
| 6,521,411 B2 | 2/2003 | Hecker et al. |
| 7,691,569 B2 | 4/2010 | Wohlgemuth et al. |
| 7,745,391 B2 | 6/2010 | Mintz et al. |
| 8,093,367 B2 | 1/2012 | Kore et al. |
| 8,664,194 B2 | 3/2014 | de Fougerolles et al. |
| 8,680,069 B2 | 3/2014 | de Fougerolles et al. |
| 8,691,750 B2 | 4/2014 | Constien et al. |
| 8,710,200 B2 | 4/2014 | Schrum et al. |
| 8,716,465 B2 | 5/2014 | Rossi et al. |
| 8,802,438 B2 | 8/2014 | Rossi et al. |
| 8,822,663 B2 | 9/2014 | Schrum et al. |
| 8,883,506 B2 | 11/2014 | Rossi et al. |
| 8,898,864 B1 | 12/2014 | Porter |
| 8,969,353 B2 | 3/2015 | Mahon et al. |
| 8,980,864 B2 | 3/2015 | Hoge et al. |
| 8,999,380 B2 | 4/2015 | Bancel et al. |
| 9,050,297 B2 | 6/2015 | Chakraborty et al. |
| 9,061,059 B2 | 6/2015 | Chakraborty et al. |
| 9,089,604 B2 | 7/2015 | Chakraborty et al. |
| 9,095,552 B2 | 8/2015 | Chakraborty et al. |

(Continued)

FOREIGN PATENT DOCUMENTS

| | | |
|---|---|---|
| CA | 2028849 A1 | 9/1991 |
| CA | 2473135 A1 | 6/2003 |

(Continued)

OTHER PUBLICATIONS

Qi et al.; Repurposing CRISPR as an RNA-Guided Platform for Sequence-Specific Control of Gene Expression; Cell 152, 1173-1183, Feb. 28, 2013.*

Moretti et al.; Mechanism of translational regulation by miR-2 from sites in the 5' untranslated region or the open reading frame; RNA (2010), 16:2493-2502 (Year: 2010).*

Henke et al. (microRNA-122 stimulates translation of hepatitis C virus RNA; The EMBO Journal (2008) 27, 3300-3310 (Year: 2008).*

Qi et al. (Repurposing CRISPR as an RNA-Guided Platform for Sequence-Specific Control of Gene Expression; Cell 152, 1173-1183, Feb. 28, 2013; supplemental information (Year: 2013).*

(Continued)

*Primary Examiner* — Antonio Galisteo Gonzalez
(74) *Attorney, Agent, or Firm* — Clark & Elbing LLP

(57) ABSTRACT

The present invention relates to compositions comprising and methods of using synthetic polynucleotides, e.g., modified mRNA, encoding CRISPR related proteins including dCAS9 and synthetic sgRNAs targeting a gene of interest.

3 Claims, 5 Drawing Sheets
Specification includes a Sequence Listing.

(56) References Cited

U.S. PATENT DOCUMENTS

| | | |
|---|---|---|
| 9,107,886 B2 | 8/2015 | Chakraborty et al. |
| 9,114,113 B2 | 8/2015 | Chakraborty et al. |
| 9,149,506 B2 | 10/2015 | Chakraborty et al. |
| 9,428,535 B2 | 8/2016 | de Fougerolles et al. |
| 9,533,047 B2 | 1/2017 | de Fougerolles et al. |
| 9,675,668 B2 | 6/2017 | Bancel et al. |
| 9,751,925 B2 | 9/2017 | Hoge et al. |
| 9,803,177 B2 | 10/2017 | Rossi et al. |
| 9,872,900 B2 | 1/2018 | Ciaramella et al. |
| 10,022,435 B2 | 7/2018 | Ciaramella et al. |
| 10,064,935 B2 | 9/2018 | Ciaramella et al. |
| 10,072,057 B2 | 9/2018 | Hoge et al. |
| 10,286,086 B2 | 5/2019 | Roy et al. |
| 2001/0025097 A1 | 9/2001 | Sheridan et al. |
| 2002/0001812 A1 | 1/2002 | Smith et al. |
| 2002/0058256 A1 | 5/2002 | Rothberg et al. |
| 2002/0062017 A1 | 5/2002 | Hecker et al. |
| 2002/0114784 A1 | 8/2002 | Li et al. |
| 2002/0130430 A1 | 9/2002 | Castor |
| 2002/0153312 A1 | 10/2002 | Gjerde et al. |
| 2002/0164635 A1 | 11/2002 | Salerno |
| 2003/0120035 A1 | 6/2003 | Gao et al. |
| 2003/0170876 A1 | 9/2003 | Widner et al. |
| 2003/0170891 A1 | 9/2003 | McSwiggen |
| 2003/0180779 A1 | 9/2003 | Lofton-Day et al. |
| 2004/0038278 A1 | 2/2004 | Tzertzinis et al. |
| 2004/0076978 A1 | 4/2004 | Verfaillie |
| 2004/0142433 A1 | 7/2004 | Padgett et al. |
| 2004/0220127 A1 | 11/2004 | Sternberg et al. |
| 2004/0259097 A1 | 12/2004 | De Backer et al. |
| 2005/0003496 A1 | 1/2005 | McGall et al. |
| 2005/0053942 A1 | 3/2005 | Kauppinen et al. |
| 2005/0130196 A1 | 6/2005 | Hofstadler et al. |
| 2006/0058266 A1 | 3/2006 | Manoharan et al. |
| 2006/0121441 A1 | 6/2006 | Spira |
| 2006/0223081 A1 | 10/2006 | Jarrell et al. |
| 2007/0020678 A1 | 1/2007 | Ault-Riche et al. |
| 2007/0037148 A1 | 2/2007 | Fong et al. |
| 2007/0037770 A1 | 2/2007 | Gryaznov et al. |
| 2007/0244062 A1 | 10/2007 | Laux et al. |
| 2007/0281336 A1 | 12/2007 | Jendrisak et al. |
| 2008/0171711 A1 | 7/2008 | Hoerr et al. |
| 2008/0274463 A1 | 11/2008 | Chen et al. |
| 2008/0311140 A1 | 12/2008 | Lee et al. |
| 2009/0215125 A1 | 8/2009 | Reed et al. |
| 2009/0264511 A1 | 10/2009 | de Fougerolles et al. |
| 2009/0286852 A1 | 11/2009 | Kariko et al. |
| 2010/0015232 A1 | 1/2010 | Besenbacher et al. |
| 2010/0047261 A1 | 2/2010 | Hoerr et al. |
| 2010/0159456 A1 | 6/2010 | Albitar |
| 2010/0178272 A1 | 7/2010 | Hartmann et al. |
| 2010/0183639 A1 | 7/2010 | Uhlmann et al. |
| 2010/0255574 A1 | 10/2010 | Rosen et al. |
| 2010/0261228 A1 | 10/2010 | Gharib et al. |
| 2010/0261231 A1 | 10/2010 | Kore et al. |
| 2010/0317532 A1 | 12/2010 | Liu et al. |
| 2011/0130440 A1 | 6/2011 | Manoharan et al. |
| 2011/0143397 A1 | 6/2011 | Kariko et al. |
| 2011/0218170 A1 | 9/2011 | Thottassery et al. |
| 2011/0244026 A1 | 10/2011 | Guild et al. |
| 2011/0281938 A1 | 11/2011 | Schaub et al. |
| 2012/0046346 A1 | 2/2012 | Rossi et al. |
| 2012/0100136 A1 | 4/2012 | Patel et al. |
| 2012/0129261 A1 | 5/2012 | Eberwine et al. |
| 2012/0251618 A1 | 10/2012 | Schrum et al. |
| 2012/0309053 A1 | 12/2012 | Wellings |
| 2013/0046083 A1 | 2/2013 | Brown et al. |
| 2013/0046084 A1 | 2/2013 | Brown et al. |
| 2013/0052721 A1 | 2/2013 | Hollander et al. |
| 2013/0058894 A1 | 3/2013 | Maldonado et al. |
| 2013/0115272 A1 | 5/2013 | de Fougerolles et al. |
| 2013/0115274 A1* | 5/2013 | Knopov .............. A61K 31/7105 424/450 |
| 2013/0123481 A1 | 5/2013 | de Fougerolles et al. |
| 2013/0156849 A1 | 6/2013 | de Fougerolles et al. |
| 2013/0165504 A1 | 6/2013 | Bancel et al. |
| 2013/0197068 A1 | 8/2013 | Kariko et al. |
| 2013/0203115 A1 | 8/2013 | Schrum et al. |
| 2013/0244282 A1 | 9/2013 | Schrum et al. |
| 2013/0245103 A1 | 9/2013 | de Fougerolles et al. |
| 2013/0245105 A1 | 9/2013 | de Fougerolles et al. |
| 2013/0245106 A1 | 9/2013 | de Fougerolles et al. |
| 2013/0251618 A1 | 9/2013 | Li et al. |
| 2013/0259923 A1 | 10/2013 | Bancel et al. |
| 2013/0259924 A1 | 10/2013 | Bancel et al. |
| 2014/0010861 A1 | 1/2014 | Bancel et al. |
| 2014/0105964 A1 | 4/2014 | Bancel et al. |
| 2014/0105966 A1 | 4/2014 | Bancel et al. |
| 2014/0147454 A1 | 5/2014 | Chakraborty et al. |
| 2014/0200261 A1 | 7/2014 | Hoge et al. |
| 2014/0206752 A1 | 7/2014 | Afeyan et al. |
| 2014/0206852 A1 | 7/2014 | Hoge et al. |
| 2014/0243399 A1 | 8/2014 | Schrum et al. |
| 2014/0273230 A1* | 9/2014 | Chen .................. C12N 15/902 435/462 |
| 2014/0275227 A1 | 9/2014 | Hoge et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0030576 A1 | 1/2015 | Bancel |
| 2015/0050354 A1 | 2/2015 | Bouchon et al. |
| 2015/0050738 A1 | 2/2015 | Ozsolak et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0141269 A1 | 5/2015 | Soldatov et al. |
| 2015/0141499 A1 | 5/2015 | Bancel et al. |
| 2015/0166616 A1 | 6/2015 | Bancel et al. |
| 2015/0167017 A1 | 6/2015 | Roy et al. |
| 2015/0211039 A1 | 7/2015 | Wang et al. |
| 2015/0291678 A1 | 10/2015 | Rudolph et al. |
| 2015/0307542 A1 | 10/2015 | Roy et al. |
| 2016/0017313 A1 | 1/2016 | Spivak et al. |
| 2016/0024140 A1 | 1/2016 | Issa et al. |
| 2016/0024141 A1 | 1/2016 | Issa et al. |
| 2016/0024492 A1 | 1/2016 | Issa et al. |
| 2016/0024547 A1 | 1/2016 | Bancel et al. |
| 2016/0032273 A1 | 2/2016 | Shahrokh et al. |
| 2016/0038612 A1 | 2/2016 | Hoge et al. |
| 2016/0177295 A1 | 6/2016 | Rudolph et al. |
| 2016/0194368 A1 | 7/2016 | Hoge et al. |
| 2016/0194625 A1 | 7/2016 | Hoge et al. |
| 2016/0237108 A1 | 8/2016 | Fraley et al. |
| 2016/0244742 A1 | 8/2016 | Linnarsson et al. |
| 2016/0326575 A1 | 11/2016 | Von Der Mulbe et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2017/0136131 A1 | 5/2017 | Roy et al. |
| 2017/0136132 A1 | 5/2017 | Roy et al. |
| 2017/0175129 A1 | 6/2017 | Roy et al. |

FOREIGN PATENT DOCUMENTS

| | | |
|---|---|---|
| DE | 10 2006 051 516 A1 | 5/2008 |
| EP | 0366400 A2 | 5/1990 |
| EP | 1083232 B1 | 2/2005 |
| EP | 1611899 A1 | 1/2006 |
| EP | 1619254 A1 | 1/2006 |
| EP | 1383556 B9 | 3/2008 |
| EP | 1831160 B1 | 6/2010 |
| EP | 2092064 B1 | 9/2010 |
| EP | 2377938 A1 | 10/2011 |
| EP | 2484770 A1 | 8/2012 |
| EP | 2188379 B1 | 1/2013 |
| EP | 2548960 A1 | 1/2013 |
| JP | 2011-130725 A | 7/2011 |
| RU | 2540017 C2 | 1/2015 |
| WO | WO-91/05058 A1 | 4/1991 |

(56) References Cited

FOREIGN PATENT DOCUMENTS

| WO | WO-93/03052 A1 | 2/1993 | | |
|---|---|---|---|---|
| WO | WO-93/13121 A1 | 7/1993 | | |
| WO | WO-01/55306 A2 | 8/2001 | | |
| WO | WO-02/44399 A2 | 6/2002 | | |
| WO | WO-02/098443 A2 | 12/2002 | | |
| WO | WO-03/039523 A2 | 5/2003 | | |
| WO | WO-03/051881 A1 | 6/2003 | | |
| WO | WO-2004/020575 A2 | 3/2004 | | |
| WO | WO-2004/020576 A2 | 3/2004 | | |
| WO | WO-2004/064782 A2 | 8/2004 | | |
| WO | WO-2006/015445 A1 | 2/2006 | | |
| WO | WO-2007/024708 A2 | 3/2007 | | |
| WO | WO-2007/024798 A2 | 3/2007 | | |
| WO | WO-2007/089607 A2 | 8/2007 | | |
| WO | WO-2007/120863 A2 | 10/2007 | | |
| WO | WO-2008/039669 A1 | 4/2008 | | |
| WO | WO-2008/045505 A2 | 4/2008 | | |
| WO | WO-2008/083949 A2 | 7/2008 | | |
| WO | WO-2008/120016 A1 | 10/2008 | | |
| WO | WO-2009/042971 A2 | 4/2009 | | |
| WO | WO-2009/127060 A1 | 10/2009 | | |
| WO | WO-2009/127230 A1 | 10/2009 | | |
| WO | WO-2009/147519 A1 | 12/2009 | | |
| WO | WO-2009/149253 A2 | 12/2009 | | |
| WO | WO-2010/014895 A2 | 2/2010 | | |
| WO | WO-2010/017510 A1 | 2/2010 | | |
| WO | WO-2010/109289 A1 | 9/2010 | | |
| WO | WO-2010144740 A1 | * 12/2010 | ........... | A61K 9/1272 |
| WO | WO-2011/005850 A1 | 1/2011 | | |
| WO | WO-2011/012316 A3 | 2/2011 | | |
| WO | WO-2011/068810 A1 | 6/2011 | | |
| WO | WO-2011/071931 A2 | 6/2011 | | |
| WO | WO-2011/127933 A1 | 10/2011 | | |
| WO | WO-2011/130624 A2 | 10/2011 | | |
| WO | WO-2011/133868 A2 | 10/2011 | | |
| WO | WO-2011/140627 A1 | 11/2011 | | |
| WO | WO-2012/019168 A2 | 2/2012 | | |
| WO | WO-2012/031043 A1 | 3/2012 | | |
| WO | WO-2012/138530 A1 | 10/2012 | | |
| WO | WO 2012135805 A2 | * 10/2012 | ......... | A61K 31/7088 |
| WO | WO-2012/158736 A1 | 11/2012 | | |
| WO | WO-2012/164565 A1 | 12/2012 | | |
| WO | WO-2013/036748 A1 | 3/2013 | | |
| WO | WO-2013/039857 A1 | 3/2013 | | |
| WO | WO-2013/039861 A2 | 3/2013 | | |
| WO | WO-2013/052523 A1 | 4/2013 | | |
| WO | WO-2013/064911 A2 | 5/2013 | | |
| WO | WO-2013/086354 A1 | 6/2013 | | |
| WO | WO-2013/090186 A1 | 6/2013 | | |
| WO | WO-2013/090294 A1 | 6/2013 | | |
| WO | WO-2013/090648 A1 | 6/2013 | | |
| WO | WO-2013/090897 A1 | 6/2013 | | |
| WO | WO-2013/096709 A2 | 6/2013 | | |
| WO | WO-2013/101690 A1 | 7/2013 | | |
| WO | WO-2013/103659 A1 | 7/2013 | | |
| WO | WO-2013/113326 A1 | 8/2013 | | |
| WO | WO-2013/113501 A1 | 8/2013 | | |
| WO | WO-2013/113502 A1 | 8/2013 | | |
| WO | WO-2013/130161 A1 | 9/2013 | | |
| WO | WO-2013/151663 A1 | 10/2013 | | |
| WO | WO-2013/151664 A1 | 10/2013 | | |
| WO | WO-2013/151665 A2 | 10/2013 | | |
| WO | WO-2013/151666 A2 | 10/2013 | | |
| WO | WO-2013/151667 A1 | 10/2013 | | |
| WO | WO-2013/151668 A2 | 10/2013 | | |
| WO | WO-2013/151669 A1 | 10/2013 | | |
| WO | WO-2013/151670 A2 | 10/2013 | | |
| WO | WO-2013/151671 A1 | 10/2013 | | |
| WO | WO-2013/151672 A2 | 10/2013 | | |
| WO | WO-2013/151736 A2 | 10/2013 | | |
| WO | WO-2013/184976 A2 | 12/2013 | | |
| WO | WO-2013/185069 A1 | 12/2013 | | |
| WO | WO-2014/028429 A2 | 2/2014 | | |
| WO | WO-2014/081507 A1 | 5/2014 | | |
| WO | WO-2014/093574 A1 | 6/2014 | | |
| WO | WO-2014/093622 A2 | 6/2014 | | |
| WO | WO-2014/093924 A1 | 6/2014 | | |
| WO | WO-2014093712 A1 | * 6/2014 | ............ | C12N 15/86 |
| WO | WO-2014/113089 A2 | 7/2014 | | |
| WO | WO-2014/144039 A1 | 9/2014 | | |
| WO | WO-2014/144711 A1 | 9/2014 | | |
| WO | WO-2014/144767 A1 | 9/2014 | | |
| WO | WO-2014/152027 A1 | 9/2014 | | |
| WO | WO-2014/152030 A1 | 9/2014 | | |
| WO | WO-2014/152031 A1 | 9/2014 | | |
| WO | WO-2014/152211 A1 | 9/2014 | | |
| WO | WO-2014/152513 A1 | 9/2014 | | |
| WO | WO-2014/152540 A1 | 9/2014 | | |
| WO | WO-2014/160243 A1 | 10/2014 | | |
| WO | WO-2014/160284 A1 | 10/2014 | | |
| WO | WO-2014/164253 A1 | 10/2014 | | |
| WO | WO-2015/006747 A2 | 1/2015 | | |
| WO | WO-2015/034925 A1 | 3/2015 | | |
| WO | WO-2015/034928 A1 | 3/2015 | | |
| WO | WO-2015/038892 A1 | 3/2015 | | |
| WO | WO-2015/048744 A2 | 4/2015 | | |
| WO | WO-2015/051169 A2 | 4/2015 | | |
| WO | WO-2015/051173 A2 | 4/2015 | | |
| WO | WO-2015/051214 A1 | 4/2015 | | |
| WO | WO-2015/058069 A1 | 4/2015 | | |
| WO | WO-2015/070413 A1 | 5/2015 | | |
| WO | WO-2015/085318 A2 | 6/2015 | | |
| WO | WO-2015/089511 A2 | 6/2015 | | |
| WO | WO-2015/101414 A2 | 7/2015 | | |
| WO | WO-2015/105926 A1 | 7/2015 | | |
| WO | WO-2015/196118 A1 | 12/2015 | | |
| WO | WO-2015/196128 A2 | 12/2015 | | |
| WO | WO-2015/196130 A2 | 12/2015 | | |
| WO | WO-2016/010840 A1 | 1/2016 | | |
| WO | WO-2016/011222 A2 | 1/2016 | | |
| WO | WO-2016/011226 A1 | 1/2016 | | |
| WO | WO-2016/036902 A1 | 3/2016 | | |
| WO | WO-2016/077125 A1 | 5/2016 | | |
| WO | WO-2016/118724 A1 | 7/2016 | | |
| WO | WO-2016/118725 A1 | 7/2016 | | |

OTHER PUBLICATIONS

Finn et al., A Single Administration of CRISPR/Cas9 Lipid Nanoparticles Achieves Robust and Persistent In Vivo Genome Editing; Cell Reports; vol. 22, pp. 2227-2235, Feb. 27, 2018 (Year: 2018).*

Anderson et al., "Incorporation of pseudouridine into mRNA enhances translation by diminishing PKR activation," Nucleic Acids Res. 38(17):5884-92 (2010).

Bynum et al., "Characterization of subcellular poly(a) RNA populations by poly(U) sepharose chromatography and discontinuous elution," Anal Biochem. 107(2):406-16 (1980).

Chen et al., "LC/MS analysis of cellular RNA reveals NAD-linked RNA," Nat Chem Biol. 5(12):879-81 (2009).

Ditcheva et al. "CRISPR RNA maturation by trans-encoded small RNA and host factor RNase III," available in PMC Sep. 30, 2011, published in final edited form as: Nature 471(7340):602-7 (2011) (54 pages).

Derrigo et al., "RNA-protein interactions in the control of stability and localization of messenger RNA (review)," Int J Mol Med. 5(2):111-23 (2000).

Extended European Search Report for European Application No. 14823392.7, dated Dec. 14, 2016 (11 pages).

Farrow et al., "Combinatorial recombination of gene fragments to construct a library of chimeras," Curr Protoc Protein Sci. Chapter 26, Unit 26.2 (2010) (20 pages).

Gaj et al., "ZFN, TALEN, and CRISPR/Cas-based methods for genome engineering," Trends Biotechnol. 31(7):397-405 (2013).

Gilbert et al., "CRISPR-mediated modular RNA-guided regulation of transcription in eukaryotes," Cell 154(2):442-51 (2013) (15 pages).

Grosjean, Modification and editing of RNA: historical overview and important facts to remember. *Fine-Tuning of RNA Functions by Modification and Editing.* Grosjean H, 1-22 (2005).

Hamaguchi et al., "Direct reverse transcription-PCR on oligo(dT)-immobilized polypropylene microplates after capturing total mRNA from crude cell lysates," Clin Chem. 44(11):2256-63 (1998).

(56) References Cited

OTHER PUBLICATIONS

Hansen et al., "Circular RNA and miR-7 in Cancer," Cancer Res. 73(18):5609-12 (2013).
Hansen et al., "Natural RNA circles function as efficient microRNA sponges," Nature. 495(7441):384-8 (2013) (7 pages).
Jakobsen et al., "Direct mRNA Isolation Using Magnetic Oligo (dT) Beads: A Protocol for All Types of Cell Cultures, Animal and Plant Tissues," Advances in Biomagnetic Separation. ed. Uhlén et al., Eaton Publishing, 61-71 (1994) (15 pages).
Jani et al., "In vitro transcription and capping of Gaussia luciferase mRNA followed by HeLa cell transfection," J Vis Exp. 61:e3702 (2012) (9 pages).
Kanwar et al., "Chimeric aptamers in cancer cell-targeted drug delivery," Crit Rev Biochem Mol Bio. 46(6):459-77 (2011).
Karikó et al., "Incorporation of pseudouridine into mRNA yields superior nonimmunogenic vector with increased translational capacity and biological stability." Mol Ther. 16(11):1833-40 (2008).
Karikó et al., "mRNA is an endogenous ligand for Toll-like receptor 3," J Biol Chem. 279(13): 12542-50 (2004).
Kluiver et al., "Rapid generation of MicroRNA Sponges for MicroRNA Inhibition ," PLoS One. 7(1):E29275(2012) (8 pages).
Kore et al., "Synthesis and application of 2'-fluoro-substituted cap analogs." Bioorg Med Chem Letters. 17:5295-9 (2007).
Kormann et al., "Expression of therapeutic proteins after delivery of chemically modified mRNA in mice," Nat Biotechnol. 29(2):154-7 (2011) (6 pages).
Kuwahara et al., "Molecular evolution of functional nucleic acids with chemical modifications," Molecules. 15(8):5423-44 (2010).
Liu et al., "Construction of circular miRNA sponges targeting miR-21 or miR-221 and demonstration of their excellent anticancer effects on malignant melanoma cells," Int J Biochem Cell Biol. 45(11):2643-50 (2013).
Maeder et al., "CRISPR RNA-guided activation of endogenous human genes," Nat Methods 10(10):977-9 (2013).
Melton et al., "Efficient in vitro synthesis of biologically active RNA and RNA hybridization probes from plasmids containing a bacteriophage SP6 promoter," Nucleic Acids Res. 12(18):7035-56 (1984).
Memczak et al., "Circular RNAs are a large class of animal RNAs with regulatory potency," Nature. 495(7441):333-8 (2013) (10 pages).
Mestas et al., "Of mice and not men: differences between mouse and human immunology," J Immunol. 172(5):2731-8 (2004).
Mészáros et al., "Subtractive hybridization strategy using paramagnetic oligo(dT) beads and PCR," Biotechniques 20(3):413-9 (1996).
Park et al., "Reverse transcriptase-coupled quantitative real time PCR analysis of cell-free transcription on the chromatin-assembled p21 promoter," PLoS One 6(8):e23617 (2011) (6 pages).
Pascolo, Chapter 3: Vaccination With Messenger RNA. *Methods in Molecular Medicine, vol. 127: DNA Vaccines: Methods and Protocols: Second Edition*. Saltzman et al., Humana Press Inc., 23-40 (2006).
Perez-Pinera et al., "RNA-guided gene activation by CRISPR-Cas9-based transcription factors," Nat Methods 10(10):973-6 (2013).
PubChem Compound Summary for CID 262692, created Mar. 26, 2005. <URL: http://pubchem.ncbi.nlm.nih.gov/compound/262692> (11 pages).
PubChem Compound Summary for CID 479886, created Aug. 1, 2005. <URL: http://pubchem.ncbi.nlm.nih.gov/compound/479886> (12 pages).
Qiu et al., "Creating a flexible multiple microRNA expression vector by linking precursor microRNAs," Biochem Biophys Res Commun. 411(2):276-80 (2011).
Salfen et al., "Effects of exogenous ghrelin on feed intake, weight gain, behavior, and endocrine responses in weanling pigs," J Anim Sci. 82(7):1957-66 (2004).
Sasaki et al., "Construction of a normalized cDNA library by introduction of a semi-solid mRNA-cDNA hybridization system," Nucleic Acids Res. 22(6):987-92 (1994).
Shimelis et al., "Nuclease P1 digestion/high-performance liquid chromatography, a practical method for DNA quantitation," J Chromatogr A. 1117(2):132-6 (2006).
Slater, Chapter 16: The Purification of Poly(A)-Containing RNA by Affinity Chromatography. Methods in Molecular Biology. ed. Walker, Springer Verlag,117-20 (1985).
Smith et al., "Purification of polynucleotide phosphorylase by affinity chromatography and some properties of the purified enzymes," Nucleic Acids Res. 1(12):1763-73 (1974).
St. Claire, "Positive ion electrospray ionization tandem mass spectrometry coupled to ion-pairing high-performance liquid chromatography with a phosphate buffer for the quantitative analysis of intracellular nucleotides," Rapid Commun Mass Spectrom. 14(17):1625-34 (2000).
Tavernier et al., "mRNA as gene therapeutic: how to control protein expression," J Control Release. 150(3):238-47 (2011).
Vomelová et al., "Methods of RNA purification. All ways (should) lead to Rome," Folia Biol (Praha) 55(6):243-51 (2009).
Wang et al., "One-step generation of mice carrying mutations in multiple genes by CRISPR/Cas-mediated genome engineering," Cell 153(4):910-8 (2013).
Warren et al., "Highly efficient reprogramming to pluripotency and directed differentiation of human cells with synthetic modified mRNA," Cell Stem Cell. 7(5):618-30 (2010).
Weiss et al., "Prophylactic mRNA vaccination against allergy," Curr Opin Allergy Clin Immunol. 10(6):567-74 (2010) (8 pages).
Wilusz et al., "Molecular Biology. A circuitous route to noncoding RNA," Science. 340(6131):440-1 (2013).
Yamamoto et al., "Current prospects for mRNA gene delivery," Eur J Pharm Biopharm. 71(3):484-9 (2009).
Yanagawa et al., "Overexpression of autocrine motility factor in metastatic tumor cells: possible association with augmented expression of KIF3A and GDI-beta," Lab Invest. 84(4):513-22 (2004).
Fath et al., "Multiparameter RNA and codon optimization: a standardized tool to assess and enhance autologous mammalian gene expression," PLoS One 6(3):e17596 (2011) (14 pages).
Anderson et al., "Nucleoside modifications in RNA limit activation of 2'-5'-oligoadenylate synthetase and increase resistance to cleavage by RNase L," Nucleic Acids Res. 39(21): 9329-38 (2011) (10 pages).
Andries et al., "N1-methylpseudouridine-incorporated mRNA outperforms pseudouridine-incorporated mRNA by providing enhanced protein expression and reduced immunogenicity in mammalian cell lines and mice," J Control Release. 217:337-44 (2015).
Hikishima et al., "Synthesis of 1,8-naphthyridine C-nucleosides and their base-pairing properties in oligodeoxynucleotides: thermally stable naphthyridine:imidazopyridopyrimidine base-pairing motifs," Angew Chem Int Ed. 44:596-8 (2005).
Irier et al., "Translational regulation of GluR2 mRNAs in rat hippocampus by alternative 3' untranslated regions," available in PMC Aug. 17, 2009, published in final edited form as: J Neurochem. 109(2):584-594 (2009) (18 pages).
Kariko, K. et al., mRNA is an endogenous ligand for Toll-like receptor 3. J Biol Chem. Mar. 26, 2004;279(13):12542-50. Epub Jan. 16, 2004.
Karikóet al., "Generating the optimal mRNA for therapy: HPLC purification eliminates immune activation and improves translation of nucleoside-modified, protein-encoding mRNA," Nucleic Acids Res. 39(21):e142, DOI: 10.1093/nar/gkr695 (2011) (10 pages).
Karikó et al., "Suppression of RNA recognition by Toll-like receptors: the impact of nucleoside modification and the evolutionary origin of RNA," Immunity. 23(2):165-75 (2005).
Kumar et al., "Template-directed oligonucleotide strand ligation, covalent intramolecular DNA circularization and catenation using click chemistry," J Am Chem Soc. 129(21):6859-64 (2007).
Loomis et al., "Strategies for modulating innate immune activation and protein production of in vitro transcribed mRNAs," J Mater Chem B. 4(9):1619-32 (2016).
Nakazato et al., "Purification of messenger RNA and heterogeneous nuclear RNA containing poly(A) sequences," Methods Enzymol. 29:431-443 (1974).
Nielsen et al., "An mRNA is capped by a 2',5' lariat catalyzed by a group I-like ribozyme," Science. 309(5740):1584-7 (2005).

(56) References Cited

OTHER PUBLICATIONS

Notification of Reasons for Rejection for Japanese Application No. 2016-525829, dated Aug. 28, 2018 (13 pages).
Olesiak et al., "The synthesis of di- and oligo-nucleotides containing a phosphorodithioate internucleotide linkage with one of the sulfur atoms in a 5'-bridging position," Org Biomol Chem. 7(10):2162-9 (2009).
Pardi et al., "Expression kinetics of nucleoside-modified mRNA delivered in lipid nanoparticles to mice by various routes," available in PMC Nov. 10, 2016, published in final edited form as: J Control Release. 217:345-51 (2015) (18 pages).
Quabius et al., "Synthetic mRNAs for manipulating cellular phenotypes: an overview," N Biotechnol. 32(1):229-35 (2015).
Rodriguez et al., "Magnetic poly (styrene/divinylbenzene/acrylic acid)-based hybrid microspheres for bio-molecular recognition," Micro Nano Lett. 6(6):349-352 (2011).
Semple et al., "Rational design of cationic lipids for siRNA delivery," Nat Biotechnol. 28(2):172-6 (2010) (26 pages).
Stewart et al., "Effect of azide position on the rate of azido glucose-cyclooctyne cycloaddition," Journal of Carbohydrate Chemistry. 33(7-8):408-19 (2014).
Supplementary Material for Thess et al., "Sequence-engineered mRNA Without Chemical Nucleoside Modifications Enables an Effective Protein Therapy in Large Animals," Mol Ther. 23(9):1456-64 (2015), accessed <http://www.sciencedirect.com/sdfe/arp/media/1-s2.0-S1525001616302738.mmc1-pdf>. (11 Pages).
Takita et al., "Precise sequential DNA ligation on a solid substrate: solid-based rapid sequential ligation of multiple DNA molecules," DNA Res. 20(6):583-92 (2013).
Thess et al., "Sequence-engineered mRNA Without Chemical Nucleoside Modifications Enables an Effective Protein Therapy in Large Animals," Mol Ther. 23(9):1456-64 (2015).
Valadi et al., "Exosome-mediated transfer of mRNAs and microRNAs is a novel mechanism of genetic exchange between cells," Nat Cell Biol. 9(6):654-9 (2007) (17 pages).
Virnekäs et al., "Trinucleotide phosphoramidites: ideal reagents for the synthesis of mixed oligonucleotides for random mutagenesis," Nucleic Acids Res. 22(25):5600-7 (1994).
Weissman et al., "mRNA: Fulfilling the Promise of Gene Therapy," Mol Ther. 23(9):1416-7 (2015).
Jinek et al., "RNA-programmed genome editing in human cells" Elife. 2:e00471 (2013) (9 pages).
Miyoshi-Akiyama et al., "Complete genome sequence of *Streptococcus pyogenes* M1 476, isolated from a patient with streptococcal toxic shock syndrome," J Bacteriol. 194(19):5466 (2012).

Notification of Reasons for Rejection for Japanese Patent Application No. 2016-525829, dated Jun. 18, 2019 (9 pages).
Kormann et al., "Expression of therapeutic proteins after delivery of chemically modified mRNA in mice," Nat Biotechnol. 29(2):154-7 (including supplement) (2011) (6 pages).
"AutoImmune shares collapse on Colloral data in rheumatoid arthritis," Pharma MarketLetter, *Marketletter Publications Ltd.* ISSN:0951-3175 (1999).
Anderson, Bart R., Dissertation: "Nucleoside Modifications Suppress RNA Activation of Cytoplasmic RNA Sensors," Doctor of Philosophy, Cell & Molecular Biology, University of Pennsylvania, 2010 (197 pages).
Bell et al., "In trans T cell tolerance diminishes autoantibody responses and exacerbates experimental allergic encephalomyelitis," J Immunol. 180(3):1508-16 (2008).
El-Sagheer et al., "Click nucleic acid ligation: applications in biology and nanotechnology," Acc Chem Res. 45(8):1258-67 (2012).
Examination Report for Australian Patent Application No. 2014287009, dated Nov. 8, 2019 (4 pages).
Goodnow, "Pathways for self-tolerance and the treatment of autoimmune diseases," Lancet. 357(9274):2115-21 (2001).
Haseltine et al., "Rous sarcoma virus genome is terminally redundant: the 5' sequence," Proc Natl Acad Sci USA. 74(3):989-93 (1977).
Jawalekar et al., "Oligonucleotide tagging for copper-free click conjugation," Molecules. 18(7):7346-63 (2013).
Kraus et al., "Oral tolerance and inflammatory bowel disease," Curr Opin Gatroenterol. 21(6):692-6 (2005).
Kuribayashi-Ohta et al., "Application of oligo(dT)30-latex for rapid purification of poly(A)+ mRNA and for hybrid subtraction with the in situ reverse transcribed cDNA," Biochim Biophys Acta. 1156(2):204-12 (1993).
Lietard et al., "New strategies for cyclization and bicyclization of oligonucleotides by click chemistry assisted by microwaves," J Org Chem. 73(1):191-200 (2008).
Pozzilli et al., "No effect of oral insulin on residual beta-cell function in recent-onset type I diabetes (the IMDIAB VII)," Diabetologia. 43(8):1000-4 (2000).
Santner et al., "Efficient access to 3'-terminal azide-modified RNA for inverse click-labeling patterns," Bioconjug Chem. 25(1):188-95 (2014).
Skyler et al., "Effects of oral insulin in relatives of patients with type 1 diabetes: The Diabetes Prevention Trial—Type 1," Diabetes Care 28(5):1068-76 (2005).
Weiner et al.,"Oral tolerance," available in PMC May 1, 2012, published in final edited form as: Immunol Rev. 241(1):241-59 (2011) (14 pages).

\* cited by examiner

SEQUENCE LISTING

```
<160> NUMBER OF SEQ ID NOS: 137

<210> SEQ ID NO 1
<211> LENGTH: 4140
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 1
auggacaaga aguacuccau ugggcucgau aucggcacaa acagcgucgg cugggccguc       60
auuacggacg aguacaaggu gccgagcaaa aaauucaaag uucugggcaa uaccgaucgc      120
cacagcauaa agaagaaccu cauuggcgcc cuccuguucg acuccgggga cggccgaa       180 gccacgcggc ucaaaagaac agcacggcgc agauauaccc gcagaaagaa ucggaucugc      240
uaccugcagg agaucuuuag uaaugagaug gcuaaggugg augacucuuu cuuccauagg      300
cuggaggagu ccuuuuuggu ggaggaggau aaaaagcacg agcgccaccc aaucuuuggc      360
aauaucgugg acgaggugac guaccaugaa aaguacccaa ccauauauca ucugaggaag      420
aagcuuguag acaguacuga uaaggcgac uugcgguuga ucuaucucgc gcuggcgcau      480
augaucaaau uucggggaca cuuccucauc gaggggacc ugaacccaga caacagcgau      540
gucgacaaac ucuuuaucca acugguucag acuuacaauc agcuuuucga agagaacccg      600
aucaacgcau ccggaguuga cgccaaagca auccugagcg cuaggcuguc caaaucccgg      660
cggcucgaaa accucaucgc acagcucccu ggggagaaga gaacggccu guuugguaau      720 cuuaucgccc ugucacucgg gcugaccccc aacuuuaaau cuaacuucga ccuggccgaa      780
gaugccaagc uucaacugag caaagacacc uacgaugaug aucgacaa ucugcuggcc      840 cagaucggcg accaguacgc agaccuuuuu uuggcggcaa agaaccuguc agacgccauu      900
cugcugagug auauucugcg agugaacacg gagaucacca aagcuccgcu gagcgcuagu      960
augaucaagc gcuaugauga gcaccaccaa gacuugacuu ugcugaaggc ccuugucaga     1020
```

```
cagcaacugc cugagaagua caaggaaauu ucuucgauc agucuaaaaa uggcuacgcc   1080
ggauacauug acggcggagc aagccaggag gaauuuuaca aauuuauuaa gcccaucuug   1140
gaaaaaaugg acggcaccga ggagcugcug guaaagcuua acagagaaga ucuguugcgc   1200
aaacagcgca cuuucgacaa uggaagcauc ccccaccaga uucaccuggg cgaacugcac   1260
gcuauccuca ggcggcaaga ggauuucuac cccuuuuuga aagauaacag ggaaaagauu   1320
gagaaaauuc ucacauuucg gauacccuac uauguaggcc cccucgcccg gggaaauucc   1380
agauucgcgu ggaugacucg caaucagaa gagaccauca cucccuggaa cuucgaggaa   1440
gucguggaua aggggggccuc ugcccaaguccc uucaucgaaa ggaugacuaa cuuugauaaa   1500
aaucugccua acgaaaaggu gcuuccuaaa cacucucugc guacgaguaa cuucacaguu   1560
uauaacgagc ucaccaaggu caaauacguc acagaaggga ugagaaagcc agcauuccug   1620
ucuggagagc agaagaaagc uaucguggac cuccucuuca agacgaaccg gaaaguuacc   1680
gugaaacagc ucaagaaga cauuucaaa aagauugaau guucgacuc uguugaaauc   1740 agcggagugg aggaucgcuu caacgcaucc cuggaacgu aucacgaucu ccugaaaauc   1800
auuaaagaca aggacuuccu ggacaaugag gagaacgagg acauucuuga ggacauuguc   1860
cucacccuua cguuguuuga agauaggagg augauugaag aacgcuugaa aacuuacgcu   1920
caucucuucg acgacaaagu caugaaacag cucaagaggc gccgauauac aggauggggg   1980
cggcugucaa gaaaacugau caaugggauc cgagacaagc agaguggaaa gacaauccug   2040 gauuucuua aguccgaugg auuugccaac cggaacuuca ugcaguugau ccaugaugac   2100
ucucucaccu uuaaggagga cauccagaaa gcacaaguuu cuggccaggg ggacagucuu   2160
cacgagcaca ucgcuaaucu gcagguagc ccagcuauca aaaagggaau acugcagacc   2220
guuaaggucg uggaugaacu cgucaaagua auggaaggc auaagcccga gaauaucguu   2280
aucgagaugg cccgagagaa ccaaacuacc cagaagggac agaagaacag uagggaaagg   2340
augaagagga uugaagaggg uauaaaagaa cugggguccc aaauccuuaa ggaacaccca   2400
guugaaaaca cccagcuuca gaaugagaag cucuaccugu acuaccugca gaacggcagg   2460
gacauguacg uggaucagga acuggacauc aaucggcucu ccgacuacga cguggaucau   2520
aucgugcccc agucuuuucu caaagaugau ucuauugaua auaaaguguu gacaagaucc   2580
gauaaaaaua gagggaagag ugauaacguc cccucagaag aaguugcaa gaaaaugaaa   2640 aauuauuggc ggcagcugcu gaacgccaaa cugaucacac aacggaaguu cgauaaucug   2700
acuaaggcug aacgaggugg ccugucgag uuggauaaag ccggcuucau caaaaggcag   2760
cuuguugaga cacgccagau caccaagcac guggcccaaa uucucgauuc acgcaugaac   2820
accaaguacg augaaaauga caaacugauu cgagagguga aguuauuac ucugaagucu   2880 aagcuggucu cagauuucag aaaggacuuu caguuuuaua aggugagaga gaucaacaau   2940
uaccaccaug cgcaugaugc cuaccugaau gcaguggag gcacugcacu uaucaaaaaa   3000
uaucccaagc uugaaucuga auugguuuac ggagacuaua aaguguacga guuaggaaa   3060 augaucgcaa agucugagca ggaaauaggc aaggccaccg cuaaguacuu cuuuuacagc   3120
aauauuauga auuuuucaa gaccgagauu acacuggcca auggagagau cggaagcga   3180 ccacuuaucg aaacaaacgg agaaacagga gaaaucgugu gggacaaggg uagggauuuc   3240 gcgacaguc ggaaggucuu guccaugccg caggugaaca ucguuaaaaa gaccgaagua   3300
cagaccggag gcuucuccaa ggaaaguauc cucccgaaaa ggaacagcga caagcugauc   3360
gcacgcaaaa aagauuggga ccccaagaaa uacggcggau ucgauucucc uacagucgcu   3420
```

```
uacaguguac ugguugugge caaaguggag aaagggaagu cuaaaaaacu caaaagcguc    3480
aaggaacugc ugggcaucac aaucauggag cgaucaagcu ucgaaaaaaa ccccaucgac    3540
uuucucgagg cgaaaggaua uaaagagguc aaaaagacc ucaucauuaa gcuucccaag     3600
uacucucucu uugagcuuga aaacggccgg aaacgaaugc ucgcuagugc gggcgagcug    3660
cagaaaggua acgagcuggc acugcccucu aaauacguua auuucuugua ucuggccagc    3720
cacuaugaaa agcucaaagg gucucccgaa gauaaugagc agaagcagcu guucguggaa    3780
caacacaaac acuaccuuga ugagaucauc gagcaaauaa gcgaauucuc caaaagagug    3840
auccucgccg acgcuaaccu cgauaaggug cuuucugcuu acaauaagca cagggauaag    3900
cccaucaggg agcaggcaga aaacauuauc cacuuguuua cucugaccaa cuugggcgcg    3960
ccugcagccu ucaaguacuu cgacaccacc auagacagaa agcgguacac cucuacaaag    4020
gagguccugg acgccacacu gauucaucag ucaauuacgg ggcucuauga aacaagaauc    4080
gaccucucuc agcucggugg agacagcagg gcugaccccca agaagaagag gaagguguga   4140
```

<210> SEQ ID NO 2
<211> LENGTH: 4269
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 2

```
auggacuaua aggaccacga cggagacuac aaggaucaug auauugauua caaagacgau    60
gacgauaaga ugccccaaa gaagaagcgg aaggucggua uccacggagu cccagcagcc    120
gacaagaagu acagcaucgg ccuggacauc ggcaccaacu cuguggguu ggccgugauc     180 accgacgagu acaaggugcc cagcaagaaa uucaaggugc ugggcaacac cgaccggcac    240
agcaucaaga gaaccugau cggagcccug cuguucgaca cggcgaaac agccgaggcc     300 acccggcuga agagaaccgc cagaagaaga uacaccagac ggaagaaccg gaucugcuau    360
cugcaagaga ucuucagcaa cgagauggcc aaggugacg acagcuucu ccacagacug      420 gaagaguccu uccugguga agaggauaag aagcacgagc ggcaccccau cuucggcaac    480
aucguggacg agguggccua ccacgagaag uaccccacca ucuaccaccu gagaaagaaa    540 cuggugggaca gcaccgacaa ggccgaccug cggcugaucu aucuggcccu ggcccacaug    600
aucaaguucc ggggccacuu ccugaucgag ggcgaccuga acccccgacaa cagcgacgug    660 gacaagcugu ucauccagcu ggugcagacc uacaaccagc uguucgagga aaaccccauc    720
aacgccagcg gcguggacgc caaggccauc cugucugcca acugagcaa gagcagacgg    780 cuggaaaauc ugaucgcca gcugcccggc gagaagaaga uggccuguu cggcaaccug    840 auugcccuga gccugggccu gaccccaac uucaagagca acuucgaccu ggccgaggau    900
gccaaacugc agcugagcaa ggacaccuac gacgacgacc uggacaaccu gcuggccag    960 aucggcgacc aguacgccga ccuguuucug gccgccaaga accugucga cgccauccug    1020 cugagcgaca uccugagagu gaacaccgag aucaccaagg cccccgag cgccucuaug    1080 aucaagagau acgacgagca ccaccaggac cugacccugc ugaaagcucu cgugcggcag    1140
cagcugcccg agaaguacaa agagauuuc uucgaccaga gcaagaacgg cuacgccggc    1200
uacauugacg gcggagccag ccaggaagag uucuacaagu caucaagcc caucuggaa    1260 aagauggacg gcaccgagga acugcucgug aagcugaaca gagaggaccu gcugcggaag    1320
```

```
cagcggaccu ucgacaacgg cagcaucccc caccagaucc accugggaga gcugcacgcc   1380
auucugcggc ggcaggaaga uuuuuaccca uccugaagg acaaccggga aaagaucgag    1440
aagauccuga ccuuccgcau ccccuacuac gugggcccuc uggccagggg aaacagcaga   1500
uucgccugga ugaccagaaa gagcgaggaa accaucaccc ccuggaacuu cgaggaagug   1560
guggacaagg gcgcuuccgc ccagagcuuc aucgagcgga ugaccaacuu cgauaagaac   1620
cugcccaacg agaaggugcu gcccaagcac agccugcugu acgaguacuu caccguguau   1680
aacgagcuga ccaaagugaa auacgugacc gagggaauga gaaagcccgc cuuccugagc   1740
ggcgagcaga aaaaggccau cguggaccug cuguucaaga ccaaccggaa agugaccgug   1800
aagcagcuga agaggacua cuucaagaaa aucgagugcu ucgacuccgu ggaaaucucc    1860
ggcguggaag aucgguucaa cgccucccug ggcacauacc acgaucugcu gaaaauuauc   1920
aaggacaagg acuuccugga caaugaggaa aacgaggaca uucuggaaga uaucgugcug   1980
acccugacac uguuugagga cagagagaug aucgaggaac ggcugaaaac cuaugcccac   2040
cuguucgacg acaaagugau gaagcagcug aagcggcgga gauacaccgg cugggcagg    2100 cugagccgga agcugaucaa cggcauccgg gacaagcagu ccggcaagac aauccuggau   2160
uuccugaagu ccgacggcuu cgccaacaga aacuucaugc agcugaucca cgacgacagc   2220
cugaccuuua agaggacau ccagaaagcc caggugccg gccagggcga uagccugcac    2280
gagcacauug ccaaucuggc cggcagcccc gccauuaaga agggcauccu gcagacagug   2340 aaggugugg acgagcucgu gaaagugaug ggccggcaca gcccgagaa caucgugauc    2400 gaaauggcca gagagaacca gaccacccag aagggacaga agaacagccg cgagagaaug   2460
aagcggaucg aagagggcau caaagagcug ggcagccaga uccugaaaga acaccccgug   2520
gaaacacccc agcugcagaa cgagaagcug uaccuguacu accugcagaa ugggcgggau   2580
auguacgugg accaggaacu ggacaucaac cggcugucca cuacgaugu ggaccauauc    2640 gugccucaga gcuuucugaa ggacgaccc aucgacaaca aggugcugac cagaagcgac   2700
aagaaccggg gcaagagcga caacgugccc uccgaagagg ucgugaagaa gaugaagaac   2760
uacuggcggc agcugcugaa cgccaagcug auuacccaga gaaaguucga caaucugacc   2820
aaggccgaga gaggcggccu gagcgaacug gauaaggccg gcuucaucaa gagacagcug   2880
guggaaaccc ggcagaucac aaagcacgug gcacagaucc uggacucccg gaugaacacu   2940
aaguacgacg agaaugacaa gcugauccgg gaagugaaag ugaucacccu gaaguccaag   3000
cuggugaccg auuccggaa ggauuuccag uuuuacaaag ugcgcgagau caacaacuac   3060
caccacgccc acgacgccua ccugaacgcc gucgugggaa ccgcccugau caaaaaguac   3120
ccuaagcugg aaagcgaguu cguguacggc gacuacaagg uguacgacgu gcggaagaug   3180
aucgccaaga gcgagcagga aaucggcaag gcuaccgcca aguacuucuu cuacagcaac   3240
aucaugaacu uuucaagac cgagauuacc cuggccaacg gcgagauccg gaagcggccu   3300
cugaucgaga caaacggcga aaccggggag aucgugugg auaagggccg ggauuuugcc    3360
accgugcgga agugcugag caugcccaa gugaauaucg ugaaaaagac cgaggugcag    3420
acaggcggcu ucagcaaaga gucuauccug cccaagagga cagcgauaa gcugaucgcc    3480 agaaagaagg acugggaccc uaagaaguac ggcggcuucg acagcccac cguggccuau   3540 ucugugcugg ugguggccaa aguggaaaag ggcaaguccaa agaaacugaa gagugugaaa   3600
gagcugcugg ggaucaccau caugggaaga agcagcuucg agaagaaucc caucgacuuu   3660
```

| | |
|---|---|
| cuggaagcca agggcuacaa agaagugaaa aaggaccuga ucaucaagcu gccuaaguac | 3720 |
| ucccuguucg agcuggaaaa cggccggaag agaaugcugg ccucugccgg cgaacugcag | 3780 |
| aagggaaacg aacuggcccu gcccuccaaa uaugugaacu uccuguaccu ggccagccac | 3840 |
| uaugagaagc ugaagggcuc ccccgaggau aaugagcaga acagcuguu ugggaacag | 3900 |
| cacaagcacu accuggacga gaucaucgag cagaucagcg aguuccaa gagagugauc | 3960 |
| cuggccgacg cuaaucugga caaagucug uccgccuaca caagcaccg ggauaagccc | 4020 |
| aucagagagc aggccgagaa uaucauccac cuguuuaccc ugaccaaucu gggagccccu | 4080 |
| gccgccuuca aguacuuuga caccaccauc gaccggaaga gguacaccag caccaaagag | 4140 |
| gugcuggacg ccacccugau ccaccagagc aucaccggcc uguacgagac acggaucgac | 4200 |
| cugucucagc ugggaggcga caagcguccu gcugcuacua agaaagcugg ucaagcuaag | 4260 |
| aaaaagaaa | 4269 |

<210> SEQ ID NO 3
<211> LENGTH: 4956
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 3

| | |
|---|---|
| auggacaaga aguacagcau cggccuggac aucggcacca acucuguggg cugggccgug | 60 |
| aucaccgacg aguacaaggu gcccagcaag aaauucaagg ugcugggcaa caccgaccgg | 120 |
| cacagcauca agaagaaccu gaucggcgcc cugcuguucg acagcggaga acagccgag | 180 |
| gccacccggc ugaagagaac cgccagaaga agauacacca acggaagaa ccggaucugc | 240 |
| uaucugcaag agaucuucag caacgagaug gccaaggugg acgacagcuu cuuccacaga | 300 |
| cuggaagagu ccuuccuggu ggaagaggau aagaagcacg agcggcaccc caucuucggc | 360 |
| aacaucgugg acgaggugc cuaccacgag aaguacccca ccaucuacca ccugagaaag | 420 |
| aaacuggugg acagcaccga caaggccgac cucggcuga ucuaucggc ccuggcccac | 480 |
| augaucaagu ccggggcca cuuccugauc gagggcgacc ugaaccccga caacagcgac | 540 |
| guggacaagc uguucaucca gcuggugcag accuacaacc agcuguucga ggaaaacccc | 600 |
| aucaacgcca gcggcgugga cgccaaggcc auccugucug ccagacugag caagagcaga | 660 |
| cggcuggaaa aucgaucgc ccagcugccc ggcgagaaga gaauggccu guucggcaac | 720 |
| cugauugccc ugagccuggg ccugaccccc aacuucaaga caacuucga ccuggccgag | 780 |
| gaugccaaac ugcagcugag caaggacacc uacgacgacg accuggacaa ccugcuggcc | 840 |
| cagaucggcg accaguacgc cgaccuguuu cuggccgcca gaaccuguc cgacgccauc | 900 |
| cugcugagcg acauccugag agugaacacc gagaucacca aggccccccu gagcgccucu | 960 |
| augaucaaga gauacgacga gcaccaccag gaccugaccc ugcugaaagc ucucgugcgg | 1020 |
| cagcagcugc cugagaagua caaagagauu ucuucgacc agagcaagaa cggcuacgcc | 1080 |
| ggcuacaucg auggcggagc cagccaggaa gaguucuaca aguucaucaa gcccauccug | 1140 |
| gaaaagaugg acggcaccga ggaacugcuc gugaagcuga cagagagga ccugcugcgg | 1200 |
| aagcagcgga ccuucgacaa cggcagcauc ccccaccaga uccaccuggg agagcugcac | 1260 |
| gccauucugc ggcggcagga agauuuuuac ccauuccuga aggacaaccg ggaaaagauc | 1320 |
| gagaagaucc ugaccuuccg cauccccuac uacguggggcc cucuggccag ggaaacagc | 1380 |

```
agauucgccu ggaugaccag aaagagcgag gaaaccauca cccccuggaa cuucgaggaa    1440
gugguggaca agggcgccag cgcccagagc uucaucgagc ggaugaccaa cuucgauaag    1500
aaccugccca acgagaaggu gcugcccaag cacagccugc uguacgagua cuucaccgug    1560
uacaacgagc ugaccaaagu gaaauacgug accgagggaa ugagaaagcc cgccuuccug    1620
agcggcgagc agaaaaaagc caucguggac cugcuguuca agaccaaccg gaaagugacc    1680
gugaagcagc ugaaagagga cuacuucaag aaaucgagu gcuucgacuc cguggaaauc    1740
uccggcgugg aagaucgguu caacgccucc cugggcacau accacgaucu gcugaaaauu    1800
aucaaggaca aggacuuccu ggacaaugag gaaaacgagg acauucugga agauaucgug    1860
cugacccuga cacuguuuga ggacagagag augaucgagg aacggcugaa aaccuaugcc    1920
caccuguucg acgacaaagu gaugaagcag cugaagcggc ggagauacac cggcugggc    1980 aggcugagcc ggaagcugau caacggcauc cgggacaagc aguccggcaa acaauccug    2040 gauuuccuga aguccgacgg cuucgccaac agaaacuuca gcagcugau ccacgacgac    2100 agccugaccu uuaaagagga caucagaaa gcccaggugu ccggccaggg cgauagccug    2160
cacgagcaca uugccaaucu ggccggcagc cccgccauua agaagggcau ccugcagaca    2220
gugaaggugu ggacgagcu cgugaaagug augggccggc acaagcccga gaacaucgug    2280
aucgaaaugg ccagagagaa ccagaccacc cagaagggac agaagaacag ccgcgagaga    2340 augagcgga ucaagagggg caucaaagag cugggcagcc agauccugaa gaacaccccc    2400
guggaaaaca cccagcugca gaacgagaag cuguaccugu acuaccugca gaaugggcgg    2460
gauauguacg uggaccagga acuggacauc aaccggcugu ccgacuacga uguggaccau    2520
aucgugccuc agagcuuucu gaaggacgac uccaucgaua caaagugcu gacucggagc    2580 gacaagaacc ggggcaagag cgacaacgug cccuccgaag guccgugaa gaagaugaag    2640 aacuacuggc gccagcugcu gaaugccaag cugauuaccc agaggaaguu cgacaaucug    2700
accaaggccg agagaggcgg ccugagcgaa cuggauaagg ccggcuucau caagagacag    2760
cugguggaaa cccggcagau cacaaagcac guggcacaga uccuggacuc ccggaugaac    2820
acuaaguacg acgagaacga caaacugauc cgggaaguga aagugaucac ccugaagucc    2880
aagcuggugu ccgauuuccg gaaggauuuc caguuuuaca agugcgcga gaucaacaac    2940 uaccaccacg cccacgacgc cuaccugaac gccgucgugg gaaccgcccu gaucaaaaag    3000
uacccuaagc uggaaagcga guucgugua ggcgacuaca aggugacga cgugcggaag    3060 augaucgcca agagcgagca ggaaaucggc aaggcuaccg ccaaguacuu cuucuacagc    3120
aacaucauga acuuuuucaa gaccgagauu acccuggcca acggcgagau ccggaagcgg    3180
ccucugaucg agacaaacgg cgaaacaggc gagaucgugu gggauaaggg ccgggacuuu    3240
gccaccgugc ggaaagugcu gucuaugccc aagugaaaua ucgugaaaaa gaccgaggug    3300
cagacaggcg gcuucagcaa agagucuauc cugcccaaga ggaacagcga caagcugaauc    3360 gccagaaaga aggacuggga cccuaagaag uacggcggcu cgacagccc caccguggcc    3420 uauucugugc uggugugc caaaguggaa agggcaagu ccaagaaacu gaagagugug    3480
aaagagcugc ugggaucac caucaaggaa agaagcagcu cgagaagaa ucccaucgac    3540 uuucuggaag ccaagggcua caaagaagug aaaaaggacc ugaucaucaa gcugccuaag    3600
uacucccugu ucgagcugga aaacggccgg aagagaaugc uggccucugc cggcgaacug    3660
cagaagggaa acgaacuggc ccugcccucc aaauaugua acuuccugua ccuggccagc    3720
cacuaugaga agcugaaggg cucccccgag gauaaugagc agaaacagcu guuuguggaa    3780
```

-continued

```
cagcacaaac acuaccugga cgagaucauc gagcagauca gcgaguucuc caagagagug    3840
auccuggccg acgcuaaucu ggacaaggug cugagcgccu acaacaagca cagagacaag    3900
ccuaucagag agcaggccga gaauaucauc caccuguuua cccugaccaa ucugggagcc    3960
ccugccgccu ucaaguacuu ugacaccacc aucgaccgga gaggauacac cagcaccaaa    4020
gaggugcugg acgccacccu gauccaccag agcaucaccg ccuguacga gacacggauc    4080 gaccugucuc agcugggagg cgacgccuau cccuaugacg ugcccgauua ugccagccug    4140
ggcagcggcu cccccaagaa aaaacgcaag guggaagauc uaagaaaaa gcggaaagug    4200 gacggcauug guaugggag caacggcagc agcggauccg ugagcaaggg cgaggagcug    4260
uucaccgggg uggugcccau ccuggucgag cuggacggcg acguaaacgg ccacaaguuc    4320
agcgugcgcg gcgagggcga gggcgaugcc accaacggca agcugacccu gaaguucauc    4380
ugcaccaccg gcaagcugcc cgugcccugg cccacccucg ugaccacccu gaccuacggc    4440
gugcagugcu ucagccgcua ccccgaccac augaagcagc acgacuucuu caagccgcc    4500 augcccgaag gcuacgucca ggagcgcacc aucuccuuca aggacgacgg caccuacaag    4560
acccgcgccg aggugaaguu cgagggcgac acccuggugaa ccgcaucga gcugaagggc    4620 aucgacuuca aggaggacgg caacauccug ggcacaagc uggaguacaa cuucaacagc    4680
cacaacgucu auaucacggc cgacaagcag aagaacggca ucaaggcgaa cuucaagauc    4740
cgccacaacg ucgaggacgg cagcgugcag cucgccgacc acuaccagca gaacaccccc    4800
aucggcgacg gccccgugcu gcugcccgac aaccacuacc ugagcaccca guccaagcug    4860
agcaaagacc ccaacgagaa gcgcgaucac augguccugc uggaguucgu gaccgccgcc    4920
gggaucacuc ucggcaugga cgagcuguac aaguag                              4956
```

<210> SEQ ID NO 4
<211> LENGTH: 1201
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4

```
ugaucgccaa gucggaacag gaaaucggaa aggcuacugc aaaguacuuc uucuacucaa      60
acaucaugaa cuucuucaaa acggagauca cgcucgcgaa cggcgaaauc cggaaaaggc     120
cgcucauuga aaccaacgga gaaaccgggg agaucgugug ggacaaggga agggauuuug     180
cgacugugag gaaggguug uccaugccgc aagucaauau ugugaaaaag acggaagugc     240
aaaccggagg auucagcaaa gaauccaucc ucccaaagcg caacucggac aaacucaucg     300
cgcgcaagaa ggauugggac cccaagaaau acgguggcuu ugacagcccu acugggcuu     360 acuccgu ccu cgucgggcu aaaguggaaa agguaaauc caaaaagcuc aaaucgguga     420
aggagcuccu gggaaucacg aucauggagc ggucgagcuu cgaaaagaau ccuauugauu     480
uccuggaggc gaagggcuac aaggaaguca agaaagaccu gaucaucaag cucccgaagu     540
acagcccucu ucgagcucgaa aacggcagaa agaggaugcu ggcaucagcg ggagaauugc     600
agaagggaaa cgaacuggca cugccguccca aguacgugaa uuuucucuau cuggcuagcc     660
acuacgaaaa gcugaaggga ucgcccgagg acaacgagca aaaacaacug uucgugagc     720 agcacaagca cuaccuggau gagaucaucg agcagaucc cgaauucucg aaacgcguga     780
uccuugccga ugccaaucug gauaaagugu ugucggcuua caacaagcau cgggauaaac     840
```

| | |
|---|---:|
| cgauccgcga acaggcagaa aacaucauuc aucuguucac uuugaccaau cugggagcgc | 900 |
| cugccgcguu uaaguacuuc gacaccacua uugauagaaa gcgcuacacc ucgaccaagg | 960 |
| aagugcugga cgcuacccug auccaccagu ccaucaccgg acucuacgaa acucgcauug | 1020 |
| accguccca gcuuggagga gauucacggg ccgauccaaa gaaaaagcgc aaggucugau | 1080 |
| aauaggcugg agcucggug gccaugcuuc uugccccuug gccucccccc cagccccucc | 1140 |
| uccccuuccu gcacccguac ccccgugguc uuugaauaaa gucgagugg gcggcucuag | 1200 |
| a | 1201 |

<210> SEQ ID NO 5
<211> LENGTH: 3153
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 5

| | |
|---|---:|
| ucaagcuuuu ggacccucgu acagaagcua auacgacuca cuauagggaa auaagagaga | 60 |
| aaagaagagu aagaagaaau auaagagcca ccauggacaa gaaauacagc aucggccugg | 120 |
| auauuggaac uaacagcguu ggaugggcag ugaucaccga cgaguacaag gugccgagca | 180 |
| agaaguucaa ggugcugggg aacacugacc gccaucaau uaagaaaaac cucauuggag | 240 |
| cacugcuuuu ugacucgggu gagacugccg aagcuaccag gcucaaacgc accgcacgca | 300 |
| gacgguacac ccgccgcaag aaucgcaucu gcuaucugca agagaucuuu ccaacgaga | 360 |
| uggcgaaggu ugacgacagc uuuuuccacc ggcuggaaga gagcuuccuc guggaagagg | 420 |
| acaaaaagca cgaaaggcau ccaaucuucg guaacaucgu ggacgaagug gcguaucacg | 480 |
| aaaaguaccc uaccaucuac caucugcgga agaagcuggu cgauuccacg gauaaggcag | 540 |
| accugagacu gaucuaccug gcuuggccc auaugaucaa auuccgcggc cauuccuga | 600 |
| ucgaggggga ccuuaacccg gauaacucgg augucgacaa gcuguucauc cagcuggucc | 660 |
| aaacguauaa ccaacuguuu gaggaaaauc ccaucaacgc uucggggug gacgccaaag | 720 |
| caauccucuc cgcgcgccug agcaagucac ggcggcucga aaaccugauc gcgcagcugc | 780 |
| cgggagaaaa gaaaaaugga cuguuuggga aucugaucgc gcugucgcuc ggccugacuc | 840 |
| caaacuuuaa gucaaauuuc gauuuggccg aagaugccaa gcugcagcug ucaaaggaca | 900 |
| cuuacgacga cgaccuggac aaucugcugg cccagauugg ggaccauac gcagaccugu | 960 |
| ucuuggccgc gaagaaccug agcgacgcca uucuucuguc cgauauucug agagucaaua | 1020 |
| ccgaaaucac uaaggcuccg cugucgcuu caaugaucaa gcgcuacgau gaacaccacc | 1080 |
| aggaucucac ucugcucaaa gcccucguga acaacaauu gccugaaaag uacaaggaga | 1140 |
| ucuucuucga ccagagcaaa aacggcuacg caggcuacau cgauggagga gcgucacaag | 1200 |
| aagaguucua caaguucauc aagccaaucu ggagaagau ggacgguacu gaagaacucc | 1260 |
| uugugaagcu gaauagggag gauuugcuca gaaagcagcg gacuuugac aacggcucga | 1320 |
| ucccucauca gauucaccuc ggugagcgc augccauccu ucggcgccaa gaggauuuuu | 1380 |
| accccuuccu gaaggauaau cgcgagaaaa ucgaaaagau ccgacguuc agaauucccu | 1440 |
| acuacguggg accgcuggcg cgcggaacu cgcgguuugc auggaugacu cgcaagucag | 1500 |
| aggaaacuau cacuccuugg aauuugagg aggucgcga uaaggagcc uccgcccagu | 1560 |
| cauucaucga acgcaugacc aacuucgaca agaaucuucc gaacgagaag guccuuccaa | 1620 |

-continued

| | |
|---|---|
| agcacucccu guuguacgaa uacuucaccg uguacaauga gcugaccaaa guuaaguaug | 1680 |
| ucaccgaggg caugagaaag ccggccuucc ucagcggcga acaaaagaag gccaucgucg | 1740 |
| accuccucuu caagaccaac cggaagguga ccgucaagca acucaaggag gacuacuuca | 1800 |
| agaagaucga augcuuugac ucggucgaaa ucagcggagu ggaggaccgg uuuaacgcgu | 1860 |
| cacugggυac cuaccaugau cuccugaaaa ucaucaaaga caaggacuuc cuggacaacg | 1920 |
| aagaaaacga ggacauccug gaagauauug uguugacccu gacgcuguuc gaggaccggg | 1980 |
| aaaugaucga ggaaaggcuu aagaccuacg cacaccucuu cgaugacaaa gugaugaagc | 2040 |
| aacugaagcg gcggagauau acuggcuggg ggaggcucuc ccggaagcuc auuaauggaa | 2100 |
| ucagagacaa acagucgggu aaaacuaucc ucgacuuccu caagucggau ggguucgcca | 2160 |
| accggaacuu caugcagcug auccacgaug auuccuugac cuucaaggaa gauaccagaa | 2220 |
| aggcgcaagu gagcggacag ggagauucgu ugcacgaaca uaucgcuaau cucgccggau | 2280 |
| ccccagccau caagaaagga auccugcaga ccgugaaggu ggggaugaa cuggugaaag | 2340 |
| ugaugggcg ccacaaacca gagaacaucg ucauugagau ggcccgcgag aaucagacca | 2400 |
| cucagaaggg acaaaagaac uccagagagc ggaugaaacg caucgaggaa ggcaucaaag | 2460 |
| agcuugguag ccaaauccug aaggaacacc cggucgagaa cacccagcuc cagaacgaaa | 2520 |
| agcuuuaccu guacuaccuc caaaauggac gggacaugua cgucgaccag gaauuggaca | 2580 |
| ucaacagacu cagcgacuac gauguggacc auauugugcc acaguccuuu cuuaaggacg | 2640 |
| acagcaucga uaacaaagug cucacuagau cagacaaaaa ucgcgggaaa ucagacaaug | 2700 |
| ugccaucgga agagguuguc aagaagauga aaaacuacug gagacagcug cucaaugcca | 2760 |
| aacuuaucac ccagcggaag uucgacaacc uuaccaaggc cgagcgcgga ggauugccg | 2820 |
| aacucgacaa ggccggcuuc aucaaaggc agcuggugga aacccggcag aucacuaaac | 2880 |
| acguggccca gauccucgau ucgcgcauga acacuaaaua cgaugagaau gacaagcuga | 2940 |
| uuagggaagu caaggucauc acucugaagu cgaaacuggu gucggacuuu agaaaggauu | 3000 |
| uccaguucua caaaguccgc gagauuaaca acuaccacca cgcucaugac gccuaccuga | 3060 |
| augcaguugu gggcaccgcg cugaucaaga aguauccgaa gcuggaaucc gaguucgugu | 3120 |
| acggagauua caaaguguac gacgugcgca aga | 3153 |

<210> SEQ ID NO 6
<211> LENGTH: 4486
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 6

| | |
|---|---|
| ucaagcuuuu ggacccucgu acagaagcua auacgacuca cuauagggaa auaagagaga | 60 |
| aaagaagagu aagaagaaau auaagagcca ccauggacua caaggaccac gacgagacu | 120 |
| acaaagacca ugacaucgau uacaaggaug acgaugacaa auggcaccg aagaagaaga | 180 |
| gaaaggucga aauucacggg gugccggccg cggacaagaa guacucaauc ggacuggaua | 240 |
| ucggcacgaa cagcguggu ugggcaguga ucaccgacga auacaaggug ccgagcaaga | 300 |
| aguucaaagu gcugggaaau accgaucgcc auucgaucaa gaaaaaucug auuggcgcgc | 360 |
| uccuguucga cucgggagag acugccgagg ccacagacu gaagaggacc gcuaggcgcc | 420 |
| gcuacacgag gcgcaaaaac cgcaucugcu aucuucaaga aaucuucuca aacgagaugg | 480 |

| | | | |
|---|---|---|---|
| ccaaggugga | cgacuccuuu | uuccaucggc uggaagaauc auuucuggug gaggaggaca | 540 |
| agaagcacga | acgccauccc | auuucggca acauugucga cgaaguggcc uaucaugaga | 600 |
| aguauccgac | uaucuaccac | uugagaaaga agcuggugga cuccacugac aaggcagauc | 660 |
| ugcgguugau | cuaccucgca | cuggcccaua ugaucaaauu ccggggacac uuccucaucg | 720 |
| agggcgaccu | uaaucccgac | aauuccgaug uggauaagcu uuucauccag cugguccaga | 780 |
| ccuacaacca | acuguuugaa | gaaaauccaa ucaaugcgag cggugucgau gcaaaggcca | 840 |
| uccugagcgc | ccgccucucg | aaaagcagaa ggcucgaaaa ccugaucgca caguugccug | 900 |
| gagagaagaa | gaacggccuc | uucggcaauc ucaucgcauu gcccgggga cugacuccaa | 960 |
| acuucaaauc | caacuucgac | uuggccgagg acgccaaacu gcaacugagc aaagauaccu | 1020 |
| acgaugauga | cuuggacaau | cuucggcuc agacggcga ccaguacgcc gaccuguucc | 1080 |
| uugcggcuaa | gaaccugucg | acgccauccc ugcuguccga cauccugcgc gucaauaccg | 1140 |
| aaauuacuaa | agcaccacuc | ucggcaucca ugaucaagag auacgaugaa caccaccagg | 1200 |
| aucucacccu | ccugaaagca | cuggugcggc agcagcuccc ugagaaauac aaggaaaucu | 1260 |
| ucuuugauca | guccaagaac | ggauacgccg gauacaucga cggcggcgcg agccaagagg | 1320 |
| aauucuacaa | guucaucaag | ccgauccugg aaaagaugga uggcacggaa gaacuccugg | 1380 |
| ucaaacugaa | uagagaggau | cugcuccgca acaacggac cuucgauaac ggaucgaucc | 1440 |
| cgcaccagau | ccaccucggc | gaacugcaug ccauccugcg gcggcaggag gacuuuuacc | 1500 |
| cguuccucaa | agacaacaga | gaaaagaucg agaagaucuu gaccuuucgc aucccguacu | 1560 |
| acgugggccc | gcucgcgaga | gguaacuccc gcuuugcuug gaugacuaga aagucagagg | 1620 |
| aaacgaucac | cccauggaac | uucgaagagg ugguugacaa aggagcgagc gcccaaucgu | 1680 |
| ucaucgaacg | gaugacuaac | uucgauaaga aucgccgaa ugagaagguc cugccuaagc | 1740 |
| acucacuucu | guaugaauac | uuuacugugu auaacgaacu caccaaaguc aaauacguga | 1800 |
| cugagggaau | gcgcaagccu | gcguuuugu ccggcgagca gaaaaaggcc aucguggacu | 1860 |
| ugcuguucaa | aaccaaccgc | aaggugacug uuaagcaacu caaagaggac uacuuuaaga | 1920 |
| agaucgaaug | cuuugacucg | gucgagauuu ccggggbuuga agauagauuc aacgcgucgc | 1980 |
| ugggaaccua | ccaugaucuc | cucaagauua ucaaggacaa agacuuccug gauaacgagg | 2040 |
| agaaugagga | cauccucgaa | gauauugugc uucccugac ccuuuucgaa gaucgcgaaa | 2100 |
| ugaucgaaga | acgccugaaa | accuacgcuc accguucga cgauaaggug augaaacagu | 2160 |
| ugaaacgccg | gcgguacacg | gguuggggc ggcugucgcg caagcugauc aacgaauuc | 2220 |
| gggacaaaca | gagcggaaag | accauccucg auuuucugaa guccgaugu uugccaacc | 2280 |
| gcaacuucau | gcagcucauc | caugacgauu cgcuuaccuu uaaggaggau uccagaagg | 2340 |
| cacaaguguc | gggacaaggg | gauucgcucc acgaacacau cgccaaucug gcgggucgc | 2400 |
| cggcaauuaa | gaagggaauc | cuccagacug uuaaggugu cgacgagcug ugaagguga | 2460 |
| ugggagaca | uaagccugaa | acauuguga ucgaugggc gagagaaaau caaacuacuc | 2520 |
| agaagggaca | gaagaauucc | cgggagcgga ugaagcgcau cgaggaggga ucaaggaac | 2580 |
| ugggcuccca | aauccugaaa | gagcaucccg uggaaauac ucagcugcag aacgagaagc | 2640 |
| uuuaccugua | cuaucuucaa | aauggcaggg acauguacgu cgaccaagaa cuggauauca | 2700 |
| aucggcucuc | cgauuacgac | gucgaucaca ucgucccca aucauuccug aaggaugaua | 2760 |
| gcaucgauaa | caagguggcuc | acuagaucag acaaaaaccg gggaaaguca gauaacgucc | 2820 |

| | | |
|---|---|---|
| ccagcgaaga agucgugaag aagaugaaga auuacuggag gcaacuucug aacgccaaac | 2880 |
| ucaucacuca gcgcaaguuc gacaaccuga ccaaagcaga aaggggagga cucagcgagc | 2940 |
| uggacaaggc ugguuucauc aaacggcagc ugguggagac ucgccaaauc acgaagcaug | 3000 |
| uggcccagau ucucgacucg cgcaugaaua cuaaguacga cgaaaacgau aagcugaucc | 3060 |
| gggaggugaa ggugaucacc cucaagagca agcucguguc cgauuuccgg aaagacuucc | 3120 |
| aguucuacaa ggugcgggag auuaacaacu accaucacgc ucacgacgcu uaccucaaug | 3180 |
| cuguggugg gacggcguug auuaagaagu acccaaaacu ggaguccgaa uucgucuacg | 3240 |
| gagauuacaa ggucuacgac gugcgcaaga ugauugccaa gucggagcag gaaauuggga | 3300 |
| aagcgacugc uaaguacuuc uucuacucga auaucaugaa cuucuucaag accgaaauca | 3360 |
| cccuggcuaa cggcgagauc aggaaacggc cgcugaucga aacuaauggu gagacugguu | 3420 |
| aaaucgugug ggauaaggga cgggacuucg ccacgguccg caagguccuc agcaugccgc | 3480 |
| aagugaauau uguuaagaaa accgaagugc agaccggugg guucucgaag gaauccaucc | 3540 |
| ugccaaagcg caacucggau aagcuuauug cccgcaagaa ggauugggac ccgaaaaagu | 3600 |
| acgguggguu cgacucccu accguggcgu acucggucgu gguggugcc aagugugaaa | 3660 |
| agggcaaauc aaagaagcuc aagagcguca aggagcugcu gggaaucacc aucauggaga | 3720 |
| gguccagcuu ugagaaaac ccgaucgacu ucuuggaagc caagggauac aagagguga | 3780 |
| agaaagaccu gaucaucaaa cuuccaaagu acucccuguu cgaacucgaa acgggagga | 3840 |
| agcgcaugcu cgccucagcc ggggaacugc aaaagggcaa cgaacuggcc cucccgucaa | 3900 |
| aauacgucaa cuuccuguac uuggcgucac acuacgaaaa gcugaaagga uccccagagg | 3960 |
| acaacgaaca gaaacagcug uucgucgagc agcacaagca cuaccuggac gagaucaucg | 4020 |
| aacagaucuc ggaauucagc aagagaguga cuuggcaga cgcuaaccuu gacaaaguc | 4080 |
| ucucggcaua caauaagcau cgcgacaagc cgaucagaga acaggcggag aacaucaucc | 4140 |
| accguucac ucucaccaac cugggcgcgc agcggcuuu uaaguacuuu gauaccacca | 4200 |
| uugaccgcaa gagauacacc ucaacuaaag aagugcugga cgcaacccug auccaucaaa | 4260 |
| gcaucaccgg acuuuaugaa acucggaucg aucucucaca gcucgaagga gacaaaagac | 4320 |
| cggcugccac caagaaggcc ggacaggcaa agaagaagaa augauaauag gcuggagccu | 4380 |
| cgguggccau gcuucuugcc ccuugggccu cccccagcc ccuccuccc uuccugcacc | 4440 |
| cguaccccg uggucuuuga auaaagucug aguggcggc ucuaga | 4486 |

<210> SEQ ID NO 7
<211> LENGTH: 1368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Tyr Thr Arg Lys Asn Arg Ile Cys
 65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr

```
                      485                 490                 495
Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910
```

```
Lys Ala Gly Phe Ile Lys Arg Gln Leu Val Glu Thr Arg Gln Ile Thr
           915                 920                 925

Lys His Val Ala Gln Ile Leu Asp Ser Arg Met Asn Thr Lys Tyr Asp
       930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
               965                 970                 975

Glu Ile Asn Asn Tyr His His Ala His Asp Ala Tyr Leu Asn Ala Val
               980                 985                 990

Val Gly Thr Ala Leu Ile Lys Lys Tyr Pro Lys Leu Glu Ser Glu Phe
           995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305
```

```
Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

<210> SEQ ID NO 8
<211> LENGTH: 1379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300
```

```
Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720
```

His Glu His Ile Ala Asn Leu Ala Gly Ser Pro Ala Ile Lys Lys Gly
                    725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val

```
                1130                1135                1140

Leu Val Val Ala Lys Val Glu Lys Gly Lys Ser Lys Lys Leu Lys
            1145                1150                1155

Ser Val Lys Glu Leu Leu Gly Ile Thr Ile Met Glu Arg Ser Ser
            1160                1165                1170

Phe Glu Lys Asn Pro Ile Asp Phe Leu Glu Ala Lys Gly Tyr Lys
            1175                1180                1185

Glu Val Lys Lys Asp Leu Ile Ile Lys Leu Pro Lys Tyr Ser Leu
            1190                1195                1200

Phe Glu Leu Glu Asn Gly Arg Lys Arg Met Leu Ala Ser Ala Gly
            1205                1210                1215

Glu Leu Gln Lys Gly Asn Glu Leu Ala Leu Pro Ser Lys Tyr Val
            1220                1225                1230

Asn Phe Leu Tyr Leu Ala Ser His Tyr Glu Lys Leu Lys Gly Ser
            1235                1240                1245

Pro Glu Asp Asn Glu Gln Lys Gln Leu Phe Val Glu Gln His Lys
            1250                1255                1260

His Tyr Leu Asp Glu Ile Ile Glu Gln Ile Ser Glu Phe Ser Lys
            1265                1270                1275

Arg Val Ile Leu Ala Asp Ala Asn Leu Asp Lys Val Leu Ser Ala
            1280                1285                1290

Tyr Asn Lys His Arg Asp Lys Pro Ile Arg Glu Gln Ala Glu Asn
            1295                1300                1305

Ile Ile His Leu Phe Thr Leu Thr Asn Leu Gly Ala Pro Ala Ala
            1310                1315                1320

Phe Lys Tyr Phe Asp Thr Thr Ile Asp Arg Lys Arg Tyr Thr Ser
            1325                1330                1335

Thr Lys Glu Val Leu Asp Ala Thr Leu Ile His Gln Ser Ile Thr
            1340                1345                1350

Gly Leu Tyr Glu Thr Arg Ile Asp Leu Ser Gln Leu Gly Gly Asp
            1355                1360                1365

Ser Arg Ala Asp Pro Lys Lys Lys Arg Lys Val
            1370                1375

<210> SEQ ID NO 9
<211> LENGTH: 1423
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Asp Lys Lys Tyr Ser Ile Gly Leu
            35                  40                  45

Asp Ile Gly Thr Asn Ser Val Gly Trp Ala Val Ile Thr Asp Glu Tyr
50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95
```

Thr Ala Glu Ala Thr Arg Leu Lys Arg Thr Ala Arg Arg Tyr Thr
                100                 105                 110

Arg Arg Lys Asn Arg Ile Cys Tyr Leu Gln Glu Ile Phe Ser Asn Glu
            115                 120                 125

Met Ala Lys Val Asp Asp Ser Phe Phe His Arg Leu Glu Glu Ser Phe
130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
    210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
        275                 280                 285

Pro Asn Phe Lys Ser Asn Phe Asp Leu Ala Glu Asp Ala Lys Leu Gln
    290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
        355                 360                 365

Gln Asp Leu Thr Leu Leu Lys Ala Leu Val Arg Gln Gln Leu Pro Glu
    370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
            420                 425                 430

Asn Arg Glu Asp Leu Leu Arg Lys Gln Arg Thr Phe Asp Asn Gly Ser
        435                 440                 445

Ile Pro His Gln Ile His Leu Gly Glu Leu His Ala Ile Leu Arg Arg
    450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
            500                 505                 510

Thr Pro Trp Asn Phe Glu Glu Val Val Asp Lys Gly Ala Ser Ala Gln

-continued

```
            515                 520                 525
Ser Phe Ile Glu Arg Met Thr Asn Phe Asp Lys Asn Leu Pro Asn Glu
530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
                580                 585                 590

Lys Thr Asn Arg Lys Val Thr Val Lys Gln Leu Lys Glu Asp Tyr Phe
                595                 600                 605

Lys Lys Ile Glu Cys Phe Asp Ser Val Glu Ile Ser Gly Val Glu Asp
610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
                660                 665                 670

Glu Arg Leu Lys Thr Tyr Ala His Leu Phe Asp Asp Lys Val Met Lys
                675                 680                 685

Gln Leu Lys Arg Arg Arg Tyr Thr Gly Trp Gly Arg Leu Ser Arg Lys
690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
                740                 745                 750

Ser Gly Gln Gly Asp Ser Leu His Glu His Ile Ala Asn Leu Ala Gly
                755                 760                 765

Ser Pro Ala Ile Lys Lys Gly Ile Leu Gln Thr Val Lys Val Val Asp
770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
                820                 825                 830

Gln Ile Leu Lys Glu His Pro Val Glu Asn Thr Gln Leu Gln Asn Glu
835                 840                 845

Lys Leu Tyr Leu Tyr Tyr Leu Gln Asn Gly Arg Asp Met Tyr Val Asp
                850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
                885                 890                 895

Thr Arg Ser Asp Lys Asn Arg Gly Lys Ser Asp Asn Val Pro Ser Glu
                900                 905                 910

Glu Val Val Lys Lys Met Lys Asn Tyr Trp Arg Gln Leu Leu Asn Ala
                915                 920                 925

Lys Leu Ile Thr Gln Arg Lys Phe Asp Asn Leu Thr Lys Ala Glu Arg
930                 935                 940
```

-continued

```
Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
                965                 970                 975

Arg Met Asn Thr Lys Tyr Asp Glu Asn Asp Lys Leu Ile Arg Glu Val
            980                 985                 990

Lys Val Ile Thr Leu Lys Ser Lys Leu Val Ser Asp Phe Arg Lys Asp
        995                 1000                1005

Phe Gln Phe Tyr Lys Val Arg Glu Ile Asn Asn Tyr His His Ala
    1010                1015                1020

His Asp Ala Tyr Leu Asn Ala Val Val Gly Thr Ala Leu Ile Lys
    1025                1030                1035

Lys Tyr Pro Lys Leu Glu Ser Glu Phe Val Tyr Gly Asp Tyr Lys
    1040                1045                1050

Val Tyr Asp Val Arg Lys Met Ile Ala Lys Ser Glu Gln Glu Ile
    1055                1060                1065

Gly Lys Ala Thr Ala Lys Tyr Phe Phe Tyr Ser Asn Ile Met Asn
    1070                1075                1080

Phe Phe Lys Thr Glu Ile Thr Leu Ala Asn Gly Glu Ile Arg Lys
    1085                1090                1095

Arg Pro Leu Ile Glu Thr Asn Gly Glu Thr Gly Glu Ile Val Trp
    1100                1105                1110

Asp Lys Gly Arg Asp Phe Ala Thr Val Arg Lys Val Leu Ser Met
    1115                1120                1125

Pro Gln Val Asn Ile Val Lys Lys Thr Glu Val Gln Thr Gly Gly
    1130                1135                1140

Phe Ser Lys Glu Ser Ile Leu Pro Lys Arg Asn Ser Asp Lys Leu
    1145                1150                1155

Ile Ala Arg Lys Lys Asp Trp Asp Pro Lys Lys Tyr Gly Gly Phe
    1160                1165                1170

Asp Ser Pro Thr Val Ala Tyr Ser Val Leu Val Val Ala Lys Val
    1175                1180                1185

Glu Lys Gly Lys Ser Lys Lys Leu Lys Ser Val Lys Glu Leu Leu
    1190                1195                1200

Gly Ile Thr Ile Met Glu Arg Ser Ser Phe Glu Lys Asn Pro Ile
    1205                1210                1215

Asp Phe Leu Glu Ala Lys Gly Tyr Lys Glu Val Lys Lys Asp Leu
    1220                1225                1230

Ile Ile Lys Leu Pro Lys Tyr Ser Leu Phe Glu Leu Glu Asn Gly
    1235                1240                1245

Arg Lys Arg Met Leu Ala Ser Ala Gly Glu Leu Gln Lys Gly Asn
    1250                1255                1260

Glu Leu Ala Leu Pro Ser Lys Tyr Val Asn Phe Leu Tyr Leu Ala
    1265                1270                1275

Ser His Tyr Glu Lys Leu Lys Gly Ser Pro Glu Asp Asn Glu Gln
    1280                1285                1290

Lys Gln Leu Phe Val Glu Gln His Lys His Tyr Leu Asp Glu Ile
    1295                1300                1305

Ile Glu Gln Ile Ser Glu Phe Ser Lys Arg Val Ile Leu Ala Asp
    1310                1315                1320

Ala Asn Leu Asp Lys Val Leu Ser Ala Tyr Asn Lys His Arg Asp
    1325                1330                1335
```

| | | | | | | | | | | | |
|---|---|---|---|---|---|---|---|---|---|---|---|
| Lys | Pro | Ile | Arg | Glu | Gln | Ala | Glu | Asn | Ile | Ile | His | Leu | Phe | Thr |
| | 1340 | | | | 1345 | | | | | 1350 | | | | |
| Leu | Thr | Asn | Leu | Gly | Ala | Pro | Ala | Ala | Phe | Lys | Tyr | Phe | Asp | Thr |
| 1355 | | | | | 1360 | | | | | 1365 | | | | |
| Thr | Ile | Asp | Arg | Lys | Arg | Tyr | Thr | Ser | Thr | Lys | Glu | Val | Leu | Asp |
| 1370 | | | | | 1375 | | | | | 1380 | | | | |
| Ala | Thr | Leu | Ile | His | Gln | Ser | Ile | Thr | Gly | Leu | Tyr | Glu | Thr | Arg |
| 1385 | | | | | 1390 | | | | | 1395 | | | | |
| Ile | Asp | Leu | Ser | Gln | Leu | Gly | Gly | Asp | Lys | Arg | Pro | Ala | Ala | Thr |
| 1400 | | | | | 1405 | | | | | 1410 | | | | |
| Lys | Lys | Ala | Gly | Gln | Ala | Lys | Lys | Lys | Lys |
| 1415 | | | | | 1420 | | | | | |

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gggaaataag agagaaaaga agagtaagaa gaaatataag agccacc                    47

<210> SEQ ID NO 16
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gggagatcag agagaaaaga agagtaagaa gaaatataag agccacc                    47

<210> SEQ ID NO 17
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
ggaataaaag tctcaacaca acatatacaa aacaaacgaa tctcaagcaa tcaagcattc        60
tacttctatt gcagcaattt aaatcatttc ttttaaagca aaagcaattt tctgaaaatt       120
ttcaccattt acgaacgata gcaac                                             145

<210> SEQ ID NO 18
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gggagacaag cuuggcauuc cgguacuguu gguaaagcca cc                           42

<210> SEQ ID NO 19
<211> LENGTH: 371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gcgcctgccc acctgccacc gactgctgga acccagccag tgggagggcc tggcccacca        60
gagtcctgct ccctcactcc tcgccccgcc ccctgtccca gagtcccacc tggggggctct      120 ctccacccctt ctcagagttc cagtttcaac cagagttcca accaatgggc tccatcctct     180
ggattctggc caatgaaata tctccctggc agggtcctct tcttttccca gagctccacc       240
ccaaccagga gctctagtta atggagagct cccagcacac tcggagcttg tgctttgtct       300
ccacgcaaag cgataaataa aagcattggt ggcctttggt ctttgaataa agcctgagta       360
ggaagtctag a                                                            371

<210> SEQ ID NO 20
<211> LENGTH: 568
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20 gccctgccg ctcccacccc cacccatctg ggccccgggt tcaagagaga gcggggtctg         60
atctcgtgta gccatataga gtttgcttct gagtgtctgc tttgtttagt agaggtgggc       120
aggaggagct gaggggctgg ggctggggtg ttgaagttgg ctttgcatgc ccagcgatgc       180
gcctccctgt gggatgtcat caccctggga accgggagtg gcccttggct cactgtgttc       240
tgcatggttt ggatctgaat taattgtcct ttcttctaaa tcccaaccga acttcttcca       300
acctccaaac tggctgtaac cccaaatcca agccattaac tacacctgac agtagcaatt      360
gtctgattaa tcactggccc cttgaagaca gcagaatgtc cctttgcaat gaggaggaga      420

```
tctgggctgg gcgggccagc tggggaagca tttgactatc tggaacttgt gtgtgcctcc    480
tcaggtatgg cagtgactca cctggtttta ataaaacaac ctgcaacatc tcatggtctt    540
tgaataaagc ctgagtagga agtctaga                                        568
```

<210> SEQ ID NO 21
<211> LENGTH: 289
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
acacactcca cctccagcac gcgacttctc aggacgacga atcttctcaa tggggggcg      60 gctgagctcc agccacccg cagtcacttt ctttgtaaca acttccgttg ctgccatcgt    120
aaactgacac agtgtttata acgtgtacat acattaactt attacctcat tttgttattt    180
ttcgaaacaa agccctgtgg aagaaaatgg aaaacttgaa gaagcattaa agtcattctg    240
ttaagctgcg taaatggtct ttgaataaag cctgagtagg aagtctaga               289
```

<210> SEQ ID NO 22
<211> LENGTH: 379
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
catcacattt aaaagcatct cagcctacca tgagaataag agaaagaaaa tgaagatcaa     60
aagcttattc atctgttttt cttttctgtt ggtgtaaagc caacaccctg tctaaaaaac    120
ataaatttct ttaatcattt tgcctctttt ctctgtgctt caattaataa aaaatggaaa    180
gaatctaata gagtggtaca gcactgttat ttttcaaaga tgtgttgcta tcctgaaaat    240
tctgtaggtt ctgtggaagt tccagtgttc tctcttattc cacttcggta gaggatttct    300
agtttcttgt gggctaatta aataaatcat taatactctt ctaatggtct ttgaataaag    360
cctgagtagg aagtctaga                                                 379
```

<210> SEQ ID NO 23
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
gctgccttct gcggggcttg ccttctggcc atgcccttct tctctccctt gcacctgtac     60
ctcttggtct ttgaataaag cctgagtagg aaggcggccg ctcgagcatg catctaga     118
```

<210> SEQ ID NO 24
<211> LENGTH: 908
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
gccaagccct ccccatccca tgtatttatc tctatttaat atttatgtct atttaagcct    60
catatttaaa gacagggaag agcagaacgg agccccaggc ctctgtgtcc ttccctgcat   120
ttctgagttt cattctcctg cctgtagcag tgagaaaaag ctcctgtcct cccatcccct   180
ggactgggag gtagataggt aaataccaag tatttattac tatgactgct ccccagccct   240
ggctctgcaa tgggcactgg gatgagccgc tgtgagcccc tggtcctgag ggtccccacc   300
tgggaccctt gagagtatca ggtctcccac gtgggagaca agaaatccct gtttaatatt   360
taaacagcag tgttccccat ctgggtcctt gcaccnctca ctctggcctc agccgactgc   420
acagcggccc ctgcatcccc ttggctgtga ggccnctgga caagcagagg tggccagagc   480
tgggaggcat ggccctgggg tcccacgaat tgctgggga atctcgtttt tcttcttaag   540
actttrggga catggtttga ctcccgaaca tcaccgacgc gtctcctgtt tttctgggtg   600
gcctcgggac acctgccctg cccccacgag ggtcaggact gtgactcttt ttagggccag   660
gcaggtgcct ggacatttgc cttgctggac ggggactggg gatgtgggag ggagcagaca   720
ggaggaatca tgtcaggcct gtgtgtgaaa ggaagctcca ctgtcaccct ccacctcttc   780
accccccact caccagtgtc ccctccactg tcacattgta actgaacttc aggataataa   840
agtgtttgcc tccatggtct ttgaataaag cctgagtagg aaggcggccg ctcgagcatg   900
catctaga                                                            908
```

<210> SEQ ID NO 25
<211> LENGTH: 835
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
actcaatcta aattaaaaaa gaaagaaatt tgaaaaaact ttctctttgc catttcttct    60
tcttcttttt taactgaaag ctgaatcctt ccatttcttc tgcacatcta cttgcttaaa   120
ttgtgggcaa aagagaaaaa gaaggattga tcagagcatt gtgcaataca gtttcattaa   180
ctccttcccc cgctccccca aaaatttgaa ttttttttc aacactctta cacctgttat   240
ggaaaatgtc aacctttgta agaaaaccaa aataaaaatt gaaaataaa aaccataaac   300 atttgcacca cttgtggctt ttgaatatct tccacagagg gaagtttaaa acccaaactt   360
ccaaaggttt aaactacctc aaaacacttt cccatgagtg tgatccacat tgttaggtgc   420
tgacctagac agagatgaac tgaggtcctt gttttgtttt gttcataata caaaggtgct   480
aattaatagt atttcagata cttgaagaat gttgatggtg ctagaagaat ttgagaagaa   540
atactcctgt attgagttgt atcgtgtggt gtatttttta aaaaatttga tttagcattc   600
atattttcca tcttattccc aattaaaagt atgcagatta tttgcccaaa tcttcttcag   660
attcagcatt tgttctttgc cagtctcatt ttcatcttct tccatggttc acagaaagct   720
ttgtttcttg ggcaagcaga aaaattaaat tgtacctatt ttgtatatgt gagatgttta   780
aataaattgt gaaaaaaatg aaataaagca tgtttggttt tccaaaagaa catat        835
```

<210> SEQ ID NO 26
<211> LENGTH: 297
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

| cgccgccgcc cgggcccgc agtcgagggt cgtgagccca ccccgtccat ggtgctaagc | 60 |
| gggcccgggt cccacacggc cagcaccgct gctcactcgg acgacgccct gggcctgcac | 120 |
| ctctccagct cctcccacgg ggtccccgta gccccggccc ccgcccagcc ccaggtctcc | 180 |
| ccaggccctc cgcaggctgc ccggcctccc tcccctgca gccatcccaa ggctcctgac | 240 |
| ctacctggcc cctgagctct ggagcaagcc ctgacccaat aaaggctttg aacccat | 297 |

<210> SEQ ID NO 27
<211> LENGTH: 602
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

| ggggctagag ccctctccgc acagcgtgga gacggggcaa ggaggggggt tattaggatt | 60 |
| ggtggttttg ttttgctttg tttaaagccg tgggaaaatg gcacaacttt acctctgtgg | 120 |
| gagatgcaac actgagagcc aaggggtggg agttgggata attttatat aaagaagtt | 180 |
| tttccacttt gaattgctaa aagtggcatt tttcctatgt gcagtcactc ctctcatttc | 240 |
| taaaataggg acgtggccag gcacggtggc tcatgcctgt aatcccagca ctttgggagg | 300 |
| ccgaggcagg cggctcacga ggtcaggaga tcgagactat cctggctaac acggtaaaac | 360 |
| cctgtctcta ctaaaagtac aaaaaattag ctgggcgtgg tggtgggcac ctgtagtccc | 420 |
| agctactcgg gaggctgagg caggagaaag gcatgaatcc aagaggcaga gcttgcagtg | 480 |
| agctgagatc acgccattgc actccagcct gggcaacagt gttaagactc tgtctcaaat | 540 |
| ataaataaat aaataaataa ataaataaat aaataaaaat aaagcgagat gttgccctca | 600 |
| aa | 602 |

<210> SEQ ID NO 28
<211> LENGTH: 785
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

| ggccctgccc cgtcggactg cccccagaaa gcctcctgcc cctgccagt gaagtccttc | 60 |
| agtgagcccc tccccagcca gcccttccct ggccccgccg gatgtataaa tgtaaaaatg | 120 |
| aaggaattac attttatatg tgagcagca agccggcaag cgagcacagt attatttctc | 180 |
| catcccctcc ctgcctgctc cttggcaccc ccatgctgcc ttcagggaga caggcaggga | 240 |
| gggcttgggg ctgcacctcc taccctccca ccagaacgca cccactggg agagctggtg | 300 |
| gtgcagcctt cccctccctg tataagacac tttgccaagg ctctcccctc tcgccccatc | 360 |
| cctgcttgcc cgctcccaca gcttcctgag ggctaattct gggaagggag agttctttgc | 420 |
| tgcccctgtc tggaagacgt ggctctgggt gaggtaggcg ggaaaggatg gagtgtttta | 480 |
| gttcttgggg gaggccaccc caaaccccag ccccaactcc aggggcacct atgagatggc | 540 |
| catgctcaac ccccctccca gacaggccct cctgtctccc agggccccca ccgaggttcc | 600 |
| cagggctgga gacttcctct ggtaaacatt cctccagcct cccctcccct ggggacgcca | 660 |

```
aggaggtgggg ccacacccag gaagggaaag cgggcagccc cgttttgggg acgtgaacgt      720
tttaataatt tttgctgaat tcctttacaa ctaaataaca cagatattgt tataaataaa      780
attgt                                                                   785
```

<210> SEQ ID NO 29
<211> LENGTH: 3001
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
atattaagga tcaagctgtt agctaataat gccacctctg cagttttggg aacaggcaaa       60
taaagtatca gtatacatgg tgatgtacat ctgtagcaaa gctcttggag aaaatgaaga      120
ctgaagaaag caaagcaaaa actgtataga gagattttc aaaagcagta atccctcaat       180
tttaaaaaag gattgaaaat tctaaatgtc tttctgtgca tatttttgt gttaggaatc       240 aaaagtattt tataaaagga gaagaacag cctcattta gatgtagtcc tgttggattt        300
tttatgcctc ctcagtaacc agaaatgttt taaaaaacta agtgtttagg atttcaagac      360
aacattatac atggctctga aatatctgac acaatgtaaa cattgcaggc acctgcattt      420 tatgttttt ttttcaacaa atgtgactaa tttgaaactt ttatgaactt ctgagctgtc       480
cccttgcaat tcaaccgcag tttgaattaa tcatatcaaa tcagttttaa ttttttaaat      540
tgtacttcag agtctatatt tcaagggcac attttctcac tactattta atacattaaa      600 ggactaaata atctttcaga gatgctggaa acaaatcatt tgctttatat gtttcattag      660
aataccaatg aaacatacaa cttgaaaatt agtaatagta tttttgaaga tcccatttct      720
aattggagat ctcttaatt tcgatcaact tataatgtgt agtactatat taagtgcact       780
tgagtggaat tcaacatttg actaataaaa tgagttcatc atgttggcaa gtgatgtggc      840
aattatctct ggtgacaaaa gagtaaaatc aaatatttct gcctgttaca aatatcaagg      900
aagacctgct actatgaaat agatgacatt aatctgtctt cactgtttat aatacggatg      960 gattttttt caaatcagtg tgtgttttga ggtcttatgt aattgatgac atttgagaga     1020
aatggtggct ttttttagct acctctttgt tcatttaagc accagtaaag atcatgtctt     1080
tttatagaag tgtagatttt ctttgtgact ttgctatcgt gcctaaagct ctaaatatag     1140
gtgaatgtgt gatgaatact cagattattt gtctctctat ataattagtt tggtactaag     1200
tttctcaaaa aattattaac acatgaaaga caatctctaa accagaaaaa gaagtagtac     1260 aaatttgtt actgtaatgc tcgcgtttag tgagtttaaa acacacagta tcttttggtt      1320
ttataatcag tttctatttt gctgtgcctg agattaagat ctgtgtatgt gtgtgtgtgt     1380
gtgtgtgcgt ttgtgtgtta aagcagaaaa gactttttta aaagttttaa gtgataaatg     1440
caatttgtta attgatctta gatcactagt aaactcaggg ctgaattata ccatgtatat     1500
tctattagaa gaaagtaaac accatcttta ttcctgccct ttttcttctc tcaaagtagt     1560
tgtagttata tctagaaaga agcaatttg atttcttgaa aaggtagttc ctgcactcag      1620
tttaaactaa aaataatcat acttggattt tatttatttt tgtcatagta aaaatttaa      1680 tttatatata tttttattta gtattatctt attctttgct atttgccaat cctttgtcat     1740
caattgtgtt aaatgaattg aaaattcatg ccctgttcat tttatttac tttattggtt      1800 aggatatttta aaggatttt gtatatataa tttcttaaat taatattcca aaaggttagt    1860
```

| | |
|---|---|
| ggacttagat tataaattat ggcaaaaatc taaaaacaac aaaaatgatt tttatacatt | 1920 |
| ctatttcatt attcctcttt ttccaataag tcatacaatt ggtagatatg acttatttta | 1980 |
| tttttgtatt attcactata tctttatgat atttaagtat aaataattaa aaaaatttat | 2040 |
| tgtaccttat agtctgtcac caaaaaaaaa aaattatctg taggtagtga aatgctaatg | 2100 |
| ttgatttgtc tttaagggct tgttaactat cctttatttt ctcatttgtc ttaaattagg | 2160 |
| agtttgtgtt taaattactc atctaagcaa aaaatgtata taaatcccat tactgggtat | 2220 |
| atacccaaag gattataaat catgctgcta taaagacaca tgcacacgta tgtttattgc | 2280 |
| agcactattc acaatagcaa agacttggaa ccaacccaaa tgtccatcaa tgatagactt | 2340 |
| gattaagaaa atgtgcacat atacaccatg gaatactatg cagccataaa aaaggatgag | 2400 |
| ttcatgtcct ttgtagggac atggataaag ctggaaacca tcattctgag caaactattg | 2460 |
| caaggacaga aaaccaaaca ctgcatgttc tcactcatag gtgggaattg aacaatgaga | 2520 |
| acacttggac acaaggtggg gaacaccaca caccagggcc tgtcatgggg tgggggagt | 2580 |
| ggggagggat agcattagga gatataccta atgtaaatga tgagttaatg ggtgcagcac | 2640 |
| accaacatgg cacatgtata catatgtagc aaacctgcac gttgtgcaca tgtaccctag | 2700 |
| aacttaaagt ataattaaaa aaaaaagaa aacagaagct atttataaag aagttatttg | 2760 |
| ctgaaataaa tgtgatcttt cccattaaaa aataaagaa attttggggt aaaaaaacac | 2820 |
| aatatattgt attcttgaaa aattctaaga gagtggatgt gaagtgttct caccacaaaa | 2880 |
| gtgataacta attgaggtaa tgcacatatt aattagaaag attttgtcat tccacaatgt | 2940 |
| atatatactt aaaaatatgt tatacacaat aaatacatac attaaaaaat aagtaaatgt | 3000 |
| a | 3001 |

<210> SEQ ID NO 30
<211> LENGTH: 1037
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 30

| | |
|---|---|
| cccaccctgc acgccggcac caaaccctgt cctcccaccc ctccccactc atcactaaac | 60 |
| agagtaaaat gtgatgcgaa ttttcccgac caacctgatt cgctagattt ttttttaagga | 120 |
| aaagcttgga aagccaggac acaacgctgc tgcctgctttt gtgcagggtc ctccggggct | 180 |
| cagccctgag ttggcatcac ctgcgcaggg ccctctgggg ctcagccctg agctagtgtc | 240 |
| acctgcacag ggccctctga ggctcagccc tgagctggcg tcacctgtgc agggccctct | 300 |
| ggggctcagc cctgagctgg cctcacctgg gttccccacc ccgggctctc ctgccctgcc | 360 |
| ctcctgcccg ccctccctcc tgcctgcgca gctccttccc taggcacctc tgtgctgcat | 420 |
| cccaccagcc tgagcaagac gccctctcgg ggctgtgcc gcactagcct ccctctcctc | 480 |
| tgtccccata gctggttttt cccaccaatc ctcacctaac agttacttta caattaaaact | 540 |
| caaagcaagc tcttctcctc agcttggggc agccattggc ctctgtctcg ttttgggaaa | 600 |
| ccaaggtcag gaggccgttg cagacataaa tctcggcgac tcggcccgt ctcctgaggg | 660 |
| tcctgctggt gaccggcctg gaccttggcc ctacagccct ggaggccgct gctgaccagc | 720 |
| actgaccccg acctcagaga gtactcgcag gggcgctggc tgcactcaag accctcgaga | 780 |
| ttaacggtgc taacccccgtc tgctcctccc tcccgcagag actggggcct ggactggaca | 840 |

| tgagagcccc ttggtgccac agagggctgt gtcttactag aaacaacgca aacctctcct | 900 |
| tcctcagaat agtgatgtgt tcgacgtttt atcaaaggcc cccttctat gttcatgtta | 960 |
| gttttgctcc ttctgtgttt ttttctgaac catatccatg ttgctgactt ttccaaataa | 1020 |
| aggttttcac tcctctc | 1037 |

<210> SEQ ID NO 31
<211> LENGTH: 577
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

| agaggcctgc ctccagggct ggactgaggc ctgagcgctc ctgccgcaga gctggccgcg | 60 |
| ccaaataatg tctctgtgag actcgagaac tttcattttt ttccaggctg gttcggattt | 120 |
| ggggtggatt ttggttttgt tcccctcctc cactctcccc cacccctcc ccgccctttt | 180 |
| tttttttttt tttaaactg gtattttatc tttgattctc cttcagccct caccctggt | 240 |
| tctcatcttt cttgatcaac atcttttctt gcctctgtcc ccttctctca tctcttagct | 300 |
| cccctccaac ctgggggca gtggtgtgga aagccacag gcctgagatt tcatctgctc | 360 |
| tccttcctgg agcccagagg agggcagcag aaggggtgg tgtctccaac cccccagcac | 420 |
| tgaggaagaa cggggctctt ctcatttcac ccctcccttt ctccctgcc cccaggactg | 480 |
| ggccacttct gggtgggca gtgggtccca gattggctca cactgagaat gtaagaacta | 540 |
| caaacaaaat ttctattaaa ttaaattttg tgtctcc | 577 |

<210> SEQ ID NO 32
<211> LENGTH: 2212
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

| ctccctccat cccaacctgg ctccctccca cccaaccaac tttcccccca acccggaaac | 60 |
| agacaagcaa cccaaactga accccctcaa aagccaaaaa atgggagaca atttcacatg | 120 |
| gactttggaa atatttttt cctttgcat tcatctctca aacttagttt ttatctttga | 180 |
| ccaaccgaac atgaccaaaa accaaaagtg cattcaacct taccaaaaaa aaaaaaaaa | 240 |
| aaagaataaa taaataactt tttaaaaag gaagcttggt ccacttgctt gaagacccat | 300 |
| gcggggtaa gtccctttct gcccgttggg cttatgaaac cccaatgctg ccctttctgc | 360 |
| tcctttctcc acacccccct tggggcctcc cctccactcc ttcccaaatc tgtctcccca | 420 |
| gaagacacag gaaacaatgt attgtctgcc cagcaatcaa aggcaatgct caaacaccca | 480 |
| agtggccccc accctcagcc cgctcctgcc cgcccagcac cccagggccc tgggggacct | 540 |
| ggggttctca gactgccaaa gaagccttgc catctggcgc tcccatggct cttgcaacat | 600 |
| ctcccccttcg ttttttgaggg ggtcatgccg ggggagccac cagcccctca ctgggttcgg | 660 |
| aggagagtca ggaagggcca cgacaaagca gaaacatcgg atttggggaa cgcgtgtcaa | 720 |
| tcccttgtgc cgcagggctg ggcgggagag actgttctgt tccttgtgta actgtgttgc | 780 |
| tgaaagacta cctcgttctt gtcttgatgt gtcaccgggg caactgcctg ggggcgggga | 840 |
| tggggggcagg gtggaagcgg ctccccattt tataccaaag gtgctacatc tatgtgatgg | 900 |

```
gtggggtggg gagggaatca ctggtgctat agaaattgag atgcccccc  aggccagcaa    960
atgttccttt ttgttcaaag tctattttta ttccttgata ttttttcttt tttttttttt   1020
tttttgtgga tggggacttg tgaattttc  taaaggtgct atttaacatg ggaggagagc   1080
gtgtgcggct ccagcccagc ccgctgctca ctttccaccc tctctccacc tgcctctggc   1140
ttctcaggcc tctgctctcc gacctctctc ctctgaaacc ctcctccaca gctgcagccc   1200
atcctcccgg ctccctccta gtctgtcctg cgtcctctgt ccccgggttt cagagacaac   1260
ttcccaaagc acaaagcagt ttttccccct aggggtggga ggaagcaaaa gactctgtac   1320
ctattttgta tgtgtataat aatttgagat gttttaatt  attttgattg ctggaataaa   1380
gcatgtggaa atgacccaaa cataatccgc agtggcctcc taatttcctt ctttggagtt   1440
gggggagggg tagacatggg gaaggggctt tggggtgatg ggcttgcctt ccattcctgc   1500
cctttccctc cccactattc tcttctagat ccctccataa ccccactccc ctttctctca   1560
cccttcttat accgcaaacc tttctacttc ctctttcatt ttctattctt gcaatttcct   1620
tgcaccttt  ccaaatcctc ttctccctg  caataccata caggcaatcc acgtgcacaa   1680
cacacacaca cactcttcac atctggggtt gtccaaacct catcccact  ccccttcaag   1740
cccatccact ctccaccccc tggatgccct gcacttggtg gcggtgggat gctcatggat   1800
actgggaggg tgagggagt  ggaacccgtg aggaggacct gggggcctct ccttgaactg   1860
acatgaaggg tcatctggcc tctgctccct tctcacccac gctgacctcc tgccgaagga   1920
gcaacgcaac aggagagggg tctgctgagc ctggcgaggg tctgggaggg accaggagga   1980
aggcgtgctc cctgctcgct gtcctggccc tgggggagtg agggagacag acacctggga   2040
gagctgtggg gaaggcactc gcaccgtgct cttgggaagg aaggagacct ggccctgctc   2100
accacggact gggtgcctcg acctcctgaa tccccagaac acaaccccc  tgggctgggg   2160
tggtctgggg aaccatcgtg ccccgcctc ccgcctactc cttttaagc tt            2212
```

<210> SEQ ID NO 33  
<211> LENGTH: 729  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 33

```
ttggccaggc ctgaccctct tggaccttc  ttctttgccg acaaccactg cccagcagcc     60
tctgggacct cggggtccca gggaacccag tccagcctcc tggctgttga cttcccattg    120
ctcttggagc caccaatcaa agagattcaa agagattcct gcaggccaga ggcggaacac    180
acctttatgg ctggggctct ccgtggtgtt ctggacccag cccctggaga caccattcac    240
ttttactgct tgtagtgac  tcgtgctctc caacctgtct tcctgaaaaa ccaaggcccc    300
cttcccccac ctcttccatg gggtgagact tgagcagaac aggggcttcc ccaagttgcc    360
cagaaagact gtctgggtga aagccatgg  ccagagcttc tcccaggcac aggtgttgca    420
ccagggactt ctgcttcaag ttttgggta  aagacacctg gatcagactc caagggctgc    480
cctgagtctg ggacttctgc ctccatggct ggtcatgaga gcaaaccgta gtcccctgga    540
gacagcgact ccagagaacc tcttgggaga cagaagaggc atctgtgcac agctcgatct    600
tctacttgcc tgtggggagg ggagtgacag gtccacacac cacactgggt caccctgtcc    660
tggatgcctc tgaagagagg gacagaccgt cagaaactgg agagtttcta ttaaaggtca    720
``` tttaaacca 729

<210> SEQ ID NO 34
<211> LENGTH: 847
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

| tcctccggga cccagccct caggattcct gatgctccaa ggcgactgat gggcgctgga | 60 |
| tgaagtggca cagtcagctt ccctgggggc tggtgtcatg ttgggctcct ggggcggggg | 120 |
| cacggcctgg catttcacgc attgctgcca ccccaggtcc acctgtctcc actttcacag | 180 |
| cctccaagtc tgtggctctt cccttctgtc ctccgagggg cttgccttct ctcgtgtcca | 240 |
| gtgaggtgct cagtgatcgg cttaacttag agaagcccgc cccctcccct tctccgtctg | 300 |
| tcccaagagg gtctgctctg agcctgcgtt cctaggtggc tcggcctcag ctgcctgggt | 360 |
| tgtggccgcc ctagcatcct gtatgccac agctactgga atccccgctg ctgctccggg | 420 |
| ccaagcttct ggttgattaa tgagggcatg gggtggtccc tcaagacctt ccctacctt | 480 |
| ttgtggaacc agtgatgcct caaagacagt gtcccctcca cagctgggtg ccaggggcag | 540 |
| gggatcctca gtatagccgg tgaaccctga taccaggagc ctgggcctcc ctgaacccct | 600 |
| ggcttccagc catctcatcg ccagcctcct cctggacctc ttggccccca gccccttccc | 660 |
| cacacagccc cagaagggtc ccagagctga ccccactcca ggacctaggc ccagcccctc | 720 |
| agcctcatct ggagcccctg aagaccagtc ccacccacct ttctggcctc atctgacact | 780 |
| gctccgcatc ctgctgtgtg tcctgttcca tgttccggtt ccatccaaat acactttctg | 840 |
| gaacaaa | 847 |

<210> SEQ ID NO 35
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

| gctggagcct cggtggccat gcttcttgcc ccttgggcct cccccagcc cctcctcccc | 60 |
| ttcctgcacc cgtaccccg tggtctttga ataaagtctg agtgggcggc | 110 |

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 4354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
tcaagctttt ggaccctcgt acagaagcta atacgactca ctatagggaa ataagagaga      60
aaagaagagt aagaagaaat ataagagcca ccatggacaa gaaatacagc atcggcctgg     120
atattggaac taacagcgtt ggatgggcag tgatcaccga cgagtacaag gtgccgagca     180
agaagttcaa ggtgctgggg aacactgacc gccattcaat taagaaaaac ctcattggag     240
cactgctttt tgactcgggt gagactgccg aagctaccag gctcaaacgc accgcacgca     300
gacggtacac ccgccgcaag aatcgcatct gctatctgca agagatcttt tccaacgaga     360
tggcgaaggt tgacgacagc ttttccacc ggctggaaga gagcttcctc gtggaagagg      420
acaaaaagca cgaaaggcat ccaatcttcg gtaacatcgt ggacgaagtg gcgtatcacg     480
aaaagtaccc taccatctac catctgcgga agaagctggt cgattccacg ataaggcag      540 acctgagact gatctacctg gctttggccc atatgatcaa attccgcggc catttcctga     600 tcgagggga ccttaacccg ataactcgg atgtcgacaa gctgttcatc cagctggtcc       660
aaacgtataa ccaactgttt gaggaaaatc ccatcaacgc ttcggggtg gacgccaaag      720 caatcctctc cgcgcgcctg agcaagtcac ggcggctcga aaacctgatc gcgcagctgc     780
cgggagaaaa gaaaaatgga ctgtttggga atctgatcgc gctgtcgctc ggcctgactc     840
caaactttaa gtcaaatttc gatttggccg aagatgccaa gctgcagctg tcaaaggaca     900
cttacgacga cgacctggac aatctgctgg cccagattgg ggaccaatac gcagacctgt     960
tcttggccgc gaagaacctg agcgacgcca ttcttctgtc cgatattctg agagtcaata    1020
ccgaaatcac taaggctccg ctgtccgctt caatgatcaa gcgctacgat gaacaccacc    1080
aggatctcac tctgctcaaa gccctcgtga caacaatt gcctgaaaag tacaaggaga     1140
tcttcttcga ccagagcaaa aacggctacg caggctacat cgatggagga gcgtcacaag    1200
aagagttcta caagttcatc aagccaatct tggagaagat ggacggtact gaagaactcc    1260
ttgtgaagct gaatagggag gatttgctca gaaagcagcg gactttgac aacggctcga     1320 tccctcatca gattcacctc ggtgagctgc atgccatcct tcggcgccaa gaggattttt    1380
accccttcct gaaggataat cgcgagaaaa tcgaaaagat cctgacgttc agaattccct    1440
actacgtggg accgctggcg cgcggtaact cgcggtttgc atggatgact cgcaagtcag    1500
aggaaactat cactccttgg aattttgagg aggtcgtcga taagggagcc tccgcccagt    1560
cattcatcga acgcatgacc aacttcgaca agaatcttcc gaacgagaag gtccttccaa    1620
```

```
agcactccct gttgtacgaa tacttcaccg tgtacaatga gctgaccaaa gttaagtatg    1680
tcaccgaggg catgagaaag ccggccttcc tcagcggcga acaaaagaag gccatcgtcg    1740
acctcctctt caagaccaac cggaaggtga ccgtcaagca actcaaggag gactacttca    1800
agaagatcga atgctttgac tcggtcgaaa tcagcggagt ggaggaccgg tttaacgcgt    1860
cactgggtac ctaccatgat ctcctgaaaa tcatcaaaga caaggacttc ctggacaacg    1920
aagaaaacga ggacatcctg gaagatattg tgttgaccct gacgctgttc gaggaccggg    1980
aaatgatcga ggaaaggctt aagacctacg cacacctctt cgatgacaaa gtgatgaagc    2040
aactgaagcg gcggagatat actggctggg ggaggctctc ccggaagctc attaatggaa    2100
tcagagacaa acagtcgggt aaaactatcc tcgacttcct caagtcggat gggttcgcca    2160
accggaactt catgcagctg atccacgatg attccttgac cttcaaggaa gatatccaga    2220
aggcgcaagt gagcggacag ggagattcgt tgcacgaaca tatcgctaat ctcgccggat    2280
ccccagccat caagaaagga atcctgcaga ccgtgaaggt ggtggatgaa ctggtgaaag    2340
tgatggggcg ccacaaacca gagaacatcg tcattgagat ggcccgcgag aatcagacca    2400
ctcagaaggg acaaaagaac tccagagagc ggatgaaacg catcgaggaa ggcatcaaag    2460
agcttggtag ccaaatcctg aaggaacacc cggtcgagaa cacccagctc cagaacgaaa    2520
agctttacct gtactacctc caaaatggac gggacatgta cgtcgaccag gaattggaca    2580
tcaacagact cagcgactac gatgtggacc atattgtgcc acagtccttt cttaaggacg    2640
acagcatcga taacaaagtg ctcactagat cagacaaaaa tcgcgggaaa tcagacaatg    2700
tgccatcgga agaggttgtc aagaagatga aaaactactg gagacagctg ctcaatgcca    2760
aacttatcac ccagcggaag ttcgacaacc ttaccaaggc cgagcgcgga ggattgtccg    2820
aactcgacaa ggccggcttc atcaaaaggc agctggtgga acccggcag atcactaaac    2880 acgtggccca gatcctcgat tcgcgcatga acactaaata cgatgagaat gacaagctga    2940
ttagggaagt caaggtcatc actctgaagt cgaaactggt gtcggacttt agaaaggatt    3000
tccagttcta caaagtccgc gagattaaca actaccacca cgctcatgac gcctacctga    3060
atgcagttgt gggcaccgcg ctgatcaaga agtatccgaa gctggaatcc gagttcgtgt    3120
acggagatta caaagtgtac gacgtgcgca agatgatcgc caagtcggaa caggaaatcg    3180
gaaaggctac tgcaaagtac ttcttctact caaacatcat gaacttcttc aaaacggaga    3240
tcacgctcgc gaacggcgaa atccggaaaa ggccgctcat tgaaaccaac ggagaaaccg    3300
gggagatcgt gtgggacaag ggaagggatt ttgcgactgt gaggaaggtg ttgtccatgc    3360
cgcaagtcaa tattgtgaaa aagacggaag tgcaaaccgg aggattcagc aaagaatcca    3420
tcctcccaaa gcgcaactcg gacaaactca tcgcgcgcaa gaaggattgg gaccccaaga    3480
aatacggtgg ctttgacagc cctactgtgg cttactccgt cctcgtcgtg gctaaagtgg    3540
aaaagggtaa atccaaaaag ctcaaatcgg tgaaggagct cctgggaatc acgatcatgg    3600
agcggtcgag cttcgaaaag aatcctattg atttcctgga ggcgaagggc tacaaggaag    3660
tcaagaaaga cctgatcatc aagctcccga agtacagcct cttcgagctc gaaaacggca    3720
gaaagaggat gctggcatca gcgggagaat tgcagaaggg aaacgaactg gcactgccgt    3780
ccaagtacgt gaattttctc tatctggcta gccactacga aaagctgaag ggatcgcccg    3840
aggacaacga gcaaaaacaa ctgttcgtgg agcagcacaa gcactacctg gatgagatca    3900
tcgagcagat ctccgaattc tcgaaacgcg tgatccttgc cgatgccaat ctggataaag    3960
```

```
tgttgtcggc ttacaacaag catcgggata aaccgatccg cgaacaggca gaaaacatca    4020
ttcatctgtt cactttgacc aatctgggag cgcctgccgc gtttaagtac ttcgacacca    4080
ctattgatag aaagcgctac acctcgacca aggaagtgct ggacgctacc ctgatccacc    4140
agtccatcac cggactctac gaaactcgca ttgacctgtc ccagcttgga ggagattcac    4200
gggccgatcc aaagaaaaag cgcaaggtct gataataggc tggagcctcg gtggccatgc    4260
ttcttgcccc ttgggcctcc ccccagcccc tcctcccctt cctgcacccg taccccgtg     4320 gtctttgaat aaagtctgag tgggcggctc taga                                4354
```

<210> SEQ ID NO 42
<211> LENGTH: 4486
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
tcaagctttt ggaccctcgt acagaagcta atacgactca ctatagggaa ataagagaga      60
aaagaagagt aagaagaaat ataagagcca ccatggacta caaggaccac gacggagact     120
acaaagacca tgacatcgat tacaaggatg acgatgacaa aatggcaccg aagaagaaga     180
gaaaggtcgg aattcacggg gtgccggccg cggacaagaa gtactcaatc ggactggata     240
tcggcacgaa cagcgtgggt tggcagtgat caccgacga atacaaggtg ccgagcaaga     300
agttcaaagt gctgggaaat accgatcgcc attcgatcaa gaaaaatctg attggcgcgc     360
tcctgttcga ctcgggagag actgccgagg ccactagact gaagaggacc gctaggcgcc     420
gctacacgag gcgcaaaaac cgcatctgct atcttcaaga aatcttctca acgagatgg     480 ccaaggtgga cgactccttt ttccatcggc tggaagaatc atttctggtg gaggaggaca     540
agaagcacga acgccatccc attttcggca acattgtcga cgaagtggcc tatcatgaga     600
agtatccgac tatctaccac ttgagaaaga agctggtgga ctccactgac aaggcagatc     660
tgcggttgat ctacctcgca ctggcccata tgatcaaatt ccggggacac ttcctcatcg     720
agggcgacct taatcccgac aattccgatg tggataagct tttcatccag ctggtccaga     780
cctacaacca actgtttgaa gaaaatccaa tcaatgcgag cggtgtcgat gcaaaggcca     840
tcctgagcgc ccgcctctcg aaaagcagaa ggctcgaaaa cctgatcgca cagttgcctg     900
gagagaagaa gaacggcctc ttcggcaatc tcatcgcatt gtccctggga ctgactccaa     960
acttcaaatc caacttcgac ttggccgagg acgccaaact gcaactgagc aaagatacct    1020
acgatgatga cttggacaat cttctggctc agatcggcga ccagtacgcc gacctgttcc    1080
ttgcggctaa gaacctgtcg gacgccatcc tgctgtccga catcctgcgc gtcaataccg    1140
aaattactaa agcaccactc tcggcatcca tgatcaagag atacgatgaa caccaccagg    1200
atctcaccct cctgaaagca ctggtgcggc agcagctccc tgagaaatac aaggaaatct    1260
tctttgatca gtccaagaac ggatacgccg gatacatcga cggcggcgcg agccaagagg    1320
aattctacaa gttcatcaag ccgatcctgg aaaagatgga tggcacggaa gaactcctgg    1380
tcaaactgaa tagagaggat ctgctccgca acaacggac cttcgataac ggatcgatcc    1440
cgcaccagat ccacctcggc gaactgcatg ccatcctgcg gcggcaggag gacttttacc    1500
cgttcctcaa agacaacaga gaaaagatcg agaagatctt gaccttcgc atcccgtact    1560 acgtgggccc gctcgcgaga ggtaactccc gctttgcttg gatgactaga aagtcagagg    1620
```

```
aaacgatcac cccatggaac ttcgaagagg tggttgacaa aggagcgagc gcccaatcgt   1680
tcatcgaacg gatgactaac ttcgataaga atctgccgaa tgagaaggtc ctgcctaagc   1740
actcacttct gtatgaatac tttactgtgt ataacgaact caccaaagtc aaatacgtga   1800
ctgagggaat gcgcaagcct gcgttttttgt ccggcgagca gaaaaaggcc atcgtggact   1860
tgctgttcaa aaccaaccgc aaggtgactg ttaagcaact caaagaggac tactttaaga   1920
agatcgaatg cttttgactcg gtcgagattt ccggggttga agatagattc aacgcgtcgc   1980
tgggaaccta ccatgatctc ctcaagatta tcaaggacaa agacttcctg gataacgagg   2040
agaatgagga catcctcgaa gatattgtgc ttaccctgac ccttttcgaa gatcgcgaaa   2100
tgatcgaaga acgcctgaaa acctacgctc acctgttcga cgataaggtg atgaaacagt   2160
tgaaacgccg gcggtacacg ggttgggggc ggctgtcgcg caagctgatc aacggaattc   2220
gggacaaaca gagcggaaag accatcctcg attttctgaa gtccgatggt tttgccaacc   2280
gcaacttcat gcagctcatc catgacgatt cgcttacctt taaggaggat atccagaagg   2340
cacaagtgtc gggacaaggg gattcgctcc acgaacacat cgccaatctg gcggggtcgc   2400
cggcaattaa gagggaatc ctccagactg ttaaggtggt cgacgagctg gtgaaggtga   2460
tggggagaca taagcctgaa aacattgtga tcgagatggc gagagaaaat caaactactc   2520
agaagggaca gaagaattcc cgggagcgga tgaagcgcat cgaggaggga atcaaggaac   2580
tgggctccca aatcctgaaa gagcatcccg tggaaaatac tcagctgcag aacgagaagc   2640
tttacctgta ctatcttcaa aatggcaggg acatgtacgt cgaccaagaa ctggatatca   2700
atcggctctc cgattacgac gtcgatcaca tcgtccccca atcattcctg aaggatgata   2760
gcatcgataa caaggtgctc actagatcag acaaaaaccg gggaaagtca gataacgtcc   2820
ccagcgaaga agtcgtgaag aagatgaaga attactggag gcaacttctg aacgccaaac   2880
tcatcactca gcgcaagttc gacaacctga ccaaagcaga aggggagga ctcagcgagc   2940 tggacaaggc tggtttcatc aaacggcagc tggtggagac tcgccaaatc acgaagcatg   3000
tggcccagat tctcgactcg cgcatgaata ctaagtacga cgaaaacgat aagctgatcc   3060
gggaggtgaa ggtgatcacc ctcaagagca agctcgtgtc cgatttccgg aaagacttcc   3120
agttctacaa ggtgcgggag attaacaact accatcacgc tcacgacgct tacctcaatg   3180
ctgtggtggg gacggcgttg attaagaagt acccaaaact ggagtccgaa ttcgtctacg   3240
gagattacaa ggtctacgac gtgcgcaaga tgattgccaa gtcggagcag gaaattggga   3300
aagcgactgc taagtacttc ttctactcga atatcatgaa cttcttcaag accgaaatca   3360
ccctggctaa cggcgagatc aggaaacggc cgctgatcga aactaatggt gagactggtg   3420
aaatcgtgtg ggataaggga cgggacttcg ccacggtccg caaggtcctc agcatgccgc   3480
aagtgaatat tgttaagaaa accgaagtgc agaccggtgg gttctcgaag gaatccatcc   3540
tgccaaagcg caactcggat aagcttattg cccgcaagaa ggattgggac ccgaaaaagt   3600
acggtgggtt cgactcccct accgtggcgt actcggtgtt ggtggtggcc aaagtggaaa   3660
agggcaaatc aaagaagctc aagagcgtca aggagctgct gggaatcacc atcatggaga   3720
ggtccagctt tgagaaaaac ccgatcgact tcttggaagc caagggatac aaagaggtga   3780
agaaagacct gatcatcaaa cttccaaagt actccctgtt cgaactcgaa aacgggagga   3840
agcgcatgct cgcctcagcc ggggaactgc aaaagggcaa cgaactggcc ctcccgtcaa   3900
aatacgtcaa cttcctgtac ttggcgtcac actacgaaaa gctgaaagga tcccagagg   3960 acaacgaaca gaaacagctg ttcgtcgagc agcacaagca ctacctggac gagatcatcg   4020
```

```
aacagatctc ggaattcagc aagagagtga tcttggcaga cgctaacctt gacaaagtcc   4080
tctcggcata caataagcat cgcgacaagc cgatcagaga acaggcggag aacatcatcc   4140
acctgttcac tctcaccaac ctgggcgcgc cagcggcttt taagtacttt gataccacca   4200
ttgaccgcaa gagatacacc tcaactaaag aagtgctgga cgcaaccctg atccatcaaa   4260
gcatcaccgg actttatgaa actcggatcg atctctcaca gctcggagga gacaaaagac   4320
cggctgccac caagaaggcc ggacaggcaa agaagaagaa atgataatag gctggagcct   4380
cggtggccat gcttcttgcc ccttgggcct ccccccagcc cctcctcccc ttcctgcacc   4440
cgtaccccg tggtctttga ataaagtctg agtgggcggc tctaga                  4486
```

<210> SEQ ID NO 43
<211> LENGTH: 4684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
tcaagctttt ggaccctcgt acagaagcta atacgactca ctataggaa ataagagaga    60
aaagaagagt aagaagaaat ataagagcca ccatggacaa gaaatactca atcggacttg   120
ctatcggaac taacagcgtg ggatgggccg tcattactga cgaatacaag gtgccctcaa   180
agaagttcaa ggtcctggga ataccgata gacactccat caaaaagaac ctgatcgggg   240
cactgttgtt cgactcggga gagactgcag aagcaaccag gctcaagcgc actgcgaggc   300
gccggtacac ccggaggaag aaccgcatct gctacctcca agagattttc agcaacgaga   360
tggcaaaggt cgatgattcg ttcttcacc gccttgagga gtcgttcctt gtcgaggagg   420
acaaaaagca tgaaagacat ccgatcttcg gaaacatcgt ggacgaagtc gcataccatg   480
aaaagtaccc taccatctac catctcagaa agaaactcgt cgattcaact gataaggccg   540
acttgcggct gatctacctg gctctggcgc acatgatcaa gtttcggggt cactttctca   600
tcgagggtga tctcaacccg gacaattccg acgttgacaa actcttcatc caactggtcc   660
agacgtacaa ccagctgttc gaagaaatc cgatcaacgc aagcggagtg acgccaaag   720
ccattctgtc ggcccgcctc tcgaagtcgc gtcgcctgga aaatctgatt gctcagctcc   780
cgggcgaaaa gaagaatggc ctgtttggaa acctcatcgc actgtccctc gggctgactc   840
ccaacttcaa atcgaacttt gacttggctg aggatgcaaa gctgcaactc tccaaagaca   900
cttacgatga tgacctggac aatctcctgg cgcagatcgg ggatcagtat gctgacctgt   960
tcctggcggc caagaacctg tctgatgcca tcctgctctc cgatatcctg agagtgaaca  1020
ctgagatcac caaggcgcct ctgagcgcct cgatgatcaa acgctacgat gaacaccatc  1080
aggacctcac tcttctgaag gctttggtgc ggcagcagct tccggaaaag tacaaagaga  1140
tcttcttcga ccagtcgaaa aacggctacg ccggatacat tgatggcggc gcaagccagg  1200
aggaattcta taagtttatc aaaccgatcc tggagaagat ggacggcact gaagaacttc  1260
tggtcaagct gaatcgagag gatctgctcc ggaagcagcg gaccttcgac aatgggtcta  1320
tccctcacca aatccatctc ggcgagctgc atgcgattct gaggcgccag gaggacttct  1380
acccattcct gaaagacaat cgggagaaaa tcgaaaagat tctgacgttc cgcattccat  1440
actacgtcgg gccacttgcg cggggtaatt cgagattcgc ctggatgacg cggaagtccg  1500
aagaaaccat cacgccgtgg aatttcgaag aagtggtcga caagggagcc agcgcacagt  1560
```

```
ccttcattga gcgcatgacc aatttcgaca aaaatctgcc gaacgagaag gtcctgccga    1620
agcattcact gctgtacgaa tactttaccg tgtacaacga actgaccaag gtgaagtacg    1680
tcaccgaggg aatgagaaag cctgctttcc tgagcggaga acagaagaag gccattgttg    1740
acctcctctt caagactaat cgcaaagtga ccgtgaagca gcttaaagag gattacttca    1800
aaaagatcga atgtttcgac tccgtggaaa tcagcggcgt ggaggataga ttcaacgcgt    1860
cccttgggac ttaccacgac ctccttaaga tcatcaagga taaggatttc ctcgacaatg    1920
aggaaaacga agatatcctg gaggacatcg ttctgactct gaccctcttt gaggaccggg    1980
agatgatcga ggagagactc aagacctacg cgcacctgtt tgacgacaaa gtgatgaagc    2040
aacttaaacg caggcgctac accggctggg gcagactgtc acgcaagttg atcaacggaa    2100
ttagagataa acagtccgga aagaccatcc tggacttcct gaagtccgat ggattcgcca    2160
accggaattt catgcagctc atccatgacg actcattgac tttcaaggag gatatccaaa    2220
aggcccaagt gagcggccaa ggggactccc ttcacgaaca catcgcaaat ttggccggat    2280
caccagcgat taagaaggga atcctgcaga ccgtgaaggt ggtggacgag ctggtgaaag    2340
tgatgggacg gcacaagccg gaaaacatcg tgatcgagat ggccagagag aaccagacga    2400
ctcaaaaggg ccagaagaac tcgcgcgaac gcatgaagag aatagaagag ggaattaagg    2460
aactgggatc gcagatcttg aaggagcacc ctgtcgaaaa tactcaactc cagaacgaga    2520
agctgtacct gtactatctt caaaacggca gggacatgta tgtcgaccaa gagctcgaca    2580
ttaaccgcct gtccgattat gacgtggacg ccatcgtgcc gcagagcttt ctcaaggacg    2640
attccatcga caacaaagtg ctcacccgca gcgacaagaa tagagggaag tcggataacg    2700
tcccttcgga agaggtggtg aaaaagatga agaattactg gcggcagctc ctgaatgcaa    2760
agctcatcac ccaacggaag tttgacaacc tcaccaaggc agaaagagga ggactgtcgg    2820
aattggataa ggccggtttc atcaagcgac aattggtgga aactcggcaa attaccaagc    2880
atgtggcaca gattctggac tcccgtatga acaccaagta cgacgagaac gataagctga    2940
tccgcgaggt caaggtgatc accctcaaaa gcaaacttgt gtcagacttc cggaaggact    3000
tccaattcta caaggtccgc gaaatcaaca actaccacca cgctcatgac gcatacctga    3060
acgctgtggt cgggactgcc ctcatcaaga gtaccctaa actcgaaagc gaatttgtgt    3120
acggcgacta caaagtgtac gatgtccgga agatgatcgc gaaatccgag caggagatcg    3180
gaaaggcgac tgctaagtac ttttttctact cgaacatcat gaacttcttc aaaaccgaaa    3240
tcaccctggc taatggcgag atcagaaagc gcccgctgat cgaaaccaac ggcgaaaccg    3300
gtgaaatcgt gtgggacaag ggccgcgatt tcgctactgt gagaaaggtc ctttccatgc    3360
cgcaagtgaa tatcgtcaaa aagactgagg tgcagactgg cggattttcc aaggaatcga    3420
tcctcccaaa gaggaactca gataagctca tcgcgcggaa aaaggattgg gaccctaaga    3480
agtacggagg atttgatagc ccaactgtgg cctactctgt gctcgtggtg gccaaagtcg    3540
agaaaggaaa gtcgaagaag ttgaaatccg tgaaagaact cttgggaatc actatcatgg    3600
agcggtcgtc atttgaaaag aacccaatcg acttcctgga agccaaggga tacaaagaag    3660 tcaagaagaga cctgatcatc aagctcccta agtacagcct gttcgaactg gagaacggaa    3720
ggaaacggat gctggcttcc gccggcgaac tgcaaaaggg caatgagctg gccctcccat    3780
cgaaatacgt gaacttcctc tacccttgcct cccattacga aaagttgaag ggctcacccg    3840
aggacaatga gcagaaacag ctctttgttg aacaacacaa acactacctg gacgaaatca    3900
```

| | | |
|---|---|---|
| tcgaacaaat cagcgagttc agcaagcgcg tcattctggc ggacgcgaac ctggataaag | 3960 |
| tgctgtccgc gtacaacaag caccgcgata agccgatacg ggaacaggct gagaacatca | 4020 |
| ttcacctctt cactctcact aatctgggag cccccgccgc cttcaagtac tttgatacta | 4080 |
| ccatcgaccg caagagatac acgagcacca aggaagtgct cgatgccacc ctgatccacc | 4140 |
| agtccattac tggtctgtac gaaacgcgaa tcgatctgtc acagctcgga ggagatgcgt | 4200 |
| accccctacga tgtccccgac tacgcgtcac tcggtagcgg cagcccgaag aagaaaagaa | 4260 |
| aggtggagga cccgaagaaa aagaggaagg ttgacgggat cggaagcgga tcgaatggat | 4320 |
| cgtcaggggg aggtggcgga ggtatggacg caaaatcact tacggcctgg tcacggacct | 4380 |
| tggtgacctt taaagacgtg ttcgtggatt tcaccaggga agaatggaaa ctgttggaca | 4440 |
| ccgcccagca gatcgtgtac cggaatgtga tgctggagaa ctacaaaaac ttggtgtccc | 4500 |
| tggggtatca actcactaag ccagatgtca ttcttagact ggaaaaggga gaagaaccgt | 4560 |
| gataataggc tggagcctcg gtggccatgc ttcttgcccc ttgggcctcc ccccagcccc | 4620 |
| tcctcccctt cctgcacccg taccccgtg gtctttgaat aaagtctgag tgggcggctc | 4680 |
| taga | 4684 |

<210> SEQ ID NO 44
<211> LENGTH: 4600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

| | | |
|---|---|---|
| tcaagctttt ggaccctcgt acagaagcta atacgactca ctatagggaa ataagagaga | 60 |
| aaagaagagt aagaagaaat ataagagcca ccatggacaa gaaatactca atcggacttg | 120 |
| ctatcggaac taacagcgtg ggatgggccg tcattactga cgaatacaag gtgccctcaa | 180 |
| agaagttcaa ggtcctggga ataccgata gacactccat caaaaagaac ctgatcgggg | 240 |
| cactgttgtt cgactcggga gagactgcag aagcaaccag gctcaagcgc actgcgaggc | 300 |
| gccggtacac ccggaggaag aaccgcatct gctacctcca agagattttc agcaacgaga | 360 |
| tggcaaaggt cgatgattcg ttctttcacc gccttgagga gtcgttcctt gtcgaggagg | 420 |
| acaaaaagca tgaaagacat ccgatcttcg gaaacatcgt ggacgaagtc gcataccatg | 480 |
| aaaagtaccc taccatctac catctcagaa agaaactcgt cgattcaact gataaggccg | 540 |
| acttgcggct gatctacctg gctctggcgc acatgatcaa gtttcggggt cactttctca | 600 |
| tcgagggtga tctcaacccg gacaattccg acgttgacaa actcttcatc caactggtcc | 660 |
| agacgtacaa ccagctgttc gaagaaaatc cgatcaacgc aagcggagtg gacgccaaag | 720 |
| ccattctgtc ggcccgcctc tcgaagtcgc gtcgcctgga aaatctgatt gctcagctcc | 780 |
| cgggcgaaaa gaagaatggc ctgtttggaa acctcatcgc actgtccctc gggctgactc | 840 |
| ccaacttcaa atcgaacttt gacttggctg aggatgcaaa gctgcaactc tccaaagaca | 900 |
| cttacgatga tgacctggac aatctcctgg cgcagatcgg ggatcagtat gctgacctgt | 960 |
| tcctggcggc caagaacctg tctgatgcca tcctgctctc cgatatcctg agagtgaaca | 1020 |
| ctgagatcac caaggcgcct ctgagcgcct cgatgatcaa acgctacgat gaacaccatc | 1080 |
| aggacctcac tcttctgaag gctttggtgc ggcagcagct tccggaaaag tacaaagaga | 1140 |
| tcttcttcga ccagtcgaaa aacggctacg ccggatacat tgatggcggc gcaagccagg | 1200 |

```
aggaattcta taagtttatc aaaccgatcc tggagaagat ggacggcact gaagaacttc    1260
tggtcaagct gaatcgagag gatctgctcc ggaagcagcg gaccttcgac aatgggtcta    1320
tccctcacca aatccatctc ggcgagctgc atgcgattct gaggcgccag gaggacttct    1380
acccattcct gaaagacaat cgggagaaaa tcgaaaagat tctgacgttc cgcattccat    1440
actacgtcgg gccacttgcg cggggtaatt cgagattcgc ctggatgacg cggaagtccg    1500
aagaaaccat cacgccgtgg aatttcgaag aagtggtcga caaggagcc agcgcacagt    1560 ccttcattga gcgcatgacc aatttcgaca aaaatctgcc gaacgagaag gtcctgccga    1620
agcattcact gctgtacgaa tactttaccg tgtacaacga actgaccaag gtgaagtacg    1680
tcaccgaggg aatgagaaag cctgctttcc tgagcggaga acagaagaag gccattgttg    1740
acctcctctt caagactaat cgcaaagtga ccgtgaagca gcttaaagag gattacttca    1800
aaaagatcga atgtttcgac tccgtggaaa tcagcggcgt ggaggataga ttcaacgcgt    1860
cccttgggac ttaccacgac ctccttaaga tcatcaagga taaggatttc ctcgacaatg    1920
aggaaaacga agatatcctg gaggacatcg ttctgactct gaccctcttt gaggaccggg    1980
agatgatcga ggagagactc aagacctacg cgcacctgtt tgacgacaaa gtgatgaagc    2040
aacttaaacg caggcgctac accggctggg gcagactgtc acgcaagttg atcaacggaa    2100
ttagagataa acagtccgga aagaccatcc tggacttcct gaagtccgat ggattcgcca    2160
accggaattt catgcagctc atccatgacg actcattgac tttcaaggag atatccaaa    2220 aggcccaagt gagcggccaa ggggactccc ttcacgaaca catcgcaaat ttggccggat    2280
caccagcgat taagaaggga atcctgcaga ccgtgaaggt ggtggacgag ctggtgaaag    2340
tgatgggacg gcacaagccg gaaaacatcg tgatcgagat ggccagagag aaccagacga    2400
ctcaaaaggg ccagaagaac tcgcgcgaac gcatgaagag aatagaagag ggaattaagg    2460
aactgggatc gcagatcttg aaggagcacc ctgtcgaaaa tactcaactc cagaacgaga    2520
agctgtacct gtactatctt caaaacggca gggacatgta tgtcgaccaa gagctcgaca    2580
ttaaccgcct gtccgattat gacgtggacg ccatcgtgcc gcagagcttt ctcaaggacg    2640
attccatcga caacaaagtg ctcacccgca gcgacaagaa tagagggaag tcggataacg    2700
tccccttcga agaggtggtg aaaaagatga gaattactg gcggcagctc ctgaatgcaa    2760
agctcatcac ccaacggaag tttgacaacc tcaccaaggc agaaagagga ggactgtcgg    2820
aattggataa ggccggtttc atcaagcgac aattggtgga aactcggcaa attaccaagc    2880
atgtggcaca gattctggac tcccgtatga acaccaagta cgacgagaac gataagctga    2940
tccgcgaggt caaggtgatc accctcaaaa gcaaacttgt gtcagacttc cggaaggact    3000
tccaattcta caaggtccgc gaaatcaaca actaccacca cgctcatgac gcatacctga    3060
acgctgtggt cgggactgcc ctcatcaaga agtaccctaa actcgaaagc gaatttgtgt    3120
acggcgacta caaagtgtac gatgtccgga agatgatcgc gaaatccgag caggagatcg    3180
gaaaggcgac tgctaagtac tttttctact cgaacatcat gaacttcttc aaaaccgaaa    3240 tcacccctggc taatggcgag atcagaaagc gcccgctgat cgaaaccaac ggcgaaaccg    3300
gtgaaatcgt gtgggacaag ggccgcgatt tcgctactgt gagaaaggtc ctttccatgc    3360
cgcaagtgaa tatcgtcaaa aagactgagg tgcagactgg cggattttcc aaggaatcga    3420
tcctcccaaa gaggaactca gataagctca tcgcgcggaa aaaggattgg gaccctaaga    3480 agtacgagg atttgatagc ccaactgtgg cctactctgt gctcgtggtg gccaaagtcg    3540
agaaaggaaa gtcgaagaag ttgaaatccg tgaaagaact cttgggaatc actatcatgg    3600
```

| | |
|---|---|
| agcggtcgtc atttgaaaag aacccaatcg acttcctgga agccaaggga tacaaagaag | 3660 |
| tcaagaaaga cctgatcatc aagctcccta agtacagcct gttcgaactg agaacggaa | 3720 |
| ggaaacggat gctggcttcc gccggcgaac tgcaaaaggg caatgagctg ccctcccat | 3780 |
| cgaaatacgt gaacttcctc taccttgcct cccattacga aaagttgaag gctcacccg | 3840 |
| aggacaatga gcagaaacag ctctttgttg aacaacacaa acactacctg gacgaaatca | 3900 |
| tcgaacaaat cagcgagttc agcaagcgcg tcattctggc ggacgcgaac ctggataaag | 3960 |
| tgctgtccgc gtacaacaag caccgcgata agccgatacg ggaacaggct gagaacatca | 4020 |
| ttcacctctt cactctcact aatctgggag cccccgccgc cttcaagtac tttgatacta | 4080 |
| ccatcgaccg caagagatac acgagcacca aggaagtgct cgatgccacc ctgatccacc | 4140 |
| agtccattac tggtctgtac gaaacgcgaa tcgatctgtc acagctcgga ggagatgggt | 4200 |
| caccgaaaaa gaaacggaaa gtcagctcgg attacaagga tcacgacgga gactacaagg | 4260 |
| accatgacat cgactataag gacgacgacg acaaggccgc tggaggcggt ggatcgggac | 4320 |
| gcgcggacgc cttggatgac ttcgaccttg acatgctggg atccgacgca cttgatgatt | 4380 |
| ttgatctcga tatgcttggc agcgacgcac tggacgattt cgacctcgac atgctcggat | 4440 |
| cggatgcgct cgacgacttc gatctggata tgctgtgata taggctgga gcctcggtgg | 4500 |
| ccatgcttct tgccccttgg gcctcccccc agccctcct cccttcctg cacccgtacc | 4560 |
| cccgtggtct ttgaataaag tctgagtggg cggctctaga | 4600 |

<210> SEQ ID NO 45
<211> LENGTH: 4706
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

| | |
|---|---|
| tcaagctttt ggaccctcgt acagaagcta atacgactca ctatagggaa ataagagaga | 60 |
| aaagaagagt aagaagaaat ataagagcca ccatggacaa gaagtactca atcggactcg | 120 |
| caatcggaac caattcagtc ggctgggcag tcattaccga tgaatacaag gtgccgtcga | 180 |
| agaagttcaa agtcctgggt aacactgaca gacattcgat caaaagaac ctgatcggag | 240 |
| ccttgctgtt tgattcaggc gaaaccgccg aagctacccg gttgaaacga actgctagac | 300 |
| gccgctacac gcgccgcaag aaccggatct gctacctcca agaaatcttc tcgaacgaaa | 360 |
| tggctaaggt ggacgactcg ttctttcacc ggctcgagga gtcattcctt gtggaggaag | 420 |
| ataagaagca cgaaagacac ccgatcttcg gcaacatcgt ggacgaagtc gcgtaccacg | 480 |
| aaaagtaccc gactatctac catctccgga agaagctcgt ggatagcacc gataaggccg | 540 |
| atctgcgact gatctacctc gcgctggccc atatgattaa gttccgcggg cacttcctca | 600 |
| tcgaagggga cctgaatcca gacaactcgg acgtggataa gctgtttatc cagctggtgc | 660 |
| agacttacaa tcaattgttt gaagaaaacc ctatcaacgc gtctggggtg gacgcaaagg | 720 |
| ccatcctgag cgcgcggctg tcaaaatcca gacggctgga aaatctgata gcccaactgc | 780 |
| cgggcgagaa gaaaaacggc ctgtttggaa atcttatcgc cctgtccctg ggactgaccc | 840 |
| ccaacttcaa gtcgaacttc gacttggccg aggatgcgaa gctccagctc agcaaagaca | 900 |
| cctacgacga tgacctcgat aacctgttgg cccagatcgg tgaccagtat gctgatctct | 960 |
| tcttggcggc caagaacctg tcagacgcaa ttctgctctc cgacatcctg cgggtgaata | 1020 |

```
ctgagatcac taaagcccca ttgagcgcgt cgatgatcaa agatacgac gagcaccacc    1080 aggatctgac tctcctcaag gcactggtcc gccaacagct cccggaaaag tacaaagaga    1140
tcttctttga ccaatccaaa aacggatacg ctggttacat agacggcgga gcgtcacaag    1200
aagagttcta caagttcatc aagcctatcc tggaaaagat ggacgggacc gaggaactcc    1260
tggttaagct caatagggag gatctgctgc gcaagcaacg cacgttcgac aatggaagca    1320
tcccccatca gatccacctg ggggagctcc acgcgatcct gaggcgccag gaagatttct    1380
acccatttct gaaggacaat agagagaaaa tcgaaaagat cctgactttc gaatcccgt    1440 actacgtggg cccgctcgca cggggaaact cacggtttgc ctggatgact cgcaaatccg    1500
aagaaaccat tacccctgg aatttcgagg aggtggtcga taaaggcgcc tcagcccagt    1560
cgttcatcga aagaatgacc aactttgaca agaacctccc aaatgagaag gtgctgccaa    1620
aacatagcct gctgtacgag tactttactg tgtataacga actcaccaag gtgaaatacg    1680
tgaccgaggg aatgcgcaag ccggcatttc tgtcgggcga acagaagaag gcaattgtgg    1740
acttgctgtt caaaaccaac cggaaggtga ccgtgaaaca gctcaaggaa gattacttta    1800
agaagatcga gtgtttcgat agcgtcgaaa tttcggggt ggaagatcgc ttcaatgcaa    1860
gccttgggac gtaccacgat ctgcttaaga tcattaagga caaggatttc cttgacaacg    1920
aagagaacga ggatattctc gaggatatcg tcctgaccct gactctgttt gaggatagag    1980
aaatgatcga ggagagattg aaaacttacg cacacctctt cgacgataag gtgatgaaac    2040
agctgaaaag gcgtagatac actggttggg gaaggctgtc gagaaagctg atcaacggaa    2100
ttagggacaa gcagtccgga aaaaccatcc tggatttcct caagtccgac ggtttcgcca    2160
accgcaactt catgcagctg atccacgatg attccctgac gttcaaagag gatatccaga    2220
aggcacaagt gtccggacaa ggagactcac tccacgagca tatcgctaat ctcgccggat    2280
cgccagctat caagaaggga atcttgcaga ctgtcaaggt ggtggacgaa ctggtgaaag    2340
tgatgggaag gcataagccg gagaatatcg tgatcgagat ggcgagggaa aaccagacga    2400
cccagaaagg acagaaaaac agccgggaac gcatgaagcg catcgaagag ggaatcaaag    2460
agcttgggag ccaaatcctc aaagaacacc ctgtggaaaa tacccaactg cagaatgaga    2520
agctttacct gtattacctc caaaacgggc gcgacatgta cgttgaccag gaattggaca    2580
ttaaccggct ttccgactac gatgtggacg ctatcgtccc gcagtccttc ctgaaagacg    2640
attcgatcga caataaggtc ctgactagat cagacaagaa tcggggaaag tcagacaacg    2700
tgcctagcga agaggtcgtt aagaagatga agaattactg gcgccagctg ctgaacgcga    2760
agcttatcac tcagcgcaag ttcgacaacc tcaccaaggc agaaagaggc ggattgtcgg    2820
agctcgacaa agctggcttc atcaagcgcc agctcgtcga aactcgccag attactaagc    2880
atgtggcgca gatcctggac agccgcatga atactaagta tgatgagaat gacaagctca    2940
tccgggaggt gaaggtcatc accctgaagt ccaagctggt gtccgacttc cggaaggact    3000
tccaattcta caaagtcaga gaaatcaaca attaccatca cgcgcatgac gcctacttga    3060
atgcagtggt gggtactgcc ctcatcaaga aatacccaaa gcttgaaagc gagtttgtct    3120
acggagacta caaggtgtac gacgtccgga agatgatcgc caaatcggaa caggaaattg    3180
ggaaggcgac cgctaagtac ttcttctact cgaatatcat gaatttcttc aagaccgaga    3240
tcacgcttgc aaatggcgaa atccggaagc ggccctcat cgaaaccaac ggagaaaccg    3300
gagaaatcgt gtgggacaag ggtcgcgatt ttgcgaccgt ccgaaaggtt cttagcatgc    3360
```

| | |
|---|---|
| ctcaagtgaa catcgtcaag aaaacggaag tgcagactgg aggcttcagc aaggagtcca | 3420 |
| ttctcccgaa acgcaactcc gacaaactga tcgcacgcaa gaaagactgg gacccgaaga | 3480 |
| aatacggagg cttcgattcg ccgactgtgg cttactcggt cctggttgtg gccaaggtgg | 3540 |
| aaaagggaaa gtccaagaag ctgaagtccg tcaaggagct cctcggaatc accatcatgg | 3600 |
| aacggtcaag cttcgagaaa aacccaattg acttcctgga ggcaaagggg tacaaggagg | 3660 |
| tgaagaagga tctgatcatc aaactgccga agtacagcct ctttgagctc gaaaacggac | 3720 |
| gcaaaaggat gctggcctcc gccggagagc tgcaaaaggg aaacgagctt gccttgcctt | 3780 |
| ccaagtacgt gaacttcctg tacctggcat cccactacga aaaactgaag ggatcgccgg | 3840 |
| aggacaacga acagaagcag ctgtttgtgg aacaacacaa gcattatctg gatgaaatca | 3900 |
| tcgaacaaat cagcgaattc tcaaaaaggg tgatcttggc cgacgccaac ctggataaag | 3960 |
| tgctttccgc ctacaacaaa catcgcgaca gccgatccg ggagcaggcc gaaaacatca | 4020 |
| ttcacctgtt taccctgact aatctgggtg cgcccgcggc tttcaaatac ttcgatacca | 4080 |
| cgatcgaccg gaagagatac accagcacca agaggtgtt ggacgcgacc ctcatccacc | 4140 |
| aatctattac cggcctctat gaaactagga tcgacctcag ccagctggga ggcgatgcct | 4200 |
| acccttacga tgtcccggac tacgcctcgc tgggatccgg atctccgaag aagaagcgga | 4260 |
| aggtcgagga cccaaagaaa aagcgcaaag tggatgggat cggtagcggt tccaacggtt | 4320 |
| cctcgggtgg cggcggaggc ggcatggatg ctaagtcact taccgcctgg tcgcggacgc | 4380 |
| tggtgacttt caaagatgtg ttcgtggatt tcactcgtga ggaatggaaa ttgctggaca | 4440 |
| ctgcccaaca gatcgtctac cgcaacgtca tgcttgaaaa ctacaaaaac ctcgtgtcgc | 4500 |
| tgggatatca gctgaccaag cccgacgtga ttctgagact ggagaagggc gaagaacctt | 4560 |
| gataataggc tggagcctcg gtggccatgc ttcttgcccc ttgggcctcc ccccagccc | 4620 |
| tcctcccctt cctgcacccg tacccccaa acaccattgt cacactccag tggtctttga | 4680 |
| ataaagtctg agtgggcggc tctaga | 4706 |

<210> SEQ ID NO 46
<211> LENGTH: 4622
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 46

| | |
|---|---|
| tcaagctttt ggaccctcgt acagaagcta atacgactca ctatagggaa ataagagaga | 60 |
| aaagaagagt aagaagaaat ataagagcca ccatggacaa gaagtactca atcggactcg | 120 |
| caatcggaac caattcagtc ggctgggcag tcattaccga tgaatacaag gtgccgtcga | 180 |
| agaagttcaa agtcctgggt aacactgaca gcattcgat caaaaagaac ctgatcggag | 240 |
| ccttgctgtt tgattcaggc gaaaccgccg aagctacccg gttgaaacga actgctagac | 300 |
| gccgctacac gcgccgcaag aaccggatct gctacctcca agaaatcttc tcgaacgaaa | 360 |
| tggctaaggt ggacgactcg ttcttcacc ggctcgagga gtcattcctt gtggaggaag | 420 |
| ataagaagca cgaaagacac ccgatcttcg gcaacatcgt ggacgaagtc gcgtaccacg | 480 |
| aaaagtaccc gactatctac catctccgga agaagctcgt ggatagcacc gataaggccg | 540 |
| atctgcgact gatctacctc gcgctggccc atatgattaa gttccgcggg cacttcctca | 600 |
| tcgaagggga cctgaatcca gacaactcgg acgtggataa gctgtttatc cagctggtgc | 660 |

```
agacttacaa tcaattgttt gaagaaaacc ctatcaacgc gtctggggtg gacgcaaagg    720
ccatcctgag cgcgcggctg tcaaaatcca gacggctgga aaatctgata gcccaactgc    780
cgggcgagaa gaaaaacggc ctgtttggaa atcttatcgc cctgtccctg ggactgaccc    840
ccaacttcaa gtcgaacttc gacttggccg aggatgcgaa gctccagctc agcaaagaca    900
cctacgacga tgacctcgat aacctgttgg cccagatcgg tgaccagtat gctgatctct    960
tcttggcggc caagaacctg tcagacgcaa ttctgctctc cgacatcctg cgggtgaata   1020
ctgagatcac taaagcccca ttgagcgcgt cgatgatcaa agatacgac gagcaccacc    1080 aggatctgac tctcctcaag gcactggtcc gccaacagct cccggaaaag tacaaagaga   1140
tcttctttga ccaatccaaa aacggatacg ctggttacat agacggcgga gcgtcacaag   1200
aagagttcta caagttcatc aagcctatcc tggaaaagat ggacgggacc gaggaactcc   1260
tggttaagct caatagggag gatctgctgc gcaagcaacg cacgttcgac aatggaagca   1320
tcccccatca gatccacctg ggggagctcc acgcgatcct gaggcgccag gaagatttct   1380
acccatttct gaaggacaat agagagaaaa tcgaaaagat cctgactttc cgaatcccgt   1440
actacgtggg cccgctcgca cggggaaact cacggtttgc ctggatgact cgcaaatccg   1500
aagaaaccat taccccctgg aatttcgagg aggtggtcga taaaggcgcc tcagcccagt   1560
cgttcatcga aagaatgacc aactttgaca agaacctccc aaatgagaag gtgctgccaa   1620
aacatagcct gctgtacgag tactttactg tgtataacga actcaccaag gtgaaatacg   1680
tgaccgaggg aatgcgcaag ccggcatttc tgtcgggcga acagaagaag gcaattgtgg   1740
acttgctgtt caaaaccaac cggaaggtga ccgtgaaaca gctcaaggaa gattacttta   1800
agaagatcga gtgtttcgat agcgtcgaaa tttcggggt ggaagatcgc ttcaatgcaa   1860
gccttgggac gtaccacgat ctgcttaaga tcattaagga caaggatttc cttgacaacg   1920
aagagaacga ggatattctc gaggatatcg tcctgaccct gactctgttt gaggatagag   1980
aaatgatcga ggagagattg aaaacttacg cacacctctt cgacgataag gtgatgaaac   2040
agctgaaaag gcgtagatac actggttggg gaaggctgtc gagaaagctg atcaacggaa   2100
ttagggacaa gcagtccgga aaaaccatcc tggatttcct caagtccgac ggtttcgcca   2160
accgcaactt catgcagctg atccacgatg attccctgac gttcaaagag gatatccaga   2220
aggcacaagt gtccggacaa ggagactcac tccacgagca tatcgctaat ctcgccggat   2280
cgccagctat caagaaggga atcttgcaga ctgtcaaggt ggtggacgaa ctggtgaaag   2340
tgatgggaag gcataagccg gagaaatatcg tgatcgagat ggcgagggaa aaccagacga   2400
cccagaaagg acagaaaaac agccgggaac gcatgaagcg catcgaagag ggaatcaaag   2460
agctggggag ccaaatcctc aaagaacacc ctgtggaaaa tacccaactg cagaatgaga   2520
agctttacct gtattacctc caaaacgggc gcgacatgta cgttgaccag gaattggaca   2580
ttaaccggct ttccgactac gatgtggacg ctatcgtccc gcagtccttc ctgaaagacg   2640
attcgatcga caataaggtc ctgactagat cagacaagaa tcgggaaag tcagacaacg   2700 tgcctagcga agaggtcgtt aagaagatga aaaattactg gcgccagctg ctgaacgcga   2760
agcttatcac tcagcgcaag ttcgacaacc tcaccaaggc agaaagaggc ggattgtcgg   2820
agctcgacaa agctggcttc atcaagcgcc agctcgtcga aactcgccag attactaagc   2880
atgtggcgca gatcctggac agccgcatga atactaagta tgatgagaat gacaagctca   2940
tccgggaggt gaaggtcatc accctgaagt ccaagctggt gtccgacttc cggaaggact   3000
tccaattcta caaagtcaga gaaatcaaca attaccatca cgcgcatgac gcctacttga   3060
```

-continued

```
atgcagtggt gggtactgcc ctcatcaaga aatacccaaa gcttgaaagc gagtttgtct    3120
acggagacta caaggtgtac gacgtccgga agatgatcgc caaatcggaa caggaaattg    3180
ggaaggcgac cgctaagtac ttcttctact cgaatatcat gaatttcttc aagaccgaga    3240
tcacgcttgc aaatggcgaa atccggaagc ggccccctcat cgaaaccaac ggagaaaccg    3300
gagaaatcgt gtgggacaag ggtcgcgatt ttgcgaccgt ccgaaaggtt cttagcatgc    3360
ctcaagtgaa catcgtcaag aaaacggaag tgcagactgg aggcttcagc aaggagtcca    3420
ttctcccgaa acgcaactcc gacaaactga tcgcacgcaa aaagactgg gacccgaaga    3480
aatacggagg cttcgattcg ccgactgtgg cttactcggt cctggttgtg gccaaggtgg    3540
aaaagggaaa gtccaagaag ctgaagtccg tcaaggagct cctcggaatc accatcatgg    3600
aacggtcaag cttcgagaaa aacccaattg acttcctgga ggcaaagggg tacaaggagg    3660
tgaagaagga tctgatcatc aaactgccga agtacagcct ctttgagctc gaaaacggac    3720
gcaaaaggat gctggcctcc gccggagagc tgcaaaaggg aaacgagctt gccttgcctt    3780
ccaagtacgt gaacttcctg tacctggcat cccactacga aaaactgaag ggatcgccgg    3840
aggacaacga acagaagcag ctgtttgtgg aacaacacaa gcattatctg gatgaaatca    3900
tcgaacaaat cagcgaattc tcaaaaaggg tgatcttggc cgacgccaac ctggataaag    3960
tgctttccgc ctacaacaaa catcgcgaca agccgatccg ggagcaggcc gaaaacatca    4020
ttcacctgtt taccctgact aatctgggtg cgcccgcggc tttcaaatac ttcgatacca    4080
cgatcgaccg gaagagatac accagcacca aagaggtgtt ggacgcgacc ctcatccacc    4140
aatctattac cggcctctat gaaactagga tcgacctcag ccagctggga ggcgatggat    4200
ccccaaagaa gaagagaaaa gtgtcctccg actacaagga tcatgatggg gactataaag    4260
atcatgatat tgattacaag gacgacgacg acaaggccgc tggaggagga ggttccggcc    4320
gcgccgatgc tctcgacgac ttcgacctcg acatgctggg atccgacgcc ctggacgact    4380
ttgatctgga tatgctgggc tcggacgccc ttgatgactt cgatctggac atgctggggt    4440
cggatgcact ggacgacttc gaccttgata tgctgtgata ataggctgga gcctcggtgg    4500
ccatgcttct tgccccttgg gcctccccc agccctcct cccttcctg cacccgtacc    4560
ccccaaacac cattgtcaca ctccagtggt ctttgaataa agtctgagtg ggcggctcta    4620
ga                                                                   4622
```

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51
<211> LENGTH: 4777
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 51

| | | | | | |
|---|---|---|---|---|---|
| gggaaauuaa | gagagaaaag | aagaguuaag | aagaaauuau | uaagagccac | cauggacaag | 60 |
| aaauacucaa | ucggacuugc | uaucggaacu | aacagcgugg | gaugggccgu | cauuacugac | 120 |
| gaauacaagg | ugcccucaaa | gaaguucaag | guccugggaa | auaccgauag | acacuccauc | 180 |
| aaaaagaacc | ugaucggggc | acuguuguuc | gacucgggag | agacugcaga | agcaaccagg | 240 |
| cucaagcgca | cugcgaggcg | ccgguacacc | cggaggaaga | accgcaucug | cuaccuccaa | 300 |
| gagauuuuca | gcaacgagau | ggcaaagguc | gaugauucgu | ucuuucaccg | ccuugaggag | 360 |
| ucguuccuug | ucgaggagga | caaaaagcau | gaaagacauc | cgaucuucgg | aaacaucgug | 420 |
| gacgaagucg | cauaccauga | aaaguacccu | accaucuacc | aucucagaaa | gaaacucguc | 480 |
| gauucaacug | auaaggccga | cuugcggcug | aucuaccugg | cucuggcgca | caugaucaag | 540 |
| uuucgggguc | acuuucucau | cgagggugau | cucaacccgg | acaauuccga | cguugacaaa | 600 |
| cucuucaucc | aacuguccag | gacguacaac | cagcuguucg | aagaaaaucc | gaucaacgca | 660 |
| agcggagugg | acgccaaagc | cauucugucg | gcccgccucu | cgaagucgcg | ucgccuggaa | 720 |
| aaucugauug | cucagcuccc | gggcgaaaag | aagaauggcc | uguuuggaaa | ccucaucgca | 780 |
| cugucccucg | ggcugacucc | caacuucaaa | ucgaacuuug | acuggcuga | ggaugcaaag | 840 |
| cugcaacucu | ccaaagacac | uuacgaugau | gaccuggaca | ucuccggc | gcagaucggg | 900 |
| gaucaguaug | cugaccuguu | ccuggcggcc | aagaaccugu | cugaugccau | ccugcucucc | 960 |
| gauauccuga | gagugaacac | ugagaucacc | aaggcgccuc | ugagcgccuc | gaugaucaaa | 1020 |
| cgcuacgaug | aacaccauca | ggaccucacu | cuucugaagg | cuuggugcg | gcagcagcuu | 1080 |
| ccggaaaagu | acaaagagau | cuucuucgac | cagucgaaaa | acggcuacgc | cggauacauu | 1140 |
| gauggcggcg | caagccagga | ggaauucuau | aaguuuauca | aaccgauccu | ggagaagaug | 1200 |
| gacggcacug | aagaacuucu | ggucaagcug | aaucgagagg | aucugcuccg | gaagcagcgg | 1260 |
| accuucgaca | augggucuau | cccucaccaa | auccaucucg | gcgagcugca | ugcgauucg | 1320 |
| aggcgccagg | aggacuucua | cccauuccug | aaagacaauc | gggagaaaau | cgaaaagauu | 1380 |
| cugacguucc | gcauuccaua | cuacgucggg | ccacuugcgc | gggguaauuc | gagauucgcc | 1440 |
| uggaugacgc | ggaagccga | agaaaccauc | acgccgugga | auucgaaga | aguggucgac | 1500 |
| aagggagcca | cgcacagu | cuucauugag | cgcaugacca | auucgacaa | aaaucugccg | 1560 |
| aacgagaagg | uccugccgaa | gcauucacug | cuguacgaau | acuuuaccgu | guacaacgaa | 1620 |
| cugaccaagg | ugaaguacgu | caccgaggga | augagaaagc | cugcuuuccu | gagcggagaa | 1680 |
| cagaagaagg | ccauuguuga | ccuccucuuc | aagacuaauc | gcaaagugac | cgugaagcag | 1740 |
| cuuaagagg | auuacuucaa | aaagaucgaa | uguucgacu | ccguggaaau | cagcggcgug | 1800 |
| gaggauagau | ucaacgcguc | ccuugggacu | uaccacgacc | uccuuaagau | caucaaggau | 1860 |
| aaggauuucc | ucgacaauga | ggaaaacgaa | gauauccugg | aggacaucgu | ucugacucug | 1920 |

|  |  |
|---|---|
| acccucuuug aggaccggga gaugaucgag gagagacuca agaccuacgc gcaccuguuu | 1980 |
| gacgacaaag ugaugaagca acuuaaacgc aggcgcuaca ccggcugggg cagacuguca | 2040 |
| cgcaaguuga ucaacggaau uagagauaaa caguccggaa agaccauccu ggacuuccug | 2100 |
| aaguccgaug gauucgccaa ccggaauuuc augcagcuca ccaugacga cucauugacu | 2160 |
| uucaaggagg auauccaaaa ggcccaagug agcggccaag gggacucccu ucacgaacac | 2220 |
| aucgcaaauu uggccggauc accagcgauu aagaagggaa uccugcagac cgugaaggug | 2280 |
| guggacgagc uggugaaagu gaugggacgg cacaagccgg aaaacaucgu gaucgagaug | 2340 |
| gccagagaga accagacgac ucaaaagggc cagaagaacu cgcgcgaacg caugaagaga | 2400 |
| auagaagagg gaauuaagga acugggaucg cagaucuuga aggagcaccc ugucgaaaau | 2460 |
| acucaacucc agaacgagaa gcuguaccug uacuaucuuc aaaacggcag ggacauguau | 2520 |
| gucgaccaag agcucgacau uaaccgccug uccgauuaug acguggacgc caucgugccg | 2580 |
| cagagcuuuc ucaaggacga uuccaucgac aacaaagugc ucacccgcag cgacaagaau | 2640 |
| agagggaagu cggauaacgu cccuucgaaa gagguggugu aaaagaugaa gaauuacugg | 2700 |
| cggcagcucc ugaaugcaaa gcucaucacc caacggaagu uugacaaccu caccaaggca | 2760 |
| gaaagaggag gacugucgga auuggauaag gccgguuuca ucaagcgaca auggugggaa | 2820 |
| acucggcaaa uuaccaagca uguggcacag auucuggacu cccgaugaa caccaaguac | 2880 |
| gacgagaacg auaagcugau ccgcgagguc aaggugauca cccucaaaag caaacuugug | 2940 |
| ucagacuucc ggaaggacuu ccaauucuac aagguccgcg aaaucaacaa cuaccaccac | 3000 |
| gcucaugacg cauaccugaa cgcuguguc gggacugccc ucaucaagaa gucccuaaa | 3060 |
| cucgaaagcg aauuugugua cggcgacuac aaaguguacg auguccggaa gaugaucgcg | 3120 |
| aaauccgagc aggagaucgg aaaggcgacu gcuaaguacu uuuucuacuc gaacaucaug | 3180 |
| aacuucuuca aaccgaaau caccccuggcu aauggcgaga ucagaaagcg cccgcugauc | 3240 |
| gaaaccaacg gcgaaaccgg ugaaaucgug ugggacaagg gccgcgauuu cgcuacugug | 3300 |
| agaaaggucc uuccaugcc gcaagugaau cgucaaaaa gacugaggu gcagacuggc | 3360 |
| ggauuuucca aggaaucgau ccucccaaag aggaacucag auaagcucau cgcgcggaaa | 3420 |
| aaggauuggg acccuaagaa guacggagga uuugauagcc caacuguggc cuacucugug | 3480 |
| cucguggugg ccaaagucga aaggaaag ucgaagaagu ugaaauccgu gaaagaacuc | 3540 |
| uugggaauca cuaucaugga gcggucguca uuugaaaaga acccaaucga cuuccuggaa | 3600 |
| gccaagggau acaagaagu caagaaagac cugaucauca agcucccuaa guacagccug | 3660 |
| uucgaacugg agaacggaag gaaacggaug cuggcuuccg ccggcgaacu gcaaaagggc | 3720 |
| aaugagcugg cccucccauc gaaauacgug aacuuccucu accuugccuc ccauuacgaa | 3780 |
| aaguugaagg gcucacccga ggacaaugag cagaaacagc ucuuuguuga acaacacaaa | 3840 |
| cacuaccugg acgaaaucau cgaacaaauc agcgaguuca gcaagcgcgu cauucuggcg | 3900 |
| gacgcgaacc uggauaaagu gcugucegcg uacaacaagc accgcgauaa gccgauacgg | 3960 |
| gaacaggcug agaacaucau ucacccucuuc acucuacua aucuggagc ccccgccgcc | 4020 |
| uucaaguacu uugauacuac caucgaccgc aagagauaca cgagcaccaa ggaagugcuc | 4080 |
| gaugccaccc ugauccacca guccauuacu ggucuguacg aaacgcgaau cgaucugcua | 4140 |
| cagcucggag gagaugcgua ccccuacgau guccccgacu acgcgucacu cgguagcggc | 4200 |
| agcccgaaga gaaaagaaa ggugaggac ccgaagaaaa agaggaaggu ugacgggauc | 4260 |
| ggaagcggau cgaauggauc gucaggggga ggugggcggag guauggacgc aaaaucacuu | 4320 |

```
acggccuggu cacggaccuu ggugaccuuu aaagacgugu ucguggauuu caccagggaa    4380
gaauggaaac uguuggacac cgcccagcag aucguguacc ggaaugugau gcuggagaac    4440
uacaaaaacu uggugucccu gggguaucaa cucacuaagc cagaugucau ucuuagacug    4500 gaaagggag aagaaccgug auaauaggcu ggagccucgg uggccaugcu ucuugccccu     4560
ugggccuccc cccagccccu ccuccccuuc cugcacccgu accccgugg ucuuugauaa     4620 aagucugagu gggcggcaaa aaaaaaaaa aaaaaaaaa aaaaaaaaa aaaaaaaaa        4680 aaaaaaaaaa aaaaaaaaa aaaaaaaaa aaaaaaa                               4777
```

<210> SEQ ID NO 52
<211> LENGTH: 4689
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 52

```
gggaauaag agagaaaaga agaguaagaa gaaauauaag agccaccaug acaagaaau      60 acucaaucgg acuugcuauc ggaacuaaca gcgugggaug ggccgucauu acugacgaau    120
acaaggugcc cucaaagaag uucaaggucc ugggaaauac cgauagacac uccaucaaaa    180
agaaccugau cggggcacug uuguucgacu cgggagagac ugcagaagca accaggcuca    240
agcgcacugc gaggcgccgg uacacccgga ggaagaaccg caucugcuac cuccaagaga    300 uuucagcaa cgagauggca aaggucgaug auucguucuu ucaccgccuu gaggagucgu     360 uccuugcga ggaggacaaa aagcaugaaa gacauccgau cuucggaaac aucguggacg     420
aagucgcaua ccaugaaaag uacccuacca ucuaccaucu cagaaagaaa cucgucgauu    480
caacugauaa ggccgacuug cggcugaucu accggcucu ggcgcacaug ucaaguuuc      540 ggggucacuu ucucaucgag ggugaucuca acccggacaa uucgacguu gacaaacucu     600 ucauccaacu ggccagacg uacaaccagc uguucgaaga aaauccgauc aacgcaagcg     660
gaguggacgc caaagccauu cugucggccc gccucucgaa gucgcgucgc cuggaaaauc    720
ugauugcuca gcucccgggc gaaaagaaga auggccuguu uggaaaccuc aucgcacugu    780
cccucgggcu gacucccaac uucaaaucga cuuugacuu ggcugaggau gcaaagcugc     840
aacucuccaa agacacuuac gaugaugacc uggacaaucu ccuggcgcag aucggggauc    900
aguaugcuga ccuguuccug gcggccaaga accugucuga ugccauccug cucuccgaua    960
uccugagagu gaacacugag aucaccaagg cgccucugag cgccucgaug aucaaacgcu    1020
acgaugaaca ccaucaggac cucacucuuc ugaaggcuuu ggugcggcag cagcuuccgg    1080
aaaaguacaa agagaucuuc uucgaccagu cgaaaacgg cuacgccgga uacauugaug    1140
gcggcgcaag ccaggaggaa uucuauaagu uuaucaaacc gauccuggag aagauggacg    1200
gcacugaaga acuucggguc aagcugaauc gagaggaucu gcuccggaag cagcggaccu    1260
ucgacaaugg gucuauccu caccaaaucc aucucggcga gcugcaugcg auucugaggc    1320
gccaggagga cuucuacccca uuccugaaag acaaucggga gaaaucgaa aagauucuga    1380 cguuccgcau uccauacuac gucgggccac uugcgcgggg uaauucgaga uucgccugga   1440
ugacgcggaa guccgaagaa accaucacgc cguggaauuu cgaagaagug gucgacaagg    1500
gagccagcgc acaguccuuc auugagcgca ugaccaauuu cgacaaaau cugccgaacg     1560
```

```
agaagguccu gccgaagcau ucacugcugu acgaauacuu uaccguguac aacgaacuga      1620
ccaaggugaa guacgucacc gagggaauga gaaagccugc uuuccugagc ggagaacaga      1680
agaaggccau uguugaccuc cucuucaaga cuaaucgcaa agugaccgug aagcagcuua      1740
aagaggauua cuucaaaaag aucgaauguu cgacuccgu ggaaaucagc ggcguggagg       1800
auagauucaa cgcgucccuu gggacuuacc acgaccuccu uaagaucauc aaggauaagg      1860
auuuccucga caaugaggaa aacgaagaua uccuggagga caucguucug acucugaccc      1920
ucuuugagga ccgggagaug aucgaggaga gacucaagac cuacgcgcac cuguuugacg      1980
acaaagugau gaagcaacuu aaacgcaggc gcuacaccgg cuggggcaga cugucacgca      2040
aguugaucaa cggaauuaga gauaaacagu ccggaaagac cauccuggac uuccugaagu      2100
ccgauggauu cgccaaccgg aauuucaugc agcucaucca ugacgacuca uugacuuuca      2160
aggaggauau ccaaaaggcc aagugagcg gccaagggga cucccuucac gaacacaucg      2220
caaauuuggc cggaucacca gcgauuaaga agggaauccu gcagaccgug aaggugguug      2280
acgagcuggu gaaagugaug ggacggcaca agccggaaaa caucgugauc gagauggcca      2340
gagagaacca gacgacucaa aagggccaga gaacucgcg cgaacgcaug aagagaauag      2400
aagagggaau uaaggaacug ggaucgcaga ucuugaagga gcacccuguc gaaaauacuc      2460
aacuccagaa cgagaagcug uaccuguacu aucuucaaaa cggcagggac auguaugucg      2520
accaagagcu cgacauuaac cgccugccg auuaugacgu ggacgccauc gugccgcaga      2580
gcuuucucaa ggacgauucc aucgacaaca aagugcucac ccgcagcgac aagaauagag      2640
ggaagucgga uaacgucccu ucggaagagg uggugaaaaa gaugaagaau acuggcggc       2700 agccuccugaa ugcaaagcuc aucacccaac ggaaguuuga caaccucacc aaggcagaaa     2760
gaggaggacu gucggaauug gauaaggccg guuucaucaa gcgacaauug guggaaacuc      2820
ggcaaauuac caagcaugug gcacagauuc uggacucccg uaugaacacc aaguacgacg      2880
agaacgauaa gcugauccgc gaggucaagg ugaucacccu caaaagcaaa cuugugucag      2940
acuuccggaa ggacuuccaa uucuacaagg uccgcgaaau caacaacuac caccacgcuc      3000
augacgcaua ccugaacgcu guggucggga cugcccucau caagaaguac ccuaaacucg      3060
aaagcgaauu uguguacggc gacuacaaag uacgaugu ccggaagaug aucgcgaaau        3120
ccgagcagga gaucggaaag gcgacugcua aguacuuuuu cuacucgaac aucaugaacu      3180
ucuucaaaac cgaaaucacc cuggcuaaug gcgagaucag aaagcgcccg cugaucgaaa      3240
ccaacggcga aaccgugaa aucgugggg acaagggccg cgauuucgcu acugugaaga       3300
agguccuuuc caugccgcaa gugaauaucg ucaaaaagac ugaggugcag acuggcggau      3360 uuccaagga aucgauccuc ccaaagagga acucagauaa gcucaucgcg cggaaaaagg      3420
auugggaccc uaagaaguac ggaggauuug auagcccaac uguggccuac ucugugcucg      3480
ugguggccaa agucgagaaa ggaaagucga agaaguugaa auccgugaaa gaacucuugg      3540
gaaucacuau cauggagcgg ucgucauuug aaaagaaccc aaucgacuuc cuggaagcca      3600
agggauacaa agaagucaag aaagaccuga ucaucaagcu cccuaaguac agccuguucg      3660
aacuggagaa cggaaggaaa cggaugcugg cuuccgccgg cgaacugcaa aagggcaaug      3720
agcuggcccu cccaucgaaa uacgugaacu uccucuaccu ugccucccau uacgaaaagu      3780
ugaagggcuc acccgaggac aaugagcaga aacagcucuu uguugaacaa cacaaacacu      3840
accuggacga aaucaucgaa caaucagcg aguucagcaa gcgcgucauu cuggcggacg      3900
```

| | |
|---|---|
| cgaaccugga uaaagugcug uccgcguaca acaagcaccg cgauaagccg auacgggaac | 3960 |
| aggcugagaa caucauucac cucuucacuc ucacuaaucu gggagccccc gccgccuuca | 4020 |
| aguacuuuga uacuaccauc gaccgcaaga gauacacgag caccaaggaa gugcucgaug | 4080 |
| ccacccugau ccaccagucc auuacugguc uguacgaaac gcgaaucgau cugucacagc | 4140 |
| ucggaggaga ugggucaccg aaaagaaac ggaaagucag cucggauuac aaggaucacg | 4200 |
| acggagacua caaggaccau gacaucgacu auaaggacga cgacgacaag gccgcuggag | 4260 |
| gcggugauc gggacgcgcg gacgccuugg augacuucga ccuugacaug cugggauccg | 4320 |
| acgcacuuga ugauuuugau cucgauaugc uggcagcga cgcacuggac gauuucgacc | 4380 |
| ucgacaugcu cggaucggau gcgcucgacg acuucgaucu ggauaugcug ugauaauagg | 4440 |
| cuggagccuc gguggccaug cuucuugccc cuugggccuc cccccagccc cuccucccu | 4500 |
| uccugcaccc guaccccgu ggucuuugaa uaaagucuga gugggcggca aaaaaaaaa | 4560 |
| aaaaaaaaaa aaaaaaaaaa aaaaaaaaaa aaaaaaaaaa aaaaaaaaaa aaaaaaaaaa | 4620 |
| aaaaaaaaaa aaaaaaaaaa aaaaaaaaaa aaaaaaaaaa aaaaaaaaaa aaaaaaaaaa | 4680 |
| aaaaaaaaa | 4689 |

<210> SEQ ID NO 53
<211> LENGTH: 4795
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 53

| | |
|---|---|
| gggaaauaag agagaaaaga agaguaagaa gaaauauaag agccaccaug gacaagaagu | 60 |
| acucaaucgg acucgcaauc ggaaccaauu cagucggcug ggcagucauu accgaugaau | 120 |
| acaaggugcc gucgaagaag uucaaagucc uggguaacac ugacagacau cgaucaaaa | 180 |
| agaaccugau cggagccuug cuguuugauu caggcgaaac cgccgaagcu acccgguuga | 240 |
| aacgaacugc uagacgccgc uacacgcgcg gcaagaaccg gaucugcuac cuccaagaaa | 300 |
| ucuucucgaa cgaaauggcu aaggugacg acucguucuu ucaccggcuc gaggagucau | 360 |
| uccuugugga ggaagauaag aagcacgaaa gacacccgau cuucggcaac aucguggacg | 420 |
| aagucgcgua ccacgaaaag uacccgacua ucuaccaucu ccggaagaag cucguggaua | 480 |
| gcaccgauaa ggccgaucug cgacugaucu accucgcgcu ggcccauaug auuaaguucc | 540 |
| gcgggcacuu ccucaucgaa ggggaccuga auccagacaa cucggacgug auaagcugu | 600 |
| uuauccagcu ggugcagacu acaaucaau uguuugaaga aaacccuauc aacgcgucug | 660 |
| gggugacgc aaaggccauc cugagcgcgc ggcugucaaa auccagacgg cuggaaaauc | 720 |
| ugauagccca acugccgggc gagaagaaaa acggccuguu uggaaaucuu aucgcccugu | 780 |
| cccugggacu gaccccaac uucaagucga cuucgacuu ggccgaggau gcgaagcucc | 840 |
| agcucagcaa agacaccuac gacgaugacc ucgauaaccu guuggccag aucggugacc | 900 |
| aguaugcuga ucucuucuug gcggccaaga accugucaga cgcaauucug cucuccgaca | 960 |
| uccugcgggu gaauacugag aucacuaaag ccccauugga cgcgucgaug aucaaaagau | 1020 |
| acgacgagca ccaccaggau cugacucucc ucaaggcacu gguccgccaa cagcucccgg | 1080 |
| aaaaguacaa agagaucuuc uuugaccaau ccaaaaacgg auacgcuggu acauagacg | 1140 |
| gcggagcguc acaagaagag uucuacaagu ucaucaagcc uauccuggaa aagauggacg | 1200 |

-continued

```
ggaccgagga acuccugguu aagcucaaua gggaggaucu gcugcgcaag caacgcacgu      1260
ucgacaaugg aagcauccccc caucagaucc accuggggga gcuccacgcg auccugaggc     1320
gccaggaaga uuucuaccca uuucugaagg acaauagaga gaaaaucgaa aagauccuga      1380
cuuuccgaau cccguacuac gugggcccgc ucgcacgggg aaacucacgg uuugccugga     1440
ugacucgcaa auccgaagaa accauuaccc ccuggaauuu cgaggaggug gucgauaaag     1500
gcgccucagc ccagucguuc aucgaaagaa ugaccaacuu ugacaagaac ucccaaaug      1560 agaaggugcu gccaaaacau agccugcugu acgaguacuu uacuguguau aacgaacuca     1620
ccaaggugaa auacgugacc gagggaaugc gcaagccggc auuucugucg ggcgaacaga     1680
agaaggcaau uguggacuug cuguucaaaa ccaaccggaa ggugaccgug aaacagcuca     1740
aggaagauua cuuuaagaag aucgagugu ucgauagcgu cgaaauuucg ggguggaag       1800 aucgcuucaa ugcaagccuu gggacguacc acgaucugcu uaagaucauu aaggacaagg     1860
auuuccuuga caacgaagag aacgaggaua uucucgagga uaucguccug acccugacuc     1920
uguuugagga uagagaaaug aucgaggaga gauugaaaac uuacgcacac cucuucgacg     1980
auaaggugau gaaacagcug aaaaggcgua gauacacugg uuggggaagg cugucgagaa     2040
agcugaucaa cggaauuagg gacaagcagu ccggaaaaac cauccuggau uuccucaagu     2100
ccgacgguuu cgccaaccgc aacuucaugc agcugaucca cgaugauucc cugacguuca     2160
aagaggauau ccagaaggca caagguguccg gacaaggaga cucacuccac gagcauaucg     2220
cuaaucucgc cggaucgcca gcuaucaaga agggaaucuu gcagacuguc aaggugguug     2280
acgaacuggu gaaagugaug ggaaggcaua agccggagaa uaucgugauc gagaauggcga     2340 gggaaaacca gacgacccag aaaggacaga aaacagccg ggaacgcaug aagcgcaucg       2400
aagagggaau caaagagcuu gggagccaaa uccucaaaga acacccugug gaaaauaccc      2460
aacugcagaa ugagaagcuu uaccuguauu accuccaaaa cgggcgcgac auguacguug      2520
accaggaauu ggacauuaac cggcuuuccg acuacgaugu ggacgcuauc ucccgcagu      2580 ccuuccugaa agacgauucg aucgacaaua aggccugac uagaucagac aagaaucggg      2640
gaaagucaga caacgugccu agcgaagagg ucguuaagaa gaugaagaau uacuggcgcc      2700
agcugcugaa cgcgaagcuu aucacucagc gcaaguucga caaccucacc aaggcagaaa      2760
gaggcggauu gucggagcuc gacaaagcug gcuucaucaa cgccagcuc gucgaaacuc       2820 gccagauuac uaagcaugug gcgcagaucc uggacagccg caugaauacu aaguaugaug      2880
agaaugacaa gcuauccgg gaggugaagg ucaucccu gaaguccaag cuggugccg          2940 acuuccggaa ggacuuccaa uucuacaaag ucagagaaau caacaauuac caucacgcgc      3000
augacgccua cuugaaugca guggugggua cugccuucau caagaaauac ccaaagcuug     3060
aaagcgaguu ugucuacgga gacuacaagg uguacgacgu ccggaagaug aucgccaaau     3120
cggaacagga aauugggaag gcgaccgcua aguacuucuu cuacucgaau ucaugaauu       3180 ucuucaagac cgagaucacg cuugcaaaug gcgaaauccg gaagcggccc cucaucgaaa     3240
ccaacggaga aaccggagaa aucgugggg acaagggucg cgauuuugcg accgguccgaa     3300 agguucuuag caugccucaa gugaacaucg ucaagaaaac ggaagugcag acugaggcu     3360 ucagcaagga guccauucuc ccgaaacgca acuccgacaa acugaucgca cgcaagaaag    3420
acugggaccc gaagaaauac ggaggcuucu auucgccgac uguggcuuac ucggcucgg     3480 uuguggccaa gguggaaaag ggaaaguccca agaagcugaa guccgucaag gagcucccg    3540 gaaucaccau caauggaacgg ucaagcuucg agaaaaaccc aauugacuuc cuggaggcaa    3600
```

| | |
|---|---|
| aggggu acaa ggaggugaag aaggaucuga ucaucaaacu gccgaaguac agccucuuug | 3660 |
| agcucgaaaa cggacgcaaa aggaugcugg ccuccgccgg agagcugcaa aagggaaacg | 3720 |
| agcuugccuu gccuuccaag uacgugaacu uccuguaccu ggcaucccac uacgaaaaac | 3780 |
| ugaagggauc gccggaggac aacgaacaga agcagcuguu uguggaacaa cacaagcauu | 3840 |
| aucuggauga aaucaucgaa caaucagcg aauucucaaa aagggugauc uuggccgacg | 3900 |
| ccaaccugga uaaagugcuu uccgccuaca caaacaucg cgacaagccg auccgggagc | 3960 |
| aggccgaaaa caucauucac cuguuuaccc ugacuaaucu gggugcgccc gcggcuuuca | 4020 |
| aauacuucga uaccacgauc gaccggaaga gauacaccag caccaaagag guguuggacg | 4080 |
| cgacccucau ccaccaaucu auuaccggcc ucaugaaac uaggaucgac cucagccagc | 4140 |
| ugggaggcga ugccuacccu uacgaugucc cggacuacgc cucgcuggga uccggaucuc | 4200 |
| cgaagaagaa gcggaagguc gaggacccaa agaaaaagcg caaaguggau gggaucggua | 4260 |
| gcgguccaa cgguuccucg gguggcgcg gaggcggcau ggaugcuaag ucacuuaccg | 4320 |
| ccuggucgcg gacgcuggug acuuucaaag augu guucgu ggauuucacu cgugaggaau | 4380 |
| ggaaauugcu ggacacugcc caacagaucg ucuaccgcaa cgucaugcuu gaaaacuaca | 4440 |
| aaaaccucgu gucgcuggga uaucagcuga ccaagcccga cgugauucug agacuggaga | 4500 |
| agggcgaaga accuugauaa uaggcuggag ccucggguggc caugcuucuu gccccuuggg | 4560 |
| ccucccccca gccccuccuc cccuccugc accguaccc cccaaacacc auugucacac | 4620 |
| uccagugguc uuugaauaaa gucugagugg gcggcaaaaa aaaaaaaaa aaaaaaaaa | 4680 |
| aaaaaaaaa aaaaaaaaa aaaaaaaaa aaaaaaaaa aaaaaaaaa aaaaaaaaa | 4740 |
| aaaaaaaaa aaaaaaaaa aaaaaaaaa aaaaaaaaa aaaaaaaaa aaaaa | 4795 |

<210> SEQ ID NO 54
<211> LENGTH: 4711
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 54

| | |
|---|---|
| gggaaauaag agagaaaaga agaguaagaa gaaauauaag agccaccaug gacaagaagu | 60 |
| acucaaucgg acucgcaauc ggaaccaauu cagucggcug ggcagucauu accgaugaau | 120 |
| acaaggugcc gucgaagaag uucaaaaugucc ugggaacac ugacagacau ucgaucaaaa | 180 |
| agaaccugau cggagccuug cuguuugauu caggcgaaac cgccgaagcu acccgguuga | 240 |
| aacgaacugc uagacgccgc uacacgcgcc gcaagaaccg gaucugcuac cuccaagaaa | 300 |
| ucuucucgaa cgaaauggcu aagguggacg acucguucuu ucaccggcuc gaggagucau | 360 |
| uccuugugga ggaagauaag aagcacgaaa gacacccgau cuuccgcaac aucguggacg | 420 |
| aagucgcgua ccacgaaaag uacccgacua ucuaccaucu ccggaagaag cucgugggaua | 480 |
| gcaccgauaa ggccgaucug cgacugaucu accucgcgcu ggcccauaug auuaaguucc | 540 |
| gcgggcacuu ccucaucgaa ggggaccuga accagacaa cucggacgug auaagcugu | 600 |
| uuaccagcu ggugcagacu acaaucaau uguuugaaga aaacccuauc aacgcgucug | 660 |
| ggugggacgc aaaggccauc cugagcgcgc ggcugcaaa uccagacgg cuggaaaauc | 720 |
| ugauagccca acugcgggc gagaagaaaa acggccuguu uggaaaucuu aucgcccugu | 780 |
| cccugggacu gaccccccaac uucaagucga acuucgacuu ggccgaggau gcgaagcucc | 840 |

```
agcucagcaa agacaccuac gacgaugacc ucgauaaccu guuggcccag aucggugacc     900
aguaugcuga ucucuucuug gcggccaaga accugucaga cgcaauucug cucuccgaca     960
uccugcgggu gaauacugag aucacuaaag ccccaugag cgcgucgaug aucaaaagau    1020
acgacgagca ccaccaggau cugacucucc ucaaggcacu gguccgccaa cagcucccgg    1080
aaaaguacaa agagaucuuc uuugaccaau ccaaaaacgg auacgcuggu uacauagacg    1140
gcggagcguc acaagaagag uucuacaagu ucaucaagcc uaccuggaa aagauggacg     1200 ggaccgagga acuccugguu aagcucaaua ggggaggaucu gcugcgcaag caacgcacgu    1260
ucgacaaugg aagcaucccc caucagaucc accuggggga gcuccacgcg auccugaggc    1320
gccaggaaga uucuacccca uuucugaagg acaauagaga gaaaaucgaa aagauccuga    1380
cuuuccgaau cccguacuac gugggccccgc ucgcacgggg aaacucacgg uuugccugga    1440
ugacucgcaa auccgaagaa accauuaccc ccuggaauuu cgaggaggug ucgauaaag     1500 gcgcccuagc ccagucguuc aucgaaagaa ugaccaacuu ugacaagaac ucccaaaug     1560 agaaggugcu gccaaaacau agccugcugu acgaguacuu uacuguguau aacgaacuca    1620
ccaaggugaa auacgugacc gagggaaugc gcaagccggc auuucugucg ggcgaacaga    1680
agaaggcaau uguggacuug cuguucaaaa ccaaccggaa ggugaccgug aaacagcuca    1740
aggaagauua cuuuaagaag aucgaguguu ucgauagcgu cgaaauuucg ggguggaag     1800 aucgcuucaa ugcaagccuu gggacguacc acgaucugcu uaagaucauu aaggacaagg    1860
auuuccuuga caacgaagag aacgaggaua uucucgagga uaucguccug acccugacuc    1920
uguuugagga uagagaaaug aucgaggaga gauugaaaac uuacgcacac cucuucgacg    1980
auaaggugau gaaacagcug aaaaggcgua gauacacugg uuggggaagg cgucgagaa     2040 agcugaucaa cggaauuagg acaagcagu ccggaaaaac cauccuggau uuccucaagu    2100
ccgacgguuu cgccaaccgc aacuucaugc agcugaucca cgaugauccc ugacguuca    2160 aagaggauau ccagaaggca caagugucccg gacaaggaga cucacuccac gagcauaucg    2220
cuaaucucgc cggaucgcca gcuaucaaga agggaaucuu gcagacuguc aaggugugg     2280 acgaacuggu gaaagugaug ggaaggcaua agccggagaa uaucgugauc gagauggcga    2340
gggaaaacca gacgacccag aaaggacaga aaaacagccg ggaacgcaug aagcgcaucg    2400
aagagggaau caaagagcuu gggagccaaa uccucaaaga acacccugug gaaaauaccc    2460
aacugcagaa ugagaagcuu uaccuguauu accuccaaaa cgggcgcgac auguacguug    2520
accaggaauu ggacauuaac cggcuuuccg acuacgaugu ggacgcuauc gucccgcagu    2580
ccuuccugaa agacgauucg aucgacaaua aggucctgac uagaucagac aagaaucggg    2640
gaaagucaga caacgugccu agcgaagagg ucguuaagaa gaugaagaau uacuggcgcc    2700
agcugcugaa cgcgaagcuu aucacucagc gcaaguucga caaccucacc aaggcagaaa    2760
gaggcggauu gucggagcuc gacaaagcug gcuucaucaa gcgccagcuc gucgaaacuc    2820
gccagauuac uaagcaugug gcgcagaucc uggacagccg caugaauacu aaguaugaug    2880
agaaugacaa gcucauccgg gaggugaagg ucaucacccu gaaguccaag cugguguccg    2940
acuuccggaa ggacuuccaa uucuacaaag ucagagaaau caacaauuac caucacgcgc    3000
augacgccua cuugaaugca guguggua cugcccucau caagaaauac ccaaagcuug    3060
aaagcgaguu ugucuacgga gacuacaagg uguacgacgu ccggaagaug aucgccaaau    3120
cggaacagga aauugggaag gcgaccgcua aguacuucuu cuacucgaau aucaugaauu    3180
```

| | |
|---|---|
| ucuucaagac cgagaucacg cuugcaaaug gcgaaauccg gaagcggccc cucaucgaaa | 3240 |
| ccaacggaga aaccggagaa aucguguggg acaagggucg cgauuuugcg accguccgaa | 3300 |
| agguucuuag caugccucaa gugaacaucg ucaagaaaac ggaagugcag acuggaggcu | 3360 |
| ucagcaagga guccauucuc ccgaaacgca acuccgacaa acugaucgca cgcaagaaag | 3420 |
| acugggaccc gaagaaauac ggaggcuucg auucgccgac uguggcuuac ucgguccugg | 3480 |
| uuguggccaa ggugaaaaag ggaaagucca agaagcugaa guccgucaag gagcucccucg | 3540 |
| gaaucaccau cauggaacgg ucaagcuucg agaaaacccc aauugacuuc cuggaggcaa | 3600 |
| aggggguacaa ggaggugaag aaggaucuga ucaucaaacu gccgaaguac agccucuuug | 3660 |
| agcucgaaaa cggacgcaaa aggaugcugg ccuccgccgg agagcugcaa aagggaaacg | 3720 |
| agcuugccuu gccuuccaag uacgugaacu uccuguaccu ggcaucccac uacgaaaaac | 3780 |
| ugaagggauc gccggaggac aacgaacaga agcagcuguu guggaacaa cacaagcauu | 3840 |
| aucuggauga aaucaucgaa caaaucagca auucucaaa aagggugauc uuggccgacg | 3900 |
| ccaaccugga uaaagugcuu uccgccuaca acaaacaucg cgacaagccg auccgggagc | 3960 |
| aggccgaaaa caucauucac cuguuuaccc ugacuaaucu ggugcgcccc gcggcuuuca | 4020 |
| aauacuucga uaccacgauc gaccggaaga gauacaccag caccaaagag guguuggacg | 4080 |
| cgacccucau ccaccaaucu auuaccggcc ucuaugaaac uaggaucgac cucagccagc | 4140 |
| ugggaggcga uggaucccca agaagaaga gaaaagugc cuccgacuac aaggaucaug | 4200 |
| augggaacua uaaagaucau gauauugauu acaaggacga cgacgacaag gccgcuggag | 4260 |
| gaggaggguuc cggccgcgcc gaugcucucg acgacuucga ccucgacaug cugggauccg | 4320 |
| acgcccugga cgacuuugau cuggauaugc ugggcucgga cgcccuugau gacuucgauc | 4380 |
| uggacaugcu gggucggau gcacuggacg acuucgaccu ugauaugcug ugauaauagg | 4440 |
| cuggagccuc gguggccaug cuucuugccc cuugggccuc ccccagccc cuccucccccu | 4500 |
| uccugcaccc guaccccca aacaccauug ucacacucca gugucuuug aauaaagucu | 4560 |
| gaguggggcgg caaaaaaaaa aaaaaaaaaa aaaaaaaaaa aaaaaaaaaa aaaaaaaaaa | 4620 |
| aaaaaaaaaa aaaaaaaaaa aaaaaaaaaa aaaaaaaaaa aaaaaaaaaa aaaaaaaaaa | 4680 |
| aaaaaaaaaa aaaaaaaaaa aaaaaaaaaa a | 4711 |

<210> SEQ ID NO 55
<211> LENGTH: 4443
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 55

| | |
|---|---|
| gggaaauaag agagaaaaga agaguaagaa gaaauauaag agccaccaug gacaagaaau | 60 |
| acagcaucgg ccuggauauu ggaacuaaca gcguuggau ggcagugauc accgacgagu | 120 |
| acaaggugcc gagcaagaag uucaaggugc uggggaacac ugaccgccau ucaauuaaga | 180 |
| aaaaccucau uggagcacug cuuuuugacu cgggugagac ugccgaagcu accaggcuca | 240 |
| aacgaccgc acgcagacgg uacacccgcc gcaagaaucg caucugcuau cugcaagaga | 300 |
| ucuuuuccaa cgagauggcg aagguugacg acagcuuuuu ccaccggcug aagagagcu | 360 |
| uccucgugga agaggacaaa aagcacgaaa ggcauccaau cuucgguaac aucguggacg | 420 |
| aaguggcgua ucacgaaaag uacccuacca ucuaccaucu gcggaagaag cugguccgauu | 480 |

-continued

```
ccacggauaa ggcagaccug agacugaucu accuggcuuu ggcccauaug aucaaauucc    540
gcggccauuu ccugaucgag ggggaccuua acccggauaa ucucggaugu cgacaagcugu   600 ucauccagcu gguccaaacg uauaaccaac uguuugagga aaaucccauc aacgcuucgg    660
ggguggacgc caaagcaauc cucuccgcgc gccugagcaa gucacggcgg cucgaaaacc    720
ugaucgcgca gcugccggga gaaaagaaaa auggacuguu ugggaaucug aucgcgcugu    780
cgcucggccu gacuccaaac uuuaagucaa auuucgauuu ggccgaagau gccaagcugc    840
agcugucaaa ggacacuuac gacgacgacc uggacaaucu gcuggcccag auuggggacc    900
aauacgcaga ccuguucuug gccgcgaaga accugagcga cgccauucuu cuguccgaua    960
uucugagagu caauaccgaa aucacuaagg uccgcugucc cgcuucaaug ucaagcgcu    1020 acgaugaaca ccaccaggau cucacucugc ucaaagcccu cgugagacaa caauugccug    1080
aaaaguacaa ggagaucuuc uucgaccaga gcaaaaacgg cuacgcaggc uacaucgaug   1140
gaggagcguc acaagaagag uucuacaagu caucaagcc aaucuuggag aagauggacg    1200
guacugaaga acuccuugug aagcugaaua gggaggauuu gcucagaaag cagcggacuu    1260
uugacaacgg cucgaucccu caucagauuc accucgguga gcugcaugcc auccuucggc   1320 gccaaggagga uuuuuacccc uuccugaagg auaaucgcga gaaaaucgaa aagauccuga   1380
cguucagaau ucccuacuac gugggaccgc uggcgcgcgg uaacucgcgg uuugcaugga   1440
ugacucgcaa gucagaggaa acuaucacuc cuuggaauuu ugaggagguc gucgauaagg   1500
gagccuccgc ccagucauuc aucgaacgca ugaccaacuu cgacaagaau cuuccgaacg   1560
agaagguccu uccaaagcac ucccuguugu acgaauacuu caccguguac aaugagcuga   1620
ccaaaguuaa guaugucacc gagggcauga aaagccggc cuuccucagc ggcgaacaaa    1680
agaaggccau cgucgaccuc cucuucaaga ccaaccggaa ggugaccguc aagcaacuca   1740
aggaggacua cuucaagaag aucgaaugcu uugacucggu cgaaaucagc ggaguggagg   1800
accgguuuaa cgcgucacug gguaccuacc augaucccu gaaaaucauc aaagacaagg   1860
acuuccugga caacgaagaa aacgaggaca uccuggaaga uauugucuug acccugacgc   1920
uguucgagga ccgggaaaug aucgaggaaa ggcuuaagac cuacgcacac cucuucgaug   1980
acaaagugau gaagcaacug aagcggcgga gauauacugg cugggggagg cucucccgga   2040
agcucauuaa uggaaucaga gacaaacagu cggguaaaac uauccucgac uuccucaagu   2100
cggauggguu cgccaaccgg aacuucaugc agcugaucca cgaugauucc uugaccuuca   2160
aggaagauau ccagaaggcg caagugagcg gacaggagga uucguugcac gaacauaucg   2220
cuaaucucgc cggauccca gccaucaaga aaggaauccu gcagaccgug aaggugguggg   2280 augaacuggu gaaagugaug gggcgccaca accagagaa cauegucauu gagaugggccc   2340 gcgagaauca gaccacucag aagggacaaa agaauccag agagcggaug aaacgcaucg   2400
aggaaggcau caaagagcuu ggagccaaa uccugaagga acaccccguc gagaacaccc   2460
agcuccagaa cgaaaagcuu uaccuguacu acuccaaaaa uggacgggac auguacgucg   2520
accaggaauu ggacaucaac agacucagcg acuacgaugu ggaccauauu gugccacagu   2580 ccuucuuaa ggacgacagc aucgauaaca aagugcucac uagaucagac aaaaaucgcg   2640
ggaaaucaga caaugugcca ucggaagagg uugucaagaa gaugaaaaac uacuggagac   2700
agcugcucaa ugccaaacuu aucccccagc ggaaguucga caaccuuacc aaggccgagc   2760
gcggaggauu guccgaacuc gacaaggcg gcuuaucaca aaggcagcug guggaaaccc    2820
ggcagaucac uaaacacgug gcccagaucc ucgauucgcg caugaacacu aaauacgaug   2880
```

```
agaaugacaa gcugauuagg gaagucaagg ucaucacucu gaagucgaaa cuggugucgg    2940
acuuuagaaa ggauuuccag uucuacaaag uccgcgagau uaacaacuac caccacgcuc    3000
augacgccua ccugaaugca guuguggca ccgcgcugau caagaaguau ccgaagcugg     3060
aauccgaguu cguguacgga gauuacaaag uguacgacgu gcgcaagaug aucgccaagu    3120
cggaacagga aaucggaaag gcuacugcaa aguacuucuu cuacucaaac aucaugaacu    3180
ucuucaaaac ggagaucacg cucgcgaacg gcgaaauccg gaaaaggccg cucauugaaa    3240
ccaacggaga aaccggggag aucgugugg acaaggaag ggauuuugcg acugugagga    3300
agguuguguc caugccgcaa gucaauauug ugaaaaagac ggaagugcaa accggaggau   3360
ucagcaaaga auccauccuc ccaaagcgca acucggacaa acucaucgcg cgcaagaagg    3420
auugggaccc caagaaauac gguggcuuug acagcccuac uguggcuuac uccguccucg    3480
ucguggcuaa aguggaaaag gguaaaucca aaaagcucaa aucggugaag gagcuccugg    3540
gaaucacgau caugagcgg ucgagcuucg aaaagaaucc uauugauuuc cuggaggcga    3600
agggcuacaa ggaagucaag aaagaccuga ucaucaagcu cccgaaguac agccucuucg    3660
agcucgaaaa cggcagaaag aggaugcugg caucagcggg agaauugcag aagggaaacg    3720
aacuggcacu gccguccaag uacgugaauu uucucuaucu ggcuagccac uacgaaaagc    3780
ugaagggauc gcccgaggac aacgagcaaa acaacuguu cguggagcag cacaagcacu     3840
accuggauga gaucaucgag cagaucuccg aauucucgaa acgcgugauc cuugccgaug    3900
ccaaucugga uaaaguguug ucggcuuaca caagcaucg ggauaaaccg auccgcgaac     3960
aggcagaaaa caucauucau cuguucacuu ugaccaaucu gggagcgccu gccgcguuua    4020
aguacuucga caccacuauu gauagaaagc gcuacaccuc gaccaaggaa gugcuggacg    4080
cuacccugau ccaccagucc aucaccggac ucuacgaaac ucgcauugac cugucccagc    4140
uuggaggaga uucacgggcc gauccaaaga aaaagcgcaa ggucugauaa uaggcuggag    4200 ccucggugc caugcuucuu gccccuuggg ccuccccca gccccuccuc cccuccugc       4260 acccguaccc ccgugugucuu ugaauaaagu cugaguggg ggcaaaaaaa aaaaaaaaa    4320 aaaaaaaaa aaaaaaaaa aaaaaaaaa aaaaaaaaa aaaaaaaaa aaaaaaaaa          4380 aaaaaaaaa aaaaaaaaa aaaaaaaaa aaaaaaaaa aaaaaaaaa aaaaaaaaa          4440 aaa                                                                  4443
```

<210> SEQ ID NO 56
<211> LENGTH: 4575
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 56

```
gggaaauaag agagaaaaga agaguaagaa gaaauauaag agccaccaug gacuacaagg    60
accacgacgg agacuacaaa gaccaugaca ucgauuacaa ggaugacgau gacaaaaugg   120
caccgaagaa gaagagaaag gucggaauuc acggggugcc ggccgcggac aagaaguacu    180
caaucggacu ggauaucggc acgaacagcg ugguuggc agugaucacc gacgaauaca     240
aggugccgag caagaaguuc aaagugcugg gaaauaccga ucgccauucg aucaagaaaa    300
aucgauuggg cgcgcuccug uucgacucgg gagagacugc cgaggccacu agacugaaga    360
ggaccgcuag gcgccgcuac acgaggcgca aaaaccgcau cugcuaucuu caagaaaucu    420
```

-continued

```
ucucaaacga gauggccaag guggacgacu ccuuuuucca ucggcuggaa gaaucauuuc     480 uggugagga ggacaagaag cacgaacgcc aucccauuuu cggcaacauu gucgacgaag      540
uggccuauca ugagaaguau ccgacuaucu accacuugag aaagaagcug guggacucca    600
cugacaaggc agaucugcgg uugaucuacc ucgcacuggc ccauaugauc aaauuccggg    660
gacacuuccu caucgagggc gaccuuaauc ccgacaauuc cgauguggau aagcuuuuca    720
uccagcuggu ccagaccuac aaccaacugu uugaagaaaa uccaaucaau gcagcggug     780 ucgaugcaaa ggccauccug agcgcccgcc ucucgaaaag cagaaggcuc gaaaaccuga    840
ucgcacaguu gccuggagag aagaagaacg gccucuucgg caaucucauc gcauugsccc    900
ugggacugac uccaaacuuc aaauccaacu cgacuuggc cgaggacgcc aaacugcaac     960
ugagcaaaga uaccuacgau gaugacuugg acaaucuucu ggcucagauc ggcgaccagu   1020
acgccgaccu guuccuugcg gcuaagaacc ugucggacgc cauccugcug uccgacaucc   1080
ugcgcgucaa uaccgaaauu acuaaagcac cacucucggc auccaugauc aagagauacg   1140
augaacacca ccaggaucuc acccuccuga agcacuggu gcggcagcag cucccugaga    1200
aauacaagga aaucuucuuu gaucaguccaa agaacgauua cgccggauac aucgacggcg  1260
gcgcgagcca agaggaauuc uacaaguuca ucaagccgau ccuggaaaag auggauggca   1320
cggaagaacu ccuggucaaa cugaauagag aggaucugcu ccgcaaacaa cggaccuucg   1380
auaacggauc gaucccgcac cagauccacc ucggcgaacu gcaugccauc cugcggcggc   1440
aggaggacuu uuacccgauc cucaaagaca acagagaaaa gaucgagaag aucuugaccu   1500
uucgcauccc guacuacgug ggcccgcucg cgagagguaa cucccgcuuu gcuuggauga   1560
cuagaaaguc agaggaaacg aucaccccau ggaacuucga agaggugguu gacaaaggag   1620
cgagcgccca aucguucauc gaacggauga cuaacuucga uaagaaucug ccgaugaga    1680 aggcucugcc uaagcacuca cuucuguaug aauacuuuac uguguauaac gaacucacca   1740
aagucaaaua cgugacugag ggaaugcgca agccugcguu uuuguccggc gagcagaaaa   1800
aggccaucgu ggacuugcug uucaaaacca ccgcaaggu gacuguuaag caacucaaag    1860
aggacuacuu uaagaagauc gaaugcuuug acucggucga gauuuccggg guugaagaua   1920
gauucaacgc gucgcuggga accuaccaug aucccucaa gauuaucaag gacaaagacu    1980
uccuggauaa cgaggagaau gaggacaucc ucgaagauau ugugcuuacc cugacccuuu  2040
ucgaagaucg cgaaaugauc gaagaacgcc ugaaaaccua cgcucaccug uucgacgaua  2100
aggugaugaa acaguugaaa cgccggcggu acacggguug ggggcggcug ucgcgcaagc  2160
ugaucaacgg aauucgggac aaacagagcg gaaagaccau ccucgauuuu cugaaguccg  2220
augguuuugc caaccgcaac uucaugcagc ucauccauga cgauucgcuu accuuuaagg  2280 aggauauucca gaaggcacaa gugucgggac aagggauuc gcuccacgaa cacaucgcca   2340
aucuggcggg gucgccggca auuaagaagg gaauccucca gacuguuaag guggucgacg   2400 agcugguagaa ggugaugggg agacauaagc cugaaaacau gugaucgag auggcgagag   2460 aaaaucaaac uacucagaag ggacagaaga auucccggga gcggaugaag cgcaucgagg  2520
agggaaucaa ggaacugggc ucccaaaucc ugaaagagca uccggguggaa aauacucagc  2580 ugcagaacga gaagcuuuac cuguacuauc uucaaaaugg cagggacaug uacgucgacc   2640
aagaacugga uaucaaucgg cucuccgauu acgacgucga ucacaucguc ccccaaucau   2700
uccugaagga ugauagcauc gauaacaagg ugcucacuag aucagacaaa aaccggggaa   2760
```

| | |
|---|---|
| agucagauaa cguccccagc gaagaagucg ugaagaagau gaagaauuac uggaggcaac | 2820 |
| uucugaacgc caaacucauc acucagcgca aguucgacaa ccugaccaaa gcagaaaggg | 2880 |
| gaggacucag cgagcuggac aaggcugguu ucaucaaacg gcagcuggug gagacucgcc | 2940 |
| aaaucacgaa gcauguggcc cagauucucg acucgcgcau gaauacuaag ucgacgaaa | 3000 |
| acgauaagcu gauccgggag gugaaggug ucacccucaa gagcaagcuc guguccgauu | 3060 |
| uccggaaaga cuuccaguuc uacaaggugc gggagauuaa caacuaccau cacgcucacg | 3120 |
| acgcuuaccu caaugcugug guggggacgg cguugauuaa gaaguaccca aaacuggagu | 3180 |
| ccgaauucgu cuacggagau uacaaggucu acgacgugcg caagaugauu gccaagucgg | 3240 |
| agcaggaaau ugggaaagcg acugcuaagu acuucuucua cucgaauauc augaacuucu | 3300 |
| ucaagaccga aaucacccug gcuaacggcg agaucaggaa acggccgcug aucgaaacua | 3360 |
| auggugagac uggugaaauc guguggaua agggacggga cuucgccacg guccgcaagg | 3420 |
| uccucagcau gccgcaagug aauauuguua agaaaaccga agucagacc gguggguucu | 3480 |
| cgaaggaauc cauccugcca aagcgcaacu cggauaagcu uauugccgc aagaaggauu | 3540 |
| gggacccgaa aaaguacggu ggguucgacu ccccuaccgu ggcguacucg uguuggugg | 3600 |
| uggccaaagu ggaaaaggc aaaucaaaga agcucaagag cgucaaggag cugcugggaa | 3660 |
| ucaccaucau ggagaggucc agcuuugaga aaaccccgau cgacuucuug gaagccaagg | 3720 |
| gaucaaaga ggugaagaaa gaccugauca ucaaacuucc aaaguacucc cuguucgaac | 3780 |
| ucgaaaacgg gaggaagcgc augcucgccu cagccgggga acugcaaaag ggcaacgaac | 3840 |
| uggcccuccc gucaaaauac gucaacuucc uguacuuggc gucacacuac gaaaagcuga | 3900 |
| aaggaucccc agaggacaac gaacagaaac agcuguucgu cgagcagcac aagcacuacc | 3960 |
| uggacgagau caucgaacag aucucggaau ucagcaagag agugaucuug gcagacgcua | 4020 |
| accuugacaa aguccucucg gcauacaaua agcaucgcga caagccgauc agagaacagg | 4080 |
| cggaaacau cauccaccug uucacucuca ccaaccuggg cgcgccagcg gcuuuuaagu | 4140 |
| acuuugauac caccauugac cgcaagagau acaccucaac uaaagaagug cuggacgcaa | 4200 |
| cccugaucca ucaaagcauc accggacuuu augaaacucg gaucgaucuc ucacagcucg | 4260 |
| gaggagacaa aagaccggcu gccaccaaga aggccggaca ggcaaagaag aagaaaugau | 4320 |
| aauaggcugg agccucggug gccaugcuuc uugccccuug ggccucccc cagccccucc | 4380 |
| ucccuuccu gcacccguac cccgugguc uuugaauaaa gucugagugg gcggcaaaaa | 4440 |
| aaaaaaaaaa aaaaaaaaaa aaaaaaaaaa aaaaaaaaaa aaaaaaaaaa aaaaaaaaaa | 4500 |
| aaaaaaaaaa aaaaaaaaaa aaaaaaaaaa aaaaaaaaaa aaaaaaaaaa aaaaaaaaaa | 4560 |
| aaaaaaaaaa aaaaa | 4575 |

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61
<211> LENGTH: 1368
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300
```

```
Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
    595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
```

```
                725                 730                 735
Ile Leu Gln Thr Val Lys Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
                835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140
```

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 62
<211> LENGTH: 1489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr

```
            115                 120                 125
His Glu Lys Tyr Pro Thr Ile Tyr His Leu Arg Lys Lys Leu Val Asp
130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
530                 535                 540
```

```
Lys Lys Ala Ile Val Asp Leu Leu Phe Lys Thr Asn Arg Lys Val Thr
545                 550                 555                 560

Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
                770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
                850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960
```

-continued

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp

```
                1355                1360                1365
Ala Tyr Pro Tyr Asp Val Pro Asp Tyr Ala Ser Leu Gly Ser Gly
        1370                1375                1380

Ser Pro Lys Lys Lys Arg Lys Val Glu Asp Pro Lys Lys Lys Arg
        1385                1390                1395

Lys Val Asp Gly Ile Gly Ser Gly Ser Asn Gly Ser Ser Gly Gly
        1400                1405                1410

Gly Gly Gly Gly Met Asp Ala Lys Ser Leu Thr Ala Trp Ser Arg
        1415                1420                1425

Thr Leu Val Thr Phe Lys Asp Val Phe Val Asp Phe Thr Arg Glu
        1430                1435                1440

Glu Trp Lys Leu Leu Asp Thr Ala Gln Gln Ile Val Tyr Arg Asn
        1445                1450                1455

Val Met Leu Glu Asn Tyr Lys Asn Leu Val Ser Leu Gly Tyr Gln
        1460                1465                1470

Leu Thr Lys Pro Asp Val Ile Leu Arg Leu Glu Lys Gly Glu Glu
        1475                1480                1485

Pro

<210> SEQ ID NO 63
<211> LENGTH: 1722
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
```

```
                 210                 215                 220
Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640
```

His Leu Phe Asp Asp Lys Val Met Lys Gln Leu Lys Arg Arg Tyr
            645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
            1010                1015                1020

Lys Ser Glu Gln Glu Ile Gly Lys Ala Thr Ala Lys Tyr Phe Phe
            1025                1030                1035

Tyr Ser Asn Ile Met Asn Phe Phe Lys Thr Glu Ile Thr Leu Ala
            1040                1045                1050

-continued

| | | | | | | | | | | | |
|---|---|---|---|---|---|---|---|---|---|---|---|
|Asn|Gly|Glu|Ile|Arg|Lys|Arg|Pro|Leu|Ile|Glu|Thr|Asn|Gly|Glu|
| |1055| | | |1060| | | |1065| | |

Asn Gly Glu Ile Arg Lys Arg Pro Leu Ile Glu Thr Asn Gly Glu
     1055            1060            1065

Thr Gly Glu Ile Val Trp Asp Lys Gly Arg Asp Phe Ala Thr Val
     1070            1075            1080

Arg Lys Val Leu Ser Met Pro Gln Val Asn Ile Val Lys Lys Thr
     1085            1090            1095

Glu Val Gln Thr Gly Gly Phe Ser Lys Glu Ser Ile Leu Pro Lys
     1100            1105            1110

Arg Asn Ser Asp Lys Leu Ile Ala Arg Lys Lys Asp Trp Asp Pro
     1115            1120            1125

Lys Lys Tyr Gly Gly Phe Asp Ser Pro Thr Val Ala Tyr Ser Val
     1130            1135            1140

Leu Val Val Ala Lys Val Glu Lys Gly Lys Ser Lys Lys Leu Lys
     1145            1150            1155

Ser Val Lys Glu Leu Leu Gly Ile Thr Ile Met Glu Arg Ser Ser
     1160            1165            1170

Phe Glu Lys Asn Pro Ile Asp Phe Leu Glu Ala Lys Gly Tyr Lys
     1175            1180            1185

Glu Val Lys Lys Asp Leu Ile Ile Lys Leu Pro Lys Tyr Ser Leu
     1190            1195            1200

Phe Glu Leu Glu Asn Gly Arg Lys Arg Met Leu Ala Ser Ala Gly
     1205            1210            1215

Glu Leu Gln Lys Gly Asn Glu Leu Ala Leu Pro Ser Lys Tyr Val
     1220            1225            1230

Asn Phe Leu Tyr Leu Ala Ser His Tyr Glu Lys Leu Lys Gly Ser
     1235            1240            1245

Pro Glu Asp Asn Glu Gln Lys Gln Leu Phe Val Glu Gln His Lys
     1250            1255            1260

His Tyr Leu Asp Glu Ile Ile Glu Gln Ile Ser Glu Phe Ser Lys
     1265            1270            1275

Arg Val Ile Leu Ala Asp Ala Asn Leu Asp Lys Val Leu Ser Ala
     1280            1285            1290

Tyr Asn Lys His Arg Asp Lys Pro Ile Arg Glu Gln Ala Glu Asn
     1295            1300            1305

Ile Ile His Leu Phe Thr Leu Thr Asn Leu Gly Ala Pro Ala Ala
     1310            1315            1320

Phe Lys Tyr Phe Asp Thr Thr Ile Asp Arg Lys Arg Tyr Thr Ser
     1325            1330            1335

Thr Lys Glu Val Leu Asp Ala Thr Leu Ile His Gln Ser Ile Thr
     1340            1345            1350

Gly Leu Tyr Glu Thr Arg Ile Asp Leu Ser Gln Leu Gly Gly Asp
     1355            1360            1365

Ala Tyr Pro Tyr Asp Val Pro Asp Tyr Ala Ser Leu Gly Ser Gly
     1370            1375            1380

Ser Pro Lys Lys Lys Arg Lys Val Glu Asp Pro Lys Lys Lys Arg
     1385            1390            1395

Lys Val Asp Gly Ile Gly Ser Gly Ser Asn Gly Ser Ser Gly Ser
     1400            1405            1410

Ser Glu Leu Ile Lys Glu Asn Met His Met Lys Leu Tyr Met Glu
     1415            1420            1425

Gly Thr Val Asp Asn His His Phe Lys Cys Thr Ser Glu Gly Glu
     1430            1435            1440

Gly Lys Pro Tyr Glu Gly Thr Gln Thr Met Arg Ile Lys Val Val

Glu Gly Gly Pro Leu Pro Phe Ala Phe Asp Ile Leu Ala Thr Ser
            1460                1465                1470

Phe Leu Tyr Gly Ser Lys Thr Phe Ile Asn His Thr Gln Gly Ile
    1475                1480                1485

Pro Asp Phe Phe Lys Gln Ser Phe Pro Glu Gly Phe Thr Trp Glu
1490                1495                1500

Arg Val Thr Thr Tyr Glu Asp Gly Gly Val Leu Thr Ala Thr Gln
    1505                1510                1515

Asp Thr Ser Leu Gln Asp Gly Cys Leu Ile Tyr Asn Val Lys Ile
1520                1525                1530

Arg Gly Val Asn Phe Thr Ser Asn Gly Pro Val Met Gln Lys Lys
    1535                1540                1545

Thr Leu Gly Trp Glu Ala Phe Thr Glu Thr Leu Tyr Pro Ala Asp
1550                1555                1560

Gly Gly Leu Glu Gly Arg Asn Asp Met Ala Leu Lys Leu Val Gly
    1565                1570                1575

Gly Ser His Leu Ile Ala Asn Ile Lys Thr Thr Tyr Arg Ser Lys
1580                1585                1590

Lys Pro Ala Lys Asn Leu Lys Met Pro Gly Val Tyr Tyr Val Asp
    1595                1600                1605

Tyr Arg Leu Glu Arg Ile Lys Glu Ala Asn Asn Glu Thr Tyr Val
1610                1615                1620

Glu Gln His Glu Val Ala Val Ala Arg Tyr Cys Asp Leu Pro Ser
    1625                1630                1635

Lys Leu Gly His Lys Leu Asn Gly Gly Gly Gly Met Asp Ala
1640                1645                1650

Lys Ser Leu Thr Ala Trp Ser Arg Thr Leu Val Thr Phe Lys Asp
    1655                1660                1665

Val Phe Val Asp Phe Thr Arg Glu Glu Trp Lys Leu Leu Asp Thr
1670                1675                1680

Ala Gln Gln Ile Val Tyr Arg Asn Val Met Leu Glu Asn Tyr Lys
    1685                1690                1695

Asn Leu Val Ser Leu Gly Tyr Gln Leu Thr Lys Pro Asp Val Ile
1700                1705                1710

Leu Arg Leu Glu Lys Gly Glu Glu Pro
    1715                1720

<210> SEQ ID NO 64
<211> LENGTH: 1461
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

```
Lys Arg Thr Ala Arg Arg Tyr Thr Arg Lys Asn Arg Ile Cys
 65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
```

-continued

```
                485                 490                 495
Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
                690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
                770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp Ala Ile Val Pro Gln Ser Phe Leu Lys
                835                 840                 845

Asp Asp Ser Ile Asp Asn Lys Val Leu Thr Arg Ser Asp Lys Asn Arg
                850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910
```

```
Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305
```

```
Ile Ile His Leu Phe Thr Leu Thr Asn Leu Gly Ala Pro Ala Ala
    1310            1315                1320

Phe Lys Tyr Phe Asp Thr Thr Ile Asp Arg Lys Arg Tyr Thr Ser
    1325            1330                1335

Thr Lys Glu Val Leu Asp Ala Thr Leu Ile His Gln Ser Ile Thr
    1340            1345                1350

Gly Leu Tyr Glu Thr Arg Ile Asp Leu Ser Gln Leu Gly Gly Asp
    1355            1360                1365

Gly Ser Pro Lys Lys Arg Lys Val Ser Ser Asp Tyr Lys Asp
    1370            1375                1380

His Asp Gly Asp Tyr Lys Asp His Asp Ile Asp Tyr Lys Asp Asp
    1385            1390                1395

Asp Asp Lys Ala Ala Gly Gly Gly Gly Ser Gly Arg Ala Asp Ala
    1400            1405                1410

Leu Asp Asp Phe Asp Leu Asp Met Leu Gly Ser Asp Ala Leu Asp
    1415            1420                1425

Asp Phe Asp Leu Asp Met Leu Gly Ser Asp Ala Leu Asp Asp Phe
    1430            1435                1440

Asp Leu Asp Met Leu Gly Ser Asp Ala Leu Asp Asp Phe Asp Leu
    1445            1450                1455

Asp Met Leu
    1460

<210> SEQ ID NO 65
<211> LENGTH: 1483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
                20                  25                  30

Gly Arg Gly Met Asp Lys Lys Tyr Ser Ile Gly Leu Ala Ile Gly Thr
            35                  40                  45

Asn Ser Val Gly Trp Ala Val Ile Thr Asp Glu Tyr Lys Val Pro Ser
        50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Arg Tyr Thr Arg Arg Lys Asn
            100                 105                 110

Arg Ile Cys Tyr Leu Gln Glu Ile Phe Ser Asn Glu Met Ala Lys Val
        115                 120                 125

Asp Asp Ser Phe Phe His Arg Leu Glu Glu Ser Phe Leu Val Glu Glu
    130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
            180                 185                 190
```

```
Leu Ala His Met Ile Lys Phe Arg Gly His Phe Leu Ile Glu Gly Asp
            195                 200                 205

Leu Asn Pro Asp Asn Ser Asp Val Asp Lys Leu Phe Ile Gln Leu Val
        210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
            260                 265                 270

Phe Gly Asn Leu Ile Ala Leu Ser Leu Gly Leu Thr Pro Asn Phe Lys
        275                 280                 285

Ser Asn Phe Asp Leu Ala Glu Asp Ala Lys Leu Gln Leu Ser Lys Asp
290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
            340                 345                 350

Ser Ala Ser Met Ile Lys Arg Tyr Asp Glu His His Gln Asp Leu Thr
        355                 360                 365

Leu Leu Lys Ala Leu Val Arg Gln Gln Leu Pro Glu Lys Tyr Lys Glu
        370                 375                 380

Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
            420                 425                 430

Leu Leu Arg Lys Gln Arg Thr Phe Asp Asn Gly Ser Ile Pro His Gln
        435                 440                 445

Ile His Leu Gly Glu Leu His Ala Ile Leu Arg Arg Gln Glu Asp Phe
        450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
            500                 505                 510

Phe Glu Glu Val Val Asp Lys Gly Ala Ser Ala Gln Ser Phe Ile Glu
        515                 520                 525

Arg Met Thr Asn Phe Asp Lys Asn Leu Pro Asn Glu Lys Val Leu Pro
530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
            580                 585                 590

Lys Val Thr Val Lys Gln Leu Lys Glu Asp Tyr Phe Lys Lys Ile Glu
        595                 600                 605
```

```
Cys Phe Asp Ser Val Glu Ile Ser Gly Val Glu Asp Arg Phe Asn Ala
610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
            660                 665                 670

Thr Tyr Ala His Leu Phe Asp Asp Lys Val Met Lys Gln Leu Lys Arg
            675                 680                 685

Arg Arg Tyr Thr Gly Trp Gly Arg Leu Ser Arg Lys Leu Ile Asn Gly
690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
            740                 745                 750

Asp Ser Leu His Glu His Ile Ala Asn Leu Ala Gly Ser Pro Ala Ile
            755                 760                 765

Lys Lys Gly Ile Leu Gln Thr Val Lys Val Val Asp Glu Leu Val Lys
770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
            835                 840                 845

Tyr Tyr Leu Gln Asn Gly Arg Asp Met Tyr Val Asp Gln Glu Leu Asp
850                 855                 860

Ile Asn Arg Leu Ser Asp Tyr Asp Val Asp Ala Ile Val Pro Gln Ser
865                 870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
            900                 905                 910

Lys Met Lys Asn Tyr Trp Arg Gln Leu Leu Asn Ala Lys Leu Ile Thr
            915                 920                 925

Gln Arg Lys Phe Asp Asn Leu Thr Lys Ala Glu Arg Gly Gly Leu Ser
930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
            980                 985                 990

Leu Lys Ser Lys Leu Val Ser Asp Phe Arg Lys Asp Phe Gln Phe Tyr
            995                 1000                1005

Lys Val Arg Glu Ile Asn Asn Tyr His His Ala His Asp Ala Tyr
    1010                1015                1020

Leu Asn Ala Val Val Gly Thr Ala Leu Ile Lys Lys Tyr Pro Lys
```

-continued

```
           1025                1030                1035
Leu Glu Ser Glu Phe Val Tyr Gly Asp Tyr Lys Val Tyr Asp Val
           1040                1045                1050
Arg Lys Met Ile Ala Lys Ser Glu Gln Glu Ile Gly Lys Ala Thr
           1055                1060                1065
Ala Lys Tyr Phe Phe Tyr Ser Asn Ile Met Asn Phe Phe Lys Thr
           1070                1075                1080
Glu Ile Thr Leu Ala Asn Gly Glu Ile Arg Lys Arg Pro Leu Ile
           1085                1090                1095
Glu Thr Asn Gly Glu Thr Gly Glu Ile Val Trp Asp Lys Gly Arg
           1100                1105                1110
Asp Phe Ala Thr Val Arg Lys Val Leu Ser Met Pro Gln Val Asn
           1115                1120                1125
Ile Val Lys Lys Thr Glu Val Gln Thr Gly Gly Phe Ser Lys Glu
           1130                1135                1140
Ser Ile Leu Pro Lys Arg Asn Ser Asp Lys Leu Ile Ala Arg Lys
           1145                1150                1155
Lys Asp Trp Asp Pro Lys Lys Tyr Gly Gly Phe Asp Ser Pro Thr
           1160                1165                1170
Val Ala Tyr Ser Val Leu Val Val Ala Lys Val Glu Lys Gly Lys
           1175                1180                1185
Ser Lys Lys Leu Lys Ser Val Lys Glu Leu Leu Gly Ile Thr Ile
           1190                1195                1200
Met Glu Arg Ser Ser Phe Glu Lys Asn Pro Ile Asp Phe Leu Glu
           1205                1210                1215
Ala Lys Gly Tyr Lys Glu Val Lys Lys Asp Leu Ile Ile Lys Leu
           1220                1225                1230
Pro Lys Tyr Ser Leu Phe Glu Leu Glu Asn Gly Arg Lys Arg Met
           1235                1240                1245
Leu Ala Ser Ala Gly Glu Leu Gln Lys Gly Asn Glu Leu Ala Leu
           1250                1255                1260
Pro Ser Lys Tyr Val Asn Phe Leu Tyr Leu Ala Ser His Tyr Glu
           1265                1270                1275
Lys Leu Lys Gly Ser Pro Glu Asp Asn Glu Gln Lys Gln Leu Phe
           1280                1285                1290
Val Glu Gln His Lys His Tyr Leu Asp Glu Ile Ile Glu Gln Ile
           1295                1300                1305
Ser Glu Phe Ser Lys Arg Val Ile Leu Ala Asp Ala Asn Leu Asp
           1310                1315                1320
Lys Val Leu Ser Ala Tyr Asn Lys His Arg Asp Lys Pro Ile Arg
           1325                1330                1335
Glu Gln Ala Glu Asn Ile Ile His Leu Phe Thr Leu Thr Asn Leu
           1340                1345                1350
Gly Ala Pro Ala Ala Phe Lys Tyr Phe Asp Thr Thr Ile Asp Arg
           1355                1360                1365
Lys Arg Tyr Thr Ser Thr Lys Glu Val Leu Asp Ala Thr Leu Ile
           1370                1375                1380
His Gln Ser Ile Thr Gly Leu Tyr Glu Thr Arg Ile Asp Leu Ser
           1385                1390                1395
Gln Leu Gly Gly Asp Pro Ile Ala Gly Ser Lys Ala Ser Pro Lys
           1400                1405                1410
Lys Lys Arg Lys Val Gly Arg Ala Asp Ala Leu Asp Asp Phe Asp
           1415                1420                1425
```

Leu Asp Met Leu Gly Ser Asp Ala Leu Asp Phe Asp Leu Asp
         1430                1435                1440

Met Leu Gly Ser Asp Ala Leu Asp Phe Asp Leu Asp Met Leu
         1445                1450                1455

Gly Ser Asp Ala Leu Asp Phe Asp Leu Asp Met Leu Ile Asn
     1460                1465                1470

Tyr Pro Tyr Asp Val Pro Asp Tyr Ala Ser
     1475                1480

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
tcaagctttt ggaccctcgt acagaagcta atacgactca ctatagggaa ataagagaga    60
aaagaagagt aagaagaaat ataagagcca cc                                  92

<210> SEQ ID NO 72
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tcaagctttt ggaccctcgt acagaagcta atacgactca ctataggg                 48

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
tgataatagg ctggagcctc ggtggccatg cttcttgccc cttgggcctc cccccagccc      60
ctcctcccct tcctgcaccc gtaccccgt ggtctttgaa taaagtctga gtgggcggct     120
ctaga                                                                 125

<210> SEQ ID NO 82
<211> LENGTH: 147
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
tgataatagg ctggagcctc ggtggccatg cttcttgccc cttgggcctc ccccagccc       60 ctcctcccct tcctgcaccc gtaccccca aacaccattg tcacactcca gtggtctttg      120
aataaagtct gagtgggcgg ctctaga                                          147

<210> SEQ ID NO 83
<400> SEQUENCE: 83
000

<210> SEQ ID NO 84
<400> SEQUENCE: 84
000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88
<400> SEQUENCE: 88
000

<210> SEQ ID NO 89
<400> SEQUENCE: 89
000

<210> SEQ ID NO 90
<211> LENGTH: 107
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(28)
<223> OTHER INFORMATION: a, c, u, g, unknown or other

<400> SEQUENCE: 90
gggnnnnnnn nnnnnnnnnn nnnnnnnngu uuuagagcua gaaauagcaa guuaaaauaa       60
ggcuaguccg uuaucaacuu gaaaaagugg caccgagucg gugugc                    107

<210> SEQ ID NO 91
<211> LENGTH: 101

```
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 91
gggugugcag acggcaguca cuaggguuuu agagcuagaa auagcaaguu aaaauaaggc      60
uaguccguua ucaacuugaa aaaguggcac cgagucggug c                        101

<210> SEQ ID NO 92
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 92
gggugaguga gugugugcgu guggguuuua gagcuagaaa uagcaaguua aaauaaggcu      60
aguccguuau caacuugaaa aaguggcacc gagucggugc                          100

<210> SEQ ID NO 93
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 93
gggugaguga gugugugcgu guggguuuua gagcuagaaa uagcaaguua aaauaaggcu      60
aguccguuau caacuugaaa aaguggcacc gagucggugc                          100

<210> SEQ ID NO 94
<211> LENGTH: 101
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 94
ggguuggagc ggggagaagg ccaggguuuu agagcuagaa auagcaaguu aaaauaaggc      60
uaguccguua ucaacuugaa aaaguggcac cgagucggug c                        101

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000
```

<210> SEQ ID NO 98

<400> SEQUENCE: 98

000

<210> SEQ ID NO 99

<400> SEQUENCE: 99

000

<210> SEQ ID NO 100
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gttttagagc tagaaatagc aagttaaaat aaggctagtc cgttatcaac ttgaaaaagt      60
ggcaccgagt cggtggtgc                                                  79

<210> SEQ ID NO 101
<211> LENGTH: 146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
tcaagctttt ggaccctcgt acagaagcta atacgactca ctatagggtg tgcagacggc      60
agtcactagg gttttagagc tagaaatagc aagttaaaat aaggctagtc cgttatcaac     120
ttgaaaaagt ggcaccgagt cggtgc                                         146

<210> SEQ ID NO 102
<211> LENGTH: 146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
tcaagctttt ggaccctcgt acagaagcta atacgactca ctatagggag cagcgtcttc      60
gagagtgagg gttttagagc tagaaatagc aagttaaaat aaggctagtc cgttatcaac     120
ttgaaaaagt ggcaccgagt cggtgc                                         146

<210> SEQ ID NO 103
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
tcaagctttt ggaccctcgt acagaagcta atacgactca ctatagggtg agtgagtgtg      60
tgcgtgtggg ttttagagct agaaatagca agttaaaata aggctagtcc gttatcaact    120
tgaaaaagtg gcaccgagtc ggtgc                                          145

```
<210> SEQ ID NO 104
<211> LENGTH: 146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104
tcaagctttt ggaccctcgt acagaagcta atacgactca ctatagggtt ggagcgggga       60
gaaggccagg gttttagagc tagaaatagc aagttaaaat aaggctagtc cgttatcaac      120
ttgaaaaagt ggcaccgagt cggtgc                                           146

<210> SEQ ID NO 105
<211> LENGTH: 152
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (49)..(73)
<223> OTHER INFORMATION: a, c, t, g, unknown or other

<400> SEQUENCE: 105
tcaagctttt ggaccctcgt acagaagcta atacgactca ctatagggnn nnnnnnnnn       60 nnnnnnnnnn nnngttttag agctagaaat agcaagttaa ataaggcta gtccgttatc      120 aacttgaaaa agtggcaccg agtcggtggt gc                                    152

<210> SEQ ID NO 106
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tcaagctttt ggaccctcgt acagaagcta atacgactca ctataggg                    48

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110
<211> LENGTH: 6705
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 110

```
gacgtcttaa gacccacttt cacatttaag ttgttttttct aatccgcata tgatcaattc        60
aaggccgaat aagaaggctg gctctgcacc ttggtgatca ataattcga tagcttgtcg         120
taataatggc ggcatactat cagtagtagg tgtttcccctt tcttctttag cgacttgatg       180
ctcttgatct tccaatacgc aacctaaagt aaaatgcccc acagcgctga gtgcatataa       240
tgcattctct agtgaaaaac cttgttggca taaaaaggct aattgattttt cgagagtttc     300
atactgtttt tctgtaggcc gtgtacctaa atgtacttt gctccatcgc gatgacttag        360
taaagcacat ctaaaacttt tagcgttatt acgtaaaaaa tcttgccagc tttcccttc       420
taaagggcaa aagtgagtat ggtgcctatc taacatctca atggctaagg cgtcgagcaa      480
agcccgctta ttttttacat gccaatacaa tgtaggctgc tctacaccta gcttctgggc     540
gagtttacgg gttgttaaac cttcgattcc gacctcatta agcagctcta atgcgctgtt      600
aatcacttta cttttatcta atctagacat cattaattcc taatttttgt tgacactcta      660
tcgttgatag agttatttta ccactccccta tcagtgatag agaaaagaat tcaaagatc      720
taaagaggag aaaggatcta tggataagaa atactcaata ggcttagcta tcggcacaaa      780
tagcgtcgga tgggcggtga tcactgatga atataaggtt ccgtctaaaa agttcaaggt     840
tctgggaaat acagaccgcc acagtatcaa aaaaatctt ataggggctc ttttatttga      900
cagtggagag acagcggaag cgactcgtct caaacggaca gctcgtagaa ggtatacacg      960
tcggaagaat cgtatttgtt atctacagga gattttttca aatgagatgg cgaaagtaga     1020
tgatagtttc tttcatcgac ttgaagagtc tttttggtg gaagaagaca agaagcatga      1080
acgtcatcct atttttggaa atatagtaga tgaagttgct tatcatgaga aatatccaac     1140
tatctatcat ctgcgaaaaa aattggtaga ttctactgat aaagcggatt gcgcttaat      1200
ctatttggcc ttagcgcata tgattaagtt tcgtggtcat ttttttgattg agggagattt    1260
aaatcctgat aatagtgatg tggacaaact atttatccag ttggtacaaa cctacaatca    1320
attatttgaa gaaaccccta ttaacgcaag tggagtagat gctaaagcga ttctttctgc    1380
acgattgagt aaatcaagac gattagaaaa tctcattgct cagctccccg gtgagaagaa    1440
aaatggctta tttgggaatc tcattgcttt gtcattgggt ttgacccccta attttaaatc   1500
aaattttgat ttggcagaag atgctaaatt acagctttca aaagatactt acgatgatga     1560
tttagataat ttattggcgc aaattggaga tcaatatgct gatttgtttt tggcagctaa    1620
gaatttatca gatgctattt tactttcaga tatcctaaga gtaaatactg aaataactaa    1680
ggctccccta tcagcttcaa tgattaaacg ctacgatgaa catcatcaag acttgactct    1740
tttaaaagct ttagttcgac aacaacttcc agaaaagtat aaagaaatct ttttttgatca   1800
atcaaaaaac ggatatgcag gttatattga tgggggagct agccaagaag aattttataa    1860
atttatcaaa ccaattttag aaaaaatgga tggtactgag gaattattgg tgaaactaaa    1920
tcgtgaagat ttgctgcgca agcaacggac ctttgacaac ggctctattc cccatcaaat    1980
tcacttgggt gagctgcatg ctattttgag aagacaagaa gacttttatc cattttttaaa   2040
agacaatcgt gagaagattg aaaaaatctt gactttttcga attccttatt atgttggtcc   2100
attggcgcgt ggcaatagtc gttttgcatg gatgactcgg aagtctgaag aaacaattac    2160
cccatggaat tttgaagaag ttgtcgataa aggtgcttca gctcaatcat ttattgaacg   2220
catgacaaac tttgataaaa atcttccaaa tgaaaaagta ctaccaaaac atagtttgct    2280
```

```
ttatgagtat tttacggttt ataacgaatt gacaaaggtc aaatatgtta ctgaaggaat    2340
gcgaaaacca gcatttcttt caggtgaaca gaagaaagcc attgttgatt tactcttcaa    2400
aacaaatcga aaagtaaccg ttaagcaatt aaaagaagat tatttcaaaa aaatagaatg    2460
ttttgatagt gttgaaattt caggagttga agatagattt aatgcttcat taggtaccta    2520
ccatgatttg ctaaaaatta ttaaagataa agattttttg gataatgaag aaaatgaaga    2580
tatcttagag gatattgttt taacattgac cttatttgaa gatagggaga tgattggaga    2640
aagacttaaa acatatgctc acctctttga tgataaggtg atgaaacagc ttaaacgtcg    2700
ccgttatact ggttggggac gttttgtctcg aaaattgatt aatggtatta gggataagca    2760
atctggcaaa acaatattag attttttgaa atcagatggt tttgccaatc gcaattttat    2820
gcagctgatc catgatgata gtttgacatt taaagaagac attcaaaaag cacaagtgtc    2880
tggacaaggc gatagtttac atgaacatat tgcaaattta gctggtagcc ctgctattaa    2940
aaaaggtatt ttacagactg taaaagttgt tgatgaattg gtcaaagtaa tggggcggca    3000
taagccagaa aatatcgtta ttgaaatggc acgtgaaaat cagacaactc aaaagggcca    3060
gaaaaattcg cgagagcgta tgaaacgaat cgaagaaggt atcaaagaat taggaagtca    3120
gattcttaaa gagcatcctg ttgaaaatac tcaattgcaa aatgaaaagc tctatctcta    3180
ttatctccaa aatggaagag acatgtatgt ggaccaagaa ttagatatta atcgtttaag    3240
tgattatgat gtcgatgcca ttgttccaca aagtttcctt aaagacgatt caatagacaa    3300
taaggtctta acgcgttctg ataaaaatcg tggtaaatcg ataacgttc caagtgaaga    3360 agtagtcaaa aagatgaaaa actattggag acaacttcta aacgccaagt taatcactca    3420
acgtaagttt gataatttaa cgaaagctga acgtggaggt ttgagtgaac ttgataaagc    3480
tggttttatc aaacgccaat tggttgaaac tcgccaaatc actaagcatg tggcacaaat    3540
tttggatagt cgcatgaata ctaaatacga tgaaaatgat aaacttattc gagaggttaa    3600
agtgattacc ttaaaatcta aattagtttc tgacttccga aaagatttcc aattctataa    3660
agtacgtgag attaacaatt accatcatgc ccatgatgcg tatctaaatg ccgtcgttgg    3720
aactgctttg attaagaaat atccaaaact tgaatcggag tttgtctatg gtgattataa    3780
agtttatgat gttcgtaaaa tgattgctaa gtctgagcaa gaaataggca agcaaccgc    3840 aaaatatttc ttttactcta atatcatgaa cttcttcaaa acagaaatta cacttgcaaa    3900
tggagagatt cgcaaacgcc ctctaatcga aactaatggg gaaactggag aaattgtctg    3960
ggataaaggg cgagattttg ccacagtgcg caaagtattg tccatgcccc aagtcaatat    4020
tgtcaagaaa acagaagtac agacaggcgg attctccaag gagtcaattt taccaaaaag    4080
aaattcggac aagcttattg ctcgtaaaaa agactgggat ccaaaaaaat atggtggttt    4140
tgatagtcca acggtagctt attcagtcct agtggttgct aaggtggaaa aagggaaatc    4200
gaagaagtta aaatccgtta aagagttact agggatcaca attatggaaa gaagttcctt    4260
tgaaaaaaat ccgattgact ttttagaagc taaaggatat aaggaagtta aaaaagactt    4320
aatcattaaa ctacctaaat atagtctttt tgagttagaa aacggtcgta acggatgct    4380 ggctagtgcc ggagaattac aaaaaggaaa tgagctggct ctgccaagca aatatgtgaa    4440 tttttatat ttagctagtc attatgaaaa gttgaagggt agtccagaag ataacgaaca    4500
aaaacaattg tttgtggagc agcataagca ttatttagat gagattattg agcaaatcag    4560 tgaatttttct aagcgtgtta ttttagcaga tgccaattta gataaagttc ttagtgcata    4620
```

| | |
|---|---|
| taacaaacat agagacaaac caatacgtga acaagcagaa aatattattc atttatttac | 4680 |
| gttgacgaat cttggagctc ccgctgcttt taaatatttt gatacaacaa ttgatcgtaa | 4740 |
| acgatatacg tctacaaaag aagttttaga tgccactctt atccatcaat ccatcactgg | 4800 |
| tctttatgaa acacgcattg atttgagtca gctaggaggt gactaactcg agtaaggatc | 4860 |
| tccaggcatc aaataaaacg aaaggctcag tcgaaagact gggcctttcg ttttatctgt | 4920 |
| tgtttgtcgg tgaacgctct ctactagagt cacactggct caccttcggg tgggcctttc | 4980 |
| tgcgtttata cctagggata tattccgctt cctcgctcac tgactcgcta cgctcggtcg | 5040 |
| ttcgactgcg gcgagcggaa atggcttacg aacggggcgg agatttcctg gaagatgcca | 5100 |
| ggaagatact aacagggaa gtgagagggc gcgggcaaag ccgttttcc ataggctccg | 5160 |
| cccccctgac aagcatcacg aaatctgacg ctcaaatcag tggtggcgaa acccgacagg | 5220 |
| actataaaga taccaggcgt ttccccctgg cggctccctc gtgcgctctc ctgttcctgc | 5280 |
| ctttcggttt accggtgtca ttccgctgtt atggccgcgt ttgtctcatt ccacgcctga | 5340 |
| cactcagttc cgggtaggca gttcgctcca agctggactg tatgcacgaa ccccccgttc | 5400 |
| agtccgaccg ctgcgcctta tccggtaact atcgtcttga gtccaacccg gaaagacatg | 5460 |
| caaaagcacc actggcagca gccactggta attgatttag aggagttagt cttgaagtca | 5520 |
| tgcgccggtt aaggctaaac tgaaaggaca gtttggtg actgcgctcc tccaagccag | 5580 |
| ttacctcggt tcaaagagtt ggtagctcag agaaccttcg aaaaaccgcc ctgcaaggcg | 5640 |
| gttttttcgt tttcagagca agagattacg cgcagaccaa aacgatctca agaagatcat | 5700 |
| cttattaatc agataaaata tttctagatt tcagtgcaat ttatctcttc aaatgtagca | 5760 |
| cctgaagtca gccccatacg atataagttg ttactagtgc ttggattctc accaataaaa | 5820 |
| aacgcccggc ggcaaccgag cgttctgaac aaatccagat ggagttctga ggtcattact | 5880 |
| ggatctatca acaggagtcc aagcgagctc gatatcaaat tacgccccgc cctgccactc | 5940 |
| atcgcagtac tgttgtaatt cattaagcat tctgccgaca tggaagccat cacaaacggc | 6000 |
| atgatgaacc tgaatcgcca gcggcatcag caccttgtcg ccttgcgtat aatatttgcc | 6060 |
| catggtgaaa acggggcga agaagttgtc catattggcc acgtttaaat caaaactggt | 6120 |
| gaaactcacc cagggattgg ctgagacgaa aaacatattc tcaataaacc ctttagggaa | 6180 |
| ataggccagg ttttcaccgt aacacgccac atcttgcgaa tatatgtgta gaaactgccg | 6240 |
| gaaatcgtcg tggtattcac tccagagcga tgaaaacgtt tcagtttgct catggaaaac | 6300 |
| ggtgtaacaa gggtgaacac tatcccatat caccagctca ccgtctttca ttgccatacg | 6360 |
| aaattccgga tgagcattca tcaggcgggc aagaatgtga ataaaggccg gataaaactt | 6420 |
| gtgcttattt ttctttacgg tctttaaaaa ggccgtaata tccagctgaa cggtctggtt | 6480 |
| ataggtacat tgagcaactg actgaaatgc ctcaaaatgt tctttacgat gccattggga | 6540 |
| tatatcaacg gtggtatatc cagtgatttt tttctccatt ttagcttcct tagctcctga | 6600 |
| aaatctcgat aactcaaaaa atacgcccgg tagtgatctt atttcattat ggtgaaagtt | 6660 |
| ggaacctctt acgtgccgat caacgtctca ttttcgccag atatc | 6705 |

<210> SEQ ID NO 111
<211> LENGTH: 4146
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111

```
gccaccatgg acaagaagta ctccattggg ctcgatatcg gcacaaacag cgtcggctgg      60
gccgtcatta cggacgagta caaggtgccg agcaaaaaat tcaaagttct gggcaatacc     120
gatcgccaca gcataaagaa gaacctcatt ggcgccctcc tgttcgactc cggggagacg     180
gccgaagcca cgcggctcaa agaacagca cggcgcagat atacccgcag aaagaatcgg     240
atctgctacc tgcaggagat ctttagtaat gagatggcta aggtggatga ctctttcttc     300
cataggctgg aggagtcctt tttggtggag gaggataaaa agcacgagcg ccacccaatc     360
tttggcaata tcgtggacga ggtggcgtac catgaaaagt acccaaccat atatcatctg     420
aggaagaagc ttgtagacag tactgataag gctgacttgc ggttgatcta tctcgcgctg     480
gcgcatatga tcaaatttcg gggacacttc ctcatcgagg gggacctgaa cccagacaac     540
agcgatgtcg acaaactctt tatccaactg gttcagactt acaatcagct tttcgaagag     600
aacccgatca cgcatccgg agttgacgcc aaagcaatcc tgagcgctag gctgtccaaa     660
tcccggcggc tcgaaaacct catcgcacag ctccctgggg agaagaagaa cggcctgttt     720
ggtaatctta tcgccctgtc actcgggctg accccccaact ttaaatctaa cttcgacctg     780
gccgaagatg ccaagcttca actgagcaaa gacacctacg atgatgatct cgacaatctg     840
ctggcccaga tcggcgacca gtacgcagac ctttttttgg cggcaaagaa cctgtcagac     900
gccattctgc tgagtgatat tctgcgagtg aacacggaga tcaccaaagc tccgctgagc     960
gctagtatga tcaagcgcta tgatgagcac caccaagact tgactttgct gaaggccctt    1020
gtcagacagc aactgcctga gaagtacaag gaaattttct tcgatcagtc taaaaatggc    1080
tacgccggat acattgacgg cggagcaagc caggaggaat tttacaaatt tattaagccc    1140
atcttggaaa aaatggacgg caccgaggag ctgctggtaa agcttaacag agaagatctg    1200
ttgcgcaaac agcgcacttt cgacaatgga agcatccccc accagattca cctgggcgaa    1260
ctgcacgcta tcctcaggcg gcaagaggat ttctaccccct ttttgaaaga taacaggaa    1320
aagattgaga aaatcctcac atttcggata ccctactatg taggcccct cgcccgggga    1380
aattccagat tcgcgtggat gactcgcaaa tcagaagaga ccatcactcc ctggaacttc    1440
gaggaagtcg tggataaggg ggcctctgcc cagtccttca tcgaaaggat gactaacttt    1500
gataaaaatc tgcctaacga aaaggtgctt cctaaacact ctctgctgta cgagtacttc    1560
acagtttata acgagctcac caaggtcaaa tacgtcacag aagggatgag aaagccagca    1620
ttcctgtctg gagagcagaa gaaagctatc gtggacctcc tcttcaagac gaaccggaaa    1680
gttaccgtga acagctcaa agaagactat ttcaaaaaga ttgaatgttt cgactctgtt    1740
gaaatcagcg gagtggagga tcgcttcaac gcatccctgg gaacgtatca cgatctcctg    1800
aaaatcatta agacaagga cttcctggac aatgaggaga cgaggacat tcttgaggac    1860
attgtcctca cccttacgtt gttttgaagat agggagatga ttgaagaacg cttgaaaact    1920
tacgctcatc tcttcgacga caaagtcatg aaacagctca gaggcgccg atatacagga    1980
tggggggcgc tgtcaagaaa actgatcaat gggatccgag acaagcagag tggaaagaca    2040
atcctggatt tcttaagtc cgatggattt gccaaccgga acttcatgca gttgatccat    2100
gatgactctc tcacctttaa ggaggacatc cagaaagcac aagtttctgg ccaggggac    2160
agtcttcacg agcacatcgc taatcttgca ggtagcccag ctatcaaaaa gggaatactg    2220
cagaccgtta aggtcgtgga tgaactcgtc aaagtaatgg gaaggcataa gcccgagaat    2280
atcgttatcg agatggcccg agagaaccaa actacccaga agggacagaa gaacagtagg    2340
```

```
gaaaggatga agaggattga agagggtata aaagaactgg ggtcccaaat ccttaaggaa     2400
cacccagttg aaaacaccca gcttcagaat gagaagctct acctgtacta cctgcagaac     2460
ggcagggaca tgtacgtgga tcaggaactg gacatcaatc ggctctccga ctacgacgtg     2520
gatcatatcg tgccccagtc tttctcaaa gatgattcta ttgataataa agtgttgaca      2580
agatccgata aaaatagagg gaagagtgat aacgtcccct cagaagaagt tgtcaagaaa     2640
atgaaaaatt attggcggca gctgctgaac gccaaactga tcacacaacg gaagttcgat     2700
aatctgacta aggctgaacg aggtggcctg tctgagttgg ataaagccgg cttcatcaaa     2760
aggcagcttg ttgagacacg ccagatcacc aagcacgtgg cccaaattct cgattcacgc     2820
atgaacacca gtacgatga aaatgacaaa ctgattcgag aggtgaaagt tattactctg      2880
aagtctaagc tggtctcaga tttcagaaag gactttcagt tttataaggt gagagagatc     2940
aacaattacc accatgcgca tgatgcctac ctgaatgcag tggtaggcac tgcacttatc     3000
aaaaaatatc ccaagcttga atctgaattt gtttacggag actataaagt gtacgatgtt     3060
aggaaaatga tcgcaaagtc tgagcaggaa ataggcaagg ccaccgctaa gtacttcttt     3120
tacagcaata ttatgaattt tttcaagacc gagattacac tggccaatgg agagattcgg     3180
aagcgaccac ttatcgaaac aaacggagaa acaggagaaa tcgtgtggga caagggtagg     3240
gatttcgcga cagtccggaa ggtcctgtcc atgccgcagg tgaacatcgt taaaaagacc     3300
gaagtacaga ccggaggctt ctccaaggaa agtatcctcc cgaaaaggaa cagcgacaag     3360
ctgatcgcac gcaaaaaaga ttgggacccc aagaaatacg gcggattcga ttctcctaca     3420
gtcgcttaca gtgtactggt tgtggccaaa gtggagaaag ggaagtctaa aaaactcaaa     3480
agcgtcaagg aactgctggg catcacaatc atggagcgat caagcttcga aaaaaacccc     3540
atcgactttc tcgaggcgaa aggatataaa gaggtcaaaa aagacctcat cattaagctt     3600
cccaagtact ctctctttga gcttgaaaac ggccggaaac gaatgctcgc tagtgcgggc     3660
gagctgcaga aaggtaacga gctggcactg ccctctaaat acgttaattt cttgtatctg     3720
gccagccact atgaaaagct caaagggtct cccgaagata tgagcagaa gcagctgttc      3780 gtggaacaac acaaacacta ccttgatgag atcatcgagc aaataagcga attctccaaa     3840
agagtgatcc tcgccgacgc taacctcgat aaggtgcttt ctgcttacaa taagcacagg     3900
gataagccca tcagggagca ggcagaaaac attatccact tgtttactct gaccaacttg     3960
ggcgcgcctg cagccttcaa gtacttcgac accaccatag acagaaagcg gtacacctct     4020
acaaaggagg tcctggacgc cacactgatt catcagtcaa ttacgggct ctatgaaaca      4080 agaatcgacc tctctcagct cggtggagac agcagggctg accccaagaa gaagaggaag     4140
gtgtga                                                                4146
```

<210> SEQ ID NO 112
<211> LENGTH: 4212
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 112

```
atgggaccta agaaaaagag gaaggtgcct aagaaaaaga ggaaggtgcc taagaaaaag      60
aggaaggtgg cggccgctga ctacaaggat gacgacgata atctagaga caagaaatac      120 tctattggac tggatatcgg gacaaactcc gttggctggg ccgtcataac cgacgagtat     180
```

```
aaggtgccaa gcaagaaatt caaggtgctg ggtaatactg accgccattc aatcaagaag    240
aacctgatcg gagcactcct cttcgactcc ggtgaaaccg ctgaagctac tcggctgaag    300
cggaccgcaa ggcggagata cacccgccgc aagaatcgga tatgttatct gcaagagatc    360
tttagcaacg aaatggctaa ggtggacgac tccttctttc accgcctgga agagagcttt    420
ctggtggagg aggataagaa acacgagagg caccctatat tcggaaatat cgtggatgag    480
gtggcttacc atgaaaagta tcctacaatc taccatctga ggaagaagct ggtggacagc    540
accgataaag cagacctgag gctcatctat ctggccctgg ctcatatgat aaagtttaga    600
ggacactttc tgatcgaggg cgacctgaat cccgataatt ccgatgtgga taaactcttc    660
attcaactgg tgcagacata taccaactg ttcgaggaga atcccataaa cgcttctggt    720
gtggatgcca aggctattct gtccgctcgg ctgtccaagt cacgcagact ggagaatctg    780
attgcccaac tgccaggaga aaagaagaac ggcctgtttg gaacctcat cgccctgagc    840 ctgggcctga cacctaactt caagtccaat tttgatctgg ccgaagatgc taaactccag    900
ctctccaagg acacctatga cgatgatctg gacaacctgc tcgcacagat aggcgaccag    960
tacgccgatc tctttctggc tgctaagaat ctctccgacg ccattctgct gagcgacata   1020
ctccgggtca acactgagat caccaaagca cctctgagcg cctccatgat aaaacgctat   1080
gatgaacacc atcaagacct gactctgctc aaagccctcg tgaggcaaca gctgccagag   1140
aagtacaaag agatattctt cgaccagagc aagaatggat atgccggata catcgatggc   1200
ggagcatcac aggaagaatt ttacaagttc atcaaaccaa tcctcgagaa gatggacggt   1260
actgaagagc tgctggtgaa gctgaacagg gaggacctgc tgaggaagca gaggaccttt   1320
gataatggct ccattccaca tcagatacac ctgggagagc tgcatgcaat cctccgcagg   1380
caggaggatt tctatccttt cctgaaggat aaccgggaga agatagagaa gatcctgacc   1440
ttcaggatcc cttattacgt cggccctctg gctagaggca actcccgctt cgcttggatg   1500
accaggaaat ctgaggagac aattactcct tggaacttcg aagaggtcgt ggataagggc   1560
gcaagcgccc agtcattcat cgaacggatg accaatttcg ataagaacct gcccaacgag   1620
aaggtcctgc ccaaacattc actcctgtac gagtatttca ccgtctataa cgagctgact   1680
aaagtgaagt acgtgaccga gggcatgagg aagcctgcct tcctgtccgg agagcagaag   1740
aaggctatcg ttgatctgct cttcaagact aatagaaagg tgacagtgaa gcagctcaag   1800
gaggattact ttaagaagat cgaatgcttt gactcagtgg aaatctctgg cgtggaggac   1860
cgctttaatg ccagcctggg cacttaccat gatctgctga agataatcaa agacaaagat   1920
ttcctcgata tgaggagaa cgaggacatc ctggaagata tcgtgctgac cctgactctg   1980
ttcgaggata gagagatgat cgaagagcgc ctgaagacct atgcccatct gtttgacgat   2040
aaagtcatga acagctcaa gcggcggcgc tacactgggt ggggtagact ctccaggaaa   2100
ctcataaacg gcatccgcga caaacagagc ggaaagacca tcctggattt cctgaaatcc   2160
gacggattcg ctaacaggaa cttcatgcaa ctgattcacg atgactctct gacatttaaa   2220
gaggacatcc agaaggcaca ggtgagcggt caaggcgaca gcctgcacga gcacatcgcc   2280
aacctcgctg gatcacccgc cataaagaag ggaatactgc agacagtcaa ggtcgtggac   2340
gaactcgtca aagtgatggg tcggcacaag ccagagaata tcgttatcga aatggcaagg   2400
gagaaccaaa ccacccagaa gggccagaag aactctcggg aacggatgaa aagaatcgaa   2460
gagggaatta aggagctggg atctcagata ctgaaggagc accctgtgga gaatacacag   2520
```

```
ctccagaacg agaaactcta cctgtactac ctccagaacg ggcgggacat gtacgttgac    2580
caggaactcg acatcaaccg gctgtccgat tatgacgtgg accatattgt tccacagtcc    2640
ttcctcaaag atgactccat tgacaacaag gtgctgacca gatccgataa gaatcgcggt    2700
aagtctgaca atgttccatc agaagaggtg gtcaagaaga tgaagaatta ctggcggcag    2760
ctcctcaacg ccaaactgat cacccagcgg aagtttgaca atctgactaa ggcagaaaga    2820
ggaggtctga gcgaactcga caaggccggc tttattaaga ggcaactggt cgaaacacgc    2880
cagattacca aacacgtggc acaaatcctc gactctagga tgaacactaa gtacgatgag    2940
aacgataagc tgatcaggga agtgaaagtg ataactctga gagcaagct ggtgtctgac    3000 ttccggaagg actttcaatt ctacaaagtt cgcgaaataa acaattacca tcatgctcac    3060
gatgcctatc tcaatgctgt cgttggcacc gccctgatca gaaatacccc taaactggag    3120
tctgagttcg tgtacggtga ctataaagtc tacgatgtga ggaagatgat agcaaagtct    3180
gagcaagaga ttggcaaagc caccgccaag tacttcttct actctaatat catgaatttc    3240
tttaagactg agataaccct ggctaacggc gaaatccgga agcgcccact gatcgaaaca    3300
aacggagaaa caggagaaat cgtgtgggat aaaggcaggg acttcgcaac tgtgcggaag    3360
gtgctgtcca tgccacaagt caatatcgtg aagaagaccg aagtgcagac cggcggattc    3420
tcaaaggaga gcatcctgcc aaagcggaac tctgacaagc tgatcgccag gaagaaagat    3480
tgggacccaa agaagtatgg cggtttcgat tcccctacag tggcttattc cgttctggtc    3540
gtggcaaaag tggagaaagg caagtccaag aaactcaagt ctgttaagga gctgctcgga    3600
attactatta tggagagatc cagcttcgag aagaatccaa tcgatttcct ggaagctaag    3660
ggctataaag aagtgaagaa agatctcatc atcaaactgc ccaagtactc tctctttgag    3720
ctggagaatg gtaggaagcg gatgctggcc tccgccggag agctgcagaa aggaaacgag    3780
ctggctctgc cctccaaata cgtgaacttc ctgtatctgg cctcccacta cgagaaactc    3840
aaaggtagcc ctgaagacaa tgagcagaag caactctttg ttgagcaaca taaacactac    3900
ctggacgaaa tcattgaaca gattagcgag ttcagcaagc gggttattct ggccgatgca    3960
aacctcgata aagtgctgag cgcatataat aagcacaggg acaagccaat cgcgaacaa    4020 gcagagaata ttatccacct ctttactctg actaatctgg gcgctcctgc tgccttcaag    4080
tatttcgata caactattga caggaagcgg tacacctcta ccaaagaagt tctcgatgcc    4140
accctgatac accagtcaat taccggactg tacgagactc gcatcgacct gtctcagctc    4200
ggcggcgact ag                                                        4212
```

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Asn Glu Leu Ala Leu Pro Ser Lys
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Tyr Phe Asp Thr Thr Ile Asp Arg
1               5

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ile Pro Tyr Tyr Val Gly Pro Leu Ala Arg
1               5                   10

<210> SEQ ID NO 123
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 123 atcg                                                            4

<210> SEQ ID NO 124
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5meC

<400> SEQUENCE: 124 atcg                                                            4

<210> SEQ ID NO 125
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125 atcccg                                                          6

<210> SEQ ID NO 126
<211> LENGTH: 9
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126 ccrccaugg                                                       9

<210> SEQ ID NO 127
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127 gggaga                                                          6

<210> SEQ ID NO 128
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(160)
<223> OTHER INFORMATION: This sequence may encompass 80-160 bases

<400> SEQUENCE: 128
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
```

```
aaaaaaaaaa aaaaaaaaaa aaaaaaaaaa aaaaaaaaaa                          160

<210> SEQ ID NO 129
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(250)
<223> OTHER INFORMATION: This sequence may encompass 100-250 bases

<400> SEQUENCE: 129
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa aaaaaaaaaa aaaaaaaaaa aaaaaaaaaa    180
aaaaaaaaaa aaaaaaaaaa aaaaaaaaaa aaaaaaaaaa aaaaaaaaaa aaaaaaaaaa    240
aaaaaaaaaa                                                           250

<210> SEQ ID NO 130
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: See specification as filed for detailed
      description of substitutions and preferred embodiments

<400> SEQUENCE: 130
aaaaaaaaaa aaaaaaaaaa aaaaaaaaaa                                      30

<210> SEQ ID NO 131
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120

<210> SEQ ID NO 132
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
tttttttttt tttttttttt tttttttttt tttttttttt tttttttttt tttttttttt     60
tttttttttt tttttttttt tttttttttt tttttttttt tttttttttt tttttttttt    120

<210> SEQ ID NO 133
<211> LENGTH: 165
<212> TYPE: DNA
<213> ORGANISM: Artificial Sequence
<220> FEATURE:
```

<223> OTHER INFORMATION: Description of Artificial Sequence: Synthetic
      polynucleotide
<220> FEATURE:
<221> NAME/KEY: misc_feature
<222> LOCATION: (1)..(165)
<223> OTHER INFORMATION: This sequence may encompass 150-165 bases; See
      specification as filed for detailed description of substitutions
      and preferred embodiments

<400> SEQUENCE: 133
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaa                     165

<210> SEQ ID NO 134
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa                                                 140

<210> SEQ ID NO 135
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(140)
<223> OTHER INFORMATION: This sequence may encompass 80-140 bases

<400> SEQUENCE: 135
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa                                                 140

<210> SEQ ID NO 136
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa                           100

<210> SEQ ID NO 137
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 137
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
aaaaaaaaaa aaaaaaaaaa aaaaaaaaaa aaaaaaaaaa                             160
```

COMPOSITIONS COMPRISING SYNTHETIC POLYNUCLEOTIDES ENCODING CRISPR RELATED PROTEINS AND SYNTHETIC SGRNAS AND METHODS OF USE

CROSS-REFERENCE TO RELATED APPLICATION

This application claims the benefit of U.S. Provisional Patent Application No. 61/844,890, filed Jul. 11, 2013, and U.S. Provisional Patent Application No. 61/886,545, filed Oct. 3, 2013, the disclosures of which are incorporated herein by reference.

FIELD OF THE INVENTION

The present invention is directed to compositions comprising and methods of using synthetic polynucleotides and short guide RNAs (sgRNAs). The synthetic polynucleotides are, e.g., synthetic modified RNA encoding CRISPR related proteins, e.g., dCAS9 and dCAS9-effector domain fusion proteins. The synthetic sgRNAs target a gene of interest. The synthetic polynucleotides and synthetic sgRNAs can be used to modulate transcription, e.g., in therapeutics and/or clinical and research settings.

BACKGROUND OF THE INVENTION

Bacterial and archaeal Clustered Regularly Interspaced Short Palindromic Repeats (CRISPR) systems rely on CRISPR RNAs (crRNAs) in complex with CRISPR-associated (CAS) proteins to direct degradation of complementary sequences present within invading viral and plasmid DNA (Mali et al. Science. 2013. 339:823-826; herein incorporated by reference in its entirety).

In type II CRISPR systems, the pre-crRNAs are processed by trans-activating crRNA (tracrRNA) complementary to the repeat sequences in pre-crRNA which triggers processing by the double-stranded (ds) RNA-specific ribonuclease RNase III in the presence of the CAS9 protein. CAS9 (formerly CSN1) is the key protein in the type II CRISPR systems and is thought to be the sole protein responsible for crRNA-guided silencing of foreign DNA (Jinek et al. Science. 2012. 337:816-821; herein incorporated by reference in its entirety). The CAS9 protein is also hypothesized to be involved in both crRNA maturation and crRNA-guided DNA interference (Jinek et al. Science. 2012. 337:816-821; herein incorporated by reference in its entirety).

The CAS9 endonuclease family can be programmed with single RNA molecules to cleave specific DNA sites which may be used to develop a versatile RNA-directed system to generate dsDNA breaks for genome targeting and editing (Jinek et al. Science. 2012. 337:816-821; herein incorporated by reference in its entirety). This use of CAS9 could enhance the ease of genome engineering.

The Church Lab engineered the bacterial and archaeal type II CRISPR system to function with custom guide RNA (gRNA) in human cells (Mali et al. Science. 2013. 339:823-826; herein incorporated by reference in its entirety).

It has been shown that fusion of CRISPR-associated catalytically inactive dCas9 protein to distinct effector domains (e.g. VP64, p65AD, KRAB, and Mxi1) enables repression or activation of transcription in human and yeast cells, with the site of delivery determined solely by a co-expressed short guide RNA (sgRNA). Coupling of dCas9 to a transcriptional repressor domain can silence expression of multiple endogenous genes, with no detectable off-targets as verified by RNA-seq analysis. (Qi et al. Cell. 2013. 152:1173-1183)

One example of a catalytically inactive Cas9 protein is the mutant (D10A, H840A) Streptococcus pyogenes Cas9 protein, typically referred to as dCAS9 (Qi et al. Cell. 2013. 152:1173-1183; Gilbert et al. Cell. 2013. 154:1-10). A Streptococcus thermophiles Cas9 with 2 endonuclease domains and single amino acid substitution (D31A, H858A) has been described which also resulted in catalytically inactive Cas9 (Sapranauskas et al. Nucleic Acids Research. 2011. 39:9275-9282).

Other publications describing the CRISPR systems, Cas9, and dCas9 include the following Cong et al (2013); Jinek et al (2012); Lei et al (2013); Gilbert et al (2013); Perez-Pinela et al (2013); Maider et al (2013).

It has been shown that certain modified mRNA sequences have the potential as therapeutics with benefits beyond just evading, avoiding or diminishing the immune response. Such studies are detailed in published co-pending applications International Publication No WO2012019168 filed Aug. 5, 2011 and International Publication No WO2012045075 filed Oct. 3, 2011, International Publication No WO2013052523 filed Oct. 3, 2011, the contents of which are incorporated herein by reference in their entirety.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIG. 4 shows the results of a LC-PRM Cas9 peptide quantification in cell lysates of HeLa cells transfected with Maeder and Gilbert Cas9 constructs versus untreated HeLa cells. Each chart shows the quantification of a peptide fragment of the Cas9 construct.

DETAILED DESCRIPTION

Figure 1:
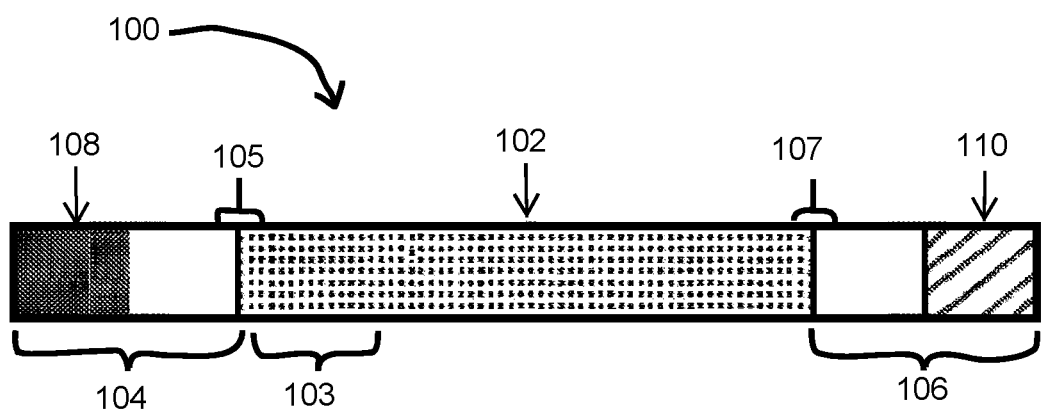
FIG. 1 is a schematic of a synthetic polynucleotide of the present invention.

The present invention is based, at least in part, on the surprising discovery that mRNAs can be expressed in the cytoplasm and translocated to the nucleus. The mRNA technology of the invention is surprisingly suited for delivery of intracellular proteins. The mRNA technology of the invention is also desirable suited for delivery of multiple mRNAs. The methodologies of the invention avoid or circumvent problems associated with conventional gene therapy approaches, such as toxicity, integration of DNA into host genome, and the like. The methodologies of the invention are particularly suited to the delivery of a plurality of mRNAs, without inducing an innate immune and without undesirable side effects associated with conventional gene therapy approaches. In particular, the mRNA delivery technology of the invention facilitates the expression both the mRNA encoding CRISPR-related proteins, e.g., Cas9, dCas9 and variants thereof, in combination with one or more guide RNAs (sgRNAs) to enable gene regulation in vitro and in vivo. Using mRNA-based pharmaceutical compositions, the technology provides for therapeutic applications of the CRISPR technologies that were previously unattainable The data presented herein evidence that it is possible to achieve intracellular expression of CRISPR-related proteins, including proteins engineered to include regulatory sequence facilitating regulation of protein expression, and the corresponding mRNA targeting sequences (i.e., sgRNAs). The data presented herein demonstrate that is it possible to achieve intracellular protein expression of CRISPR-related proteins, in particular, via in vivo administration of pharmaceutical compositions containing modified mRNAs encoding such proteins.

The details of various embodiments of the invention are set forth in the description below. Other features, objects, and advantages of the invention will be apparent from the description and the drawings, and from the claims.

Described herein are compositions (including pharmaceutical compositions) and methods for the design, preparation, manufacture and/or formulation of synthetic polynucleotides encoding one or more one or more CRISPR related proteins, e.g., dCAS9 and/or dCAS9-effector fusion proteins. Also described herein are compositions (including pharmaceutical compositions) and methods for the design, preparation, manufacture and/or formulation of one or more synthetic small guide RNAs ("sgRNAs") targeting a gene of interest. Both the synthetic polynucleotides and sgRNAs are typically manufactures using in vitro transcription. In one embodiment the synthetic polynucleotide and sgRNA are modified, e.g., comprise at least one modified nucleotide. Also described herein are method of modulation of expression of a gene of interest using a synthetic polynucleotide encoding a CRISPR related protein and an sgRNA targeting the gene of interest. Included are in vitro and in vivo methods, e.g., methods of treatment of a disease state correlated with expression of the gene of interest. Also provided are systems, processes, devices and kits for the selection, design and/or utilization of the synthetic polynucleotides and synthetic sgRNAs described herein.

A key limitation of the CRISPR/Inhibition/Activation (CRISPR/I/A) systems described to date is their dependence on delivery of DNA by viral vectors to drive intracellular transcription (of the sgRNA) and transcription and translation of Cas9, dCas9 or dCas9-fusion proteins such as dCas9-VP64, and dCas9-KRAB. There are several implications of this limitation for in vivo systems using transcriptional activation/repression as this will require repeat dosing. First, delivery of DNA by pseudo virus will induce measurable innate immune activation (e.g., thru TLRs) and these will impact transfection efficiency and have undesirable side effects. Second, the repeat dosing of viral capsids could and likely will induce an adaptive immune response on repeat dosing. Third, the use of DNA—and the risk of chronically activated dCas9 represent a significant safety and toxicity risk for in vivo therapeutics.

Modified synthetic polynucleotide (e.g., modified mRNA) presents an ideal platform for the clinical translation of this prokaryotic platform. Technologies are disclosed herein to safely delivery modified mRNA in vivo that encodes for CRISPR related protein, e.g., dCA9, in a time limited and—potentially cell-type—targeted fashion. Moreover, the use of modified mRNA will avoid the risk of significant innate immune activation, and diminish the risk of adaptive responses.

I. Synthetic Polynucleotides Encoding CRISPR Related Proteins

The present invention provides synthetic polynucleotides which encode one or more CRISPR related proteins, e.g., dCAS9 and dCAS9 fusion proteins. The term "polynucleotide," in its broadest sense, includes any compound and/or substance that comprise a polymer of nucleotides. Exemplary polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

In one embodiment, the synthetic polynucleotide is a synthetic messenger RNA (mRNA). As used herein, the term "messenger RNA" (mRNA) refers to any polynucleotide, which may be synthetic, which encodes a polypeptide, e.g., a CRISPR related protein, and which is capable of being translated to produce the encoded polypeptide in vitro, in vivo, in situ or ex vivo. In the present invention, the mRNA encodes a CRISPR related protein, e.g., dCAS9 and dCA9-effector (activator or inhibitor) fusion proteins. Additional description of and sequences for CRISPR related proteins are below.

The present invention expands the scope of functionality of traditional mRNA molecules by providing synthetic polynucleotides which comprise one or more structural and/or chemical modifications or alterations which impart useful properties to the polynucleotides including, in some embodiments, the lack of a substantial induction of the innate immune response of a cell into which the polynucleotide is introduced. As used herein, a "structural" feature or modification is one in which two or more linked nucleotides are inserted, deleted, duplicated, inverted or randomized in a synthetic polynucleotide, primary construct or mmRNA without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" (SEQ ID NO: 123) may be chemically modified to "AT-5meC-G" (SEQ ID NO: 124). The same polynucleotide may be structurally modified from "ATCG" (SEQ ID NO: 123) to "ATCCCG" (SEQ ID NO: 125). Here, the dinucleotide "CC" has been inserted, resulting in a structural modification to the polynucleotide.

CRISPR Related Proteins

The synthetic polynucleotides of the invention encode a CRISPR related protein. The term "CRISPR related protein"

includes but is not limited to CAS9, CSY4, dCAS9, and dCAS9-effector domain (activator and/or inhibitor domain) fusion proteins. Examples of CRISPR related protein polypeptide sequences and polynucleotide sequences are found in the Tables below.

The CRISPR related protein can be from any number of species including but not limited to *Streptococcus pyogenes, Listeria innocua*, and *Streptococcus thermophilus*.

The synthetic polynucleotide can encode the wild-type sequence of the CRISPR related protein or a variant CRISPR related protein. Variants are described in further details herein. As described in more detail herein, the synthetic polynucleotide can include either the wild-type codon usage or codon usage optimized for a particular application, e.g., human codon optimization for human therapeutics.

According to the present invention, the synthetic polynucleotides comprise at least a first region of linked nucleosides encoding at least one CRISPR related proteins. Example of CRISPR related proteins are listed in the Tables below. For any particular CRISPR related protein there may exist one or more variants or isoforms. It will be appreciated by those of skill in the art that disclosed in the Tables are potential flanking regions. These are encoded in each transcript either to the 5' (upstream) or 3' (downstream) of the ORF or coding region. The coding region is definitively and specifically disclosed by teaching the protein sequence. Consequently, the sequences taught flanking that encoding the protein are considered flanking regions. It is also possible to further characterize the 5' and 3' flanking regions by utilizing one or more available databases or algorithms. Databases have annotated the features contained in the flanking regions of the transcripts and these are available in the art.

In one embodiment the CRISPR related protein is dCAS9. Typical sequences are included in the Tables below.

In another embodiment the CRISPR related protein is a dCAS9-effector domain fusion protein. The effector domain can be an activation domain or an inhibition domain, depending on the application. Examples of effector domains are well known to one of skill in the art and include, e.g., KRAB, CSD, WRPW, VP64, or p65AD.

In some embodiments, the CRISPR related protein is dCAS9-KRAB or dCAS9-VP64 fusion proteins. Examples of sequences are provided in the Tables below and the Sequence Listing.

Further constructs useful in various aspects of the invention include those set forth as SEQ ID NOs: 1-9. These include the nucleotide sequence encoding Cas9, serotype M1 (SEQ ID NO: 1); nucleotide sequence encoding FLAG-tagged (i.e., trimer-FLAG) CAS9 having a nuclear localization sequence (NLS) (SEQ ID NO:2); nucleotide sequence encoding HA-tagged Cas9 having a NLS (Cas9-HAtag/2× NLS) conjugated to GFP (SEQ ID NO:3); nucleotide sequence encoding Cas9 C-terminal fragment having a NLS (SEQ ID NO:4); nucleotide sequence encoding Cas9 N-terminal fragment (SEQ ID NO:5); nucleotide sequence encoding FLAG-tagged Cas9 having NLSs (FLAG-NLS-Cas9-NLS) (SEQ ID NO:6); as well as Cas9 protein sequences (Cas9—SEQ ID NO:8, Cas9 serotype M1—SEQ ID NO:9) and FLAG-tagged (i.e., trimer-FLAG) CAS9 having a nuclear localization sequence (NLS) (SEQ ID NO:9.)

Synthetic Polynucleotide Architecture

The modified synthetic polynucleotides or of the present invention are distinguished from wild type mRNA in their functional and/or structural design features which serve to, as evidenced herein, overcome existing problems of effective polypeptide production using nucleic acid-based therapeutics.

FIG. 1 shows a representative polynucleotide primary construct 100 of the present invention. As used herein, the term "primary construct" or "primary mRNA construct" refers to a polynucleotide transcript which encodes one or more polypeptides of interest and which retains sufficient structural and/or chemical features to allow the polypeptide of interest encoded therein to be translated. Primary constructs may be polynucleotides of the invention. When structurally or chemically modified, the primary construct may be referred to as an modified synthetic polynucleotides or mmRNA.

Returning to FIG. 1, the primary construct 100 here contains a first region of linked nucleotides 102 that is flanked by a first flanking region 104 and a second flanking region 106. As used herein, the "first region" may be referred to as a "coding region" or "region encoding" or simply the "first region." This first region may include, but is not limited to, the encoded polypeptide of interest, i.e., the CRISPR related protein. The polypeptide of interest may comprise at its 5' terminus one or more signal sequences encoded by a signal sequence region 103. The first flanking region 104 may comprise a region of linked nucleotides comprising one or more complete or incomplete 5' UTRs sequences. The first flanking region 104 may also comprise a 5' terminal capping region 108. The second flanking region 106 may comprise a region of linked nucleotides comprising one or more complete or incomplete 3' UTRs. The second flanking region 106 may also comprise a 3' tailing sequence 110.

Bridging the 5' terminus of the first region 102 and the first flanking region 104 is a first operational region 105. Traditionally this first operational region comprises a Start codon. The operational region may alternatively comprise any translation initiation sequence or signal including a Start codon.

Bridging the 3' terminus of the first region 102 and the second flanking region 106 is a second operational region 107. Traditionally this second operational region comprises a Stop codon. The second operational region may alternatively comprise any translation initiation sequence or signal including a Stop codon. According to the present invention, multiple serial stop codons may also be used.

In some embodiments, the synthetic polynucleotide, primary construct, or mmRNA includes from about 30 to about 100,000 nucleotides (e.g., from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 30 to 25,000, from 30 to 50,000, from 30 to 70,000, from 100 to 250, from 100 to 500, from 100 to 1,000, from 100 to 1,500, from 100 to 3,000, from 100 to 5,000, from 100 to 7,000, from 100 to 10,000, from 100 to 25,000, from 100 to 50,000, from 100 to 70,000, from 100 to 100,000, from 500 to 1,000, from 500 to 1,500, from 500 to 2,000, from 500 to 3,000, from 500 to 5,000, from 500 to 7,000, from 500 to 10,000, from 500 to 25,000, from 500 to 50,000, from 500 to 70,000, from 500 to 100,000, from 1,000 to 1,500, from 1,000 to 2,000, from 1,000 to 3,000, from 1,000 to 5,000, from 1,000 to 7,000, from 1,000 to 10,000, from 1,000 to 25,000, from 1,000 to 50,000, from 1,000 to 70,000, from 1,000 to 100,000, from 1,500 to 3,000, from 1,500 to 5,000, from 1,500 to 7,000, from 1,500 to 10,000, from 1,500 to 25,000, from 1,500 to 50,000, from 1,500 to 70,000, from 1,500 to 100,000, from 2,000 to 3,000, from 2,000 to 5,000, from 2,000 to 7,000, from 2,000 to 10,000, from 2,000 to 25,000, from 2,000 to 50,000, from 2,000 to 70,000, and from 2,000 to 100,000).

Generally, the length of the first region encoding the polypeptide of interest, e.g., CRISPR related protein of the present invention is greater than about 30 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000, 4,000, 5,000, 6,000, 7,000, 8,000, 9,000, 10,000, 20,000, 30,000, 40,000, 50,000, 60,000, 70,000, 80,000, 90,000 or up to and including 100,000 nucleotides).

According to the present invention, the first and second flanking regions may range independently from 15-1,000 nucleotides in length (e.g., greater than 30, 40, 45, 50, 55, 60, 70, 80, 90, 100, 120, 140, 160, 180, 200, 250, 300, 350, 400, 450, 500, 600, 700, 800, and 900 nucleotides or at least 30, 40, 45, 50, 55, 60, 70, 80, 90, 100, 120, 140, 160, 180, 200, 250, 300, 350, 400, 450, 500, 600, 700, 800, 900, and 1,000 nucleotides).

According to the present invention, the 3' tailing sequence may range from absent to 500 nucleotides in length (e.g., at least 60, 70, 80, 90, 120, 140, 160, 180, 200, 250, 300, 350, 400, 450, or 500 nucleotides). Where the tailing sequence is a polyA tail, the length may be determined in units of or as a function of polyA Binding Protein binding. In this embodiment, the polyA tail is long enough to bind at least 4 monomers of PolyA Binding Protein. PolyA Binding Protein monomers bind to stretches of approximately 38 nucleotides. As such, it has been observed that polyA tails of about 80 nucleotides and 160 nucleotides are functional.

According to the present invention, the 5' terminal capping region may comprise a single cap or a series of nucleotides forming the cap. In this embodiment the capping region may be from 1 to 10, e.g. 2-9, 3-8, 4-7, 1-5, 5-10, or at least 2, or 10 or fewer nucleotides in length. In some embodiments, the capping region is absent.

According to the present invention, the first and second operational regions may range from 3 to 40, e.g., 5-30, 10-20, 15, or at least 4, or 30 or fewer nucleotides in length and may comprise, in addition to a Start and/or Stop codon, one or more signal and/or restriction sequences.

Cyclic Synthetic Polynucleotides

According to the present invention, a synthetic polynucleotide may be cyclized, or concatemerized, to generate a translation competent molecule to assist interactions between poly-A binding proteins and 5'-end binding proteins. The mechanism of cyclization or concatemerization may occur through at least 3 different routes: 1) chemical, 2) enzymatic, and 3) ribozyme catalyzed. The newly formed 5'-/3'-linkage may be intramolecular or intermolecular.

In the first route, the 5'-end and the 3'-end of the nucleic acid contain chemically reactive groups that, when close together, form a new covalent linkage between the 5'-end and the 3'-end of the molecule. The 5'-end may contain an NHS-ester reactive group and the 3'-end may contain a 3'-amino-terminated nucleotide such that in an organic solvent the 3'-amino-terminated nucleotide on the 3'-end of a synthetic mRNA molecule will undergo a nucleophilic attack on the 5'-NHS-ester moiety forming a new 5'-/3'-amide bond.

In the second route, T4 RNA ligase may be used to enzymatically link a 5'-phosphorylated nucleic acid molecule to the 3'-hydroxyl group of a nucleic acid forming a new phosphorodiester linkage. In an example reaction, 1 μg of a nucleic acid molecule is incubated at 37° C. for 1 hour with 1-10 units of T4 RNA ligase (New England Biolabs, Ipswich, Mass.) according to the manufacturer's protocol. The ligation reaction may occur in the presence of a split oligonucleotide capable of base-pairing with both the 5'- and 3'-region in juxtaposition to assist the enzymatic ligation reaction.

In the third route, either the 5'- or 3'-end of the cDNA template encodes a ligase ribozyme sequence such that during in vitro transcription, the resultant nucleic acid molecule can contain an active ribozyme sequence capable of ligating the 5'-end of a nucleic acid molecule to the 3'-end of a nucleic acid molecule. The ligase ribozyme may be derived from the Group I Intron, Group I Intron, Hepatitis Delta Virus, Hairpin ribozyme or may be selected by SELEX (systematic evolution of ligands by exponential enrichment). The ribozyme ligase reaction may take 1 to 24 hours at temperatures between 0 and 37° C.

Synthetic Polynucleotide Multimers

According to the present invention, multiple distinct synthetic polynucleotides may be linked together through the 3'-end using nucleotides which are modified at the 3'-terminus. Chemical conjugation may be used to control the stoichiometry of delivery into cells. For example, the glyoxylate cycle enzymes, isocitrate lyase and malate synthase, may be supplied into HepG2 cells at a 1:1 ratio to alter cellular fatty acid metabolism. This ratio may be controlled by chemically linking polynucleotides, primary constructs or mmRNA using a 3'-azido terminated nucleotide on one polynucleotide, primary construct or mmRNA species and a C5-ethynyl or alkynyl-containing nucleotide on the opposite polynucleotide, primary construct or mmRNA species. The modified nucleotide is added post-transcriptionally using terminal transferase (New England Biolabs, Ipswich, Mass.) according to the manufacturer's protocol. After the addition of the 3'-modified nucleotide, the two polynucleotide, primary construct or mmRNA species may be combined in an aqueous solution, in the presence or absence of copper, to form a new covalent linkage via a click chemistry mechanism as described in the literature.

In another example, more than two polynucleotides may be linked together using a functionalized linker molecule. For example, a functionalized saccharide molecule may be chemically modified to contain multiple chemical reactive groups (SH—, $NH_2$—, $N_3$, etc . . . ) to react with the cognate moiety on a 3'-functionalized mRNA molecule (i.e., a 3'-maleimide ester, 3'-NHS-ester, alkynyl). The number of reactive groups on the modified saccharide can be controlled in a stoichiometric fashion to directly control the stoichiometric ratio of conjugated polynucleotide, primary construct or mmRNA.

Synthetic Polynucleotide Conjugates and Combinations

In order to further enhance protein production, synthetic polynucleotides of the present invention can be designed to be conjugated to other polynucleotides, dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases, proteins, e.g., glycoproteins, or peptides, e.g., molecules having a specific affinity for a co-ligand, or antibodies e.g., an antibody, that binds to a specified cell type such as a cancer cell, endothelial cell, or bone cell, hormones and hormone receptors, non-peptidic species, such as lipids, lectins, carbohydrates, vitamins, cofactors, or a drug.

Conjugation may result in increased stability and/or half life and may be particularly useful in targeting the polynucleotides, primary constructs or mmRNA to specific sites in the cell, tissue or organism.

According to the present invention, the mmRNA or primary constructs may be administered with, or further encode one or more of RNAi agents, siRNAs, shRNAs, miRNAs, miRNA binding sites, antisense RNAs, ribozymes, catalytic DNA, tRNA, RNAs that induce triple helix formation, aptamers or vectors, and the like.

Bifunctional Synthetic Polynucleotides

In one embodiment of the invention are bifunctional polynucleotides (e.g., bifunctional primary constructs or bifunctional mmRNA). As the name implies, bifunctional polynucleotides are those having or capable of at least two functions. These molecules may also by convention be referred to as multi-functional.

The multiple functionalities of bifunctional polynucleotides may be encoded by the RNA (the function may not manifest until the encoded product is translated) or may be a property of the polynucleotide itself. It may be structural or chemical. Bifunctional modified polynucleotides may comprise a function that is covalently or electrostatically associated with the polynucleotides. Further, the two functions may be provided in the context of a complex of a mmRNA and another molecule.

Bifunctional polynucleotides may encode peptides which are anti-proliferative. These peptides may be linear, cyclic, constrained or random coil. They may function as aptamers, signaling molecules, ligands or mimics or mimetics thereof. Anti-proliferative peptides may, as translated, be from 3 to 50 amino acids in length. They may be 5-40, 10-30, or approximately 15 amino acids long. They may be single chain, multichain or branched and may form complexes, aggregates or any multi-unit structure once translated.

Noncoding Polynucleotides and Primary Constructs

As described herein, provided are polynucleotides and primary constructs having sequences that are partially or substantially not translatable, e.g., having a noncoding region. Such noncoding region may be the "first flanking region" of the primary construct. Alternatively, the noncoding region may be a region other than the first region. Such molecules are generally not translated, but can exert an effect on protein production by one or more of binding to and sequestering one or more translational machinery components such as a ribosomal protein or a transfer RNA (tRNA), thereby effectively reducing protein expression in the cell or modulating one or more pathways or cascades in a cell which in turn alters protein levels. The polynucleotide or primary construct may contain or encode one or more long noncoding RNA (lncRNA, or lincRNA) or portion thereof, a small nucleolar RNA (sno-RNA), micro RNA (miRNA), small interfering RNA (siRNA) or Piwi-interacting RNA (piRNA).

Polypeptide of Interest (CRISPR Related Proteins)

According to the present invention, the synthetic polynucleotide is designed to encode one or more polypeptides of interest or fragments thereof. The polypeptides of interest include CRISPR related proteins, e.g., CAS9, dCAS9, and dCAS9-effector domain (activator and/or inhibitor domain) fusion proteins. CRISPR related proteins are described in more detail herein.

A polypeptide of interest may include, but is not limited to, whole polypeptides, a plurality of polypeptides or fragments of polypeptides, which independently may be encoded by one or more nucleic acids, a plurality of nucleic acids, fragments of nucleic acids or variants of any of the aforementioned. As used herein, the term "polypeptides of interest" refers to any polypeptides which are selected to be encoded in the primary construct of the present invention. As used herein, "polypeptide" means a polymer of amino acid residues (natural or unnatural) linked together most often by peptide bonds. The term, as used herein, refers to proteins, polypeptides, and peptides of any size, structure, or function. In some instances the polypeptide encoded is smaller than about 50 amino acids and the polypeptide is then termed a peptide. If the polypeptide is a peptide, it will be at least about 2, 3, 4, or at least 5 amino acid residues long. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. They may also comprise single chain or multichain polypeptides such as antibodies or insulin and may be associated or linked. Most commonly disulfide linkages are found in multichain polypeptides. The term polypeptide may also apply to amino acid polymers in which one or more amino acid residues are an artificial chemical analogue of a corresponding naturally occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants will possess at least about 50% identity (homology) to a native or reference sequence, and preferably, they will be at least about 80%, more preferably at least about 90% identical (homologous) to a native or reference sequence.

In some embodiments "variant mimics" are provided. As used herein, the term "variant mimic" is one which contains one or more amino acids which would mimic an activated sequence. For example, glutamate may serve as a mimic for phosphoro-threonine and/or phosphoro-serine. Alternatively, variant mimics may result in deactivation or in an inactivated product containing the mimic, e.g., phenylalanine may act as an inactivating substitution for tyrosine; or alanine may act as an inactivating substitution for serine.

"Homology" as it applies to amino acid sequences is defined as the percentage of residues in the candidate amino acid sequence that are identical with the residues in the amino acid sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation.

By "homologs" as it applies to polypeptide sequences means the corresponding sequence of other species having substantial identity to a second sequence of a second species.

"Analogs" is meant to include polypeptide variants which differ by one or more amino acid alterations, e.g., substitutions, additions or deletions of amino acid residues that still maintain one or more of the properties of the parent or starting polypeptide.

The present invention contemplates several types of compositions which are polypeptide based including variants and derivatives. These include substitutional, insertional, deletion and covalent variants and derivatives. The term "derivative" is used synonymously with the term "variant" but generally refers to a molecule that has been modified and/or changed in any way relative to a reference molecule or starting molecule.

As such, mmRNA encoding polypeptides containing substitutions, insertions and/or additions, deletions and covalent modifications with respect to reference sequences, in particular the polypeptide sequences disclosed herein, are included within the scope of this invention. For example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to polypeptides are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to polypeptides are those with one or more amino acids in the native or starting amino acid sequence removed. Ordinarily, deletional variants will have one or more amino acids deleted in a particular region of the molecule.

"Covalent derivatives" when referring to polypeptides include modifications of a native or starting protein with an organic proteinaceous or non-proteinaceous derivatizing agent, and/or post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the polypeptides produced in accordance with the present invention.

Other post-translational modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)).

"Features" when referring to polypeptides are defined as distinct amino acid sequence-based components of a molecule. Features of the polypeptides encoded by the mmRNA of the present invention include surface manifestations, local conformational shape, folds, loops, half-loops, domains, half-domains, sites, termini or any combination thereof.

As used herein when referring to polypeptides the term "surface manifestation" refers to a polypeptide based component of a protein appearing on an outermost surface.

As used herein when referring to polypeptides the term "local conformational shape" means a polypeptide based structural manifestation of a protein which is located within a definable space of the protein.

As used herein when referring to polypeptides the term "fold" refers to the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein the term "turn" as it relates to protein conformation means a bend which alters the direction of the backbone of a peptide or polypeptide and may involve one, two, three or more amino acid residues.

As used herein when referring to polypeptides the term "loop" refers to a structural feature of a polypeptide which may serve to reverse the direction of the backbone of a peptide or polypeptide. Where the loop is found in a polypeptide and only alters the direction of the backbone, it may comprise four or more amino acid residues. Oliva et al. have identified at least 5 classes of protein loops (J. Mol Biol 266 (4): 814-830; 1997). Loops may be open or closed. Closed loops or "cyclic" loops may comprise 2, 3, 4, 5, 6, 7, 8, 9, 10 or more amino acids between the bridging moieties. Such bridging moieties may comprise a cysteine-cysteine bridge (Cys-Cys) typical in polypeptides having disulfide bridges or alternatively bridging moieties may be non-protein based such as the dibromozylyl agents used herein.

As used herein when referring to polypeptides the term "half-loop" refers to a portion of an identified loop having at least half the number of amino acid resides as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the term "half-domain" means a portion of an identified domain having at least half the number of amino acid resides as the domain from which it is derived. It is understood that domains may not always contain an even number of amino acid residues. Therefore, in those cases where a domain contains or is identified to comprise an odd number of amino acids, a half-domain of the odd-numbered domain will comprise the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that subdomains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain).

As used herein when referring to polypeptides the terms "site" as it pertains to amino acid based embodiments is used synonymously with "amino acid residue" and "amino acid side chain." A site represents a position within a peptide or polypeptide that may be modified, manipulated, altered, derivatized or varied within the polypeptide based molecules of the present invention.

As used herein the terms "termini" or "terminus" when referring to polypeptides refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus (terminated by an amino acid with a free amino group (NH2)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Once any of the features have been identified or defined as a desired component of a polypeptide to be encoded by the primary construct or mmRNA of the invention, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full length molecule would.

Modifications and manipulations can be accomplished by methods known in the art such as, but not limited to, site directed mutagenesis. The resulting modified molecules may then be tested for activity using in vitro or in vivo assays such as those described herein or any other suitable screening assay known in the art.

According to the present invention, the polypeptides may comprise a consensus sequence which is discovered through rounds of experimentation. As used herein a "consensus" sequence is a single sequence which represents a collective population of sequences allowing for variability at one or more sites.

As recognized by those skilled in the art, protein fragments, functional protein domains, and homologous proteins are also considered to be within the scope of polypeptides of interest of this invention. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of about 20, about 30, about 40, about 50, or about 100 amino acids which are about 40%, about 50%, about 60%, about 70%, about 80%, about 90%, about 95%, or about 100% identical to any of the sequences described herein can be utilized in accordance with the invention. In certain embodiments, a polypeptide to be utilized in accordance with the invention includes 2, 3, 4, 5, 6, 7, 8, 9, 10, or more mutations as shown in any of the sequences provided or referenced herein.

Variant Polypeptides of Interest

In one embodiment, synthetic polypeptides of the invention may encode variant polypeptides, e.g., variant CRISPR related proteins which have a certain identity with a reference polypeptide sequence. As used herein, a "reference polypeptide sequence" refers to a starting polypeptide sequence. Reference sequences may be wild type sequences or any sequence to which reference is made in the design of another sequence. A "reference polypeptide sequence" may be, e.g., any encoding CAS9, dCAS9, a dCAS9-activator domain fusion protein, a dCAS9-inhibitor domain fusion protein, and/or variants thereof.

The term "identity" as known in the art, refers to a relationship between the sequences of two or more peptides, as determined by comparing the sequences. In the art, identity also means the degree of sequence relatedness between peptides, as determined by the number of matches between strings of two or more amino acid residues. Identity measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

In some embodiments, the polypeptide variant may have the same or a similar activity as the reference polypeptide. Alternatively, the variant may have an altered activity (e.g., increased or decreased) relative to a reference polypeptide. Generally, variants of a particular polynucleotide or polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.) Other tools are described herein, specifically in the definition of "Identity."

Default parameters in the BLAST algorithm include, for example, an expect threshold of 10, Word size of 28, Match/Mismatch Scores 1, -2, Gap costs Linear. Any filter can be applied as well as a selection for species specific repeats, e.g., *Homo sapiens*.

Flanking Regions: Untranslated Regions (UTRs)

As described herein, the synthetic polynucleotides of the invention include untranslated regions. Untranslated regions (UTRs) of a gene are transcribed but not translated. The 5'UTR starts at the transcription start site and continues to the start codon but does not include the start codon; whereas, the 3'UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides, primary constructs and/or mmRNA of the present invention to enhance the stability of the molecule. The specific features can also be incorporated to ensure controlled down-regulation of the transcript in case they are misdirected to undesired organs sites.

Examples of UTRs include but are not limited to those found in the Tables below.

Tables 2 and 3 of co-pending U.S. Provisional Patent Application No. 61/737,130 filed Dec. 14, 2012 provide a listing of exemplary UTRs which may be utilized in the primary construct of the present invention as flanking regions. Variants of 5' or 3'UTRs may be utilized wherein one or more nucleotides are added or removed to the termini, including A, T, C or G.

It should be understood that those listed are examples and that any UTR from any gene may be incorporated into the respective first or second flanking region of the primary construct. Furthermore, multiple wild-type UTRs of any known gene may be utilized. It is also within the scope of the present invention to provide artificial UTRs which are not variants of wild type genes. These UTRs or portions thereof may be placed in the same orientation as in the transcript from which they were selected or may be altered in orientation or location. Hence a 5' or 3' UTR may be inverted, shortened, lengthened, made chimeric with one or more other 5' UTRs or 3' UTRs. As used herein, the term "altered" as it relates to a UTR sequence, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In one embodiment, the UTR may be selected from the UTRs described in Lengthy Table 21 in co-pending US Provisional Application No. U.S. 61/775,509, filed Mar. 9, 2013, entitled Heterologous Untranslated Regions for mRNA and in Lengthy Table 21 and in Table 22 in co-pending US Provisional Application No. U.S. 61/829,372, filed May 31, 2013, entitled Heterologous Untranslated Regions for mRNA; each of which is herein incorporated by reference in its entirety.

In one embodiment, a double, triple or quadruple UTR such as a 5' or 3' UTR may be used. As used herein, a "double" UTR is one in which two copies of the same UTR are encoded either in series or substantially in series. For example, a double beta-globin 3' UTR may be used as described in US Patent publication 20100129877, the contents of which are incorporated herein by reference in its entirety.

It is also within the scope of the present invention to have patterned UTRs. As used herein "patterned UTRs" are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In one embodiment, flanking regions are selected from a family of transcripts whose proteins share a common function, structure, feature of property. For example, polypeptides of interest may belong to a family of proteins which are expressed in a particular cell, tissue or at some time during development. The UTRs from any of these genes may be swapped for any other UTR of the same or different family of proteins to create a new chimeric primary transcript. As used herein, a "family of proteins" is used in the broadest sense to refer to a group of two or more polypeptides of interest which share at least one function, structure, feature, localization, origin, or expression pattern.

In one embodiment, the synthetic polynucleotides of the invention may comprise an untranslated region that is not heterologous to the encoded protein of interest. As a non-limiting example, the untranslated region may comprise all or a portion or fragment thereof of one or more of the untranslated regions described in co-pending US Provisional Application No. U.S. 61/775,509, filed Mar. 9, 2013, entitled Heterologous Untranslated Regions for mRNA and US Provisional Application No. U.S. 61/829,372, filed Mar. 15, 2013, entitled Heterologous Untranslated Regions for mRNA, each of which is herein incorporated by reference in its entirety.

5' UTR and Translation Initiation

The synthetic polynucleotides of the invention typically include a 5' UTR. Natural 5'UTRs bear features which play roles in for translation initiation. They harbor signatures like Kozak sequences which are commonly known to be involved in the process by which the ribosome initiates translation of many genes. Kozak sequences have the consensus CCR(A/G)CCAUGG (SEQ ID NO: 126), where R is a purine (adenine or guanine) three bases upstream of the start codon (AUG), which is followed by another 'G'. 5'UTR also have been known to form secondary structures which are involved in elongation factor binding.

By engineering the features typically found in abundantly expressed genes of specific target organs, one can enhance the stability and protein production of the synthetic polynucleotides, primary constructs or mmRNA of the invention. For example, introduction of 5' UTR of liver-expressed mRNA, such as albumin, serum amyloid A, Apolipoprotein A/B/E, transferrin, alpha fetoprotein, erythropoietin, or Factor VIII, could be used to enhance expression of a nucleic acid molecule, such as a mmRNA, in hepatic cell lines or liver. Likewise, use of 5' UTR from other tissue-specific mRNA to improve expression in that tissue is possible—for muscle (MyoD, Myosin, Myoglobin, Myogenin, Herculin), for endothelial cells (Tie-1, CD36), for myeloid cells (C/EBP, AML, G-CSF, GM-CSF, CD11b, MSR, Fr-1, i-NOS), for leukocytes (CD45, CD18), for adipose tissue (CD36, GLUT4, ACRP30, adiponectin) and for lung epithelial cells (SP-A/B/C/D).

Other non-UTR sequences may be incorporated into the 5' (or 3' UTR) UTRs. For example, introns or portions of introns sequences may be incorporated into the flanking regions of the polynucleotides, primary constructs or mmRNA of the invention. Incorporation of intronic sequences may increase protein production as well as mRNA levels.

The 5'UTR may selected for use in the present invention may be a structured UTR such as, but not limited to, 5'UTRs to control translation. As a non-limiting example, a structured 5'UTR may be beneficial when using any of the terminal modifications described in copending U.S. Provisional Application No. 61/758,921 filed Jan. 31, 2013, entitled Differential Targeting Using RNA Constructs; U.S. Provisional Application No. 61/781,139 filed Mar. 14, 2013, entitled Differential Targeting Using RNA Constructs; U.S. Provisional Application No. 61/729,933, filed Nov. 26, 2012 entitled Terminally Optimized RNAs; U.S. Provisional Application No. 61/737,224 filed Dec. 14, 2012 entitled Terminally Optimized RNAs and U.S. Provisional Application No. 61/829,359 filed May 31, 2013 entitled Terminally Optimized RNAs, each of which is herein incorporated by reference in their entirety.

3' UTR and the AU Rich Elements

The synthetic polynucleotides of the invention typically include a 3' UTR. 3'UTRs are known to have stretches of Adenosines and Uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) nonamers. Molecules containing this type of AREs include GM-CSF and TNF-a. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of polynucleotides, primary constructs or mmRNA of the invention. When engineering specific polynucleotides, primary constructs or mmRNA, one or more copies of an ARE can be introduced to make polynucleotides, primary constructs or mmRNA of the invention less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using polynucleotides, primary constructs or mmRNA of the invention and protein production can be assayed at various time points post-transfection. For example, cells can be transfected with different ARE-engineering molecules and by using an ELISA kit to the relevant protein and assaying protein produced at 6 hr, 12 hr, 24 hr, 48 hr, and 7 days post-transfection.

3' UTR and microRNA Binding Sites

In some embodiments, the synthetic polynucleotides of the invention include a miRNA binding site in the 3'UTR. A microRNA (or miRNA) is a 19-25 nucleotide long noncoding RNA that binds to the 3'UTR of nucleic acid molecules and down-regulate gene expression either by reducing nucleic acid molecule stability or by inhibiting translation. The polynucleotides, primary constructs or mmRNA of the invention may comprise one or more microRNA target sequences, microRNA sequences, microRNA binding sites, or microRNA seeds. Such sequences may correspond to any known microRNA such as those taught in US Publication US2005/0261218 and US Publication US2005/0059005, or those listed in Table 7 of co-pending application U.S. Ser. No. 61/758,921 filed Jan. 31, 2013, the contents of which are incorporated herein by reference in their entirety.

Examples of 3'UTRs containing miRNA binding sites include but are not limited to those found in the Tables below.

A microRNA sequence comprises a "seed" region, i.e., a sequence in the region of positions 2-8 of the mature microRNA, which sequence has perfect Watson-Crick complementarity to the miRNA target sequence. A microRNA seed may comprise positions 2-8 or 2-7 of the mature microRNA. In some embodiments, a microRNA seed may comprise 7 nucleotides (e.g., nucleotides 2-8 of the mature microRNA), wherein the seed-complementary site in the corresponding miRNA target is flanked by an adenine (A) opposed to microRNA position 1. In some embodiments, a microRNA seed may comprise 6 nucleotides (e.g., nucleotides 2-7 of the mature microRNA), wherein the seed-complementary site in the corresponding miRNA target is flanked by an adenine (A) opposed to microRNA position 1. See for example, Grimson A, Farh K K, Johnston W K, Garrett-Engele P, Lim L P, Bartel D P; Mol Cell. 2007 Jul. 6; 27(1):91-105. The bases of the microRNA seed have complete complementarity with the target sequence. By engineering microRNA target sequences into the 3'UTR of polynucleotides, primary constructs or mmRNA of the invention one can target the molecule for degradation or reduced translation, provided the microRNA in question is available. This process will reduce the hazard of off target effects upon nucleic acid molecule delivery. Identification of microRNA, microRNA target regions, and their expression patterns and role in biology have been reported (Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414).

For example, if the nucleic acid molecule is an mRNA and is not intended to be delivered to the liver but ends up there, then miR-122, a microRNA abundant in liver, can inhibit the expression of the gene of interest if one or multiple target sites of miR-122 are engineered into the 3'UTR of the polynucleotides, primary constructs or mmRNA. Introduction of one or multiple binding sites for different microRNA can be engineered to further decrease the longevity, stability, and protein translation of a polynucleotides, primary constructs or mmRNA.

As used herein, the term "microRNA site" refers to a microRNA target site or a microRNA recognition site, or any nucleotide sequence to which a microRNA binds or associates. It should be understood that "binding" may follow traditional Watson-Crick hybridization rules or may reflect any stable association of the microRNA with the target sequence at or adjacent to the microRNA site.

Conversely, for the purposes of the polynucleotides, primary constructs or mmRNA of the present invention, microRNA binding sites can be engineered out of (i.e. removed from) sequences in which they naturally occur in order to increase protein expression in specific tissues. For example, miR-122 binding sites may be removed to improve protein expression in the liver. Regulation of expression in multiple tissues can be accomplished through introduction or removal or one or several microRNA binding sites.

Examples of tissues where microRNA are known to regulate mRNA, and thereby protein expression, include, but are not limited to, liver (miR-122), muscle (miR-133, miR-206, miR-208), endothelial cells (miR-17-92, miR-126), nervous system (mir-124a, miR-9), pluripotent cells (miR-302, miR-367, miR-290, miR-371, miR-373), pancreatic islet cells (miR-375), myeloid cells (miR-142-3p, miR-142-5p, miR-16, miR-21, miR-223, miR-24, miR-27), adipose tissue (let-7, miR-30c), heart (miR-id, miR-149), kidney (miR-192, miR-194, miR-204), and lung epithelial cells (let-7, miR-133, miR-126).

MicroRNA can also regulate complex biological processes such as angiogenesis (miR-132) (Anand and Cheresh Curr Opin Hematol 2011 18:171-176). In the polynucleotides, primary constructs or mmRNA of the invention, binding sites for microRNAs that are involved in such processes may be removed or introduced, in order to tailor the expression of the polynucleotides, primary constructs or mmRNA expression to biologically relevant cell types or to the context of relevant biological processes.

MicroRNAs are also known to be expressed in the immune cells (also called hematopoietic cells), for example, the antigen presenting cells (e.g. dendritic cells and macrophage). Immune cell specific microRNAs are involved in immunogenicity, autoimmunity, the immune-response to infection, inflammation, as well as unwanted immune response after gene therapy and tissue/organ transplantation. For example, miR-142 and miR-146 are exclusively expressed in the immune cells, particularly abundant in myeloid dendritic cells. Introducing the miR-142 binding site into the 3'-UTR of a polynucleotide or a gene delivery construct can selectively suppress the gene expression in the antigen presenting cells through miR-142 mediated mRNA degradation, limiting antigen presentation in professional APCs (e.g. dendritic cells) and thereby preventing antigen-mediated immune response after gene delivery (see, Annoni A et al., blood, 2009, 114, 5152-5161, the content of which is herein incorporated by reference in its entirety.). In the polynucleotides, primary constructs or mmRNA of the present invention, binding sites for microRNAs that are involved in such processes may be introduced, in order to reduce the expression of the polynucleotides, primary constructs or mmRNA of the present invention in APCs and to subdue the antigen mediated immune response.

Lastly, through an understanding of the expression patterns of microRNA in different cell types, polynucleotides, primary constructs or mmRNA can be engineered for more targeted expression in specific cell types or only under specific biological conditions. Through introduction of tissue-specific microRNA binding sites, polynucleotides, primary constructs or mmRNA could be designed that would be optimal for protein expression in a tissue or in the context of a biological condition.

Transfection experiments can be conducted in relevant cell lines, using engineered polynucleotides, primary constructs or mmRNA and protein production can be assayed at various time points post-transfection. For example, cells can be transfected with different microRNA binding site-engineering polynucleotides, primary constructs or mmRNA and by using an ELISA kit to the relevant protein and assaying protein produced at 6 hr, 12 hr, 24 hr, 48 hr, 72 hr and 7 days post-transfection. In vivo experiments can also be conducted using microRNA-binding site-engineered molecules to examine changes in tissue-specific expression of formulated polynucleotides, primary constructs or mmRNA.

Viral Sequences

Additional viral sequences such as, but not limited to, the translation enhancer sequence of the barley yellow dwarf virus (BYDV-PAV) can be engineered and inserted in the 3' UTR of the synthetic polynucleotides, polynucleotides, primary constructs or mmRNA of the invention and can stimulate the translation of the construct in vitro and in vivo. Transfection experiments can be conducted in relevant cell lines at and protein production can be assayed by ELISA at 12 hr, 24 hr, 48 hr, 72 hr and day 7 post-transfection.

5' Capping

The synthetic polynucleotides of the invention can include a 5' capping region or 5' cap. The 5' cap structure of an mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns removal during mRNA splicing.

Endogenous mRNA molecules may be 5'-end capped generating a 5'-ppp-5'-triphosphate linkage between a terminal guanosine cap residue and the 5'-terminal transcribed sense nucleotide of the mRNA molecule. This 5'-guanylate cap may then be methylated to generate an N7-methyl-guanylate residue. The ribose sugars of the terminal and/or anteterminal transcribed nucleotides of the 5' end of the mRNA may optionally also be 2'-O-methylated. 5'-decapping through hydrolysis and cleavage of the guanylate cap structure may target a nucleic acid molecule, such as an mRNA molecule, for degradation.

Modifications to the polynucleotides, primary constructs, and mmRNA of the present invention may generate a non-hydrolyzable cap structure preventing decapping and thus increasing mRNA half-life. Because cap structure hydrolysis requires cleavage of 5'-ppp-5' phosphorodiester linkages, modified nucleotides may be used during the capping reaction. For example, a Vaccinia Capping Enzyme from New England Biolabs (Ipswich, Mass.) may be used with α-thio-guanosine nucleotides according to the manufacturer's instructions to create a phosphorothioate linkage in the 5'-ppp-5' cap. Additional modified guanosine nucleotides may be used such as α-methyl-phosphonate and seleno-phosphate nucleotides.

Additional modifications include, but are not limited to, 2'-O-methylation of the ribose sugars of 5'-terminal and/or 5'-anteterminal nucleotides of the mRNA (as mentioned above) on the 2'-hydroxyl group of the sugar ring. Multiple distinct 5'-cap structures can be used to generate the 5'-cap of a nucleic acid molecule, such as an mRNA molecule.

Cap analogs, which herein are also referred to as synthetic cap analogs, chemical caps, chemical cap analogs, or structural or functional cap analogs, differ from natural (i.e. endogenous, wild-type or physiological) 5'-caps in their chemical structure, while retaining cap function. Cap analogs may be chemically (i.e. non-enzymatically) or enzymatically synthesized and/linked to a nucleic acid molecule.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine (m$^7$G-3'mppp-G; which may equivalently be designated 3' O-Me-m7G(5')ppp(5')G). The 3'-O atom of the other, unmodified, guanine becomes linked to the 5'-terminal nucleotide of the capped nucleic acid molecule (e.g. an mRNA or mmRNA). The N7- and 3'-O-methlyated guanine provides the terminal moiety of the capped nucleic acid molecule (e.g. mRNA or mmRNA).

Another exemplary cap is mCAP, which is similar to ARCA but has a 2'-O-methyl group on guanosine (i.e., N7,2'-O-dimethyl-guanosine-5'-triphosphate-5'-guanosine, m$^7$Gm-ppp-G).

While cap analogs allow for the concomitant capping of a nucleic acid molecule in an in vitro transcription reaction, up to 20% of transcripts remain uncapped. This, as well as the structural differences of a cap analog from an endogenous 5'-cap structures of nucleic acids produced by the endogenous, cellular transcription machinery, may lead to reduced translational competency and reduced cellular stability.

Polynucleotides, primary constructs and mmRNA of the invention may also be capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present invention are those which, among other things, have enhanced binding of cap binding proteins, increased half life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of an mRNA and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include 7mG(5')ppp(5')N,pN2p (cap 0), 7mG(5')ppp(5')N1mpNp (cap 1), and 7mG(5')-ppp(5')N1mpN2mp (cap 2).

Because the polynucleotides, primary constructs or mmRNA may be capped post-transcriptionally, and because this process is more efficient, nearly 100% of the polynucleotides, primary constructs or mmRNA may be capped. This is in contrast to ~80% when a cap analog is linked to an mRNA in the course of an in vitro transcription reaction.

According to the present invention, 5' terminal caps may include endogenous caps or cap analogs. According to the present invention, a 5' terminal cap may comprise a guanine analog. Useful guanine analogs include inosine, N1-methyl-guanosine, 2'fluoro-guanosine, 7-deaza-guanosine, 8-oxo-guanosine, 2-amino-guanosine, LNA-guanosine, and 2-azido-guanosine.

IRES Sequences

Further, provided are synthetic polynucleotides, primary constructs or mmRNA which may contain an internal ribosome entry site (IRES). First identified as a feature Picorna virus RNA, IRES plays an important role in initiating protein synthesis in absence of the 5' cap structure. An IRES may act as the sole ribosome binding site, or may serve as one of multiple ribosome binding sites of an mRNA. Synthetic polynucleotides, primary constructs or mmRNA containing more than one functional ribosome binding site may encode several peptides or polypeptides that are translated independently by the ribosomes ("multicistronic nucleic acid molecules"). When polynucleotides, primary constructs or mmRNA are provided with an IRES, further optionally provided is a second translatable region. Examples of IRES sequences that can be used according to the invention include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

Stop Codons

In one embodiment, the primary constructs of the present invention may include at least two stop codons before the 3' untranslated region (UTR). The stop codon may be selected from TGA, TAA and TAG. In one embodiment, the primary constructs of the present invention include the stop codon TGA and one additional stop codon. In a further embodiment the addition stop codon may be TAA.

In another embodiment, the primary constructs of the present invention may include three stop codons before the 3' untranslated region (UTR).

Signal Sequences

The primary constructs or mmRNA may also encode additional features which facilitate trafficking of the polypeptides to therapeutically relevant sites. One such feature which aids in protein trafficking is the signal sequence. As used herein, a "signal sequence" or "signal peptide" is a polynucleotide or polypeptide, respectively, which is from about 9 to 200 nucleotides (3-60 amino acids) in length which is incorporated at the 5' (or N-terminus) of the coding region or polypeptide encoded, respectively. Addition of these sequences result in trafficking of the encoded polypeptide to the endoplasmic reticulum through one or more secretory pathways. Some signal peptides are cleaved from the protein by signal peptidase after the proteins are transported.

Signal sequences may be selected from any of those listed in co-pending patent applications: U.S. Provisional Patent Application No. 61/618,862, filed Apr. 2, 2012, entitled Modified Polynucleotides for the Production of Biologics; U.S. Provisional Patent Application No. 61/681,645, filed Aug. 10, 2012, entitled Modified Polynucleotides for the Production of Biologics; U.S. Provisional Patent Application No. 61/737,130, filed Dec. 14, 2012, entitled Modified Polynucleotides for the Production of Biologics; U.S. Provisional Patent Application No. 61/618,866, filed Apr. 2, 2012, entitled Modified Polynucleotides for the Production of Antibodies; U.S. Provisional Patent Application No. 61/681,647, filed Aug. 10, 2012, entitled Modified Polynucleotides for the Production of Antibodies; U.S. Provisional Patent Application No. 61/737,134, filed Dec. 14, 2012, entitled Modified Polynucleotides for the Production of Antibodies; U.S. Provisional Patent Application No. 61/618,868, filed Apr. 2, 2012, entitled Modified Polynucleotides for the Production of Vaccines; U.S. Provisional Patent Application No. 61/681,648, filed Aug. 10, 2012, entitled Modified Polynucleotides for the Production of Vaccines; U.S. Provisional Patent Application No. 61/737,135, filed Dec. 14, 2012, entitled Modified Polynucleotides for the Production of Vaccines; U.S. Provisional Patent Application No. 61/618,870, filed Apr. 2, 2012, entitled Modified Polynucleotides for the Production of Therapeutic Proteins and Peptides; U.S. Provisional Patent Application No. 61/681,649, filed Aug. 10, 2012, entitled Modified Polynucleotides for the Production of Therapeutic Proteins and Peptides; U.S. Provisional Patent Application No. 61/737,139, filed Dec. 14, 2012, Modified Polynucleotides for the Production of Therapeutic Proteins and Peptides; U.S. Provisional Patent Application No. 61/618,873, filed Apr. 2, 2012, entitled Modified Polynucleotides for the Production of Secreted Proteins; U.S. Provisional Patent Application No. 61/681,650, filed Aug. 10, 2012, entitled Modified Polynucleotides for the Production of Secreted Proteins; U.S. Provisional Patent Application No. 61/737,147, filed Dec. 14, 2012, entitled Modified Polynucleotides for the Production of Secreted Proteins; U.S. Provisional Patent Application No. 61/618,878, filed Apr. 2, 2012, entitled Modified Polynucleotides for the Production of Plasma Membrane Proteins; U.S. Provisional Patent Application No. 61/681,654, filed Aug. 10, 2012, entitled Modified Polynucleotides for the Production of Plasma Membrane Proteins; U.S. Provisional Patent Application No. 61/737,152, filed Dec. 14, 2012, entitled Modified Polynucleotides for the Production of Plasma Membrane Proteins; U.S. Provisional Patent Application No. 61/618,885, filed Apr. 2, 2012, entitled Modified Polynucleotides for the Production of Cytoplasmic and Cytoskeletal Proteins; U.S. Provisional Patent Application No. 61/681,658, filed Aug. 10, 2012, entitled Modified Polynucleotides for the Production of Cytoplasmic and Cytoskeletal Proteins; U.S. Provisional Patent Application No. 61/737,155, filed Dec. 14, 2012, entitled Modified Polynucleotides for the Production of Cytoplasmic and Cytoskeletal Proteins; U.S. Provisional Patent Application No. 61/618,896, filed Apr. 2, 2012, entitled Modified Polynucleotides for the Production of Intracellular Membrane Bound Proteins; U.S. Provisional Patent Application No. 61/668,157, filed Jul. 5, 2012, entitled Modified Polynucleotides for the Production of Intracellular Membrane Bound Proteins; U.S. Provisional Patent Application No. 61/681,661, filed Aug. 10, 2012, entitled Modified Polynucleotides for the Production of Intracellular Membrane Bound Proteins; U.S. Provisional Patent Application No. 61/737,160, filed Dec. 14, 2012, entitled Modified Polynucleotides for the Production of Intracellular Membrane Bound Proteins; U.S. Provisional Patent Application No. 61/618,911, filed Apr. 2, 2012, entitled Modified Polynucleotides for the Production of Nuclear Proteins; U.S. Provisional Patent Application No. 61/681,667, filed Aug. 10, 2012, entitled Modified Polynucleotides for the Production of Nuclear Proteins; U.S. Provisional Patent Application No. 61/737,168, filed Dec. 14, 2012, entitled Modified Polynucleotides for the Production of Nuclear Proteins; U.S. Provisional Patent Application No. 61/618,922, filed Apr. 2, 2012, entitled Modified Polynucleotides for the Production of Proteins; U.S. Provisional Patent Application No. 61/681,675, filed Aug. 10, 2012, entitled Modified Polynucleotides for the Production of Proteins; U.S. Provisional Patent Application No. 61/737,174, filed Dec. 14, 2012, entitled Modified Polynucleotides for the Production of Proteins; U.S. Provisional Patent Application No. 61/618,935, filed Apr. 2, 2012, entitled Modified Polynucleotides for the Production of Proteins Associated with Human Disease; U.S. Provisional Patent Application No. 61/681,687, filed Aug. 10, 2012, entitled Modified Polynucleotides for the Production of Proteins Associated with Human Disease; U.S. Provisional Patent Application No. 61/737,184, filed Dec. 14, 2012, entitled Modified Polynucleotides for the Production of Proteins Associated with Human Disease; U.S. Provisional Patent Application No. 61/618,945, filed Apr. 2, 2012, entitled Modified Polynucleotides for the Production of Proteins Associated with Human Disease; U.S. Provisional Patent Application No. 61/681,696, filed Aug. 10, 2012, entitled Modified Polynucleotides for the Production of Proteins Associated with Human Disease; U.S. Provisional Patent Application No. 61/737,191, filed Dec. 14, 2012, entitled Modified Polynucleotides for the Production of Proteins Associated with Human Disease; U.S. Provisional Patent Application No. 61/618,953, filed Apr. 2, 2012, entitled Modified Polynucleotides for the Production of Proteins Associated with Human Disease; U.S. Provisional Patent Application No. 61/681,704, filed Aug. 10, 2012, entitled Modified Polynucleotides for the Production of Proteins Associated with Human Disease; U.S. Provisional Patent Application No. 61/737,203, filed Dec. 14, 2012, entitled Modified Polynucleotides for the Production of Proteins Associated with Human Disease, International Application No PCT/US2013/030062, filed Mar. 9, 2013, entitled Modified Polynucleotides for the Production of Biologics and Proteins Associated with Human Disease; International Application No PCT/US2013/030063, filed Mar. 9, 2013, entitled Modified Polynucleotides; International Application No. PCT/US2013/030064, entitled Modified Polynucleotides for the Production of Secreted Proteins; International Application No PCT/US2013/030059, filed Mar. 9, 2013, entitled Modified Polynucleotides for the Production of Membrane Proteins; International Application No. PCT/US2013/030066, filed Mar. 9, 2013, entitled Modified Polynucleotides for the Production of Cytoplasmic and Cytoskeletal Proteins; International Application No. PCT/US2013/030067, filed Mar. 9, 2013, entitled Modified Polynucleotides for the Production of Nuclear Proteins; International Application No. PCT/US2013/030060, filed Mar. 9, 2013, entitled Modified Polynucleotides for the Production of Proteins; International Application No. PCT/US2013/030061, filed Mar. 9, 2013, entitled Modified Polynucleotides for the Production of Proteins Associated with Human Disease; International Application No. PCT/US2013/030068, filed Mar. 9, 2013, entitled Modified Polynucleotides for the Production of Cosmetic Proteins and Peptides; and International Application No. PCT/US2013/030070, filed Mar. 9, 2013, entitled Modified Polynucleotides for the Production of Oncology-Related Proteins and Peptides; International Patent Application No. PCT/US2013/031821, filed Mar. 15, 2013, entitled In Vivo Production of Proteins, the contents of which are incorporated herein by reference. Protein signal sequences which may be incorporated for encoding by the polynucleotides, primary constructs or mmRNA of the invention include signal sequences from α-1-antitrypsin, G-CSF, Factor IX, Prolactin, Albumin, HMMSP38, ornithine carbamoyltransferase, Cytochrome C Oxidase subunit 8A, Type III, bacterial, viral, secretion signals, Vrg-6, PhoA, OmpA, STI, STII, Amylase, Alpha Factor, Endoglucanase V, Secretion signal, fungal, fibronectin and interleukins (e.g., IL12).

In the table of the co-pending patent applications, SS is secretion signal and MLS is mitochondrial leader signal. The primary constructs or mmRNA of the present invention may be designed to encode any of the signal sequences or fragments or variants thereof. These sequences may be included at the beginning of the polypeptide coding region, in the middle or at the terminus or alternatively into a flanking region.

Additional signal sequences which may be utilized in the present invention include those taught in, for example, databases such as those found at www.signalpeptide.de/ or proline.bic.nus.edu.sg/spdb/. Those described in U.S. Pat. Nos. 8,124,379; 7,413,875 and 7,385,034 are also within the scope of the invention, and the contents of each are incorporated herein by reference in their entirety.

Protein Cleavage Signals and Sites

In one embodiment, the polypeptides of the present invention may include at least one protein cleavage signal containing at least one protein cleavage site. The protein cleavage site may be located at the N-terminus, the C-terminus, at any space between the N- and the C-termini such as, but not limited to, half-way between the N- and C-termini, between the N-terminus and the half way point, between the half way point and the C-terminus, and combinations thereof.

The polypeptides of the present invention may include, but is not limited to, a proprotein convertase (or prohormone convertase), thrombin or Factor Xa protein cleavage signal. Proprotein convertases are a family of nine proteinases, comprising seven basic amino acid-specific subtilisin-like serine proteinases related to yeast kexin, known as prohormone convertase 1/3 (PC1/3), PC2, furin, PC4, PC5/6, paired basic amino-acid cleaving enzyme 4 (PACE4) and PC7, and two other subtilases that cleave at non-basic residues, called subtilisin kexin isozyme 1 (SKI-1) and proproteinconvertase subtilisin kexin 9 (PCSK9).

In one embodiment, the primary constructs and mmRNA of the present invention may be engineered such that the primary construct or mmRNA contains at least one encoded protein cleavage signal. The encoded protein cleavage signal may be located before the start codon, after the start codon, before the coding region, within the coding region such as, but not limited to, half way in the coding region, between the start codon and the half way point, between the half way point and the stop codon, after the coding region, before the stop codon, between two stop codons, after the stop codon and combinations thereof.

In one embodiment, the primary constructs or mmRNA of the present invention may include at least one encoded protein cleavage signal containing at least one protein cleavage site. The encoded protein cleavage signal may include, but is not limited to, a proprotein convertase (or prohormone convertase), thrombin and/or Factor Xa protein cleavage signal. One of skill in the art may use Table 1 below or other known methods to determine the appropriate encoded protein cleavage signal to include in the primary constructs or mmRNA of the present invention. For example, starting with a signal sequence and considering the codons of Table 1 one can design a signal for the primary construct which can produce a protein signal in the resulting polypeptide.

In one embodiment, the polypeptides of the present invention include at least one protein cleavage signal and/or site.

As a non-limiting example, U.S. Pat. No. 7,374,930 and U.S. Pub. No. 20090227660, herein incorporated by reference in their entireties, use a furin cleavage site to cleave the N-terminal methionine of GLP-1 in the expression product from the Golgi apparatus of the cells. In one embodiment, the polypeptides of the present invention include at least one protein cleavage signal and/or site with the proviso that the polypeptide is not GLP-1.

In one embodiment, the primary constructs or mmRNA of the present invention includes at least one encoded protein cleavage signal and/or site.

In one embodiment, the primary constructs or mmRNA of the present invention includes at least one encoded protein cleavage signal and/or site with the proviso that the primary construct or mmRNA does not encode GLP-1.

In one embodiment, the primary constructs or mmRNA of the present invention may include more than one coding region. Where multiple coding regions are present in the primary construct or mmRNA of the present invention, the multiple coding regions may be separated by encoded protein cleavage sites. As a non-limiting example, the primary construct or mmRNA may be signed in an ordered pattern. On such pattern follows AXBY form where A and B are coding regions which may be the same or different coding regions and/or may encode the same or different polypeptides, and X and Y are encoded protein cleavage signals which may encode the same or different protein cleavage signals. A second such pattern follows the form AXYBZ where A and B are coding regions which may be the same or different coding regions and/or may encode the same or different polypeptides, and X, Y and Z are encoded protein cleavage signals which may encode the same or different protein cleavage signals. A third pattern follows the form ABXCY where A, B and C are coding regions which may be the same or different coding regions and/or may encode the same or different polypeptides, and X and Y are encoded protein cleavage signals which may encode the same or different protein cleavage signals.

In one embodiment, the polypeptides, primary constructs and mmRNA can also contain sequences that encode protein cleavage sites so that the polypeptides, primary constructs and mmRNA can be released from a carrier region or a fusion partner by treatment with a specific protease for said protein cleavage site.

Poly-A Tails

The synthetic polynucleotides of the invention typically include a 3' tailing sequences, e.g., a poly-A tail. During RNA processing, a long chain of adenine nucleotides (poly-A tail) may be added to a polynucleotide such as an mRNA molecules in order to increase stability. Immediately after transcription, the 3' end of the transcript may be cleaved to free a 3' hydroxyl. Then poly-A polymerase adds a chain of adenine nucleotides to the RNA. The process, called polyadenylation, adds a poly-A tail that can be between 100 and 250 residues long.

It has been discovered that unique poly-A tail lengths provide certain advantages to the polynucleotides, primary constructs or mmRNA of the present invention.

Generally, the length of a poly-A tail of the present invention is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides). In some embodiments, the polynucleotide, primary construct, or mmRNA includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In one embodiment, the poly-A tail is designed relative to the length of the overall polynucleotides, primary constructs or mmRNA. This design may be based on the length of the coding region, the length of a particular feature or region (such as the first or flanking regions), or based on the length of the ultimate product expressed from the polynucleotides, primary constructs or mmRNA.

In this context the poly-A tail may be 10, 20, 30, 40, 50, 60, 70, 80, 90, or 100% greater in length than the polynucleotides, primary constructs or mmRNA or feature thereof. The poly-A tail may also be designed as a fraction of polynucleotides, primary constructs or mmRNA to which it belongs. In this context, the poly-A tail may be 10, 20, 30, 40, 50, 60, 70, 80, or 90% or more of the total length of the construct or the total length of the construct minus the poly-A tail. Further, engineered binding sites and conjugation of polynucleotides, primary constructs or mmRNA for Poly-A binding protein may enhance expression.

Additionally, multiple distinct polynucleotides, primary constructs or mmRNA may be linked together to the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In one embodiment, the polynucleotide primary constructs of the present invention are designed to include a polyA-G Quartet. The G-quartet is a cyclic hydrogen bonded array of four guanine nucleotides that can be formed by G-rich sequences in both DNA and RNA. In this embodiment, the G-quartet is incorporated at the end of the poly-A tail. The resultant mmRNA construct is assayed for stability, protein production and other parameters including half-life at various time points. It has been discovered that the polyA-G quartet results in protein production equivalent to at least 75% of that seen using a poly-A tail of 120 nucleotides alone.

II. Synthetic Small Guide RNAs (sgRNA)

The invention also includes synthetic small guide RNAs or sgRNAs. A synthetic sgRNA targets a gene of interest, e.g., a gene where modulation of transcription is desired. A synthetic sgRNA includes a sequence, typically 20-25 nucleotides long, that is complementary to one strand of the 5'UTR of the gene of interest upstream of the transcription start site. The synthetic sgRNA also includes a guide scaffold sequence. A typical guide scaffold sequence is as follows:

```
                                    (SEQ ID NO: 100)
GTTTTAGAGCTAGAAATAGCAAGTTAAAATAAGGCTAGTCC

GTTATCAACTTGAAAAAGTGGCACCGAGTCGGTGGTGC
```

A description of sgRNA design can be found at, e.g., Mali et al. Science. 2013. 339:823-826.

Examples of sgRNA sequences can be found in the Tables below.

Genes of Interest

The sgRNA target a gene of interest, directing the CRISPR related protein encoded by the synthetic polynucleotide to interact with the gene of interest. The gene of interest is selected depending on the application. Examples genes of interest include VEGF, TPO, and/or genes apoptosis or senescence genes.

III. Design and Synthesis of Synthetic Polynucleotides and sgRNAs

Synthetic polynucleotides and sgRNAs of the invention may be prepared according to any available technique including, but not limited to chemical synthesis; enzymatic synthesis, which is generally termed in vitro transcription (IVT); or enzymatic or chemical cleavage of a longer precursor, etc. Methods of synthesizing RNAs are known in the art (see, e.g., Gait, M. J. (ed.) *Oligonucleotide synthesis: a practical approach*, Oxford [Oxfordshire], Washington, D.C.: IRL Press, 1984; and Herdewijn, P. (ed.) *Oligonucleotide synthesis: methods and applications*, Methods in Molecular Biology, v. 288 (Clifton, N.J.) Totowa, N.J.: Humana Press, 2005; both of which are incorporated herein by reference).

The process of design and synthesis of the primary constructs, e.g. synthetic polynucleotides encoding a CRISPR related protein or synthetic sgRNA, of the invention generally includes the steps of gene construction, synthetic mRNA production (either with or without modifications) and purification. In the enzymatic synthesis method, a polynucleotide sequence encoding the CRISPR related protein or sgRNA is first selected for incorporation into a vector which will be amplified to produce a cDNA template. Optionally, the CRISPR related protein polynucleotide sequence and/or any flanking sequences may be codon optimized. The cDNA template is then used to produce mRNA or sgRNA through in vitro transcription (IVT). After production, the mRNA or sgRNA may undergo purification and clean-up processes. The steps of which are provided in more detail below.

Gene Construction of the Synthetic Polynucleotide Encoding a CRISPR Related Protein The step of gene construction may include, but is not limited to gene synthesis, vector amplification, plasmid purification, plasmid linearization and clean-up, and cDNA template synthesis and clean-up.

Once a polypeptide of interest, e.g., a CRISPR related protein, e.g., dCAS9 or a dCAS9-effector domain fusion protein, is selected for production, a primary construct is designed. Within the primary construct, a first region of linked nucleosides encoding the polypeptide of interest may be constructed using an open reading frame (ORF) of a selected nucleic acid (DNA or RNA) transcript. The ORF may comprise the wild type ORF, an isoform, variant or a fragment thereof. As used herein, an "open reading frame" or "ORF" is meant to refer to a nucleic acid sequence (DNA or RNA) which is capable of encoding a polypeptide of interest. ORFs often begin with the start codon, ATG and end with a nonsense or termination codon or signal.

Further, the nucleotide sequence of the first region may be codon optimized. Codon optimization methods are known in the art and may be useful in efforts to achieve one or more of several goals. These goals include to match codon frequencies in target and host organisms to ensure proper folding, bias GC content to increase mRNA stability or reduce secondary structures, minimize tandem repeat codons or base runs that may impair gene construction or expression, customize transcriptional and translational control regions, insert or remove protein trafficking sequences, remove/add post translation modification sites in encoded protein (e.g. glycosylation sites), add, remove or shuffle protein domains, insert or delete restriction sites, modify ribosome binding sites and mRNA degradation sites, to adjust translational rates to allow the various domains of the protein to fold properly, or to reduce or eliminate problem secondary structures within the mRNA. Codon optimization tools, algorithms and services are known in the art, non-limiting examples include services from GeneArt (Life Technologies) and/or DNA2.0 (Menlo Park Calif.). In one embodiment, the ORF sequence is optimized using optimization algorithms. Codon options for each amino acid are given in Table 1.

TABLE 1

Codon Options

| Amino Acid | Single Letter Code | Codon Options |
|---|---|---|
| Isoleucine | I | ATT, ATC, ATA |
| Leucine | L | CTT, CTC, CTA, CTG, TTA, TTG |
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |
| Selenocysteine | Sec | UGA in mRNA in presence of Selenocystein insertion element (SECIS) |
| Stop codons | Stop | TAA, TAG, TGA |

After a sequence has been codon optimized it may be further evaluated for regions containing restriction sites. At least one nucleotide within the restriction site regions may be replaced with another nucleotide in order to remove the restriction site from the sequence but the replacement of nucleotides does alter the amino acid sequence which is encoded by the codon optimized nucleotide sequence.

In some embodiments and as described in more detail herein, a 5' UTR and/or a 3' UTR may be provided as flanking regions. Multiple 5' or 3' UTRs may be included in the flanking regions and may be the same or of different sequences. Any portion of the flanking regions, including none, may be codon optimized and any may independently contain one or more different structural or chemical modifications, before and/or after codon optimization. Combinations of features may be included in the first and second flanking regions and may be contained within other features. For example, the ORF may be flanked by a 5' UTR which may contain a strong Kozak translational initiation signal and/or a 3' UTR which may include an oligo(dT) sequence for templated addition of a poly-A tail.

After optimization (if desired), the primary construct components are reconstituted and transformed into a vector such as, but not limited to, plasmids, viruses, cosmids, and artificial chromosomes. For example, the optimized construct may be reconstituted and transformed into chemically competent *E. coli*, yeast, *neurospora*, maize, *drosophila*, etc. where high copy plasmid-like or chromosome structures occur by methods described herein.

Vector Amplification

The vector containing the primary construct, encoding either the synthetic polynucleotide encoding a CRISPR related protein or the sgRNA, is then amplified and the plasmid isolated and purified using methods known in the art such as, but not limited to, a maxi prep using the Invitrogen PURELINK™ HiPure Maxiprep Kit (Carlsbad, Calif.).

Plasmid Linearization

The plasmid may then be linearized using methods known in the art such as, but not limited to, the use of restriction enzymes and buffers. The linearization reaction may be purified using methods including, for example Invitrogen's PURELINK™ PCR Micro Kit (Carlsbad, Calif.), and HPLC based purification methods such as, but not limited to, strong anion exchange HPLC, weak anion exchange HPLC, reverse phase HPLC (RP-HPLC), and hydrophobic interaction HPLC (HIC-HPLC) and Invitrogen's standard PURELINK™ PCR Kit (Carlsbad, Calif.). The purification method may be modified depending on the size of the linearization reaction which was conducted. The linearized plasmid is then used to generate cDNA for in vitro transcription (IVT) reactions.

cDNA Template Synthesis

A cDNA template may be synthesized by having a linearized plasmid undergo polymerase chain reaction (PCR). Table 4 of U.S. patent application Ser. No. 13/791,922 filed Mar. 9, 2013 provides a listing of primers and probes that may be usefully in the PCR reactions of the present invention. It should be understood that the listing is not exhaustive and that primer-probe design for any amplification is within the skill of those in the art. Probes may also contain chemically modified bases to increase base-pairing fidelity to the target molecule and base-pairing strength.

In one embodiment, the cDNA may be submitted for sequencing analysis before undergoing transcription.

mRNA Production

The process of synthetic polynucleotide or sgRNA production may include, but is not limited to, in vitro transcription, cDNA template removal and RNA clean-up, and RNA capping and/or tailing reactions. Alternatively the synthetic polynucleotide or sgRNA can be chemically synthesized.

In Vitro Transcription

The cDNA produced in the previous step may be transcribed using an in vitro transcription (IVT) system. The system typically comprises a transcription buffer, nucleotide triphosphates (NTPs), an RNase inhibitor and a polymerase. The NTPs may be manufactured in house, may be selected from a supplier, or may be synthesized as described herein. The NTPs may be selected from, but are not limited to, those described herein including natural and unnatural (modified)

NTPs. The polymerase may be selected from, but is not limited to, T7 RNA polymerase, T3 RNA polymerase and mutant polymerases such as, but not limited to, polymerases able to incorporate modified nucleic acids. Inorganic pyrophosphatase can be included in the transcription system.

RNA Polymerases

Any number of RNA polymerases or variants may be used in the design of the primary constructs of the present invention.

RNA polymerases may be modified by inserting or deleting amino acids of the RNA polymerase sequence. As a non-limiting example, the RNA polymerase may be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants may be obtained by evolving an RNA polymerase, optimizing the RNA polymerase amino acid and/or nucleic acid sequence and/or by using other methods known in the art. As a non-limiting example, T7 RNA polymerase variants may be evolved using the continuous directed evolution system set out by Esvelt et al. (Nature (2011) 472(7344):499-503; herein incorporated by reference in its entirety) where clones of T7 RNA polymerase may encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M267I, G280C, H300R, D351A, A354S, E356D, L360P, A383V, Y385C, D388Y, S397R, M401T, N410S, K450R, P45 IT, G452V, E484A, H523L, H524N, G542V, E565K, K577E, K577M, N601S, S684Y, L699I, K713E, N748D, Q754R, E775K, A827V, D851N or L864F. As another non-limiting example, T7 RNA polymerase variants may encode at least mutation as described in U.S. Pub. Nos. 20100120024 and 20070117112; herein incorporated by reference in their entireties. Variants of RNA polymerase may also include, but are not limited to, substitutional variants, conservative amino acid substitution, insertional variants, deletional variants and/or covalent derivatives.

In one embodiment, the primary construct may be designed to be recognized by the wild type or variant RNA polymerases. In doing so, the primary construct may be modified to contain sites or regions of sequence changes from the wild type or parent primary construct.

In one embodiment, the primary construct may be designed to include at least one substitution and/or insertion upstream of an RNA polymerase binding or recognition site, downstream of the RNA polymerase binding or recognition site, upstream of the TATA box sequence, downstream of the TATA box sequence of the primary construct but upstream of the coding region of the primary construct, within the 5'UTR, before the 5'UTR and/or after the 5'UTR.

In one embodiment, the 5'UTR of the primary construct may be replaced by the insertion of at least one region and/or string of nucleotides of the same base. The region and/or string of nucleotides may include, but is not limited to, at least 3, at least 4, at least 5, at least 6, at least 7 or at least 8 nucleotides and the nucleotides may be natural and/or unnatural. As a non-limiting example, the group of nucleotides may include 5-8 adenine, cytosine, thymine, a string of any of the other nucleotides disclosed herein and/or combinations thereof.

In one embodiment, the 5'UTR of the primary construct may be replaced by the insertion of at least two regions and/or strings of nucleotides of two different bases such as, but not limited to, adenine, cytosine, thymine, any of the other nucleotides disclosed herein and/or combinations thereof. For example, the 5'UTR may be replaced by inserting 5-8 adenine bases followed by the insertion of 5-8 cytosine bases. In another example, the 5'UTR may be replaced by inserting 5-8 cytosine bases followed by the insertion of 5-8 adenine bases.

In one embodiment, the primary construct may include at least one substitution and/or insertion downstream of the transcription start site which may be recognized by an RNA polymerase. As a non-limiting example, at least one substitution and/or insertion may occur downstream the transcription start site by substituting at least one nucleic acid in the region just downstream of the transcription start site (such as, but not limited to, +1 to +6). Changes to region of nucleotides just downstream of the transcription start site may affect initiation rates, increase apparent nucleotide triphosphate (NTP) reaction constant values, and increase the dissociation of short transcripts from the transcription complex curing initial transcription (Brieba et al, Biochemistry (2002) 41: 5144-5149; herein incorporated by reference in its entirety). The modification, substitution and/or insertion of at least one nucleic acid may cause a silent mutation of the nucleic acid sequence or may cause a mutation in the amino acid sequence.

In one embodiment, the primary construct may include the substitution of at least 1, at least 2, at least 3, at least 4, at least 5, at least 6, at least 7, at least 8, at least 9, at least 10, at least 11, at least 12 or at least 13 guanine bases downstream of the transcription start site.

In one embodiment, the primary construct may include the substitution of at least 1, at least 2, at least 3, at least 4, at least 5 or at least 6 guanine bases in the region just downstream of the transcription start site. As a non-limiting example, if the nucleotides in the region are GGGAGA (SEQ ID NO: 127) the guanine bases may be substituted by at least 1, at least 2, at least 3 or at least 4 adenine nucleotides. In another non-limiting example, if the nucleotides in the region are GGGAGA (SEQ ID NO: 127) the guanine bases may be substituted by at least 1, at least 2, at least 3 or at least 4 cytosine bases. In another non-limiting example, if the nucleotides in the region are GGGAGA (SEQ ID NO: 127) the guanine bases may be substituted by at least 1, at least 2, at least 3 or at least 4 thymine, and/or any of the nucleotides described herein.

In one embodiment, the primary construct may include at least one substitution and/or insertion upstream of the start codon. For the purpose of clarity, one of skill in the art would appreciate that the start codon is the first codon of the protein coding region whereas the transcription start site is the site where transcription begins. The primary construct may include, but is not limited to, at least 1, at least 2, at least 3, at least 4, at least 5, at least 6, at least 7 or at least 8 substitutions and/or insertions of nucleotide bases. The nucleotide bases may be inserted or substituted at 1, at least 1, at least 2, at least 3, at least 4 or at least 5 locations upstream of the start codon. The nucleotides inserted and/or substituted may be the same base (e.g., all A or all C or all T or all G), two different bases (e.g., A and C, A and T, or C and T), three different bases (e.g., A, C and T or A, C and T) or at least four different bases. As a non-limiting example, the guanine base upstream of the coding region in the primary construct may be substituted with adenine, cytosine, thymine, or any of the nucleotides described herein. In another non-limiting example the substitution of guanine bases in the primary construct may be designed so as to leave one guanine base in the region downstream of the transcription start site and before the start codon (see Esvelt et al. Nature (2011) 472(7344):499-503; herein incorporated by reference in its entirety). As a non-limiting example, at least 5 nucleotides may be inserted at 1 location downstream of the transcription start site but upstream of the start codon and the at least 5 nucleotides may be the same base type.

cDNA Template Removal and Clean-Up

The cDNA template may be removed using methods known in the art such as, but not limited to, treatment with Deoxyribonuclease I (DNase I). RNA clean-up may also include a purification method such as, but not limited to, AGENCOURT® CLEANSEQ® system from Beckman Coulter (Danvers, Mass.), HPLC based purification methods such as, but not limited to, strong anion exchange HPLC, weak anion exchange HPLC, reverse phase HPLC (RP-HPLC), and hydrophobic interaction HPLC (HIC-HPLC).

Capping and/or Tailing Reactions

The primary construct or mmRNA may also undergo capping and/or tailing reactions. A capping reaction may be performed by methods known in the art to add a 5' cap to the 5' end of the primary construct. Methods for capping include, but are not limited to, using a Vaccinia Capping enzyme (New England Biolabs, Ipswich, Mass.).

A poly-A tailing reaction may be performed by methods known in the art, such as, but not limited to, 2' O-methyltransferase and by methods as described herein. If the primary construct generated from cDNA does not include a poly-T, it may be beneficial to perform the poly-A-tailing reaction before the primary construct is cleaned.

Samples undergoing capping reactions may have varying amounts of 5' capped structures ranging from 0 to 100%. In some embodiments, the sample comprises 0, 5, 10, 20, 30, 40, 50, 60, 70, 80, 90, 95, 99, or 100% 5' capped RNA.

Synthetic Polynucleotide and sgRNA Purification

Purification of the synthetic polynucleotide or sgRNA may include, but is not limited to, RNA clean-up, quality assurance and quality control. RNA clean-up may be performed by methods known in the arts such as, but not limited to, AGENCOURT® beads (Beckman Coulter Genomics, Danvers, Mass.), poly-T beads, LNA™ oligo-T capture probes (EXIQON® Inc, Vedbaek, Denmark), HPLC based purification methods such as, but not limited to, strong anion exchange HPLC, weak anion exchange HPLC, reverse phase HPLC (RP-HPLC), and hydrophobic interaction HPLC (HIC-HPLC) or RNAse III treatment (a non-limiting example of treating mRNA with RNAse III is described by Meis et al. in International Publication No. WO2013102203, herein incorporated by reference in its entirety). The term "purified" when used in relation to a polynucleotide such as a "purified RNA" refers to one that is separated from at least one contaminant. As used herein, a "contaminant" is any substance which makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In another embodiment, the RNA may be sequenced by methods including, but not limited to reverse-transcriptase-PCR.

In one embodiment, the mRNA or mmRNA may be quantified using methods such as, but not limited to, ultraviolet visible spectroscopy (UV/Vis). A non-limiting example of a UV/Vis spectrometer is a NANODROP® spectrometer (ThermoFisher, Waltham, Mass.). The quantified mRNA or mmRNA may be analyzed in order to determine if the mRNA or mmRNA may be of proper size, check that no degradation of the mRNA or mmRNA has occurred. Degradation of the mRNA and/or mmRNA may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

IV. Modified Synthetic Polynucleotides and sgRNAs

The synthetic polynucleotides and sgRNAs of the invention are typically modified. Herein, in a polynucleotide (such as synthetic polynucleotide or sgRNA), the terms "modification" or, as appropriate, "modified" refer to modification with respect to A, G, U or C ribonucleotides. Generally, herein, these terms are not intended to refer to the ribonucleotide modifications in naturally occurring 5'-terminal mRNA cap moieties. Examples of modifications can be found in U.S. patent application Ser. No. 13/644,072, filed 3 Oct. 2012 and published as US20130115272, e.g., the contents of which are incorporated by reference for all purposes.

The modifications may be various distinct modifications. In some embodiments, the coding region, the flanking regions and/or the terminal regions may contain one, two, or more (optionally different) nucleoside or nucleotide modifications. In some embodiments, a modified polynucleotide, primary construct, or mmRNA introduced to a cell may exhibit reduced degradation in the cell, as compared to an unmodified polynucleotide, primary construct, or mmRNA.

The polynucleotides, primary constructs, and mmRNA can include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications according to the present invention may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

As described herein, the polynucleotides, primary constructs, and mmRNA of the invention do not substantially induce an innate immune response of a cell into which the mRNA is introduced. Features of an induced innate immune response include 1) increased expression of pro-inflammatory cytokines, 2) activation of intracellular PRRs (RIG-I, MDA5, etc, and/or 3) termination or reduction in protein translation.

In certain embodiments, it may desirable to intracellularly degrade a modified nucleic acid molecule introduced into the cell. For example, degradation of a modified nucleic acid molecule may be preferable if precise timing of protein production is desired. Thus, in some embodiments, the invention provides a modified nucleic acid molecule containing a degradation domain, which is capable of being acted on in a directed manner within a cell.

The polynucleotides, primary constructs, and mmRNA can optionally include other agents (e.g., RNAi-inducing agents, RNAi agents, siRNAs, shRNAs, miRNAs, antisense RNAs, ribozymes, catalytic DNA, tRNA, RNAs that induce triple helix formation, aptamers, vectors, etc.).

In some embodiments, the polynucleotide, primary construct, or mmRNA (e.g., the first region, first flanking region, or second flanking region) includes n number of linked nucleosides having any base, sugar, backbone, building block or other structure or formula, including but not limited to those of Formulas I through IX or any substructures thereof as described in International Publication No WO2013052523 filed Oct. 3, 2012, entitled Modified Nucleosides, Nucleotides, and Nucleic Acids, and Uses Thereof, the contents of which are incorporated herein by reference in their entirety. Such structures include modifications to the sugar, nucleobase, internucleoside linkage, or combinations thereof.

Combinations of chemical modifications include those taught in including but not limited to those described in International Publication No WO2013052523 filed Oct. 3, 2012, entitled Modified Nucleosides, Nucleotides, and Nucleic Acids, and Uses Thereof, the contents of which are incorporated herein by reference in their entirety.

The synthesis of polynucleotides, primary constructs or mmRNA of the present invention may be according to the methods described in International Publication No WO2013052523 filed Oct. 3, 2012, entitled Modified Nucleosides, Nucleotides, and Nucleic Acids, and Uses Thereof, the contents of which are incorporated herein by reference in their entirety.

In some embodiments, the nucleobase selected from the group consisting of cytosine, guanine, adenine, and uracil.

In some embodiments, the modified nucleobase is a modified uracil.

Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), 3-methyl-uridine ($m^3U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine ($\tau m^5s^2U$), 1-taurinomethyl-4-thio-pseudouridine, 5-methyl-uridine ($m^5U$, i.e., having the nucleobase deoxythymine), 1-methyl-pseudouridine ($m^1\psi$), 5-methyl-2-thio-uridine ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3\psi$), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine ($m^3C$), N4-acetyl-cytidine ($ac^4C$), 5-formyl-cytidine ($f^5C$), N4-methyl-cytidine ($m^4C$), 5-methyl-cytidine ($m^5C$), 5-halo-cytidine (e.g., 5-iodo-cytidine), 5-hydroxymethyl-cytidine ($hm^5C$), 1-methyl-pseudoisocytidine, pyrrolo-cytidine, pyrrolo-pseudoisocytidine, 2-thio-cytidine ($s^2C$), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine ($k_2C$), α-thio-cytidine, 2'-O-methyl-cytidine (Cm), 5,2'-O-dimethyl-cytidine ($m^5Cm$), N4-acetyl-2'-O-methyl-cytidine ($ac^4Cm$), N4,2'-O-dimethyl-cytidine ($m^4Cm$), 5-formyl-2'-O-methyl-cytidine ($f^5Cm$), N4,N4,2'-O-trimethyl-cytidine ($m^4{}_2Cm$), 1-thio-cytidine, 2'-F-ara-cytidine, 2'-F-cytidine, and 2'-OH-ara-cytidine.

In exemplary embodiments, the modified nucleobase is a modified uracil selected from pseudouridine (ψ) and 1-methylpseudouridine. In some embodiments, the modified nucleobase is a modified uracil in combination with a modified cytosine, e.g., 5-methylcytosine.

In some embodiments, a polynucleotide of the invention is fully modified with pseudouridine (ω), optionally in combination with 5-methylcytosine. In some embodiments, a polynucleotide of the invention is fully modified with 1-methylpseudouridine ($m^1\psi$), optionally in combination with 5-methylcytosine.

In some embodiments, the mRNA molecules are codon optimized.

In some embodiments, the modified nucleobase is a modified adenine. Exemplary nucleobases and nucleosides having a modified adenine include 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine ($m^1A$), 2-methyl-adenine ($m^2A$), N6-methyl-adenosine ($m^6A$), 2-methylthio-N6-methyl-adenosine ($ms^2m^6A$), N6-isopentenyl-adenosine ($i^6A$), 2-methylthio-N6-isopentenyl-adenosine ($ms^2i^6A$), N6-(cis-hydroxyisopentenyl)adenosine ($io^6A$), 2-methylthio-N6-(cis-hydroxyisopentenyl) adenosine ($ms^2io^6A$), N6-glycinylcarbamoyl-adenosine ($g^6A$), N6-threonylcarbamoyl-adenosine ($t^6A$), N6-methyl- N6-threonylcarbamoyl-adenosine ($m^6t^6A$), 2-methylthio-N6-threonylcarbamoyl-adenosine ($ms^2g^6A$), N6,N6-dimethyl-adenosine ($m^6_2A$), N6-hydroxynorvalylcarbamoyl-adenosine ($hn^6A$), 2-methylthio-N6-hydroxynorvalylcarbamoyl-adenosine ($ms^2hn^6A$), N6-acetyl-adenosine ($ac^6A$), 7-methyl-adenine, 2-methylthio-adenine, 2-methoxy-adenine, α-thio-adenosine, 2'-O-methyl-adenosine (Am), N6,2'-O-dimethyl-adenosine ($m^6Am$), N6,N6,2'-O-trimethyl-adenosine ($m^6_2Am$), 1,2'-O-dimethyl-adenosine ($m^1Am$), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include inosine (I), 1-methyl-inosine ($m^1I$), wyosine (imG), methylwyosine (mimG), 4-demethyl-wyosine (imG-14), isowyosine (imG2), wybutosine (yW), peroxywybutosine ($o_2yW$), hydroxywybutosine (OHyW), undermodified hydroxywybutosine (OHyW*), 7-deaza-guanosine, queuosine (Q), epoxyqueuosine (oQ), galactosyl-queuosine (galQ), mannosyl-queuosine (manQ), 7-cyano-7-deaza-guanosine ($preQ_0$), 7-aminomethyl-7-deaza-guanosine ($preQ_1$), archaeosine ($G^+$), 7-deaza-8-aza-guanosine, 6-thio-guanosine, 6-thio-7-deaza-guanosine, 6-thio-7-deaza-8-aza-guanosine, 7-methyl-guanosine ($m^7G$), 6-thio-7-methyl-guanosine, 7-methyl-inosine, 6-methoxy-guanosine, 1-methyl-guanosine ($m^1G$), N2-methyl-guanosine ($m^2G$), N2,N2-dimethyl-guanosine ($m^2_2G$), N2,7-dimethyl-guanosine ($m^{2,7}G$), N2, N2,7-dimethyl-guanosine ($m^{2,2,7}G$), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine ($m^2Gm$), N2,N2-dimethyl-2'-O-methyl-guanosine ($m^2_2Gm$), 1-methyl-2'-O-methyl-guanosine ($m^1Gm$), N2,7-dimethyl-2'-O-methyl-guanosine ($m^{2,7}Gm$), 2'-O-methyl-inosine (Im), 1,2'-O-dimethyl-inosine ($m^1Im$), and 2'-O-ribosylguanosine (phosphate) (Gr(p)).

The nucleobase of the nucleotide can be independently selected from a purine, a pyrimidine, a purine or pyrimidine analog. For example, the nucleobase can each be independently selected from adenine, cytosine, guanine, uracil, or hypoxanthine. In another embodiment, the nucleobase can also include, for example, naturally-occurring and synthetic derivatives of a base, including pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

Modified nucleosides and nucleotides (e.g., building block molecules) can be prepared according to the synthetic methods described in Ogata et al., J. Org. Chem. 74:2585-2588 (2009); Purmal et al., Nucl. Acids Res. 22(1): 72-78, (1994); Fukuhara et al., Biochemistry, 1(4): 563-568 (1962); and Xu et al., Tetrahedron, 48(9): 1729-1740 (1992), each of which are incorporated by reference in their entirety.

The polypeptides, primary constructs, and mmRNA of the invention may or may not be uniformly modified along the entire length of the molecule. For example, one or more or all types of nucleotide (e.g., purine or pyrimidine, or any one or more or all of A, G, U, C) may or may not be uniformly modified in a polynucleotide of the invention, or in a given predetermined sequence region thereof (e.g. one or more of the sequence regions represented in FIG. 1). In some embodiments, all nucleotides X in a polynucleotide of the invention (or in a given sequence region thereof) are modified, wherein X may any one of nucleotides A, G, U, C, or any one of the combinations A+G, A+U, A+C, G+U, G+C, U+C, A+G+U, A+G+C, G+U+C or A+G+C.

Different sugar modifications, nucleotide modifications, and/or internucleoside linkages (e.g., backbone structures) may exist at various positions in the polynucleotide, primary construct, or mmRNA. One of ordinary skill in the art will appreciate that the nucleotide analogs or other modification(s) may be located at any position(s) of a polynucleotide, primary construct, or mmRNA such that the function of the polynucleotide, primary construct, or mmRNA is not substantially decreased. A modification may also be a 5' or 3' terminal modification. The polynucleotide, primary construct, or mmRNA may contain from about 1% to about 100% modified nucleotides (either in relation to overall nucleotide content, or in relation to one or more types of nucleotide, i.e. any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, the polynucleotide, primary construct, or mmRNA includes a modified pyrimidine (e.g., a modified uracil/uridine/U or modified cytosine/cytidine/C). In some embodiments, the uracil or uridine (generally: U) in the polynucleotide, primary construct, or mmRNA molecule may be replaced with from about 1% to about 100% of a modified uracil or modified uridine (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100% of a modified uracil or modified uridine). The modified uracil or uridine can be replaced by a compound having a single unique structure or by a plurality of compounds having different structures (e.g., 2, 3, 4 or more unique structures, as described herein).

In some embodiments, the cytosine or cytidine (generally: C) in the polynucleotide, primary construct, or mmRNA molecule may be replaced with from about 1% to about 100% of a modified cytosine or modified cytidine (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100% of a modified cytosine or modified cytidine). The modified cytosine or cytidine can be replaced by a compound having a single unique structure or by a plurality of compounds having different structures (e.g., 2, 3, 4 or more unique structures, as described herein).

In some embodiments, at least 25% of the cytosines are replaced by a compound of Formula (b10)-(b14) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the uracils are replaced by a compound of Formula (b1)-(b9) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the cytosines are replaced by a compound of Formula (b10)-(b14), and at least 25% of the uracils are replaced by a compound of Formula (b1)-(b9) (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In one embodiment, the synthetic polynucleotide and/or sgRNA includes a terminal modification. The terminal modification may be a modification described in US Provisional Application No. U.S. 61/729,933, filed Nov. 26, 2012, entitled Terminally Optimized RNAs; US Provisional Application No. U.S. 61/737,224, filed Dec. 14, 2012, entitled Terminally Optimized RNAs; US Provisional Application No. U.S. 61/758,921, filed Jan. 31, 2013, entitled Differential Targeting Using RNA Constructs; US Provisional Application No. U.S. 61/781,139, filed Mar. 14, 2013, entitled Differential Targeting Using RNA Constructs; US Provisional Application No. U.S. 61/829,359, filed May 31, 2013, entitled Differential Targeting Using RNA Constructs; US Provisional Application No. U.S. 61/839,903, filed Jun. 27, 2013, entitled Differential Targeting Using RNA Constructs; U.S. Provisional Application No. 61/842,709, filed Jul. 3, 2013, entitled Differential Targeting Using RNA Constructs; each of which is herein incorporated by reference in its entirety.

In another embodiment, the chemical modification may be a modification described in International Publication No. WO2013052523, herein incorporated by reference in its entirety.

V. Pharmaceutical Compositions: Formulation, Administration, Delivery and Dosing In one embodiment, the invention includes synthetic polynucleotide and/or sgRNA compositions and complexes in combination with one or more pharmaceutically acceptable excipients. Pharmaceutical compositions may optionally comprise one or more additional active substances, e.g. therapeutically and/or prophylactically active substances. General considerations in the formulation and/or manufacture of pharmaceutical agents may be found, for example, in *Remington: The Science and Practice of Pharmacy* 21$^{st}$ ed., Lippincott Williams & Wilkins, 2005 (incorporated herein by reference in its entirety). synthetic polynucleotides and/or synthetic sgRNAs In one embodiment, the synthetic polynucleotide and/or sgRNA are formulated. As a non-limiting example the synthetic polynucleotides and/or synthetic sgRNAs may be formulated by the methods described in International Publication No. WO2013090648 and/or co-pending US Provisional Application No. U.S. 61/821,406, filed Mar. 14, 2013, entitled Formulation and Delivery of Modified Nucleoside, Nucleotide, and Nucleic Acid Compositions, US Provisional Application No. U.S. 61/821,406, filed May 9, 2013, entitled Formulation and Delivery of Modified Nucleoside, Nucleotide, and Nucleic Acid Compositions and US Provisional Application No. U.S. 61/840,510, filed Jun. 28, 2013, entitled Formulation and Delivery of Modified Nucleoside, Nucleotide, and Nucleic Acid Compositions, each of which is herein incorporated by reference in its entirety.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient Formulations The synthetic polynucleotides and/or synthetic sgRNAs of the invention can be formulated using one or more excipients to: (1) increase stability; (2) increase cell transfection; (3) permit the sustained or delayed release (e.g., from a depot formulation of the polynucleotide, primary construct, or mmRNA); (4) alter the biodistribution (e.g., target the polynucleotide, primary construct, or mmRNA to specific tissues or cell types); (5) increase the translation of encoded protein in vivo; and/or (6) alter the release profile of encoded protein in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present invention can include, without limitation, lipidoids, liposomes, lipid nanoparticles, polymers, lipoplexes, core-shell nanoparticles, peptides, proteins, cells transfected with polynucleotide, primary construct, or mmRNA (e.g., for transplantation into a subject), hyaluronidase, nanoparticle mimics and combinations thereof. Accordingly, the formulations of the invention can include one or more excipients, each in an amount that together increases the stability of the polynucleotide, primary construct, or mmRNA, increases cell transfection by the polynucleotide, primary construct, or mmRNA, increases the expression of polynucleotide, primary construct, or mmRNA encoded protein, and/or alters the release profile of polynucleotide, primary construct, or mmRNA encoded proteins. Further, the primary construct and mmRNA of the present invention may be formulated using self-assembled nucleic acid nanoparticles.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient may generally be equal to the dosage of the active ingredient which would be administered to a subject and/or a convenient fraction of such a dosage including, but not limited to, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient.

In some embodiments, the formulations described herein may contain at least one synthetic polynucleotide. As a non-limiting example, the formulations may contain 1, 2, 3, 4 or 5 mmRNA. In one embodiment the formulation may contain modified mRNA encoding proteins selected from categories such as, but not limited to, human proteins, veterinary proteins, bacterial proteins, biological proteins, antibodies, immunogenic proteins, therapeutic peptides and proteins, secreted proteins, plasma membrane proteins, cytoplasmic and cytoskeletal proteins, intracellular membrane bound proteins, nuclear proteins, proteins associated with human disease and/or proteins associated with non-human diseases. In one embodiment, the formulation contains at least three modified mRNA encoding proteins. In one embodiment, the formulation contains at least five modified mRNA encoding proteins.

Pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

In some embodiments, the particle size of the lipid nanoparticle may be increased and/or decreased. The change in particle size may be able to help counter biological reaction such as, but not limited to, inflammation or may increase the biological effect of the modified mRNA delivered to mammals.

Pharmaceutically acceptable excipients used in the manufacture of pharmaceutical compositions include, but are not limited to, inert diluents, surface active agents and/or emulsifiers, preservatives, buffering agents, lubricating agents, and/or oils. Such excipients may optionally be included in the pharmaceutical formulations of the invention.

Lipidoids

The synthesis of lipidoids has been extensively described and formulations containing these compounds are particularly suited for delivery of polynucleotides, primary constructs or mmRNA (see Mahon et al., Bioconjug Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

While these lipidoids have been used to effectively deliver double stranded small interfering RNA molecules in rodents and non-human primates (see Akinc et al., Nat Biotechnol. 2008 26:561-569; Frank-Kamenetsky et al., Proc Natl Acad Sci USA. 2008 105:11915-11920; Akinc et al., Mol Ther. 2009 17:872-879; Love et al., Proc Natl Acad Sci USA. 2010 107:1864-1869; Leuschner et al., Nat Biotechnol. 2011 29:1005-1010; all of which is incorporated herein in their entirety), the present disclosure describes their formulation and use in delivering single stranded polynucleotides, primary constructs, or mmRNA. Complexes, micelles, liposomes or particles can be prepared containing these lipidoids and therefore, can result in an effective delivery of the polynucleotide, primary construct, or mmRNA, as judged by the production of an encoded protein, following the injection of a lipidoid formulation via localized and/or systemic routes of administration. Lipidoid complexes of polynucleotides, primary constructs, or mmRNA can be administered by various means including, but not limited to, intravenous, intramuscular, or subcutaneous routes.

In vivo delivery of nucleic acids may be affected by many parameters, including, but not limited to, the formulation composition, nature of particle PEGylation, degree of loading, oligonucleotide to lipid ratio, and biophysical parameters such as particle size (Akinc et al., Mol Ther. 2009 17:872-879; herein incorporated by reference in its entirety). As an example, small changes in the anchor chain length of poly(ethylene glycol) (PEG) lipids may result in significant effects on in vivo efficacy. Formulations with the different lipidoids, including, but not limited to penta[3-(1-laurylaminopropionyl)]-triethylenetetramine hydrochloride (TETA-5LAP; aka 98N12-5, see Murugaiah et al., Analytical Biochemistry, 401:61 (2010)), C12-200 (including derivatives and variants), and MD1, can be tested for in vivo activity.

The lipidoid referred to herein as "98N12-5" is disclosed by Akinc et al., Mol Ther. 2009 17:872-879 and is incorporated by reference in its entirety. (See FIG. 2)

The lipidoid referred to herein as "C12-200" is disclosed by Love et al., Proc Natl Acad Sci USA. 2010 107:1864-1869 (see FIG. 2) and Liu and Huang, Molecular Therapy. 2010 669-670 (see FIG. 2); both of which are herein incorporated by reference in their entirety. The lipidoid formulations can include particles comprising either 3 or 4 or more components in addition to polynucleotide, primary construct, or mmRNA. As an example, formulations with certain lipidoids, include, but are not limited to, 98N12-5 and may contain 42% lipidoid, 48% cholesterol and 10% PEG (C14 alkyl chain length). As another example, formulations with certain lipidoids, include, but are not limited to, C12-200 and may contain 50% lipidoid, 10% disteroylphosphatidyl choline, 38.5% cholesterol, and 1.5% PEG-DMG.

In one embodiment, a polynucleotide, primary construct, or mmRNA formulated with a lipidoid for systemic intravenous administration can target the liver. For example, a final optimized intravenous formulation using polynucleotide, primary construct, or mmRNA, and comprising a lipid molar composition of 42% 98N12-5, 48% cholesterol, and 10% PEG-lipid with a final weight ratio of about 7.5 to 1 total lipid to polynucleotide, primary construct, or mmRNA, and a C14 alkyl chain length on the PEG lipid, with a mean particle size of roughly 50-60 nm, can result in the distribution of the formulation to be greater than 90% to the liver (see, Akinc et al., Mol Ther. 2009 17:872-879; herein incorporated in its entirety). In another example, an intravenous formulation using a C12-200 (see U.S. provisional application 61/175,770 and published international application WO2010129709, each of which is herein incorporated by reference in their entirety) lipidoid may have a molar ratio of 50/10/38.5/1.5 of C12-200/disteroylphosphatidyl choline/cholesterol/PEG-DMG, with a weight ratio of 7 to 1 total lipid to polynucleotide, primary construct, or mmRNA, and a mean particle size of 80 nm may be effective to deliver polynucleotide, primary construct, or mmRNA to hepatocytes (see, Love et al., Proc Natl Acad Sci USA. 2010 107:1864-1869 herein incorporated by reference). In another embodiment, an MD1 lipidoid-containing formulation may be used to effectively deliver polynucleotide, primary construct, or mmRNA to hepatocytes in vivo. The characteristics of optimized lipidoid formulations for intramuscular or subcutaneous routes may vary significantly depending on the target cell type and the ability of formulations to diffuse through the extracellular matrix into the blood stream. While a particle size of less than 150 nm may be desired for effective hepatocyte delivery due to the size of the endothelial fenestrae (see, Akinc et al., Mol Ther. 2009 17:872-879 herein incorporated by reference), use of a lipidoid-formulated polynucleotide, primary construct, or mmRNA to deliver the formulation to other cells types including, but not limited to, endothelial cells, myeloid cells, and muscle cells may not be similarly size-limited. Use of lipidoid formulations to deliver siRNA in vivo to other non-hepatocyte cells such as myeloid cells and endothelium has been reported (see Akinc et al., Nat Biotechnol. 2008 26:561-569; Leuschner et al., Nat Biotechnol. 2011 29:1005-1010; Cho et al. Adv. Funct. Mater. 2009 19:3112-3118; 8$^{th}$ International Judah Folkman Conference, Cambridge, Mass. Oct. 8-9, 2010 herein incorporated by reference in its entirety). Effective delivery to myeloid cells, such as monocytes, lipidoid formulations may have a similar component molar ratio. Different ratios of lipidoids and other components including, but not limited to, disteroylphosphatidyl choline, cholesterol and PEG-DMG, may be used to optimize the formulation of the polynucleotide, primary construct, or mmRNA for delivery to different cell types including, but not limited to, hepatocytes, myeloid cells, muscle cells, etc. For example, the component molar ratio may include, but is not limited to, 50% C12-200, 10% disteroylphosphatidyl choline, 38.5% cholesterol, and %1.5 PEG-DMG (see Leuschner et al., Nat Biotechnol 2011 29:1005-1010; herein incorporated by reference in its entirety). The use of lipidoid formulations for the localized delivery of nucleic acids to cells (such as, but not limited to, adipose cells and muscle cells) via either subcutaneous or intramuscular delivery, may not require all of the formulation components desired for systemic delivery, and as such may comprise only the lipidoid and the polynucleotide, primary construct, or mmRNA.

Combinations of different lipidoids may be used to improve the efficacy of polynucleotide, primary construct, or mmRNA directed protein production as the lipidoids may be able to increase cell transfection by the polynucleotide, primary construct, or mmRNA; and/or increase the translation of encoded protein (see Whitehead et al., Mol. Ther. 2011, 19:1688-1694, herein incorporated by reference in its entirety).

Liposomes, Lipoplexes, and Lipid Nanoparticles

The polynucleotide, primary construct, and mmRNA of the invention can be formulated using one or more liposomes, lipoplexes, or lipid nanoparticles. In one embodiment, pharmaceutical compositions of polynucleotide, primary construct, or mmRNA include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

In one embodiment, pharmaceutical compositions described herein may include, without limitation, liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120; herein incorporated by reference in its entirety) and liposomes which may deliver small molecule drugs such as, but not limited to, DOXIL® from Janssen Biotech, Inc. (Horsham, Pa.).

In one embodiment, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles *Hum Gene Ther.* 2008 19:125-132; all of which are incorporated herein in their entireties). The original manufacture method by Wheeler et al. was a detergent dialysis method, which was later improved by Jeffs et al. and is referred to as the spontaneous vesicle formation method. The liposome formulations are composed of 3 to 4 lipid components in addition to the polynucleotide, primary construct, or mmRNA. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al.

In one embodiment, the polynucleotides, primary constructs and/or mmRNA may be formulated in a lipid vesicle which may have crosslinks between functionalized lipid bilayers.

In one embodiment, the polynucleotides, primary constructs and/or mmRNA may be formulated in a lipid-polycation complex. The formation of the lipid-polycation complex may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyomithine and/or polyarginine. In another embodiment, the polynucleotides, primary constructs and/or mmRNA may be formulated in a lipid-polycation complex which may further include a neutral lipid such as, but not limited to, cholesterol or dioleoyl phosphatidylethanolamine (DOPE).

The liposome formulation may be influenced by, but not limited to, the selection of the cationic lipid component, the degree of cationic lipid saturation, the nature of the PEGylation, ratio of all components and biophysical parameters such as size. In one example by Semple et al. (Semple et al. Nature Biotech. 2010 28:172-176), the liposome formulation was composed of 57.1% cationic lipid, 7.1% dipalmitoylphosphatidylcholine, 34.3% cholesterol, and 1.4% PEG-c-DMA. As another example, changing the composition of the cationic lipid could more effectively deliver siRNA to various antigen presenting cells (Basha et al. Mol Ther. 2011 19:2186-2200; herein incorporated by reference in its entirety).

In some embodiments, the ratio of PEG in the LNP formulations may be increased or decreased and/or the carbon chain length of the PEG lipid may be modified from C14 to C18 to alter the pharmacokinetics and/or biodistribution of the LNP formulations. As a non-limiting example, LNP formulations may contain 1-5% of the lipid molar ratio of PEG-c-DOMG as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol) or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In one embodiment, the cationic lipid may be selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865 and WO2008103276, U.S. Pat. Nos. 7,893,302 and 7,404,969 and US Patent Publication No. US20100036115; each of which is herein incorporated by reference in their entirety. In another embodiment, the cationic lipid may be selected from, but not limited to, formula A described in International Publication Nos. WO2012040184, WO2011153120, WO2011149733, WO2011090965, WO2011043913, WO2011022460, WO2012061259, WO2012054365 and WO2012044638; each of which is herein incorporated by reference in their entirety. In yet another embodiment, the cationic lipid may be selected from, but not limited to, formula CLI-CLXXIX of International Publication No. WO2008103276, formula CLI-CLXXIX of U.S. Pat. No. 7,893,302, formula CLI-CLXXXII of U.S. Pat. No. 7,404,969 and formula I-VI of US Patent Publication No. US20100036115; each of which is herein incorporated by reference in their entirety. As a non-limiting example, the cationic lipid may be selected from (20Z,23Z)—N,N-dimethylnonacosa-20,23-dien-10-amine, (17Z,20Z)—N,N-dimemylhexacosa-17,20-dien-9-amine, (1 Z, 19Z)—N5N~dimethylpentacosa~16, 19-dien-8-amine, (13 Z, 16Z)—N,N-dimethyldocosa-13J16-dien-5-amine, (12Z,15Z)—NJN-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21 Z)—N,N-dimethylheptacosa-18,21-dien-8-amine, (17Z,20Z)—N,N-dimethylhexacosa-17,20-dien-7-amine, (16Z; 19Z)—N,N-dimethylpentacosa-16,19-dien-6-amine, (22Z,25Z)—N,N-dimethylhentriaconta-22,25-dien-10-amine, (21 Z,24Z)—N;N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—NJN-dimethyloctacosa-19,22-dien-7-amine, N,N-dimethyl-heptacosan-10-amine, (20Z,23Z)—N-ethyl-N-methylnona-cosa-20J23-dien-10-amine, 1-[(11Z,14Z)-1-nonylicosa-11,14-dien-1-yl] pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dim-ethylnonacos-20-en-10-amine, (22Z)—N,N-dimethylhen-triacont-22-en-10-amine, (16Z)—N,N-dimethylpentacos-16-en-8-amine, (12Z, 15Z)—N,N-dimethyl-2-nonylhenicosa-12, 15-dien-1-amine, (13Z, 16Z)—N,N-dimethyl-3-nonyldocosa-13, 16-dien-1-amine, N,N-dimethyl-1-[(1 S,2R)-2-octylcyclopropyl] eptadecan-8-amine, 1-[(1 S,2R)-2-hexylcyclopropyl]-N,N-dimethylnonadecan-10-amine, N,N-dimethyl-1-[(1 S,2R)-2-octylcyclopropyl]nonadecan-10-amine, N,N-dimethyl-21~[(1S,2R)-2-octylcyclopropyl]henicosan-10-amine, N,N-dimethyl-1-[(1 S,2S)-2-{[(1R,2R)-2-pentylcyclopropyl] methyl} cyclopropyl]nonadecan-10-amine, N,N-dimethyl-1-[(1 S,2R)-2-octylcyclopropyl]hexadecan-8-amine, N,N-dimethyH-[(1R,2S)-2-undecyIcyclopropyl]tetradecan-5-amine, N,N-dimethyl-3-{7-[(1 S,2R)-2-octylcyclopropyl] heptyl} dodecan-1-amine, 1-[(1 R,2 S)-2-heptylcyclopropy 1]-N,N-dimethyloctadecan-9-amine, 1-[(1 S,2R)-2-decylcy-clopropyl]-N,N-dimethylpentadecan-6-amine, N,N-dim-ethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)pro-pan-2-amine, 1-{2-[(9Z,12Z)-octadeca-9,12-dien-1-yloxy]-1-[(octyloxy) methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy) methyl] ethyl}azetidine, (2S)-1-(hexyloxy)-N,N-dimethyl-3-[(9Z,12Z)-octadeca-9,12-dien-1-yloxy]propan-2-amine, (2 S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-amine (Compound 9); (2S)—N,N-dimethyl-1-[(6Z,9Z,12Z)-octadeca-6,9,12-trien-1-yloxy]-3-(octyloxy) propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z, 12Z)-octadeca-9,12-dien-1-yloxy]propan-2-amine, N,N-di-methyl-1-(octyloxy)-3-({8-[(1S,2S)-2-{[(1R,2R)-2-pentyl-cyclopropyl]methyl}cyclopropyl]octyl}oxy)propan-2-amine, N,N-dimethyl-1-{[8-(2-oclylcyclopropyl)octyl] oxy}-3-(octyloxy)propan-2-amine and (11E,20Z,23Z)—N;N-dimethylnonacosa-11,20,2-trien-10-amine or a pharmaceutically acceptable salt or stereoisomer thereof.

In one embodiment, the cationic lipid may be synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724 and WO201021865; each of which is herein incorporated by reference in their entirety.

In one embodiment, the LNP formulations of the polynucleotides, primary constructs and/or mmRNA may contain PEG-c-DOMG 3% lipid molar ratio. In another embodiment, the LNP formulations of the polynucleotides, primary constructs and/or mmRNA may contain PEG-c-DOMG 1.5% lipid molar ratio.

In one embodiment, the pharmaceutical compositions of the polynucleotides, primary constructs and/or mmRNA may include at least one of the PEGylated lipids described in International Publication No. 2012099755, herein incorporated by reference.

In one embodiment, the LNP formulation may contain PEG-DMG 2000 (1,2-dimyristoyl-sn-glycero-3-phopho-ethanolamine-N-[methoxy(polyethylene glycol)-2000). In one embodiment, the LNP formulation may contain PEG-DMG 2000, a cationic lipid known in the art and at least one other component. In another embodiment, the LNP formulation may contain PEG-DMG 2000, a cationic lipid known in the art, DSPC and cholesterol. As a non-limiting example, the LNP formulation may contain PEG-DMG 2000, DLin-DMA, DSPC and cholesterol. As another non-limiting example the LNP formulation may contain PEG-DMG 2000, DLin-DMA, DSPC and cholesterol in a molar ratio of 2:40:10:48 (see Geall et al., Nonviral delivery of self-amplifying RNA vaccines, PNAS 2012; PMID: 22908294).

In one embodiment, the LNP formulation may be formulated by the methods described in International Publication Nos. WO2011127255 or WO2008103276, each of which is herein incorporated by reference in their entirety. As a non-limiting example, modified RNA described herein may be encapsulated in LNP formulations as described in WO2011127255 and/or WO2008103276; each of which is herein incorporated by reference in their entirety.

In one embodiment, LNP formulations described herein may comprise a polycationic composition. As a non-limiting example, the polycationic composition may be selected from formula 1-60 of US Patent Publication No. US20050222064; herein incorporated by reference in its entirety. In another embodiment, the LNP formulations comprising a polycationic composition may be used for the delivery of the modified RNA described herein in vivo and/or in vitro.

In one embodiment, the LNP formulations described herein may additionally comprise a permeability enhancer molecule. Non-limiting permeability enhancer molecules are described in US Patent Publication No. US20050222064; herein incorporated by reference in its entirety.

In one embodiment, the pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713)) and hyaluronan-coated liposomes (Quiet Therapeutics, Israel).

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In one embodiment, the internal ester linkage may be located on either side of the saturated carbon. Non-limiting examples of reLNPs include, tion No. 20120189700 and International Publication No. WO2012099805; each of which is herein incorporated by reference in their entirety). The polymer may encapsulate the nanospecies or partially encapsulate the nanospecies.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosal tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. PNAS 2007 104(5):1482-487; Lai et al. Adv Drug Deliv Rev. 2009 61(2): 158-171; each of which is herein incorporated by reference in their entirety). The transport of nanoparticles may be determined using rates of permeation and/or fluorescent microscopy techniques including, but not limited to, fluorescence recovery after photobleaching (FRAP) and high resolution multiple particle tracking (MPT).

The lipid nanoparticle engineered to penetrate mucus may comprise a polymeric material (i.e. a polymeric core) and/or a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyim-

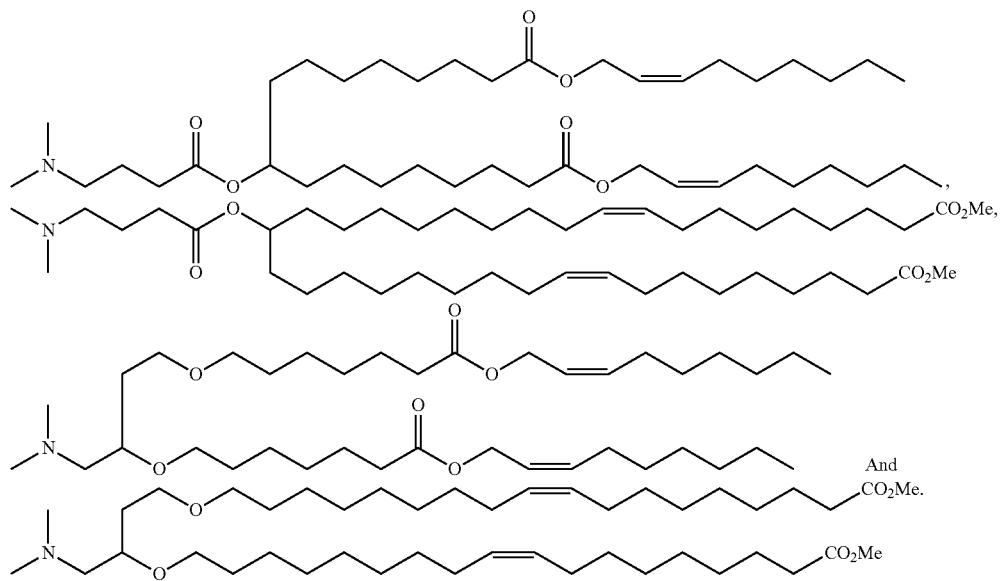

In one embodiment, an immune response may be elicited by delivering a lipid nanoparticle which may include a nanospecies, a polymer and an immunogen. (U.S. Publicaides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), and trimethylene carbonate, polyvinylpyrrolidone. The lipid nanoparticle may be coated or associated with a co-polymer such as, but not limited to, a block co-polymer, and (poly(ethylene glycol))-(poly(propylene oxide))-(poly(ethylene glycol)) triblock copolymer (see US Publication 20120121718 and US Publication 20100003337; each of which is herein incorporated by reference in their entirety). The co-polymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. Angew. Chem. Int. Ed. 2011 50:2597-2600; herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus may include surface altering agents such as, but not limited to, mmRNA, anionic protein (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase. The surface altering agent may be embedded or enmeshed in the particle's surface or disposed (e.g., by coating, adsorption, covalent linkage, or other process) on the surface of the lipid nanoparticle. (see US Publication 20100215580 and US Publication 20080166414; each of which is herein incorporated by reference in their entirety).

The mucus penetrating lipid nanoparticles may comprise at least one mmRNA described herein. The mmRNA may be encapsulated in the lipid nanoparticle and/or disposed on the surface of the particle. The mmRNA may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion which may increase the delivery of the mucus penetrating lipid nanoparticles to the mucosal tissue.

In one embodiment, the polynucleotide, primary construct, or mmRNA is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In one embodiment such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. Mol Ther. 2010 18:1357-1364; Song et al., Nat Biotechnol. 2005 23:709-717; Judge et al., J Clin Invest. 2009 119:661-673; Kaufmann et al., Microvasc Res 2010 80:286-293; Santel et al., Gene Ther 2006 13:1222-1234; Santel et al., Gene Ther 2006 13:1360-1370; Gutbier et al., Pulm Pharmacol. Ther. 2010 23:334-344; Basha et al., Mol. Ther. 2011 19:2186-2200; Fenske and Cullis, Expert Opin Drug Deliv. 2008 5:25-44; Peer et al., Science. 2008 319: 627-630; Peer and Lieberman, Gene Ther. 2011 18:1127-1133; all of which are incorporated herein by reference in its entirety). One example of passive targeting of formulations to liver cells includes the DLin-DMA, DLin-KC2-DMA and MC3-based lipid nanoparticle formulations which have been shown to bind to apolipoprotein E and promote binding and uptake of these formulations into hepatocytes in vivo (Akinc et al. Mol Ther. 2010 18:1357-1364; herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., Curr Drug Discov Technol. 2011 8:197-206; Musacchio and Torchilin, *Front Biosci*. 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714 Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721:339-353; Subramanya et al., Mol Ther. 2010 18:2028-2037; Song et al., Nat Biotechnol. 2005 23:709-717; Peer et al., Science. 2008 319:627-630; Peer and Lieberman, Gene Ther. 2011 18:1127-1133; all of which are incorporated herein by reference in its entirety).

In one embodiment, the polynucleotide, primary construct, or mmRNA is formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In a further embodiment, the lipid nanoparticle may be a self-assembly lipid-polymer nanoparticle (see Zhang et al., ACS Nano, 2008, 2 (8), pp 1696-1702; herein incorporated by reference in its entirety).

Liposomes, lipoplexes, or lipid nanoparticles may be used to improve the efficacy of polynucleotide, primary construct, or mmRNA directed protein production as these formulations may be able to increase cell transfection by the polynucleotide, primary construct, or mmRNA; and/or increase the translation of encoded protein. One such example involves the use of lipid encapsulation to enable the effective systemic delivery of polyplex plasmid DNA (Heyes et al., Mol Ther. 2007 15:713-720; herein incorporated by reference in its entirety). The liposomes, lipoplexes, or lipid nanoparticles may also be used to increase the stability of the polynucleotide, primary construct, or mmRNA.

In one embodiment, the polynucleotides, primary constructs, and/or the mmRNA of the present invention can be formulated for controlled release and/or targeted delivery. As used herein, "controlled release" refers to a pharmaceutical composition or compound release profile that conforms to a particular pattern of release to effect a therapeutic outcome. In one embodiment, the polynucleotides, primary constructs or the mmRNA may be encapsulated into a delivery agent described herein and/or known in the art for controlled release and/or targeted delivery. As used herein, the term "encapsulate" means to enclose, surround or encase. As it relates to the formulation of the compounds of the invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention may be enclosed, surrounded or encased within the delivery agent. "Partially encapsulation" means that less than 10, 10, 20, 30, 40 50 or less of the pharmaceutical composition or compound of the invention may be enclosed, surrounded or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the invention are encapsulated in the delivery agent.

In another embodiment, the polynucleotides, primary constructs, or the mmRNA may be encapsulated into a lipid nanoparticle or a rapidly eliminating lipid nanoparticle and the lipid nanoparticles or a rapidly eliminating lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.).

In one embodiment, the lipid nanoparticle may be encapsulated into any polymer or hydrogel known in the art which may form a gel when injected into a subject. As another non-limiting example, the lipid nanoparticle may be encapsulated into a polymer matrix which may be biodegradable.

In one embodiment, the polynucleotide, primary construct, or mmRNA formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In one embodiment, the controlled release and/or targeted delivery formulation may comprise at least one degradable polyester which may contain polycationic side chains. Degradable polyesters include, but are not limited to, poly (serine ester), poly(L-lactide-co-L-lysine), poly(4-hydroxy-L-proline ester), and combinations thereof. In another embodiment, the degradable polyesters may include a PEG conjugation to form a PEGylated polymer.

In one embodiment, the polynucleotides, primary constructs, and/or the mmRNA of the present invention may be encapsulated in a therapeutic nanoparticle. Therapeutic nanoparticles may be formulated by methods described herein and known in the art such as, but not limited to, International Pub Nos. WO2010005740, WO2010030763, WO2010005721, WO2010005723, WO2012054923, US Pub. Nos. US20110262491, US20100104645, US20100087337, US20100068285, US20110274759, US20100068286, and U.S. Pat. No. 8,206,747; each of which is herein incorporated by reference in their entirety. In another embodiment, therapeutic polymer nanoparticles may be identified by the methods described in US Pub No. US20120140790, herein incorporated by reference in its entirety.

In one embodiment, the therapeutic nanoparticle of may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the polynucleotides, primary constructs, and mmRNA of the present invention (see International Pub No.

2010075072 and US Pub No. US20100216804 and US20110217377, each of which is herein incorporated by reference in their entirety).

In one embodiment, the therapeutic nanoparticles may be formulated to be target specific. As a non-limiting example, the therapeutic nanoparticles may include a corticosteroid (see International Pub. No. WO2011084518). In one embodiment, the therapeutic nanoparticles may be formulated to be cancer specific. As a non-limiting example, the therapeutic nanoparticles may be formulated in nanoparticles described in International Pub No. WO2008121949, WO2010005726, WO2010005725, WO2011084521 and US Pub No. US20100069426, US20120004293 and US20100104655, each of which is herein incorporated by reference in their entirety.

In one embodiment, the nanoparticles of the present invention may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In one embodiment, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In one embodiment, the therapeutic nanoparticle comprises a diblock copolymer. As a non-limiting example the therapeutic nanoparticle comprises a PLGA-PEG block copolymer (see US Pub. No. US20120004293 and U.S. Pat. No. 8,236,330, herein incorporated by reference in their entireties). In another non-limiting example, the therapeutic nanoparticle is a stealth nanoparticle comprising a diblock copolymer of PEG and PLA or PEG and PLGA (see U.S. Pat. No. 8,246,968, each of which is herein incorporated by reference in its entirety).

In one embodiment, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly (acrylic acid), poly(methacrylic acid), polycyanoacrylates and combinations thereof.

In one embodiment, the therapeutic nanoparticles may comprise at least one cationic polymer described herein and/or known in the art.

In one embodiment, the therapeutic nanoparticles may comprise at least one amine-containing polymer such as, but not limited to polylysine, polyethylene imine, poly(amidoamine) dendrimers and combinations thereof.

In one embodiment, the therapeutic nanoparticles may comprise at least one degradable polyester which may contain polycationic side chains. Degradable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In another embodiment, the therapeutic nanoparticle may include a conjugation of at least one targeting ligand.

In one embodiment, the therapeutic nanoparticle may be formulated in an aqueous solution which may be used to target cancer (see International Pub No. WO2011084513 and US Pub No. US20110294717, each of which is herein incorporated by reference in their entirety).

In one embodiment, the polynucleotides, primary constructs, or mmRNA may be encapsulated in, linked to and/or associated with synthetic nanocarriers. The synthetic nanocarriers may be formulated using methods known in the art and/or described herein. As a non-limiting example, the synthetic nanocarriers may be formulated by the methods described in International Pub Nos. WO2010005740, WO2010030763 and US Pub. Nos. US20110262491, US20100104645 and US20100087337, each of which is herein incorporated by reference in their entirety. In another embodiment, the synthetic nanocarrier formulations may be lyophilized by methods described in International Pub. No. WO2011072218 and U.S. Pat. No. 8,211,473; each of which is herein incorporated by reference in their entireties.

In one embodiment, the synthetic nanocarriers may contain reactive groups to release the polynucleotides, primary constructs and/or mmRNA described herein (see International Pub. No. WO20120952552 and US Pub No. US20120171229, each of which is herein incorporated by reference in their entirety).

In one embodiment, the synthetic nanocarriers may contain an immunostimulatory agent to enhance the immune response from delivery of the synthetic nanocarrier. As a non-limiting example, the synthetic nanocarrier may comprise a Th1 immunostimulatory agent which may enhance a Th1-based response of the immune system (see International Pub No. WO2010123569 and US Pub. No. US20110223201, each of which is herein incorporated by reference in its entirety).

In one embodiment, the synthetic nanocarriers may be formulated for targeted release. In one embodiment, the synthetic nanocarrier is formulated to release the polynucleotides, primary constructs and/or mmRNA at a specified pH and/or after a desired time interval. As a non-limiting example, the synthetic nanoparticle may be formulated to release the polynucleotides, primary constructs and/or mmRNA after 24 hours and/or at a pH of 4.5 (see International Pub. Nos. WO2010138193 and WO2010138194 and US Pub Nos. US20110020388 and US20110027217, each of which is herein incorporated by reference in their entireties).

In one embodiment, the synthetic nanocarriers may be formulated for controlled and/or sustained release of the polynucleotides, primary constructs and/or mmRNA described herein. As a non-limiting example, the synthetic nanocarriers for sustained release may be formulated by methods known in the art, described herein and/or as described in International Pub No. WO2010138192 and US Pub No. 20100303850, each of which is herein incorporated by reference in their entireties.

Polymers, Biodegradable Nanoparticles, and Core-Shell Nanoparticles

The polynucleotide, primary construct, and mmRNA of the invention can be formulated using natural and/or synthetic polymers. Non-limiting examples of polymers which may be used for delivery include, but are not limited to, Dynamic POLYCONJUGATE™ formulations from MIRUS® Bio (Madison, Wis.) and Roche Madison (Madison, Wis.), PHASERX™ polymer formulations such as, without limitation, SMARTT POLYMER TECHNOLOGY™ (Seattle, Wash.), DMRI/DOPE, poloxamer, VAXFECTIN® adjuvant from Vical (San Diego, Calif.), chitosan, cyclodextrin from Calando Pharmaceuticals (Pasadena, Calif.), dendrimers and poly(lactic-co-glycolic acid) (PLGA) polymers. RONDEL™ (RNAi/Oligonucleotide Nanoparticle Delivery) polymers (Arrowhead Research Corporation, Pasadena, Calif.) and pH responsive co-block polymers such as, but not limited to, PHASERX™ (Seattle, Wash.).

A non-limiting example of PLGA formulations include, but are not limited to, PLGA injectable depots (e.g., ELIGARD® which is formed by dissolving PLGA in 66% N-methyl-2-pyrrolidone (NMP) and the remainder being aqueous solvent and leuprolide. Once injected, the PLGA and leuprolide peptide precipitates into the subcutaneous space).

Many of these polymer approaches have demonstrated efficacy in delivering oligonucleotides in vivo into the cell cytoplasm (reviewed in deFougerolles *Hum Gene Ther.* 2008 19:125-132; herein incorporated by reference in its entirety). Two polymer approaches that have yielded robust in vivo delivery of nucleic acids, in this case with small interfering RNA (siRNA), are dynamic polyconjugates and cyclodextrin-based nanoparticles. The first of these delivery approaches uses dynamic polyconjugates and has been shown in vivo in mice to effectively deliver siRNA and silence endogenous target mRNA in hepatocytes (Rozema et al., Proc Natl Acad Sci USA. 2007 104:12982-12887). This particular approach is a multicomponent polymer system whose key features include a membrane-active polymer to which nucleic acid, in this case siRNA, is covalently coupled via a disulfide bond and where both PEG (for charge masking) and N-acetylgalactosamine (for hepatocyte targeting) groups are linked via pH-sensitive bonds (Rozema et al., Proc Natl Acad Sci USA. 2007 104:12982-12887). On binding to the hepatocyte and entry into the endosome, the polymer complex disassembles in the low-pH environment, with the polymer exposing its positive charge, leading to endosomal escape and cytoplasmic release of the siRNA from the polymer. Through replacement of the N-acetylgalactosamine group with a mannose group, it was shown one could alter targeting from asialoglycoprotein receptor-expressing hepatocytes to sinusoidal endothelium and Kupffer cells. Another polymer approach involves using transferrin-targeted cyclodextrin-containing polycation nanoparticles. These nanoparticles have demonstrated targeted silencing of the EWS-FLI1 gene product in transferrin receptor-expressing Ewing's sarcoma tumor cells (Hu-Lieskovan et al., Cancer Res. 2005 65: 8984-8982) and siRNA formulated in these nanoparticles was well tolerated in non-human primates (Heidel et al., Proc Natl Acad Sci USA 2007 104: 5715-21). Both of these delivery strategies incorporate rational approaches using both targeted delivery and endosomal escape mechanisms.

The polymer formulation can permit the sustained or delayed release of the polynucleotide, primary construct, or mmRNA (e.g., following intramuscular or subcutaneous injection). The altered release profile for the polynucleotide, primary construct, or mmRNA can result in, for example, translation of an encoded protein over an extended period of time. The polymer formulation may also be used to increase the stability of the polynucleotide, primary construct, or mmRNA. Biodegradable polymers have been previously used to protect nucleic acids other than mmRNA from degradation and been shown to result in sustained release of payloads in vivo (Rozema et al., Proc Natl Acad Sci USA. 2007 104:12982-12887; Sullivan et al., Expert Opin Drug Deliv. 2010 7:1433-1446; Convertine et al., Biomacromolecules. 2010 Oct. 1; Chu et al., Acc Chem Res. 2012 Jan. 13; Manganiello et al., Biomaterials. 2012 33:2301-2309; Benoit et al., Biomacromolecules. 2011 12:2708-2714; Singha et al., Nucleic Acid Ther. 2011 2:133-147; deFougerolles Hum Gene Ther. 2008 19:125-132; Schaffert and Wagner, Gene Ther. 2008 16:1131-1138; Chaturvedi et al., Expert Opin Drug Deliv. 2011 8:1455-1468; Davis, Mol Pharm. 2009 6:659-668; Davis, Nature 2010 464:1067-1070; each of which is herein incorporated by reference in its entirety).

In one embodiment, the pharmaceutical compositions may be sustained release formulations. In a further embodiment, the sustained release formulations may be for subcutaneous delivery. Sustained release formulations may include, but are not limited to, PLGA microspheres, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TISSELL® (Baxter International, Inc Deerfield, Ill.), PEG-based sealants, and COSEAL® (Baxter International, Inc Deerfield, Ill.).

As a non-limiting example modified mRNA may be formulated in PLGA microspheres by preparing the PLGA microspheres with tunable release rates (e.g., days and weeks) and encapsulating the modified mRNA in the PLGA microspheres while maintaining the integrity of the modified mRNA during the encapsulation process. EVAc are non-biodegradable, biocompatible polymers which are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C. PEG-based surgical sealants comprise two synthetic PEG components mixed in a delivery device which can be prepared in one minute, seals in 3 minutes and is reabsorbed within 30 days. GELSITE® and natural polymers are capable of in-situ gelation at the site of administration. They have been shown to interact with protein and peptide therapeutic candidates through ionic interaction to provide a stabilizing effect.

Polymer formulations can also be selectively targeted through expression of different ligands as exemplified by, but not limited by, folate, transferrin, and N-acetylgalactosamine (GalNAc) (Benoit et al., Biomacromolecules. 2011 12:2708-2714; Rozema et al., Proc Natl Acad Sci USA. 2007 104:12982-12887; Davis, Mol Pharm. 2009 6:659-668; Davis, Nature 2010 464:1067-1070; each of which is herein incorporated by reference in its entirety).

The polynucleotides, primary constructs and/or mmRNA of the invention may be formulated with or in a polymeric compound. The polymer may include at least one polymer such as, but not limited to, polyethenes, polyethylene glycol (PEG), poly(l-lysine)(PLL), PEG grafted to PLL, cationic lipopolymer, biodegradable cationic lipopolymer, polyethyleneimine (PEI), cross-linked branched poly(alkylene imines), a polyamine derivative, a modified poloxamer, a biodegradable polymer, biodegradable block copolymer, biodegradable random copolymer, biodegradable polyester copolymer, biodegradable polyester block copolymer, biodegradable polyester block random copolymer, linear biodegradable copolymer, poly[α-(4-aminobutyl)-L-glycolic acid) (PAGA), biodegradable cross-linked cationic multi-block copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester), acrylic polymers, amine-containing polymers or combinations thereof.

As a non-limiting example, the polynucleotides, primary constructs and/or mmRNA of the invention may be formulated with the polymeric compound of PEG grafted with PLL as described in U.S. Pat. No. 6,177,274 herein incorporated by reference in its entirety. The formulation may be used for transfecting cells in vitro or for in vivo delivery of the polynucleotides, primary constructs and/or mmRNA. In another example, the polynucleotides, primary constructs and/or mmRNA may be suspended in a solution or medium with a cationic polymer, in a dry pharmaceutical composition or in a solution that is capable of being dried as described in U.S. Pub. Nos. 20090042829 and 20090042825 each of which are herein incorporated by reference in their entireties.

As another non-limiting example the polynucleotides, primary constructs or mmRNA of the invention may be formulated with a PLGA-PEG block copolymer (see US Pub. No. US20120004293 and U.S. Pat. No. 8,236,330, each of which is herein incorporated by reference in their entireties). As a non-limiting example, the polynucleotides, primary constructs or mmRNA of the invention may be formulated with a diblock copolymer of PEG and PLA or PEG and PLGA (see U.S. Pat. No. 8,246,968, herein incorporated by reference in its entirety).

A polyamine derivative may be used to deliver nucleic acids or to treat and/or prevent a disease or to be included in an implantable or injectable device (U.S. Pub. No. 20100260817 herein incorporated by reference in its entirety). As a non-limiting example, a pharmaceutical composition may include the modified nucleic acids and mmRNA and the polyamine derivative described in U.S. Pub. No. 20100260817 (the contents of which are incorporated herein by reference in its entirety.

The polynucleotides, primary constructs or mmRNA of the invention may be formulated with at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), polycyanoacrylates and combinations thereof.

In one embodiment, the polynucleotides, primary constructs or mmRNA of the present invention may be formulated with at least one polymer described in International Publication Nos. WO201115862, WO2012082574 and WO2012068187, each of which is herein incorporated by reference in their entireties. In another embodiment the polynucleotides, primary constructs or mmRNA of the present invention may be formulated with a polymer of formula Z as described in WO201115862, herein incorporated by reference in its entirety. In yet another embodiment, the polynucleotides, primary constructs or mmRNA may be formulated with a polymer of formula Z, Z' or Z" as described in WO2012082574 or WO2012068187, each of which are herein incorporated by reference in their entireties. The polymers formulated with the modified RNA of the present invention may be synthesized by the methods described in WO2012082574 or WO2012068187, each of which is herein incorporated by reference in their entireties.

Formulations of polynucleotides, primary constructs or mmRNA of the invention may include at least one amine-containing polymer such as, but not limited to polylysine, polyethylene imine, poly(amidoamine) dendrimers or combinations thereof.

For example, the polynucleotides, primary constructs and/or mmRNA of the invention may be formulated in a pharmaceutical compound including a poly(alkylene imine), a biodegradable cationic lipopolymer, a biodegradable block copolymer, a biodegradable polymer, or a biodegradable random copolymer, a biodegradable polyester block copolymer, a biodegradable polyester polymer, a biodegradable polyester random copolymer, a linear biodegradable copolymer, PAGA, a biodegradable cross-linked cationic multi-block copolymer or combinations thereof. The biodegradable cationic lipopolymer may be made my methods known in the art and/or described in U.S. Pat. No. 6,696,038, U.S. App. Nos. 20030073619 and 20040142474 each of which is herein incorporated by reference in their entireties. The poly(alkylene imine) may be made using methods known in the art and/or as described in U.S. Pub. No. 20100004315, herein incorporated by reference in its entirety. The biodegradable polymer, biodegradable block copolymer, the biodegradable random copolymer, biodegradable polyester block copolymer, biodegradable polyester polymer, or biodegradable polyester random copolymer may be made using methods known in the art and/or as described in U.S. Pat. Nos. 6,517,869 and 6,267,987, the contents of which are each incorporated herein by reference in its entirety. The linear biodegradable copolymer may be made using methods known in the art and/or as described in U.S. Pat. No. 6,652,886. The PAGA polymer may be made using methods known in the art and/or as described in U.S. Pat. No. 6,217,912 herein incorporated by reference in its entirety. The PAGA polymer may be copolymerized to form a copolymer or block copolymer with polymers such as but not limited to, poly-L-lysine, polyarginine, polyornithine, histones, avidin, protamines, polylactides and poly(lactide-co-glycolides). The biodegradable cross-linked cationic multi-block copolymers may be made my methods known in the art and/or as described in U.S. Pat. No. 8,057,821 or U.S. Pub. No. 2012009145 each of which is herein incorporated by reference in their entireties. For example, the multi-block copolymers may be synthesized using linear polyethyleneimine (LPEI) blocks which have distinct patterns as compared to branched polyethyleneimines. Further, the composition or pharmaceutical composition may be made by the methods known in the art, described herein, or as described in U.S. Pub. No. 20100004315 or U.S. Pat. Nos. 6,267,987 and 6,217,912 each of which is herein incorporated by reference in their entireties.

The polynucleotides, primary constructs, and mmRNA of the invention may be formulated with at least one degradable polyester which may contain polycationic side chains. Degradable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In one embodiment, the polymers described herein may be conjugated to a lipid-terminating PEG. As a non-limiting example, PLGA may be conjugated to a lipid-terminating PEG forming PLGA-DSPE-PEG. As another non-limiting example, PEG conjugates for use with the present invention are described in International Publication No. WO2008103276, herein incorporated by reference in its entirety.

In one embodiment, the polynucleotides, primary constructs and/or mmRNA described herein may be conjugated with another compound. Non-limiting examples of conjugates are described in U.S. Pat. Nos. 7,964,578 and 7,833,992, each of which are herein incorporated by reference in their entireties. In another embodiment, the polynucleotides, primary constructs and/or mmRNA of the present invention may be conjugated with conjugates of formula 1-122 as described in U.S. Pat. Nos. 7,964,578 and 7,833,992, each of which are herein incorporated by reference in their entireties.

As described in U.S. Pub. No. 20100004313, herein incorporated by reference in its entirety, a gene delivery composition may include a nucleotide sequence and a poloxamer. For example, the polynucleotide, primary construct and/or mmRNA of the present invention may be used in a gene delivery composition with the poloxamer described in U.S. Pub. No. 20100004313.

In one embodiment, the polymer formulation of the present invention may be stabilized by contacting the polymer formulation, which may include a cationic carrier, with a cationic lipopolymer which may be covalently linked to cholesterol and polyethylene glycol groups. The polymer formulation may be contacted with a cationic lipopolymer using the methods described in U.S. Pub. No. 20090042829 herein incorporated by reference in its entirety. The cationic carrier may include, but is not limited to, polyethylenimine, poly(trimethylenimine), poly(tetramethylenimine), polypropylenimine, aminoglycoside-polyamine, dideoxy-diamino-b-cyclodextrin, spermine, spermidine, poly(2-dimethylamino)ethyl methacrylate, poly(lysine), poly(histidine), poly(arginine), cationized gelatin, dendrimers, chitosan, 1,2-Dioleoyl-3-Trimethylammonium-Propane (DOTAP), N-[1-(2,3-dioleoyloxy)propyl]-N,N,N-trimethylammonium chloride (DOTMA), 1-[2-(oleoyloxy)ethyl]-2-oleyl-3-(2-hydroxyethyl)imidazolinium chloride (DOTIM), 2,3-dioleyloxy-N-[2(sperminecarboxamido)ethyl]-N,N-dimethyl-1-propanaminium trifluoroacetate (DOSPA), 3B—[N—(N',N'-Dimethylaminoethane)-carbamoyl]Cholesterol Hydrochloride (DC-Cholesterol HCl) diheptadecylamidoglycyl spermidine (DOGS), N,N-distearyl-N,N-dimethylammonium bromide (DDAB), N-(1,2-dimyristyloxyprop-3-yl)-N,N-dimethyl-N-hydroxyethyl ammonium bromide (DMRIE), N,N-dioleyl-N,N-dimethylammonium chloride DODAC) and combinations thereof.

The polynucleotide, primary construct, and mmRNA of the invention can also be formulated as a nanoparticle using a combination of polymers, lipids, and/or other biodegradable agents, such as, but not limited to, calcium phosphate. Components may be combined in a core-shell, hybrid, and/or layer-by-layer architecture, to allow for fine-tuning of the nanoparticle so to delivery of the polynucleotide, primary construct and mmRNA may be enhanced (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in its entirety).

Biodegradable calcium phosphate nanoparticles in combination with lipids and/or polymers have been shown to deliver polynucleotides, primary constructs and mmRNA in vivo. In one embodiment, a lipid coated calcium phosphate nanoparticle, which may also contain a targeting ligand such as anisamide, may be used to deliver the polynucleotide, primary construct and mmRNA of the present invention. For example, to effectively deliver siRNA in a mouse metastatic lung model a lipid coated calcium phosphate nanoparticle was used (Li et al., J Contr Rel. 2010 142: 416-421; Li et al., J Contr Rel. 2012 158:108-114; Yang et al., Mol Ther. 2012 20:609-615). This delivery system combines both a targeted nanoparticle and a component to enhance the endosomal escape, calcium phosphate, in order to improve delivery of the siRNA.

In one embodiment, calcium phosphate with a PEG-polyanion block copolymer may be used to delivery polynucleotides, primary constructs and mmRNA (Kazikawa et al., J Contr Rel. 2004 97:345-356; Kazikawa et al., J Contr Rel. 2006 111:368-370).

In one embodiment, a PEG-charge-conversional polymer (Pitella et al., Biomaterials. 2011 32:3106-3114) may be used to form a nanoparticle to deliver the polynucleotides, primary constructs and mmRNA of the present invention. The PEG-charge-conversional polymer may improve upon the PEG-polyanion block copolymers by being cleaved into a polycation at acidic pH, thus enhancing endosomal escape.

The use of core-shell nanoparticles has additionally focused on a high-throughput approach to synthesize cationic cross-linked nanogel cores and various shells (Siegwart et al., Proc Natl Acad Sci USA. 2011 108:12996-13001). The complexation, delivery, and internalization of the polymeric nanoparticles can be precisely controlled by altering the chemical composition in both the core and shell components of the nanoparticle. For example, the core-shell nanoparticles may efficiently deliver siRNA to mouse hepatocytes after they covalently attach cholesterol to the nanoparticle.

In one embodiment, a hollow lipid core comprising a middle PLGA layer and an outer neutral lipid layer containing PEG may be used to delivery of the polynucleotide, primary construct and mmRNA of the present invention. As a non-limiting example, in mice bearing a luciferase-expressing tumor, it was determined that the lipid-polymer-lipid hybrid nanoparticle significantly suppressed luciferase expression, as compared to a conventional lipoplex (Shi et al, Angew Chem Int Ed. 2011 50:7027-7031).

Peptides and Proteins

The synthetic polynucleotides and/or synthetic sgRNAs of the invention can be formulated with peptides and/or proteins in order to increase transfection of cells by the polynucleotide, primary construct, or mmRNA. In one embodiment, peptides such as, but not limited to, cell penetrating peptides and proteins and peptides that enable intracellular delivery may be used to deliver pharmaceutical formulations. A non-limiting example of a cell penetrating peptide which may be used with the pharmaceutical formulations of the present invention includes a cell-penetrating peptide sequence attached to polycations that facilitates delivery to the intracellular space, e.g., HIV-derived TAT peptide, penetratins, transportans, or hCT derived cell-penetrating peptides (see, e.g., Caron et al., Mol. Ther. 3(3): 310-8 (2001); Langel, Cell-Penetrating Peptides: Processes and Applications (CRC Press, Boca Raton Fla., 2002); El-Andaloussi et al., Curr. Pharm. Des. 11(28):3597-611 (2003); and Deshayes et al., Cell. Mol. Life Sci. 62(16): 1839-49 (2005), all of which are incorporated herein by reference). The compositions can also be formulated to include a cell penetrating agent, e.g., liposomes, which enhance delivery of the compositions to the intracellular space. polynucleotides, primary constructs, and mmRNA of the invention may be complexed to peptides and/or proteins such as, but not limited to, peptides and/or proteins from Aileron Therapeutics (Cambridge, Mass.) and Permeon Biologics (Cambridge, Mass.) in order to enable intracellular delivery (Cronican et al., ACS Chem. Biol. 2010 5:747-752; McNaughton et al., Proc. Natl. Acad. Sci. USA 2009 106: 6111-6116; Sawyer, Chem Biol Drug Des. 2009 73:3-6; Verdine and Hilinski, Methods Enzymol. 2012; 503:3-33; all of which are herein incorporated by reference in its entirety).

In one embodiment, the cell-penetrating polypeptide may comprise a first domain and a second domain. The first domain may comprise a supercharged polypeptide. The second domain may comprise a protein-binding partner. As used herein, "protein-binding partner" includes, but are not limited to, antibodies and functional fragments thereof, scaffold proteins, or peptides. The cell-penetrating polypeptide may further comprise an intracellular binding partner for the protein-binding partner. The cell-penetrating polypeptide may be capable of being secreted from a cell where the polynucleotide, primary construct, or mmRNA may be introduced.

Formulations of the including peptides or proteins may be used to increase cell transfection by the polynucleotide, primary construct, or mmRNA, alter the biodistribution of the polynucleotide, primary construct, or mmRNA (e.g., by targeting specific tissues or cell types), and/or increase the translation of encoded protein.

Cells

The polynucleotide, primary construct, and mmRNA of the invention can be transfected ex vivo into cells, which are subsequently transplanted into a subject. As non-limiting examples, the pharmaceutical compositions may include red blood cells to deliver modified RNA to liver and myeloid cells, virosomes to deliver modified RNA in virus-like particles (VLPs), and electroporated cells such as, but not limited to, from MAXCYTE® (Gaithersburg, Md.) and from ERYTECH® (Lyon, France) to deliver modified RNA. Examples of use of red blood cells, viral particles and electroporated cells to deliver payloads other than mmRNA have been documented (Godfrin et al., Expert Opin Biol Ther. 2012 12:127-133; Fang et al., Expert Opin Biol Ther. 2012 12:385-389; Hu et al., Proc Natl Acad Sci USA. 2011 108:10980-10985; Lund et al., Pharm Res. 2010 27:400-420; Huckriede et al., J Liposome Res. 2007; 17:39-47; Cusi, Hum Vaccin. 2006 2:1-7; de Jonge et al., Gene Ther. 2006 13:400-411; all of which are herein incorporated by reference in its entirety).

The polynucleotides, primary constructs and mmRNA may be delivered in synthetic VLPs synthesized by the methods described in International Pub No. WO2011085231 and US Pub No. 20110171248, each of which is herein incorporated by reference in their entireties.

Cell-based formulations of the polynucleotide, primary construct, and mmRNA of the invention may be used to ensure cell transfection (e.g., in the cellular carrier), alter the biodistribution of the polynucleotide, primary construct, or mmRNA (e.g., by targeting the cell carrier to specific tissues or cell types), and/or increase the translation of encoded protein.

A variety of methods are known in the art and suitable for introduction of nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

The technique of sonoporation, or cellular sonication, is the use of sound (e.g., ultrasonic frequencies) for modifying the permeability of the cell plasma membrane. Sonoporation methods are known to those in the art and are used to deliver nucleic acids in vivo (Yoon and Park, Expert Opin Drug Deliv. 2010 7:321-330; Postema and Gilja, Curr Pharm Biotechnol. 2007 8:355-361; Newman and Bettinger, Gene Ther. 2007 14:465-475; all herein incorporated by reference in their entirety). Sonoporation methods are known in the art and are also taught for example as it relates to bacteria in US Patent Publication 20100196983 and as it relates to other cell types in, for example, US Patent Publication 20100009424, each of which are incorporated herein by reference in their entirety.

Electroporation techniques are also well known in the art and are used to deliver nucleic acids in vivo and clinically (Andre et al., Curr Gene Ther. 2010 10:267-280; Chiarella et al., Curr Gene Ther. 2010 10:281-286; Hojman, Curr Gene Ther. 2010 10:128-138; all herein incorporated by reference in their entirety). In one embodiment, polynucleotides, primary constructs or mmRNA may be delivered by electroporation as described in Example 26.

Hyaluronidase

The intramuscular or subcutaneous localized injection of polynucleotide, primary construct, or mmRNA of the invention can include hyaluronidase, which catalyzes the hydrolysis of hyaluronan. By catalyzing the hydrolysis of hyaluronan, a constituent of the interstitial barrier, hyaluronidase lowers the viscosity of hyaluronan, thereby increasing tissue permeability (Frost, Expert Opin. Drug Deliv. (2007) 4:427-440; herein incorporated by reference in its entirety). It is useful to speed their dispersion and systemic distribution of encoded proteins produced by transfected cells. Alternatively, the hyaluronidase can be used to increase the number of cells exposed to a polynucleotide, primary construct, or mmRNA of the invention administered intramuscularly or subcutaneously.

Nanoparticle Mimics

The polynucleotide, primary construct or mmRNA of the invention may be encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example the polynucleotide, primary construct or mmRNA of the invention may be encapsulated in a non-viron particle which can mimic the delivery function of a virus (see International Pub. No. WO2012006376 herein incorporated by reference in its entirety).

Nanotubes

The polynucleotides, primary constructs or mmRNA of the invention can be attached or otherwise bound to at least one nanotube such as, but not limited to, rosette nanotubes, rosette nanotubes having twin bases with a linker, carbon nanotubes and/or single-walled carbon nanotubes, The polynucleotides, primary constructs or mmRNA may be bound to the nanotubes through forces such as, but not limited to, steric, ionic, covalent and/or other forces.

In one embodiment, the nanotube can release one or more polynucleotides, primary constructs or mmRNA into cells. The size and/or the surface structure of at least one nanotube may be altered so as to govern the interaction of the nanotubes within the body and/or to attach or bind to the polynucleotides, primary constructs or mmRNA disclosed herein. In one embodiment, the building block and/or the functional groups attached to the building block of the at least one nanotube may be altered to adjust the dimensions and/or properties of the nanotube. As a non-limiting example, the length of the nanotubes may be altered to hinder the nanotubes from passing through the holes in the walls of normal blood vessels but still small enough to pass through the larger holes in the blood vessels of tumor tissue.

In one embodiment, at least one nanotube may also be coated with delivery enhancing compounds including polymers, such as, but not limited to, polyethylene glycol. In another embodiment, at least one nanotube and/or the polynucleotides, primary constructs or mmRNA may be mixed with pharmaceutically acceptable excipients and/or delivery vehicles.

In one embodiment, the polynucleotides, primary constructs or mmRNA are attached and/or otherwise bound to at least one rosette nanotube. The rosette nanotubes may be formed by a process known in the art and/or by the process described in International Publication No. WO2012094304, herein incorporated by reference in its entirety. At least one polynucleotide, primary construct and/or mmRNA may be attached and/or otherwise bound to at least one rosette nanotube by a process as described in International Publication No. WO2012094304, herein incorporated by reference in its entirety, where rosette nanotubes or modules forming rosette nanotubes are mixed in aqueous media with at least one polynucleotide, primary construct and/or mmRNA under conditions which may cause at least one polynucleotide, primary construct or mmRNA to attach or otherwise bind to the rosette nanotubes.

Conjugates

The polynucleotides, primary constructs, and mmRNA of the invention include conjugates, such as a polynucleotide, primary construct, or mmRNA covalently linked to a carrier or targeting group, or including two encoding regions that together produce a fusion protein (e.g., bearing a targeting group and therapeutic protein or peptide).

The conjugates of the invention include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Representative U.S. patents that teach the preparation of polynucleotide conjugates, particularly to RNA, include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; each of which is herein incorporated by reference in their entireties.

In one embodiment, the conjugate of the present invention may function as a carrier for the polynucleotides, primary constructs and/or mmRNA of the present invention. The conjugate may comprise a cationic polymer such as, but not limited to, polyamine, polylysine, polyalkylenimine, and polyethylenimine which may be grafted to with poly(ethylene glycol). As a non-limiting example, the conjugate may be similar to the polymeric conjugate and the method of synthesizing the polymeric conjugate described in U.S. Pat. No. 6,586,524 herein incorporated by reference in its entirety.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Targeting groups may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent fucose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, aptamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein.

In one embodiment, pharmaceutical compositions of the present invention may include chemical modifications such as, but not limited to, modifications similar to locked nucleic acids.

Representative U.S. patents that teach the preparation of locked nucleic acid (LNA) such as those from Santaris, include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include polynucleotides, primary constructs or mmRNA with phosphorothioate backbones and oligonucleosides with other modified backbones, and in particular —CH$_2$—NH—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —N(CH$_3$)—CH$_2$—CH$_2$— [wherein the native phosphodiester backbone is represented as —O—P(O)$_2$—O—CH$_2$—] of the above-referenced U.S. Pat. No. 5,489,677, and the amide backbones of the above-referenced U.S. Pat. No. 5,602,240. In some embodiments, the polynucleotides featured herein have morpholino backbone structures of the above-referenced U.S. Pat. No. 5,034,506.

Modifications at the 2' position may also aid in delivery. Preferably, modifications at the 2' position are not located in a polypeptide-coding sequence, i.e., not in a translatable region. Modifications at the 2' position may be located in a 5'UTR, a 3'UTR and/or a tailing region. Modifications at the 2' position can include one of the following at the 2' position: H (i.e., 2'-deoxy); F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Exemplary suitable modifications include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. In other embodiments, the polynucleotides, primary constructs or mmRNA include one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties, or a group for improving the pharmacodynamic properties, and other substituents having similar properties. In some embodiments, the modification includes a 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$, also described in examples herein below. Other modifications include 2'-methoxy (2'-OCH$_3$), 2'-aminopropoxy (2'-OCH$_2$CH$_2$CH$_2$NH$_2$) and 2'-fluoro (2'-F). Similar modifications may also be made at other positions, particularly the 3' position of the sugar on the 3' terminal nucleotide or in 2'-5' linked dsRNAs and the 5' position of 5' terminal nucleotide. Polynucleotides of the invention may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920 and each of which is herein incorporated by reference.

In still other embodiments, the polynucleotide, primary construct, or mmRNA is covalently conjugated to a cell penetrating polypeptide. The cell-penetrating peptide may also include a signal sequence. The conjugates of the invention can be designed to have increased stability; increased cell transfection; and/or altered the biodistribution (e.g., targeted to specific tissues or cell types).

Self-Assembled Nucleic Acid Nanoparticles

Self-assembled nanoparticles have a well-defined size which may be precisely controlled as the nucleic acid strands may be easily reprogrammable. For example, the optimal particle size for a cancer-targeting nanodelivery carrier is 20-100 nm as a diameter greater than 20 nm avoids renal clearance and enhances delivery to certain tumors through enhanced permeability and retention effect. Using self-assembled nucleic acid nanoparticles a single uniform population in size and shape having a precisely controlled spatial orientation and density of cancer-targeting ligands for enhanced delivery. As a non-limiting example, oligonucleotide nanoparticles are prepared using programmable self-assembly of short DNA fragments and therapeutic siRNAs. These nanoparticles are molecularly identical with controllable particle size and target ligand location and density. The DNA fragments and siRNAs self-assembled into a one-step reaction to generate DNA/siRNA tetrahedral nanoparticles for targeted in vivo delivery. (Lee et al., Nature Nanotechnology 2012 7:389-393).

Excipients

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical compositions.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEENn®60], polyoxyethylene sorbitan monooleate [TWEEN®80], sorbitan monopalmitate [SPAN®40], sorbitan monostearate [Span®60], sorbitan tristearate [Span®65], glyceryl monooleate, sorbitan monooleate [SPAN®80]), polyoxyethylene esters (e.g. polyoxyethylene monostearate [MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLUORINC®F 68, POLOXAMER®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN®II, NEOLONE™, KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Excipients such as cocoa butter and suppository waxes, coloring agents, coating agents, sweetening, flavoring, and/or perfuming agents can be present in the composition, according to the judgment of the formulator.

Delivery

The present disclosure encompasses the delivery of polynucleotides, primary constructs or mmRNA for any of therapeutic, pharmaceutical, diagnostic or imaging by any appropriate route taking into consideration likely advances in the sciences of drug delivery. Delivery may be naked or formulated.

Naked Delivery

The polynucleotides, primary constructs or mmRNA of the present invention may be delivered to a cell naked. As used herein in, "naked" refers to delivering polynucleotides, primary constructs or mmRNA free from agents which promote transfection. For example, the polynucleotides, primary constructs or mmRNA delivered to the cell may contain no modifications. The naked polynucleotides, primary constructs or mmRNA may be delivered to the cell using routes of administration known in the art and described herein.

Formulated Delivery

The polynucleotides, primary constructs or mmRNA of the present invention may be formulated, using the methods described herein. The formulations may contain polynucleotides, primary constructs or mmRNA which may be modified and/or unmodified. The formulations may further include, but are not limited to, cell penetration agents, a pharmaceutically acceptable carrier, a delivery agent, a bioerodible or biocompatible polymer, a solvent, and a sustained-release delivery depot. The formulated polynucleotides, primary constructs or mmRNA may be delivered to the cell using routes of administration known in the art and described herein.

The compositions may also be formulated for direct delivery to an organ or tissue in any of several ways in the art including, but not limited to, direct soaking or bathing, via a catheter, by gels, powder, ointments, creams, gels, lotions, and/or drops, by using substrates such as fabric or biodegradable materials coated or impregnated with the compositions, and the like.

Administration

The polynucleotides, primary constructs or mmRNA of the present invention may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compositions may be administered in a way which allows them cross the blood-brain barrier, vascular barrier, or other epithelial barrier. Non-limiting routes of administration for the polynucleotides, primary constructs or mmRNA of the present invention are described below.

Parenteral and Injectible Administration

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Rectal and Vaginal Administration

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Oral Administration

Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents.

Topical or Transdermal Administration

As described herein, compositions containing the polynucleotides, primary constructs or mmRNA of the invention may be formulated for administration topically. The skin may be an ideal target site for delivery as it is readily accessible. Gene expression may be restricted not only to the skin, potentially avoiding nonspecific toxicity, but also to specific layers and cell types within the skin.

The site of cutaneous expression of the delivered compositions will depend on the route of nucleic acid delivery. Three routes are commonly considered to deliver polynucleotides, primary constructs or mmRNA to the skin: (i) topical application (e.g. for local/regional treatment and/or cosmetic applications); (ii) intradermal injection (e.g. for local/regional treatment and/or cosmetic applications); and (iii) systemic delivery (e.g. for treatment of dermatologic diseases that affect both cutaneous and extracutaneous regions). polynucleotides, primary constructs or mmRNA can be delivered to the skin by several different approaches known in the art. Most topical delivery approaches have been shown to work for delivery of DNA, such as but not limited to, topical application of non-cationic liposome-DNA complex, cationic liposome-DNA complex, particle-mediated (gene gun), puncture-mediated gene transfections, and viral delivery approaches. After delivery of the nucleic acid, gene products have been detected in a number of different skin cell types, including, but not limited to, basal keratinocytes, sebaceous gland cells, dermal fibroblasts and dermal macrophages.

In one embodiment, the invention provides for a variety of dressings (e.g., wound dressings) or bandages (e.g., adhesive bandages) for conveniently and/or effectively carrying out methods of the present invention. Typically dressing or bandages may comprise sufficient amounts of pharmaceutical compositions and/or polynucleotides, primary constructs or mmRNA described herein to allow a user to perform multiple treatments of a subject(s).

In one embodiment, the invention provides for the polynucleotides, primary constructs or mmRNA compositions to be delivered in more than one injection.

In one embodiment, before topical and/or transdermal administration at least one area of tissue, such as skin, may be subjected to a device and/or solution which may increase permeability. In one embodiment, the tissue may be subjected to an abrasion device to increase the permeability of the skin (see U.S. Patent Publication No. 20080275468, herein incorporated by reference in its entirety). In another embodiment, the tissue may be subjected to an ultrasound enhancement device. An ultrasound enhancement device may include, but is not limited to, the devices described in U.S. Publication No. 20040236268 and U.S. Pat. Nos. 6,491,657 and 6,234,990; each of which is herein incorporated by reference in their entireties. Methods of enhancing the permeability of tissue are described in U.S. Publication Nos. 20040171980 and 20040236268 and U.S. Pat. No. 6,190,315; each of which are herein incorporated by reference in their entireties.

In one embodiment, a device may be used to increase permeability of tissue before delivering formulations of the polynucleotides, primary constructs and mmRNA described herein. The permeability of skin may be measured by methods known in the art and/or described in U.S. Pat. No. 6,190,315, herein incorporated by reference in its entirety. As a non-limiting example, a modified mRNA formulation may be delivered by the drug delivery methods described in U.S. Pat. No. 6,190,315, herein incorporated by reference in its entirety.

In another non-limiting example tissue may be treated with a eutectic mixture of local anesthetics (EMLA) cream before, during and/or after the tissue may be subjected to a device which may increase permeability. Katz et al. (Anesth Analg (2004); 98:371-76; herein incorporated by reference in its entirety) showed that using the EMLA cream in combination with a low energy, an onset of superficial cutaneous analgesia was seen as fast as 5 minutes after a pretreatment with a low energy ultrasound.

In one embodiment, enhancers may be applied to the tissue before, during, and/or after the tissue has been treated to increase permeability. Enhancers include, but are not limited to, transport enhancers, physical enhancers, and cavitation enhancers. Non-limiting examples of enhancers are described in U.S. Pat. No. 6,190,315, herein incorporated by reference in its entirety.

In one embodiment, a device may be used to increase permeability of tissue before delivering formulations of polynucleotides, primary constructs and/or mmRNA described herein, which may further contain a substance that invokes an immune response. In another non-limiting example, a formulation containing a substance to invoke an immune response may be delivered by the methods described in U.S. Publication Nos. 20040171980 and 20040236268; each of which is herein incorporated by reference in their entirety.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required.

Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 0.1% to about 10% (w/w) active ingredient, although the concentration of active ingredient may be as high as the solubility limit of the active ingredient in the solvent. Formulations for topical administration may further comprise one or more of the additional ingredients described herein.

Depot Administration

As described herein, in some embodiments, the composition is formulated in depots for extended release. Generally, a specific organ or tissue (a "target tissue") is targeted for administration.

In some aspects of the invention, the polynucleotides, primary constructs or mmRNA are spatially retained within or proximal to a target tissue. Provided are method of providing a composition to a target tissue of a mammalian subject by contacting the target tissue (which contains one or more target cells) with the composition under conditions such that the composition, in particular the nucleic acid component(s) of the composition, is substantially retained in the target tissue, meaning that at least 10, 20, 30, 40, 50, 60, 70, 80, 85, 90, 95, 96, 97, 98, 99, 99.9, 99.99 or greater than 99.99% of the composition is retained in the target tissue. Advantageously, retention is determined by measuring the amount of the nucleic acid present in the composition that enters one or more target cells. For example, at least 1, 5, 10, 20, 30, 40, 50, 60, 70, 80, 85, 90, 95, 96, 97, 98, 99, 99.9, 99.99 or greater than 99.99% of the nucleic acids administered to the subject are present intracellularly at a period of time following administration. For example, intramuscular injection to a mammalian subject is performed using an aqueous composition containing a ribonucleic acid and a transfection reagent, and retention of the composition is determined by measuring the amount of the ribonucleic acid present in the muscle cells.

Aspects of the invention are directed to methods of providing a composition to a target tissue of a mammalian subject, by contacting the target tissue (containing one or more target cells) with the composition under conditions such that the composition is substantially retained in the target tissue. The composition contains an effective amount of a polynucleotide, primary construct or mmRNA such that the polypeptide of interest is produced in at least one target cell. The compositions generally contain a cell penetration agent, although "naked" nucleic acid (such as nucleic acids without a cell penetration agent or other agent) is also contemplated, and a pharmaceutically acceptable carrier.

In some circumstances, the amount of a protein produced by cells in a tissue is desirably increased. Preferably, this increase in protein production is spatially restricted to cells within the target tissue. Thus, provided are methods of increasing production of a protein of interest in a tissue of a mammalian subject. A composition is provided that contains polynucleotides, primary constructs or mmRNA characterized in that a unit quantity of composition has been determined to produce the polypeptide of interest in a substantial percentage of cells contained within a predetermined volume of the target tissue.

In some embodiments, the composition includes a plurality of different polynucleotides, primary constructs or mmRNA, where one or more than one of the polynucleotides, primary constructs or mmRNA encodes a polypeptide of interest. Optionally, the composition also contains a cell penetration agent to assist in the intracellular delivery of the composition. A determination is made of the dose of the composition required to produce the polypeptide of interest in a substantial percentage of cells contained within the predetermined volume of the target tissue (generally, without inducing significant production of the polypeptide of interest in tissue adjacent to the predetermined volume, or distally to the target tissue). Subsequent to this determination, the determined dose is introduced directly into the tissue of the mammalian subject.

In one embodiment, the invention provides for the polynucleotides, primary constructs or mmRNA to be delivered in more than one injection or by split dose injections.

In one embodiment, the invention may be retained near target tissue using a small disposable drug reservoir or patch pump. Non-limiting examples of patch pumps include those manufactured and/or sold by BD® (Franklin Lakes, N.J.), Insulet Corporation (Bedford, Mass.), SteadyMed Therapeutics (San Francisco, Calif.), Medtronic (Minneapolis, Minn.), UniLife (York, Pa.), Valeritas (Bridgewater, N.J.), and SpringLeaf Therapeutics (Boston, Mass.).

Pulmonary Administration

A pharmaceutical composition may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are suitably in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Intranasal, Nasal and Buccal Administration

Formulations described herein as being useful for pulmonary delivery are useful for intranasal delivery of a pharmaceutical composition. Another formulation suitable for intranasal administration is a coarse powder comprising the active ingredient and having an average particle from about 0.2 µm to 500 µm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

Ophthalmic Administration

A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Ear drops and/or eye drops are contemplated as being within the scope of this invention.

Payload Administration: Detectable Agents and Therapeutic Agents

The polynucleotides, primary constructs or mmRNA described herein can be used in a number of different scenarios in which delivery of a substance (the "payload") to a biological target is desired, for example delivery of detectable substances for detection of the target, or delivery of a therapeutic agent. Detection methods can include, but are not limited to, both imaging in vitro and in vivo imaging methods, e.g., immunohistochemistry, bioluminescence imaging (BLI), Magnetic Resonance Imaging (MRI), positron emission tomography (PET), electron microscopy, X-ray computed tomography, Raman imaging, optical coherence tomography, absorption imaging, thermal imaging, fluorescence reflectance imaging, fluorescence microscopy, fluorescence molecular tomographic imaging, nuclear magnetic resonance imaging, X-ray imaging, ultrasound imaging, photoacoustic imaging, lab assays, or in any situation where tagging/staining/imaging is required.

The polynucleotides, primary constructs or mmRNA can be designed to include both a linker and a payload in any useful orientation. For example, a linker having two ends is used to attach one end to the payload and the other end to the nucleobase, such as at the C-7 or C-8 positions of the deaza-adenosine or deaza-guanosine or to the N-3 or C-5 positions of cytosine or uracil. The polynucleotide of the invention can include more than one payload (e.g., a label and a transcription inhibitor), as well as a cleavable linker. In one embodiment, the modified nucleotide is a modified 7-deaza-adenosine triphosphate, where one end of a cleavable linker is attached to the C7 position of 7-deaza-adenine, the other end of the linker is attached to an inhibitor (e.g., to the C5 position of the nucleobase on a cytidine), and a label (e.g., Cy5) is attached to the center of the linker (see, e.g., compound 1 of A*pCp C5 Parg Capless in FIG. 5 and columns 9 and 10 of U.S. Pat. No. 7,994,304, incorporated herein by reference). Upon incorporation of the modified 7-deaza-adenosine triphosphate to an encoding region, the resulting polynucleotide will have a cleavable linker attached to a label and an inhibitor (e.g., a polymerase inhibitor). Upon cleavage of the linker (e.g., with reductive conditions to reduce a linker having a cleavable disulfide moiety), the label and inhibitor are released. Additional linkers and payloads (e.g., therapeutic agents, detectable labels, and cell penetrating payloads) are described herein.

For example, the polynucleotides, primary constructs or mmRNA described herein can be used in induced pluripotent stem cells (iPS cells), which can directly track cells that are transfected compared to total cells in the cluster. In another example, a drug that may be attached to the polynucleotides, primary constructs or mmRNA via a linker and may be fluorescently labeled can be used to track the drug in vivo, e.g. intracellularly. Other examples include, but are not limited to, the use of a polynucleotide, primary construct or mmRNA in reversible drug delivery into cells.

The polynucleotides, primary constructs or mmRNA described herein can be used in intracellular targeting of a payload, e.g., detectable or therapeutic agent, to specific organelle. Exemplary intracellular targets can include, but are not limited to, the nuclear localization for advanced mRNA processing, or a nuclear localization sequence (NLS) linked to the mRNA containing an inhibitor.

In addition, the polynucleotides, primary constructs or mmRNA described herein can be used to deliver therapeutic agents to cells or tissues, e.g., in living animals. For example, the polynucleotides, primary constructs or mmRNA attached to the therapeutic agent through a linker can facilitate member permeation allowing the therapeutic agent to travel into a cell to reach an intracellular target.

In some embodiments, the payload may be a therapeutic agent such as a cytotoxin, radioactive ion, chemotherapeutic, or other therapeutic agent. A cytotoxin or cytotoxic agent includes any agent that may be detrimental to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020 incorporated herein in its entirety), rachelmycin (CC-1065, see U.S. Pat. Nos. 5,475,092, 5,585,499, and 5,846,545, all of which are incorporated herein by reference), and analogs or homologs thereof. Radioactive ions include, but are not limited to iodine (e.g., iodine 125 or iodine 131), strontium 89, phosphorous, palladium, cesium, iridium, phosphate, cobalt, yttrium 90, samarium 153, and praseodymium. Other therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

In some embodiments, the payload may be a detectable agent, such as various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., $^{18}$F, $^{67}$Ga, $^{81m}$Kr, $^{82}$Rb, $^{111}$In, $^{123}$I, $^{133}$Xe, $^{201}$Tl, $^{125}$I, $^{35}$S, $^{14}$C, $^{3}$H, or $^{99m}$Tc (e.g., as pertechnetate (technetate (VII), TcO$_4^-$)), and contrast agents (e.g., gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons). Such optically-detectable labels include for example, without limitation, 4-acetamido-4'-isothiocyanatostilbene-2,2'disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5' 5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives (e.g., eosin and eosin isothiocyanate); erythrosin and derivatives (e.g., erythrosin B and erythrosin isothiocyanate); ethidium; fluorescein and derivatives (e.g., 5-carboxyfluorescein (FAM), 5-(4,6-dichlorotriazin-2-yl)aminofluorescein (DTAF), 2',7'-dimethoxy-4' 5'-dichloro-6-carboxyfluorescein, fluorescein, fluorescein isothiocyanate, X-rhodamine-5-(and-6)-isothiocyanate (QFITC or XRITC), and fluorescamine); 2-[2-[3-[[1,3-dihydro-1,1-dimethyl-3-(3-sulfopropyl)-2H-benz[e]indol-2-ylidene]ethylidene]-2-[4-(ethoxycarbonyl)-1-piperazinyl]-1-cyclopenten-1-yl]ethenyl]-1,1-dimethyl-3-(3-sulforpropyl)-1H-benz[e]indolium hydroxide, inner salt, compound with n,n-diethylethanamine (1:1) (IR144); 5-chloro-2-[2-[3-[(5-chloro-3-ethyl-2(3H)-benzothiazol-ylidene)ethylidene]-2-(diphenylamino)-1-cyclopenten-1-yl] ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycoerythrin; o-phthaldialdehyde; pyrene and derivatives (e.g., pyrene, pyrene butyrate, and succinimidyl 1-pyrene); butyrate quantum dots; Reactive Red 4 (CIBA-CRON™ Brilliant Red 3B-A); rhodamine and derivatives (e.g., 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'tetramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5 (Cy5.5), Cyanine-7 (Cy7); IRD 700; IRD 800; Alexa 647; La Jolta Blue; phthalo cyanine; and naphthalo cyanine.

In some embodiments, the detectable agent may be a non-detectable pre-cursor that becomes detectable upon activation (e.g., fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE® (VisEn Medical))). In vitro assays in which the enzyme labeled compositions can be used include, but are not limited to, enzyme linked immunosorbent assays (ELISAs), immunoprecipitation assays, immunofluorescence, enzyme immunoassays (EIA), radio-immunoassays (RIA), and Western blot analysis.

Combinations

The polynucleotides, primary constructs or mmRNA may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that may improve their bioavailability, reduce and/or modify their metabolism, inhibit their excretion, and/or modify their distribution within the body. As a non-limiting example, the polynucleotides, primary constructs and/or mmRNA may be used in combination with a pharmaceutical agent for the treatment of cancer or to control hyperproliferative cells. In U.S. Pat. No. 7,964,571, herein incorporated by reference in its entirety, a combination therapy for the treatment of solid primary or metastasized tumor is described using a pharmaceutical composition including a DNA plasmid encoding for interleukin-12 with a lipopolymer and also administering at least one anticancer agent or chemotherapeutic. Further, the polynucleotides, primary constructs and/or mmRNA of the present invention that encodes anti-proliferative molecules may be in a pharmaceutical composition with a lipopolymer (see e.g., U.S. Pub. No. 20110218231, herein incorporated by reference in its entirety, claiming a pharmaceutical composition comprising a DNA plasmid encoding an antiproliferative molecule and a lipopolymer) which may be administered with at least one chemotherapeutic or anticancer agent.

Dosing

The present invention provides methods comprising administering polynucleotides, primary constructs and/or mmRNA and their encoded proteins or complexes in accordance with the invention to a subject in need thereof. nucleic acids, proteins or complexes, or pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In certain embodiments, compositions in accordance with the present invention may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

According to the present invention, it has been discovered that administration of mmRNA in split-dose regimens produce higher levels of proteins in mammalian subjects. As used herein, a "split dose" is the division of single unit dose or total daily dose into two or more doses, e.g., two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in 24 hr period. It may be administered as a single unit dose. In one embodiment, the mmRNA of the present invention are administered to a subject in split doses. The mmRNA may be formulated in buffer only or in a formulation described herein.

Dosage Forms

A pharmaceutical composition described herein can be formulated into a dosage form described herein, such as a topical, intranasal, intratracheal, or injectable (e.g., intravenous, intraocular, intravitreal, intramuscular, intracardiac, intraperitoneal, subcutaneous).

Liquid Dosage Forms

Liquid dosage forms for parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art including, but not limited to, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments for parenteral administration, compositions may be mixed with solubilizing agents such as CREMOPHOR®, alcohols, oils, modified oils, glycols, polysorbates, cyclodextrins, polymers, and/or combinations thereof.

Injectable

Injectable preparations, for example, sterile injectable aqueous or oleaginous suspensions may be formulated according to the known art and may include suitable dispersing agents, wetting agents, and/or suspending agents. Sterile injectable preparations may be sterile injectable solutions, suspensions, and/or emulsions in nontoxic parenterally acceptable diluents and/or solvents, for example, a solution in 1,3-butanediol. Among the acceptable vehicles and solvents that may be employed include, but are not limited to, are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it may be desirable to slow the absorption of the active ingredient from subcutaneous or intramuscular injection. This may be accomplished by the use of a liquid suspension of crystalline or amorphous material with poor water solubility. The rate of absorption of the polynucleotide, primary construct or mmRNA then depends upon its rate of dissolution which, in turn, may depend upon crystal size and crystalline form. Alternatively, delayed absorption of a parenterally administered polynucleotide, primary construct or mmRNA may be accomplished by dissolving or suspending the polynucleotide, primary construct or mmRNA in an oil vehicle. Injectable depot forms are made by forming microencapsule matrices of the polynucleotide, primary construct or mmRNA in biodegradable polymers such as polylactide-polyglycolide. Depending upon the ratio of polynucleotide, primary construct or mmRNA to polymer and the nature of the particular polymer employed, the rate of polynucleotide, primary construct or mmRNA release can be controlled. Examples of other biodegradable polymers include, but are not limited to, poly(orthoesters) and poly(anhydrides). Depot injectable formulations may be prepared by entrapping the polynucleotide, primary construct or mmRNA in liposomes or microemulsions which are compatible with body tissues.

Pulmonary

Formulations described herein as being useful for pulmonary delivery may also be use for intranasal delivery of a pharmaceutical composition. Another formulation suitable for intranasal administration may be a coarse powder comprising the active ingredient and having an average particle from about 0.2 μm to 500 μm. Such a formulation may be administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, contain about 0.1% to 20% (w/w) active ingredient, where the balance may comprise an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

General considerations in the formulation and/or manufacture of pharmaceutical agents may be found, for example, in Remington: The Science and Practice of Pharmacy $21^{st}$ ed., Lippincott Williams & Wilkins, 2005 (incorporated herein by reference).

Coatings or Shells

Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Properties of Pharmaceutical Compositions

The pharmaceutical compositions described herein can be characterized by one or more of bioavailability, therapeutic window and/or volume of distribution.

Bioavailability

The polynucleotides, primary constructs or mmRNA, when formulated into a composition with a delivery agent as described herein, can exhibit an increase in bioavailability as compared to a composition lacking a delivery agent as described herein. As used herein, the term "bioavailability" refers to the systemic availability of a given amount of polynucleotides, primary constructs or mmRNA administered to a mammal. Bioavailability can be assessed by measuring the area under the curve (AUC) or the maximum serum or plasma concentration ($C_{max}$) of the unchanged form of a compound following administration of the compound to a mammal. AUC is a determination of the area under the curve plotting the serum or plasma concentration of a compound along the ordinate (Y-axis) against time along the abscissa (X-axis). Generally, the AUC for a particular compound can be calculated using methods known to those of ordinary skill in the art and as described in G. S. Banker, Modern Pharmaceutics, Drugs and the Pharmaceutical Sciences, v. 72, Marcel Dekker, New York, Inc., 1996, herein incorporated by reference.

The $C_{max}$ value is the maximum concentration of the compound achieved in the serum or plasma of a mammal following administration of the compound to the mammal. The $C_{max}$ value of a particular compound can be measured using methods known to those of ordinary skill in the art. The phrases "increasing bioavailability" or "improving the pharmacokinetics," as used herein mean that the systemic availability of a first polynucleotide, primary construct or mmRNA, measured as AUC, $C_{max}$, or $C_{min}$ in a mammal is greater, when co-administered with a delivery agent as described herein, than when such co-administration does not take place. In some embodiments, the bioavailability of the polynucleotide, primary construct or mmRNA can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Therapeutic Window

The polynucleotides, primary constructs or mmRNA, when formulated into a composition with a delivery agent as described herein, can exhibit an increase in the therapeutic window of the administered polynucleotide, primary construct or mmRNA composition as compared to the therapeutic window of the administered polynucleotide, primary construct or mmRNA composition lacking a delivery agent as described herein. As used herein "therapeutic window" refers to the range of plasma concentrations, or the range of levels of therapeutically active substance at the site of action, with a high probability of eliciting a therapeutic effect. In some embodiments, the therapeutic window of the polynucleotide, primary construct or mmRNA when co-administered with a delivery agent as described herein can increase by at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%.

Volume of Distribution

The polynucleotides, primary constructs or mmRNA, when formulated into a composition with a delivery agent as described herein, can exhibit an improved volume of distribution ($V_{dist}$), e.g., reduced or targeted, relative to a composition lacking a delivery agent as described herein. The volume of distribution ($V_{dist}$) relates the amount of the drug in the body to the concentration of the drug in the blood or plasma. As used herein, the term "volume of distribution" refers to the fluid volume that would be required to contain the total amount of the drug in the body at the same concentration as in the blood or plasma: $V_{dist}$ equals the amount of drug in the body/concentration of drug in blood or plasma. For example, for a 10 mg dose and a plasma concentration of 10 mg/L, the volume of distribution would be 1 liter. The volume of distribution reflects the extent to which the drug is present in the extravascular tissue. A large volume of distribution reflects the tendency of a compound to bind to the tissue components compared with plasma protein binding. In a clinical setting, $V_{dist}$ can be used to determine a loading dose to achieve a steady state concentration. In some embodiments, the volume of distribution of the polynucleotide, primary construct or mmRNA when co-administered with a delivery agent as described herein can decrease at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%.

Biological Effect

In one embodiment, the biological effect of the modified mRNA delivered to the animals may be categorized by analyzing the protein expression in the animals. The reprogrammed protein expression may be determined from analyzing a biological sample collected from a mammal administered the modified mRNA of the present invention. In one embodiment, the expression protein encoded by the modified mRNA administered to the mammal of at least 50 pg/ml may be preferred. For example, a protein expression of 50-200 pg/ml for the protein encoded by the modified mRNA delivered to the mammal may be seen as a therapeutically effective amount of protein in the mammal.

Quantification

In one embodiment, the polynucleotides, primary constructs or mmRNA of the present invention may be quantified in exosomes derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

In the quantification method, a sample of not more than 2 mL is obtained from the subject and the exosomes isolated by size exclusion chromatography, density gradient centrifugation, differential centrifugation, nanomembrane ultrafiltration, immunoabsorbent capture, affinity purification, microfluidic separation, or combinations thereof. In the analysis, the level or concentration of a polynucleotide, primary construct or mmRNA may be an expression level, presence, absence, truncation or alteration of the administered construct. It is advantageous to correlate the level with one or more clinical phenotypes or with an assay for a human disease biomarker. The assay may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of polynucleotides, primary constructs or mmRNA remaining or delivered. This is possible because the polynucleotides, primary constructs or mmRNA of the present invention differ from the endogenous forms due to the structural or chemical modifications.

Detection of Modified Polynucleotides by Mass Spectrometry

Mass spectrometry (MS) is an analytical technique that can provide structural and molecular mass/concentration information on molecules after their conversion to ions. The molecules are first ionized to acquire positive or negative charges and then they travel through the mass analyzer to arrive at different areas of the detector according to their mass/charge (m/z) ratio.

Mass spectrometry is performed using a mass spectrometer which includes an ion source for ionizing the fractionated sample and creating charged molecules for further analysis. For example ionization of the sample may be performed by electrospray ionization (ESI), atmospheric pressure chemical ionization (APCI), photoionization, electron ionization, fast atom bombardment (FAB)/liquid secondary ionization (LSIMS), matrix assisted laser desorption/ionization (MALDI), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc.

After the sample has been ionized, the positively charged or negatively charged ions thereby created may be analyzed to determine a mass-to-charge ratio (i.e., m/z). Suitable analyzers for determining mass-to-charge ratios include quadropole analyzers, ion traps analyzers, and time-of-flight analyzers. The ions may be detected using several detection modes. For example, selected ions may be detected (i.e., using a selective ion monitoring mode (SIM)), or alternatively, ions may be detected using a scanning mode, e.g., multiple reaction monitoring (MRM) or selected reaction monitoring (SRM).

Liquid chromatography-multiple reaction monitoring (LC-MS/MRM) coupled with stable isotope labeled dilution of peptide standards has been shown to be an effective method for protein verification (e.g., Keshishian et al., Mol Cell Proteomics 2009 8: 2339-2349; Kuhn et al., Clin Chem 2009 55:1108-1117; Lopez et al., Clin Chem 2010 56:281-290). Unlike untargeted mass spectrometry frequently used in biomarker discovery studies, targeted MS methods are peptide sequence-based modes of MS that focus the full analytical capacity of the instrument on tens to hundreds of selected peptides in a complex mixture. By restricting detection and fragmentation to only those peptides derived from proteins of interest, sensitivity and reproducibility are improved dramatically compared to discovery-mode MS methods. This method of mass spectrometry-based multiple reaction monitoring (MRM) quantitation of proteins can dramatically impact the discovery and quantitation of biomarkers via rapid, targeted, multiplexed protein expression profiling of clinical samples.

In one embodiment, a biological sample which may contain at least one protein encoded by at least one modified mRNA of the present invention may be analyzed by the method of MRM-MS. The quantification of the biological sample may further include, but is not limited to, isotopically labeled peptides or proteins as internal standards.

According to the present invention, the biological sample, once obtained from the subject, may be subjected to enzyme digestion. As used herein, the term "digest" means to break apart into shorter peptides. As used herein, the phrase "treating a sample to digest proteins" means manipulating a sample in such a way as to break down proteins in a sample. These enzymes include, but are not limited to, trypsin, endoproteinase Glu-C and chymotrypsin. In one embodiment, a biological sample which may contain at least one protein encoded by at least one modified mRNA of the present invention may be digested using enzymes.

In one embodiment, a biological sample which may contain protein encoded by modified mRNA of the present invention may be analyzed for protein using electrospray ionization. Electrospray ionization (ESI) mass spectrometry (ESIMS) uses electrical energy to aid in the transfer of ions from the solution to the gaseous phase before they are analyzed by mass spectrometry. Samples may be analyzed using methods known in the art (e.g., Ho et al., Clin Biochem Rev. 2003 24(1):3-12). The ionic species contained in solution may be transferred into the gas phase by dispersing a fine spray of charge droplets, evaporating the solvent and ejecting the ions from the charged droplets to generate a mist of highly charged droplets. The mist of highly charged droplets may be analyzed using at least 1, at least 2, at least 3 or at least 4 mass analyzers such as, but not limited to, a quadropole mass analyzer. Further, the mass spectrometry method may include a purification step. As a non-limiting example, the first quadrapole may be set to select a single m/z ratio so it may filter out other molecular ions having a different m/z ratio which may eliminate complicated and time-consuming sample purification procedures prior to MS analysis.

In one embodiment, a biological sample which may contain protein encoded by modified mRNA of the present invention may be analyzed for protein in a tandem ESIMS system (e.g., MS/MS). As non-limiting examples, the droplets may be analyzed using a product scan (or daughter scan) a precursor scan (parent scan) a neutral loss or a multiple reaction monitoring.

In one embodiment, a biological sample which may contain protein encoded by modified mRNA of the present invention may be analyzed using matrix-assisted laser desorption/ionization (MALDI) mass spectrometry (MALDIMS). MALDI provides for the nondestructive vaporization and ionization of both large and small molecules, such as proteins. In MALDI analysis, the analyte is first co-crystallized with a large molar excess of a matrix compound, which may also include, but is not limited to, an ultraviolet absorbing weak organic acid. Non-limiting examples of matrices used in MALDI are α-cyano-4-hydroxycinnamic acid, 3,5-dimethoxy-4-hydroxycinnamic acid and 2,5-dihydroxybenzoic acid. Laser radiation of the analyte-matrix mixture may result in the vaporization of the matrix and the analyte. The laser induced desorption provides high ion yields of the intact analyte and allows for measurement of compounds with high accuracy. Samples may be analyzed using methods known in the art (e.g., Lewis, Wei and Siuzdak, Encyclopedia of Analytical Chemistry 2000:5880-5894). As non-limiting examples, mass analyzers used in the MALDI analysis may include a linear time-of-flight (TOF), a TOF reflectron or a Fourier transform mass analyzer.

In one embodiment, the analyte-matrix mixture may be formed using the dried-droplet method. A biologic sample is mixed with a matrix to create a saturated matrix solution where the matrix-to-sample ratio is approximately 5000:1. An aliquot (approximately 0.5-2.0 uL) of the saturated matrix solution is then allowed to dry to form the analyte-matrix mixture.

In one embodiment, the analyte-matrix mixture may be formed using the thin-layer method. A matrix homogeneous film is first formed and then the sample is then applied and may be absorbed by the matrix to form the analyte-matrix mixture.

In one embodiment, the analyte-matrix mixture may be formed using the thick-layer method. A matrix homogeneous film is formed with a nitro-cellulose matrix additive. Once the uniform nitro-cellulose matrix layer is obtained the sample is applied and absorbed into the matrix to form the analyte-matrix mixture.

In one embodiment, the analyte-matrix mixture may be formed using the sandwich method. A thin layer of matrix crystals is prepared as in the thin-layer method followed by the addition of droplets of aqueous trifluoroacetic acid, the sample and matrix. The sample is then absorbed into the matrix to form the analyte-matrix mixture.

VI. Uses of Synthetic Polynucleotides and/or Synthetic sgRNAs

The synthetic polynucleotides and/or synthetic sgRNAs of the present invention may be used to alter the phenotype of cells. The polynucleotides, primary constructs and mmRNA of the invention may encode peptides, polypeptides or multiple proteins to produce polypeptides of interest. The polypeptides of interest may be used in therapeutics and/or clinical and research settings. As a non-limiting example, the polypeptides of interest may include reprogramming factors, differentiation factors and de-differentiation factors.

Therapeutic Agents

The polynucleotides, primary constructs or mmRNA of the present invention, such as modified nucleic acids and modified RNAs, and the proteins translated from them described herein can be used as therapeutic or prophylactic agents. They are provided for use in medicine, therapy and preventative treatments. For example, a polynucleotide, primary construct or mmRNA described herein (e.g., a modified mRNA encoding a CRISPR-related polypeptide or protein) can be administered to a subject, wherein the polynucleotide, primary construct or mmRNA is translated in vivo to produce a therapeutic or prophylactic polypeptide in the subject. Likewise, and optionally in combination with the above, a polynucleotide, primary construct or mmRNA described herein (e.g., a modified sgRNA or plurality of same) can be administered to a subject, wherein the polynucleotide, primary construct or mmRNA guides gene-editing by a CRISPR-related polypeptide or protein.) Provided are compositions, methods, kits, and reagents for diagnosis, treatment or prevention of a disease or condition in humans and other mammals. The active therapeutic agents of the invention include polynucleotides, primary constructs or mmRNA, cells containing the polynucleotides, primary constructs or mmRNA or polypeptides translated from the polynucleotides, primary constructs or mmRNA.

In certain embodiments, provided herein are combination therapeutics containing one or more polynucleotide, primary construct or mmRNA containing translatable regions that encode for a protein or proteins. In certain embodiments, provided herein are combination therapeutics containing one or more polynucleotide, primary construct or mmRNA containing non-translatable regions, for example, regions complementary to target gene sequences, e.g., sgRNAs.

Provided herein are methods of inducing translation of a recombinant polypeptide in a cell population using the polynucleotide, primary construct or mmRNA described herein. Such translation can be in vivo, ex vivo, in culture, or in vitro. The cell population is contacted with an effective amount of a composition containing a nucleic acid that has at least one nucleoside modification, and a translatable region encoding the recombinant polypeptide. The cell population is optionally also contacted with an effective amount of a composition containing a nucleic acid that has at least one nucleoside modification, and has complementarity to a target gene sequence, e.g., a sgRNA. The population is contacted under conditions such that the nucleic acid is localized into one or more cells of the cell population and the recombinant polypeptide is translated in the cell from the nucleic acid and or the sgRNA (or plurality thereof) is also is localized into one or more cells of the cell population.

An "effective amount" of the composition is provided based, at least in part, on the target tissue, target cell type, means of administration, physical characteristics of the nucleic acid (e.g., size, and extent of modified nucleosides), and other determinants. In general, an effective amount of the composition provides efficient protein production in the cell, preferably more efficient than a composition containing a corresponding unmodified nucleic acid. Increased efficiency may be demonstrated by increased cell transfection (i.e., the percentage of cells transfected with the nucleic acid), increased protein translation from the nucleic acid, decreased nucleic acid degradation (as demonstrated, e.g., by increased duration of protein translation from a modified nucleic acid), or reduced innate immune response of the host cell.

Aspects of the invention are directed to methods of inducing in vivo translation of a recombinant polypeptide in a mammalian subject in need thereof, e.g., a recombinant CRISPR-related protein. Further aspects of the invention are directed to methods of inducing gene editing in vivo in a mammalian subject in need thereof. Therein, an effective amount of a composition containing a nucleic acid that has at least one structural or chemical modification and a translatable region encoding the recombinant polypeptide, optionally in combination with an effective amount of a composition containing one or more nucleic acids having at least one structural or chemical modification and/or having sequence complementarity to a target gene, e.g., one or more sgRNAs, is administered to the subject using the delivery methods described herein. The nucleic acid is provided in an amount and under other conditions such that the nucleic acid is localized into a cell of the subject and (1) the recombinant polypeptide is translated in the cell from the nucleic acid and/or (2) the sgRNA(s) bind complementary sequences within target genes. The cell in which a nucleic acid of the invention is localized, or the tissue in which the cell is present, may be targeted with one or more than one rounds of nucleic acid administration.

In certain embodiments, the administered polynucleotide, primary construct or mmRNA directs production of one or more recombinant polypeptides and/or regulatory RNA, e.g., sgRNA, that provides a functional activity which is substantially absent in the cell, tissue or organism in which the recombinant polypeptide is translated, e.g., a gene editing activity. In certain embodiments, an administered polynucleotide, primary construct or mmRNA directs production of one or more recombinant polypeptides and/or regulatory RNA, e.g., sgRNA, involved in gene editing, and is administered in combination with one or more additional polynucleotide, primary construct or mmRNA that directs production of one or more additional recombinant polypeptides having therapeutic utility, e.g., providing a functional activity which is substantially absent in the cell, tissue or organism in which the recombinant polypeptide is translated. For example, the missing functional activity may be enzymatic, structural, or gene regulatory in nature. In related embodiments, the administered polynucleotide, primary construct or mmRNA directs production of one or more recombinant polypeptides that increases (e.g., synergistically) a functional activity which is present but substantially deficient in the cell in which the recombinant polypeptide is translated.

In other embodiments, the administered polynucleotide, primary construct or mmRNA directs production of one or more recombinant polypeptides that replace a polypeptide (or multiple polypeptides) that is substantially absent in the cell in which the recombinant polypeptide is translated. Such absence may be due to genetic mutation of the encoding gene or regulatory pathway thereof. In some embodiments, the recombinant polypeptide increases the level of an endogenous protein in the cell to a desirable level; such an increase may bring the level of the endogenous protein from a subnormal level to a normal level or from a normal level to a super-normal level.

Alternatively, the recombinant polypeptide functions to antagonize the activity of an endogenous protein present in, on the surface of, or secreted from the cell. Usually, the activity of the endogenous protein is deleterious to the subject; for example, due to mutation of the endogenous protein resulting in altered activity or localization. Additionally, the recombinant polypeptide antagonizes, directly or indirectly, the activity of a biological moiety present in, on the surface of, or secreted from the cell. Examples of antagonized biological moieties include lipids (e.g., cholesterol), a lipoprotein (e.g., low density lipoprotein), a nucleic acid, a carbohydrate, a metabolite (e.g. bilirubin), a protein toxin such as shiga and tetanus toxins, or a small molecule toxin such as botulinum, cholera, and diphtheria toxins. Additionally, the antagonized biological molecule may be an endogenous protein that exhibits an undesirable activity, such as a cytotoxic or cytostatic activity.

Without being bound in theory, it is proposed that the CRISPR gene-editing process can reverse disease symptoms in vivo. As such, this methodology has potential for treating many genetic disorders.

In certain embodiments, a mmRNA encoding a CRISPR-related polypeptide or protein is administered in combination with one or more sgRNAs, optionally in combination with a corrected DNA template. The DNA template includes a correct sequence of corresponding to a mutated gene associated with a disease. Exemplary DNA templates correspond to single-mutation disease causing genes. A cell into which the requisite components are introduced repairs the damaged gene using the CRISPER-related protein. In doing so, it copies from the template, introducing new genetic material into the genome.

The data presented herein demonstrate effective liver delivery of components of the invention. As such, the methodology described herein is particularly suited to treatment of metabolic disease, e.g., metabolic disease caused by inborn genetic errors, e.g., ornithine transcarbamylase deficiency-related diseases. The methods of the invention can also serve to attenuate disease progression. It is also proposed that intramuscular delivery, e.g., via multiple muscle injection, can serve to treat muscle diseases, for example, muscular dystrophy, by inclusion of appropriate corrected DNA templates. In yet other embodiments, ex vivo approaches are envisioned involving, for example, administration of agents to hematopoetic cells ex vivo (e.g., via electroporation), followed optionally by selection of cells expressing the proper components, followed by administration of treated cells, where recolonization can subsequently occur.

The recombinant proteins, mmRNAs encoding same, and/or sgRNAs, described herein may be engineered for localization within the cell, potentially within a specific compartment such as the nucleus, or are engineered for secretion from the cell or translocation to the plasma membrane of the cell. In exemplary embodiments, the recombinant proteins, mmRNAs encoding same, and/or sgRNAs, are engineered for nuclear localization.

Other aspects of the present disclosure relate to transplantation of cells containing polynucleotide, primary construct, or mmRNA to a mammalian subject. Administration of cells to mammalian subjects is known to those of ordinary skill in the art, and include, but is not limited to, local implantation (e.g., topical or subcutaneous administration), organ delivery or systemic injection (e.g., intravenous injection or inhalation), and the formulation of cells in pharmaceutically acceptable carrier. Such compositions containing polynucleotide, primary construct, or mmRNA can be formulated for administration intramuscularly, transarterially, intraperitoneally, intravenously, intranasally, subcutaneously, endoscopically, transdermally, or intrathecally. In some embodiments, the composition may be formulated for extended release.

The subject to whom the therapeutic agent may be administered suffers from or may be at risk of developing a disease, disorder, or deleterious condition. Provided are methods of identifying, diagnosing, and classifying subjects on these bases, which may include clinical diagnosis, biomarker levels, genome-wide association studies (GWAS), and other methods known in the art.

VII. Kits and Devices

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments, and contact cells and/or a population of cells at least once.

In one aspect, the present invention provides kits comprising the molecules (polynucleotides, primary constructs or mmRNA) of the invention. In one embodiment, the kit comprises one or more functional antibodies or function fragments thereof.

Kits and devices useful in combination with the polynucleotides, primary constructs or mmRNA) of the invention include those disclosed in co-pending U.S. Provisional Patent Application No. 61/737,130 filed Dec. 14, 2012, the contents of which are incorporated herein by reference in their entirety.

VIII. Definitions

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

About: As used herein, the term "about" means +/−10% of the recited value.

Administered in combination: As used herein, the term "administered in combination" or "combined administration" means that two or more agents are administered to a subject at the same time or within an interval such that there may be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Bifunctional: As used herein, the term "bifunctional" refers to any substance, molecule or moiety which is capable of or maintains at least two functions. The functions may affect the same outcome or a different outcome. The structure that produces the function may be the same or different. For example, bifunctional modified RNAs of the present invention may encode a cytotoxic peptide (a first function) while those nucleosides which comprise the encoding RNA are, in and of themselves, cytotoxic (second function). In this example, delivery of the bifunctional modified RNA to a cancer cell would produce not only a peptide or protein molecule which may ameliorate or treat the cancer but would also deliver a cytotoxic payload of nucleosides to the cell should degradation, instead of translation of the modified RNA, occur.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide, primary construct or mmRNA of the present invention may be considered biologically active if even a portion of the polynucleotide, primary construct or mmRNA is biologically active or mimics an activity considered biologically relevant.

Cancer stem cells: As used herein, "cancer stem cells" are cells that can undergo self-renewal and/or abnormal proliferation and differentiation to form a tumor.

Chemical terms: Chemical terms not otherwise defined herein, will conform to the chemical term definitions provided in co-pending U.S. Provisional Patent Application No. 61/737,130 filed Dec. 14, 2012, the contents of which are incorporated herein by reference in their entirety.

The term "diastereomer," as used herein means stereoisomers that are not mirror images of one another and are non-superimposable on one another.

The term "effective amount" of an agent, as used herein, is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

Compound: As used herein, the term "compound," is meant to include all stereoisomers, geometric isomers, tautomers, and isotopes of the structures depicted.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond and the concomitant migration of a proton. Tautomeric forms include prototropic tautomers which are isomeric protonation states having the same empirical formula and total charge. Examples prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

The compounds and salts of the present disclosure can be prepared in combination with solvent or water molecules to form solvates and hydrates by routine methods.

Committed: As used herein, the term "committed" means, when referring to a cell, when the cell is far enough into the differentiation pathway where, under normal circumstances, it will continue to differentiate into a specific cell type or subset of cell type instead of into a different cell type or reverting to a lesser differentiated cell type.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence may apply to the entire length of an oligonucleotide or polypeptide or may apply to a portion, region or feature thereof.

Controlled Release: As used herein, the term "controlled release" refers to a pharmaceutical composition or compound release profile that conforms to a particular pattern of release to effect a therapeutic outcome.

Cyclic or Cyclized: As used herein, the term "cyclic" refers to the presence of a continuous loop. Cyclic molecules need not be circular, only joined to form an unbroken chain of subunits. Cyclic molecules such as the engineered RNA or mRNA of the present invention may be single units or multimers or comprise one or more components of a complex or higher order structure.

Cytostatic: As used herein, "cytostatic" refers to inhibiting, reducing, suppressing the growth, division, or multiplication of a cell (e.g., a mammalian cell (e.g., a human cell)), bacterium, virus, fungus, protozoan, parasite, prion, or a combination thereof.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivery: As used herein, "delivery" refers to the act or manner of delivering a compound, substance, entity, moiety, cargo or payload.

Delivery Agent: As used herein, "delivery agent" refers to any substance which facilitates, at least in part, the in vivo delivery of a polynucleotide, primary construct or mmRNA to targeted cells.

Destabilized: As used herein, the term "destable," "destabilize," or "destabilizing region" means a region or molecule that is less stable than a starting, wild-type or native form of the same region or molecule.

Detectable label: As used herein, "detectable label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the peptides or proteins disclosed herein. They may be within the amino acids, the peptides, or proteins, or located at the N- or C-termini.

Developmental Potential: As used herein, "developmental potential" or "developmental potency" refers to the total of all developmental cell fates or cell types that can be achieved by a cell upon differentiation.

Developmental Potential Altering Factor: As used herein, "developmental potential altering factor" refers to a protein or RNA which can alter the developmental potential of a cell.

Digest: As used herein, the term "digest" means to break apart into smaller pieces or components. When referring to polypeptides or proteins, digestion results in the production of peptides.

Differentiated cell: As used herein, the term "differentiated cell" refers to any somatic cell that is not, in its native form, pluripotent. Differentiated cell also encompasses cells that are partially differentiated.

Differentiation: As used herein, the term "differentiation factor" refers to a developmental potential altering factor such as a protein, RNA or small molecule that can induce a cell to differentiate to a desired cell-type.

Differentiate: As used herein, "differentiate" refers to the process where an uncommitted or less committed cell acquires the features of a committed cell.

Disease: As used herein, the term "disease" refers to an abnormal condition affecting the body of an organism often showing specific bodily symptoms.

Disorder: As used herein, the term "disorder," refers to a disruption of or an interference with normal functions or established systems of the body.

Distal: As used herein, the term "distal" means situated away from the center or away from a point or region of interest.

Dose splitting factor (DSF)-ratio of PUD of dose split treatment divided by PUD of total daily dose or single unit dose. The value is derived from comparison of dosing regimens groups.

Embryonic stem cell: As used herein, the term "embryonic stem cell" refers to naturally occurring pluripotent stem cells of the inner cell mass of the embryonic blastocyst.

Encapsulate: As used herein, the term "encapsulate" means to enclose, surround or encase.

Encoded protein cleavage signal: As used herein, "encoded protein cleavage signal" refers to the nucleotide sequence which encodes a protein cleavage signal.

Engineered: As used herein, embodiments of the invention are "engineered" when they are designed to have a feature or property, whether structural or chemical, that varies from a starting point, wild type or native molecule.

Exosome: As used herein, "exosome" is a vesicle secreted by mammalian cells or a complex involved in RNA degradation.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Feature: As used herein, a "feature" refers to a characteristic, a property, or a distinctive element.

Formulation: As used herein, a "formulation" includes at least a polynucleotide, primary construct or mmRNA and a delivery agent.

Fragment: A "fragment," as used herein, refers to a portion. For example, fragments of proteins may comprise polypeptides obtained by digesting full-length protein isolated from cultured cells.

Functional: As used herein, a "functional" biological molecule is a biological molecule in a form in which it exhibits a property and/or activity by which it is characterized.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the invention, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the invention, two protein sequences are considered to be homologous if the proteins are at least about 50%, 60%, 70%, 80%, or 90% identical for at least one stretch of at least about 20 amino acids.

Identity: As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research*, 12(1), 387 (1984)), BLASTP, BLASTN, and FASTA Altschul, S. F. et al., *J. Molec. Biol.*, 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Linker: As used herein, a linker refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker may be of sufficient length as to not interfere with incorporation into a nucleic acid sequence. The linker can be used for any useful purpose, such as to form mmRNA multimers (e.g., through linkage of two or more polynucleotides, primary constructs, or mmRNA molecules) or mmRNA conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers, Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

MicroRNA (miRNA) binding site: As used herein, a microRNA (miRNA) binding site represents a nucleotide location or region of a nucleic acid transcript to which at least the "seed" region of a miRNA binds.

Modified: As used herein "modified" refers to a changed state or structure of a molecule of the invention. Molecules may be modified in many ways including chemically, structurally, and functionally. In one embodiment, the mRNA molecules of the present invention are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Mucus: As used herein, "mucus" refers to the natural substance that is viscous and comprises mucin glycoproteins.

Multipotent: As used herein, "multipotent" or "partially differentiated cell" when referring to a cell refers to a cell that has a developmental potential to differentiate into cells of one or more germ layers, but not all three germ layers.

Naturally occurring: As used herein, "naturally occurring" means existing in nature without artificial aid.

Non-human vertebrate: As used herein, a "non human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Off-target: As used herein, "off target" refers to any unintended effect on any one or more target, gene, or cellular transcript.

Oligopotent: As used herein, "oligopotent" when referring to a cell means to give rise to a more restricted subset of cell lineages than multipotent stem cells.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g. alkyl) per se is optional.

Peptide: As used herein, "peptide" is less than or equal to 50 amino acids long, e.g., about 5, 10, 15, 20, 25, 30, 35, 40, 45, or 50 amino acids long.

Paratope: As used herein, a "paratope" refers to the antigen-binding site of an antibody.

Patient: As used herein, "patient" refers to a subject who may seek or be in need of treatment, requires treatment, is receiving treatment, will receive treatment, or a subject who is under care by a trained professional for a particular disease or condition.

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17*th* ed., Mack Publishing Company, Easton, Pa., 1985, p. 1418, *Pharmaceutical Salts: Properties, Selection, and Use,* P. H. Stahl and C. G. Wermuth (eds.), Wiley-VCH, 2008, and Berge et al., *Journal of Pharmaceutical Science,* 66, 1-19 (1977), each of which is incorporated herein by reference in its entirety.

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Physicochemical: As used herein, "physicochemical" means of or relating to a physical and/or chemical property.

Pluripotent: As used herein, "pluripotent" refers to a cell with the developmental potential, under different conditions, to differentiate to cell types characteristic of all three germ layers.

Pluripotency: As used herein, "pluripotency" or "pluripotent state" refers to the developmental potential of a cell where the cell has the ability to differentiate into all three embryonic germ layers (endoderm, mesoderm and ectoderm).

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Prodrug: The present disclosure also includes prodrugs of the compounds described herein. As used herein, "prodrugs" refer to any substance, molecule or entity which is in a form predicate for that substance, molecule or entity to act as a therapeutic upon chemical or physical alteration. Prodrugs may by covalently bonded or sequestered in some way and which release or are converted into the active drug moiety prior to, upon or after administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Preparation and use of prodrugs is discussed in T. Higuchi and V. Stella, "Prodrugs as Novel Delivery Systems," Vol. 14 of the A.C.S. Symposium Series, and in *Bioreversible Carriers in Drug Design,* ed. Edward B. Roche, American Pharmaceutical Association and Pergamon Press, 1987, both of which are hereby incorporated by reference in their entirety.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Progenitor cell: As used herein, the term "progenitor cell" refers to cells that have greater developmental potential relative to a cell which it can give rise to by differentiation.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Purified: As used herein, "purify," "purified," "purification" means to make substantially pure or clear from unwanted components, material defilement, admixture or imperfection.

Repeated transfection: As used herein, the term "repeated transfection" refers to transfection of the same cell culture with a polynucleotide, primary construct or mmRNA a plurality of times. The cell culture can be transfected at least twice, at least 3 times, at least 4 times, at least 5 times, at least 6 times, at least 7 times, at least 8 times, at least 9 times, at least 10 times, at least 11 times, at least 12 times, at least 13 times, at least 14 times, at least 15 times, at least 16 times, at least 17 times at least 18 times, at least 19 times, at least 20 times, at least 25 times, at least 30 times, at least 35 times, at least 40 times, at least 45 times, at least 50 times or more.

Reprogramming: As used herein, "reprogramming" refers to a process that reverses the developmental potential of a cell or population of cells.

Reprogramming factor: As used herein, the term "reprogramming factor" refers to a developmental potential altering factor such as a protein, RNA or small molecule, the expression of which contributes to the reprogramming of a cell to a less differentiated or undifferentiated state.

Sample: As used herein, the term "sample" or "biological sample" refers to a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A sample further may include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which may contain cellular components, such as proteins or nucleic acid molecule.

Signal Sequences: As used herein, the phrase "signal sequences" refers to a sequence which can direct the transport or localization of a protein.

Single unit dose: As used herein, a "single unit dose" is a dose of any therapeutic administered in one dose/at one time/single route/single point of contact, i.e., single administration event.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Somatic cell: As used herein, "somatic cells" refers to any cell other than a germ cell, a cell present in or obtained from a pre-implantation embryo, or a cell resulting from proliferation of such a cell in vitro.

Somatic stem cell: As used herein, a "somatic stem cell" refers to any pluripotent or multipotent stem cell derived from non-embryonic tissue including fetal, juvenile and adult tissue.

Somatic pluripotent cell: As used herein, a "somatic pluripotent cell" refers to a somatic cell that has had its developmental potential altered to that of a pluripotent state.

Split dose: As used herein, a "split dose" is the division of single unit dose or total daily dose into two or more doses.

Stable: As used herein "stable" refers to a compound that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable.

Stem cell: As used herein, the term "stem cell" refers to a cell in an undifferentiated or partially differentiated state that has the property of self-renewal and ahs the developmental potential to differentiate into multiple cell types, without a specific developmental potential. A stem cell may be able capable of proliferation and giving rise to more such stem cells while maintaining its developmental potential.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially equal: As used herein as it relates to time differences between doses, the term means plus/minus 2%.

Substantially simultaneously: As used herein and as it relates to plurality of doses, the term means within 2 seconds.

Suffering from: An individual who is "suffering from" a disease, disorder, and/or condition has been diagnosed with or displays one or more symptoms of a disease, disorder, and/or condition.

Susceptible to: An individual who is "susceptible to" a disease, disorder, and/or condition has not been diagnosed with and/or may not exhibit symptoms of the disease, disorder, and/or condition but harbors a propensity to develop a disease or its symptoms. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or polypeptides or other molecules of the present invention may be chemical or enzymatic.

Targeted Cells: As used herein, "targeted cells" refers to any one or more cells of interest. The cells may be found in vitro, in vivo, in situ or in the tissue or organ of an organism. The organism may be an animal, preferably a mammal, more preferably a human and most preferably a patient.

Therapeutic Agent: The term "therapeutic agent" refers to any agent that, when administered to a subject, has a therapeutic, diagnostic, and/or prophylactic effect and/or elicits a desired biological and/or pharmacological effect.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr period. It may be administered as a single unit dose.

Totipotency: As used herein, "totipotency" refers to a cell with a developmental potential to make all of the cells found in the adult body as well as the extra-embryonic tissues, including the placenta.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Transcription: As used herein, the term "transcription" refers to methods to introduce exogenous nucleic acids into a cell. Methods of transfection include, but are not limited to, chemical methods, physical treatments and cationic lipids or mixtures.

Transdifferentiation: As used herein, "transdifferentiation" refers to the capacity of differentiated cells of one type to lose identifying characteristics and to change their phenotype to that of other fully differentiated cells.

Treating: As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incor-

EXAMPLES

Example 1. DNA Constructs for Synthetic Polynucleotide and sgRNA Production

Synthetic polynucleotides and sgRNA of the invention are produced via creation of a DNA construct; PCR amplification of a cDNA template; in-vitro transcription of the cDNA template (using, in some embodiments, modified nucleotides); if necessary, post-in vitro transcription enzymatic poly-A tailing and/or 5' capping; and purification and analysis.

The DNA construct for the synthetic polynucleotide includes an open reading frame. The open reading frame (ORF) coding for the CRISPR related protein, e.g., dCAS9 or dCAS9-activator fusion protein, may be flanked by a 5' untranslated region (UTR) which may contain a strong Kozak translational initiation signal and/or an alpha-globin 3' UTR which may include an oligo(dT) sequence for templated addition of a poly-A tail.

The ORF may also include various upstream or downstream additions (such as, but not limited to, β-globin, tags, etc.) may be ordered from an optimization service such as, but limited to, DNA2.0 (Menlo Park, Calif.) and may contain multiple cloning sites which may have XbaI recognition.

The DNA construct for the sgRNA of the invention is made using similar methods. The plasmid construct includes an insert with a sgRNA sequence including the N(20-25) guides sequence and the guide scaffold sequence flanked on the 5' end with a RNA polymerase specific 5'UTR, e.g., a T7 polymerase 5' UTR.

The DNA construct for the synthetic polynucleotide and/or the sgRNA is transformed in *E. coli*. For the present invention, NEB DH5-alpha Competent *E. coli* are used. Transformations are performed according to NEB instructions using 100 ng of plasmid. The protocol is as follows:
1. Thaw a tube of NEB 5-alpha Competent *E. coli* cells on ice for 10 minutes.
2. Add 1-5 μl containing 1 pg-100 ng of plasmid DNA to the cell mixture. Carefully flick the tube 4-5 times to mix cells and DNA. Do not vortex.
3. Place the mixture on ice for 30 minutes. Do not mix.
4. Heat shock at 42° C. for exactly 30 seconds. Do not mix.
5. Place on ice for 5 minutes. Do not mix.
6. Pipette 950 μl of room temperature SOC into the mixture.
7. Place at 37° C. for 60 minutes. Shake vigorously (250 rpm) or rotate.
8. Warm selection plates to 37° C.
9. Mix the cells thoroughly by flicking the tube and inverting.

Alternatively, incubate at 30° C. for 24-36 hours or 25° C. for 48 hours.

A single colony is then used to inoculate 5 ml of LB growth media using the appropriate antibiotic and then allowed to grow (250 RPM, 37° C.) for 5 hours. This is then used to inoculate a 200 ml culture medium and allowed to grow overnight under the same conditions.

To isolate the plasmid (up to 850 μg), a maxi prep is performed using the Invitrogen PURELINK™ HiPure Maxiprep Kit (Carlsbad, Calif.), following the manufacturer's instructions.

In order to generate cDNA for In Vitro Transcription (IVT), the plasmid is first linearized using a restriction enzyme such as XbaI. A typical restriction digest with XbaI will comprise the following: Plasmid 1.0 μg; 10× Buffer 1.0 μl; XbaI 1.5 μl; dH$_2$0 up to 10 μl; incubated at 37° C. for 1 hr. If performing at lab scale (<5 μg), the reaction is cleaned up using Invitrogen's PURELINK™ PCR Micro Kit (Carlsbad, Calif.) per manufacturer's instructions. Larger scale purifications may need to be done with a product that has a larger load capacity such as Invitrogen's standard PURELINK™ PCR Kit (Carlsbad, Calif.). Following the cleanup, the linearized vector is quantified using the NanoDrop and analyzed to confirm linearization using agarose gel electrophoresis.

Example 2. PCR for cDNA Production

The linearized plasmid (encoding the synthetic polynucleotide encoding the CRISPR related protein or encoding the sgRNA) is amplified using PCR for preparation of cDNA, e.g., a transcription template. PCR procedures for the preparation of cDNA are performed using 2×KAPA HIFI™ HotStart ReadyMix by Kapa Biosystems (Woburn, Mass.). This system includes 2×KAPA ReadyMix 12.5 μl; Forward Primer (10 uM); 0.75 μl; Reverse Primer (10 uM) 0.75 μl; Template cDNA; 100 ng; and dH20 diluted to 25.0 μl. The reaction conditions are at 95° C. for 5 min. and 25 cycles of 98° C. for 20 sec, then 58° C. for 15 sec, then 72° C. for 45 sec, then 72° C. for 5 min. then 4° C. to termination.

In some embodiments, the reverse primer of the instant invention incorporates a poly-T$_{120}$ for a poly-A$_{120}$ in the mRNA. Other reverse primers with longer or shorter poly(T) tracts can be used to adjust the length of the poly(A) tail in the mRNA.

The reaction is cleaned up using Invitrogen's PURELINK™ PCR Micro Kit (Carlsbad, Calif.) per manufacturer's instructions (up to 5 μg). Larger reactions will require a cleanup using a product with a larger capacity. Following the cleanup, the cDNA is quantified using the NanoDrop and analyzed by agarose gel electrophoresis to confirm the cDNA is the expected size. The cDNA is then submitted for sequencing analysis before proceeding to the in vitro transcription reaction.

Example 3. In Vitro Transcription (IVT)

The amplified product cDNA is used as a template for in vitro transcription to generate synthetic polynucleotides and/or synthetic sgRNAs. The input nucleotide triphosphate (NTP) mix is made in-house using natural and un-natural NTPs. The in vitro transcription reaction generates modified synthetic polynucleotides and/or sgRNA.

A typical in vitro transcription reaction includes the following:

| | |
|---|---|
| Template cDNA | 1.0 μg |
| 10x transcription buffer (400 mM Tris-HCl pH 8.0, 190 mM MgCl2, 50 mM DTT, 10 mM Spermidine) | 2.0 μl |
| Custom NTPs (25 mM each) | 7.2 μl |
| RNase Inhibitor | 20 U |
| T7 RNA polymerase | 3000 U |

| | |
|---|---|
| dH20 | Up to 20.0 µl |
| Incubation at 37° C. for 3 hr-5 hrs. | |

The synthetic polynucleotide and/or synthetic sgRNA may be modified to reduce the cellular innate immune response. The modifications to reduce the cellular response may include those described herein, e.g., pseudouridine (ψ) and 5-methyl-cytidine (5meC, 5mc or m5C). (See, Kariko K et al. Immunity 23:165-75 (2005), Kariko K et al. Mol Ther 16:1833-40 (2008), Anderson B R et al. NAR (2010); each of which is herein incorporated by reference in their entirety).

The crude IVT mix may be stored at 4° C. overnight for cleanup the next day. 1 U of RNase-free DNase is then used to digest the original template. After 15 minutes of incubation at 37° C., the mRNA is purified using Ambion's MEGACLEAR™ Kit (Austin, Tex.) following the manufacturer's instructions. This kit can purify up to 500 µg of RNA. Following the cleanup, the RNA is quantified using the NanoDrop and analyzed by agarose gel electrophoresis to confirm the RNA is the proper size and that no degradation of the RNA has occurred.

Example 4. PolyA Tailing Reaction

In some embodiments, the synthetic polynucleotide is synthesized without a poly-A tail, i.e., the cDNA construct is amplified without a poly-T. Without a poly-T in the cDNA, a poly-A tailing reaction must be performed before cleaning the final product. This is done by mixing Capped IVT RNA (100 µl); RNase Inhibitor (20 U); 10× Tailing Buffer (0.5 M Tris-HCl (pH 8.0), 2.5 M NaCl, 100 mM MgCl$_2$)(12.0 µl); 20 mM ATP (6.0 µl); Poly-A Polymerase (20 U); dH$_2$0 up to 123.5 µl and incubation at 37° C. for 30 min. If the poly-A tail is already in the transcript, then the tailing reaction may be skipped and proceed directly to cleanup with Ambion's MEGACLEAR™ kit (Austin, Tex.) (up to 500 µg). Poly-A Polymerase is preferably a recombinant enzyme expressed in yeast.

For studies performed and described herein, the poly-A tail is encoded in the IVT template to comprise 160 nucleotides in length. However, it should be understood that the processivity or integrity of the polyA tailing reaction may not always result in exactly 160 nucleotides. Hence polyA tails of approximately 160 nucleotides, e.g., about 150-165, 155, 156, 157, 158, 159, 160, 161, 162, 163, 164 or 165 are within the scope of the invention.

Example 5.5' Capping of the Synthetic Polynucleotide

5'-capping of the synthetic polynucleotide (modified RNA) may be completed concomitantly during the in vitro-transcription reaction or alternatively enzymatically capped post-transcription.

5'-capping of the synthetic polynucleotide (modified RNA) may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5') A; m7G(5')ppp(5')G (New England BioLabs, Ipswich, Mass.).

5'-capping of modified RNA may be completed post-transcriptionally using a Vaccinia Virus Capping Enzyme to generate the "Cap 0" structure: m7G(5')ppp(5')G (New England BioLabs, Ipswich, Mass.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

Post-transcription capping of the synthetic polynucleotide is performed as follows. The reaction mixture includes: IVT RNA 60 µg-180 µg and dH$_2$0 up to 72 µl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM MgCl$_2$) (10.0 µl); 20 mM GTP (5.0 µl); 20 mM S-Adenosyl Methionine (2.5 µl); RNase Inhibitor (100 U); 2'-O-Methyltransferase (400U); Vaccinia capping enzyme (Guanylyl transferase) (40 U); dH$_2$0 (Up to 28 µl); and incubation at 37° C. for 30 minutes for 60 µg RNA or up to 2 hours for 180 µg of RNA.

The capped synthetic polynucleotide is then purified using Ambion's MEGACLEAR™ Kit (Austin, Tex.) following the manufacturer's instructions. Following the cleanup, the capped synthetic polynucleotide is quantified using the NANODROP™ (ThermoFisher, Waltham, Mass.) and analyzed by agarose gel electrophoresis to confirm the RNA is the proper size and that no degradation of the RNA has occurred. The RNA product may also be sequenced by running a reverse-transcription-PCR to generate the cDNA for sequencing.

The capping efficiency of the synthetic polynucleotide is assayed using a number of experimental techniques. The capped synthetic polynucleotide is transfected into cells and the amount of CRISPR related protein is assayed using, e.g., ELISA. Higher levels of protein expression correlates with higher capping efficiency. The capped synthetic polynucleotide is run on an agarose-urea gel-electrophoresis; a synthetic polynucleotide with a single, consolidated band by electrophoresis corresponds to a higher purity product compared to a synthetic polynucleotide with multiple bands or streaking bands. The capped synthetic polynucleotide is run on an HPLC column; synthetic polynucleotide with a single HPLC peak corresponds to a higher purity product. The capped synthetic polynucleotide is transfected into human primary keratinocytes at multiple concentrations. At 6, 12, 24 and 36 hours post-transfection the amount of pro-inflammatory cytokines such as TNF-alpha and IFN-beta secreted into the culture medium are assayed by ELISA. Synthetic mRNAs that secrete higher levels of pro-inflammatory cytokines into the medium correspond to a synthetic mRNA containing an immune-activating cap structure. The capped synthetic polynucleotide is analyzed for capping reaction efficiency by LC-MS after capped mRNA nuclease treatment. Nuclease treatment of capped mRNAs yields a mixture of free nucleotides and the capped 5'-5-triphosphate cap structure detectable by LC-MS. The amount of capped product on the LC-MS spectra is expressed as a percent of total mRNA from the reaction and would correspond to capping reaction efficiency. The cap structure with higher capping reaction efficiency would have a higher amount of capped product by LC-MS.

Example 6. Methods for Analysis of Synthetic Polynucleotides and Synthetic sgRNA Agarose Gel Electrophoresis of Modified RNA or RT PCR Products: Individual modified RNAs (200-400 ng in a 20 µl volume) or reverse transcribed PCR products (200-400 ng) are loaded into a well on a non-denaturing 1.2% Agarose E-Gel (Invitrogen, Carlsbad, Calif.) and run for 12-15 minutes according to the manufacturer protocol.

Nanodrop Modified RNA Quantification and UV Spectral Data: Modified RNAs in TE buffer (1 µl) are used for Nanodrop UV absorbance readings to quantitate the yield of each modified RNA from an in vitro transcription reaction.

Example 7. Method of Screening for Protein Expression

After transfection of cells with synthetic polynucleotide encoding a CRISPR related protein, protein expression is analyzed.

A. Electrospray Ionization

A biological sample which may contain proteins encoded by synthetic polynucleotides administered to the cells or subject is prepared and analyzed according to the manufacturer protocol for electrospray ionization (ESI) using 1, 2, 3 or 4 mass analyzers. A biologic sample may also be analyzed using a tandem ESI mass spectrometry system.

Patterns of protein fragments, or whole proteins, are compared to known controls for a given protein and identity is determined by comparison.

B. Matrix-Assisted Laser Desorption/Ionization

A biological sample which may contain proteins encoded by synthetic polynucleotides administered to the cells or subject is prepared and analyzed according to the manufacturer protocol for matrix-assisted laser desorption/ionization (MALDI).

Patterns of protein fragments, or whole proteins, are compared to known controls for a given protein and identity is determined by comparison.

C. Liquid Chromatography-Mass Spectrometry-Mass Spectrometry

A biological sample, which may contain proteins encoded by synthetic polynucleotides, may be treated with a trypsin enzyme to digest the proteins contained within. The resulting peptides are analyzed by liquid chromatography-mass spectrometry-mass spectrometry (LC/MS/MS). The peptides are fragmented in the mass spectrometer to yield diagnostic patterns that can be matched to protein sequence databases via computer algorithms. The digested sample may be diluted to achieve 1 ng or less starting material for a given protein. Biological samples containing a simple buffer background (e.g. water or volatile salts) are amenable to direct in-solution digest; more complex backgrounds (e.g. detergent, non-volatile salts, glycerol) require an additional clean-up step to facilitate the sample analysis.

Patterns of protein fragments, or whole proteins, are compared to known controls for a given protein and identity is determined by comparison.

Example 8. Microphysiological Systems

Synthetic polynucleotides encoding CRISPR related proteins are formulated using one of the methods described herein such as in buffer, lipid nanoparticles and PLGA. These formulations are then administered to or contacted with microphysiological systems created from organ chips as described in International Publication Nos. WO2013086502, WO2013086486 and WO2013086505, the contents of each of which are herein incorporated by reference in its entirety.

Example 9: Design of DNA Templates for Synthetic Polynucleotides Encoding Cas9 and dCas9-Effector Domain Fusion Proteins Plasmids were designed for use as in vitro transcription templates to manufacture chemically synthetic polynucleotides as described herein. Two plasmids were designed to contain codon optimized Cas9 as described by Cong and Mali, respectively (Science (2013) 339:819-23 and Science (2013) 339:823-6.) The first plasmid encoded FLAG-tagged Cas9 and the second plasmid encoded untagged Cas9. Two plasmids were designed to contain codon optimized dcas9 that is fused to different effector domains (see Cell (2013) 154:442-51 and Nature Methods (2013) 10:977-979). Coding sequences were places under the control of T7 polymerase promoter for in vitro transcription of modified mRNA.

Sequences of the Cas9, dCAS9 gene and effector domains are found in the Tables below.

The following 5'UTR and 3'UTR sequences were used:

```
5' UTR
                                          (SEQ ID NO: 71)
TCAAGCTTTTGGACCCTCGTACAGAAGCTAATACGACTCACTATAGGGAA

ATAAGAGAGAAAAGAAGAGTAAGAAGAAATATAAGAGCCACC

3' UTR
                                          (SEQ ID NO: 81)
TGATAATAGgctg gagcctcggtggccatgctt cttgcccctt gggcctcccc ccagccccctc ctccccttcc tgcacccgtaccc ccgtggt ctttgaataa agtctgagtg ggcggc TCTAGA
```

The following constructs were created: (3) dCas9-HA tag-2×SV40NLS-KRAB and (4) dCas9-NLS-FLAG-VP64.

In other embodiments, the sequence-encoding codon-optimized *Streptococcus pyogenes* dCas9 gene can be fused with an HA-tag, one or more NLSs (e.g., SV40 NLSs, for example, one or two NLSs, optionally at the N- and/or C-terminus) and/or a detection tag (e.g., HA tag, FLAG tag, tagBFP, or the like). Any of the above can be featured alone or in combination with an effector domain (KRAB, CSD, WRPW, VP64, or p65AD domains) in the Cas9 constructs of the invention, for example, to facilitate up or down-regulation). Sequences of various Cas9, dCAS9 gene and effector domains are found in the Tables below.

Cas9 or dCas9 expression can be regulated further by engineering of miR regulatory sequences into UTR of the various constructs. Two miR-122 regulatory sequence-containing constructs are made by replacing the standard 3' UTR with a miR-122 regulatory site-containing 3' UTR. miR-122 is highly expressed in the hepatocytes and not in other tissues; therefore, translation of mRNA containing miR-122 regulatory (binding) sites in its 3' UTR is selectively down-regulated in hepatocytes but not in other cells.

The following constructs were designed: (5) dCas9-KRAB-miR-122 and (6) dCas9-NLS-FLAG-VP64-miR-122).

Constructs 1-4 (DNA cassettes) were synthesized and inserted into a vector (pJ364 from DNA 2.0, Inc., Menlo Park, Calif.). The plasmid was transfected into *E. coli* as described above, plasmid DNA was purified and linearized using a restriction enzyme (XbaI). The linearized plasmid was PCR amplified and used as a template for in vitro transcription to produce the synthetic polynucleotides of the invention.

Example 10: Design of DNA Templates for Synthetic sgRNAs Targeting VEGF

Four constructs each encoding a sgRNA targeting a gene of interest, i.e., a VEGF gene, were created for use as templates for in vitro transcription.

The constructs each included a 5'UTR (T7), a GGG, a 20-25 nucleotide sequence complementary to a sequence upstream of the VEGF gene transcriptional start, and a guide RNA scaffold sequence. The VEGF sgRNA sequences were based on Maeder et al.

The following sequence was used as the 5'UTR sequence:

```
                                          (SEQ ID NO: 72)
TCAAGCTTTTGGACCCTCGTACAGAAGCTAATACGACTCACTATAGGG
```

The following four sgRNA constructs were created; the sequences in bold italic are those complementary to the VEGF gene.

```
VEGF V1 sgRNA construct sequence
                                         (SEQ ID NO: 101)
TCAAGCTTTTGGACCCTCGTACAGAAGCTAATACGACTCACTAT

AGGGTGTGCAGACGGCAGTCACTAGG

GTTTTAGAGCTAGAAATAGCAAGTTAAAATAAGG

CTAGTCCGTTATCAACTTGAAAAAGTGGCACCGAGTCGGTGC

VEGF V2 sgRNA construct sequence
                                         (SEQ ID NO: 102)
TCAAGCTTTTGGACCCTCGTACAGAAGCTAATACGACTCACTAT

AGGGAGCAGCGTCTTCGAGAGTGAGG

GTTTTAGAGCTAGAAATAGCAAGTTAAAATAAGG

CTAGTCCGTTATCAACTTGAAAAAGTGGCACCGAGTCGGTGC

VEGF V3 sgRNA construct sequence
                                         (SEQ ID NO: 103)
TCAAGCTTTTGGACCCTCGTACAGAAGCTAATACGACTCACTAT

AGGGTGAGTGAGTGTGTGCGTGTGG

GTTTTAGAGCTAGAAATAGCAAGTTAAAATAAGG

CTAGTCCGTTATCAACTTGAAAAAGTGGCACCGAGTCGGTGC

VEGF V4 sgRNA construct sequence
                                         (SEQ ID NO: 104)
TCAAGCTTTTGGACCCTCGTACAGAAGCTAATACGACTCACTAT

AGGGTTGGAGCGGGGAGAAGGCCAGG

GGTTTTAGAGCTAGAAATAGCAAGTTAAAATAAG

GCTAGTCCGTTATCAACTTGAAAAAGTGGCACCGAGTCGGTGC
```

The four constructs (DNA cassettes) were synthesized and inserted into a vector (pJ224 from DNA 2.0, Inc., Menlo Park, Calif.). The plasmid was transfected into *E. coli* as described above and plasmid DNA was purified and linearized using a restriction enzyme (XbaI). The linearized plasmid was PCR amplified as described herein and used as a template for in vitro transcription to produce the synthetic sgRNA.

Example 11: Production of Synthetic Polynucleotides and sgRNAs Via In Vitro Transcription Using the methods described herein the two synthetic polynucleotides encoding Cas9, the two synthetic polynucleotides encoding the dCAS9-effector gene fusion proteins, and the four synthetic sgRNAs targeting VEGF were synthesized using in vitro transcription of the constructs described above. Synthetic polynucleotides and synthetic sgRNAs with the following sequences were synthesized.

```
mRNA sequence of dCas9-HA tag-2xSV40NLS-KRAB
                                          (SEQ ID NO: 51)
GGGAAAUAAGAGAGAAAAGAAGAGUAAGAAGAAAUAUAAGAGCCACCAUGGACAAGAAAUAC

UCAAUCGGACUUGCUAUCGGAACUAACAGCGUGGGAUGGGCCGUCAUUACUGACGAAUACAA

GGUGCCCUCAAAGAAGUUCAAGGUCCUGGGAAAUACCGAUAGACACUCCAUCAAAAAGAACC

UGAUCGGGGCACUGUUGUUCGACUCGGGAGAGACUGCAGAAGCAACCAGGCUCAAGCGCACU

GCGAGGCGCCGGUACACCCGGAGGAAGAACCGCAUCUGCUACCUCCAAGAGAUUUUCAGCAA

CGAGAUGGCAAAGGUCGAUGAUUCGUUCUUUCACCGCCUUGAGGAGUCGUUCCUUGUCGAGG

AGGACAAAAAGCAUGAAAGACAUCCGAUCUUCGGAAACAUCGUGGACGAAGUCGCAUACCAU

GAAAAGUACCCUACCAUCUACCAUCUCAGAAAGAAACUCGUCGAUUCAACUGAUAAGGCCGA

CUUGCGGCUGAUCUACCUGGCUCUGGCGCACAUGAUCAAGUUUCGGGGUCACUUUCUCAUCG

AGGGUGAUCUCAACCCGGACAAUUCCGACGUUGACAAACUCUUCAUCCAACUGGUCCAGACG

UACAACCAGCUGUUCGAAGAAAAUCCGAUCAACGCAAGCGGAGUGGACGCCAAAGCCAUUCU

GUCGGCCCGCCUCUCGAAGUCGCGUCGCCUGGAAAAUCUGAUUGCUCAGCUCCCGGGCGAAA

AGAAGAAUGGCCUGUUUGGAAACCUCAUCGCACUGUCCCUCGGGCUGACUCCCAACUUCAAA

UCGAACUUUGACUUGGCUGAGGAUGCAAAGCUGCAACUCUCCAAAGACACUUACGAUGAUGA

CCUGGACAAUCUCCUGGCGCAGAUCGGGGAUCAGUAUGCUGACCUGUUCCUGGCGGCCAAGA
```

-continued

```
ACCUGUCUGAUGCCAUCCUGCUCUCCGAUAUCCUGAGAGUGAACACUGAGAUCACCAAGGCG

CCUCUGAGCGCCUCGAUGAUCAAACGCUACGAUGAACACCAUCAGGACCUCACUCUUCUGAA

GGCUUUGGUGCGGCAGCAGCUUCCGGAAAAGUACAAAGAGAUCUUCUUCGACCAGUCGAAAA

ACGGCUACGCCGGAUACAUUGAUGGCGGCGCAAGCCAGGAGGAAUUCUAUAAGUUUAUCAAA

CCGAUCCUGGAGAAGAUGGACGGCACUGAAGAACUUCUGGUCAAGCUGAAUCGAGAGGAUCU

GCUCCGGAAGCAGCGGACCUUCGACAAUGGGUCUAUCCCUCACCAAAUCCAUCUCGGCGAGC

UGCAUGCGAUUCUGAGGCGCCAGGAGGACUUCUACCCAUUCCUGAAAGACAAUCGGGAGAAA

AUCGAAAAGAUUCUGACGUUCCGCAUUCCAUACUACGUCGGGCCACUUGCGCGGGGUAAUUC

GAGAUUCGCCUGGAUGACGCGGAAGUCCGAAGAAACCAUCACGCCGUGGAAUUUCGAAGAAG

UGGUCGACAAGGGAGCCAGCGCACAGUCCUUCAUUGAGCGCAUGACCAAUUUCGACAAAAAU

CUGCCGAACGAGAAGGUCCUGCCGAAGCAUUCACUGCUGUACGAAUACUUUACCGUGUACAA

CGAACUGACCAAGGUGAAGUACGUCACCGAGGGAAUGAGAAAGCCUGCUUUCCUGAGCGGAG

AACAGAAGAAGGCCAUUGUUGACCUCCUCUUCAAGACUAAUCGCAAAGUGACCGUGAAGCAG

CUUAAAGAGGAUUACUUCAAAAAGAUCGAAUGUUUCGACUCCGUGGAAAUCAGCGGCGUGGA

GGAUAGAUUCAACGCGUCCCUUGGGACUUACCACGACCUCCUUAAGAUCAUCAAGGAUAAGG

AUUUCCUCGACAAUGAGGAAAACGAAGAUAUCCUGGAGGACAUCGUUCUGACUCUGACCCUC

UUUGAGGACCGGGAGAUGAUCGAGGAGAGACUCAAGACCUACGCGCACCUGUUUGACGACAA

AGUGAUGAAGCAACUUAAACGCAGGCGCUACACCGGCUGGGGCAGACUGUCACGCAAGUUGA

UCAACGGAAUUAGAGAUAAACAGUCCGGAAAGACCAUCCUGGACUUCCUGAAGUCCGAUGGA

UUCGCCAACCGGAAUUUCAUGCAGCUCAUCCAUGACGACUCAUUGACUUUCAAGGAGGAUAU

CCAAAAGGCCCAAGUGAGCGGCCAAGGGGACUCCCUUCACGAACACAUCGCAAAUUUGGCCG

GAUCACCAGCGAUUAAGAAGGGAAUCCUGCAGACCGUGAAGGUGGUGGACGAGCUGGUGAAA

GUGAUGGGACGGCACAAGCCGGAAAACAUCGUGAUCGAGAUGGCCAGAGAGAACCAGACGAC

UCAAAAGGGCCAGAAGAACUCGCGCGAACGCAUGAAGAGAAUAGAAGAGGGAAUUAAGGAAC

UGGGAUCGCAGAUCUUGAAGGAGCACCCUGUCGAAAAUACUCAACUCCAGAACGAGAAGCUG

UACCUGUACUAUCUUCAAAACGGCAGGGACAUGUAUGUCGACCAAGAGCUCGACAUUAACCG

CCUGUCCGAUUAUGACGUGGACGCCAUCGUGCCGCAGAGCUUUCUCAAGGACGAUUCCAUCG

ACAACAAAGUGCUCACCCGCAGCGACAAGAAUAGAGGGAAGUCGGAUAACGUCCCUUCGGAA

GAGGUGGUGAAAAAGAUGAAGAAUUACUGGCGGCAGCUCCUGAAUGCAAAGCUCAUCACCCA

ACGGAAGUUUGACAACCUCACCAAGGCAGAAAGAGGAGGACUGUCGGAAUUGGAUAAGGCCG

GUUUCAUCAAGCGACAAUUGGUGGAAACUCGGCAAAUUACCAAGCAUGUGGCACAGAUUCUG

GACUCCCGUAUGAACACCAAGUACGACGAGAACGAUAAGCUGAUCCGCGAGGUCAAGGUGAU

CACCCUCAAAAGCAAACUUGUGUCAGACUUCCGGAAGGACUUCCAAUUCUACAAGGUCCGCG

AAAUCAACAACUACCACCACGCUCAUGACGCAUACCUGAACGCUGUGGUCGGGACUGCCCUC

AUCAAGAAGUACCCUAAACUCGAAAGCGAAUUUGUGUACGGCGACUACAAAGUGUACGAUGU

CCGGAAGAUGAUCGCGAAAUCCGAGCAGGAGAUCGGAAAGGCGACUGCUAAGUACUUUUUCU

ACUCGAACAUCAUGAACUUCUUCAAAACCGAAAUCACCCUGGCUAAUGGCGAGAUCAGAAAG

CGCCCGCUGAUCGAAACCAACGGCGAAACCGGUGAAAUCGUGUGGGACAAGGGCCGCGAUUU

CGCUACUGUGAGAAAGGUCCUUUCCAUGCCGCAAGUGAAUAUCGUCAAAAAGACUGAGGUGC

AGACUGGCGGAUUUUCCAAGGAAUCGAUCCUCCCAAAGAGGAACUCAGAUAAGCUCAUCGCG
```

-continued

CGGAAAAAGGAUUGGGACCCUAAGAAGUACGGAGGAUUUGAUAGCCCAACUGUGGCCUACUC
UGUGCUCGUGGUGGCCAAAGUCGAGAAAGGAAAGUCGAAGAAGUUGAAAUCCGUGAAAGAAC
UCUUGGGAAUCACUAUCAUGGAGCGGUCGUCAUUUGAAAAGAACCCAAUCGACUUCCUGGAA
GCCAAGGGAUACAAAGAAGUCAAGAAAGACCUGAUCAUCAAGCUCCCUAAGUACAGCCUGUU
CGAACUGGAGAACGGAAGGAAACGGAUGCUGGCUUCCGCCGGCGAACUGCAAAAGGGCAAUG
AGCUGGCCCUCCCAUCGAAAUACGUGAACUUCCUCUACCUUGCCUCCCAUUACGAAAAGUUG
AAGGGCUCACCCGAGGACAAUGAGCAGAAACAGCUCUUUGUUGAACAACACAAACACUACCU
GGACGAAAUCAUCGAACAAAUCAGCGAGUUCAGCAAGCGCGUCAUUCUGGCGGACGCGAACC
UGGAUAAAGUGCUGUCCGCGUACAACAAGCACCGCGAUAAGCCGAUACGGGAACAGGCUGAG
AACAUCAUUCACCUCUUCACUCUCACUAAUCUGGGAGCCCCCGCCGCCUUCAAGUACUUUGA
UACUACCAUCGACCGCAAGAGAUACACGAGCACCAAGGAAGUGCUCGAUGCCACCCUGAUCC
ACCAGUCCAUUACUGGUCUGUACGAAACGCGAAUCGAUCUGUCACAGCUCGGAGGAGAUGCG
UACCCCUACGAUGUCCCCGACUACGCGUCACUCGGUAGCGGCAGCCCGAAGAAGAAAAGAAA
GGUGGAGGACCCGAAGAAAAGAGGAAGGUUGACGGGAUCGGAAGCGGAUCGAAUGGAUCGU
CAGGGGGAGGUGGCGGAGGUAUGGACGCAAAAUCACUUACGGCCUGGUCACGGACCUUGGUG
ACCUUUAAAGACGUGUUCGUGGAUUUCACCAGGGAAGAAUGGAAACUGUUGGACACCGCCCA
GCAGAUCGUGUACCGGAAUGUGAUGCUGGAGAACUACAAAAACUUGGUGUCCCUGGGGUAUC
AACUCACUAAGCCAGAUGUCAUUCUUAGACUGGAAAAGGGAGAAGAACCGUGAUAAUAGGCU
GGAGCCUCGGUGGCCAUGCUUCUUGCCCCUUGGGCCUCCCCCCAGCCCCUCCUCCCCUUCCU
GCACCCGUACCCCCGUGGUCUUUGAAUAAAGUCUGAGUGGGCGGC+A(140nt) tail mRNA sequence of dCas9-NLS-FLAG-VP64
(SEQ ID NO: 52)
GGGAAAUAAGAGAGAAAAGAAGAGUAAGAAGAAAUAUAAGAGCCACCAUGGACAAGAAAUAC
UCAAUCGGACUUGCUAUCGGAACUAACAGCGUGGGAUGGGCCGUCAUUACUGACGAAUACAA
GGUGCCCUCAAAGAAGUUCAAGGUCCUGGGAAAUACCGAUAGACACUCCAUCAAAAAGAACC
UGAUCGGGGCACUGUUGUUCGACUCGGGAGAGACUGCAGAAGCAACCAGGCUCAAGCGCACU
GCGAGGCGCCGGUACACCCGGAGGAAGAACCGCAUCUGCUACCUCCAAGAGAUUUUCAGCAA
CGAGAUGGCAAAGGUCGAUGAUUCGUUCUUUCACCGCCUUGAGGAGUCGUUCCUUGUCGAGG
AGGACAAAAAGCAUGAAAGACAUCCGAUCUUCGGAAACAUCGUGGACGAAGUCGCAUACCAU
GAAAAGUACCCUACCAUCUACCAUCUCAGAAAGAAACUCGUCGAUUCAACUGAUAAGGCCGA
CUUGCGGCUGAUCUACCUGGCUCUGGCGCACAUGAUCAAGUUUCGGGGUCACUUUCUCAUCG
AGGGUGAUCUCAACCCGGACAAUUCCGACGUUGACAAACUCUUCAUCCAACUGGUCCAGACG
UACAACCAGCUGUUCGAAGAAAAUCCGAUCAACGCAAGCGGAGUGGACGCCAAAGCCAUUCU
GUCGGCCCGCCUCUCGAAGUCGCGUCGCCUGGAAAAUCUGAUUGCUCAGCUCCCGGGCGAAA
AGAAGAAUGGCCUGUUUGGAAACCUCAUCGCACUGUCCCUCGGGCUGACUCCCAACUUCAAA
UCGAACUUUGACUUGGCUGAGGAUGCAAAGCUGCAACUCUCCAAAGACACUUACGAUGAUGA
CCUGGACAAUCUCCUGGCGCAGAUCGGGGAUCAGUAUGCUGACCUGUUCCUGGCGGCCAAGA
ACCUGUCUGAUGCCAUCCUGCUCUCCGAUAUCCUGAGAGUGAACACUGAGAUCACCAAGGCG
CCUCUGAGCGCCUCGAUGAUCAAACGCUACGAUGAACACCAUCAGGACCUCACUCUUCUGAA
GGCUUUGGUGCGGCAGCAGCUUCCGGAAAAGUACAAAGAGAUCUUCUUCGACCAGUCGAAAA
ACGGCUACGCCGGAUACAUUGAUGGCGGCGCAAGCCAGGAGGAAUUCUAUAAGUUUAUCAAA
CCGAUCCUGGAGAAGAUGGACGGCACUGAAGAACUUCUGGUCAAGCUGAAUCGAGAGGAUCU

```
GCUCCGGAAGCAGCGGACCUUCGACAAUGGGUCUAUCCCUCACCAAAUCCAUCUCGGCGAGC

UGCAUGCGAUUCUGAGGCGCCAGGAGGACUUCUACCCAUUCCUGAAAGACAAUCGGGAGAAA

AUCGAAAAGAUUCUGACGUUCCGCAUUCCAUACUACGUCGGGCCACUUGCGCGGGGUAAUUC

GAGAUUCGCCUGGAUGACGCGGAAGUCCGAAGAAACCAUCACGCCGUGGAAUUUCGAAGAAG

UGGUCGACAAGGGAGCCAGCGCACAGUCCUUCAUUGAGCGCAUGACCAAUUUCGACAAAAAU

CUGCCGAACGAGAAGGUCCUGCCGAAGCAUUCACUGCUGUACGAAUACUUUACCGUGUACAA

CGAACUGACCAAGGUGAAGUACGUCACCGAGGGAAUGAGAAAGCCUGCUUUCCUGAGCGGAG

AACAGAAGAAGGCCAUUGUUGACCUCCUCUUCAAGACUAAUCGCAAAGUGACCGUGAAGCAG

CUUAAAGAGGAUUACUUCAAAAAGAUCGAAUGUUUCGACUCCGUGGAAAUCAGCGGCGUGGA

GGAUAGAUUCAACGCGUCCCUUGGGACUUACCACGACCUCCUUAAGAUCAUCAAGGAUAAGG

AUUUCCUCGACAAUGAGGAAAACGAAGAUAUCCUGGAGGACAUCGUUCUGACUCUGACCCUC

UUUGAGGACCGGGAGAUGAUCGAGGAGAGACUCAAGACCUACGCGCACCUGUUUGACGACAA

AGUGAUGAAGCAACUUAAACGCAGGCGCUACACCGGCUGGGGCAGACUGUCACGCAAGUUGA

UCAACGGAAUUAGAGAUAAACAGUCCGGAAAGACCAUCCUGGACUUCCUGAAGUCCGAUGGA

UUCGCCAACCGGAAUUUCAUGCAGCUCAUCCAUGACGACUCAUUGACUUUCAAGGAGGAUAU

CCAAAAGGCCCAAGUGAGCGGCCAAGGGGACUCCCUUCACGAACACAUCGCAAAUUUGGCCG

GAUCACCAGCGAUUAAGAAGGGAAUCCUGCAGACCGUGAAGGUGGUGGACGAGCUGGUGAAA

GUGAUGGGACGGCACAAGCCGGAAAACAUCGUGAUCGAGAUGGCCAGAGAGAACCAGACGAC

UCAAAAGGGCCAGAAGAACUCGCGCGAACGCAUGAAGAGAAUAGAAGAGGGAAUUAAGGAAC

UGGGAUCGCAGAUCUUGAAGGAGCACCCUGUCGAAAAUACUCAACUCCAGAACGAGAAGCUG

UACCUGUACUAUCUUCAAAACGGCAGGGACAUGUAUGUCGACCAAGAGCUCGACAUUAACCG

CCUGUCCGAUUAUGACGUGGACGCCAUCGUGCCGCAGAGCUUUCUCAAGGACGAUUCCAUCG

ACAACAAAGUGCUCACCCGCAGCGACAAGAAUAGAGGGAAGUCGGAUAACGUCCCUUCGGAA

GAGGUGGUGAAAAAGAUGAAGAAUUACUGGCGGCAGCUCCUGAAUGCAAAGCUCAUCACCCA

ACGGAAGUUUGACAACCUCACCAAGGCAGAAAGAGGAGGACUGUCGGAAUUGGAUAAGGCCG

GUUUCAUCAAGCGCACAAUUGGUGGAAACUCGGCAAAUUACCAAGCAUGUGGCACAGAUUCUG

GACUCCCGUAUGAACACCAAGUACGACGAGAACGAUAAGCUGAUCCGCGAGGUCAAGGUGAU

CACCCUCAAAAGCAAACUUGUGUCAGACUUCCGGAAGGACUUCCAAUUCUACAAGGUCCGCG

AAAUCAACAACUACCACCACGCUCAUGACGCAUACCUGAACGCUGUGGUCGGGACUGCCCUC

AUCAAGAAGUACCCUAAACUCGAAAGCGAAUUUGUGUACGGCGACUACAAAGUGUACGAUGU

CCGGAAGAUGAUCGCGAAAUCCGAGCAGGAGAUCGGAAAGGCGACUGCUAAGUACUUUUUCU

ACUCGAACAUCAUGAACUUCUUCAAAACCGAAAUCACCCUGGCUAAUGGCGAGAUCAGAAAG

CGCCCGCUGAUCGAAACCAACGGCGAAACCGGUGAAAUCGUGUGGGACAAGGGCCGCGAUUU

CGCUACUGUGAGAAAGGUCCUUUCCAUGCCGCAAGUGAAUAUCGUCAAAAAGACUGAGGUGC

AGACUGGCGGAUUUUCCAAGGAAUCGAUCCUCCCAAAGAGGAACUCAGAUAAGCUCAUCGCG

CGGAAAAAGGAUUGGGACCCUAAGAAGUACGGAGGAUUUGAUAGCCCAACUGUGGCCUACUC

UGUGCUCGUGGUGGCCAAAGUCGAGAAAGGAAAGUCGAAGAAGUUGAAAUCCGUGAAAGAAC

UCUUGGGAAUCACUAUCAUGGAGCGGUCGUCAUUUGAAAAGAACCCAAUCGACUUCCUGGAA

GCCAAGGGAUACAAAGAAGUCAAGAAAGACCUGAUCAUCAAGCUCCCUAAGUACAGCCUGUU

CGAACUGGAGAACGGAAGGAAACGGAUGCUGGCUUCCGCCGGCGAACUGCAAAAGGGCAAUG
```

-continued

```
AGCUGGCCCUCCCAUCGAAAUACGUGAACUUCCUCUACCUUGCCUCCCAUUACGAAAAGUUG

AAGGGCUCACCCGAGGACAAUGAGCAGAAACAGCUCUUUGUUGAACAACACAAACACUACCU

GGACGAAAUCAUCGAACAAAUCAGCGAGUUCAGCAAGCGCGUCAUUCUGGCGGACGCGAACC

UGGAUAAAGUGCUGUCCGCGUACAACAAGCACCGCGAUAAGCCGAUACGGGAACAGGCUGAG

AACAUCAUUCACCUCUUCACUCUCACUAAUCUGGGAGCCCCCGCCGCCUUCAAGUACUUUGA

UACUACCAUCGACCGCAAGAGAUACACGAGCACCAAGGAAGUGCUCGAUGCCACCCUGAUCC

ACCAGUCCAUUACUGGUCUGUACGAAACGCGAAUCGAUCUGUCACAGCUCGGAGGAGAUGGG

UCACCGAAAAGAAACGGAAAGUCAGCUCGGAUUACAAGGAUCACGACGGAGACUACAAGGA

CCAUGACAUCGACUAUAAGGACGACGACGACAAGGCCGCUGGAGGCGGUGGAUCGGGACGCG

CGGACGCCUUGGAUGACUUCGACCUUGACAUGCUGGGAUCCGACGCACUUGAUGAUUUUGAU

CUCGAUAUGCUUGGCAGCGACGCACUGGACGAUUUCGACCUCGACAUGCUCGGAUCGGAUGC

GCUCGACGACUUCGAUCUGGAUAUGCUGUGAUAAUAGGCUGGAGCCUCGGUGGCCAUGCUUC

UUGCCCCUUGGGCCUCCCCCCAGCCCCUCCUCCCCUUCCUGCACCCGUACCCCGUGGUCUU

UGAAUAAAGUCUGAGUGGGCGGC+A(140nt) tail
``` mRNA sequence of dCas9-KRAB-miR122

(SEQ ID NO: 53)

```
GGGAAAUAAGAGAGAAAAGAAGAGUAAGAAGAAAUAUAAGAGCCACCAUGGACAAGAAGUAC

UCAAUCGGACUCGCAAUCGGAACCAAUUCAGUCGGCUGGGCAGUCAUUACCGAUGAAUACAA

GGUGCCGUCGAAGAAGUUCAAAGUCCUGGGUAACACUGACAGACAUUCGAUCAAAAAGAACC

UGAUCGGAGCCUUGCUGUUUGAUUCAGGCGAAACCGCCGAAGCUACCCGGUUGAAACGAACU

GCUAGACGCCGCUACACGCGCCGCAAGAACCGGAUCUGCUACCUCCAAGAAAUCUUCUCGAA

CGAAAUGGCUAAGGUGGACGACUCGUUCUUUCACCGGCUCGAGGAGUCAUUCCUUGUGGAGG

AAGAUAAGAAGCACGAAAGACACCCGAUCUUCGGCAACAUCGUGGACGAAGUCGCGUACCAC

GAAAAGUACCCGACUAUCUACCAUCUCCGGAAGAAGCUCGUGGAUAGCACCGAUAAGGCCGA

UCUGCGACUGAUCUACCUCGCGCUGGCCCAUAUGAUUAAGUUCCGCGGGCACUUCCUCAUCG

AAGGGGACCUGAAUCCAGACAACUCGGACGUGGAUAAGCUGUUUAUCCAGCUGGUGCAGACU

UACAAUCAAUUGUUUGAAGAAAACCCUAUCAACGCGUCUGGGGUGGACGCAAAGGCCAUCCU

GAGCGCGCGGCUGUCAAAAUCCAGACGGCUGGAAAAUCUGAUAGCCCAACUGCCGGGCGAGA

AGAAAAACGGCCUGUUUGGAAAUCUUAUCGCCCUGUCCCUGGGACUGACCCCCAACUUCAAG

UCGAACUUCGACUUGGCCGAGGAUGCGAAGCUCCAGCUCAGCAAAGACACCUACGACGAUGA

CCUCGAUAACCUGUUGGCCCAGAUCGGUGACCAGUAUGCUGAUCUCUUCUUGGCGGCCAAGA

ACCUGUCAGACGCAAUUCUGCUCUCCGACAUCCUGCGGGUGAAUACUGAGAUCACUAAAGCC

CCAUUGAGCGCGUCGAUGAUCAAAAGAUACGACGAGCACCACCAGGAUCUGACUCUCCUCAA

GGCACUGGUCCGCCAACAGCUCCCGGAAAAGUACAAAGAGAUCUUCUUUGACCAAUCCAAAA

ACGGAUACGCUGGUUACAUAGACGGCGGAGCGUCACAAGAAGAGUUCUACAAGUUCAUCAAG

CCUAUCCUGGAAAAGAUGGACGGGACCGAGGAACUCCUGGUUAAGCUCAAUAGGGAGGAUCU

GCUGCGCAAGCAACGCACGUUCGACAAUGGAAGCAUCCCCCAUCAGAUCCACCUGGGGGAGC

UCCACGCGAUCCUGAGGCGCCAGGAAGAUUUCUACCCAUUUCUGAAGGACAAUAGAGAGAAA

AUCGAAAAGAUCCUGACUUUCCGAAUCCCGUACUACGUGGGCCCGCUCGCACGGGGAAACUC

ACGGUUUGCCUGGAUGACUCGCAAAUCCGAAGAAACCAUUACCCCCUGGAAUUUCGAGGAGG

UGGUCGAUAAAGGCGCCUCAGCCCAGUCGUUCAUCGAAAGAAUGACCAACUUUGACAAGAAC

CUCCCAAAUGAGAAGGUGCUGCCAAAACAUAGCCUGCUGUACGAGUACUUUACUGUGUAUAA
```

-continued

```
CGAACUCACCAAGGUGAAAUACGUGACCGAGGGAAUGCGCAAGCCGGCAUUUCUGUCGGGCG
AACAGAAGAAGGCAAUUGUGGACUUGCUGUUCAAAACCAACCGGAAGGUGACCGUGAAACAG
CUCAAGGAAGAUUACUUUAAGAAGAUCGAGUGUUUCGAUAGCGUCGAAAUUUCGGGGUGGA
AGAUCGCUUCAAUGCAAGCCUUGGGACGUACCACGAUCUGCUUAAGAUCAUUAAGGACAAGG
AUUUCCUUGACAACGAAGAGAACGAGGAUAUUCUCGAGGAUAUCGUCCUGACCCUGACUCUG
UUUGAGGAUAGAGAAAUGAUCGAGGAGAGAUUGAAAACUUACGCACACCUCUUCGACGAUAA
GGUGAUGAAACAGCUGAAAAGGCGUAGAUACACUGGUUGGGGAAGGCUGUCGAGAAAGCUGA
UCAACGGAAUUAGGGACAAGCAGUCCGGAAAAACCAUCCUGGAUUUCCUCAAGUCCGACGGU
UUCGCCAACCGCAACUUCAUGCAGCUGAUCCACGAUGAUUCCCUGACGUUCAAGAGGAUAU
CCAGAAGGCACAAGUGUCCGGACAAGGAGACUCACUCCACGAGCAUAUCGCUAAUCUCGCCG
GAUCGCCAGCUAUCAAGAAGGGAAUCUUGCAGACUGUCAAGGUGGUGGACGAACUGGUGAAA
GUGAUGGGAAGGCAUAAGCCGGAGAAUAUCGUGAUCGAGAUGGCGAGGGAAAACCAGACGAC
CCAGAAAGGACAGAAAAACAGCCGGGAACGCAUGAAGCGCAUCGAAGAGGGAAUCAAAGAGC
UUGGGAGCCAAAUCCUCAAAGAACACCCUGUGGAAAAUACCCAACUGCAGAAUGAGAAGCUU
UACCUGUAUUACCUCCAAAACGGGCGCGACAUGUACGUUGACCAGGAAUUGGACAUUAACCG
GCUUUCCGACUACGAUGUGGACGCUAUCGUCCCGCAGUCCUUCCUGAAAGACGAUUCGAUCG
ACAAUAAGGUCCUGACUAGAUCAGACAAGAAUCGGGGAAAGUCAGACAACGUGCCUAGCGAA
GAGGUCGUUAAGAAGAUGAAGAAUUACUGGCGCCAGCUGCUGAACGCGAAGCUUAUCACUCA
GCGCAAGUUCGACAACCUCACCAAGGCAGAAAGAGGCGGAUUGUCGGAGCUCGACAAAGCUG
GCUUCAUCAAGCGCCAGCUCGUCGAAACUCGCCAGAUUACUAAGCAUGUGGCGCAGAUCCUG
GACAGCCGCAUGAAUACUAAGUAUGAUGAGAAUGACAAGCUCAUCCGGGAGGUGAAGGUCAU
CACCCUGAAGUCCAAGCUGGUGUCCGACUUCCGGAAGGACUUCCAAUUCUACAAAGUCAGAG
AAAUCAACAAUUACCAUCACGCGCAUGACGCCUACUUGAAUGCAGUGGUGGGUACUGCCCUC
AUCAAGAAAUACCCAAAGCUUGAAAGCGAGUUUGUCUACGGAGACUACAAGGUGUACGACGU
CCGGAAGAUGAUCGCCAAAUCGGAACAGGAAAUUGGGAAGGCGACCGCUAAGUACUUCUUCU
ACUCGAAUAUCAUGAAUUUCUUCAAGACCGAGAUCACGCUUGCAAAUGGCGAAAUCCGGAAG
CGGCCCCUCAUCGAAACCAACGGAGAAACCGGAGAAAUCGUGUGGGACAAGGGUCGCGAUUU
UGCGACCGUCCGAAAGGUUCUUAGCAUGCCUCAAGUGAACAUCGUCAAGAAAACGGAAGUGC
AGACUGGAGGCUUCAGCAAGGAGUCCAUUCUCCCGAAACGCAACUCCGACAAACUGAUCGCA
CGCAAGAAAGACUGGGACCCGAAGAAAUACGGAGGCUUCGAUUCGCCGACUGUGGCUUACUC
GGUCCUGGUUGUGGCCAAGGUGGAAAAGGGAAAGUCCAAGAAGCUGAAGUCCGUCAAGGAGC
UCCUCGGAAUCACCAUCAUGGAACGGUCAAGCUUCGAGAAAAACCCAAUUGACUUCCUGGAG
GCAAAGGGGUACAAGGAGGUGAAGAAGGAUCUGAUCAUCAAACUGCCGAAGUACAGCCUCUU
UGAGCUCGAAAACGGACGCAAAAGGAUGCUGGCCUCCGCCGGAGAGCUGCAAAAGGGAAACG
AGCUUGCCUUGCCUUCCAAGUACGUGAACUUCCUGUACCUGGCAUCCCACUACGAAAAACUG
AAGGGAUCGCCGGAGGACAACGAACAGAAGCAGCUGUUUGUGGAACAACACAAGCAUUAUCU
GGAUGAAAUCAUCGAACAAAUCAGCGAAUUCUCAAAAAGGGUGAUCUUGGCCGACGCCAACC
UGGAUAAAGUGCUUUCCGCCUACAACAAACAUCGCGACAAGCCGAUCCGGGAGCAGGCCGAA
AACAUCAUUCACCUGUUUACCCUGACUAAUCUGGGUGCGCCCGCGGCUUUCAAAUACUUCGA
UACCACGAUCGACCGGAAGAGAUACACCAGCACCAAAGAGGUGUUGGACGCGACCCUCAUCC
```

-continued

ACCAAUCUAUUACCGGCCUCUAUGAAACUAGGAUCGACCUCAGCCAGCUGGGAGGCGAUGCC

UACCCUUACGAUGUCCCGGACUACGCCUCGCUGGGAUCCGGAUCUCCGAAGAAGAAGCGGAA

GGUCGAGGACCCAAAGAAAAAGCGCAAAGUGGAUGGGAUCGGUAGCGGUUCCAACGGUUCCU

CGGGUGGCGGCGGAGGCGGCAUGGAUGCUAAGUCACUUACCGCCUGGUCGCGGACGCUGGUG

ACUUUCAAAGAUGUGUUCGUGGAUUUCACUCGUGAGGAAUGGAAAUUGCUGGACACUGCCCA

ACAGAUCGUCUACCGCAACGUCAUGCUUGAAAACUACAAAAACCUCGUGUCGCUGGGAUAUC

AGCUGACCAAGCCCGACGUGAUUCUGAGACUGGAGAAGGGCGAAGAACCUUGAUAAUAGGCU

GGAGCCUCGGUGGCCAUGCUUCUUGCCCCUUGGGCCUCCCCCCAGCCCCUCCUCCCCUUCCU

GCACCCGUACCCCCCAAACACCAUUGUCACACUCCAGUGGUCUUUGAAUAAAGUCUGAGUGG

GCGGC+A(140nt) tail mRNA sequence of dCas9-VP64-miR122

(SEQ ID NO: 54)

GGGAAAUAAGAGAGAAAAGAAGAGUAAGAAGAAAUAUAAGAGCCACCAUGGACAAGAAGUAC

UCAAUCGGACUCGCAAUCGGAACCAAUUCAGUCGGCUGGGCAGUCAUUACCGAUGAAUACAA

GGUGCCGUCGAAGAAGUUCAAAGUCCUGGGUAACACUGACAGACAUUCGAUCAAAAAGAACC

UGAUCGGAGCCUUGCUGUUUGAUUCAGGCGAAACCGCCGAAGCUACCCGGUUGAAACGAACU

GCUAGACGCCGCUACACGCGCCGCAAGAACCGGAUCUGCUACCUCCAAGAAAUCUUCUCGAA

CGAAAUGGCUAAGGUGGACGACUCGUUCUUUCACCGGCUCGAGGAGUCAUUCCUUGUGGAGG

AAGAUAAGAAGCACGAAAGACACCCGAUCUUCGGCAACAUCGUGGACGAAGUCGCGUACCAC

GAAAAGUACCCGACUAUCUACCAUCUCCGGAAGAAGCUCGUGGAUAGCACCGAUAAGGCCGA

UCUGCGACUGAUCUACCUCGCGCUGGCCCAUAUGAUUAAGUUCCGCGGGCACUUCCUCAUCG

AAGGGGACCUGAAUCCAGACAACUCGGACGUGGAUAAGCUGUUUAUCCAGCUGGUGCAGACU

UACAAUCAAUUGUUUGAAGAAAACCCUAUCAACGCGUCUGGGGUGGACGCAAAGGCCAUCCU

GAGCGCGCGGCUGUCAAAAUCCAGACGGCUGGAAAAUCUGAUAGCCCAACUGCCGGGCGAGA

AGAAAAACGGCCUGUUUGGAAAUCUUAUCGCCCUGUCCCUGGGACUGACCCCCAACUUCAAG

UCGAACUUCGACUUGGCCGAGGAUGCGAAGCUCCAGCUCAGCAAAGACACCUACGACGAUGA

CCUCGAUAACCUGUUGGCCCAGAUCGGUGACCAGUAUGCUGAUCUCUUCUUGGCGGCCAAGA

ACCUGUCAGACGCAAUUCUGCUCUCCGACAUCCUGCGGGUGAAUACUGAGAUCACUAAAGCC

CCAUUGAGCGCGUCGAUGAUCAAAAGAUACGACGAGCACCACCAGGAUCUGACUCUCCUCAA

GGCACUGGUCCGCCAACAGCUCCCGGAAAAGUACAAAGAGAUCUUCUUUGACCAAUCCAAAA

ACGGAUACGCUGGUUACAUAGACGGCGGAGCGUCACAAGAAGAGUUCUACAAGUUCAUCAAG

CCUAUCCUGGAAAAGAUGGACGGGACCGAGGAACUCCUGGUUAAGCUCAAUAGGGAGGAUCU

GCUGCGCAAGCAACGCACGUUCGACAAUGGAAGCAUCCCCCAUCAGAUCCACCUGGGGGAGC

UCCACGCGAUCCUGAGGCGCCAGGAAGAUUUCUACCCAUUUCUGAAGGACAAUAGAGAGAAA

AUCGAAAAGAUCCUGACUUUCCGAAUCCCGUACUACGUGGGCCCGCUCGCACGGGGAAACUC

ACGGUUUGCCUGGAUGACUCGCAAAUCCGAAGAAACCAUUACCCCCUGGAAUUUCGAGGAGG

UGGUCGAUAAAGGCGCCUCAGCCCAGUCGUUCAUCGAAAGAAUGACCAACUUUGACAAGAAC

CUCCCAAAUGAAGGUGCUGCCAAAACAUAGCCUGCUGUACGAGUACUUUACUGUGUAUAA

CGAACUCACCAAGGUGAAAUACGUGACCGAGGGAAUGCGCAAGCCGGCAUUUCUGUCGGGCG

AACAGAAGAAGGCAAUUGUGGACUUGCUGUUCAAAACCAACCGGAAGGUGACCGUGAAACAG

CUCAAGGAAGAUUACUUUAAGAAGAUCGAGUGUUUCGAUAGCGUCGAAAUUUCGGGGUGGA

AGAUCGCUUCAAUGCAAGCCUUGGGACGUACCACGAUCUGCUUAAGAUCAUUAAGGACAAGG

-continued

```
AUUUCCUUGACAACGAAGAGAACGAGGAUAUUCUCGAGGAUAUCGUCCUGACCCUGACUCUG

UUUGAGGAUAGAGAAAUGAUCGAGGAGAGAUUGAAAACUUACGCACACCUCUUCGACGAUAA

GGUGAUGAAACAGCUGAAAAGGCGUAGAUACACUGGUUGGGAAGGCUGUCGAGAAAGCUGA

UCAACGGAAUUAGGGACAAGCAGUCCGGAAAAACCAUCCUGGAUUUCCUCAAGUCCGACGGU

UUCGCCAACCGCAACUUCAUGCAGCUGAUCCACGAUGAUUCCCUGACGUUCAAAGAGGAUAU

CCAGAAGGCACAAGUGUCCGGACAAGGAGACUCACUCCACGAGCAUAUCGCUAAUCUCGCCG

GAUCGCCAGCUAUCAAGAAGGGAAUCUUGCAGACUGUCAAGGUGGUGGACGAACUGGUGAAA

GUGAUGGGAAGGCAUAAGCCGGAGAAUAUCGUGAUCGAGAUGGCGAGGGAAAACCAGACGAC

CCAGAAAGGACAGAAAAACAGCCGGGAACGCAUGAAGCGCAUCGAAGAGGGAAUCAAAGAGC

UUGGGAGCCAAAUCCUCAAAGAACACCCUGUGGAAAAUACCCAACUGCAGAAUGAGAAGCUU

UACCUGUAUUACCUCCAAAACGGGCGCGACAUGUACGUUGACCAGGAAUUGGACAUUAACCG

GCUUUCCGACUACGAUGUGGACGCUAUCGUCCCGCAGUCCUUCCUGAAAGACGAUUCGAUCG

ACAAUAAGGUCCUGACUAGAUCAGACAAGAAUCGGGGAAAGUCAGACAACGUGCCUAGCGAA

GAGGUCGUUAAGAAGAUGAAGAAUUACUGGCGCCAGCUGCUGAACGCGAAGCUUAUCACUCA

GCGCAAGUUCGACAACCUCACCAAGGCAGAAAGAGGCGGAUUGUCGGAGCUCGACAAAGCUG

GCUUCAUCAAGCGCCAGCUCGUCGAAACUCGCCAGAUUACUAAGCAUGUGGCGCAGAUCCUG

GACAGCCGCAUGAAUACUAAGUAUGAUGAGAAUGACAAGCUCAUCCGGGAGGUGAAGGUCAU

CACCCUGAAGUCCAAGCUGGUGUCCGACUUCCGGAAGGACUUCCAAUUCUACAAAGUCAGAG

AAAUCAACAAUUACCAUCACGCGCAUGACGCCUACUUGAAUGCAGUGGUGGGUACUGCCCUC

AUCAAGAAAUACCCAAAGCUUGAAAGCGAGUUUGUCUACGGAGACUACAAGGUGUACGACGU

CCGGAAGAUGAUCGCCAAAUCGGAACAGGAAAUUGGGAAGGCGACCGCUAAGUACUUCUUCU

ACUCGAAUAUCAUGAAUUUCUUCAAGACCGAGAUCACGCUUGCAAAUGGCGAAAUCCGGAAG

CGGCCCCUCAUCGAAACCAACGGAGAAACCGGAGAAAUCGUGUGGGACAAGGGUCGCGAUUU

UGCGACCGUCCGAAAGGUUCUUAGCAUGCCUCAAGUGAACAUCGUCAAGAAAACGGAAGUGC

AGACUGGAGGCUUCAGCAAGGAGUCCAUUCUCCCGAAACGCAACUCCGACAAACUGAUCGCA

CGCAAGAAAGACUGGGACCCGAAGAAAUACGGAGGCUUCGAUUCGCCGACUGUGGCUUACUC

GGUCCUGGUUGUGGCCAAGGUGGAAAAGGGAAAGUCCAAGAAGCUGAAGUCCGUCAAGGAGC

UCCUCGGAAUCACCAUCAUGGAACGGUCAAGCUUCGAGAAAAACCCAAUUGACUUCCUGGAG

GCAAAGGGGUACAAGGAGGUGAAGAAGGAUCUGAUCAUCAAACUGCCGAAGUACAGCCUCUU

UGAGCUCGAAAACGGACGCAAAAGGAUGCUGGCCUCCGCCGGAGAGCUGCAAAAGGGAAACG

AGCUUGCCUUGCCUUCCAAGUACGUGAACUUCCUGUACCUGGCAUCCCACUACGAAAAACUG

AAGGGAUCGCCGGAGGACAACGAACAGAAGCAGCUGUUUGUGGAACAACACAAGCAUUAUCU

GGAUGAAAUCAUCGAACAAAUCAGCGAAUUCUCAAAAAGGGGUGAUCUUGGCCGACGCCAACC

UGGAUAAAGUGCUUUCCGCCUACAACAAACAUCGCGACAAGCCGAUCCGGGAGCAGGCCGAA

AACAUCAUUCACCUGUUUACCCUGACUAAUCUGGGUGCGCCCGCGGCUUUCAAAUACUUCGA

UACCACGAUCGACCGGAAGAGAUACACCAGCACCAAAGAGGUGUUGGACGCGACCCUCAUCC

ACCAAUCUAUUACCGGCCUCUAUGAAACUAGGAUCGACCUCAGCCAGCUGGGAGGCGAUGGA

UCCCCAAAGAAGAAGAGAAAAGUGUCCUCCGACUACAAGGAUCAUGAUGGGGACUAUAAAGA

UCAUGAUAUUGAUUACAAGGACGACGACGACAAGGCCGCUGGAGGAGGAGGUUCCGGCCGCG

CCGAUGCUCUCGACGACUUCGACCUCGACAUGCUGGGAUCCGACGCCCUGGACGACUUUGAU
```

-continued

CUGGAUAUGCUGGGCUCGGACGCCCUUGAUGACUUCGAUCUGGACAUGCUGGGGUCGGAUGC

ACUGGACGACUUCGACCUUGAUAUGCUGUGAUAAUAGGCUGGAGCCUCGGUGGCCAUGCUUC

UUGCCCCUUGGGCCUCCCCCCAGCCCCUCCUCCCCUUCCUGCACCCGUACCCCCCAAACACC

AUUGUCACACUCCAGUGGUCUUUGAAUAAAGUCUGAGUGGGCGGC+A(140nt) tail mRNA sequence of Cas9 (Mali)

(SEQ ID NO: 55)
GGGAAAUAAGAGAGAAAAGAAGAGUAAGAAGAAAUAUAAGAGCCACCAUGGACAAGAAAUAC

AGCAUCGGCCUGGAUAUUGGAACUAACAGCGUUGGAUGGGCAGUGAUCACCGACGAGUACAA

GGUGCCGAGCAAGAAGUUCAAGGUGCUGGGGAACACUGACCGCCAUUCAAUUAAGAAAAACC

UCAUUGGAGCACUGCUUUUUGACUCGGGUGAGACUGCCGAAGCUACCAGGCUCAAACGCACC

GCACGCAGACGGUACACCCGCCGCAAGAAUCGCAUCUGCUAUCUGCAAGAGAUCUUUUCCAA

CGAGAUGGCGAAGGUUGACGACAGCUUUUUCCACCGGCUGGAAGAGAGCUUCCUCGUGGAAG

AGGACAAAAAGCACGAAAGGCAUCCAAUCUUCGGUAACAUCGUGGACGAAGUGGCGUAUCAC

GAAAAGUACCCUACCAUCUACCAUCUGCGGAAGAAGCUGGUCGAUUCCACGGAUAAGGCAGA

CCUGAGACUGAUCUACCUGGCUUUGGCCCAUAUGAUCAAAUUCCGCGGCCAUUUCCUGAUCG

AGGGGGACCUUAACCCGGAUAACUCGGAUGUCGACAAGCUGUUCAUCCAGCUGGUCCAAACG

UAUAACCAACUGUUUGAGGAAAAUCCCAUCAACGCUUCGGGGUGGACGCCAAAGCAAUCCU

CUCCGCGCCUGAGCAAGUCACGGCGGCUCGAAAACCUGAUCGCGCAGCUGCCGGGAGAAA

AGAAAAAUGGACUGUUUGGGAAUCUGAUCGCGCUGUCGCUCGGCCUGACUCCAAACUUUAAG

UCAAAUUUCGAUUUGGCCGAAGAUGCCAAGCUGCAGCUGUCAAAGGACACUUACGACGACGA

CCUGGACAAUCUGCUGGCCCAGAUUGGGGACCAAUACGCAGACCUGUUCUUGGCCGCGAAGA

ACCUGAGCGACGCCAUUCUUCUGUCCGAUAUUCUGAGAGUCAAUACCGAAAUCACUAAGGCU

CCGCUGUCCGCUUCAAUGAUCAAGCGCUACGAUGAACACCACCAGGAUCUCACUCUGCUCAA

AGCCCUCGUGAGACAACAAUUGCCUGAAAAGUACAAGGAGAUCUUCUUCGACCAGAGCAAAA

ACGGCUACGCAGGCUACAUCGAUGGAGGAGCGUCACAAGAAGAGUUCUACAAGUUCAUCAAG

CCAAUCUUGGAGAAGAUGGACGGUACUGAAGAACUCCUUGUGAAGCUGAAUAGGGAGGAUUU

GCUCAGAAAGCAGCGGACUUUUGACAACGGCUCGAUCCCUCAUCAGAUUCACCUCGGUGAGC

UGCAUGCCAUCCUUCGGCGCCAAGAGGAUUUUUACCCCUUCCUGAAGGAUAAUCGCGAGAAA

AUCGAAAAGAUCCUGACGUUCAGAAUUCCCUACUACGUGGGACCGCUGGCGCGCGGUAACUC

GCGGUUUGCAUGGAUGACUCGCAAGUCAGAGGAAACUAUCACUCCUUGGAAUUUUGAGGAGG

UCGUCGAUAAGGGAGCCUCCGCCCAGUCAUUCAUCGAACGCAUGACCAACUUCGACAAGAAU

CUUCCGAACGAGAAGGUCCUUCCAAAGCACUCCCUGUUGUACGAAUACUUCACCGUGUACAA

UGAGCUGACCAAAGUUAAGUAUGUCACCGAGGGCAUGAGAAAGCCGGCCUUCCUCAGCGGCG

AACAAAAGAAGGCCAUCGUCGACCUCCUCUUCAAGACCAACCGGAAGGUGACCGUCAAGCAA

CUCAAGGAGGACUACUUCAAGAAGAUCGAAUGCUUUGACUCGGUCGAAAUCAGCGGAGUGGA

GGACCGGUUUAACGCGUCACUGGGUACCUACCAUGAUCUCCUGAAAAUCAUCAAAGACAAGG

ACUUCCUGGACAACGAAGAAACGAGGACAUCCUGGAAGAUAUUGUGUUGACCCUGACGCUG

UUCGAGGACCGGGAAAUGAUCGAGGAAAGGCUUAAGACCUACGCACACCUCUUCGAUGACAA

AGUGAUGAAGCAACUGAAGCGGCGAGAUAUACUGGCUGGGGAGGCUCUCCCGGAAGCUCA

UUAAUGGAAUCAGAGACAAACAGUCGGGUAAAACUAUCCUCGACUUCCUCAAGUCGGAUGGG

UUCGCCAACCGGAACUUCAUGCAGCUGAUCCACGAUGAUUCCUUGACCUUCAAGGAAGAUAU

CCAGAAGGCGCAAGUGAGCGGACAGGGAGAUUCGUUGCACGAACAUAUCGCUAAUCUCGCCG

-continued

```
GAUCCCCAGCCAUCAAGAAAGGAAUCCUGCAGACCGUGAAGGUGGUGGAUGAACUGGUGAAA
GUGAUGGGGCGCCACAAACCAGAGAACAUCGUCAUUGAGAUGGCCCGCGAGAAUCAGACCAC
UCAGAAGGGACAAAAGAACUCCAGAGAGCGGAUGAAACGCAUCGAGGAAGGCAUCAAAGAGC
UUGGUAGCCAAAUCCUGAAGGAACACCCGGUCGAGAACACCCAGCUCCAGAACGAAAAGCUU
UACCUGUACUACCUCCAAAAUGGACGGGACAUGUACGUCGACCAGGAAUUGGACAUCAACAG
ACUCAGCGACUACGAUGUGGACCAUAUUGUGCCACAGUCCUUUCUUAAGGACGACAGCAUCG
AUAACAAAGUGCUCACUAGAUCAGACAAAAAUCGCGGGAAAUCAGACAAUGUGCCAUCGGAA
GAGGUUGUCAAGAAGAUGAAAAACUACUGGAGACAGCUGCUCAAUGCCAAACUUAUCACCCA
GCGGAAGUUCGACAACCUUACCAAGGCCGAGCGCGGAGGAUUGUCCGAACUCGACAAGGCCG
GCUUCAUCAAAAGGCAGCUGGUGGAAACCCGGCAGAUCACUAAACACGUGGCCCAGAUCCUC
GAUUCGCGCAUGAACACUAAAUACGAUGAGAAUGACAAGCUGAUUAGGGAAGUCAAGGUCAU
CACUCUGAAGUCGAAACUGGUGUCGGACUUUAGAAAGGAUUUCCAGUUCUACAAAGUCCGCG
AGAUUAACAACUACCACCACGCUCAUGACGCCUACCUGAAUGCAGUUGUGGGCACCGCGCUG
AUCAAGAAGUAUCCGAAGCUGGAAUCCGAGUUCGUGUACGGAGAUUACAAAGUGUACGACGU
GCGCAAGAUGAUCGCCAAGUCGGAACAGGAAAUCGGAAAGGCUACUGCAAAGUACUUCUUCU
ACUCAAACAUCAUGAACUUCUUCAAAACGGAGAUCACGCUCGCGAACGGCGAAAUCCGGAAA
AGGCCGCUCAUUGAAACCAACGGAGAAACCGGGGAGAUCGUGUGGGACAAGGGAAGGGAUUU
UGCGACUGUGAGGAAGGUGUUGUCCAUGCCGCAAGUCAAUAUUGUGAAAAAGACGGAAGUGC
AAACCGGAGGAUUCAGCAAAGAAUCCAUCCUCCCAAAGCGCAACUCGGACAAACUCAUCGCG
CGCAAGAAGGAUUGGGACCCCAAGAAAUACGGUGGCUUUGACAGCCCUACUGUGGCUUACUC
CGUCCUCGUCGUGGCUAAAGUGGAAAAGGGUAAAUCCAAAAAGCUCAAAUCGGUGAAGGAGC
UCCUGGGAAUCACGAUCAUGGAGCGGUCGAGCUUCGAAAAGAAUCCUAUUGAUUUCCUGGAG
GCGAAGGGCUACAAGGAAGUCAAGAAAGACCUGAUCAUCAAGCUCCCGAAGUACAGCCUCUU
CGAGCUCGAAAACGGCAGAAAGAGGAUGCUGGCAUCAGCGGGAGAAUUGCAGAAGGGAAACG
AACUGGCACUGCCGUCCAAGUACGUGAAUUUUCUCUAUCUGGCUAGCCACUACGAAAAGCUG
AAGGGAUCGCCCGAGGACAACGAGCAAAAACAACUGUUCGUGGAGCAGCACAAGCACUACCU
GGAUGAGAUCAUCGAGCAGAUCUCCGAAUUCUCGAAACGCGUGAUCCUUGCCGAUGCCAAUC
UGGAUAAAGUGUUGUCGGCUUACAACAAGCAUCGGGAUAAACCGAUCCGCGAACAGGCAGAA
AACAUCAUUCAUCUGUUCACUUUGACCAAUCUGGGAGCGCCUGCCGCGUUUAAGUACUUCGA
CACCACUAUUGAUAGAAAGCGCUACACCUCGACCAAGGAAGUGCUGGACGCUACCCUGAUCC
ACCAGUCCAUCACCGGACUCUACGAAACUCGCAUUGACCUGUCCCAGCUUGGAGGAGAUUCA
CGGGCCGAUCCAAAGAAAAAGCGCAAGGUCUGAUAAUAGGCUGGAGCCUCGGUGGCCAUGCU
UCUUGCCCCUUGGGCCUCCCCCCAGCCCCUCCUCCCCUUCCUGCACCCGUACCCCCGUGGUC
UUUGAAUAAAGUCUGAGUGGGCGGC+A(140nt) tail
```
mRNA sequence of Cas9 (Cong)
(SEQ ID NO: 56)
```
GGGAAAUAAGAGAGAAAAGAAGAGUAAGAAGAAAUAUAAGAGCCACCAUGGACUACAAGGAC
CACGACGGAGACUACAAAGACCAUGACAUCGAUUACAAGGAUGACGAUGACAAAAUGGCACC
GAAGAAGAAGAGAAAGGUCGGAAUUCACGGGGUGCCGGCCGCGGACAAGAAGUACUCAAUCG
GACUGGAUAUCGGCACGAACAGCGUGGGUUGGGCAGUGAUCACCGACGAAUACAAGGUGCCG
AGCAAGAAGUUCAAAGUGCUGGGAAAUACCGAUCGCCAUUCGAUCAAGAAAAAUCUGAUUGG
```

-continued

```
CGCGCUCCUGUUCGACUCGGGAGAGACUGCCGAGGCCACUAGACUGAAGAGGACCGCUAGGC

GCCGCUACACGAGGCGCAAAAACCGCAUCUGCUAUCUUCAAGAAAUCUUCUCAAACGAGAUG

GCCAAGGUGGACGACUCCUUUUUCCAUCGGCUGGAAGAAUCAUUUCUGGUGGAGGAGGACAA

GAAGCACGAACGCCAUCCCAUUUUCGGCAACAUUGUCGACGAAGUGGCCUAUCAUGAGAAGU

AUCCGACUAUCUACCACUUGAGAAAGAAGCUGGUGGACUCCACUGACAAGGCAGAUCUGCGG

UUGAUCUACCUCGCACUGGCCCAUAUGAUCAAAUUCCGGGGACACUUCCUCAUCGAGGGCGA

CCUUAAUCCCGACAAUUCCGAUGUGGAUAAGCUUUUCAUCCAGCUGGUCCAGACCUACAACC

AACUGUUUGAAGAAAAUCCAAUCAAUGCGAGCGGUGUCGAUGCAAAGGCCAUCCUGAGCGCC

CGCCUCUCGAAAAGCAGAAGGCUCGAAAACCUGAUCGCACAGUUGCCUGGAGAGAAGAAGAA

CGGCCUCUUCGGCAAUCUCAUCGCAUUGUCCCUGGGACUGACUCCAAACUUCAAAUCCAACU

UCGACUUGGCCGAGGACGCCAAACUGCAACUGAGCAAAGAUACCUACGAUGAUGACUUGGAC

AAUCUUCUGGCUCAGAUCGGCGACCAGUACGCCGACCUGUUCCUUGCGGCUAAGAACCUGUC

GGACGCCAUCCUGCUGUCCGACAUCCUGCGCGUCAAUACCGAAAUUACUAAAGCACCACUCU

CGGCAUCCAUGAUCAAGAGAUACGAUGAACACCACCAGGAUCUCACCCUCCUGAAAGCACUG

GUGCGGCAGCAGCUCCCUGAGAAAUACAAGGAAAUCUUCUUUGAUCAGUCCAAGAACGGAUA

CGCCGGAUACAUCGACGGCGGCGCGAGCCAAGAGGAAUUCUACAAGUUCAUCAAGCCGAUCC

UGGAAAAGAUGGAUGGCACGGAAGAACUCCUGGUCAAACUGAAUAGAGAGGAUCUGCUCCGC

AAACAACGGACCUUCGAUAACGGAUCGAUCCCGCACCAGAUCCACCUCGGCGAACUGCAUGC

CAUCCUGCGGCGGCAGGAGGACUUUUACCCGUUCCUCAAAGACAACAGAGAAAAGAUCGAGA

AGAUCUUGACCUUUCGCAUCCCGUACUACGUGGGCCCGCUCGCGAGAGGUAACUCCCGCUUU

GCUUGGAUGACUAGAAAGUCAGAGGAAACGAUCACCCCAUGGAACUUCGAAGAGGUGGUUGA

CAAAGGAGCGAGCGCCCAAUCGUUCAUCGAACGGAUGACUAACUUCGAUAAGAAUCUGCCGA

AUGAGAAGGUCCUGCCUAAGCACUCACUUCUGUAUGAAUACUUUACUGUGUAUAACGAACUC

ACCAAAGUCAAAUACGUGACUGAGGGAAUGCGCAAGCCUGCGUUUUUGUCCGGCGAGCAGAA

AAAGGCCAUCGUGGACUUGCUGUUCAAAACCAACCGCAAGGUGACUGUUAAGCAACUCAAAG

AGGACUACUUUAAGAAGAUCGAAUGCUUUGACUCGGUCGAGAUUUCCGGGGUUGAAGAUAGA

UUCAACGCGUCGCUGGGAACCUACCAUGAUCUCCUCAAGAUUAUCAAGGACAAAGACUUCCU

GGAUAACGAGGAGAAUGAGGACAUCCUCGAAGAUAUUGUGCUUACCCUGACCCUUUUCGAAG

AUCGCGAAAUGAUCGAAGAACGCCUGAAAACCUACGCUCACCUGUUCGACGAUAAGGUGAUG

AAACAGUUGAAACGCCGGCGGUACACGGGUUGGGGCGGCUGUCGCGCAAGCUGAUCAACGG

AAUUCGGGACAAACAGAGCGGAAAGACCAUCCUCGAUUUUCUGAAGUCCGAUGGUUUUGCCA

ACCGCAACUUCAUGCAGCUCAUCCAUGACGAUUCGCUUACCUUUAAGGAGGAUAUCCAGAAG

GCACAAGUGUCGGGACAAGGGGAUUCGCUCCACGAACACAUCGCCAAUCUGGCGGGGUCGCC

GGCAAUUAAGAAGGGAAUCCUCCAGACUGUUAAGGUGGUCGACGAGCUGGUGAAGGUGAUGG

GGAGACAUAAGCCUGAAAACAUUGUGAUCGAGAUGGCGAGAGAAAAUCAAACUACUCAGAAG

GGACAGAAGAAUUCCCGGGAGCGGAUGAAGCGCAUCGAGGAGGGAAUCAAGGAACUGGGCUC

CCAAAUCCUGAAAGAGCAUCCCGUGGAAAAUACUCAGCUGCAGAACGAGAAGCUUUACCUGU

ACUAUCUUCAAAAUGGCAGGGACAUGUACGUCGACCAAGAACUGGAUAUCAAUCGGCUCUCC

GAUUACGACGUCGAUCACAUCGUCCCCCAAUCAUUCCUGAAGGAUGAUAGCAUCGAUAACAA

GGUGCUCACUAGAUCAGACAAAAACCGGGGAAAGUCAGAUAACGUCCCCAGCGAAGAAGUCG

UGAAGAAGAUGAAGAAUUACUGGAGGCAACUUCUGAACGCCAAACUCAUCACUCAGCGCAAG
```

-continued

UUCGACAACCUGACCAAAGCAGAAAGGGGAGGACUCAGCGAGCUGGACAAGGCUGGUUUCAU

CAAACGGCAGCUGGUGGAGACUCGCCAAAUCACGAAGCAUGUGGCCCAGAUUCUCGACUCGC

GCAUGAAUACUAAGUACGACGAAAACGAUAAGCUGAUCCGGGAGGUGAAGGUGAUCACCCUC

AAGAGCAAGCUCGUGUCCGAUUUCCGGAAAGACUUCCAGUUCUACAAGGUGCGGGAGAUUAA

CAACUACCAUCACGCUCACGACGCUUACCUCAAUGCUGUGGUGGGACGGCGUUGAUUAAGA

AGUACCCAAAACUGGAGUCCGAAUUCGUCUACGGAGAUUACAAGGUCUACGACGUGCGCAAG

AUGAUUGCCAAGUCGGAGCAGGAAAUUGGGAAAGCGACUGCUAAGUACUUCUUCUACUCGAA

UAUCAUGAACUUCUUCAAGACCGAAAUCACCCUGGCUAACGGCGAGAUCAGGAAACGGCCGC

UGAUCGAAACUAAUGGUGAGACUGGUGAAAUCGUGUGGGAUAAGGGACGGGACUUCGCCACG

GUCCGCAAGGUCCUCAGCAUGCCGCAAGUGAAUAUUGUUAAGAAAACCGAAGUGCAGACCGG

UGGGUUCUCGAAGGAAUCCAUCCUGCCAAAGCGCAACUCGGAUAAGCUUAUUGCCCGCAAGA

AGGAUUGGGACCCGAAAAAGUACGGUGGGUUCGACUCCCCUACCGUGGCGUACUCGGUGUUG

GUGGUGGCCAAAGUGGAAAAGGGCAAAUCAAAGAAGCUCAAGAGCGUCAAGGAGCUGCUGGG

AAUCACCAUCAUGGAGAGGUCCAGCUUUGAGAAAAACCCGAUCGACUUCUUGGAAGCCAAGG

GAUACAAAGAGGUGAAGAAAGACCUGAUCAUCAAACUUCCAAAGUACUCCCUGUUCGAACUC

GAAAACGGGAGGAAGCGCAUGCUCGCCUCAGCCGGGGAACUGCAAAAGGGCAACGAACUGGC

CCUCCCGUCAAAAUACGUCAACUUCCUGUACUUGGCGUCACACUACGAAAAGCUGAAAGGAU

CCCCAGAGGACAACGAACAGAAACAGCUGUUCGUCGAGCAGCACAAGCACUACCUGGACGAG

AUCAUCGAACAGAUCUCGGAAUUCAGCAAGAGAGUGAUCUUGGCAGACGCUAACCUUGACAA

AGUCCUCUCGGCAUACAAUAAGCAUCGCGACAAGCCGAUCAGAGAACAGGCGGAGAACAUCA

UCCACCUGUUCACUCUCACCAACCUGGGCGCGCCAGCGGCUUUUAAGUACUUUGAUACCACC

AUUGACCGCAAGAGAUACACCUCAACUAAAGAAGUGCUGGACGCAACCCUGAUCCAUCAAAG

CAUCACCGGACUUUAUGAAACUCGGAUCGAUCUCUCACAGCUCGGAGGAGACAAAAGACCGG

CUGCCACCAAGAAGGCCGGACAGGCAAAGAAGAAGAAAUGAUAAUAGGCUGGAGCCUCGGUG

GCCAUGCUUCUUGCCCCUUGGGCCUCCCCCCAGCCCCUCCUCCCCUUCCUGCACCCGUACCC

CCGUGGUCUUUGAAUAAAGUCUGAGUGGGCGGC+A(140nt) tail

VEGF V1 sgRNA
(SEQ ID NO: 91)
GGGTGTGCAGACGGCAGTCACTAGGGTTTTAGAGCTAGAAATAGCAAGTTAAAATAAGGCTA

GTCCGTTATCAACTTGAAAAAGTGGCACCGAGTCGGTGC

VEGF V2 sgRNA
(SEQ ID NO: 92)
GGGTGAGTGAGTGTGTGCGTGTGGGTTTTAGAGCTAGAAATAGCAAGTTAAAATAAGGCTAG

TCCGTTATCAACTTGAAAAAGTGGCACCGAGTCGGTGC

VEGF V3 sgRNA
(SEQ ID NO: 93)
GGGTGAGTGAGTGTGTGCGTGTGGGTTTTAGAGCTAGAAATAGCAAGTTAAAATAAGGCTAG

TCCGTTATCAACTTGAAAAAGTGGCACCGAGTCGGTGC

VEGF V4 sgRNA
(SEQ ID NO: 94)
GGGTTGGAGCGGGGAGAAGGCCAGGGTTTTAGAGCTAGAAATAGCAAGTTAAAATAAGGCTA

GTCCGTTATCAACTTGAAAAAGTGGCACCGAGTCGGTGC

In Vitro Expression of CRISPR-Related Proteins from mRNA Constructs

HeLa cells were transfected with various tagged dCas9 mRNAs and cellular extracts were subjected to Western, Immunoprecipitation, and LC/MS analysis to detect expression of protein expressed by said RNAs.

A FLAG tagged Cas9 mRNA constructs containing Cong Cas9 (SEQ ID NO: 55), an untagged Cas9 mRNA construct containing Mali Cas9 (SEQ ID NO: 56), a HA-tagged dCas9 construct containing Gilbert dCas9 (SEQ ID NO: 55), a FLAG-tagged dCas9 construct containing Maeder dCas9 (SEQ ID NO: 52), and a HA-tagged Trilink Cas9 construct (Trilink) were transfected into HeLa cells according to the following protocol:

$3 \times 10^6$ HeLa cells were plated on 10 cm plates on the day prior to transfection. 30 μL of Lipofectamine 2000 was diluted into a tube containing 200 μL Opti-MEM for each sample to be transfected and was held at room temperature for 2-5 minutes. 7.5 ug Cas9 mRNA was diluted into another tube containing 200 μL Opti-MEM. Then the two dilutions were combined for each sample and mixed. The final solution was allowed to stand at room temperature for 20-25 minutes before the transfection solution was overlayed onto the plated HeLa cells.

After seven hours post-transfection, cells were lysed with lysis buffer in the presence of 1×HALT protease inhibitors (Pierce). Protein from cell lysates was isolated and reserved for western, immunoprecipitation, or LC-MS assays.

For immunoprecipitation, lysates normalized for protein concentration were added to Sigma M2 agarose beads and washed. Immunoprecipitation was performed at 4° C. overnight. Beads were then washed and resuspended in 1×LDS protein sample buffer. Samples were then run on a 4-12% Bis-Tris gel with MES buffer (Life Technologies) using See BluePlus 2™ prestained protein standards (Life Technologies). The nitrocellulose was blocked with 5% milk in PBS for one hour, then blotted with 1:2000 anti-FLAG (Cell Signaling Technologies) (FIG. 2) or 1:1000 anti-HA (Covance HA.11 ascites) (FIG. 3) in PBS+0.05% Tween for 4 hours overnight at 4° C. Membranes were then washed and incubated with anti-rabbit (Sigma) or anti-mouse (Sigma) conjugated to HRP for 45 minutes at room temperature and detected with Pierce Super Signal West Femto (Pierce) according to the manufacturer's instructions.

Figure 2:
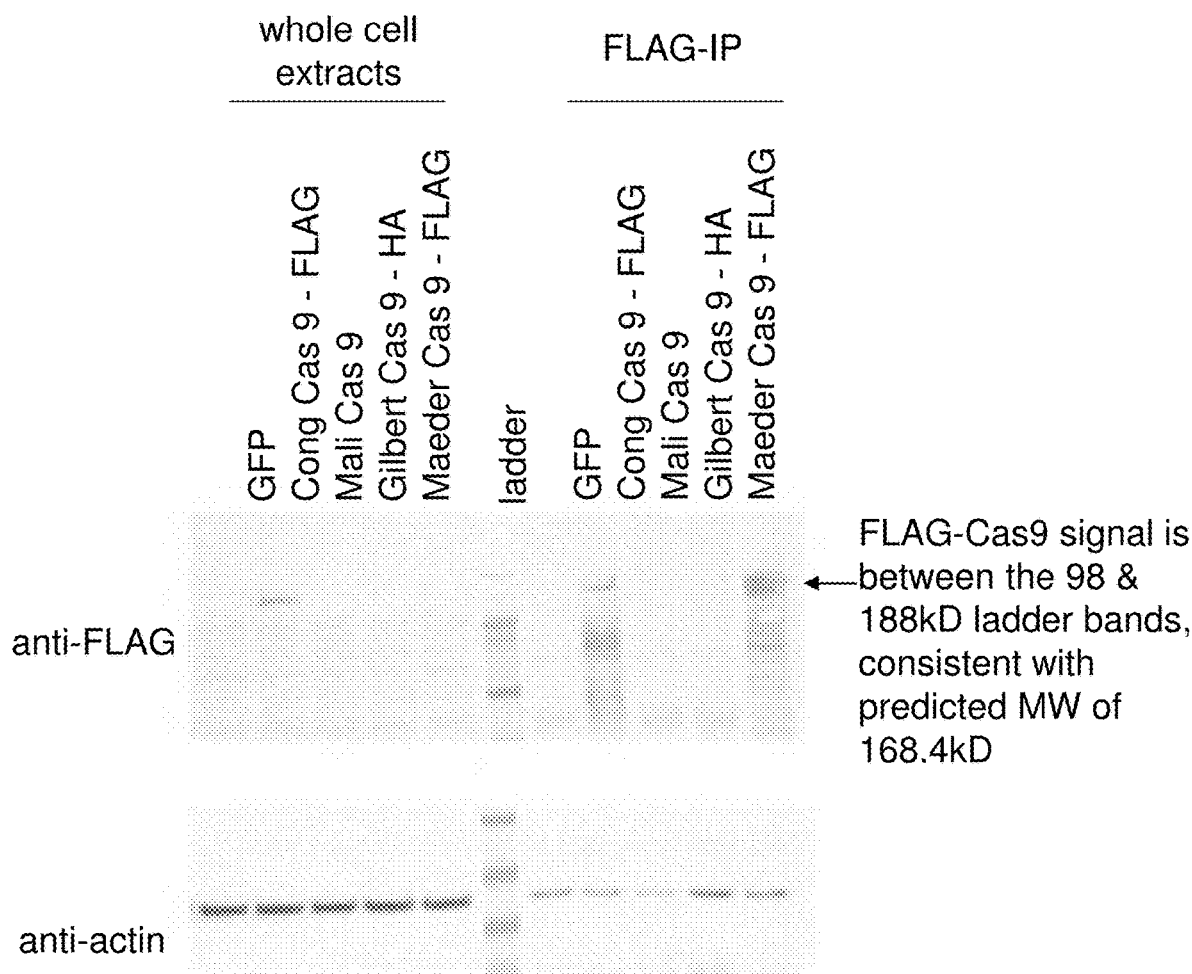
FIG. 2 shows the results of an anti-FLAG Western and Immunoprecipitation performed on the lysates of HeLa cells transfected with FLAG-tagged Cas9 constructs or controls.

Cong Cas9-FLAG protein was detected in HeLa cells transfected with Cong Cas9-FLAG mRNA (SEQ ID NO: 55) via both direct anti-FLAG western and immunoprecipitation anti-FLAG western (FIG. 2). Maeder Cas9-FLAG protein was detected in HeLA cells transfected with Maeder Cas9-FLAG mRNA (SEQ ID NO: 52) via immunoprecipitation anti-FLAG western (FIG. 2). Both Mali Cas9 and Gilbert Cas9-HA did not have a FLAG domain and thus did not show up on the anti-FLAG western or immunoprecipitation (FIG. 2).

Figure 3:
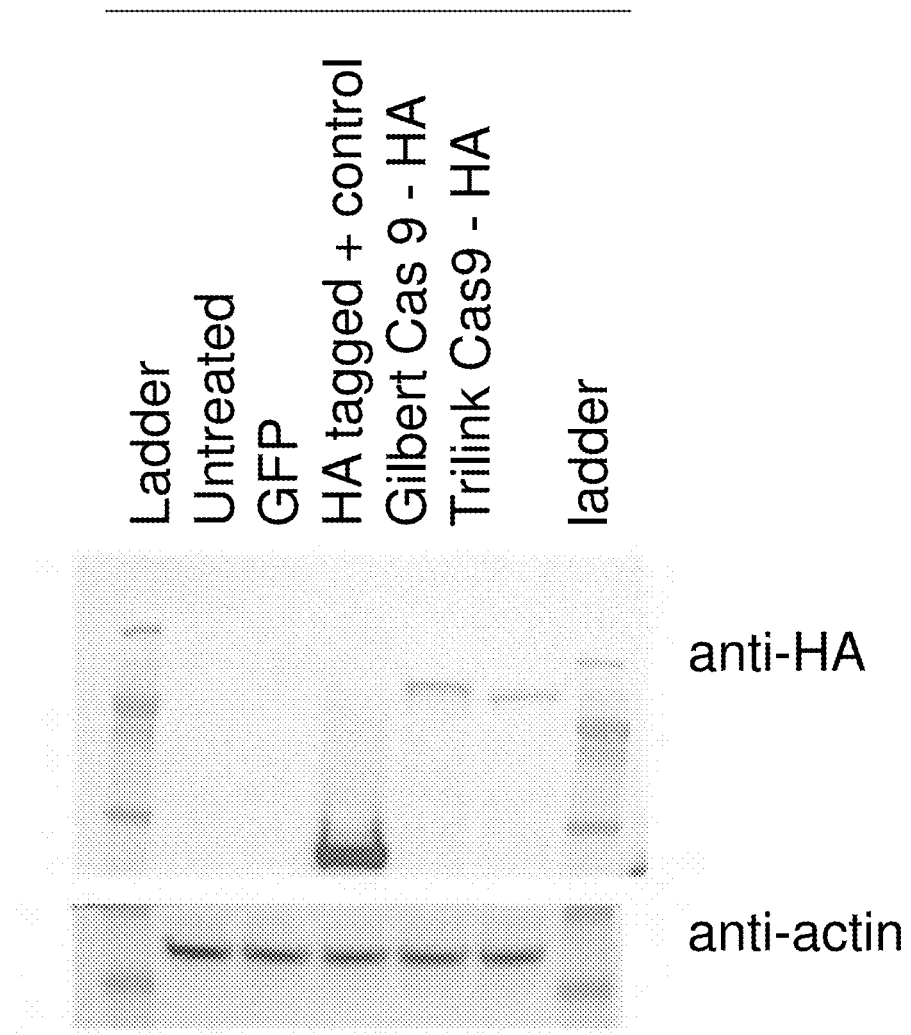
FIG. 3 shows the results of a western analysis of HeLa cells that were transfected with HA-tagged Gilbert Cas9 mRNA using Trilink-HA-tagged Cas9 mRNA as a positive control.

Gilbert dCas9-HA protein was detected in HeLA cells transfected with Gilbert dCas9-HA mRNA (SEQ ID NO: 51) via direct anti-HA western (FIG. 3). Trilink Cas9-HA was used as a positive control for dCas9 expression.

Protein extracts of HeLa cells transfected with Gilbert dCas9-HA mRNA (SEQ ID NO: 51) and Maeder dCas9-FLAG (SEQ ID NO: 52) were analyzed for protein expression of the Cas9 constructs via LC-PRM peptide quantification and compared to an untreated control HeLa cell protein extracts.

All solvents were HPLC-grade from Sigma-Aldrich and all chemicals where not stated otherwise were obtained from Sigma-Aldrich.

Samples were prepared in cell lysis buffer containing 8M urea and 0.1M ammonium bicarbonate. BCA assays to determine total protein content were carried out. Samples with 30 μg of protein were reduced using and digested overnight with trypsin. C18 cleanup for mass spectrometry was carried out using MICROSpin™ columns (The Nest Group) according to the manufacturer's instructions. Peptides were dried down redissolved in 30 μl to the final concentration of 1 μg/ul in LC solvent A (1% acetonitrile in water with 0.1% formic acid (FA)) containing a control peptide mix for retention time calibration.

Peptides (1 μg per sample) were analyzed on C18 chromatography columns on a Thermo Scientific Easy nLC nano-liquid chromatography system for all mass spectrometric analysis. LC solvents were A: 1% acetonitrile in water with 0.1% FA; B: 3% water in acetonitrile with 0.1% FA (gradient elution).

LC-MS/MS runs for peptide discovery were carried out on a Thermo Scientific Q Exactive™ mass spectrometer equipped with a standard nano-electrospray source.

LC-PRM for was carried out using a predetermined inclusion list containing target peptides precursor masses on a Thermo Scientific Q Exactive™ mass spectrometer equipped with a standard nano-electrospray source as described before (gradient elution).

The LC gradient for LC-PRM was 5-35% solvent B in 50 minutes followed by 35-100% B in 2 minutes and 100% B for 8 minutes (total gradient length was 60 minutes).

LC-MS/MS datasets were analyzed using the MaxQuant software package and searches were performed against the UniProt HUMAN database and other databases. For all peptides of target proteins that were successfully detected in LC-MS/MS, LC-PRM assays were generated using the most intense fragment ions from LC-MS/MS analysis. Top 10 most intense assays were selected.

Data were processed using SpectroDive™ (Biognosys) software for the analysis of LC-MRM and LC-PRM data based on mProphet (Reiter, Rinner et al., Nature Methods 8 (2011), 430-435). 10 peptides representing housekeeping proteins were quantified in every sample to assess sample loading on the column.

Figure 4A:
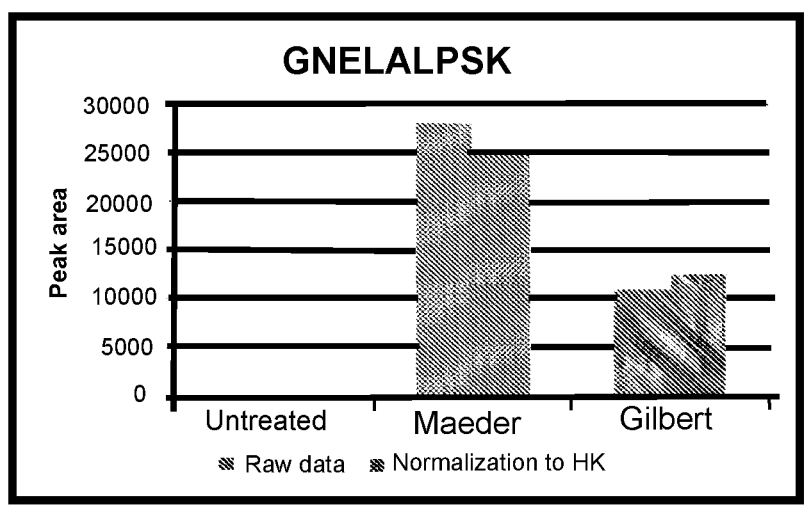
FIG. 4A represents quantification of GNELALPSK peptide (SEQ ID NO: 120).
Figure 4B:
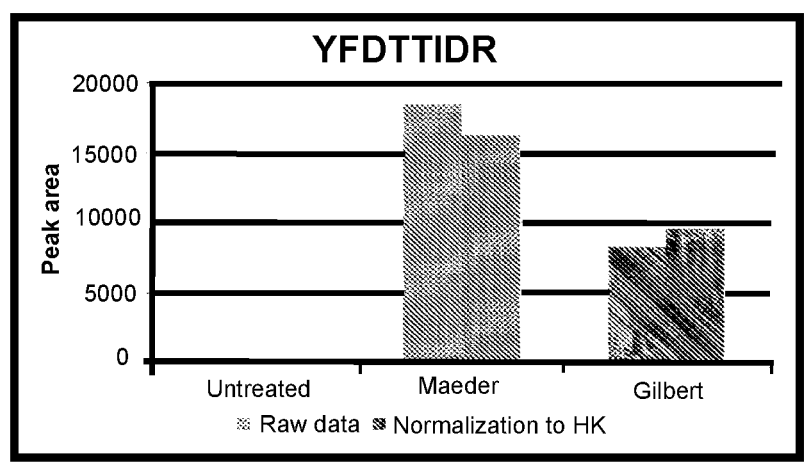
FIG. 4B represents quantification of the YFDTTIDR peptide (SEQ ID NO: 121).
Figure 4C:
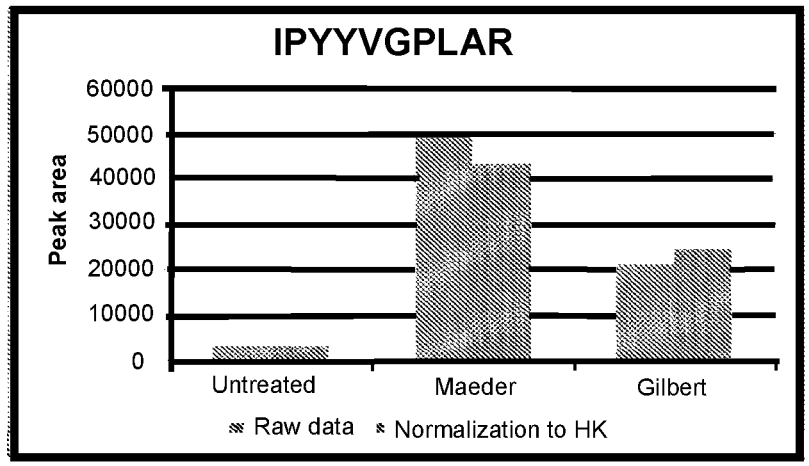
FIG. 4C represents quantification of the IPYYVGPLAR peptide (SEQ ID NO: 122).

Relative quantification of peptide segments of Cas9 was carried out for each of the protein extracts via LC-PRM. Quantification of the Cas9 peptide segments: "GNELALPSK" (SEQ ID NO: 120), "YFDTTIDR" (SEQ ID NO: 121), and "IPYYVGPLAR" (SEQ ID NO: 122) is shown in FIGS. 4A, 4B, and 4C, respectively. Table 2 shows relative quantification for each:

TABLE 2

LC-PRM Cas9 Peptide Quantification in Cell Lysate Samples

| | | Raw Data | | Normalization to housekeepers | |
|---|---|---|---|---|---|
| Peptides | Untreated | Maeder | Gilbert | Maeder | Gilbert |
| GNELALPSK (SEQ ID NO: 120) | None | 28079 | 10848 | 24712 | 12559 |
| YFDTTIDR (SEQ ID NO: 121) | None | 18405 | 8277 | 16198 | 9583 |
| IPYYVGPLAR (SEQ ID NO: 122) | 3071 | 49031 | 21150 | 43152 | 24486 |

In Vivo

Mice (n=1) (8 wk old female BalbC) were administered 350 ul intravenously of 0.04 mg/mL (14 μg) FLAG-Cas9 Cong mRNA as described as set forth in SEQ ID NO:55_

(polyA tail of approximately 140 nucleotides not shown in sequence; 5'cap, Cap1; fully modified with 1-methylpseudouridine) formulated in a lipid nanoparticle comprising the lipid DLin-MC3-DMA described in Table 3 or a control of PBS (mock).

TABLE 3

Lipid Nanoparticle Formulation

| Ionizable Amino Lipid (Lipid/Mol %) | Non-Cationic Lipid (Lipid/Mol %) | Cholesterol (Mol %) | PEG Lipid (Lipid/Mol %) |
| --- | --- | --- | --- |
| Dlin-MC3-DMA 50 | DSPC 10 | Cholesterol 38.5 | PEG-DOMG 1.5 |

6 hours after administration the mice were humanely euthanized. Livers were collected from the mice and Cas9 expression was determined by immunoprecipitation as described in detail below.

Liver tissue was lysed in a Tissue lyser formulation in the presence of protease inhibitors. Protein was extracted and quantitated using a BCA protein assay (Pierce). Samples were normalized by total protein quantification. Approximately 88 mg of protein extract was added to M2 agarose beads (Sigma) for immunoprecipitation. After gently mixing for 3-4 hours at 4° C., beads were aspirated and washed with RIPA buffer to remove supernatant. RIPA buffer supplemented with 200 μg/mL 3×FLAG peptide (Sigma) was added to the beads and incubated at 4° C. for 30 minutes with shaking at 1100 rpm in a thermomixer. Peptide elution was then performed by spinning down beads and removing supernatant. Samples were incubated at 72° C. for 12 minutes on 4-12% Bis Tris gel using MES running buffer (LifeTech) along with prestained protein standards (LifeTech). The gel was transferred onto nitrocellulose using an iBlot™ apparatus for 6 minutes according to manufacturer's instructions. Membrane was removed and placed in a vessel suitable for blotting and washed 2× with ddH$_2$O. Nitrocellulose was then blocked for 45 minutes with 5% nonfat dry milk in PBS. Nitrocellulose was then blotted with anti-M2 HRP at 1:15,000 in 1% milk PBS 0.05% Tween for 30 minutes at room temperature. The primary antibody solution was then removed and the nitrocellulose was washed with PBS 00.05% Tween. FLAG-Cas9 peptides were detected with Pierce Super Signal Femto™. The nitrocellulose membrane was then exposed for imaging.

Figure 5:
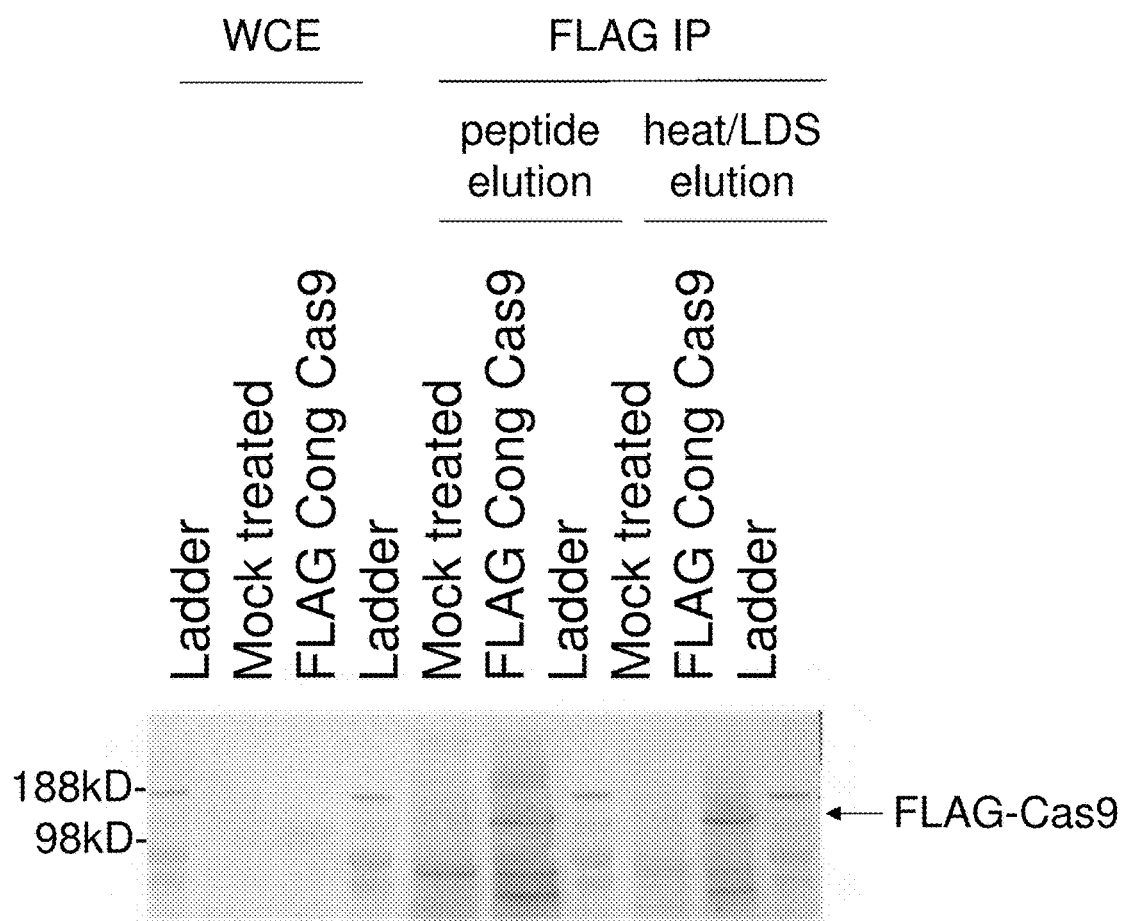
FIG. 5 shows the results of an anti-FLAG Western and Immunoprecipitation performed on the lysates of mouse livers from animals dosed with 14 ug Cas9 LNP (MC3) or mock. WCE=whole cell extract. IP=immunoprecipitation with M2-agarose beads (Sigma). Ladder=See Blue Plus 2™ prestained protein marker (LifeTech).

Results of the immunoprecipitation are shown in FIG. 5. As shown in FIG. 5, a band is present at 150 kD only in the Cas9 LNP sample and not in the PBS control treated sample. These data provide evidence of Cas9 protein expression from LNP formulated synthetic mRNA in vivo in mice dosed with Cas9-LNP.

Example 12: In Vitro Modulation of Transcription with Synthetic Polynucleotides Encoding dCas9-Effector Fusion Proteins and Synthetic sgRNA VEGF (vascular endothelial growth factor), one of the most potent angiogenic factors, has recently been identified as an inducer of neoangiogenesis in many tumors including gliomas. U-87 MG and A-172 are two established glioblastoma cell lines. Basal VEGF expression was an order of magnitude higher in U-87 MG compared to A-172. (Int J Dev Neurosci. 1999 August-October; 17(5-6):565-77). This provides a system to test gene regulation by dCas9-KRAB and dCas9-VP64 with sgRNA directed to 5' flanking genomic sequence of VEGF.

Inhibition of Transcription with dCas9-KRAB

Gilbert 2013 described gene down-regulation using dCas9-kRAB fusion protein. KRAB is a category of transcriptional repression domains present in approximately 400 human zinc finger protein-based transcription factors (KRAB zinc finger proteins) (Huntley 2006). KRAB domains have been shown to be effective repressors of transcription.

The U-87MG cell line produces endogenous VEGF. The dCas9-kRAB synthetic polynucleotide together with the 4 synthetic sgRNA targeting VEGF described above are used to inhibit transcription of a VEGF gene in U-87MG cells. The following experimental protocol is used.

1. U-87MG are maintained in Dulbecco's modified Eagle medium (DMEM) in 10% FBS, 2 mM glutamine, 100 units/ml streptomycin, and 100 mg/ml penicillin.
2. All transfections are performed in triplicate using Lipofectamine and using transfection protocol described in U.S. patent publication no. US 2013/0259924 (U.S. patent application Ser. No. 13/791,922, filed on Mar. 9, 2013) incorporated by reference.
3. 160,000 cells are seeded into 24-well plates the day before transfection.
4. Transfect U-87MG cells with 100 ng of dCas9-KRAB mRNA and 100 ng of VEGF V1-V4 sgRNAs. For synergy experiments, transfect 100 ng of dCas9-KRAB mRNA with 25 ng each of VEGF V1-V4 sgRNAs (a total of 100 ng of four different VEGF sgRNA)
5. Incubate cells for 8 hours and wash cells to remove transfection agent.
6. Continue to incubate cells in DMEM
7. Culture medium of U-87MG transfected with mRNA encoding VEGFA-targeted sgRNA and dCas9-KRAB was collected 0 h, 12 h, 24 h, 48 h after transfection
8. VEGFA protein expression is measured by ELISA.

Introduction of synthetic polynucleotides encoding dCas9-KRAB with sgRNA targeting VEGF genomic sequence inhibits VEGF transcription compared to untreated cells.

Activation of Transcription with dCas9-VP64

Maeder 2013 and Perez-Pinera 2013 describe an RNA-guided transcriptional activator, created by fusing dCas9 (D10A, H840A) to the VP64 transactivation domain.dCas9-VP64 recognizes genomic target sites through the hybridization of a sgRNA to a target sequence.

The HEK293 cell line does not produces endogenous VEGF. The dCas9-VP-64 synthetic polynucleotide together with the 4 synthetic sgRNA targeting VEGF described above are used to activate transcription of a VEGF gene in HEK293 cells. The following experimental protocol is used.

1. HEK293 are maintained in Dulbecco's modified Eagle medium (DMEM) in 10% FBS, 2 mM glutamine, 100 units/ml streptomycin, and 100 mg/ml penicillin.
2. All transfections are performed in triplicate using Lipofectamine and using transfection protocol described in U.S. patent publication no. US 2013/0259924 (U.S. patent application Ser. No. 13/791,922, filed on Mar. 9, 2013).
3. 160,000 cells were seeded into 24-well plates the day before transfection.
4. HEK293 cells are transfected with 100 ng of dCas9-VP64 mRNA and 100 ng of VEGF V1-V4 sgRNAs. For synergy experiments, transfect 100 ng of dCas9-VP64 mRNA with 25 ng each of VEGF V1-V4 sgRNAs (a total of 100 ng of four different VEGF sgRNA)

5. Incubate cells for 8 hours and wash cells to remove transfection agent.
6. Continue to incubate cells in DMEM.
7. Culture medium of HEK293 transfected with mRNA encoding VEGFA-targeted sgRNA and dCas9-VP64 is collected 0 h, 12 h, 24 h, 48 h after transfection
8. VEGFA protein expression is measured by ELISA.
9. VEGFA mRNA is measured by RT-PCR or Taqman or Q-PCR Introduction of synthetic polynucleotides encoding dCas9-VP64 with sgRNA targeting VEGF genomic sequence activates VEGF transcription in HEK293 cells compared to untreated cells.

Example 13: Tissue Specific Modulation of In Vitro Protein Expression miR-122 is present in primary human hepatocytes and is not present in hepatocellular carcinoma cell lines such as HepG2, Hep3B, and SK-Hep-1 cells. It has been shown that miR-122 can down-regulate protein production encoded by an mRNA containing miR-122 binding sites in the 3' UTR in primary hepatocytes, but not in HepG2 and Hep3B Primary hepatocytes and HepG2 cells are transfected with dCas9-KRAB, dCas9-KRAB-miR122, dCas9-VP64, dCas9-VP64-miR122 synthetic polynucleotides along with a combination of the four synthetic sgRNA targeting VEGF.

Transfection of primary hepatocytes is performed as described herein. Table 4 and 5 provide the results.

TABLE 4

Results of primary hepatocyte transfection.

| Synthetic sgRNA | dCas9-KRAB | dCas9-KRAB-miR122 | dCas9-VP64 | dCas9-VP64-miR122 | Untreated |
|---|---|---|---|---|---|
| VEGF V1 sgRNA | Potential decrease in protein expression and mRNA transcript | Potentially no change because miR-122 down-regulate the translation of dCas9-KRAB-miR122 mRNA | Potential increase in protein expression and mRNA transcript | Potentially no change because miR-122 down-regulate the translation of dCas9-VP64-miR122 mRNA | |
| VEGF V2 sgRNA | Potential decrease in protein expression and mRNA transcript | Potentially no change because miR-122 down-regulate the translation of dCas9-KRAB-miR122 mRNA | Potential increase in protein expression and mRNA transcript | Potentially no change because miR-122 down-regulate the translation of dCas9-VP64-miR122 mRNA | |
| VEGF V3 sgRNA | Potential decrease in protein expression and mRNA transcript | Potentially no change because miR-122 down-regulate the translation of dCas9-KRAB-miR122 mRNA | Potential increase in protein expression and mRNA transcript | Potentially no change because miR-122 down-regulate the translation of dCas9-VP64-miR122 mRNA | |
| VEGF V4 sgRNA | Potential decrease in protein expression and mRNA transcript | Potentially no change because miR-122 down-regulate the translation of dCas9-KRAB-miR122 mRNA | Potential increase in protein expression and mRNA transcript | Potentially no change because miR-122 down-regulate the translation of dCas9-VP64-miR122 mRNA | |
| VEGF V1-V4 sgRNA | Potential decrease in protein expression and mRNA transcript | Potentially no change because miR-122 down-regulate the translation of dCas9-KRAB-miR122 mRNA | Potential increase in protein expression and mRNA transcript | Potentially no change because miR-122 down-regulate the translation of dCas9-VP64-miR122 mRNA | |

Transfection of HEpG2 cells is performed as described herein. The following table provides the results.

TABLE 5

Results of HEpG2 transfection.

| | dCas9-KRAB | dCas9-KRAB-miR122 | dCas9-VP64 | dCas9-VP64-miR122 | Untreated |
|---|---|---|---|---|---|
| VEGF V1 sgRNA | Potential decrease in protein expression and | Potential decrease in protein expression and | Potential increase in protein expression and | Potential increase in protein expression and | |

TABLE 5-continued

Results of HEpG2 transfection.

| | dCas9-KRAB | dCas9-KRAB-miR122 | dCas9-VP64 | dCas9-VP64-miR122 | Untreated |
|---|---|---|---|---|---|
| VEGF V2 sgRNA | Potential decrease in protein expression and mRNA transcript | Potential decrease in protein expression and mRNA transcript | Potential increase in protein expression and mRNA transcript | Potential increase in protein expression and mRNA transcript | |
| VEGF V3 sgRNA | Potential decrease in protein expression and mRNA transcript | Potential decrease in protein expression and mRNA transcript | Potential increase in protein expression and mRNA transcript | Potential increase in protein expression and mRNA transcript | |
| VEGF V4 sgRNA | Potential decrease in protein expression and mRNA transcript | Potential decrease in protein expression and mRNA transcript | Potential increase in protein expression and mRNA transcript | Potential increase in protein expression and mRNA transcript | |
| VEGF V1-V4 sgRNA | Potential decrease in protein expression and mRNA transcript | Potential decrease in protein expression and mRNA transcript | Potential increase in protein expression and mRNA transcript | Potential increase in protein expression and mRNA transcript | |

Example 14: Modulation of In Vivo Protein Expression with dCas9

Delivery of synthetic polynucleotides encoding dCAS9-effector fusion proteins and synthetic sgRNA targeting a gene of interest to the liver using lipid-nucleic acid particle formulation is performed following procedures described U.S. patent publication no. US 2013/0259924 (U.S. patent application Ser. No. 13/791,922, filed on Mar. 9, 2013). Delivery of synthetic polynucleotides encoding dCAS9-effector fusion proteins and synthetic sgRNA targeting a gene of interest to muscle cells via intramuscular injection is performed as described in U.S. patent publication no. US 2013/0259924 (U.S. patent application Ser. No. 13/791,922, filed on Mar. 9, 2013).

a. In Vivo Inhibition of TPO Gene Transcription with dCas9-KRAB

Thrombopoietin (TPO) is produced mainly by the liver. Synthetic polynucleotides encoding dCas9-KRAB or dCas9-KRAB-miR122 along with sgRNA targeting the 5' flanking sequence of thrombopoietin are formulated in an LNP formulation. 0.005 mg/kg to 0.5 mg/kg of LNP formulated dCas9-KRAB and TPO sgRNA is administered intravenously to mice. Blood and liver samples are collected at 8 h, 24 hr, 48 hr, 72 hr post administration. TPO protein level is measured by ELISA and TPO mRNA is measured by RT-PCR or q-PCR.

With dCas9-KRAB mediated suppression with TPO sgRNA, TPO protein and mRNA expression will decrease. However, because of the presence of miR-122, groups treated with dCas9-KRAB-miR122 TPO sgRNA will not show significant down regulation of TPO protein production and mRNA expression.

b. In Vivo Inhibition of Reporter Gene Transcription with dCas9-KRAB

An exogenous DNA plasmid comprising a reporter molecule, such as luciferase, GFP, or human VEGF, and a specific 5' flanking sequence containing VEGF V1-V4 sgRNA sequences and a constitutively active promoter to drive protein expression is co-administered with the synthetic polynucleotide encoding dCas9-KRAB/dCas9-KRAB-miR122 and with the 4 synthetic sgRNA targeting VEGF. Polynucleotides are LNP formulated and administered as described herein.

There is a decrease in expression of the reporter molecule in groups treated with dCas9-KRAB/VEGF sgRNA. There is not a significant decrease in expression of the reporter molecule in groups treated with dCas9-KRAB-mir122/VEGF sgRNA.

c. In Vivo Activation of LDHC Gene Transcription with dCas9-VP64

To demonstrate activation of transcription and protein expression using synthetic polynucleotide encoding dCas9-VP64, proteins that are not typically expressed by the liver are targeted. Lactate dehydrogenase C (LDHC) is a testis specific enzyme. Administration of LNP formulated synthetic polynucleotide encoding dCas9-VP64 along with synthetic sgRNA targeting 5' genomic sequence of mouse LDHC induces the expression of LDHC in the liver. The LDHC mRNA transcript is measured by RT-PCR or qPCR and the protein expression is measured by ELISA or western blot. Administration of LNP formulated synthetic polynucleotide encoding dCas9-VP64-miR122 and sgRNA targeting the 5' genomic sequence of the mouse LDHC does not activate LDHC expression because of the presence of miR-122 in the liver cells.

d. In Vivo Activation of Reporter Gene Transcription with dCas9-VP64

An exogenous DNA plasmid comprising a reporter molecule, such as luciferase, GFP, or human VEGF, and a specific 5' flanking sequence containing VEGF V1-V4 sgRNA sequences and a constitutively inactive promoter is co-administered with the synthetic polynucleotide encoding dCas9-VP64/dCas9-VP64-miR122 with and the synthetic sgRNA targeting VEGF. There is an increase in expression of the reporter molecule in groups treated with dCas9-VP64/

VEGF sgRNA. There is not a significant increase in expression of the reporter molecule in groups treated with dCas9-VP64-mir122/VEGF sgRNA.

e. Tissue Specific In Vivo Modulation of LDHC Gene Transcription

As described herein, microRNA can provide tissue specificity. To demonstrate tissue selectivity of dCas9 system using microRNA 122, one group of mice is dosed intravenously and another group is dosed intramuscularly with LNP formulated synthetic polynucleotide encoding dCas9-VP64-mir122 and synthetic sgRNA targeting LDHC. Due to the presence of miR-122 in the liver cells, the synthetic polynucleotide encoding dCas9-VP64 will not be expressed; thus, no dCas9-VP64 mediated activation of LDHC expression. Since muscle cells do not contain miR-122, the group receiving intramuscular injection of dCas9-VP64-miR122 and LDHC sgRNA will show expression of a testis-specific protein.

f. Tissue Specific In Vivo Modulation of Reporter Gene Transcription

Another example is to co-administer a DNA plasmid described in Gilbert et al as a target for gene suppression of dCas9-KRAB. A formulated LNP carrying 1) SV40-GFP DNA plasmid (described in Gilbert et al), 2) sgGFP-NT1 sgRNA (described in Gilbert et al), and 3) mRNA encoding either dCas9-KRAB or dCas9-KRAB-miR122 is administered via IV to the liver, which contain miR-122. The group receiving dCas9-KRAB will show a reduced GFP expression compared to the control group that received no dCas9-KRAB mRNA as measure by flow cytometry or immunohistochemistry because the translation of dCas9-KRAB will not be reduced by miR122. The group receiving dCas9-KRAB-miR122 will show GFP expression similar to the control group receiving no dCas9-KRAB-miR122 mRNA because of the presence of miR-122 in the hepatocytes which inhibits the translation of the dCas9-KRAB-miR122 mRNA. To compared IM delivery to the muscle cells which do not contain miR-122, a formulated LNP carrying 1) SV40-GFP DNA plasmid (described in Gilbert et al), 2) sgGFP-NT1 sgRNA (described in Gilbert et al), and 3) mRNA encoding either dCas9-KRAB or dCas9-KRAB-miR122 is administered via IM injection. We expect to see both the dCas9-KRAB and the dCas9-KRAB-miR122 groups to show GPF expression in the muscle cells as measure by flow cytometry or immunohistochemistry.

Another example is to co-administer a DNA plasmid described in Gilbert et al as a target for gene activation of dCas9-VP64. A formulated LNP carrying 1) GAL4 UAS GFP DNA plasmid (described in Gilbert et al), 2) sgGAL4-1 sgRNA (described in Gilbert et al), and 3) mRNA encoding either dCas9-VP64 or dCas9-VP64-miR122 is administered via IV to the liver. The group receiving dCas9-VP64 mRNA will show GFP expression as measure by flow cytometry or immunohistochemistry whereas the group receiving dCas9-VP64-miR122 will not show GFP expression because of the presence of miR-122 in the hepatocytes suppressing the translation of dCas9-VP64-miR122 mRNA. To compared IM delivery to the muscle cells which do not contain miR-122, A formulated LNP carrying 1) GAL4 UAS GFP DNA plasmid (described in Gilbert et al), 2) sgGAL4-1 sgRNA (described in Gilbert et al), and 3) mRNA encoding either dCas9-VP64 or dCas9-VP64-miR12 is administered via IM injection. We expect to see both the dCas9-VP64 and the dCas9-VP64-miR122 groups to activate GPF expression in the muscle cells as measure by flow cytometry or immunohistochemistry.

Example 15: Use of 3 Different Delivery Systems

A combination of targeting mechanism is used to allow for a significant safety window when administering synthetic polynucleotides encoding a CRISPR related protein and sgRNA.

First, a synthetic polynucleotide encoding a dCAS9-effector domain fusion protein is designed using a miR-142.3p targeted 3'UTR to prevent expression in APCs.

Second, the synthetic polynucleotide is formulated in an ionizable LNP that targets LDL-R mediated uptake into hepatocytes. This leads to expression of the dCAS9-effector domain fusion protein in the liver.

Third, the synthetic sgRNA targeting the hepatic gene of interest is conjugated with, e.g., a GalNac conjugate or similar targeting moiety that is preferentially be taken up by hepatocytes. The synthetic sgRNA can be administered separately and after a 2-3 hour delay.

The combination of targeting mechanisms (in this case 3: mir-3'UTR, LNP, GalNac) and the absence of DNA would allow for significant safety window.

The result could be transcriptional activation or inhibition of any protein target (our first in vivo experiments will focus on IHC to confirm localization of dCas9 fusion into the liver and functional read outs using reporters like luciferase and/or GFP.

Other Embodiments

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

Sequence Tables

TABLE 5

CRISPR related proteins

| Description | Sequence | | SEQ ID NO |
|---|---|---|---|
| CRISPR-associated endonuclease CAS9/Csn1 protein | MDKKYSIGLDIGTNSVGWAVITDEYKVPSKKFKVLGNTDRHSIKKNLIGALLFDSGETAE<br>ATRLKRTARRRYTRRKNRICYLQEIFSNEMAKVDDSFFHRLEESFLVEEDKKHERHPIFG<br>NIVDEVAYHEKYPTIYHLRKKLVDSTDKADLRLIYLALAHMIKFRGHFLIEGDLNPDNSD<br>VDKLFIQLVQTYNQLFEENPINASGVDAKAILSARLSKSRRLENLIAQLPGEKKNGLFGN<br>LIALSLGLTPNFKSNFDLAEDAKLQLSKDTYDDDLDNLLAQIGDQYADLFLAAKNLSDAI<br>LLSDILRVNTEITKAPLSASMIKRYDEHHQDLTLLKALVRQQLPEKYKEIFFDQSKNGYA<br>GYIDGGASQEEFYKFIKPILEKMDGTEELLVKLNREDLLRKQRTFDNGSIPHQIHLGELH<br>AILRRQEDFYPFLKDNREKIEKILTFRIPYYVGPLARGNSRFAWMTRKSEETITPWNFEE<br>VVDKGASAQSFIERMTNFDKNLPNEKVLPKHSLLYEYFTVYNELTKVKYVTEGMRKPAFL<br>SGEQKKAIVDLLFKTNRKVTVKQLKEDYFKKIECFDSVEISGVEDRFNASLGTYHDLLKI<br>IKDKDFLDNEENEDILEDIVLTLTLFEDREMIEERLKTYAHLFDDKVMKQLKRRRYTGWG<br>RLSRKLINGIRDKQSGKTILDFLKSDGFANRNFMQLIHDDSLTFKEDIQKAQVSGQGDSL<br>HEHIANLAGSPAIKKGILQTVKVVDELVKVMGRHKPENIVIEMARENQTTQKGQKNSRER<br>MKRIEEGIKELGSQILKEHPVENTQLQNEKLYLYYLQNGRDMYVDQELDINRLSDYDVDH<br>IVPQSFLKDDSIDNKVLTRSDKNRGKSDNVPSEEVVKKMKNYWRQLLNAKLITQRKFDNL<br>TKAERGGLSELDKAGFIKRQLVETRQITKHVAQILDSRMNTKYDENDKLIREVKVITLKS<br>KLVSDFRKDFQFYKVREINNYHHAHDAYLNAVVGTALIKKYPKLESEFVYGDYKVYDVRK<br>MIAKSEQEIGKATAKYFFYSNIMNFFKTEITLANGEIRKRPLIETNGETGEIVWDKGRDF<br>ATVRKVLSMPQVNIVKKTEVQTGGFSKESILPKRNSDKLIARKKDWDPKKYGGFDSPTVA<br>YSVLVVAKVEKGKSKKLKSVKELLGITIMERSSFEKNPIDFLEAKGYKEVKKDLIIKLPK<br>YSLFELENGRKRMLASAGELQKGNELALPSKYVNFLYLASHYEKLKGSPEDNEQKQLFVE<br>QHKHYLDEIIEQISEFSKRVILADANLDKVLSAYNKHRDKPIREQAENIIHLFTLTNLGA<br>PAAFKYFDTTIDRKRYTSTKEVLDATLIHQSITGLYETRIDLSQLGGD | | 7 |
| CRISPR-associated endonuclease CAS9/Csn1 mRNA | auggacaaga aguacccau ugggcucgau aucggcacaa acagcgucgg cugggccguc | 60 | 1 |
| | auuacggacg aguacaaggu gccgagcaaa aaauucaaag uucugggcaa uaccgaucgc | 120 | |
| | cacagcauaa agaagaaccu cauuggcgcc cuccuguucg acuccgggga cggccgaa | 180 | |
| | gccacgcggc ucaaaagaac agcacggcgc agauauaccc gcagaaagaa ucggaucugc | 240 | |
| | uaccugcagg agaucuuuag uaaugagaug gcuaaggugg augacucuuu cuuccauagg | 300 | |
| | cuggaggagu ccuuuuuggu ggaggaggau aaaaagcacg agcgccaccc aaucuuuggc | 360 | |
| | aauaucgugg acgaggugcu guaccaugaa aaguacccaa ccauauauca ucugaggaag | 420 | |
| | aagcuuguag acaguacuga uaaggcugac uugcgguuga ucuaucucgc gcuggcgcau | 480 | |
| | augaucaaau ucggggaca cuuccucauc gaggggggacc ugaaccagau caacagcgau | 540 | |
| | gucgacaaac ucuuuaucca acugguucag acuuacaauc agcuuuuga agagaaccga | 600 | |
| | aucaacgcau ccggaguuga cgccaaagca auccugagcg cuaggcuguc caaaucccgg | 660 | |
| | cggcucgaaa accucaucgc acagcucccu ggggagaaga agaacggccu guuugguaau | 720 | |
| | cuuaucgccc ugucacucgg gcugaccccc aacuuuaaau cuaacuucga ccuggccgaa | 780 | |
| | gaugccaagc uucaacugag caaagacacc uacgacgacg acuugcuggc caaauccgug | 840 | |
| | cagaucggcc accaguacgc agaccuuuuu uggcggcaa agaaccuguc agacgccauu | 900 | |
| | cugcugagug auauucugcg agugaacacg gagaucacca agcucccgcu gagcgcuagu | 960 | |
| | augaucagc gcuaugauga gcaccaccaa gacuugacuu ugcugaaggc ccuugucaga | 1020 | |
| | cagcaacugc cugagaagua caaggaaaau uucuccgacc agucuaaaaa uggcuacgcc | 1080 | |
| | ggauacauug acggcggagc aagccaggag gaauuuuaca aauuuauuaa gcccaucuug | 1140 | |
| | gaaaaaaugg acggcaccga ggagcugcug uaaagcuua acagagaaga ucuguugcgc | 1200 | |
| | aaacagcgca cuuucgacaa uggaagcauc cccaccaga uucaccuggg cgaacugcac | 1260 | |
| | gcuauccuca ggcggcaaga cgauuucuac ccuuuuuga aagauaacag ggaaaagauu | 1320 | |
| | gagaaaaucc ucacauuucg gauccccuac uauguaggcc ccucgccccg gggaaauucc | 1380 | |
| | agauucgcgu ggaugacucg caaaucagaa gagaccauca cucccuggaa cuucgaggaa | 1440 | |
| | gucguggaua agggggccuc ugcccagucc uucaucgaaa ggaugacuaa cuuugauaaa | 1500 | |
| | aaucugccua acgaaaaggu gcuuccuaaa cacucucuguc ugucagagua cuucacaguu | 1560 | |
| | uauaacgagc ucaccaaggu caaauacguc acagaagguc ugagaaagcc agcauuccug | 1620 | |
| | ucuggagagc agaagaaagc uaucguggac cuccuuuuca gacgaaccg gaaaguuacc | 1680 | |
| | gugaaacagc ucaagaagac cauuucaaa agauuugaau guuucgacuc uguugaaauc | 1740 | |
| | agcggagugg aggaucgcuu caacgccauc cugggaacgu aucacgacuu ccugaaaauc | 1800 | |
| | auuaaagaca acgaaaagu gcuuccaaa cacucugagu ugaccgagua cuucacaguu | 1860 | |
| | cucacccuua cguuguuuga agauaggag augauugag aacgcuugaa acuuacgcu | 1920 | |
| | caucucuucg acgacaaagu caugaaacag ucaagaggc gccgauauac aggauggggg | 1980 | |
| | cggcugucaa gaaaacugau caauggggauc cgagacaagc agaguggaaa gacaauccug | 2040 | |
| | gauuuucua agucccgauuu caagucccau ugcauuugac cauugaugau | 2100 | |
| | ucucucaccu uuaaggagga cauccagaaa gcaaguuu cuggccaggg ggacagucuu | 2160 | |
| | cacgagcaca ucgcuaaucu gcaggucacgc ccagcuauca aaagggaau acugcagacc | 2220 | |
| | guuaaggucu uggaugaacu cguaaaagua uggggaggc auaagcccga gaauaucguu | 2280 | |
| | aucgagaugg cccaaacucc cagaacucag gagaaacag uagggaaggu | 2340 | |
| | augaagagga uugaagaggg uauaaaagaa cuggggccca aaaaucuuaa ggaacaccca | 2400 | |
| | guugaaaaca cccagcuuca gaaugagaag cucuaccugu acuaccugca acgggcagg | 2460 | |
| | gacauguacg uggaucagga acuggacauc aaucggcucu ccgacuacga cguggaucau | 2520 | |
| | aucguggccc cagcuuuuua caaggaugau ucaauuguaca aaugaaacgu gacaaucccc | 2580 | |
| | gauaaaaaua gagggaagag ugauaacguc cccucagaag aaguugucaa gaaaaugaaa | 2640 | |
| | aauuauggc ggcagcugcu gaacgccaaa cugaucacaa acggaaguu cgauaaucug | 2700 | |
| | acuaaggcug aacgagguggg ccugucugag uuggauaaag ccggcuucau caaaaggcag | 2760 | |
| | cuuguugaga cgccagau caccaagcac guggcccaaa uucucgauuc acgcaugaac | 2820 | |
| | accaaguacg augaaaauga caaacugauu cgagaggugaa aguuauuac ucugaagucu | 2880 | |

TABLE 5-continued

CRISPR related proteins

| Description | Sequence | | SEQ ID NO |
|---|---|---|---|
| | aagcuggucu cagauuucag aaaggacuuu caguuuuaua aggugagaga gaucaacaau | 2940 | |
| | uaccaccaug cgcaugaugc cuaccugaau gcagugguag gcacugcacu uaucaaaaaa | 3000 | |
| | uaucccaagc uugaaucuga auuuguuuac ggagacuaua aagugacga uguuaggaaa | 3060 | |
| | augaucgcaa agcucgagca ggaaauaggc aaggccaccg cuaaguacuu cuuuuacagc | 3120 | |
| | aauauuauga auuuuucaa gaccgagauu acacuggcca auggagagau ucggaagcga | 3180 | |
| | ccacuuaucg aaacaaacgg agaaacagga gaaaucgugu gggacaaggg uagggauuuc | 3240 | |
| | gcgacaguec ggaaggucc guccaguccg cagguagaca ucguuaaaaa gaccgaagua | 3300 | |
| | cagaccggag gcuuccucca ggaaaguauc cuccegaaaa ggaacagcga caagcugauc | 3360 | |
| | gcacgcaaaa aagauggga ccccaagaaa uacggcggau cgauucucc uacagucgcu | 3420 | |
| | uacaguguac ugguugugc caaaguggag aaagggaagu cuaaaaaaacu caaaagcguc | 3480 | |
| | aaggaacugc ugggcaucac aaucauggag cgaucagcu ucgaaaaaaa cccaucgac | 3540 | |
| | uuucucgagg cgaaaggaua uaagagguc aaaaaagacc ucaucauuaa gcucccaaag | 3600 | |
| | uacucucucu uugagcuuga aaacggccgg aaacgaaugc ucgcuagugc gggcgagcug | 3660 | |
| | cagaaaggua acgagcuggc acugcccucu aaauacguua uuucuugua ucuggccagc | 3720 | |
| | cacuaugaaa agcucaaagg gucucccgaa gauaaugaac agaagcagcu guucguggaa | 3780 | |
| | caacacaaac acuaccuuga ugagaucauc gagcaaauaa gcgaauucuc caaaagagug | 3840 | |
| | auccucgccg acgcuaaccu cgauaaggug cuuucgcuu acaauaagca cagggauaag | 3900 | |
| | cccaucaggg agcaggcaga aaacauuauc cacuuguuua cucugaccaa cuuggggcgcg | 3960 | |
| | ccugcagccu ucaaguacuu cgacaccacc auagacagc agcguacac cucuacaaag | 4020 | |
| | gagguccugg acgccacacu gauucaucag ucaauuacgg ggcucuauga aacaagaauc | 4080 | |
| | gaccucucuc agcucgguugg agacagcagg gcugaccca agaagaagag gaaggugga | 4140 | |
| CRISPR- associated endonuclease CAS9/Csn1 protein | MDKKYSIGLDIGTNSVGWAVITDEYKVPSKKFKVLGNTDRHSIKKNLIGALLFDSGETAE ATRLKRTARRRYTRRKNRICYLQEIFSNEMAKVDDSFFHRLEESFLVEEDKKHERHPIFG NIVDEVAYHEKYPTIYHLRKKLVDSTDKADLRLIYLALAHMIKFRGHFLIEGDLNPDNSD VDKLFIQLVQTYNQLFEENPINASGVDAKAILSARLSKSRRLENLIAQLPGEKKNGLFGN LIALSLGLTPNFKSNFDLAEDAKLQLSKDTYDDDLDNLLAQIGDQYADLFLAAKNLSDAI LLSDILRVNTEITKAPLSASMIKRYDEHHQDLTLLKALVRQQLPEKYKEIFFDQSKNGYA GYIDGGASQEEFYKFIKPILEKMDGTEELLVKLNREDLLRKQRTFDNGSIPHQIHLGELH AILRRQEDFYPFLKDNREKIEKILTFRIPYYVGPLARGNSRFAWMTRKSEETITPWNFEE VVDKGASAQSFIERMTNFDKNLPNEKVLPKHSLLYEYFTVYNELTKVKYVTEGMRKPAFL SGEQKKAIVDLLFKTNRKVTVKQLKEDYFKKIECFDSVEISGVEDRFNASLGTYHDLLKI IKDKDFLDNEENEDILEDIVLTLTLFEDREMIEERLKTYAHLFDDKVMKQLKRRRYTGWG RLSRKLINGIRDKQSGKTILDFLKSDGFANRNFMQLIHDDSLTFKEDIQKAQVSGQGDSL HEHIANLAGSPAIKKGILQTVKVVDELVKVMGRHKPENIVIEMARENQTTQKGQKNSRER MKRIEEGIKELGSQILKEHPVENTQLQNEKLYLYYLQNGRDMYVDQELDINRLSDYDVDH IVPQSFLKDDSIDNKVLTRSDKNRGKSDNVPSEEVVKKMKNYWRQLLNAKLITQRKFDNL TKAERGGLSELDKAGFIKRQLVETRQITKHVAQILDSRMNTKYDENDKLIREVKVITLKS KLVSDFRKDFQFYKVREINNYHHAHDAYLNAVVGTALIKKYPKLESEFVYGDYKVYDVRK MIAKSEQEIGKATAKYFFYSNIMNFFKTEITLANGEIRKRPLIETNGETGEIVWDKGRDF ATVRKVLSMPQVNIVKKTEVQTGGFSKESILPKRNSDKLIARKKDWDPKKYGGFDSPTVA YSVLVVAKVEKGKSKKLKSVKELLGITIMERSSFEKNPIDFLEAKGYKEVKKDLIIKLPK YSLFELENGRKRMLASAGELQKGNELALPSKYVNFLYLASHYEKLKGSPEDNEQKQLFVE QHKHYLDEIIEQISEFSKRVILADANLDKVLSAYNKHRDKPIREQAENIIHLFTLTNLGA PAAFKYFDTTIDRKRYTSTKEVLDATLIHQSITGLYETRIDLSQLGGDSRADPKKKRKV | | 8 |
| CRISPR- associated endonuclease CAS9/Csn1 mRNA | auggacuaua aggaccacga cggagacuac aaggaucaug auauugauua caaagacgau | 60 | 2 |
| | gacgauaaga uggccccaaa gaagaagcgg aaggucggua uccgcggagu cccagcugcc | 120 | |
| | gacaaggcaa acagcaucgg ggcaccaacu cugugggcug ggccgugauc | 180 | |
| | accgacgagu acaaggugcc cagcaagaaa uucaaggugc ugggcaacac cgaccggcac | 240 | |
| | agcaucaaga agaaccugau cggagcccug cuguucgaca gcggcgaaac agccgaggcc | 300 | |
| | acccggcuga agagaaccgc cagaagaaga uacaccgac ggaagaaccg gaucugcuau | 360 | |
| | cugcaagaga ucuuucagca agagauggcc aaggucgacg acagcuuccu ccacagacug | 420 | |
| | gaagaguccu uccugguga agaggauaag aagcacgagc ggcaccccau uucggcaac | 480 | |
| | aucguggacg agguggccua ccacgagaag uaccccacca ucuaccaccu gagaaagaaa | 540 | |
| | cugguggaca gcaccgacaa ggccgaccug cggcuaucu aucuggcccu ggcccacaug | 600 | |
| | aucaaguucc ggggccacuu ccugaucgag ggcgaccua cagcgacgug | 660 | |
| | gacaagcugu ucauccagcu ggugcagacc uacaaccagc uguucgagga aaacccccauc | 720 | |
| | aacgccagcg gcguggacgc caaggccauc cugucugcca cucgagcaa gagccgacgg | 780 | |
| | cuggaaaauc ugaucgcccca gcucccggc gagaagaaga auggccuguu cggcaaccug | 840 | |
| | auugcccuga gccuggcccu gacccccaac uucaagagca cuucgacc ggccgagagc | 900 | |
| | gccaaacugc agcugagcaa ggacaccuac gacgacgacu uggacaaccu gcuggcccag | 960 | |
| | aucggcgacc aguacgccga ccuguuucug gccgccaaga accugccga cgccauccug | 1020 | |
| | cugagcgaca uccugagagu gaacaccgag aucaccaagg cccccugag cgccucaug | 1080 | |
| | aucaagagau acgacgagca ccaccaggac cugacccugc ugaaggccu cgucggcag | 1140 | |
| | cagcugccug agaaguacaa agagauuuuc uucgaccaga gcaagaacgg cuacgccggc | 1200 | |
| | uacauugacg gcggagccag ccaggaagag uucuacaagu ucaucaagcc caucuggaa | 1260 | |
| | aagauggacg gcaccgagga acugcucgug aagcugaaca gagggaccu gcucggaag | 1320 | |
| | cagcggaccu ucgacaaugg cagcaucccc caccagaauc acggggaga gcugcacgcc | 1380 | |
| | auucugcggc ggcaggaaga uuuuuaccca uuccuuaagg acaacgggga aagaucgcc | 1440 | |
| | aagauccuga ccuuccgcau ccccuacuac guggggccc ucuggcaggggg aaacagcaga | 1500 | |
| | uucgccugga ugaccagaaa gagcgaggaa accaucaccc ccuggaacuu cgaggaagug | 1560 | |
| | guggacaagg gcgcuuccgc ccagagcuuc aucgagcgga ugaccaacuu cgauaagaac | 1620 | |
| | cugcccaacg agaagguugcu gcccaagcac agccugcugu acgaguacuu caccguguau | 1680 | |

TABLE 5-continued

CRISPR related proteins

| Description | Sequence | | SEQ ID NO |
|---|---|---|---|
| | aacgagcuga ccaaagugaa auacgugacc gagggaauga gaaagcccgc cuuccugagc | 1740 | |
| | ggcgagcaga aaaaggccau cguggaccug cuguucaaga ccaaccggaa agugaccgug | 1800 | |
| | aagcagcuga aaucucggcu cuucaagaaa aucgagucgu ucgaaucccu ggaaaucucc | 1860 | |
| | ggcguggaag aucgguucaa cgccuccccg ggcacauacc acgaucugcu gaaaauuauc | 1920 | |
| | aaggacaagg acuuccugga caaugaggaa aacgaggaca uucuggaaga uaucgugcug | 1980 | |
| | acccugacac uguuugagga cagagagaug aucgaggaac ggcugaaaac cuaugcccac | 2040 | |
| | cuguucgacg acaaagugau gaagcagcug aagcggcgga gauacaccgg cuggggccagg | 2100 | |
| | cugagccgga agcugaucaa cggcaucagu ccggcaagac aauccuggau | 2160 | |
| | uuccugaagu ccgacggcuu cgccaacaga aacuucaugc agcugaucca cgacgacagc | 2220 | |
| | cugaccuuua aggaggacau ccagaaagcc cagguguccg gccagggcga uagccugcac | 2280 | |
| | gagcacaugg ccaaucuggc cggcagcccc gccauuaaga agggcauccu gcagacaguc | 2340 | |
| | aaggugguug acgagcucgu gaaaagugaug ggccggcaca agcccgagaa caucgugauc | 2400 | |
| | gaaauggcca gagagaacca gaccacccag aagggacaga gaacagccg cgagagaaug | 2460 | |
| | aagcggaucu aagagggcau caaagagcug ggcagccaga uccugaaaga acaccccgug | 2520 | |
| | gaaaacaccc agcugcagaa cgagaagcug uaccuguacu accugcagaa uggccgggau | 2580 | |
| | auguacgugg accaggaacu ggacaucaac cggcugucccg acuacgaugu ggaccauauc | 2640 | |
| | gugcccuaga gcuuucgaa ggcgacuccc aucgacaaca aggucugacu cagaagcgac | 2700 | |
| | aagaaccggg gcaagagcga caacgugccc uccgaagagg ucgugaagaa gaugaagaac | 2760 | |
| | uacuggcggc agcugcugaa cgccaaacug auuacccaga gaaaguucga caaucugacc | 2820 | |
| | aaggccgaga gaggcggccu gagcgaacug gauaaggccg gcuucaucaa gagacagcug | 2880 | |
| | guggaaaccc ggcagaucac aaagcacgug gcacagaucc uggacuccccg gaugaacacu | 2940 | |
| | aaguacgacg agaaugacaa gcugaucgg gaagugaaag ugaucacccu gaaguccaag | 3000 | |
| | cuggugcccg auuuccggga ggauuucgga uuuuacaagg ugcgcgagau caacaacuac | 3060 | |
| | caccacgccc acgacgccua ccugaacgcc gucgugggaa ccgcccugau caaaaaguac | 3120 | |
| | ccuaagcugg aaagcgaguu cgugacggc gacuacaagg uguacgacgu gcggaagaug | 3180 | |
| | aucgccaaga gcgagcagga aaucggcaag gcuaccgcca aguacuucuu cuacagcaac | 3240 | |
| | aucaugaacu uuuucaagac cgagauuacc cuggccaacg gcgagauccg gaagcggccu | 3300 | |
| | cugaucgaga caaacggcga aaccggggag aucguggggg auaaggggcg ggauuuugcc | 3360 | |
| | accgugcgga aagugcugag caugccccaa gugaauaucg ugaaaaagac cgaggugcag | 3420 | |
| | acaggcggcu ucagcaaaga gucuauccug cccaagagga caagcgauaa gcugaucgcc | 3480 | |
| | agaaagaagg acugggaccc uaagaaguac ggcggcuucg acagcccac cguggccuau | 3540 | |
| | ucuguggucg ugguggccaa aguggaaaag ggcaagucca agaaacugaa gagugugaaa | 3600 | |
| | gagcugcugg ggaucaccau cauggaaaga agcagcuuca agaauccc aucgacuuuu | 3660 | |
| | cuggaagcca agggcuacaa agaagugaaa aaggaccuga ucaucaagcu gccuaaguac | 3720 | |
| | ucccuguucg agcuggaaaa cggccggaag agaaugcugg ccucugccgg cgaacugcag | 3780 | |
| | aagggaaacg aacuggcccu gcccuccaaa uauguaacu uccgcaccg ggcagcugcan | 3840 | |
| | uaugagaagc ugaaggcgcuc ccccgaggau aaugagcaga aacagcuguu uugggaacag | 3900 | |
| | cacaagcacu accuggacga gaucgaucag caugcagcg aguuccaa gagugugauc | 3960 | |
| | cuggccgacg cuaaucugga caaagugcug uccgccuaca acaagcaccg ggauaagccc | 4020 | |
| | aucagagagc aggccgagaa uauucaccuc ugcuuuuaccc ugaccaaucu gggagcccgu | 4080 | |
| | gccgccuuca aguacuuuga caccaccauc gaccggaaga ggacaccag caccaaagag | 4140 | |
| | gugcuggacg ccaccccugau ccaccagagc aucaccggcc uguacgagac acggaucgac | 4200 | |
| | cugcucagc ugggaggcga caagcgaccu gcugcuacua gaaagcuggu caagcuaagg | 4260 | |
| | aaaaagaaa | 4269 | |
| CRISPR-associated endonuclease CAS9/Csn1 protein | MDYKDHDGDYKDHDIDYKDDDDKMAPKKKRKVGIHGVPAADKKYSIGLDIGTNSVGWAVI TDEYKVPSKKFKVLGNTDRHSIKKNLIGALLFDSGETAEATRLKRTARRRYTRRKNRICY LQEIFSNEMAKVDDSFFHRLEESFLVEEDKKHERHPIFGNIVDEVAYHEKYPTIYHLRKK LVDSTDKADLRLIYLALAHMIKFRGHFLIEGDLNPDNSDVDKLFIQLVQTYNQLFEENPI NASGVDAKAILSARLSKSRRLENLIAQLPGEKKNGLFGNLIALSLGLTPNFKSNFDLAED AKLQLSKDTYDDDLDNLLAQIGDQYADLFLAAKNLSDAILLSDILRVNTEITKAPLSASM IKRYDEHHQDLTLLKALVRQQLPEKYKEIFFDQSKNGYAGYIDGGASQEEFYKFIKPILE KMDGTEELLVKLNREDLLRKQRTFDNGSIPHQIHLGELHAILRRQEDFYPFLKDNREKIE KILTFRIPYYVGPLARGNSRFAWMTRKSEETITPWNFEEVVDKGASAQSFIERMTNFDKN LPNEKVLPKHSLLYEYFTVYNELTKVKYVTEGMRKPAFLSGEQKKAIVDLLFKTNRKVTV KQLKEDYFKKIECFDSVEISGVEDRFNASLGTYHDLLKIIKDKDFLDNEENEDILEDIVL TLTLFEDREMIEERLKTYAHLFDDKVMKQLKRRRYTGWGRLSRKLINGIRDKQSGKTILD FLKSDGFANRNFMQLIHDDSLTFKEDIQKAQVSGQGDSLHEHIANLAGSPAIKKGILQTV KVVDELVKVMGRHKPENIVIEMARENQTTQKGQKNSRERMKRIEEGIKELGSQILKEHPV ENTQLQNEKLYLYYLQNGRDMYVDQELDINRLSDYDVDHIVPQSFLKDDSIDNKVLTRSD KNRGKSDNVPSEEVVKKMKNYWRQLLNAKLITQRKFDNLTKAERGGLSELDKAGFIKRQL VETRQITKHVAQILDSRMNTKYDENDKLIREVKVITLKSKLVSDFRKDFQFYKVREINNY HHAHDAYLNAVVGTALIKKYPKLESEFVYGDYKVYDVRKMIAKSEQEIGKATAKYFFYSN IMNFFKTEITLANGEIRKRPLIETNGETGEIVWDKGRDFATVRKVLSMPQVNIVKKTEVQ TGGFSKESILPKRNSDKLIARKKDWDPKKYGGFDSPTVAYSVLVVAKVEKGKSKKLKSVK ELLGITIMERSSFEKNPIDFLEAKGYKEVKKDLIIKLPKYSLFELENGRKRMLASAGELQ KGNELALPSKYVNFLYLASHYEKLKGSPEDNEQKQLFVEQHKHYLDEIIEQISEFSKRVI LADANLDKVLSAYNKHRDKPIREQAENIIHLFTLTNLGAPAAFKYFDTTIDRKRYTSTKE VLDATLIHQSITGLYETRIDLSQLGGDKRPAATKKAGQAKKKK | | 9 |
| CRISPR-associated endonuclease | auggacaaga aguacagcau cggccuggac aucggcacca cucugugggg cugggccgug aucaccgacg aguacaaggu gcccagcaag aaauucaagg ugcugggcaa caccgaccgg cacagcauca agaagaaccu gaucggcgcc cugcuguuca cagcggaga aacagccgag | 60<br>120<br>180 | 3 |

TABLE 5-continued

CRISPR related proteins

| Description | Sequence | SEQ ID NO |
|---|---|---|
| CAS9/Csn1 mRNA | gccacccggc ugaagagaac cgccagaaga agauacacca gacggaagaa ccggaucugc | 240 |
| | uaucugcaag agaucuucag caacgagaug gccaaggugg acgacagcuu cuuccacaga | 300 |
| | cuggaagagu ccuuccuggu ggaagaggau aagaagcacg agcggcaccc caucuucggc | 360 |
| | aacaucgugg acgaggugge cuaccacgag aaguacccca ccaucuacca ccugagaaag | 420 |
| | aaacugguqg acagcaccga caaggccgac cugcggcuga ucuaucuggc ccuggcccac | 480 |
| | augaucaagu uccggggcca cuuccugauc gagggcgacc ugaaccccga caacagcgac | 540 |
| | guggacaagc uguucaucca gcuggugcag accuacaacc agcuguucga ggaaaacccc | 600 |
| | aucaacgcca gcggcgugga cgccaaggcc auccugucug ccagacugag caagagcaga | 660 |
| | cggcuggaaa aucugaucgc ccagcugccc ggcgagaaga agaauggccu guucggcaac | 720 |
| | cugauugccc ugagccuggg ccugaccccc aacuucaaga gcaacuucga ccuggccgag | 780 |
| | gaugccaaac ugcagcugag caaggacacc uacgacgacg accuggacaa ccugcuggcc | 840 |
| | cagaucggcg accaguacgc cgaccuguuu cuggccgcca agaaccuguc cgacgccauc | 900 |
| | cugcugagcg acauccugag agugaacacc gagaucacca aggccccccu gagcgccucu | 960 |
| | augaucaaga gauacgacga gcaccaccag gaccugaccc ugcugaaagc ucucgugcgg | 1020 |
| | cagcagcugc cugagaagua caaagagauu uucuucgacc agagcaagaa cggcuacgcc | 1080 |
| | ggcuacaucg auggcggagc cagccaggaa gaguucuaca aguucaucaa gcccauccug | 1140 |
| | gaaaagaugg acggcaccga ggaacugcuc gugaagcuga acagagagga ccugcugcgg | 1200 |
| | aagcagcgga ccuucgacaa cggcagcauc ccccaccaga uccaccuggg agagcugcac | 1260 |
| | gccauucugc ggcggcagga agauuuuuac ccauucugga ggaucaaccg ggaaaagauc | 1320 |
| | gagaagaucc ugaccuuccg caucccauac uacguggqcc cucuggccag gggaaacagc | 1380 |
| | agauucgccu ggaugaccag aaagagcgag gaaaccauca cccccuggaa cuucgaggaa | 1440 |
| | guggucgaca agggcgccag cgcccagagc uucaucgagc ggaugaccaa cuucgauaag | 1500 |
| | aaccugccca acgagaaggu gcugcccaag cacagccugc uguacgagua cuucaccgug | 1560 |
| | uacaacgagc ugaccaaagu gaaauacgug accagggaa ugagaaagcc cgccuuccug | 1620 |
| | agcggcgagc agaaaaaagc caucguggac cugcuguuca gaccaaccg gaaagugacc | 1680 |
| | gugaagcagc ugaaagagga cuacuucaag aaaaucgagu gcuucgacuc cguggaaauc | 1740 |
| | uccggcgugg aagaucgguu caacgccucc cugggcacau accacgaucu gcugaaaauu | 1800 |
| | aucaaggaca aggacuuccu ggacaaugag acauucgga agauucugga gauaucgga | 1860 |
| | cugacccuga cacuguuuga ggacagagag augaucgagg aacggcugaa accuaugcc | 1920 |
| | caccuguucg acgacaaagu gaugaagcag cugaagcggc ggagauacac cggcuggggc | 1980 |
| | aggcugagcc ggaagcugau caacggcauc cgggacaagc aguccggcaa gacaauccug | 2040 |
| | gauuuccuga agucggacgg cuucgccaac agaaccuuca cucagcugau ccacgacgac | 2100 |
| | agccugaccu uuaaagagga cauccagaaa gccagguguu ccggccaggg cgauagccug | 2160 |
| | cacgagcaca uugccaaucu ggccggcagc cccgccauua agaagggcau ccugcagaca | 2220 |
| | gugaagguqg uggacgagcu cgugaaagug augggcggc acaagcccga aacaucgug | 2280 |
| | aucgaaaugg ccagagagaa ccagaccacc cagaagggac agaaaaacag ccgcgagaga | 2340 |
| | augaagcgga ucgaagaggg caucaaagag cugggcagcc agaucugaa agaacaccc | 2400 |
| | guggaaaaca cccagcugca aacgagaag cuguaccugu acuaccugca aaugggcgg | 2460 |
| | gauauguacg uggaccagga acuggacauc aaccggcugu ccgacuacga uguggaccau | 2520 |
| | aucgugcccc agagcuuucu gaaggacgac uccaucgaua acaaagugcu gacucggagc | 2580 |
| | gacaagaacc ggggcaagag cgacaacgug cccuccgaag gugugaa gaagaugaag | 2640 |
| | aacuacuggc gccagcugcu gaaugccaag cugauuaccc agaggaaguu cgacaaucug | 2700 |
| | accaaggccg agagaggcgg ccugagcgaa cuggauaagg ccggcuucau caagagacag | 2760 |
| | cugguggaaa cccggccggc cacaaagcac guggcacaga uccuggaccc cggaugaag | 2820 |
| | acuaaguacg acgagaacga caaacugauc cgggaaguga aagugaucac ccugaaguc | 2880 |
| | aagcugguqu ccgauuuccg gaaggauuuc caguuuuaca aagugcgcga gaucaacaac | 2940 |
| | uaccaccacg cccacgacgc cuaccugaac gccgucgugg aaccgcccu gaucaaaaag | 3000 |
| | uacccccuaagc uggaaagcga guucguguac ggcgacuaca agguguacga cgugcggaa | 3060 |
| | augaucgcca gagccgagca ggaaaucggc aagcuaccg ccaaguacuu cuuccacagc | 3120 |
| | aacaucauga acuuuuucaa gaccgagauu acccuggcca acggcgagau ccggaagcgg | 3180 |
| | ccucugaucg agacaaacgg cgaaacaggg gagaucgugu gggauaaggg ccgggacuuu | 3240 |
| | gccaccgucc ggaaagugcu gucuaugccc caagugaaua ucgugaaaaa gaccgaggug | 3300 |
| | cagacaggcg gcuucagcaa agagucuauc cugcccaaga ggaacagcga caagaugaac | 3360 |
| | gccagaaaga ggacgggga cccuaagag uacggcggcu ucgacagccc caccgugccc | 3420 |
| | uauucuguqc uggugguqgc caagugggaa aagggcaagu ccaagaaacu gaagagugug | 3480 |
| | aaagagcugc uggggaucac caucauggaa agaagcagcu ucgagaagaa ucccaucgac | 3540 |
| | uuucuggaag ccaagggcua caaagaagug aaaaaggacc ucaucaacga cgccuuaag | 3600 |
| | uacucccugu ucgagcugga aaacggccgg aagagaaugc uggcucucgc ggcgaacug | 3660 |
| | cagaaggaa acgaacuggc ccugcccucc aaauaugua acuccugua ccuggccagc | 3720 |
| | cacuaugaga gcugaagggg cuccccgag gauaaugagc agaaacagcu guuuguggaa | 3780 |
| | cagcacaaac acuaccugga cgagaucauc gagcaaauca gcgaguucuc caagagaguc | 3840 |
| | auccuggccg acgcuaaucu ggacaaggug cugagcgccu acaacaagca cagagacaag | 3900 |
| | ccuaucagag caggccga aauucauc caccuguuua cuugaccaa ucugggagcc | 3960 |
| | ccugccgccu ucaaguacuu ugacaccacc aucgaccgga agagguacac cagcaccaaa | 4020 |
| | gaggucugg acgccacccu gaucaccag gccgugcaga acaugacgauc | 4080 |
| | gaccugucuc agcugggagg cgacgccau cccauaucg ugcccgauua ugccagccug | 4140 |
| | ggcagcggcu cccccaagaa aaaacgcaag guggaagauc ucaagaaaaa gcggaaagug | 4200 |
| | gacggcauug uagugggag caacggcagc agcggauccg ugaagaaggg cgaggagcug | 4260 |
| | uucaccgggq ugggucccau ccuggcgac cuggccgg acguaaacgg ccacaaguac | 4320 |
| | agcgugcugg ucgaggcga gggcgaugcc accaacagcg agcugaccu gaaguucauc | 4380 |
| | ugcaccaccg gcaagcugcc cgugcccugg cccaccucg ugaccccu gaccuacggc | 4440 |
| | gugcagugcu ucagccgcua ccccgaccac augaagcagc acgacuucuu caagucccc | 4500 |
| | augcccgaag gcuacgucca ggagcgcacc aucccuuca aggacgacgg caccuacaag | 4560 |
| | acccgcgccg aggugaaguu cgagggcgac acccuggua accgcaucga gcugaagggc | 4620 |

TABLE 5-continued

CRISPR related proteins

| Description | Sequence | | | | | SEQ ID NO |
|---|---|---|---|---|---|---|
| | aucgacuuca | aggaggacgg | caacauccug | gggcacaagc | uggaguacaa cuucaacagc | 4680 |
| | cacaacgucu | auaucacggc | cgacaagcag | aagaacggca | ucaaggcgaa cuucaagauc | 4740 |
| | cgccacaacg | ucgaggacgg | cagcgugcag | cucgccgacc | acuaccagca gaacaccccc | 4800 |
| | aucggcgacg | gccccgugcu | gcugcccgac | aaccacuacc | ugagcaccca guccaagcug | 4860 |
| | agcaaagacc | ccaacgagaa | gcgcgaucac | augguccugc | uggaguucgu gaccgccgcc | 4920 |
| | gggaucacuc | ucggcaugga | cgagcuguac | aaguag | | 4956 |
| CRISPR-associated endonuclease CAS9/Csn1 mRNA | ugaucgccaa | gucggaacag | aaaucggaaa | aggcuacugc | aaaguacuuc uucuacucaa | 60 | 4 |
| | acaucaugaa | cuucuucaaa | acggagauca | cgcucgcgaa | cggcgaaauc cggaaaaggc | 120 |
| | cgcucauuga | aaccaacgga | gaaaccgggg | agaucgugug | ggacaaggga agggauuuug | 180 |
| | cgacugugag | gaaggugung | uccaugccgc | aaguaauau | ugugaaaaag acggaaguge | 240 |
| | aaaccggagg | auucagcaaa | gaauccaucu | ucccaaagcg | caacucggac aaacucaucg | 300 |
| | cgcgcaagaa | ggauugggac | cccaagaaau | acgguggcuu | ugacagccca acugnggcuu | 360 |
| | acuccgnccu | cgucguggcu | aaagnggaaa | agggnaaauc | caaaaagcuc aaaucggnuga | 420 |
| | aggagcuccu | gggaaucacg | aucuggagc | ggucgacguu | cgaaaagaau ccuauugauu | 480 |
| | uccuggaggc | gaaggcuac | aaggaaguca | agaaagaccu | gaucaucaag cucccgaagu | 540 |
| | acagccucuu | cgagcucgaa | aacggcagaa | agaggaugcu | ggcaucagcg ggagaauugc | 600 |
| | agaagggaaa | cgaacuggca | cugccgucca | aguacgugaa | uuuucucuau cuggcuagcc | 660 |
| | acuacgaaaa | gcugaaggga | ucgcccgagg | acaacgaagc | aaaacaacug uucguggagu | 720 |
| | agcacaagca | cuaccuggau | gagaucaucg | agcagaucc | cgaauucacg aaacgcguga | 780 |
| | uccuugccga | ugccaaucug | gauaagugu | gucggcuua | caacaagcau cgggauaaac | 840 |
| | cgauccgcga | acaggcagaa | aacaucauuc | aucuguacc | uuugaccaau cugggagcgc | 900 |
| | cugccgncgu | uaagcuacuuc | gacaccacua | uugauagaaa | gcgcuaccuc ucgaccaagg | 960 |
| | aagngccnga | cgcucacccug | auccaccagu | ccaucaccgg | acucuacgaa acucgcaung | 1020 |
| | accugcccca | gcuggagga | gauucacggg | ccgauccaaa | gaaaaagcgc aaggucugau | 1080 |
| | aauaggcugg | agccucggug | gccaugcuuc | uugcccuug | ggccncccc cagccccucc | 1140 |
| | uccccuuccn | gcaccgnac | ccccgngguc | uuugaauaaa | gucugagngg gcggcucuag | 1200 |
| | a | | | | | 1201 |
| CRISPR-associated endonuclease CAS9/Csn1 mRNA | ucaagcuuuu | ggacccucgu | acagaagcua | auacgacuca | cuauagggaa auaagagaga | 60 | 5 |
| | aaagaagagu | aagaagaaau | auaagagcca | ccauggacaa | gaaauacagc aucgccuggg | 120 |
| | auauuggaac | uaacagcgug | ggauccgug | ugaucaccga | cgaguacaag gugccgagca | 180 |
| | agaaguucaa | ggugcugggg | aacacugacc | gccauucaau | uaagaaaaac cucauuggag | 240 |
| | cacugcuuuu | ugacucgggu | gagacugccg | aagcuaccag | gcucaaacgc accgcacgca | 300 |
| | gacgnacac | ccgccgcaag | aaucgcaucu | gcuaucugca | agagaucuuu uccaacgaga | 360 |
| | uggcgaaggu | ugacgacagc | uuuuuccacc | ggcuggaaga | gagcuuccuc guggaaggga | 420 |
| | acaaaaagca | cgaaaggcau | ccaaucuucg | guaacaucgu | ggacgaagug gcguaucacg | 480 |
| | aaaaguaccc | uaccaucuac | caucgcggaa | gaagcuggu | cgauccacg gauaaggcag | 540 |
| | accugagacu | gaucuaccug | gcuuuggcc | auaugaucaa | auuccgcggc cauuccuga | 600 |
| | ucgaggggga | ccuuaacccg | gauaaacccg | augcuacuga | gcgguucugu cagcuggucc | 660 |
| | aaacguauaa | ccaacuguuu | gaggaaaauc | ccaucaacgc | uucggggug gacgccaaag | 720 |
| | caauccucuc | cgcgcgccug | agcaagcuca | ggcggcucga | aaaccugauc gcgcagcugc | 780 |
| | cgggagaaaa | gaaaaaugga | cuguuuggga | aucgaucgc | gcgucgcuc ggccugacuc | 840 |
| | caaacuuuaa | gucaaauuuc | gauuuggccg | aagaugccag | cggucagcug ucaaaggaca | 900 |
| | cuuacgacga | cgaccuggac | aaucugcugg | cccagauugg | ggaccaauac gcagaccgu | 960 |
| | ucuuggccgc | gaagaaccug | agcgacgcca | ucuucugnc | cgauauucug agagucaaua | 1020 |
| | ccgaaaucac | uaggcuccg | cuguccgcuu | caaugaucaa | gcgcuacgau gaacaccacc | 1080 |
| | aggaucucac | ucugccaaaa | gcccucguga | gacaacaauu | gccuaaaaag uacaaggaga | 1140 |
| | ucuucuucga | ccagagcaaa | aacggcuacg | caggcuacau | cgauggagga gcgucacaag | 1200 |
| | aagagucua | caaguucauc | aagccaaucu | uggagaagau | ggacggnacu gaagaacucc | 1260 |
| | uugngaagcu | gaauagggag | gauuugcuca | gaaagcagcg | gacuuuugac aacggcucga | 1320 |
| | ucccucauca | gauucaccuc | ggugagcugc | augccauccu | ucgcgccaa gaggauuuuu | 1380 |
| | acccuuccu | gaaggauaau | cgcgagaaaa | ucgaaagau | ccugacguuc agaauucccu | 1440 |
| | acuacgnggg | accgcuggcg | cgcgnaacu | cgcgguuuge | auggangacu cgcaaguccag | 1500 |
| | aggaaacuau | cacuccuugg | aauuuugagg | aggucgucga | uaaggagcc uccgccaug | 1560 |
| | cauucaucga | acgcaugacc | aacuucgaca | agaaucuucc | gaacgagaag guccuuccaa | 1620 |
| | agcacucccu | guuguacgaa | uacuucaccg | uguaccaaga | gucaccaaa guuaaguagu | 1680 |
| | ucaccgaggng | cangagaaag | ccggccuucc | ucagcggcga | caaaagaag gccaucgucg | 1740 |
| | accuccucuu | caagaccaac | cggaagguga | ccgucaagca | acucaaggag gacuacuuca | 1800 |
| | agaagaucga | augcuuugac | ucggucaaaa | ucagcggagu | ggaggaccgg uuuaacgcgu | 1860 |
| | cacuggguac | cuaccaugau | cucaucaaga | ucaucaagga | caaggacuuc cuggacaacg | 1920 |
| | aagaaaacga | ggacauccug | gaagauauug | uguugacccu | gacgcuguuc gaggaccggg | 1980 |
| | aaaugacga | ggaaaggcuu | aagaccacg | cacaccucuu | cgaugacaaa gugaugaagc | 2040 |
| | aacugaagcg | gcgagauau | acuggcuggg | ggaggcucuc | ccggaagcuc auuaauggaa | 2100 |
| | ucagagacaa | acagucggua | aaaacuaucc | ucgacuucuu | caagucggau gggucgccaa | 2160 |
| | accggaacuu | caugcagcug | auccacgaug | auuccuugac | cuucaaggag gauccaucaa | 2220 |
| | aggcgcaagu | gagcggacag | ggagauucgu | ugcacgaaca | uaucgcuaau cucgccggau | 2280 |
| | ccccagccau | caagaaagga | auccugcaga | ccgugaaggu | gguggaugaa cuggugaaag | 2340 |
| | ugauggggcg | ccacaaacca | gagaacaucg | ucauugagac | uggccgcgag aaucagacaa | 2400 |
| | cucagaaggg | acaaaagaac | uccagagagc | ggaugaaacg | caucgagaag auucagacaa | 2460 |
| | agcuggag | ccaauccug | aaggaacacc | cggucgagaa | cacccagcuc cagaacgaaa | 2520 |
| | agcuuuaccu | guacuaccuc | caaaauggac | gggacaugua | cgucgaccag gaauuggaca | 2580 |
| | ucaacagacu | cagcgacuac | gauguggacc | auauugcca | acaguccuuu cuuaaggacg | 2640 |
| | acagcaucga | uaacaaagug | cucacuagau | cagacaaaaa | ucgcgggaaa ucagacaaug | 2700 |

TABLE 5-continued

CRISPR related proteins

| Description | Sequence | | | | | | SEQ ID NO |
|---|---|---|---|---|---|---|---|
| | ugccaucgga | agagguuguc | aagaagauga | aaaacuacug | gagacagcug | cucaaugcca | 2760 | |
| | aacuuaucac | ccagcggaag | uucgacaacc | uuaccaaggc | cgagcgcgga | ggauugugccg | 2820 | |
| | aacucgacaa | ggccggcuuc | aucaaaaggc | agcugguga | aacccggcag | aucacuaaac | 2880 | |
| | acgugggccca | gauccucgau | ucgcgcauga | acacuaaaua | cgaugagaau | gacaagcuga | 2940 | |
| | uuagggaagu | caaggucauc | acucugaagu | cgaaacuggu | gucggacuuu | agaaaggauu | 3000 | |
| | uccaguucua | caaaguccgc | gagauuaaca | acuaccacca | cgcucaugac | gccuaccuga | 3060 | |
| | augcaguugu | gggcaccgcg | cugaucaaga | aguauccgaa | gcuggaaucc | gaguucgugu | 3120 | |
| | acggagauua | caaaguguac | gacgugcgca | aga | | | 3153 | |
| CRISPR-associated endonuclease CAS9/Csn1 mRNA | ucaagcuuuu | ggacccucgu | acagaagcua | auacgacuca | cuauagggaa | auaagagaga | 60 | 6 |
| | aaagaaga gu | aagaagaaau | auaagagcca | ccauggacaa | caaggaccac | gacgagacu | 120 | |
| | acaaagacca | ugacaucgau | uacaaggaug | acgaugacaa | aauggcaccg | aagaagaaga | 180 | |
| | gaaaggucgg | aauucacggg | gugccggccg | cggacaagaa | guacucaaac | ggacuggaua | 240 | |
| | ucggcacgaa | cagcgugggu | ugggcaguga | ucaccgacga | auacaaggug | ccgagcaaga | 300 | |
| | aguucaaagu | gcugggaaau | accgaucgac | aaaaaucag | auuggcgcgc | | 360 | |
| | uccuguucga | cucgggagag | acugccgagg | ccacuagacu | gaagaggacc | gcuaggcgcc | 420 | |
| | gcuacacgag | gcgcaaaaac | cgcaucugcu | aucuucaaga | aaucuucuca | aacgagaugg | 480 | |
| | ccaaggugga | cgacuccuuu | uuccaucggc | uggaagaauc | auuucgguug | gaggaggaca | 540 | |
| | agaagcacga | acgccauccc | auuuucggca | acaugucga | cgaaguggcc | uaucaugaga | 600 | |
| | aguauccgac | uaucuaccac | uugagaaaga | agcugguga | uccacugac | aaggcagauc | 660 | |
| | ugcgguugau | cuaccucgca | cuggcccaua | ugaucaaauu | ccggggacac | uuccucaucg | 720 | |
| | agggcgaccu | uaaucccgac | aauuccgaug | uggauaagcu | uuucauccag | cuggucccaga | 780 | |
| | ccuacaacca | acuguuugaa | gaaaauccaa | ucaaugcgag | cggugucgau | gcaaaggcca | 840 | |
| | uccugagcgc | ccgccucucg | aaaagcagaa | ggcucgcaaa | ccugaucga | caguugccug | 900 | |
| | gagagaagaa | gaacgccuc | uucggcaauc | ucaucgcauu | gcccuggga | cugacuccaa | 960 | |
| | acuucaaauc | caacuucgac | uuggccgagg | acgccaaacu | gcaacugagc | aaagauaccu | 1020 | |
| | acgaugauga | cuuggacaau | cuucggcuc | agacgcgca | ccaguacgcc | gaccuguucc | 1080 | |
| | uugcggcuaa | gaaccugucg | gacgccaucc | ugcugucgca | caucugcgc | gucaauaccg | 1140 | |
| | aaauuacuaa | agcaccacuc | ucggcaucca | ugaucaagag | auacgaugaa | caccaccagg | 1200 | |
| | aucucacccu | ccugaaagca | cuggugcgga | agcagcuccc | ugagaaauac | aaggaaaucu | 1260 | |
| | ucuuugauca | guccaagaac | ggauacgccg | gauacauga | cggcggcgcg | agccaagagg | 1320 | |
| | aauucuacaa | gcgaucaag | ccgaucugg | aaaagaggg | uggcacggaa | gaacuccugg | 1380 | |
| | ucaaacugaa | uagagaggau | cugcuccgca | acaacggac | cuucgauaac | ggaucgaucc | 1440 | |
| | cgcaccagau | ccaccucggc | gaacugcaug | ccauccugcg | gcgcaggag | gacuuuuacc | 1500 | |
| | cguuccucaa | agacaacaga | gaaaagaucg | agaagaucuc | ugaccuuucgc | aucccguacu | 1560 | |
| | acgugggggccc | cucgcugaga | gguaaacuccc | gcuuugcuug | gaugacugaa | aagcagaggg | 1620 | |
| | aaacgauac | cccauggaac | uucgaagagg | ugguugacaa | aggagcgagc | gcccaaucgu | 1680 | |
| | ucaucgaacg | gaugacuaac | uucgauaaga | aucugccgaa | ugagaagguc | cugccuaagc | 1740 | |
| | acucacuucu | guaugaauac | uuuacugugu | auaacgaacu | caccaaaguc | aaauacguga | 1800 | |
| | cugagggaau | gcgcaagccu | gcguuuuugu | ccggcgagca | gaaaaaggcc | aucguggcau | 1860 | |
| | ugcguuucaa | aaccaaccgc | aaggugacug | uuaagcaacu | caaagaggac | uacuuuaaga | 1920 | |
| | agaucgaaug | cuuugacucg | gucgagauuu | ccggggguga | agauagauuc | aacgcgucgc | 1980 | |
| | ugggaaccua | ccaugaucuc | cucaagauua | ucaggacaa | agacuuccug | gauaacgagg | 2040 | |
| | agaaugagga | caucucgaa | gauauuugc | uuacccgac | ccuuuucgaa | gaucgcgaaa | 2100 | |
| | ugaucgaaga | acgccugaaa | accuacgcuc | accuguuca | cgauaagug | augaaacagu | 2160 | |
| | ugaaacgccg | cgcguacagg | gguuggggc | ggcugucgcg | caagcugauc | aacgaauuc | 2220 | |
| | gggacaaaca | gagcggaaag | accauccucg | auuuucugaa | guccgauggu | uuugccaacc | 2280 | |
| | gcaacuucau | gcagcucauc | caugaugauu | ccuuaccuu | uaaggaggau | auccagaagg | 2340 | |
| | cacaagugucu | gggacaaggg | gauucgcucc | acgaacacau | cgccgaaucg | gcggggucgc | 2400 | |
| | cggcaauuaa | gaagggaauc | uccagacug | uuaaggug | cgacgagcug | gugaagguga | 2460 | |
| | uggggagaca | uaagccugaa | aacauuguga | ucgagauggc | gagagaaau | caaacuacuc | 2520 | |
| | agaagggaca | gaagaauucc | cgggagcgga | ugaagcgcau | cgaggaggga | aucaaggaac | 2580 | |
| | ugggcucccca | aauccugaaa | gagcauccc | uggaaaauc | ucagcugcag | aacgagaggu | 2640 | |
| | uuuaccugua | cuaucuucaa | aauggcaggg | acaugugacg | cgaccaagaa | cuggauauca | 2700 | |
| | aucggcucuc | cgauuacgac | gucgaucaca | ucgucccca | aucauuccug | aaggaugaua | 2760 | |
| | gcaucgauaa | caaggugcuc | acuagaucag | acaaaaaccg | gggaaaguca | gauaacgucc | 2820 | |
| | ccagcgaaga | agucgugaag | aagaugaaga | auuacuggag | gcaauucug | aacgccaaac | 2880 | |
| | ucaucacucu | gcgcaaguuc | gacaaccuga | ccaaagcaga | aggggagga | cucagcgagc | 2940 | |
| | uggacaaggc | uggggucauc | aaacggcagc | uguggagac | ucgccaaauc | acgaagcaug | 3000 | |
| | uggcccgauu | ucucgacucg | cgcaugaaua | cuaaguacga | cgaaaacgau | aagcugaucc | 3060 | |
| | gggagagugaa | ggugcaucca | agcugaagga | agcgucgugc | cgauuuccgg | aaagacuucc | 3120 | |
| | aguccuacaa | ggugcgggag | auuaacaacu | accaucacgc | ucacgacgcu | uaccucaaug | 3180 | |
| | cuguggugu | gacggcguug | auuaagaagu | acccaaaacu | ggaguccgaa | uucgucuacg | 3240 | |
| | gagauuacaa | ggucuacgac | gugcgcaaga | ugauugccaa | gucggagcag | gaauugggaa | 3300 | |
| | aagcgacugc | uaagauacuc | uucucucga | auacaaauca | cuucuucaag | accgaaaauca | 3360 | |
| | cccugggccuaa | cggcgagauc | aggaaacggc | cgcugaucga | aucuaauggu | gagacuggug | 3420 | |
| | aaaucgugug | ggauaaggga | cgggacuucg | ccacgguccuc | caaggucucu | agcaugccgc | 3480 | |
| | aagugaauau | uguuaagaaa | accgaagugc | agaccgguggg | uucucgaaag | gaauccaucc | 3540 | |
| | ugccaaagcg | caacucggau | aagcuuauug | cccgcaagaa | gauugggguc | ccgaaaaagu | 3600 | |
| | acggugugu | cgacuccccu | accgugcgu | acucgguggc | ugugaaauuu | aaagggaaa | 3660 | |
| | agggcaaauc | aaaaaagcuc | aagagcguca | aggagcugcu | gggaaucacc | aucaugaga | 3720 | |
| | gguccaguccuu | ugagaaaaac | ccgaucgacu | ucuuggaagc | caagggauac | aaagaggugaa | 3780 | |
| | agaaagaccu | gaucaucaaa | cuuccaaagu | acucccuguu | cgaacucgaa | aacgggagga | 3840 | |
| | agcgcaugcu | cgccucagcc | ggggaacugc | aaaagggcaa | cgaacuggcc | cucccgucaa | 3900 | |

TABLE 5-continued

CRISPR related proteins

| Description | Sequence | SEQ ID NO |
|---|---|---|
| | aauacgucaa cuuccuguac uuggcgucac acuacgaaaa gcugaaagga uccccagagg | 3960 |
| | acaacgaaca gaaacagcug uucgucgagc agcacaagca cuaccuggac gagaucaucg | 4020 |
| | aacagaucuc ggaauucagc aagagauga ucuuggcaga cgcuaaccuu gacaaaguuc | 4080 |
| | ucucggcaua caauaagcau cgcgacaagc cgaucagaga acaggcggag aacaucaucc | 4140 |
| | accuguuac ucucaccaac cugggcgcgc cagcggcuuu uaaguacuuu gauaccacca | 4200 |
| | uugaccgcaa gagauacacc ucaacuaaag aagugcugga cgcaaccug auccaucaaa | 4260 |
| | gcaucaccgg acuuuaugaa acucgaaucg cgucggagga gacaaagac | 4320 |
| | cggcugccac caagaaggcc ggacaggcaa agaagagaa augauaauag gcugagccu | 4380 |
| | cgguggccau gcuucuugcc ccuugggccu ccccccagcc ccuccucccc uuccugcacc | 4440 |
| | cguaccccg uggucuuuga auaaagucug aguggcggc ucuaga | 4486 |
| dCAS9 as described in Qi et al | MDKKYSIGLAIGTNSVGWAVITDEYKVPSKKFKVLGNTDRHSIKKNLIGALLFDSGETAEATRLKRTARRRYTRRKNRICYLQEIF SNEMAKVDDSFFHRLEESFLVEEDKKHERHPIFGNIVDEVAYHEKYPTIYHLRKKLVDSTDKADLRLIYLALAHMIKFRGHFLIEG DLNPDNSDVDKLFIQLVQTYNQLFEENPINASGVDAKAILSARLSKSRRLENLIAQLPGEKKNGLFGNLIALSLGLTPNFKSNFDL AEDAKLQLSKDTYDDDLDNLLAQIGDQYADLFLAAKNLSDAILLSDILRVNTEITKAPLSASMIKRYDEHHQDLTLLKALVRQQLP EKYKEIFFDQSKNGYAGYIDGGASQEEFYKFIKPILEKMDGTEELLVKLNREDLLRKQRTFDNGSIPHQIHLGELHAILRRQEDFY PFLKDNREKIEKILTFRIPYYVGPLARGNSRFAWMTRKSEETITPWNFEEVVDKGASAQSFIERMTNFDKNLPNEKVLPKHSLLYE YFTVYNELTKVKYVTEGMRKPAFLSGEQKKAIVDLLFKTNRKVTVKQLKEDYFKKIECFDSVEISGVEDRFNASLGTYHDLLKIIK DKDFLDNEENEDILEDIVLTLTLFEDREMIEERLKTYAHLFDDKVMKQLKRRRYTGWGRLSRKLINGIRDKQSGKTILDFLKSDGF ANRNFMQLIHDDSLTFKEDIQKAQVSGQGDSLHEHIANLAGSPAIKKGILQTVKVVDELVKVMGRHKPENIVIEMARENQTTQKGQ KNSRERMKRIEEGIKELGSQILKEHPVENTQLQNEKLYLYYLQNGRDMYVDQELDINRLSDYDVDAIVPQSFLKDDSIDNKVLTRS DKNRGKSDNVPSEEVVKKMKNYWRQLLNAKLITQRKFDNLTKAERGGLSELDKAGFIKRQLVETRQITKHVAQILDSRMNTKYDEN DKLIREVKVITLKSKLVSDFRKDFQFYKVREINNYHHAHDAYLNAVVGTALIKKYPKLESEFVYGDYKVYDVRKMIAKSEQEIGKA TAKYFFYSNIMNFFKTEITLANGEIRKRPLIETNGETGEIVWDKGRDFATVRKVLSMPQVNIVKKTEVQTGGFSKESILPKRNSDK LIARKKDWDPKKYGGFDSPTVAYSVLVVAKVEKGKSKKLKSVKELLGITIMERSSFEKNPIDFLEAKGYKEVKKDLIIKLPKYSLF ELENGRKRMLASAGELQKGNELALPSKYVNFLYLASHYEKLKGSPEDNEQKQLFVEQHKHYLDEIIEQISEFSKRVILADANLDKV LSAYNKHRDKPIREQAENIHLFTLTNLGAPAAFKYFDTTIDRKRYTSTKEVLDATLIHQSITGLYETRIDLSQLGGD | 61 |
| As describe in Gilbert et al 2013. Amino acid sequence of dCas9-KRAB (dCas9-HA tag-2xSV40NLS-KRAB) | MDKKYSIGLAIGTNSVGWAVITDEYKVPSKKFKVLGNTDRHSIKKNLIGALLFDSGETAEATRLKRTARRRYTRRKNRICYLQEIF SNEMAKVDDSFFHRLEESFLVEEDKKHERHPIFGNIVDEVAYHEKYPTIYHLRKKLVDSTDKADLRLIYLALAHMIKFRGHFLIEG DLNPDNSDVDKLFIQLVQTYNQLFEENPINASGVDAKAILSARLSKSRRLENLIAQLPGEKKNGLFGNLIALSLGLTPNFKSNFDL AEDAKLQLSKDTYDDDLDNLLAQIGDQYADLFLAAKNLSDAILLSDILRVNTEITKAPLSASMIKRYDEHHQDLTLLKALVRQQLP EKYKEIFFDQSKNGYAGYIDGGASQEEFYKFIKPILEKMDGTEELLVKLNREDLLRKQRTFDNGSIPHQIHLGELHAILRRQEDFY PFLKDNREKIEKILTFRIPYYVGPLARGNSRFAWMTRKSEETITPWNFEEVVDKGASAQSFIERMTNFDKNLPNEKVLPKHSLLYE YFTVYNELTKVKYVTEGMRKPAFLSGEQKKAIVDLLFKTNRKVTVKQLKEDYFKKIECFDSVEISGVEDRFNASLGTYHDLLKIIK DKDFLDNEENEDILEDIVLTLTLFEDREMIEERLKTYAHLFDDKVMKQLKRRRYTGWGRLSRKLINGIRDKQSGKTILDFLKSDGF ANRNFMQLIHDDSLTFKEDIQKAQVSGQGDSLHEHIANLAGSPAIKKGILQTVKVVDELVKVMGRHKPENIVIEMARENQTTQKGQ KNSRERMKRIEEGIKELGSQILKEHPVENTQLQNEKLYLYYLQNGRDMYVDQELDINRLSDYDVDAIVPQSFLKDDSIDNKVLTRS DKNRGKSDNVPSEEVVKKMKNYWRQLLNAKLITQRKFDNLTKAERGGLSELDKAGFIKRQLVETRQITKHVAQILDSRMNTKYDEN DKLIREVKVITLKSKLVSDFRKDFQFYKVREINNYHHAHDAYLNAVVGTALIKKYPKLESEFVYGDYKVYDVRKMIAKSEQEIGKA TAKYFFYSNIMNFFKTEITLANGEIRKRPLIETNGETGEIVWDKGRDFATVRKVLSMPQVNIVKKTEVQTGGFSKESILPKRNSDK LIARKKDWDPKKYGGFDSPTVAYSVLVVAKVEKGKSKKLKSVKELLGITIMERSSFEKNPIDFLEAKGYKEVKKDLIIKLPKYSLF ELENGRKRMLASAGELQKGNELALPSKYVNFLYLASHYEKLKGSPEDNEQKQLFVEQHKHYLDEIIEQISEFSKRVILADANLDKV LSAYNKHRDKPIREQAENIHLFTLTNLGAPAAFKYFDTTIDRKRYTSTKEVLDATLIHQSITGLYETRIDLSQLGGDAYPYDVPD YASLGSGSPKKKRKVEDPKKKRKVDGIGSGSNGSSGGGGGMDAKSLTAWSRTLVTFKDVFVDFTREEWKLLDTAQQIVYRNVMLE NYKNLVSLGYQLTKPDVILRLEKGEEP | 62 |
| Amino acid sequence of dCas9-BFP-KRAB ((dCas9-HA tag-2xSV40NLS-BFP-KRAB) | MDKKYSIGLAIGTNSVGWAVITDEYKVPSKKFKVLGNTDRHSIKKNLIGALLFDSGETAEATRLKRTARRRYTRRKNRICYLQEIF SNEMAKVDDSFFHRLEESFLVEEDKKHERHPIFGNIVDEVAYHEKYPTIYHLRKKLVDSTDKADLRLIYLALAHMIKFRGHFLIEG DLNPDNSDVDKLFIQLVQTYNQLFEENPINASGVDAKAILSARLSKSRRLENLIAQLPGEKKNGLFGNLIALSLGLTPNFKSNFDL AEDAKLQLSKDTYDDDLDNLLAQIGDQYADLFLAAKNLSDAILLSDILRVNTEITKAPLSASMIKRYDEHHQDLTLLKALVRQQLP EKYKEIFFDQSKNGYAGYIDGGASQEEFYKFIKPILEKMDGTEELLVKLNREDLLRKQRTFDNGSIPHQIHLGELHAILRRQEDFY PFLKDNREKIEKILTFRIPYYVGPLARGNSRFAWMTRKSEETITPWNFEEVVDKGASAQSFIERMTNFDKNLPNEKVLPKHSLLYE YFTVYNELTKVKYVTEGMRKPAFLSGEQKKAIVDLLFKTNRKVTVKQLKEDYFKKIECFDSVEISGVEDRFNASLGTYHDLLKIIK DKDFLDNEENEDILEDIVLTLTLFEDREMIEERLKTYAHLFDDKVMKQLKRRRYTGWGRLSRKLINGIRDKQSGKTILDFLKSDGF ANRNFMQLIHDDSLTFKEDIQKAQVSGQGDSLHEHIANLAGSPAIKKGILQTVKVVDELVKVMGRHKPENIVIEMARENQTTQKGQ KNSRERMKRIEEGIKELGSQILKEHPVENTQLQNEKLYLYYLQNGRDMYVDQELDINRLSDYDVDAIVPQSFLKDDSIDNKVLTRS DKNRGKSDNVPSEEVVKKMKNYWRQLLNAKLITQRKFDNLTKAERGGLSELDKAGFIKRQLVETRQITKHVAQILDSRMNTKYDEN DKLIREVKVITLKSKLVSDFRKDFQFYKVREINNYHHAHDAYLNAVVGTALIKKYPKLESEFVYGDYKVYDVRKMIAKSEQEIGKA TAKYFFYSNIMNFFKTEITLANGEIRKRPLIETNGETGEIVWDKGRDFATVRKVLSMPQVNIVKKTEVQTGGFSKESILPKRNSDK LIARKKDWDPKKYGGFDSPTVAYSVLVVAKVEKGKSKKLKSVKELLGITIMERSSFEKNPIDFLEAKGYKEVKKDLIIKLPKYSLF ELENGRKRMLASAGELQKGNELALPSKYVNFLYLASHYEKLKGSPEDNEQKQLFVEQHKHYLDEIIEQISEFSKRVILADANLDKV LSAYNKHRDKPIREQAENIHLFTLTNLGAPAAFKYFDTTIDRKRYTSTKEVLDATLIHQSITGLYETRIDLSQLGGDAYPYDVPD YASLGSGSPKKKRKVEDPKKKRKVDGIGSGSNGSSGGSSELIKENMHMKLYMEGTVDNHHFKCTSEGEGKPYEGTQTMRIKVVEGGP LPFAFDILATSFLYGSKTFINHTQGIPDFFKQSFPEGFTWERVTTYEDGGVLTATQDTSLQDGCLIYNVKIRGVNFTSNGPVMQKK TLGWEAFTETLYPADGGLEGRNDMALKLVGGSHLIANIKTTYRSKKPAKNLKMPGVYYVDYRLERIKEANNETYVEQHEVAVARYC DLPSKLGHKLNGGGGGMDAKSLTAWSRTLVTFKDVFVDFTREEWKLLDTAQQIVYRNVMLENYKNLVSLGYQLTKPDVILRLEKGE EP | 63 |
| Amino acid sequence of dCas9-NLS-FLAG-VP64 (as | MDKKYSIGLAIGTNSVGWAVITDEYKVPSKKFKVLGNTDRHSIKKNLIGALLFDSGETAEATRLKRTARRRYTRRKNRICYLQEIF SNEMAKVDDSFFHRLEESFLVEEDKKHERHPIFGNIVDEVAYHEKYPTIYHLRKKLVDSTDKADLRLIYLALAHMIKFRGHFLIEG DLNPDNSDVDKLFIQLVQTYNQLFEENPINASGVDAKAILSARLSKSRRLENLIAQLPGEKKNGLFGNLIALSLGLTPNFKSNFDL AEDAKLQLSKDTYDDDLDNLLAQIGDQYADLFLAAKNLSDAILLSDILRVNTEITKAPLSASMIKRYDEHHQDLTLLKALVRQQLP | 64 |

TABLE 5-continued

CRISPR related proteins

| Description | Sequence | SEQ ID NO |
|---|---|---|
| described in Maeder et al) | EKYKEIFFDQSKNGYAGYIDGGASQEEFYKFIKPILEKMDGTEELLVKLNREDLLRKQRTFDNGSIPHQIHLGELHAILRRQEDFY PPLKDNREKIEKILTFRIPYYVGPLARGNSRFAWMTRKSEETITPWNFEEVVDKGASAQSFIERMTNFDKNLPNEKVLPKHSLLYE YFTVYNELTKVKYVTEGMRKPAFLSGEQKKAIVDLLFKTNRKVTVKQLKEDYFKKIECFDSVEISGVEDRFNASLGTYHDLLKIIK DKDFLDNEENEDILEDIVLTLTLFEDREMIEERLKTYAHLFDDKVMKQLKRRRYTGWGRLSRKLINGIRDKQSGKTILDFLKSDGF ANRNFMQLIHDDSLTFKEDIQKAQVSGQGDSLHEHIANLAGSPAIKKGILQTVKVVDELVKVMGRHKPENIVIEMARENQTTQKGQ KNSRERMKRIEEGIKELGSQILKEHPVENTQLQNEKLYLYYLQNGRDMYVDQELDINRLSDYDVDAIVPQSFLKDDSIDNKVLTRS DKNRGKSDNVPSEEVVKKMKNYWRQLLNAKLITQRKFDNLTKAERGGLSELDKAGFIKRQLVETRQITKHVAQILDSRMNTKYDEN DKLIREVKVITLKSKLVSDFRKDFQFYKVREINNYHHAHDAYLNAVVGTALIKKYPKLESEFVYGDYKVYDVRKMIAKSEQEIGKA TAKYFFYSNIMNFFKTEITLANGEIRKRPLIETNGETGEIVWDKGRDFATVRKVLSMPQVNIVKKTEVQTGGFSKESILPKRNSDK LIARKKDWDPKKYGGFDSPTVAYSVLVVAKVEKGKSKKLKSVKELLGITIMERSSFEKNPIDFLEAKGYKEVKKDLIIKLPKYSLF ELENGRKRMLASAGELQKGNELALPSKYVNFLYLASHYEKLKGSPEDNEQKQLFVEQHKHYLDEIIEQISEFSKRVILADANLDKV LSAYNKHRDKPIREQAENIIHLFTLTNLGAPAAFKYFDTTIDRKRYTSTKEVLDATLIHQSITGLYETRIDLSQLGGDGSPKKKRK VSSDYKHDGDYKDHDIDYKDDDDKAAGGGGSGRADALDDFDLDMLGSDALDDFDLDMLGSDALDDFDLDMLGSDALDDFDLDML. | |
| Amino acid sequence of FLAG_NLS_dCas 9-NLS-VP64-HA (as described in Perez-Pinera et al) | MDYKDHDGDYKDHDIDYKDDDDKMAPKKKRKVGRGMDKKYSIGLAIGTNSVGWAVITDEYKVPSKKFKVLGNTDRHSIKKNLIGAL LFDSGETAEATRLKRTARRRYTRRKNRICYLQEIFSNEMAKVDDSFFHRLEESFLVEEDKKHERHPIFGNIVDEVAYHEKYPTIYH LRKKLVDSTDKADLRLIYLALAHMIKFRGHFLIEGDLNPDNSDVDKLFIQLVQTYNQLFEENPINASGVDAKAILSARLSKSRRLE NLIAQLPGEKKNGLFGNLIALSLGLTPNFKSNFDLAEDAKLQLSKDTYDDDLDNLLAQIGDQYADLFLAAKNLSDAILLSDILRVN TEITKAPLSASMIKRYDEHHQDLTLLKALVRQQLPEKYKEIFFDQSKNGYAGYIDGGASQEEFYKFIKPILEKMDGTEELLVKLN EDLLRKQRTFDNGSIPHQIHLGELHAILRRQEDFYPFLKDNREKIEKILTFRIPYYVGPLARGNSRFAWMTRKSEETITPWNFEEV VDKGASAQSFIERMTNPDKNLPNEKVLPKHSLLYEYFTVYNELTKVKYVTEGMRKPAFLSGEQKKAIVDLLFKTNRKVTVKQLKED YFKKIECFDSVEISGVEDRFNASLGTYHDLLKIIKDKDFLDNEENEDILEDIVLTLTLFEDREMIEERLKTYAHLFDDKVMKQLKR RRYTGWGRLSRKLINGIRDKQSGKTILDFLKSDGFANRNFMQLIHDDSLTFKEDIQKAQVSGQGDSLHEHIANLAGSPAIKKGILQ TVKVVDELVKVMGRHKPENIVIEMARENQTTQKGQKNSRERMKRIEEGIKELGSQILKEHPVENTQLQNEKLYLYYLQNGRDMYVD QELDINRLSDYDVDAIVPQSFLKDDSIDNKVLTRSDKNRGKSDNVPSEEVVKKMKNYWRQLLNAKLITQRKFDNLTKAERGGLSEL DKAGFIKRQLVETRQITKHVAQILDSRMNTKYDENDKLIREVKVITLKSKLVSDFRKDFQFYKVREINNYHHAHDAYLNAVVGTAL IKKYPKLESEFVYGDYKVYDVRKMIAKSEQEIGKATAKYFFYSNIMNFFKTEITLANGEIRKRPLIETNGETGEIVWDKGRDFATV RKVLSMPQVNIVKKTEVQTGGFSKESILPKRNSDKLIARKKDWDPKKYGGFDSPTVAYSVLVVAKVEKGKSKKLKSVKELLGITIM ERSSFEKNPIDFLEAKGYKEVKKDLIIKLPKYSLFELENGRKRMLASAGELQKGNELALPSKYVNFLYLASHYEKLKGSPEDNEQK QLFVEQHKHYLDEIIEQISEFSKRVILADANLDKVLSAYNKHRDKPIREQAENIIHLFTLTNLGAPAAFKYFDTTIDRKRYTSTKE VLDATLIHQSITGLYETRIDLSQLGGDPIAGSKASPKKKRKVGRADALDDFDLDMLGSDALDDFDLDMLGSDALDDFDLDMLGSDA LDDFDLDMLINYPYDVPDYAS | 65 |
| dCas9 (bacteria) S. pyogenes ">bacteria dCas9 | gacgtcttaagacccactttcacatttaagttgtttttctaatccgcatatgatcaattcaaggccgaat aagaaggctggctctgcaccttggtgatcaaataattcgatagcttgtcgtaataatggcggcatactat cagtagtaggtgtttccctttcttctttagcgacttgatgctcttgatctttccaatacgcaacctaagt aaaatgccccacagcgctgagtgcatataatgcattctctagtgaaaaacccttgttggcataaaaaggct aattgattttcgagagtttcatactgttttttctgtaggccgtgtacctaaatgtacttttgctccatcgc gatgacttagtaaagcacatctaaaactttttagcgttattacgtaaaaatcttgccagctttccccttc taaagggcaaaagtgagtatggtgcctatctaacatctcaaatggctaaggcgtcgagcaaagcccgctta tttttttacatgccaatacaatgtaggctgctctacacctagcttctgggcgagtttacgggttgttaaac cttcgattccgacctcattaagcagctctaatgcgctgttaatcactttacttttatctaatctagacat cattaattcctaatttttgttgacactctatcgttgatagagttattttaccactccctatcagtgatag agaaaagaattcaaaaGATCTAAAGAGGAGAAAGGATCTATGGATAAGAAATACTCAATAGGCTTAGCTA TCGGCACAAATAGCGTCGGATGGGCGGTGATCACTGATGAATATAAGGTTCCGTCTAAAAAGTTCAAGGT TCTGGGAAATACAGACCGCCACAGTATCAAAAAAATCTTATAGGGGCTCTTTTATTTGACAGTGGAGAG ACAGCGGAAGCGACTCGTCTCAAACGGACAGCTCGTAGAAGGTATACACGTCGGAAGAATCGTATTTGTT ATCTACAGGAGATTTTTCAAATGAGATGGCGAAAGTAGATGATAGTTTCTTTCATCGACTTGAAGAGTC TTTTTTGGTGGAAGAAGACAAGAAGCATGAACGTCATCCTATTTTTGGAAATATAGTAGATGAAGTTGCT TATCATGAGAAATATCCAACTATCTATCATCTGCGAAAAAATTGGTAGATTCTACTGATAAAGCGGATT TGCGCTTAATCTATTTGGCCTTAGCGCATATGATTAAGTTTCGTGGTCATTTTTTGATTGAGGGAGATTT AAATCCTGATAATAGTGATGTGGACAAACTATTTATCCAGTTGGTACAAACCTACAATCAATTATTTGAA GAAAACCCTATTAACGCAAGTGGAGTAGATGCTAAAGCGATTCTTTCTGCACGATTGAGTAAATCAAGAC GATTAGAAAATCTCATTGCTCAGCTCCCCGGTGAGAAGAAAATGGCTTATTTGGGAATCTCATTGCTTT GTCATTGGGTTTGACCCCTAATTTTAAATCAAATTTTGATTTGGCAGAAGATGCTAAATTACAGCTTTCA AAAGATACTTACGATGATGATTTAGATAATTTATTGGCGCAAATTGGAGATCAATATGCTGATTTGTTT TGGCAGCTAAGAATTTATCAGATGCTATTTTACTTTCAGATATCTCTAAGAGTAAATACTGAAATAACTAA GGCTCCCCTATCAGCTTCAATGATTAAACGCTACGATGAACATCATCAAGACTTGACTCTTTTAAAAGCT TTAGTTCGACAACAACTTCCAGAAAAGTATAAAGAAATCTTTTTTGATCAATCAAAAAACGGATATGCAG GTTATATTGATGGGGGAGCTAGCCAAGAAGAATTTTATAAATTTATCAAACCAATTTTAGAAAAAATGGA TGGTACTGAGGAATTATTGGTGAAACTAAATCGTGAAGATTTGCTGCGCAAGCAACGGAGCCTTTGACAAC GGCTCTATTCCCCATCAAATTCACTTGGGTGAGCTGCATGCTATTTTGAGAAGACAAGAAGACTTTTATC CATTTTTAAAAGACAATCGTGAGAAGATTGAAAAAATCTTGACTTTTCGAATTCCTTATTATGTTGGTCC ATTGGCGCGTGGCAATAGTCGTTTTGCATGGATGACTCGGAAGTCTGAAGAAACAATTACCCCATGGAAT TTTGAAGAAGTTGTCGATAAAGGTGCTTCAGCTCAATCATTTATTGAACGCATGACAAACTTTGATAAAA ATCTTCCAAATGAAAAAGTACTACCAAAACATAGTTTGCTTTATGAGTATTTTACGGTTTATAACGAATT GACAAAGGTCAAATATGTTACTGAAGGAATGCGAAAACCAGCATTTCTTTCAGGTGAACAGAAGAAAGCC ATTGTTGATTTACTCTTCAAACAAATCGAAAGTAACCGTTAAGCAATTAAAGGAAGATTATTTCAAA AAATAGAATGTTTTGATAGTGTTGAAATTTCAGGAGTTGAAGATAGATTTAATGCTTCATTAGGTACCTA CCATGATTTGCTAAAAATTATTAAAGATAAAGATTTTTTGGATAATGAAGAAAATGAAGATATCTTAGAG GATATTGTTTTAACATTGACCTTATTTGAAGATAGGGAGATGATTGAGGAAGACTTAAACATATGCTC ACCTCTTTGATGATAAGGTGATGAAACAGCTTAAACGTCGCCGTTATACTGGTTGGGGACGTTTGTCTCG AAAATTGATTAATGGTATTAGGGATAAGCAATCTGGCAAAACAATATTAGATTTTTTGAAATCAGATGGT TTTGCCAATCGCAATTTTATGCAGCTGATCCATGATGATAGTTTGACATTTAAAGAAGACATTCAAAAAG | 110 |

TABLE 5-continued

CRISPR related proteins

| Description | Sequence | SEQ ID NO |
|---|---|---|
| | CACAAGTGTCTGGACAAGGCGATAGTTTACATGAACATATTGCAAATTTAGCTGGTAGCCCTGCTATTAA<br>AAAAGGTATTTTACAGACTGTAAAAGTTGTTGATGAATTGGTCAAAGTAATGGGGCGGCATAAGCCAGAA<br>AATATCGTTATTGAAATGGCACGTGAAAATCAGACAACTCAAAAGGGCCAGAAAAATTCGCGAGAGCGTA<br>TGAAACGAATCGAAGAAGGTATCAAAGAATTAGGAAGTCAGATTCTTAAAGAGCATCCTGTTGAAAATAC<br>TCAATTGCAAAATGAAAAGCTCTATCTCTATTATCTCCAAAATGGAAGAGACATGTATGTGGACCAAGAA<br>TTAGATATTAATCGTTTAAGTGATTATGATGTCGATGCCATTGTTCCACAAAGTTTCCTTAAAGACGATT<br>CAATAGACAATAAGGTCTTAACGCGTTCTGATAAAAATCGTGGTAAATCGGATAACGTTCCAAGTGAAGA<br>AGTAGTCAAAAAGATGAAAAACTATTGGAGACAACTTCTAAACGCCAAGTTAATCACTCAACGTAAGTTT<br>GATAATTTAACGAAAGCTGAACGTGGAGGTTTGAGTGAACTTGATAAAGCTGGTTTTATCAAACGCCAAT<br>TGGTTGAAACTCGCCAAATCACTAAGCATGTGGCACAAATTTTGGATAGTCGCATGAATACTAAATACGA<br>TGAAAATGATAAACTTATTCGAGAGGTTAAAGTGATTACCTTAAAATCTAAATTAGTTTCTGACTTCCGA<br>AAAGATTTCCAATTCTATAAAGTACGTGAGATTAACAATTACCATCATGCCCATGATGCGTATCTAAATG<br>CCGTCGTTGGAACTGCTTTGATTAAGAAATATCCAAAACTTGAATCGGAGTTTGTCTATGGTGATTATAA<br>AGTTTATGATGTTCGTAAAATGATTGCTAAGTCTGAGCAAGAAATAGGCAAAGCAACCGCAAAATATTTC<br>TTTTACTCTAATATCATGAACTTCTTCAAAACAGAAATTACACTTGCAAATGGAGAGATTCGCAAACGCC<br>CTCTAATCGAAACTAATGGGGAAACTGGAGAAATTGTCTGGGATAAAGGGCGAGATTTTGCCACAGTGCG<br>CAAAGTATTGTCCATGCCCCAAGTCAATATTGTCAAGAAAACAGAAGTACAGACAGGCGGATTCTCCAAG<br>GAGTCAATTTTACCAAAAAGAAATTCGGACAAGCTTATTGCTCGTAAAAAAGACTGGGATCCAAAAAAAT<br>ATGGTGGTTTTGATAGTCCAACGGTAGCTTATTCAGTCCTAGTGGTTGCTAAGGTGGAAAAAGGGAAATC<br>GAAGAAGTTAAAATCCGTTAAAGAGTTACTAGGGATCACAATTATGGAAAGAAGTTCCTTTGAAAAAAAT<br>CCGATTGACTTTTTAGAAGCTAAAGGATATAAGGAAGTTAAAAAAGACTTAATCATTAAACTACCTAAAT<br>ATAGTCTTTTTGAGTTAGAAAACGGTCGTAAACGGATGCTGGCTAGTGCCGGAGAATTACAAAAAGGAAA<br>TGAGCTGGCTCTGCCAAGCAAATATGTGAATTTTTTATATTTAGCTAGTCATTATGAAAAGTTGAAGGGT<br>AGTCCAGAAGATAACGAACAAAAACAATTGTTTGTGGAGCAGCATAAGCATTATTTAGATGAGATTATTG<br>AGCAAATCAGTGAATTTTCTAAGCGTGTTATTTTAGCAGATGCCAATTTAGATAAAGTTCTTAGTGCATA<br>TAACAAACATAGAGACAAACCAATACGTGAACAAGCAGAAAATATTATTCATTTATTTACGTTGACGAAT<br>CTTGGAGCTCCCGCTGCTTTTAAATATTTTGATACAACAATTGATCGTAAACGATATACGTCTACAAAAG<br>AAGTTTTAGATGCCACTCTTATCCATCAATCCATCACTGGTCTTTATGAAACACGCATTGATTTGAGTCA<br>GCTAGGAGGTGACTAACtcgagtaaggatctccaggcatcaaataaaacgaaaggctcagtcgaaagact<br>gggcctttcgttttatctgttgtttgtcggtgaacgctctctactagagtcacactggctcaccttcggg<br>tgggcctttctgcgtttatacctagggatatattccgcttcctcgctcactgactcgctacgctcggtcg<br>ttcgactgcggcgagcggaaatggcttacgaacggggcggagatttcctggaagatgccaggaagatact<br>taacagggaagtgagagggccgcggcaaagccgtttttccataggctccgcccccctgacaagcatcacg<br>aaatctgacgctcaaatcagtggtggcgaaacccgacaggactataaagataccaggcgtttccccctgg<br>cggctccctcgtgcgctctcctgttcctgcctttcggtttaccggtgtcattccgctgttatggccgcgt<br>ttgtctcattccacgcctgacactcagttccgggtaggcagttcgctccaagctggactgtatgcacgaa<br>ccccccgttcagtccgaccgctgcgccttatccggtaactatcgtcttgagtccaacccggaaagacatg<br>caaaagcaccactggcagcagccactggtaattgatttagaggagttagtcttgaagtcatgcgccggtt<br>aaggctaaactgaaaggacaagttttggtgactgcgctcctccaagccagttacctcggttcaaagagtt<br>ggtagctcagagaaccttcgaaaaaccgccctgcaaggcggttttttcgttttcagagcaagagattacg<br>cgcagaccaaaacgatctcaagaagatcatcttattaatcagataaaatattctagatttcagtgcaat<br>ttatctcttcaaatgtagcacctgaagtcagcccatacgatataagttgttactagtgcttggattctc<br>accaataaaaaacgcccggcggcaaccgagcgttctgaacaaatccagatggagttctgaggtcattact<br>ggatctatcaacaggagtccaagcgagctcgatatcaaattacgccccgccctgccactcatcgcagtac<br>tgttgtaattcattaagcattctgccgacatggaagccatcacaaacggcatgatgaacctgaatcgcca<br>gcggcatcagcaccttgtcgccttgcgtataatatttgcccatggtgaaaacggggggcgaagaagttgtc<br>catattggccacgtttaaatcaaaactggtgaaactcacccagggattggctgagacgaaaaacatattc<br>tcaataaaccctttagggaaataggccaggttttcaccgtaacacgccacatcttgcgaatatatgtgta<br>gaaactgccggaaatcgtcgtggtattcactccagagcgatgaaaacgtttcagtttgctcatgggaaaac<br>ggtgtaacaagggtgaacactatcccatatcaccagctcaccgtctttcattgccatacgaaattccgga<br>tgagcattcatcaggcgggcaagaatgtgaataaaggccggataaaacttgtgcttattttttctttacgg<br>tctttaaaaaggccgtaatatccagctgaacggtctggttataggtacattgagcaactgactgaaatgc<br>ctcaaaatgttctttacgatgccattgggatatatcaacggtggtatatccagtgatttttttctccatt<br>ttagcttccttagctcctgaaaatctcgataactcaaaaaatacgcccggtagtgatcttatttcattat<br>ggtgaaagttggaacctcttacgtgccgatcaacgtctcattttcgccagatatc" | |
| Cas9<br>">Cas<br>9 Gene | gccaccATGGACAAGAAGTACTCCATTGGGCTCGATATCGGCACAAACAGCGTCGGCTGGGCCGTCATTA<br>CGGACGAGTACAAGGTGCCGAGCAAAAAATTCAAAGTTCTGGGCAATACCGATCGCCACAGCATAAAGAA<br>GAACCTCATTGGCGCCCTCCTGTTCGACTCCGGGGAGACGGCCGAAGCCACGCGGCTCAAAAGAACAGCA<br>CGGCGCAGATATACCCGCAGAAAGAATCGGATCTGCTACCTGCAGGAGATCTTTAGTAATGAGATGGCTA<br>AGGTGGATGACTCTTTCTTCCATAGGCTGGAGGAGTCCTTTTTGGTGGAGGAGGATAAAAAGCACGAGCG<br>CCACCCAATCTTTGGCAATATCGTGGACGAGGTGGCGTACCATGAAAAGTACCCAACCATATATCATCTG<br>AGGAAGAAGCTTGTAGACAGTACTGATAAGGCTGACTTGCGGTTGATCTATCTCGCGCTGGCGCATATGA<br>TCAAATTTCGGGGACACTTCCTCATCGAGGGGGACCTGAACCCAGACAACAGCGATGTCGACAAACTCTT<br>TATCCAACTGGTTCAGACTTACAATCAGCTTTTCGAAGAGAACCCGATCAACGCATCGGGAGTTGACGCC<br>AAAGCAATCCTGAGCGCTAGGCTGTCCAAATCCCGGCGGCTCGAAAACCTCATCGCACAGCTCCCTGGGG<br>AGAAGAAGAACGGCCTGTTTGGTAATCTTATCGCCCTGTCACTCGGGCTGACCCCCAACTTTAAATCTAA<br>CTTCGACCTGGCCGAAGATGCCAAGCTTCAACTGAGCAAAGACACCTACGATGATGATCTCGACAATCTG<br>CTGGCCCAGATCGGCGACCAGTACGCAGACCTTTTTTTGGCGGCAAAGAACCTGTCAGACGCCATTCTGC<br>TGAGTGATATTCTGCGAGTGAACACGGAGATCACCAAAGCTCCGCTGAGCGCTAGTATGATCAAGCGCTA<br>TGATGAGCACCACCAAGACTTGACTTTGCTGAAGGCCCTTGTCAGACAGCAACTGCCTGAGAAGTACAAG<br>GAAATTTTCTTCGATCAGTCTAAAAATGGCTACGCCGGATACATTGACGGCGGAGCAAGCCAGGAGGAAT<br>TTTACAAATTTATTAAGCCCATCTTGGAAAAAATGGACGGCACCGAGGAGCTGCTGGTAAAGCTTAACAG<br>AGAAGATCTGTTGCGCAAACAGCGCACTTTCGACAATGGAAGCATCCCCCACCAGATTCACCTGGGCGAA | 111 |

TABLE 5-continued

CRISPR related proteins

| Description | Sequence | SEQ ID NO |
|---|---|---|
| | CTGCACGCTATCCTCAGGCGGCAAGAGGATTTCTACCCCTTTTTGAAAGATAACAGGGAAAAGATTGAGA<br>AAATCCTCACATTTCGGATACCCTACTATGTAGGCCCCCTCGCCCGGGGAAATTCCAGATTCGCGTGGAT<br>GACTCGCAAATCAGAAGAGACCATCACTCCCTGGAACTTCGAGGAAGTCGTGGATAAGGGGGCCTCTGCC<br>CAGTCCTTCATCGAAAGGATGACTAACTTTGATAAAAATCTGCCTAACGAAAAGGTGCTTCCTAAACACT<br>CTCTGCTGTACGAGTACTTCACAGTTTATAACGAGCTCACCAAGGTCAAATACGTCACAGAAGGGATGAG<br>AAAGCCAGCATTCCTGTCTGGAGAGCAGAAGAAAGCTATCGTGGACCTCCTCTTCAAGACGAACCGGAAA<br>GTTACCGTGAAACAGCTCAAAGAAGACTATTTCAAAAAGATTGAATGTTTCGACTCTGTTGAAATCAGCG<br>GAGTGGAGGATCGCTTCAACGCATCCCTGGGAACGTATCACGATCTCCTGAAAATCATTAAAGACAAGGA<br>CTTCCTGGACAATGAGGAGAACGAGGACATTCTTGAGGCATTGTCCTCACCCTTACGTTGTTTGAAGAT<br>AGGGAGATGATTGAAGAACGCTTGAAAACTTACGCTCATCTCTTCGACGACAAAGTCATGAAACAGCTCA<br>AGAGGCGCCGATATACAGGATGGGGGCGGCTGTCAAGAAAACTGATCAATGGGATCCGAGACAAGCAGAG<br>TGGAAAGACAATCCTGGATTTTCTTAAGTCCGATGGATTTGCCAACCGGAACTTCATGCAGTTGATCCAT<br>GATGACTCTCTCACCTTTAAGGAGGACATCCAGAAAGCACAGTTTCTGGCCAGGGGGACAGTCTTCACG<br>AGCACATCGCTAATCTTGCAGGTAGCCCAGCTATCAAAAAGGGAATACTGCAGACCGTTAAGGTCGTGGA<br>TGAACTCGTCAAAGTAATGGGAAGGCATAAGCCCGAGAATATCGTTATCGAGATGGCCCGAGAGAACCAA<br>ACTACCCAGAAGGGACAGAAGAACAGTAGGGAAAGGATGAAGAGGATTGAAGAGGGTATAAAAGAACTGG<br>GGTCCCAAATCCTTAAGGAACACCCAGTTGAAAACACCCAGCTTCAGAATGAGAAGCTCTACCTGTACTA<br>CCTGCAGAACGGCAGGGACATGTACGTGGATCAGGAACTGGACATCAATCGGCTCTCCGACTACGACGTG<br>GATCATATCGTGCCCCAGTCTTTTCTCAAAGATGATTCTATTGATAATAAAGTGTTGACAAGATCCGATA<br>AAAATAGAGGGAAGAGTGATAACGTCCCCTCAGAAGAAGTTGTCAAGAAAATGAAAAATTATTGGCGGCA<br>GCTGCTGAACGCCAAACTGATCACACAACGGAAGTTCGATAATCTGACTAAGGCTGAACGAGGTGGCCTG<br>TCTGAGTTGGATAAAGCCGGCTTCATCAAAAGGCAGCTTGTTGAGACACGCCAGATCACCAAGCACGTGG<br>CCCAAATTCTCGATTCACGCATGAACACCAAGTACGATGAAAATGACAAACTGATTCGAGAGGTGAAAGT<br>TATTACTCTGAAGTCTAAGCTGGTCTCAGATTTCAGAAAGGACTTTCAGTTTTATAAGGTGAGAGAGATC<br>AACAATTACCACCATGCGCATGATGCCTACCTGAATGCAGTGGTAGGCACTGCACTTATCAAAAAATATC<br>CCAAGCTTGAATCTGAATTTGTTTACGGAGACTATAAAGTGTACGATGTTAGGAAAATGATCGCAAAGTC<br>TGAGCAGGAAATAGGCAAGGCCACCGCTAAGTACTTCTTTTACAGCAATATTATGAATTTTTTCAAGACC<br>GAGATTACACTGGCCAATGGAGAGATTCGGAAGCGACCACTTATCGAAACAAACGGAGAAACAGGAGAAA<br>TCGTGTGGGACAAGGGTAGGGATTTCGCGACAGTCCGGAAGGTCCTGTCCATGCCGCAGGTGAACATCGT<br>TAAAAAGACCGAAGTACAGACCGGAGGCTTCTCCAAGGAAAGTATCCTCCCGAAAAGGAACAGCGACAAG<br>CTGATCGCACGCAAAAAAGATTGGGACCCCAAGAAATACGGCGGATTCGATTCTCCTACAGTCGCTTACA<br>GTGTACTGGTTGTGGCCAAAGTGGAGAAAGGGAAGTCTAAAAAACTCAAAAGCGTCAAGGAACTGCTGGG<br>CATCACAATCATGGAGCGATCAAGCTTCGAAAAAAACCCCATCGACTTTCTCGAGGCGAAAGGATATAAA<br>GAGGTCAAAAAGACCTCATCATTAAGCTTCCCAAGTACTCTCTCTTTGAGCTTGAAAACGGCCGGAAAC<br>GAATGCTCGCTAGTGCGGGCGAGCTGCAGAAAGGTAACGAGCTGGCACTGCCCTCTAAATACGTTAATTT<br>CTTGTATCTGGCCAGCCACTATGAAAAGCTCAAAGGGTCTCCCGAAGATAATGAGCAGAAGCAGCTGTTC<br>GTGGAACAACACAAACACTACCTTGATGAGATCATCGAGCAAATAAGCGAATTCTCCAAAAGAGTGATCC<br>TCGCCGACGCTAACCTCGATAAGGTGCTTTCTGCTTACAATAAGCACAGGGATAAGCCCATCAGGGAGCA<br>GGCAGAAAACATTATCCACTTGTTTACTCTGACCAACTTGGGCGCGCCTGCAGCCTTCAAGTACTTCGAC<br>ACCACCATAGACAGAAAGCGGTACACCTCTACAAAGGAGGTCCTGGACGCCACACTGATTCATCAGTCAA<br>TTACGGGGCTCTATGAAACAAGAATCGACCTCTCTCAGCTCGGTGGAGACAGCAGGGCTGACCCCAAGAA<br>GAAGAGGAAGGTGTGA | |
| Human codon<br>optimized<br>Cas9 Human<br>">Cas<br>9 ORF | atgggacctaagaaaaagaggaaggtgcctaagaaaaagaggaaggtgcctaagaaaaagaggaaggtgg<br>cggccgctgactacaaggatgacgacgataaatctagagacaagaaatactctattggactggatatcgg<br>gacaaactccgttggctgggccgtcataaccgacgagtataaggtgccaagcaagaaattcaaggtgctg<br>ggtaatactgaccgccattcaatcaagaagaacctgatcggagcactcctcttcgactccggtgaaaccg<br>ctgaagctactcggctgaagcggaccgcaaggcggagatacaccccgcaagaatcggatatgttatct<br>gcaagagatcttagcaacgaaatggctaaggtggacgactccttctttcaccgcctggaagagagctt<br>ctggtggaggaggataagaaacacgagaggcaccctatattcggaaatatcgtggatgaggtggcttacc<br>atgaaaagtatcctacaatctaccatctgaggaagaagctggtggacagcaccgataaagcagacctgag<br>gctcatctatctggccctggctcatatgataaagtttagaggacactttctgatcgagggcgacctgaat<br>cccgataattccgatgtggataaaactcttcattcaactgtgacataggaccaacctgttcgaggaga<br>atcccataaacgcttctggtgtggatgccaaggctattctgtccgctcggctgtccaagtcacgcagact<br>ggagaatctgattgcccaactgccaggagaaaagaagaacggcctgtttgggaacctcatcgccctgagc<br>ctgggcctgacacctaacttcaagtccaattttgatctggccgaagatgctaaactccagctctccaagg<br>acacctatgacgatgatctggaaaacctgctcgcacagataggcgaccagtacgccgatctcttttctggc<br>tgctaagaatctctccgacgccattctgctgagcgacatactccgggtcaacactgagatcaccaaagca<br>cctctgagcgcctccatgataaaacgctatgatgaacaccatcaagacctgactctgctcaaagccctcg<br>tgaggcaacagctgccagagaagtacaaagagatattcttcgaccagagcaagaatggatatgccggata<br>catcgatggcggagcatcacaggaagaattttacaagttcaatcctcgagaagatgaacgat<br>actgaagagctgctggtgaagctgaacagggaggacctgctgaggaagcagaggaccttgataatggct<br>ccattccacatcagatacacctgggagagctgcatgcaatcctccgcaggcaggaggattctatcctttt<br>cctgaaggataaccgggagaagatagagaagatcctgaccttcaggatcccttattacgtcggccctctg<br>gctagaggcaactcccgcttcgcttggatgaccaggaaatctgaggagacaattactccttggaacttcg<br>aagaggtcgtggataagggcgcaagcgcccagtcattcatcgaacggatgaccaatttcgataagaacct<br>gcccaacgagaaggtcctgcccaaacattcactcctgtacgagtattccaccgtctataacgagctgact<br>aaagtgaagtacgtgaccgagggcatgaggaagcctgccttcctgtccggagagcagaagaaggctatcg<br>ttgatctgctcttcaagactaataaagtggacagtgaagcagccaaggagtattactttaagaagat<br>cgaatgctttgactcagtggaaatctctggcgtggaggaccgctttaatgccagcctgggcacttaccat<br>gatctgctgaagataatcaaagacaaagatttcctcgataatgaggagaacgaggacatcctggaagata<br>tcgtgctgaccctgactctgttcgaggatagagagatgatcgaagagcgcctgaagacctatgcccatct<br>gtttgacgataaagtcatgaaacagctcaagcggcggcgctacactggtggggtagactctccaggaaa<br>ctcataaacggcatccgcgacaaacagagcggaaagaccatcctggatttcctgaaatccgacggattcg | 112 |

TABLE 5-continued

CRISPR related proteins

| Description | Sequence | SEQ ID NO |
|---|---|---|
| | ctaacaggaacttcatgcaactgattcacgatgactctctgacatttaaagaggacatccagaaggcaca<br>ggtgagcggtcaaggcgacagcctgcacgagcacatcgccaacctcgctggatcacccgccataaagaag<br>ggaatactgcagacagtcaaggtcgtggacgaactcgtcaaagtgatgggtcggcacaagccagagaata<br>tcgttatcgaaatggcaagggagaaccaaaccacccagaagggccagaagaactctcgggaacggatgaa<br>aagaatcgaagaggaattaaggagctgggatctcagatactgaaggagcaccctgtggagaatacacag<br>ctccagaacgagaaactctacctgtactacctccagaacgggcgggacatgtacgttgaccaggaactcg<br>acatcaaccggctgtccgattatgacgtggaccatattgttccacagtccttcctcaaagatgactccat<br>tgacaacaaggtgctgaccagatccgataagaatcgcggtaagtctgacaatgttccatcagaagaggtg<br>gtcaagaagatgaagaattactggcggcagctcctcaacgccaaactgatcacccagcggaagtttgaca<br>atctgactaaggcagaaagaggaggtctgagcgaactcgacaaggccggctttattaagaggcaactggt<br>cgaaacacgccagattaccaaacacgtggcacaaatcctcgactctaggatgaacactaagtacgatgag<br>aacgataagctgatcagggaagtgaaagtgataactctgaagagcaagctggtgtctgacttccggaagg<br>actttcaattctacaaagttcgcgaaataaacaattaccatcatgctcacgatgcctatctcaatgctgt<br>cgttggcaccgcctgatcaagaaatacctaaactggagtctgagttcgtgtacggtgactataaagtc<br>tacgatgtgaggaagatgatagcaaagtctgagcaagagattggcaaagccaccgccaagtacttcttct<br>actctaatatcatgaatttctttaagactgagataaaccctggctaacggcgaaatccggaagcgcccact<br>gatcgaaacaaacgagaaacaggagaaatcgtgtgggataaaggcagggacttcgcaactgtgcggaag<br>gtgctgtccatgccacaagtcaatatcgtgaagaagaccgaagtgcagaccggcggattctcaaaggaga<br>gcatcctgccaaagcggaactctgacaagctgatcgccaggaagaaagattgggacccaaagaagtatgg<br>cggttttcgattcccctacagtggcttattccgttctggtcgtggcaaaagtggagaaaggcaagtccaag<br>aaactcaagtctgttaaggagctgctcggaattactattatggagagatccagcttcgagaagaatccaa<br>tcgatttcctggaagctaagggctataaagaagtgaagaaagatctcatcatcaaactgcccaagtactc<br>tctctttgagctggagaatggtaggaagcggatgctggcctccgccggagagctgcagaaaggaaacgag<br>ctggctctgccctccaaatacgtgaacttcctgtatctggcctcccactacgagaaactcaaaggtagcc<br>ctgaagacaatgagcagaagcaactcttgttgagccaacataaacactacctggacgaaatcattgaaca<br>gattagcgagttcagcaagcgggttattctggccgatgcaaacctcgataaagtgctgagcgcatataat<br>aagcacagggacaagccaattcgcgaacaagcagagaatattatccacctctttactctgactaatctgg<br>gcgctcctgctgccttcaagtatttcgatacaactattgacaggaagcggtacacctctaccaaagaagt<br>tctcgatgccaccctgatacaccagtcaattaccggactgtacgagactcgcatcgacctgtctcagctc<br>ggcggcgactag" | |

TABLE 6

5'UTR

| Description | Sequence | SEQ ID NO. |
|---|---|---|
| Synthetic polynucleotide 5'UTR | TCAAGCTTTTGGACCCTCGTACAGAAGCTAATACGACTCACTATAGG-<br>GAAATAAGAGAGAAAAGAAGAGTAAGAAGAAATATAA<br>GAGCCACC | 71 |
| sgRNA 5' UTR | TCAAGCTTTTGGACCCTCGTACAGAAGCTAATACGACTCACTATAGGG | 72 |
| 5UTR-001;<br>Synthetic UTR | GGGAAATAAGAGAGAAAAGAAGAGTAAGAAGAAATATAAGAGCCACC | 15 |
| 5UTR-002;<br>Upstream UTR | GGGAGATCAGAGAGAAAAGAAGAGTAAGAAGAAATATAAGAGCCACC | 16 |
| 5UTR-003;<br>Upstream UTR | GGAATAAAAGTCTCAACACAACATATACAAAACAAACGAATCTCAAGCAATCAAGCATTC-<br>TACTTCTATTGCAGCAATTTAAAT<br>CATTTCTTTTAAAGCAAAAGCAATTTTCTGAAAATTTTCACCATTTACGAACGATAGCAAC | 17 |
| 5UTR-004;<br>Upstream UTR | GGGAGACAAGCUUGGCAUUCCGGUACUGUUGGUAAAGCCACC | 18 |

TABLE 7

3'UTR

| Description | Sequence | SEQ ID NO. |
|---|---|---|
| Ex. 9 3' UTR | TGATAATAGgctg agcctcggtggccatgctt cttgccccctt gggcctcccc ccagcccctc ctccccttcc<br>tgcacccgtaccccgtggt ctttgaataa agtctgagtg gcgggc TCTAGA | 81 |

TABLE 7-continued

3'UTR

| Description | Sequence | SEQ ID NO. |
|---|---|---|
| miR122 3' UTR | TGATAATAGGCTGGAGCCTCGGTGGC-<br>CATGCTTCTTGCCCCTTGGGCCTCCCCCAGCCCCTCCTCCCCTTCCTGCACCCGTACCC<br>CCCAAACACCATTGTCACACTCCAGTGGTCTTTGAATAAAGTCTGAGTGGGCGGCTCTAGA | 82 |
| 3UTR-001;<br>Creatine<br>Kinase | GCGCCTGCCCACCTGCCACCGACTGCTGGAACCCAGCCAGTGGGAGGGCCTGGCC-<br>CACCAGAGTCCTGCTCCCTCACTCCTCGCCC<br>CGCCCCCTGTCCCAGAGTCCCACCTGGGGGCTCTCTCCACCCTTCTCAGAGTTCCAGTTT-<br>CAACCAGAGTTCCAACCAATGGGCTC<br>CATCCTCTGGATTCTGGCCAAT-<br>GAAATATCTCCCTGGCAGGGTCCTCTTCTTTTCCCAGAGCTCCACCCCAACCAGGAGCTCTAGT<br>TAATGGAGAGCTCCCAGCACACTCGGAGCTTGTGCTTTGTCTCCACGCAAAGCGA-<br>TAAATAAAAGCATTGGTGGCCTTTGGTCTTT<br>GAATAAAGCCTGAGTAGGAAGTCTAGA | 19 |
| 3UTR-002;<br>Myoglobin | GCCCCTGCCGCTCCCACCCCCACCCATCTGGGCCCCGGGTTCAAGAGAGAGCGGGGTCT-<br>GATCTCGTGTAGCCATATAGAGTTTGC<br>TTCTGAGTGTCTGCTTTGTTTAGTAGAGGTGGGCAGGAGGAGCT-<br>GAGGGGCTGGGCTGGGGTGTTGAAGTTGGCTTTGCATGCCC<br>AGCGATGCGCCTCCCTGTGGGATGTCATCACCCTGGGAACCGGGAGTGGCCCTTGGCT-<br>CACTGTGTTCTGCATGGTTTGGATCTGA<br>ATTAATTGTCCTTTCTTCTAAATCCCAACCGAACTTCTTCCAACCTC-<br>CAAACTGGCTGTAACCCCAAATCCAAGCCATTAACTACA<br>CCTGACAGTAGCAATTGTCTGATTAATCACTGGCCCCTTGAA-<br>GACAGCAGAATGTCCCTTTGCAATGAGGAGGAGATCTGGGCTGG<br>GCGGGCCAGCTGGGGAAGCATTTGACTATCTG-<br>GAACTTGTGTGTGCCTCCTCAGGTATGGCAGTGACTCACCTGGTTTTAATAAA<br>CAACCTGCAACATCTCATGGTCTTTGAATAAAGCCTGAGTAGGAAGTCTAGA | 20 |
| 3UTR-003; α-<br>actin | ACACACTCCACCTCCAGCACGCGACTTCTCAGGACGACGAATCTTCT-<br>CAATGGGGGGGCGGCTGAGCTCCAGCCACCCCGCAGTCA<br>CTTTCTTTGTAACAACTTCCGTTGCTGCCATCGTAAACTGACACAGTGTT-<br>TATAACGTGTACATACATTAACTTATTACCTCATTT<br>TGTTATTTTTCGAAACAAAGCCCTGTGGAAGAAAATGGAAAACTTGAAGAAGCAT-<br>TAAAGTCATTCTGTTAAGCTGCGTAAATGGT<br>CTTTGAATAAAGCCTGAGTAGGAAGTCTAGA | 21 |
| 3UTR-004;<br>Albumin | CATCACATTTAAAAGCATCTCAGCCTACCATGAGAATAAGAGAAAGAAAATGAAGAT-<br>CAAAAGCTTATTCATCTGTTTTTCTTTTT<br>CGTTGGTGTAAAGCCAACACCCTGTCTAAAAAACATAAATTTCTTTAATCAT-<br>TTTGCCTCTTTTCTCTGTGCTTCAATTAATAAAA<br>AATGGAAAGAATCTAATAGAGTGGTACAGCACTGTTATTTTTCAAAGATGTGTTGC-<br>TATCCTGAAAATTCTGTAGGTTCTGTGGAA<br>GTTCCAGTGTTCTCTCTTATTCCACTTCGGTAGAGGATTTCTAGTTTCTTGTGGGCTAAT-<br>TAAATAAATCATTAATACTCTTCTAA<br>TGGTCTTTGAATAAAGCCTGAGTAGGAAGTCTAGA | 22 |
| 3UTR-005; α-<br>globin | GCTGCCTTCTGCGGGGCTTGCCTTCTGGC-<br>CATGCCCTTCTTCTCTCCCTTGCACCTGTACCTCTTGGTCTTTGAATAAAGCCTGAG<br>TAGGAAGGCGGCCGCTCGAGCATGCATCTAGA | 23 |
| 3UTR-006; G-<br>CSF | GCCAAGCCCTCCCCATCCCATGTATTTATCTCTATTTAATATTTATGTCTATTTAAGCCT-<br>CATATTTAAAGACAGGGAAGAGCAGA<br>ACGGAGCCCCAGGCCTCTGTGTCCTTCCCTGCATTTCTGAGTTTCAT-<br>TCTCCTGCCTGTAGCAGTGAGAAAAAGCTCCTGTCCTCC<br>CATCCCCTGGACTGGGAGGTAGATAGGTAAATACCAAGTATTTTATTAC-<br>TATGACTGCTCCCCAGCCCTGGCTCTGCAATGGGCACT<br>GGGATGAGCCGCTGTGAGCCCCTGGTCCTGAGGGTCCCCACCTGGGACCCTT-<br>GAGAGTATCAGGTCTCCCACGTGGGAGACAAGAA<br>ATCCCTGTTTAATATTTAAACAGCAGTGTTCCCCATCTGGGTCCTTGCACCCCT-<br>CACTCTGGCCTCAGCCGACTGCACAGCGGCCC<br>CTGCATCCCCTTGGCTGTGAGGCCCCTGGACAAGCAGAGGTGGCCAGAGCTGGGAGG-<br>CATGGCCCTGGGGTCCCACGAATTTGCTG<br>GGGAATCTCGTTTTTCTTCTTAAGACTTTTGGGACATGGTTTGACTCCCGAACAT-<br>CACCGACGCGTCTCCTGTTTTTCTGGGTGGC<br>CTCGGGACACCTGCCCTGCCCCCACGAGGGTCAGGACTGTGACTCTTTT-<br>TAGGGCCAGGCAGGTGCCTGGACATTTGCCTTGCTGG<br>ACGGGGACTGGGGATGTGGGAGGGAGCAGACAGGAGGAATCATGTCAGGCCTGTGTGT-<br>GAAAGGAAGCTCCACTGTCACCCTCCAC<br>CTCTTCACCCCCCACTCACCAGTGTCCCCTCCACTGTCACATTGTAACTGAACTTCAGGA-<br>TAATAAAGTGTTTGCCTCCATGGTCT<br>TTGAATAAAGCCTGAGTAGGAAGGCGGCCGCTCGAGCATGCATCTAGA | 24 |
| 3UTR-007;<br>Col1a2;<br>collagen, | ACTCAATCTAAATTAAAAAAGAAAGAAATTTGAAAAAACTTTCTCTTTGCCAT-<br>TTCTTCTTCTTCTTTTTTAACTGAAAGCTGAAT<br>CCTTCCATTTCTTCTCTGCACATCTACTTGCTTAAAT-<br>TGTGGGCAAAAGAGAAAAGAAGGATTGATCAGAGCATTGTGCAATACAGT<br>TTCATTAACTCCTTCCCCCGCTCCCCAAAAATTTGAATTTTTTTTCAACACTCTTA-<br>CACCTGTTATGGAAAATGTCAACCTTTG | 25 |

TABLE 7-continued

3'UTR

| Description | Sequence | SEQ ID NO. |
|---|---|---|
| type I, alpha 2 | TAAGAAAACCAAAATAAAAATTGAAAAATAAAAACCATAAACATTTGCAC-<br>CACTTGTGGCTTTTGAATATCTTCCACAGAGGGAAG<br>TTTAAAACCCAAACTTCCAAAGGTTTAAACTACCTCAAAACACTTTCCCATGAGTGT-<br>GATCCACATTGTTAGGTGCTGACCTAGAC<br>AGAGATGAACTGAGGTCCTTGTTTTGTTTTGTTCATAATACAAAGGTGCTAATTAATAGT-<br>ATTTCAGATACTTGAAGAATGTTGAT<br>GGTGCTAGAAGAATTTGAGAAGAAATACTCCTGTATTGAGTTGTATCGTGTGGTGTAT-<br>TTTTTAAAAAATTTGATTTAGCATTCAT<br>ATTTTCCATCTTATTCCCAATTAAAAGTATGCAGATTATTTGCCCAAATCTTCTTCAGAT-<br>TCAGCATTTGTTCTTTGCCAGTCTCA<br>TTTTCATCTTCTTCCATGGTTCCACAGAAGCTTTGTTTCTTGGGCAAGCAGAAAAAT-<br>TAAATTGTACCTATTTTGTATATGTGAGA<br>TGTTTAAATAAATTGTGAAAAAAATGAAATAAAGCATGTTTGGTTTTCCAAAAGAACATAT | |
| 3UTR-008;<br>Col6a2;<br>collagen,<br>type VI,<br>alpha 2 | CGCCGCCGCCCGGGCCCCGCAGTCGAGGGTCGTGAGCCCACCCCGTC-<br>CATGGTGCTAAGCGGGCCCGGGTCCCACACGGCCAGCAC<br>CGCTGCTCACTCGGACGACGCCCTGGGCCTGCACCTCTCCAGCTCCTCC-<br>CACGGGGTCCCCGTAGCCCCGGCCCCCGCCCAGCCCC<br>AGGTCTCCCCAGGCCCTCCGCAGGCTGCCCGGCCTCCCTCCCCCTGCAGCCATCC-<br>CAAGGCTCCTGACCTACCTGGCCCCTGAGCT<br>CTGGAGCAAGCCCTGACCCAATAAAGGCTTTGAACCCAT | 26 |
| 3UTR-009;<br>RPN1;<br>ribophorin I | GGGGCTAGAGCCCTCTCCGCACAGCGTGGAGACGGGGCAAGGAGGGGGGTTATTAGGAT-<br>TGGTGGTTTTGTTTTGCTTTGTTTAAA<br>GCCGTGGGAAAATGGCACAACTTTACCTCTGTGGGAGATGCAACACTGAGAGC-<br>CAAGGGGTGGGAGTTGGGATAATTTTTATATAA<br>AAGAAGTTTTTCCACTTTGAATTGCTAAAAGTGGCATTTTTCCTATGTGCAGT-<br>CACTCCTCTCATTTCTAAAATAGGGACGTGGCC<br>AGGCACGGTGGCTCATGCCTGTAATCCCAGCACTTTGGGAGGCCGAGGCAGGCGGCT-<br>CACGAGGTCAGGAGATCGAGACTATCCTG<br>GCTAACACGGTAAAACCCTGTCTCTACTAAAAGTACAAAAAATT-<br>AGCTGGGCGTGGTGGTGGGCACCTGTAGTCCCAGCTACTCGG<br>GAGGCTGAGGCAGGAGAAAGGCATGAATCCAAGAGGCAGAGCTTGCAGTGAGCTGAGAT-<br>CACGCCATTGCACTCCAGCCTGGGCAA<br>CAGTGTTAAGACTCTGTCT-<br>CAAATATAAATAAATAAATAAATAAATAAATAAATAAAAATAAAGCGAGATGTTGCCCTCAAA | 27 |
| 3UTR-0010;<br>LRP1; low<br>density<br>lipoprotein<br>receptor-<br>related<br>protein 1 | GGCCCTGCCCCGTCGGACTGCCCCCAGAAAGCCTCCTGCCCCCTGCCAGT-<br>GAAGTCCTTCAGTGAGCCCCTCCCCAGCCAGCCCTT<br>CCCTGGCCCCGCCGGATGTATAAATGTAAAAATGAAGGAATTACATTTTATATGT-<br>GAGCGAGCAAGCCGGCAAGCGAGCACAGTAT<br>TATTTCTCCATCCCCTCCCTGCCTGCTCCTTGGCACCCCCATGCTGCCTTCAGGGA-<br>GACAGGCAGGGAGGGCTTGGGGCTGCACCT<br>CCTACCCTCCCACCAGAACGCACCCCACTGG-<br>GAGAGCTGGTGGTGCAGCCTTCCCCTCCCTGTATAAGACACTTTGCCAAGGCTCT<br>CCCCTCTCGCCCCATCCCTGCTTGCCCGCTCCCACAGCTTCCTGAGGGCTAATTCTGG-<br>GAAGGGAGAGTTCTTTGCTGCCCCTGTC<br>TGGAAGACGTGGCTCTGGGTGAGGTAGGCGGGAAAGGATGGAGTGTTTTAGTTCTTGGGG-<br>GAGGGCCACCCCAAACCCCAGCCCCAA<br>CTCCAGGGGCACCTATGAGATGGCCATGCTCAACCCCCCTCCCA-<br>GACAGGCCCTCCCTGTCTCCAGGGCCCCCACCGAGGTTCCCA<br>GGGCTGGAGACTTCCTCTGGTAAACATTCCTCCAGCCTCCCCTCCCCTGGGGACGC-<br>CAAGGAGGTGGGCCACACCCAGGAAGGGAA<br>AGCGGGCAGCCCCGTTTTGGGGACGTGAACGTTTTAATAATTTTTGCTGAATTCCTTTA-<br>CAACTAAATAACACAGATATTGTTATA<br>AATAAAATTGT | 28 |
| 3UTR-011;<br>Nnt1;<br>cardio-<br>trophin-like<br>cytokine<br>factor 1 | ATATTAAGGATCAAGCTGTTAGCTAATAATGCCACCTCTGCAGTTTTGG-<br>GAACAGGCAAATAAAGTATCAGTATACATGGTGATGT<br>ACATCTGTAGCAAAGCTCTTGGAGAAAATGAAGACT-<br>GAAGAAAGCAAAGCAAAACTGTATAGAGAGATTTTTCAAAAGCAGTAAT<br>CCCTCAATTTTAAAAAAGGATTGAAAATTCTAAATGTCTTTCTGTGCATATTTTTGTGT-<br>TAGGAATCAAAAGTATTTTATAAAAG<br>GAGAAAGAACAGCCTCATTTTAGATGTAGTCCTGTTGGATTTTT-<br>TATGCCTCCTCAGTAACCAGAAATGTTTTAAAAAACTAAGTG<br>TTTAGGATTTCAAGACAACATTATACATGGCTCTGAAATATCTGACACAATGTAAACAT-<br>TGCAGGCACCTGCATTTTATGTTTTTT<br>TTTTCAACAAATGTGACTAATTTGAAACTTTTATGAACTTCTGAGCTGTCCCCTTGCAAT-<br>TCAACCGCAGTTTGAATTAATCATAT<br>CAAATCAGTTTTAATTTTTTAAATTGTACTTCAGAGTCTATATTTCAAGGGCACAT-<br>TTTCTCACTACTATTTTAATACATTAAAGG<br>ACTAAATAATCTTTCAGAGATGCTGGAAACAAATCATTTGCTTTATATGTTTCATT-<br>AGAATACCAATGAAACATACAACTTGAAAA<br>TTAGTAATAGTATTTTGAAGATCCCATTTCTAATTGGAGATCTCTTTAATTTCGAT-<br>CAACTTATAATGTGTAGTACTATATTAAG<br>TGCACTTGAGTGGAATTCAACATTTGACTAATAAAATGAGTTCATCATGTTGGCAAGT-<br>GATGTGGCAATTATCTCTGGTGACAAAA | 29 |

TABLE 7-continued

3'UTR

| Description | Sequence | SEQ ID NO. |
|---|---|---|
| | GAGTAAAATCAAATATTTCTGCCTGTTACAAATATCAAGGAAGACCTGCTACTAT-GAAATAGATGACATTAATCTGTCTTCACTGT TTATAATACGGATGGATTTTTTTCAAATCAGTGTGTGTTTTGAGGTCTTATGTAATT-GATGACATTTGAGAGAAATGGTGGCTTT TTTTAGCTACCTCTTTGTTCATTTAAGCACCAGTAAAGATCATGTCTTTT-TATAGAAGTGTAGATTTTCTTTGTGACTTTGCTATC GTGCCTAAAGCTCTAAATATAGGTGAATGTGTGATGAATACTCAGATTATTTGTCTCTC-TATATAATTAGTTTGGTACTAAGTTTC TCAAAAAATTATTAACACATGAAAGACAATCTCTAAACCAGAAAAAGAAGTAGTACAAAT-TTTGTTACTGTAATGCTCGCGTTTAG TGAGTTTAAAACACACAGTATCTTTTGGTTTTATAATCAGTTTCTATTTGCTGTGCCT-GAGATTAAGATCTGTGTATGTGTGTGT GTGTGTGTGCGTTTGTGTGTTAAAGCAGAAAAGACTTTTTTAAAAGTTTTAAGTGA-TAAATGCAATTTGTTAATTGATCTTAGA TCACTAGTAAACTCAGGGCTGAATTATACCATGTATATTCTATTAGAAGAAAGTAAACAC-CATCTTTATTCCTGCCCTTTTTCTTC TCTCAAAGTAGTTGTAGTTATATCTAGAAAGAAGCAATTTTGATTTCTT-GAAAAGGTAGTTCCTGCACTCAGTTTAAACTAAAAAT AATCATACTTGGATTTTATTTATTTTTGTCATAGTAAAAATTTTAATTTATATATATTTT-TATTTAGTATTATCTTATTCTTTGCT ATTTGCCAATCCTTTGTCATCAATTGTGTTAAATGAATTGAAAATTCATGCCCTGTTCAT-TTTATTTTACTTTATTGGTTAGGATA TTTAAAGGATTTTTGTATATATAATTTCTTAAATTAATATTCCAAAAGGTTAGTGGACT-TAGATTATAAATTATGGCAAAAATCTA AAAACAACAAAAATGATTTTTATACATTCTATTTCATTATTCCTCTTTTTCCAATAAGT-CATACAATTGGTAGATATGACTTATTT TATTTTTGTATTATTCACTATATCTTTATGATATTTAAGTATAAATAATTAAAAAAATTT-ATTGTACCTTATAGTCTGTCACCAAA AAAAAAAAATTATCTGTAGGTAGTGAAATGCTAATGTTGATTTGTCTTTAAGGGCTTGT-TAACTATCCTTTATTTTCTCATTTGTC TTAAATTAGGAGTTTGTGTTTAAATTACTCATCTAAGCAAAAAATGTATATAAATCCCAT-TACTGGGTATATACCCAAAGGATTAT AAATCATGCTGCTATAAAGACACATGCACACGTATGTTTATTGCAGCACTATT-CACAATAGCAAAGACTTGGAACCAACCCAAATG TCCATCAATGATAGACTTGATTAAGAAAATGTGCACATATACACCATGGAATAC-TATGCAGCCATAAAAAAGGATGAGTTCATGTC CTTTGTAGGGACATGGATAAAGCTGGAAACCATCATTCTGAGCAAACTAT-TGCAAGGACAGAAAACCAAACACTGCATGTTCTCAC TCATAGGTGGGAATTGAACAATGAGAACACTTGGACACAAGGTGGGGAACAC-CACACACCAGGGCCTGTCATGGGGTGGGGGGAGT GGGGAGGGATAGCATTAGGAGATATACCTAATGTAAATGATGAGT-TAATGGGTGCAGCACACCAACATGGCACATGTATACATATG TAGCAAACCTGCACGTTGTGCACATGTACCCTAGAACTTAAAGTATAAT-TAAAAAAAAAAGAAAACAGAAGCTATTTATAAAGAA GTTATTTGCTGAAATAAATGTGATCTTTCCCATTAAAAAAATAAAGAAAT-TTTGGGGTAAAAAAACACAATATATTGTATTCTTGA AAAATTCTAAGAGAGTGGATGTGAAGTGTTCTCACCACAAAAGTGATAACTAATT-GAGGTAATGCACATATTAATTAGAAAGATTT TGTCATTCCACAATGTATATATACTTAAAAATATGTTATACACAATAAATACATACATTAAAAAAATAAGTAAATGTA | |
| 3UTR-012; Col6a1; collagen, type VI, alpha 1 | CCCACCCTGCACGCCGGCACCAAACCCTGTCCTCCCACCCCTCCCCACTCAT-CACTAAACAGAGTAAAATGTGATGCGAATTTTCC CGACCAACCTGATTCGCTAGATTTTTTTTAAGGAAAAGCTTG-GAAAGCCAGGACACAACGCTGCTGCCTGCTTTGTGCAGGGTCCT CCGGGGCTCAGCCCTGAGTTGGCATCACCTGCGCAGGGCCCTCTGGGGCTCAGCCCT-GAGCTAGTGTCACCTGCACAGGGCCTCT GAGGGCTCAGCCCTGAGCTGGCGTCACCTGTGCAGGGCCCTCTGGGGCTCAGCCCT-GAGCTGGCCTCACCTGGGTTCCCCACCCCGG GCTCTCCTGCCCTGCCCTCCTGCCCGCCCTCCTCCTGCCTGCGCAGCTCCTTCCCTAGGCACCTCTGTGCTGCATCCCACCAGCC TGAGCAAGACGCCCTCTCGGGGCCTGTGCCGCACTAGCCTCCCTCTCCTCTGTCCCCAT-AGCTGGTTTTTCCCACCAATCCTCACC TAACAGTTACTTTACAATTAAACTCAAAGCAAGCTCTTCTCCTCAGCTTGGGGCAGCCAT-TGGCCTCTGTCTCGTTTTGGGAAACC AAGGTCAGGAGGCCGTTGCAGACATAAATCTCGGCGACTCGGCCCCGTCTCCT-GAGGGTCCTGCTGGTGACCGGCCTGGACCTTGG CCCTACAGCCCTG-GAGGCCGCTGCTGACCAGCACTGACCCCGACCTCAGAGAGTACTCGCAGGGGCGCTGGCTGCACTCAAGACCC TCGAGATTAACGGTGCTAACCCCGTCTGCTCCTCCCTCCCGCAGA-GACTGGGGCCTGGACTGGACATGAGAGCCCCTTGGTGCCAC AGAGGGCTGTGTCTTACTAGAAACAACGCAAACCTCTCCTTCCTCAGAATAGT-GATGTGTTCGACGTTTTATCAAAGGCCCCCTTT CTATGTTCATGTTAGTTTTGCTCCTTCTGTGTTTTTTCTGAACCATATC-CATGTTGCTGACTTTTCCAAATAAAGGTTTTCACTC CTCTC | 30 |
| 3UTR-013; Calr; | AGAGGCCTGCCTCCAGGGCTGGACTGAGGCCT-GAGCGCTCCTGCCGCAGAGCTGGCCGCGCCAAATAATGTCTCTGTGAGACTCGA GAACTTTCATTTTTTTCCAGGCTGGTTCGGATTTGGGGTGGAT-TTTGGTTTTGTTCCCCTCCTCCACTCTCCCCCACCCCCTCCCC | 31 |

TABLE 7-continued

3'UTR

| Description | Sequence | SEQ ID NO. |
|---|---|---|
| calreticulin | GCCCTTTTTTTTTTTTTTTTTAAACTGGTATTTTATCTTTGATTCTCCTTCAGCCCT-<br>CACCCCTGGTTCTCATCTTTCTTGATCA<br>ACATCTTTTCTTGCCTCTGTCCCCTTCTCTCATCTCTTAGCTCCCCTC-<br>CAACCTGGGGGGCAGTGGTGTGGAGAAGCCACAGGCCT<br>GAGATTTCATCTGCTCTCCTTCCTGGAGCCCAGAG-<br>GAGGGCAGCAGAAGGGGGTGGTGTCTCCAACCCCCCAGCACTGAGGAAGAA<br>CGGGGCTCTTCTCATTTCACCCCTCCCTTTCTCCCCTGCCCCCAGGACTGGGC-<br>CACTTCTGGGTGGGGCAGTGGGTCCCAGATTGG<br>CTCACACTGAGAATGTAAGAACTACAAACAAAATTTCTATTAAATTAAATTTTGTGTCTCC | |
| 3UTR-014;<br>Col1a1;<br>collagen,<br>type I,<br>alpha 1 | CTCCCTCCATCCCAACCTGGCTCCCTCCCACCCAACCAACTTTCCCCCCAACCCG-<br>GAAACAGACAAGCAACCCAAACTGAACCCCC<br>TCAAAAGCCAAAAAATGGGAGACAATTTCACATGGACTTTGGAAAATAT-<br>TTTTTTCCTTTGCATTCATCTCTCAAACTTAGTTTTT<br>ATCTTTGACCAACCGAACATGACCAAAAACCAAAAGTGCATTCAACCTTAC-<br>CAAAAAAAAAAAAAAAAAAGAATAAATAAATAAC<br>TTTTTAAAAAAGGAAGCTTGGTCCACTTGCTTGAAGACC-<br>CATGCGGGGTAAGTCCCTTTCTGCCCGTTGGGCTTATGAAACCCCA<br>ATGCTGCCCTTTCTGCTCCTTTCTCCACACCCCCCTTGGGGCCTCCCCTCCACTCCTTCC-<br>CAAATCTGTCTCCCCAGAAGACACAG<br>GAAACAATGTATTGTCTGCCCAGCAATCAAAGGCAATGCTCAAACACCCAAGTGGCCCC-<br>CACCCCTCAGCCCGCTCCTGCCCGCCCA<br>GCACCCCAGGCCCTGGGGGACCTGGGGTTCTCAGACTGCCAAAGAAGCCTTGC-<br>CATCTGGCGCTCCCATGGCTCTTGCAACATCT<br>CCCCTTCGTTTTTGAGGGGGTCATGCCGGGGGAGCCACCAGCCCCTCACTGGGTTCGGAG-<br>GAGAGTCAGGAAGGGCACGACAAAG<br>CAGAAACATCGGATTTGGGGAACGCGTGTCAATCCCTTGTGCCGCAGGGCTGGGCGG-<br>GAGAGACTGTTCTGTTCCTTGTGTAACTG<br>TGTTGCTGAAAGACTACCTCGTTCTTGTCTTGATGTGT-<br>CACCGGGGCAACTGCCTGGGGCGGGGATGGGGGCAGGGTGGAAGCGG<br>CTCCCCATTTTATACCAAAGGTGCTACATCTATGTGATGGGTGGGGTGGGGAGGGAAT-<br>CACTGGTGCTATAGAAATTGAGATGCCC<br>CCCCAGGCCAGCAAATGTTCCTTTTTGTTCAAAGTCTATTTTTATTCCTTGATAT-<br>TTTTCTTTTTTTTTTTTTTTTTGTGGATG<br>GGGACTTGTGAATTTTTCTAAAGGTGCTATTTAACATGGGAG-<br>GAGAGCGTGTGCGGCTCCAGCCCAGCCCGCTGCTCACTTTCCAC<br>CCTCTCTCCACCTGCCTCTGGCTTCTCAGGCCTCTGCTCTCCGACCTCTCTCCTCT-<br>GAAACCCTCCTCCACAGCTGCAGCCCATCC<br>TCCCGGCTCCCTCCTAGTCTGTCCTGCGTCCTCTGTCCCCGGGTTTCAGAGACAACTTCC-<br>CAAAGCACAAAGCAGTTTTTCCCCCT<br>AGGGGTGGGAGGAAGCAAAAGACTCTGTACCTATTTTGTATGTGTATAATAATTT-<br>GAGATGTTTTTAATTATTTTGATTGCTGGAA<br>TAAAGCATGTGGAAATGACCCAACATAATCCGCAGTGGCCTCCTAATTTCCTTCTTTG-<br>GAGTTGGGGGAGGGGTAGACATGGGGA<br>AGGGGCTTTGGGGTGATGGGCTTGCCTTCCATTCCTGCCCTTTCCCTCCCCACTAT-<br>TCTCTTCTAGATCCCTCCATAACCCCACTC<br>CCCCTTTCTCTCACCCTTCTTATACCGCAAACCTTTCTACTTCCTCTTTCATTTTCTAT-<br>TCTTGCAATTTCCTTGCACCTTTTCCAA<br>ATCCTCTTCTCCCCTGCAATACCATACAGGCAATC-<br>CACGTGCACAACACACACACACACTCTTCACATCTGGGGTTGTCCAAACCT<br>CATACCCACTCCCCTTCAAGCCCATCCACTCTCCACCCCCTG-<br>GATGCCCTGCACTTGGTGGCGGTGGGATGCTCATGGATACTGGG<br>AGGGTGAGGGGAGTGGAACCCGTGAGGAGGACCTGGGGGCCTCTCCTTGAACTGACAT-<br>GAAGGGTCATCTGGCCTCTGCTCCCTTC<br>TCACCCACGCTGACCTCCTGCCGAAGGAGCAACGCAACAGGAGAGGGTCTGCT-<br>GAGCCTGGCGAGGGTCTGGGAGGGACCAGGAG<br>GAAGGCGTGCTCCCTGCTCGCTGTCCTGGCCCTGGGGGAGTGAGGGAGACAGACACCTGG-<br>GAGAGCTGTGGGAAGGCACTCGCAC<br>CGTGCTCTTGGGAAGGAAGGAGACCTGGCCCTGCTCAC-<br>CACGGACTGGGTGCCTCGACCTCCTGAATCCCCAGAACACAACCCCCC<br>TGGGCTGGGGTGGTCTGGGGAACCATCGTGCCCCCGCCTCCCGCCTACTCCTTTTTAAGCTT | 32 |
| 3UTR-015;<br>Plod1;<br>procollagen-<br>lysine, 2-<br>oxoglutarate<br>5-<br>dioxygenase<br>1 | TTGGCCAGGCCTGACCCTCTTGGACCTTTCTTCTTTGCCGACAAC-<br>CACTGCCCAGCAGCCTCTGGGACCTCGGGGTCCCAGGGAAC<br>CCAGTCCAGCCTCCTGGCTGTTGACTTCCCATTGCTCTTGGAGCCACCAATCAAAGAGAT-<br>TCAAAGAGATTCCTGCAGGCCAGAGG<br>CGGAACACACCTTTATGGCTGGGGCTCTCCGTGGTGTTCTGGACCCAGCCCCTGGA-<br>GACACCATTCACTTTTACTGCTTTGTAGTG<br>ACTCGTGCTCTCCAACCTGTCTTCCTGAAAAACCAAGGCCCCCTTCCCCCACCTCTTC-<br>CATGGGGTGAGACTTGAGCAGAACAGGG<br>GCTTCCCCAAGTTGCCCAGAAAGACTGTCTGGGTGAGAAGC-<br>CATGGCCAGAGCTTCTCCCAGGCACAGGTGTTGCACCAGGGACTT<br>CTGCTTCAAGTTTTGGGGTAAAGACACCTGGATCAGACTCCAAGGGCTGCCCT-<br>GAGTCTGGGACTTCTGCCTCCATGGCTGGTCAT<br>GAGAGCAAACCGTAGTCCCCTGGAGACGACAGCGACTCCAGAGAACCTCTTGGGA-<br>GACAGAAGAGGCATCTGTGCACAGCTCGATCTTC<br>TACTTGCCTGTGGGAGGGGAGTGACAGGTCCACACACCACACTGGGTCACCCTGTCCTG-<br>GATGCCTCTGAAGAGAGGGACAGACC<br>GTCAGAAACTGGAGAGTTTCTATTAAAGGTCATTTAAACCA | 33 |

TABLE 7-continued

3'UTR

| Description | Sequence | SEQ ID NO. |
|---|---|---|
| 3UTR-016; Nucb1; nucleobindin 1 | TCCTCCGGGACCCCAGCCCTCAGGATTCCTGATGCTCCAAGGCGACTGATGGGCGCTG-<br>GATGAAGTGGCACAGTCAGCTTCCCTGG<br>GGGCTGGTGTCATGTTGGGCTCCTGGGGCGGGGGCACGGCCTGGCATTTCACGCAT-<br>TGCTGCCACCCCAGGTCCACCTGTCTCCAC<br>TTTCACAGCCTC-<br>CAAGTCTGTGGCTCTTCCCTTCTGTCCTCCGAGGGGCTTGCCTTCTCTCGTGTCCAGTGAGGTGCTCAGTGATC<br>GGCTTAACTTAGAGAAGCCCGCCCCCTCCCCTTCTCCGTCTGTCC-<br>CAAGAGGGTCTGCTCTGAGCCTGCGTTCCTAGGTGGCTCGG<br>CCTCAGCTGCCTGGGTTGTGGCCGCCCTAGCATCCTGTATGCCCACAGCTACTG-<br>GAATCCCCGCTGCTGCTCCGGGCCAAGCTTCT<br>GGTTGATTAATGAGGGCATGGGGTGGTCCCTCAAGACCTTCCCCTACCTTTTGTG-<br>GAACCAGTGATGCCTCAAAGACAGTGTCCCC<br>TCCACAGCTGGGTGCCAGGGGCAGGGGATCCTCAGTATAGCCGGTGAACCCTGATACCAG-<br>GAGCCTGGGCCTCCCTGAACCCCTGG<br>CTTCCAGCCATCTCATCGCCAGCCTCCTCCTGGACCTCTTGGCCCCAGCCCCTTCCC-<br>CACACAGCCCCAGAAGGGTCCCAGAGCT<br>GACCCCACTCCAGGACCTAGGCCCAGCCCCTCAGCCTCATCTGGAGCCCCTGAA-<br>GACCAGTCCACCCACCTTTCTGGCCTCATCT<br>GACACTGCTCCGCATCCTGCTGTGTGTCCTGTTCCATGTTCCGGTTCCATCCAAATACACTTTCTGGAACAAA | 34 |
| 3UTR-017; α-globin | GCTGGAGCCTCGGTGGC-<br>CATGCTTCTTGCCCCTTGGGCCTCCCCCCAGCCCCTCCTCCCCTTCCTGCACCCGTACCCCCGTGGTCT<br>TTGAATAAAGTCTGAGTGGGCGGC | 35 |

TABLE 8

DNA constructs encoding synthetic polynucleotides (mRNA) coding for CRISPR related proteins

| Description | Sequence | SEQ ID NO: |
|---|---|---|
| DNA sequence coding for mRNA transcript of Cas9 (Mali) | TCAAGCTTTTGGACCCTCGTACAGAAGCTAATACGACTCACTATAGGGAAATAAGAGAGAAAAGAAGAGTAAGAAGAAATATAAGA<br>GCCACCATGGACAAGAAATACAGCATCGGCCTGGATATTGGAACTAACAGCGTTGGATGGGCAGTGATCACCGACGAGTACAAGGT<br>GCCGAGCAAGAAGTTCAAGGTGCTGGGGAACACTGACCGCCATTCAATTAAGAAAAACCTCATTGGAGCACTGCTTTTTGACTCGG<br>GTGAGACTGCCGAAGCTACCAGGCTCAAACGCACCGCACGCAGACGGTACACCCGCCGAAGAATCGCATCTGCTATCTGCAAGAG<br>ATCTTTTCCAACGAGATGGCGAAGGTTGACGACAGCTTTTTCCACCGGCTGGAAGAGAGCTTCCTCGTGGAAGAGGACAAAAAGCA<br>CGAAAGGCATCCAATCTTCGGTAACATCGTGGACGAAGTGGCGTATCACGAAAAGTACCCTCCATCTACCATCTGCGGAAGAAGC<br>TGGTCGATTCCACGGATAAGGCAGACCTGAGACTGATCTACCTGGCTTTGGCCCATATGATCAAATTCCGCGGCCATTTCCTGATC<br>GAGGGGGACCTTAACCCCGGATAACTCGGATGTCGACAAGCTGTTCATCCAGCTGGTCCAAACGTATAACCAACTGTTTGAGGAAAA<br>TCCCATCAACGCTTCGGGGGTGGACGCCAAAGCAATCCTCTCCGCGCGCCTGAGCAAGTCACGGCGGCTCGAAAACCTGATCGCGC<br>AGCTGCCGGGAGAAAAGAAAAATGGACTGTTTGGGAATCTGATCGCGCTGTCGCTCGGCCTGACTCCAAACTTTAAGTCAAATTTC<br>GATTTGGCCGAAGATGCCAAGCTGCAGCTGTCAAAGGACACTTACGACGACGACCTGGACAATCTGCTGGCCCAGATTGGGGACCA<br>ATACGCAGACCTGTTCTTGGCCGCGAAGAACCTGAGCGACGCCATTCTTCTGTCCGATATTCTGAGAGTCAATACCGAAATCACTA<br>AGGCTCCGCTGTCCGCTTCAATGATCAAGCGCTACGATGAACACCACCAGGATCTCACTCTGCTCAAAGCCCTCGTGAGACAACAA<br>TTGCCTGAAAAGTACAAGGAGATCTTCTTCGACCAGAGCAAAAACGGCTACGCAGGCTACATCGATGGAGGAGCGTCACAAGAAGA<br>GTTCTACAAGTTCATCAAGCCAATCTTGGAGAAGATGGACGGTTACTGAGAACTCCTTGTGAAGCTGAATAGGGAGGATTTGCTCA<br>GAAAGCAGCGGACTTTTGACAACGGCTCGATCCCTCATCAGATTCACCTCGGTGAGCTGCATGCCATCCTTCGGCGCCAAGAGGAT<br>TTTTACCCCTTCCTGAAGGATAATCGCGAGAAAATCGAAAAGATCCTGACGTTCAGAATTCCCTACTACGTGGGACCGCTGGCGCG<br>CGGTAACTCGCGGTTTGCATGGATGACTCGCAAGTCAGAGGAAACTATCACTCCTTGGAATTTTGAGGAGGTCGTCGATAAGGGAG<br>CCTCGCCCAGTCATTCATTCATCGAACGCATGACCAACTTCGACAAGAATCTTCCGACAAGAAGGTCCTTCCAAAGCACTCCCTGTTG<br>TACGAATACTTCACCGTGTACAATGAGCTGACCAAAGTTAAGTATGTCACCGAGGGCATGAGAAAGCCGGCCTTCCTCAGCGGCGA<br>ACAAAAGAAGGCCATCGTCGACCTCCTCTTCAAGACCAACCGGAAGGTGACCGTCAAGCAACTCAAGGAGGACTACTTCAAGAAGA<br>TCGAATGCTTTGACTCGGTCGAAATCAGCGGAGTGGAGGACCGGTTTAACGCGTCACTGGGTACCTACCATGATCTCCTGAAAATC<br>ATCAAAGACAAGGACTTCCTGGACAACGAAGAAAACGAGGACATCCTGGAAGATATTGTGTTGACCCTGACGCTGTTCGAGGACCG<br>GGAAATGATCGAGGAAAGGCTTAAGACCTACGCACACCTCTTCGATGACAAAGTGATGAAGCAACTGAAGCGGCGGAGATATACTG<br>GCTGGGGAGGCTCTCCCGGAAGCTCATTAATGGAATCAGACACAAACAGTCGGGTAAAACTATCCTCGACTTCCTCAAGTCGGAT<br>GGGTTCGCCAACCGGAACTTCATGCAGCTGATCCACGATGATTCCTTGACCTTCAAGGAAGATATCCAGAAGGCGCAAGTGAGCGG<br>ACAGGGAGATTCGTTGCACGAACATATCGCTAATCTCGCCGGATCCCCAGCCATCAAGAAAGGAATCTGCAGACCGTGAAGGTGG<br>TGGATGAACTGGTGAAAGTGATGGGGCGCCACAAACCAGAGAACATCGTCATTGAGATGGCCCGCGAGAATCAGACCACTCAGAAG<br>GGACAAAAGAACTCCAGAGAGCGGATGAAACGCATCGAGGAAGGCATCAAAGAGCTTGGTAGCCAAATCCTGAAGGAACACCCGGT<br>CGAGAACACCCAGCTCCAGAACGAAAAGCTTTACCTGTACTACCTCCAAAATGGACGGGACATGTACGTCGACCAGGAATTGGACA<br>TCAACAGGCTCAGCGACTACGATGTGGACCATATTGTGCCACAGGCCTTTCTTAAGGACGACAGCATCGATAACAAAGTGCTCACT<br>AGATCAGACAAAAATCGCGGGAAATCAGACAATGTGCCATCGGAAGAGGTTGTCAAGAAGATGAAAAACTACTGGAGACAGCTGCT<br>CAATGCCAACTTATCACCCAGCGGAAGTTCGACAACCTTACCAAGGCCGAGCGCGGAGGATTGTCCGAACTCGACAAGGCCGGCT<br>TCATCAAAAGGCAGCTGGTGGAAACCCGGCAGATCACTAAACACGTGGCCCAGATCCTCGATTCGCGCATGAACACTAAATACGAT<br>GAGAATGACAAGCTGATTAGGGAAGTCAAGGTCATCACTCTGAAGTCAAACTGGTGTCGGACTTTAGAAAGGATTTCCAGTTCTA<br>CAAAGTCCGCGAGATTAACAACTACCACCACGCTCATGACGCCTACCTGAATGCAGTTGTGGGCACCGCGTTGATCAAGAAGTATC<br>CGAAGCTGGAATCCGAGTTCGTGTACGGAGATTACAAAGTGTACGACGTGCGCAAGATGATCGCCAAGTCGGAACAGGAAATCGGA<br>AAGGCTACTGCAAAGTACTTCTTCTACTCAAACATCATGAACTTCTTCAAAACGGAGATCACGCTCGCGAACGGCGAAATCCGGAA<br>AAGGCCGCTCATTGAAACCAACGGAGAAACCGGGAGATCGTGTGGGACAAGGGAAGGGATTTTGCGACTGTGAGGAAGGTGTTGT<br>CCATGCCGCAAGTCAATATTGTGAAAAAGACGGAAGTGCAAACCGGAGGATTCAGCAAAGAATCCATCCTCCCAAAGCGCAACTCG | 41 |

TABLE 8-continued

DNA constructs encoding synthetic polynucleotides (mRNA) coding for CRISPR related proteins

| Description | Sequence | SEQ ID NO: |
|---|---|---|
| | GACAAACTCATCGCGCGCAAGAAGGATTGGGACCCCAAGAAATACGGTGGCTTTGACAGCCCTACTGTGGCTTACTCCGTCCTCGT CGTGGCTAAAGTGGAAAAGGGTAAATCCAAAAAGCTCAAATCGGTGAAGGAGCTCCTGGGAATCACGATCATGGAGCGGTCGAGCT TCGAAAAGAATCCTATTGATTTCCTGGAGGCGAAGGGCTACAAGGAAGTCAAGAAAGACCTGATCATCAAGCTCCCGAAGTACAGC CTCTTCGAGCTCGAAAACGGCAGAAAGAGGATGCTGGCATCAGCGGGAGAATTGCAGAAGGGAAACGAACTGGCACTGCCGTCCAA GTACGTGAATTTTCTCTATCTGGCTAGCCACTACGAAAAGCTGAAGGGATCGCCCGAGGACAACGAGCAAAAACAACTGTTCGTGG AGCAGCACAAGCACTACCTGGATGAGATCATCGAGCAGATCTCCGAATTCTCGAAACGCGTGATCCTTGCCGATGCCAATCTGGAT AAAGTGTTGTCGGCTTACAACAAGCATCGGGATAAACCGATCCGCGAACAGGCAGAAAACATCATTCATCTGTTCACTTTGACCAA TCTGGGAGCGCCTGCCGCGTTTAAGTACTTCGACACCACTATTGATAGAAAGCGCTACACCTCGACCAAGGAAGTGCTGGACGCTA CCCTGATCCACCAGTCCATCACCGGACTCTACGAAACTCGCATTGACCTGTCCCAGCTTGGAGGAGATTCACGGGCCGATCCAAAG AAAAAGCGCAAGGTCTGATAATAGGCTGGAGCCTCGGTGGCCATGCTTCTTGCCCCTTGGGCCTCCCCCAGCCCCTCCTCCCCCTT CCTGCACCCGTACCCCCGTGGTCTTTGAATAAAGTCTGAGTGGGCGGCTCTAGA | |
| DNA sequence coding for mRNA transcript of Cas9 (Cong) | TCAAGCTTTTGGACCCTCGTACAGAAGCTAATACGACTCACTATAGGGAAATAAGAGAGAAAAGAAGAGTAAGAAGAAATATAAGA GCCACCATGGACTACAAGGACCACGACGGAGACTACAAAGACCATGACATCGATTACAAGGATGACGATGACAAAATGGCACCGAA GAAGAAGAGAAAGGTCGGAATTCACGGGGTCCGGCCGCGACAAGAAGTACTCAATCGGACTGGATATCGGCACGAACAGCGTGG GTTGGGCAGTGATCACCGACGAATACAAGGTGCCGAGCAAGAAGTTCAAAGTGCTGGGAAATACCGATCGCCATTCGATCAAGAAG AATCTGATTGGCGCGCTCCTGTTCGACTCGGGAGAGACTGCCGAGGCCACTAGACTGAAGAGGACCGCTAGGCGCCGCTACACGAG GCGCAAAAACCGCATCTGCTATCTTAAGAAATCTTCTCAAACGAGATGGCCAAGGTGGACGACTCCTTTTTCCATCGGCTGGAAG AATCATTTCTGGTGGAGGAGGACAAGAAGCACGAACGCCATCCCATTTTCGGCAACATTGTCGACGAAGTGGCCTATCATGAGAAG TATCCGACTATCTACCACTTGAGAAGAAGCTGGTGGACTCCACTGACAAGGCAGATCTGCGGTTGATCTACCTCGCACTGGCCCA TATGATCAAATTCCGGGGACACTTCCTCATCGAGGGCGACCTTAATCCCGACAATTCCGATGTGGATAAGCTTTTCATCCAGCTGG TCCAGACCTACAACCAACTGTTTGAAGAAAATCCAATCAATGCGAGCGGTGTCGATGCAAAGGCCATCCTGAGCGCCCGCCTCTCG AAAAGCAGAAGGCTCGAAAACCTGATCGCACAGTTGCCTGGAGAGAAGAAGAACGGCCTCTTCGGCAATCTCATCGCATTGTCCCT GGGACTGACTCCAAACTTCAAATCCAACTTCGACTTGGCCGAGGACGCCAAACTGCAACTGAGCAAAGATACCTACGATGATGACT TGGACAATCTTCTGGCTCAGATCGGCGACCAGTACGCCGACCTGTTCCTTGCGGCTAAGAACCTGTCGGACGCCATCCTGCTGTCC GACATCCTGCGCGTCAATACCGAAATTACTAAAGCACCACTCTCGGCATCCATGATCAAGAGATACGATGAACACCACCAGGATCT CACCCTCCTGAAAGCACTGGTGCGGCAGCAGCTCCCTGAAAAATACAAGGAAATCTTCTTTGATCAGTCCAAGAACGGATACGCG GATACATCGACGGCGGCGCGAGCCAAGAGGAATTCTACAAGTTCATCAAGCCGATCCTGGAAAAGATGGATGGCACGGAAGAACTC CTGGTCAAACTGAATAGAGAGGATCTGCTCCGCAAACAACGGACCTTCGATAACGGATCGATCCCGCACCAGATCCACCTCGGCGA ACTGCATGCCATCCTGCGGCGGCAGGAGGACTTTTACCCGTTCCTCAAAGACAACAGAGAAAAGATCGAGAAGATCTTGACCTTTC GCATCCCGTACTACGTGGGCCCGCTCGCGAGAGGTAACTCCCGCTTTGCTTGGATGACTAGAAAGTCAGAGGAAACGATCACCCCA TGGAACTTCGAAGAGGTGGTTGACAAAGGAGCGAGCGCCCAATCGTTCATCGAACGGATGACTAACTTCGATAAGAATCTGCCGAA TGAGAAGGTCCTGCCTAAGCACTCACTTCTGTATGAATACTTTACTGTGTATAACGAACTCACCAAAGTCAAATACGTGACTGAGG GAATGCGCAAGCCTGCGTTTTTGTCCGGCGAGCAGAAAAAGGCCATCGTGGACTTGCTGTTCAAAACCAACCGCAAGGTGACTGTT AAGCAACTCAAAGAGGACTACTTTAAGAAGATCGAATGCTTTGACTCGGTCGAGATTTCCGGGTTGAAGATAGATTCAACGCGTC GCTGGGAACCTACCATGATCTCCTCAAGATTATCAAGGACAAGGACTTCCTGGATAACGAGGAGAATGAGGACATCCTCGAAGATA TTGTGCTTACCCTGACCCTTTTCGAAGATCGCGAAATGATCGAAGAACGCCTGAAAACCTACGCTCACCTGTTCGACGATAAGGTG ATGAAACAGTTGAAACGCCGGCGGTACACCGGGTGGGGCCGGCTGTCGCGCAAGCTGATCAACGGAATTCGGGACAAACAGAGCGG AAAGACCATCCTCGATTTTCTGAAGTCCGATGGTTTTGCCAACCGCAACTTCATGCAGCTCATCCATGACGATTCGCTTACCTTTA AGGAGGATATCCAGAAGGCCCAAGTGTCGGGACAAGGGGATTCGCTCCACGAACACATCGCCAATCTGGCGGGTTCGCCGGCAATT AAGAAGGGAATCCTCCAGACTGTTAAGGTGGTCGACGAGCTGGTGAAGGTGATGGGGAGACATAAGCCTGAAAACATTGTGATCGA GATGGCGAGAGAAATCAACTACTCAGAAGGGACAGAAGAATTCCCGGGAGCGGATGAAGCGCATCGAGGAGGGAATCAAGGAAC TGGGCTCCCAAATCCTGAAAGAGCATCCCGTGGAAAATACTCAGCTGCAGAACGAGAAGCTTTACCTGTACTATCTTCAAAATGGC AGGGACATGTACGTCGACCAAGAACTGGATATCAATCGGCTCTCCGATTACGACGTCGATCACATCGTCCCCCAATCATTCCTGAA GGATGATAGCATCGATAACAAGGTGCTCACTAGATCAGACAAAAACCGGGGAAAGTCAGATAACGTCCCCAGCGAAGAAGTCGTGA AGAAGATGAAGAATTACTGGAGGCAACTTCTGAACGCCAAACTCATCACTCAGCGCAAGTTCGACAACCTGACCAAAGCAGAAAGG GGAGGACTCAGCGAGCTGGACAAGGCTGGTTTCATCAAACGGCAGCTGGTGGAGACTCGCCAAATCACGAAGCATGTGGCCCAGAT TCTCGACTCGCGCATGAATACTAAGTACGACGAAAACGATAAGCTGATCCGGGAGGTGAAGGTGATCACCCTCAAGAGCAAGCTG TGTCCGATTTCCGGAAAGACTTCCAGTTCTACAAGGTGCGGGAGATTAACAACTACCATCACGCTCACGACGCTTACCTCAATGCT GTGGTGGGACGGCGTTGATTAAGAAGTACCCAAAACTGGAGTCCGAATTCGTCTACGGAGATTACAAGGTCTACGACGTGCGCAA GATGATTGCCAAGTCGGAGCAGGAAATTGGGAAAGCGACTGCTAAGTACTTCTTCTACTCGAATATCATGAACTTCTTCAAGACCG AAATCACCCTGGCTAACGGCGAGATCAGGAAACGGCCTCTGATCGAAACTAATGGTGAGACTGGTGAAATCGTGTGGGATAAGGGA CGGGACTTCGCCACGGTCCGCAAGGTCCTCAGCATGCCGCAAGTGAATATTGTTAAGAAAACCGAAGTGCAGACCGGTGGGTTCTC GAAGGAATCCATCCTGCCAAAGCGCAACTCGGATAAGCTTATTGCCCGCAAGAAGGATTGGGACCCGAAAAAGTACGGTGGGTTCG ACTCCCCTACCGTGGCGTACTCGGTGTTGGTGGTGGCCAAAGTGGAAAAGGGCAAATCAAAGAAGCTCAAGAGCGTCAAGGAGCTG CTGGGAATCACCATCATGGAGAGGTCCAGCTTTGAGAAAAACCCGATCGACTTCTTGGAAGCCAAGGGATACAAAGAGGTGAAGAA AGACCTGATCATCAAACTTCCAAAGTACTCCCTGTTCGAACTCGAAAACGGGAGGAAGCGCATGCTCGCCTCAGCCGGGGAACTGC AAAAGGGCAACGAACTGGCCCTCCCGTCAAAATACGTCAACTTCCTGTACTTGGCGTCACACTACGAAAAGCTGAAAGGGATCCCA GAGGACAACGAACAGAAACAGCTGTTCGTCGAGCAGCACAAGCACTACCTGGACGAGATCATCGAACAGATCTCGGAATTCAGCAA GAGAGTGATCTTGGCAGACGCTAACCTTGACAAAGTCCTCTCGGCATACAATAAGCATCGCGACAAGCCGATCAGAGAACAGGCGG AGAACATCATCCACCTGTTCACTCTCACCAACCTGGGCGCGCCAGCGGCGTTTAAGTACTTTGATACCACCATTGACCGCAAGAGA TACACCTCAACTAAAGAAGTGTTGGACGCAACCCTGATCCATCAAAGCATCACCGGACTTTATGAAACTCGGATCGATCTCTCACA GCTCGGAGGAGACAAAAGACCGGCTGCCACCAAGAAGGCCGGACAGGCAAAGAAGAAGAAATGATAATAGGCTGGAGCCTCGGTGG CCATGCTTCTTGCCCCTTGGGCCTCCCCCAGCCCCTCCTCCCCTTCCTGCACCCGTACCCCCGTGGTCTTTGAATAAAGTCTGAG TGGGCGGCTCTAGA | 42 |
| DNA sequence coding for mRNA transcript of dCas9-KRAB | TCAAGCTTTTGGACCCTCGTACAGAAGCTAATACGACTCACTATAGGGAAATAAGAGAGAAAAGAAGAGTAAGAAGAAATATAAGA GCCACCATGGACAAGAAATACTCAATCGGACTTGCTATCGGAACTAACAGCGTGGGATGGGCCGTCATTACTGACGAATACAAGGT GCCCTCAAAGAAGTTCAAGGTCCTGGGAAATACCGATAGACACTCCATCAAAAAGAACCTGATCGGGGCGCTGTTGTTCGACTCGG GAGAGACTGCAGAAGCAACCAGGCTCAAGCGCACTGCGAGGCGCCGGTACACCCGGAGGAAGAACCGCATCTGCTACCTCCAAGAG ATTTTCAGCAACGAGATGGCAAAGGTCGATGATTCGTTCTTCCACCGCCTTGAGGAGTCGTTCCTTGTCGAGGAGGACAAAAAGCA TGAAAGACATCCGATCTTCGGAAACATCGTGGACGAAGTCGCATACCATGAAAAGTACCCTACCATCTACCATCTCAGAAAGAAAC TCGTCGATTCAACTGATAAGGCCGACTTGCGGCTGATCTACCTGGCTCTGGCGCACATGATCAAGTTTCGGGGTCACTTTCTCATC GAGGGTGATCTCAACCCGGACAATTCCGACGTTGACAAACTCTTCATCCAACTGGTCCAGACGTACAACCAGCTGTTCGAAGAAAA | 43 |

TABLE 8-continued

DNA constructs encoding synthetic polynucleotides (mRNA) coding for CRISPR related proteins

| Description | Sequence | SEQ ID NO: |
|---|---|---|
| | TCCGATCAACGCAAGCGGAGTGGACGCCAAAGCCATTCTGTCGGCCCGCCTCTCGAAGTCGCGTCGCCTGGAAAATCTGATTGCTC<br>AGCTCCCGGGCGAAAAGAAGAATGGCCTGTTTGGAAACCTCATCGCACTGTCCCTCGGGCTGACTCCCAACTTCAAATCGAACTTT<br>GACTTGGCTGAGGATGCAAAGCTGCAACTCTCCAAAGACACTTACGATGATGACCTGGACAATCTCCTGGCGCAGATCGGGGATCA<br>GTATGCTGACCTGTTCCTGGCGGCCAAGAACCTGTCTGATGCCATCCTGCTCTCCGATATCCTGAGAGTGAACACTGAGATCACCA<br>AGGCGCCTCTGAGCGCCTCGATGATCAAACGCTACGATGAACACCATCAGGACCTCACTCTTCTGAAGGCTTTGGTGCGGCAGCAG<br>CTTCCGGAAAAGTACAAAGAGATCTTCTTCGACCAGTCGAAAAACGGCTACGCCGGATACATTGATGGCGGCGCAAGCCAGGAGGA<br>ATTCTATAAGTTTATCAAACCGATCCTGGAGAAGATGGACGGCACTGAAGAACTTCTGGTCAAGCTGAATCGAGAGGATCTGCTCC<br>GGAAGCAGCGGACCTTCGACAATGGGTCTATCCCTCACCAAATCCATCTCGGCGAGCTGCATGCGATTCTGAGGCGCCAGGAGGAC<br>TTCTACCCATTCCTGAAAGACAATCGGGAGAAAATCGAAAAGATTCTGACGTTCCGCATTCCATACTACGTCGGGCCACTTGCGCG<br>GGGTAATTCGAGATTCGCCTGGATGACGCGGAAGTCCGAAGAAACCATCACGCCGTGGAATTTCGAAGAAGTGGTCGACAAGGGAG<br>CCAGCGCACAGTCCTTCATTGAGCGCATGACCAATTTCGACAAAAATCTGCCGAACGAGAAGGTCCTGCCGAAGCATTCACTGCTG<br>TACGAATACTTTACCGTGTACAACGAACTGACCAAGGTGAAGTACGTCACCGAGGGAATGAGAAAGCCTGCTTTCCTGAGCGGAGA<br>ACAGAAGAAGGCCATTGTTGACCTCCTCTTCAAGACTAATCGCAAAGTGACCGTGAAGCAGCTTAAAGAGGATTACTTCAAAAAGA<br>TCGAATGTTTCGACTCCGTGGAAATCAGCGGCGTGGAGGATAGATTCAACGCGTCCCTTGGGACTTACCACGACCTCCTTAAGATC<br>ATCAAGGATAAGGATTTCCTCGACAATGAGGAAAACGAAGATATCCTGGAGGACATCGTTCTGACTCTGACCCTCTTTGAGGACCG<br>GGAGATGATCGAGGAGAGACTCAAGACCTACGCGCACCTGTTTGACGACAAAGTGATGAAGCAACTTAAACGCAGGCGCTACACCG<br>GCTGGGGCAGACTGTCACGCAAGTTGATCAACGGAATTAGAGATAAACAGTCCGGAAAGACCATCCTGGACTTCCTGAAGTCCGAT<br>GGATTCGCCAACCGGAATTTCATGCAGCTCATCCATGACGACTCATTGACTTTCAAGGAGGATATCCAAAAGGCCCAAGTGAGCGG<br>CCAAGGGGACTCCCTTCACGAACACATCGCAAATTTGGCCGGATCACCAGCGATTAAGAAGGGAATCCTGCAGACCGTGAAGGTGG<br>TGGACGAGCTGGTGAAAGTGATGGGACGGCACAAGCCGGAAACATCGTGATCGAGATGGCCAGAGAGAACCAGACGACTCAAAAG<br>GGCCAGAAGAACTCGCGCGAACGCATGAAGAGAATAGAAGAGGGAATTAAGGAACTGGGATCGCAGATCTTGAAGGAGCACCCTGT<br>CGAAAATACTCAACTCCAGAACGAGAAGCTGTACCTGTACTATCTTCAAAACGGCAGGGACATGTATGTCGACCAAGAGCTCGACA<br>TTAACCGCCTGTCCGATTATGACGTGGACGCCATCGTGCCGCAGCTTTCTCAAGGACGATTCCATCGACAACAAAGTGCTCACC<br>CGCAGCGACAAGAATAGAGGGAAGTCGGATAACGTCCCTTCGGAAGAGGTGGTGAAAAAGATGAAGAATTACTGGCGGCAGCTCCT<br>GAATGCAAAGCTCATCACCCAACGGAAGTTTGACAACCTCACCAAGGCAGAAAGAGGAGGACTGTCGGAATTGGATAAGGCCGGTT<br>TCATCAAGCGACAATTGGTGGAAACTCGGCAAATTACCAAGCATGTGGCACAGATTCTGGACTCCCGTATGAACACCAAGTACGAC<br>GAGAACGATAAGCTGATCCGCGAGGTCAAGGTGATCACCCTCAAAAGCAAACTTGTGTCAGACTTCCGGAAGGACTTCCAATTCTA<br>CAAGGTCCGCGAAATCAACAACTACCACCACGCTCATGACGCATACCTGAACGCTGTGGTCGGGACTGCCCTCATCAAGAAGTACC<br>CTAAACTCGAAAGCGAATTTGTGTACGGCGACTACAAAGTGTACGATGTCCGGAAGATGATCGCGAAATCCGAGCAGGAGATCGGA<br>AAGGCGACTGCTAAGTACTTTTTCTACTCGAACATCATGAACTTCTTCAAAACCGAAATCACCCTGGCTAATGGCGAGATCAGAAA<br>GCGCCCGCTGATCGAAACCAACGGCGAAACCGGTGAAATCGTGTGGGACAAGGGCCGCGATTTCGCTACTGTGAGAAAGGTCCTTT<br>CCATGCCGCAAGTGAATATCGTCAAAAAGACTGAAGGTGCAGACTGGCGGATTTTCCAAGGAATCGATCCTCCCAAAGAGGAACTCA<br>GATAAGCTCATCGCGCGGAAAAAGGATTGGGACCCTAAGAAGTACGGAGGATTTGATAGCCCAACTGTGGCCTACTCTGTGCTCGT<br>GGTGGCCAAAGTCGAGAAAGGAAAGTCGAAGAAGTTGAAATCCGTGAAAGAACTCTTGGGAATCACTATCATGGAGCGGTCGTCAT<br>TTGAAAAGAACCCAATCGACTTCCTGGAAGCCAAGGGATACAAAGAAGTCAAGAAAGACCTGATCATCAAGCTCCCTAAGTACAGC<br>CTGTTCGAACTGGAGAACGGAAGGAAACGGATGCTGGCTTCCGCCGGCGAACTGCAAAAGGGCAATGAGCTGGCCCTCCCATCGAA<br>ATACGTGAACTTCCTCTACCTTGCCTCCCATTACGAAAAGTTGAAGGGCTCACCCGAGGACAATGAGCAGAACAGCTCTTTGTTG<br>AACAACACAAACACTACCTGGACGAAATCATCGAACAAATCAGCGAGTTCAGCAAGCGCGTCATTCTGGCCGACGCGAACCTGGAT<br>AAAGTGCTGTCCGCGTACAACAAGCACCGCGATAAGCCGATACGGGAACAGGCTGAGAACATCATTCACCTCTTCACTCTCACTAA<br>TCTGGGAGCCCCCGCCGCCTTCAAGTACTTTGATACTACCATCGACCGCAAGAGATACACGAGCACCAAGGAAGTGCTCGATGCCA<br>CCCTGATCCACCAGTCCATTACTGGTCTGTACGAAACGCGAATCGATCTGTCACAGTCGGAGGAGATGCGTACCCCTACGATGTC<br>CCCGACTACGCGTCACTCGGTAGCGGCAGCCCGAAGAAGAAAGAAAGGTGGAGGACCGAAGAAAAAGAGGAAGGTTGACGGGAT<br>CGGAAGCGGATCGAATGGATCGTCAGGGGGAGGTGGCGGAGGTATGGACGCAAAATCACTTACGGCCTGGTCACGGACCTTGGTGA<br>CCTTTAAAGCGTGTTCGTGGATTTCACCAGGAAGAATGGAAACTGTTGGACACCCGCCCAGCGATCGTGTACCGGAATGTGATG<br>CTGGAGAACTACAAAAACTTGGTGTCCCTGGGGTATCAACTCACTAAGCCAGATGTCATTCTTAGACTGGAAAAGGGAGAAGAACC<br>GTGATAATAGGCTGGAGCCTCGGTGGCCATGCTTCTTGCCCCTTGGGCCTCCCCCAGCCCTCCTCCCCTTCCTGCACCCGTACC<br>CCCGTGGTCTTTGAATAAAGTCTGAGTGGGCGGCTCTAGA | |
| DNA plasmid sequence of dCas9-NLS-FLAG-VP64 | TCAAGCTTTTGGACCCTCGTACAGAAGCTAATACGACTCACTATAGGGAAATAAGAGAGAAAAGAAGAGTAAGAAGAAATATAAGA<br>GCCACCATGGACAAGAAATACTCAATCGGACTTGCTATCGGAACTAACAGCGTGGGATGGGCCGTCATTACTGACGAATACAAGGT<br>GCCCTCAAAGAAGTTCAAGGTCCTGGGAAATACCGATAGACACTCCATCAAAAAGAACCTGATCGGGGCACTGTTGTTCGACTCGG<br>GAGAGACTGCAGAAGCAACCAGGCTCAAGCGCACTGCAGGCGCCACCCGGAGGAGAACCGCATCTGCTACCTCCAAGAG<br>ATTTTCAGCAACGAGATGGCAAAGGTCGATGATTCGTTCTTTCACCGCCTTGAGGAGTCGTTCCTTGTCGAGGAGGACAAAAAGCA<br>TGAAAGACATCCGATCTTCGGAAACATCGTGGACGAAGTCGCATACCATGAAAAGTACCCTACCATCTACCATCTCAGAAAGAAAC<br>TCGTCGATTCAACTGATAAGGCCGACTTGCGGCTGATCTACCTGGCTCTGGCGCACATGATCAAGTTTCGGGGTCACTTTCTCATC<br>GAGGGTGATCTCAACCCGGACAATTCCGACGTTGACAAACTCTTCATCCAACTGGTCCAGACGTACAACCAGCTGTTCGAAGAAAA<br>TCCGATCAACGCAAGCGGAGTGGACGCCAAAGCCATTCTGTCGGCCCGCCTCTCGAAGTCGCGTCGCCTGGAAAATCTGATTGCTC<br>AGCTCCCGGGCGAAAAGAAGAATGGCCTGTTTGGAAACCTCATCGCACTGTCCCTCGGGCTGACTCCCAACTTCAAATCGAACTTT<br>GACTTGGCTGAGGATGCAAAGCTGCAACTCTCCAAAGACACTTACGATGATGACCTGGACAATCTCCTGGCGCAGATCGGGGATCA<br>GTATGCTGACCTGTTCCTGGCGGCCAAGAACCTGTCTGATGCCATCCTGCTCTCCGATATCCTGAGAGTGAACACTGAGATCACCA<br>AGGCGCCTCTGAGCGCCTCGATGATCAAACGCTACGATGAACACCATCAGGACCTCACTCTTCTGAAGGCTTTGGTGCGGCAGCAG<br>CTTCCGGAAAAGTACAAAGAGATCTTCTTCGACCAGTCGAAAAACGGCTACGCCGGATACATTGATGGCGGCGCAAGCCAGGAGGA<br>ATTCTATAAGTTTATCAAACCGATCCTGGAGAAGATGGACGGCACTGAAGAACTTCTGGTCAAGCTGAATCGAGAGGATCTGCTCC<br>GGAAGCAGCGGACCTTCGACAATGGGTCTATCCCTCACCAAATCCATCTCGGCGAGCTGCATGCGATTCTGAGGCGCCAGGAGGAC<br>TTCTACCCATTCCTGAAAGACAATCGGGAGAAAATCGAAAAGATTCTGACGTTCCGCATTCCATACTACGTCGGGCCACTTGCGCG<br>GGGTAATTCGAGATTCGCCTGGATGACGCGGAAGTCCGAAGAAACCATCACGCCGTGGAATTTCGAAGAAGTGGTCGACAAGGGAG<br>CCAGCGCACAGTCCTTCATTGAGCGCATGACCAATTTCGACAAAAATCTGCCGAACGAGAAGGTCCTGCCGAAGCATTCACTGCTG<br>TACGAATACTTTACCGTGTACAACGAACTGACCAAGGTGAAGTACGTCACCGAGGGAATGAGAAAGCCTGCTTTCCTGAGCGGAGA<br>ACAGAAGAAGGCCATTGTTGACCTCCTCTTCAAGACTAATCGCAAAGTGACCGTGAAGCAGCTTAAAGAGGATTACTTCAAAAAGA<br>TCGAATGTTTCGACTCCGTGGAAATCAGCGGCGTGGAGGATAGATTCAACGCGTCCCTTGGGACTTACCACGACCTCCTTAAGATC<br>ATCAAGGATAAGGATTTCCTCGACAATGAGGAAAACGAAGATATCCTGGAGGACATCGTTCTGACTCTGACCCTCTTTGAGGACCG<br>GGAGATGATCGAGGAGAGACTCAAGACCTACGCGCACCTGTTTGACGACAAAGTGATGAAGCAACTTAAACGCAGGCGCTACACCG<br>GCTGGGGCAGACTGTCACGCAAGTTGATCAACGGAATTAGAGATAAACAGTCCGGAAAGACCATCCTGGACTTCCTGAAGTCCGAT<br>GGATTCGCCAACCGGAATTTCATGCAGCTCATCCATGACGACTCATTGACTTTCAAGGAGGATATCCAAAAGGCCCAAGTGAGCGG | 44 |

TABLE 8-continued

DNA constructs encoding synthetic polynucleotides (mRNA) coding for CRISPR related proteins

| Description | Sequence | SEQ ID NO: |
|---|---|---|
| | CCAAGGGGACTCCCTTCACGAACACATCGCAAATTTGGCCGGATCACCAGCGATTAAGAAGGGAATCCTGCAGACCGTGAAGGTGG<br>TGGACGAGCTGGTGAAAGTGATGGGACGGCACAAGCCGGAAAATCGTGATCGAGATGGCCAGAGAGAACCAGACGACTCAAAAG<br>GGCCAGAAGAACTCGCGCGAACGCATGAAGAGAATAGAAGAGGGAATTAAGGAACTGGGATCGCAGATCTTGAAGGAGCACCCTGT<br>CGAAAATACTCAACTCCAGAACGAGAAGCTGTACCTGTACTATCTTCAAAACGGCCAGGGACATGTATGTCGACCAAGAGCTCGACA<br>TTAACCGCCTGTCCGATTATGACGTGGACGCCATCGTGCCGCAGAGCTTTCTCAAGGACGATTCCATCGACAACAAAGTGCTCACC<br>CGCAGCGACAAGAATAGAGGGAAGTCGGATAACGTCCCTTCGGAAGAGGTGGTGAAAAAGATGAAGAATTACTGGCGGCAGCTCCT<br>GAATGCAAAGCTCATCACCCAACGGAAGTTTGACAACCTCACCAAGGCAGAAAGAGGAGGACTGTCGGAATTGGATAAGGCCGGTT<br>TCATCAAGCGACAATTGGTGGAAACTCGGCAAATTACCAAGCATGTGGCACAGATTCTGGACTCCCGTATGAACACCAAGTACGAC<br>GAGAACGATAAGCTGATCCGCGAGGTCAAGGTGATCACCCTCAAAAGCAAACTTGTGTCAGACTTCCGGAAGGACTTCCAATTCTA<br>CAAGGTCCGCGAAATCAACAACTACCACCACGCTCATGACGCATACCTGAACGCTGTGGTCGGGACTGCCCTCATCAAGAAGTACC<br>CTAAACTCGAAAGCGAATTTGTGTACGGCGACTACAAAGTGTACGATGTCCGGAAGATGATCGCGAAATCCGAGCAGGAGATCGGA<br>AAGGCGACTGCTAAGTACTTTTTTCTACTCGAACATCATGAACTTCTTCAAAACCGAAATCACCCTGGCTAATGGCGAGATCAGAAA<br>GCGCCCGCTGATCGAAACCAACGGCGAAACCGGTGAAATCGTGTGGGACAAGGGCCGCGATTTCGCTACTGTGAGAAAGGTCCTTT<br>CCATGCCGCAAGTGAATATCGTCAAAAAGACTGAGGTGCAGACTGGCGGATTTTCCAAGGAATCGATCCTCCCAAAGAGGAACTCA<br>GATAAGCTCATCGCGCGGAAAAAGGATTGGGACCCTAAGAGTACGGAGGATTTGATAGCCCAACTGTGGCCTACTCTGTGCTCGT<br>GGTGGCCAAAGTCGAGAAAGGAAAGTCGAAGAAGTTGAAATCCGTGAAAGAACTCTTGGGAATCACTATCATGGAGCGGTCGTCAT<br>TTGAAAAGAACCCAATCGACTTCCTGGAAGCCAAGGGATACAAAGAAGTCAAGAAAGACCTGATCATCAAGCTCCCTAAGTACAGC<br>CTGTTCGAACTGGAGAACGGAAGGAAACGGATGCTGGCTTCCGCCGGCGAACTGCAAAAGGGCAATGAGCTGGCCCTCCCATCGAA<br>ATACGTGAACTTCCTCTACCTTGCCTCCCATTACGAAAAGTTGAAGGGCTCACCCGAGGACAATGAGCAGAAACAGCTCTTTGTTG<br>AACAACACAAACACTACCTGGACGAAATCATCGAACAAATCAGCGAGTTCAGCAAGCGCGTCATTCTGGCGGACGCGAACCTGGAT<br>AAAGTGCTGTCCGCGTACAACAAGCACCGCGATAAGCCGATACGGGAACAGGCTGAGAACATCATTCACCTCTTCACTCTCACTAA<br>TCTGGGAGCCCCCGCCGCCTTCAAGTACTTTGATACTACCATCGACCGCAAGAGATACACGAGCACCAAGGAAGTGCTCGATGCCA<br>CCCTGATCCACCAGTCCATTACTGGTCTGTACGAAACGCGAATCGTCTGTCACAGCTCGGAGGAGATGGGTCACCGAAAAAGAAA<br>CGGAAAGTCAGCTCGGATTACAAGGATCACGACGGAGACTACAAGGACCATGACATCGACTATAAGGACGACGACAAGGCCGC<br>TGGAGGCGGTGGATCGGGACGCGCGGACGCCTTGGATGACTTCGACCTTGACATGCTGGGATCCGACGCACTTGATGATTTTGATC<br>TCGATATGCTTGGCAGCGACGCACTGGACGATTTCGACCTCGACATGCTCGGATCGGATGCGCTCGACGACTTCGATCTGGATATG<br>CTGTGATAATAGGCTGGAGCCTCGGTGGCCATGCTTCTTGCCCCTTGGGCCTCCCCCCAGCCCCTCCTCCCCTTCCTGCACCCGTA<br>CCCCCGTGGTCTTTGAATAAAGTCTGAGTGGGCGGCTCTAGA | |
| Plasmid<br>sequence of<br>dCas9-KRAB-<br>miR122 | TCAAGCTTTTGGACCCTCGTACAGAAGCTAATACGACTCACTATAGGGAAATAAGAGAGAAAAGAAGAGTAAGAAGAAATATAAGA<br>GCCACCATGGACAAGAAGTACTCAATCGGACTCGCAATCGGAACCAATTCAGTCGGCTGGGCAGTCATTACCGATGAATACAAGGT<br>GCCGTCGAAGAAGTTCAAAGTCCTGGGTAACACTGACAGACATTCGATCAAAAAGAACCTGATCGGAGCCTTGCTGTTTGATTCAG<br>GCGAAACCGCCGAAGCTACCCGGTTGAAACGAACTGCTAGACGCCGCTACACGCGCCGCAAGAACCGGATCTGCTACCTCCAAGAA<br>ATCTTCTCGAACGAAATGGCTAAGGTGGACGACTCGTTCTTTCACCGGCTCGAGGAGTCATTCCTTGTGGAGGAAGATAAGAAGCA<br>CGAAAGACACCCGATCTTCGGCAACATCGTGGACGAAGTCGCGTACCACGAAAAGTACCCGACTATCTACCATCTCCGGAAGAAGC<br>TCGTGGATAGCACCGATAAGGCCGATCTGCGACTGATCTACCTTCGCCAGCGATCGCCCATATGATTAAGTTCCGCGGGCACTTCCTCATC<br>GAAGGGGACCTGAATCCAGACAACTCGGACGTGGATAAGCTGTTTATCCAGCTGGTTCAGACTTACAATCAATTGTTTGAAGAAAA<br>CCCTATCAACGCGTCTGGGGTGGACGCAAAGGCCATCCTGAGCGCGCGGCTGTCAAAATCCAGACGGCTGGAAAATCTGATAGCCC<br>AACTGCCGGGCGAGAAGAAAACGGCCTGTTTGGAAATCTTATCGCCCTGTCCCTGGGACTGACCCCCAACTTCAAGTCGAACTTC<br>GACTTGGCCGAGGATGCGAAGCTCCAGCTCAGCAAAGACACCTACGACGATGACCTTGATTGGCCCAGATCGGTGACCA<br>GTATGCTGATCTCTTCTTGGCGGCCAAGAACCTGTCAGACGCAATTCTGCTCTCCGACATCCTGCGGGTGAATACTGAGATCACTA<br>AAGCCCCATTGAGCGCGTCGATGATCAAAAGATACGACGAGCACCACCAGGATCTGACTCTCCTCAAGGCACTGGTCCGCCAACAG<br>CTCCCCGGAAAAGTACAAAGAGATCTTCTTTGACCAATCCAAAAACGGATACGCTGGTTACATAGACGGCGGAGCGTCACAAGAAGA<br>GTTCTACAAGTTCATCAAGCCTATCCTGGAAAAGATGGACGGGACCGAGGAGCTCCTGGTTAAGCTCAATAGGGAGGATCTGCTGC<br>GCAAGCAACGCACGTTCGACAATGGAAGCATCCCCCATCAGATCCACCTGGGGGAGCTCCACGCGATCCTGAGGCGCCAGGAAGAT<br>TTCTACCCATTTCTGAAGGACAATAGAGAGAAATCGAAAAGATCCTGACTTTCCGAATCCCGTACTACGTGGGCCCGCTCGCACG<br>GGGAAACTCACGGTTTGCCTGGATGACTCGCAAATCCGAAGAAACCATTACCCCCTGGAATTTCGAGGAGGTGGTCGATAAAGGCG<br>CCTCAGCCCAGTCGTTCATCGAAAGAATGACCAACTTTGACAAGAACCTCCCAAATGAGAAGGTGCTGCCAAAACATAGCCTGCTG<br>TACGAGTACTTTACTGTGTATAAGAACTCACCAAGGTGAAATACGTGACGAGGGAATGCGCAAGCCGGCATTTCTGTCGGGCGA<br>ACAGAAGAAGGCAATTGTGGACTTGCTGTTCAAAACCAACCGGAAGGTGACCGTGAAACAGCTCAAGGAAGATTACTTTAAGAAGA<br>TCGAGTGTTTCGATAGCGTCGAAATTTCGGGGGTGGAAGATCGCTTCAATGCAAGCTTGGGACGTACCACGATCTGCTTAAGATC<br>ATTAAGGACAAGGATTTCCTTGACAACGAAGAGAACGAGGATATTCTCGAGGATATCGTCCTGACGCTGACTCTGTTTGAGGATAG<br>AGAAATGATCGAGGAGATTGAAAACCTTACGCACACCTCTTCGACGATAAGGTGATGAAACAGCTGAAAAGGCGTAGATACACTG<br>GTTGGGAAGGCTGTCGAGAAAGCTGATAACGGAATTAGGGACAAGCAGTCCGGAAAAACCATCCTGGATTTCCTCAAGTCCGAC<br>GGTTTCGCCAACCGCAACTTCATGCAGCTGATCCACGATGATTCCCTGACGTTCAAAGAGGATATCCAGAAGGCACAAGTGTCCGG<br>ACAAGGAGACTCACTCCACGAGCATATCGCTAATCTCGCCGGATCGCCAGCTATCAAGAAGGGAATCTTGCAGACTGTCAAGGTGG<br>TGGACGAACTGGTGAAAGTGATGGGAAGGCATAAGCCGGAGAATATCGTGATCGAAATGGCGAGGGAAAACCAGACGACCCAGAAA<br>GGACAGAAAAACAGCCGGGAACGCATGAAGCGCATCGAAGAGGGGATCAAAGAGCTTGGGAGCCAAATCCTCAAAGAACACCCTGT<br>GGAAAATACCCAACTGCAGAATGAGAAGCTTTACCTGTATTACCTCCAAAACGGGCGCGACATGTACGTTGACCAGGAATTGGACA<br>TTAACCGGCTTTCCGACTACGATGTGGACGCTATCGTCCCGCAGTCCTTCCTGAAAGACGATTCGATCGACAATAAGGTCCTGACT<br>AGATCAGACAAGAATCGGGGAAAGTCAGACAACGTGCCTAGCGAAGAGGTCGTTAAGAAGATGAAGAATTACTGGCGCCAGCTGCT<br>GAACGCGAAGCTTATCACTCAGCGCAAGTTCGACAACCTCACCAAGGCAGAAAGAGGCGGATTGTCGGAGCTGGACAAAGCTGGCT<br>TCATCAAGCGCCAGCTCGTCGAAACTCGCCAGATTACTAAGCATGTGGCGCAGATCCTGGACAGCCGCATGAATACTAAGTATGAT<br>GAGAATGACAAGCTCATCCGGGAGGTGAAGGTCATCACCCTGAAGTCCAAGCTGGTGTCCGACTTCCGGAAGGACTTCCAATTCTA<br>CAAAGTGCGAGAAATCAACAATTACCATCACGCGCATGACGCCTACTTGAATGCAGTGGTGGGTACTGCCCTCATCAAGAAATACC<br>CAAAGCTTGAAAGCGAGTTTGTCTACGGAGACTACAAGGTGTACGACGTCCGGAAGATGATCGCCAAATCGGAACAGGAAATTGGG<br>AAGGCGACCGCTAAGTACTTCTTCTACTCGAATATCATGAATTTCTTCAAGACCGAGATCACGCTTGCAAATGGCGAAATCCGGAA<br>GCGGCCCCTCATCGAAACCAACGGAGAAACCGGAGAAATCGTGTGGGACAAGGGTCGCGATTTTGCGACCGTCCGAAAGGTCTTA<br>GCATGCCTCAAGTGAATATCGTCAAGAAAACCGAAGTTCAGACTGGAGGCTTCAGCAAGGAGTCCATTCTCCCGAAACGCAACTCC<br>GACAAACTGATCGCACGCAAGAAAGACTGGGACCCGAAGAATACGGAGGCTTCGATTCGCCGACTGTGGCTTACTCGGTCCTGGT<br>TGTGGCCAAGGTGAAAGGGAAGTCCAAGAAGCTGAAGTCCGTCAAGGAGCTCCTCGGAATCACCATCATGGAACGGTCAAGCT<br>TCGAGAAAACCCAATTGACTTCCTGGAGGCAAAGGGGTACAAGGAGGTGAAGAAGGATCTGATCATCAAACTGCCGAAGTACAGC<br>CTCTTTGAGCTCGAAAACGGACGCAAAAGGATGCTGGCCTCCGCCGGAGAGCTGCAAAAGGGAAACGAGCTTGCCTTGCCTTCCAA<br>GTACGTGAACTTCCTGTACCTGGCATCCCACTACGAAAAACTGAAGGGATCGCCGGAGGACAACGAACAGAAGCAGCTGTTTGTGG | 45 |

TABLE 8-continued

DNA constructs encoding synthetic polynucleotides (mRNA) coding for CRISPR related proteins

| Description | Sequence | SEQ ID NO: |
|---|---|---|
| | AACAACACAAGCATTATCTGGATGAAATCATCGAACAAATCAGCGAATTCTCAAAAAGGGTGATCTTGGCCGACGCCAACCTGGAT<br>AAAGTGCTTTCCGCCTACAACAAACATCGCGACAAGCCGATCCGGGAGCAGGCCGAAAACATCATTCACCTGTTTACCCTGACTAA<br>TCTGGGTGCGCCCGCGGCTTTCAAATACTTCGATACCACGATCGACCGGAAGAGATACACCAGCACCAAAGAGGTGTTGGACGCGA<br>CCCTCATCCACCAATCTATTACCGGCCTCTATGAAACTAGGATCGACCTCAGCCAGCTGGGAGGCGATGCCTACCCTTACGATGTC<br>CCGGACTACGCCTCGCTGGGATCCGGATCTCCGAAGAAGAAGCGGAAGGTCGAGGACCCAAAGAAAAAGCGCAAAGTGGATGGGAT<br>CGGTAGCGGTTCCAACGGTTCCTCGGGTGGCGGCGGAGGCGGCATGGATGCTAAGTCACTTACCGCCTGGTCGCGGACGCTGGTGA<br>CTTTCAAAGATGTGTTCGTGGATTTCACTCGTGAGGAATGGAAATTGCTGGACACTGCCCAACAGATCGTCTACCGCAACGTCATG<br>CTTGAAAACTACAAAAACCTCGTGTCGCTGGATATCAGCTGACCAAGCCCGACGTGATTCTGAGACTGGAGAAGGGCGAAGAACC<br>TTGATAATAGGCTGGAGCCTCGGTGGCCATGCTTCTTGCCCCTTGGGCCTCCCCCCAGCCCCTCCTCCCCTTCCTGCACCCGTACC<br>CCCCAAACACCATTGTCACACTCCAGTGGTCTTTGAATAAAGTCTGAGTGGGCGGCTCTAGA | |
| DNA Plasmid sequence of dCas9-VP64-miR122 | TCAAGCTTTTGGACCCTCGTACAGAAGCTAATACGACTCACTATAGGGAAATAAGAGAGAAAAGAAGAGTAAGAAGAAATATAAGA<br>GCCACCATGGACAAGAAGTACTCAATCGGACTCGCAATCGGAACCAATTCAGTCGGCTGGGCAGTCATTACCGATGAATACAAGGT<br>GCCGTCGAAGAAGTTCAAAGTCCTGGGTAACACTGACAGACATTCGATCAAAAAGAACCTGATCGGAGCCTTGCTGTTTGATTCAG<br>GCGAAACCGCCGAAGCTACCCGGTTGAAACGAACTGCTAGACGCCGCTACACGCGCCGCAAGAACCGGATCTGCTACCTCCAAGAA<br>ATCTTCTCGAACGAAATGGCTAAGGTGGACGACTCGTTCTTTCACCGGCTCGAGGAGTCATTCCTTGTGGAGGAAGATAAGAAGCA<br>CGAAAGACACCCGATCTTCGGCAACATCGTGGACGAAGTCGCGTACCACGAAAAGTACCCGACTATCTACCATCTCCGGAAGAAGC<br>TCGTGGATAGCACCGATAAGGCCGATCTGCGACTGATCTACCTCGCGCTGGCCCATATGATTAAGTTCCGCGGGCACTTCCTCATC<br>GAAGGGGACCTGAATCCAGACAACTCGGACGTGGATAAGCTGTTTTATCCAGCTGGTGCAGACTTACAATCAATTGTTTGAAGAAA<br>CCCTATCAACGCGTCTGGGGTGGACGCAAAGGCCATCCTGAGCGCGCGGCTGTCAAAATCCAGACGGCTGGAAAATCTGATAGCCC<br>AACTGCCGGGCGAGAAGAAAAACGGCCTGTTTGGAAATCTTATCGCCCTGTCCCTGGGACTGACCCCCAACTTCAAGTCGAACTTC<br>GACTTGGCCGAGGATGCGAAGCTCCAGCTCAGCAAAGACACCTACGACGATGACCTCGATAACCTGTTGGCCCAGATCGGTGACCA<br>GTATGCTGATCTCTTCTTGGCGGCCAAGAACCTGTCAGACGCAATTCTGCTCTCCGACATCCTGCGGGTGAATACTGAGATCACTA<br>AAGCCCCATTGAGCGCGTCGATGATCAAAAGATACGACGAGCACCACCAGGATCTGACTCTCCTCAAGGCACTGGTCCGCCAACAG<br>CTCCCGGAAAAGTACAAAGAGATCTTCTTTGACCAATCCAAAAACGGATACGTGGTTACATAGACGGCGGAGCGTCACAAGAAGA<br>GTTCTACAAGTTCATCAAGCCTATCCTGGAAAAGATGGACGGGACCGAGGAACTCCTGGTTAAGCTCAATAGGGAGGATCTGCTGC<br>GCAAGCAACGCACGTTCGACAATGGAAGCATCCCCCATCAGATCCACCTGGGGGAGCTCCACGCGATCCTGAGGCGCCAGGAAGAT<br>TTCTACCCATTTCTGAAGGACAATAGAGAGAAATCGAAAAGATCCTGACTTTCCGAATCCCGTACTACGTGGGCCCGCTCGCACG<br>GGGAAACTCACGGTTTGCCTGGATGACTCGCAAATCCGAAGAAACCATTACCCCCTGGAATTTCGAGGAGGTGGTCGATAAAGGCG<br>CCTCAGCCCAGTCGTTCATCGAAAGAATGACCAACTTTGACAAGAACCTCCCAAATGAGAAGGTGCTGCCAAAACATAGCCTGCTG<br>TACGAGTACTTTACTGTGTATAACGAACTCACCAAGGTGAAATACGTGACCGAGGAATGCGCAAGCCGGCATTTCTGTCGGCGA<br>ACAGAAGAAGGCAATTGTGGACTTGCTGTTCAAAACCAACCGGAAGGTGACCGTGAAACAGCTCAAGGAAGATTACTTTAAGAAGA<br>TCGAGTGTTTCGATAGCGTCGAAATTTCGGGGGTGGAAGATCGCTTCAATGCAAGCCTTGGGACGTACCACGATCTGCTTAAGATC<br>ATTAAGGACAAGGATTTCCTTGACAACGAAGAGAACGAGGATATTCTCGAGGATATCGTCCTGACCCTGACTCTGTTTGAGGATAG<br>AGAAATGATCGAGGAGAGATTGAAAACTTACGCACACCTCTTCGACGATAAGGTGATGAAACAGCTGAAAAGGCGTAGATACACTG<br>GTTGGGGAAGGCTGTCGAAAAGCTGATCAACGGAATTAGGGACAAGCAGTCCGGAAAAACCATCCTGGATTTCCTCAAGTCCGAC<br>GGTTTCGCCAACCGCAACTTCATGCAGCTGATCCACGATGATTCCCTGACGTTCAAAGAGGATATCCAGAAGGCACAAGTGTCCGG<br>ACAAGGAGACTCACTCCACGAGCATATCGTCAATCTCGCCGGATCGCAGCTATCAAGAAGGGAATCTTGCAGACTGTCAAGGTGG<br>TGGACGAACTGGTGAAAGTGATGGGAAGGCATAAGCCGGAGAATATCGTGATCGAGATGGCGAGGGAAAACCAGACGACCCAGAAA<br>GGACAGAAAAACAGCCGGGAACGCATGAAGCGCATCGAAGAGGGAATCAAAGAGCTTGGGAGCCAAATCCTCAAAGAACACCCTGT<br>GGAAAATACCCAACTGCAGAATGAGAAGCTTTACCTGTATTACCTCCAAAACGGGCGCGACATGTACGTTGACCAGGAATTGGACA<br>TTAACCGGCTTTCCGACTACGATGTGGACGCTATCGTCCCGCAGTCCTTCCTGAAAGACGATTCGATCGACAATAAGGTCCTGACT<br>AGATCAGACAAGAATCGGGGAAAGTCAGACAACGTGCCTAGCGAAGAGGTCGTTAAGAAGATGAAGAATTACTGGCGCCAGCTGCT<br>GAACGCGAAGCTTATCACTCAGCGCAAGTTCGACAACCTCACCAAGGCAGAAAGAGGCGGATTGTCGGAGCTCGACAAAGCTGGCT<br>TCATCAAGCGCCAGCTCGTCGAAACTCGCCAGATTACTAAGCATGTGGCGCAGATCCTGGACAGCCGCATGAATACTAAGTATGAT<br>GAGAATGACAAGCTCATCCGGGAGGTGAAGGTCATCACCCTGAAGTCCAAGCTGGTGTCCGACTTCCGGAAGGACTTCCAATTCTA<br>CAAAGTCAGAGAAATCAACAATTACCATCACGCGCATGACGCCTACTTGAATGCAGTGGTGGGTACTGCCCTCATCAAGAAATACC<br>CAAAGCTTGAAAGCGAGTTTGTCTACGGAGACTACAAGGTGTACGACGTCCGGAAGATGATCGCCAAATCGGAACAGGAAATTGGG<br>AAGGCGACCGCTAAGTACTTCTTCTACTCGAATATCATGAATTTCTTCAAGACCGAGATCACGCTTGCAAATGGCGAAATCCGGAA<br>GCGGCCCCTCATCGAAACCAACGGAGAAACCGGAGAAATCGTGTGGGACAAGGGTCGCGATTTTGCGACCGTCCGAAAGGTTCTTA<br>GCATGCCTCAAGTGAACATCGTCAAGAAAACGGAAGTGCAGACTGGAGGCTTCAGCAAGGAGTCCATTCTCCCGAAACGCAACTCC<br>GACAAACTGATCGCACGCAAGAAAGACTGGGACCCGAAGAAATACGGAGGCTTCGATTCGCCGACTGTGGCTTACTCGGTCCTGGT<br>TGTGGCCAAGGTGGAAAAGGGAAAGTCCAAGAAGCTGAAGTCCGTCAAGGAGCTCCTCGGAATCACCATCATGGAACGGTCAAGCT<br>TCGAGAAAAACCCAATTGACTTCCTGGAGGCAAAGGGGTACAAGGAGGTGAAGAAGGATCTGATCATCAAACTGCCGAAGTACAGC<br>CTCTTTGAGCTCGAAAACGGACGCAAAAGGATGCTGGCCTCCGCCGGAGAGCTGCAAAAGGGAAACGAGCTTGCCTTGCCTTCCAA<br>GTACGTGAACTTCCTGTACCTGGCATCCCACTACGAAAACTGAAGGGATCGCCGGAGGACAACGAACAGAAGCAGCTGTTTGTGG<br>AACAACACAAGCATTATCTGGATGAAATCATCGAACAAATCAGCGAATTCTCAAAAAGGGTGATCTTGGCCGACGCCAACCTGGAT<br>AAAGTGCTTTCCGCCTACAACAAACATCGCGACAAGCCGATCCGGGAGCAGGCCGAAAACATCATTCACCTGTTTACCCTGACTAA<br>TCTGGGTGCGCCCGCGGCTTTCAAATACTTCGATACCACGATCGACCGGAAGAGATACACCAGCACCAAAGAGGTGTTGGACGCGA<br>CCCTCATCCACCAATCTATTACCGGCCTCTATGAAACTAGGATCGACCTCAGCCAGCTGGGAGGCGATGGATCCCAAAGAAGAAG<br>AGAAAAGTGTCCTCCGACTACAAGGATCATGATGGGACTATAAAGATCATGATATTGATTACAAGGACGACGACGACAAGGCCGC<br>TGGAGGAGGAGGTTCCGGCCGCGCCGATGCTCTCGACGACTTCGACCTCGACATGCTGGGATCCGACGCCCTGGACGACTTTGATC<br>TGGATATGCTGGGCTCGGACGCCCTTGATGACTTCGATCTGGACATGCTGGGTCGGATGCACTGGACGACTTCGACCTTGATATG<br>CTGTGATAATAGGCTGGAGCCTCGGTGGCCATGCTTCTTGCCCCTTGGGCCTCCCCCCAGCCCCTCCTCCCCTTCCTGCACCCGTA<br>CCCCCCAAACACCATTGTCACACTCCAGTGGTCTTTGAATAAAGTCTGAGTGGGCGGCTCTAGA | 46 |

TABLE 9 sgRNA constructs

| Description | Sequence | SEQ ID NO: |
|---|---|---|
| VEGF V1 sgRNA construct sequence | TCAAGCTTTTGGACCCTCGTACAGAAGCTAATACGACTCACTATAGGGTGTGCAGACGGCAGTCACTAGGGTTTTAGAGCTAGAAA TAGCAAGTTAAAATAAGGCTAGTCCGTTATCAACTTGAAAAAGTGGCACCGAGTCGGTGC | 101 |
| VEGF V2 sgRNA construct sequence | TCAAGCTTTTGGACCCTCGTACAGAAGCTAATACGACTCACTATAGGGAGCAGCGTCTTCGAGAGTGAGGGTTTTAGAGCTAGAAA TAGCAAGTTAAAATAAGGCTAGTCCGTTATCAACTTGAAAAAGTGGCACCGAGTCGGTGC | 102 |
| VEGF V3 sgRNA construct sequence | TCAAGCTTTTGGACCCTCGTACAGAAGCTAATACGACTCACTATAGGGTGAGTGAGTGTGTGCGTGTGGGTTTTAGAGCTAGAAAT AGCAAGTTAAAATAAGGCTAGTCCGTTATCAACTTGAAAAAGTGGCACCGAGTCGGTGC | 103 |
| VEGF V4 sgRNA construct sequence | TCAAGCTTTTGGACCCTCGTACAGAAGCTAATACGACTCACTATAGGGTTGGAGCGGGGAGAAGGCCAGGGTTTTAGAGCTAGAAA TAGCAAGTTAAAATAAGGCTAGTCCGTTATCAACTTGAAAAAGTGGCACCGAGTCGGTGC | 104 |
| sgRNA plasmid template | TCAAGCTTTTGGACCCTCGTACAGAAGCTAATACGACTCACTATAGGGNNNNNNNNNNNNNNNNNNNNNNNNNNNNGTTTTAGAGCTAG AAATAGCAAGTTAAAATAAGGCTAGTCCGTTATCAACTTGAAAAAGTGGCACCGAGTCGGTGGTGC | 105 |
| Moderna sgRNA 5' UTR | TCAAGCTTTTGGACCCTCGTACAGAAGCTAATACGACTCACTATAGGG | 106 |
| Synthetic sgRNA guide scaffold sequence | GTTTTAGAGCTAGAAATAGCAAGTTAAAATAAGGCTAGTCCGTTATCAACTTGAAAAAGTGGCACCGAGTCG GTGGTGC | 100 |

TABLE 10

Synthetic polynucleotides encoding a CRISPR related protein and synthetic sgRNA

| Description | Sequence | SEQ ID NO |
|---|---|---|
| mRNA sequence of dCas9-HA tag-2xSV40NLS-KRAB | GGGAAAUUAAGAGAGAAAAGAAGAGUUAAGAAGAAAUUAUUAAGAGCCACCAUGGACAAGAAAUACUCAAUCGGACUUGCUAUCGG AACUAACAGCGUGGGAUGGGCCGUCAUUACUGACGAAUACAAGGUGCCCUCAAAGAAGUUCAAGGUCCUGGGAAAUACCGAUAGAC ACUCCAUCAAAAAGAACCUGAUCGGGGCACUGUUGUUCGACUCGGGAGAGACUGCAGAAGCAACCAGGCUCAAGCGCACUGCGAGG CGCCGGUACACCCGGAGGAAGAACCGCAUCUGCUACCUCCAAGAGAUUUUCAGCAACGAGAUGGCAAAGGUCGAUGAUUCGUUCUU UCACCGCCUUGAGGAGUCGUUCCUUGUCGAGGAGGACAAAAAGCAUGAAAGACAUCCGAUCUUCGGAAACAUCGUGGACGAAGUCG CAUACCAUGAAAAGUACCCCUACCAUCUACCAUCUCAGAAAGAAAUCGUCGAUGAAUUGCAACGACAUUGCGGCUGAUCUAC CUGGCUCUGGCGCACAUGAUCAAGUUUCGGGGUCACUUUCUCAUCGAGGGUGAUCUCAACCCCGACAAUUCCGACGUUGACAAACU CUUCAUCCAACUGGUCCAGACGUACAACCAGCUGUUCGAAGAAAAUCCGAUCAACGCAAGCGGAGUGGACGCCAAAGCCAUUCUGU CGGCCCGCCUCUCGAAGUCGCGUCGCCUGGAAAAUCUGAUUGCUCAGCUCCCGGGCGAAAAGAAGAAUGGCCUGUUUGGAAACCUC AUCGCACUGUCCCUCGGGCUGACUCCCAACUUCAAAUCGAACUUUGACUUGGCUGAGGAUGCAAAGCUGCAACUCUCCAAAGACAC UUACGAUGAUGACCUGGACAAUCUCCUGGCCGCAGAUCGGGAUCAGUAUGCUGACCUGUUCCUGGCGGCCAAGAACCUGUCUGAUG CCAUCCUGCUCUCCGAUAUCCUGAGAGUGAACACUGAGAUCACCAAGGCGCCUCUGAGCGCCUCGAUGAUCAAACGCUACGAUGAA CACCAUCAGGACCUCACUCUUCUGAAGGCUUUGGUGCGGCAGCAGCUUCCGGAAAAGUACAAAGAGAUCUUCUUCGACCAGUCGAA AAACGGCUACGCCGGAUACAUUGAUGGCGGCGCAAGCCAGGAGGAAUUCUAUAAGUUUAUCAAACCGAUCCUGGAGAAGAUGGACG GCACUGAAGAACUUCUGGUCAAGCUGAAUCGAGAGGAUCUGCUCCGCAAGCAGCGGACCUUCGACAAUGGGUCUAUCCCUCACCAA AUCCAUCUCGGCGAGCUGCAUGCGAUUCUGAGGCGCCAGGAGGACUUCUACCCAUUCCUGAAAGACAAUCGGGAGAAAAUCGAAAA GAUUCUGACGUUCCGCAUUCCAUACUACGUCGGGCCACUUGCGCGGGUAAAUUCGAGAUUCGCCUGGAUGACGCGGAAGUCCGAAG AAACCAUCACGCCGUGGAAUUUCGAAGAAGUGGUCGACAAGGGAGCCAGCGCACAGUCCUUCAUUGAGCGCAUGACCAAUUUCGAC AAAAAUCUGCCGAACGAGAAGGUCCUGCCGAAGCAUUCACUGCUGUACGAAUACUUUACCGUGUACAACGAACUGACCAAGGUGAA GUACGUCACCGAGGGAAUGAGAAAGCCUGCUUUCCUGAGCGGAGAACAGAAGAAGGCCAUUGUUGACCUCCUCUUCAAGACUAAUC GCAAAGUGACCGUGAAGCAGCUUAAAGAGGAUUACUUCAAAAAGAUCGAAUGUUUCGACUCCGUGGAAAUCAGCGGCGUGGAGGAU AGAUUCAACGCGUCCCUUGGGACUUACCACGACCUCCUUAAGAUCAUCAAGGAUAAGGAUUUCCUCGACAAUGAGGAAAACGAAGA UAUCCUGGAGGACAUCGUCCUGACUCUGACUCUGUUUGAGGACCGGGAGAUGAUCGAGGAGAGACUCAAGACCUACGCGCACCUGU UUGACGACAAAGUGAUGAAGCAACUUAAACGCAGGCGCUACACCGGCUGGGGCAGACUGUCACGCAAGUUGAUCAACGGAAUUAGA GAUAAACAGUCCGGAAAGACCAUCCUGGACUUCCUGAAGUCCGAUGGAUUCGCCAACCGGAAUUUCAUGCAGCUCAUCCAUGACGA CUCAUUGACUUUCAAGGAGGAUAUCCAAAAGGCCCAAGUGAGCGGCCAAGGGGACUCCCUUCACGAACACAUCGCAAAUUUGGCCG GAUCACCAGCGAUUAAGAAAGGGAUCUUGCAGACGGUGAAGGUGGUGGACGAGCUGGUGAAAGUGAUGGGGAGGCACAAGCCGGAA AACAUCGUGAUCGAGAUGGCCAGAGAGAACCAGACGACUCAAAAGGGCCAGAAGAACUCGCGCGAACGCAUGAAGAGAAUAGAAGA GGGAAUUAAGGAACUGGGAUCGCAGAUCUUGAAGGAGCACCCUGUCGAAAAAUACUCAACUCCAGAACGAGAAGCUGUACCUGUACU AUCUUCAAAACGGCAGGGACAUGUAUGUCGACCAAGAGCUCGACAUUAACCGCCUGUCCGAUUAUGACGUGGACGCCAUCGUGCCG CAGAGCUUUCUCAAGGACGAUUCCAUCGACAACAAAGUGCUCACCCGCAGCGACAAGAACAGAGGGAAGAGUGAUAACGUCCCCUUC GAAGAGGUGGUGAAAAAGAUGAAGAAUUACUGGCGGCAGCUCCUGAAUGCAAAGCUCAUCACCCAACGGAAGUUUGACAACCUCA CCAAGGCAGAAAGAGGAGGACUGUCGGAAUUGGAUAAGGCCGGUUUCAUCAAGCGACAAUUGGUGGAAAUCGGCAAAUUACCAAG CAUGUGGCACAGAUUCUGGACUCCCGUAUGAACACCAAGUACGACGAGAACGAUAAGCUGAUCCGCGAGGUCAAGGUGAUCACCCU GAAAGCAAACUUGUGUCAGACUUCCGGAAGGACUUCCAAUUCUACAAGGUCCGCGAAAUCAACAACUACCACCACGCUCAUGACG CAUACCUGAACGCUGUGGUCGGGACUGCCCCAUCAAGAAGUACCCUAAACUCGAAAGCGAAUUUGUGUACGGCGACUACAAAGUG | 51 |

TABLE 10-continued

Synthetic polynucleotides encoding a CRISPR related protein and synthetic sgRNA

| Description | Sequence | SEQ ID NO |
|---|---|---|
| | UACGAUGUCCGGAAGAUGAUCGCGAAAUCCGAGCAGGAGAUCGGAAAGGCGACUGCUAAGUACUUUUUCUACUCGAACAUCAUGAA CUUCUUCAAAACCGAAACUCACCCUGGCUAAUGGCGAGAUCAGAAAGCGCCCGCUGAACGAAACCAACGGCGAAACCGGUGAAAUCG UGUGGGACAAGGGCCGCGAUUUCGCUACUGUGAGAAAGGUCCUUUCCAUGCCGCCAAGUGAAUAUCGUCAAAAAGACUGAGGUGCAG ACUGGCGGAUUUUCCAAGGAAUCGAUCCUCCCAAAGAGGAACUCAGAUAAGCUCAUCGCGCGGAAAAAGGAUUGGGACCCUAAGAA GUACGGAGGAUUUGAUAGCCCAACUGUGGCCUACUCUGUGCUCGUGGUGGCCAAAGUCGAGAAAGGAAAGUCGAAGAAGUUGAAAU CCGUGAAAGAACUCUUGGGAAUCACUAUCAUGGAGCGGUCGUCAUUUGAAAAGAACCCAAUCGACUUCCUGGAAGCCAAGGGAUAC AAAGAAGUCAAGAAAGACCUGAUCAUCAAGCUCCCUAAGUACAGCCUGUUCGAACUGGAGAACGGAAGGAAACGGAUGCUGGCUUC CGCCGGCGAACUGCAAAAGGGCAAUGAGCUGGCCCUCCCAUCGAAAUACGUGAACUUCUCUACCUUGCCUCCCAUUACGAAAAGU UGAAGGGCUCACCCGAGGACAAUGAGCAGAAACAGCUCUUUGUUGAACAACACAAACACUACCUGGACGAAAUCAUCGAACAAAUC AGCGAGUUCAGCAAGCGCGUCAUUCUGGCGGACGCGAACCUGGAUAAAGUGCUGUCCGCGUACAACAAGCACCGCGAUAAGCCGAU ACGGGAACAGGCUGAGAACAUCAUUCACCUCUUCACUCUCACUAAUCUGGGAGCCCCCGCCGCCUUCAAGUACUUUGAUAUCUACCA UCGACCGCAAGAGAUACACGAGCACCAAGGAAGUGCUCGAUGCCACCCUGAUCCACCAGUCCAUUACUGGUCUGUACGAAACGCGA AUCGAUCUGUCACAGCUCGGAGGAGAUGCGUACCCCUACGAUGUCCCCGACUACGCGUCACUCGGUAGCGGCAGCCCGAAGAAGAA AAGAAAGGUGGAGGACCCGAAGAAAAGAGGAAGGUUGACGGGAUCGGAAGCGGAUCGAAUGGAUCGUCAGGGGGAGGUGGCGGAG GUAUGGACGCAAAAUCACUUACGGCCUGGCUGGUCACGGCCUUGGUGACCUUUAAAGACGUGUUCACGGGAUUUCACCAGGGAGAAUGG AAACUGUUGGACACCGCCCAGCAGAUCGUGUACCGGGAUGUGAUGCUGGAGAACUACAAAAACUUGGUGUCCCUGGGGUAUCAACU CACUAAGCCAGAUGUCAUUCUUAGACUGGAAAAGGGAGAAGAACCGUGAUAAUAGGCUGGAGCUCGGUGGCCAUGCUUCUUGCCC CUUGGGCCUCCCCCCAGCCCCUCCUCCCCUUCCUGCACCCGUACCCCCGUGGUCUUUGAAUAAAGUCUGAGUGGGCGGC+A (140nt) tail | |
| mRNA sequence of dCas9-NLS-FLAG-VP64 | GGGAAAUAAGAGAGAAAAGAAGAGUAAGAAGAAAUAUAAGAGCCACCAUGGACAAGAAAUACUCAAUCGGACUUGCUAUCGGAACU AACAGCGUGGGAUGGGCCGUCAUUACUGACGAAUACAAGGUGCCCUCAAAGAAGUUCAAGGUCCUGGGAAAUACCGAUAGACACUC CAUCAAAAAGAACCUGAUCGGGCACUGUUGUUCGACUCGGGAGGAGACGCAGAAGCAACCAGGCUCAAGCGCACUGCGAGGCGCC GGUACACCCGGAGGAAGAACCGCAUCUGCUACCUCCAAGAGAUUUUCAGCAACGAGAUGGCAAAGGUCGAUGAUUCGUUCUUUCAC CGCCUUGAGGAGUCGUUCCUUGUCGAGGAGGACAAAAAGCAUGAAAGACAUCCGAUCUUCGGAAACAUCGUGGACGAAGUCGCAUA CCAUGAAAAGUACCCCUACCAUCUACCAUCUCAGAAAGAAACUCGUCGAUUCAACUGAUAAGGCCGACUUGCGGCUGAUCUACCUGG CUCUGGCGCACAUGAUCAAGUUCCGGGGCCACUUUCUCAUCGAGGGUGAUCUCAACCCGGACAAUUCCGACGUUGACAAACUCUUC AUCCAACUGGUCCAGACGUACAACCAGCUGUUCGAAGAAAAUCCGAUCAACGCAAGCGGAGUGGACGCCAAAGCCAUUCUGUCGGC CCGCCUCUCGAAGUCGCGUCGCCUGGAAAAUCUGAUUGCUCAGCUCCCGGGCGAAAAGAAGAAUGGCCUGUUUGGAAACCUCAUCG CACUGUCCCUCGGGCUGACUCCCAACUUCAAAUCGAACUUUGACUUGGCUGAGGAUGCAAAGCUGCAACUCUCCAAAGACACUUAC GAUGAUGACCUGGACAAUCUCCUGGCGCAGAUCGGGGAUCAGUAUGCUGACCUGUUCCUGGCCGCCAAGAACCUGUCUGAUGCCAU CCUGCUCUCCGAUAUCCUGAGAGUGAACACUGAGAUCACCAAGGCGCCUCUGAGCGCCUCGAUGAUCAAACGCUACGAUGAACACC AUCAGGACCUCACUCUUCUGAAGGCUUUGGUGCGGCAGCAGCUUCCGGAAAAGUACAAAGAGAUCUUCUUCGACCAGUCGAAAAAC GGCUACGCCGGAUACAUUGAUGGCGGCGCAAGCCAGGAGGAAUUCUAUAAGUUUAUCAAACCGAUCCUGGAGAAGAUGGACGGCAC UGAAGAACUUCUGGUCAAGCUGAAUCGAGAGGAUCUGCUCCGGAAGCAGCGGACCUUCGACAAUGGGUCUAUCCCUCACCAAAUCC AUCUCGACCGCCUGUGCAGUGAGUCUGGAGGCGCCAGGAGGAGCACUACCGAAGAAGGCCAUUGGUGACCCUCUCGAAUGAUCGCAA AGUGACCGUGAAGCAGCUUAAAGAGGAUUACUUCAAAAAGAUCGAAUGUUUCGACUCCGUGGAAAUCAGCGGCGUGGAGGAUAGAU UCAACGCGUCCCUUGGGACUUACCACGACCUCCUUAAGAUCAUCAAGGAUAAGGAUUUCCUCGACAAUGAGGAAAACGAAGAUAUC CUGGAGGACAUCGUUCUGACUCUGACCCUCUUUGAGGACCGGGAGAUGAUCGAGGAGAGACUCAAGACCUACGCGCACCUGUUUGA CGACAAAGUGAUGAAGCAACUUAAACGCAGGCGUACACCGAGGGCAUUAAAGAGCUGGGCAGCCAGAUCCUCAAGGAACAUCCGGUU GAGAAUACCCAGCUCCAGAACGAGAAGCUGUACCUCUACUACCUCCAAAAUGGCGCGGACAUGUACGUGGACCAAGAACUGGACAU AACAGUCCGGAAAGACCAUCCUGGACUUCCUGAAGUCCGAUGGAUUCGCCAACCGGAAUUUCAUGCAGCUGAUCCAUGACGACUCA UUGACUUUCAAGGAGGAUAUCCAAAAGGCCCAAGUGAGCGGCCAAGGGACUCCCUUCACGAACACAUCCAAAUUUGGCCGGAUC ACCAGCGAUUAAGAAGGGAAUCCUGCAGACCGUGAAGGUGGUGGACGAGCUGGUGAAAGUGAUGGGACGGCACAAGCCGGAAAACA UCGUGAUCGAGAUGGCCAGAGAAAACCAGACCACGCAGAAGGGCCAGAAGAACUCCCGCGAACGCAUGAAGAGAAUAGAAGAGGGA AUUAAGGAACUGGGAUCGCAGAUCUUGAAGGAGCACCCUGUCGAAAAUACUCAACUCCAGAACGAGAAGCUGUACCUGUACUAUCU UCAAAACGGCAGGGACAUGUAUGUCGACCAAGAGCUCGACAUUAACCGCCUGUCCGAUUAUGACGUGGACGCCAUCGUGCCGCAGA GCUUUCUCAAGGACGAUUCCAUCGACAACAAAGUGCUCACCCGCAGCGACAAGAAUAGAGGGAAGUCGGAUAACGUCCCUUCGGAA GAGGUGGUGAAAAAGAUGAAGAAUUACUGGCGGCACUUGCUGAAUGCCAAAGCUGCACCCAACGGAAGUUUGACAACCUCACCAA GGCAGAAAGAGGAGGACUGUCGAAUUGGAUAAGGCCGGUUUUAUCAAGCGACAAUUGGUGGAAACUCGGCAAAUUACCAAGCAUG UGGCACAGAUUCUGGACUCCCGUAUGAACACCAAGUACGACGAGAACGAUAAGCUGAUCCGCGAGGUCAAGGUGAUCACCCUCAA AGCAAACUUGUGUCAGACUUCCGGAAGGACUUCCAAUUCUACAAGGUCCGCGAAAUCAACAACUACCACCACGCUCAUGACGCAUA CCUGACGCUGUGGUCGGGACUGCCCUCAUCAAGAAGUACCCUAAACUCGAAAGCGAAUUUGUGUACGGCGACUACAAAGUGUACG AUGUCCGGAAGAUGAUCGCGAAAUCCGAGCAGGAGAUCGGAAAAGGCGACUGCUAAGUACUUUUUCUACUCGAACAUGAACUUC UUCAAAACCGAAAUCACCCUGGCUAAUGGCGAGAUCAGAAAGCGCCCGCUGAUCGAAACCAACGGCGAAACCGGUGAAAUCGUGUG GACAAGGGCCGCGAUUUCGCUACUGUGAGAAAGGUCCUUUCCAUGCCGCAAGUGAAUAUCGUCAAAAAGACUGAGGUGCAGACUG GCGGAUUUUCCAAGGAAUCGAUCCUCCCAAAGAGGAACUCAGAUAAGCUCAUCGCGCGGAAAAAGGAUUGGGACCCUAAGAAGUAC GGAGGAUUUGAUAGCCCAACUGUGGCCUACUCUGUGCUCGUGGUGGCCAAAGUCGAGAAAGGAAAGUCGAAGAAGUUGAAAUCCGU GAAAGAACUCUUGGGAAUCACUAUCAUGGAGCGGUCGUCAUUUGAAAAGAACCCAAUCGACUUCCUGGAAGCCAAGGGAUACAAAG AAGUCAAGAAAGACCUGAUCAUCAAGCUCCCUAAGUACAGCCUGUUCGAACUGGAGAACGGAAGGAAACGGAUGCUGGCUUCCGCC GGCGAACUGCAAAAGGGCAAUGAGCUGGCCCUCCCAUCGAAAUACGUGAACUUCUCUACCUUGCCUCCCAUUACGAAAAGUUGAA GGGCUCACCCGAGGACAAUGAGCAGAAACAGCUCUUUGUUGAACAACACAAACACUACCUGGACGAAAUCAUCGAACAAAUCAGCG AGUUCAGCAAGCGCGUCAUUCUGGCGGACGCGAACCUGGAUAAAGUGCUGUCCGCGUACAACAAGCACCGCGAUAAGCCGAUACGG GAACAGGCUGAGAACAUCAUUCACCUCUUCACUCUCACUAAUCUGGGAGCCCCCGCCGCCUUCAAGUACUUUGAUAUCUACCAUCGA CCGCAAGAGAUACACGAGCACCAAGGAAGUGCUCGAUGCCACCCUGAUCCACCAGUCCAUUACUGGUCUGUACGAAACGCGAAUCG AUCUGUCACAGCUCGGAGGAGAUGGGUCGAGAAAGGCGAAAAGCUAGGGAAGGUGAUCGGGAGGCGGAGGCGGGAUCGGGAGCGCGGACGCCUUGGAUGAUCUCGA CCUUGACAUGCUGGGAUCCGACGCACUUGAUGAUUUUGAUCUCGAUAUGCUGGCAGCGACGCACUGGAGAUUUGACCUCGACA UGCUCGAUCGGAUGCGCUCGACGACUUCGAUCUGGAUAUGCUGUGAUAAUAGGCUGGAGCUCGGUGGCCAUGCUUCUUGCCCU UGGGCCUCCCCCCAGCCCCUCCUCCCCUUCCUGCACCCGUACCCCCGUGGUCUUUGAAUAAAGUCUGAGUGGGCGGC++A (140nt) tail | 52 |

TABLE 10-continued

Synthetic polynucleotides encoding a CRISPR related protein and synthetic sgRNA

| Description | Sequence | SEQ ID NO |
|---|---|---|
| mRNA sequence of dCas9-KRAB-miR122 | GGGAAAUAAGAGAGAAAAGAAGAGUAAGAAGAAAUAUAAGAGCCACCAUGGACAAGAAGUACUCAAUCGGACUCGCAAUCGGACC<br>AAUUCAGUCGGCUGGGCAGUCAUUACCGAUGAAUACAAGGUGCCGUCGAAGAAGUUCAAAGUCCUGGGUAACACUGACAGACAUUC<br>GAUCAAAAAGAACCUGAUCGGAGCCUUGCUGUUUGAUUCAGGCGAAACCGCCGAAGCUACCCGGUUGAAACGAACUGCUAGACGCC<br>GCUACACGCGCCGCAAGAACCGGAUCUGCUACCUCCAAGAAAUCUUCUCGAACGAAAUGGCUAAGGUGGACGACUCGUUCUUUCAC<br>CGGCUCGAGGGAGUCAUUCCUUGUGGAGGAAGAUAAGAAGCACGAAAGACACCCGAUCUUCGGCAACAUCGUGGACGAAGUCGCGUA<br>CCACGAAAAGUACCCGACUAUCUACCAUCUCCGGAAGAAGCUCGUGGAUAGCACCGAUAAGGCCGAUCUGCGACUGAUCUACCUCG<br>CGCUGGCCCAUAUGAUUAAGUUCCGCGGGCACUUCCUCAUCGAAGGGGACCUGAAUCCAGACAACUCGGACGUGGAUAAGCUGUUU<br>AUCCAGCUGGUGCAGACUUACAAUCAAUUGUUUGAAGAAAACCCUAUCAACGCGUCUGGGGUGGACGCAAAGGCCAUCCUGAGCGC<br>GCGGCUGUCAAAAUCCAGACGGCUGGAAAAUCUGAUAGCCCAACUGCCGGGCGAGAAGAAAAACGGCCUGUUUGGAAAUCUUAUCG<br>CCCUGUCCCUGGGACUGACCCCCAACUUCAAGUCGAACUUCGACUUGGCCGAGGAUGCGAAGCUCCAGCUCAGCAAAGACACCUAC<br>GACGAUGACCUCGAUAACCUGUUGGCCCAGAUCGGUGACCAGUAUGCUGAUCUCUUCUUGGCGGCCAAGAACCUGUCAGACGCAAU<br>UCUGCUCUCCGACAUCCUGCGGGUGAAUACUGAGAUCACUAAAGCCCCAUUGAGCGCGUCGAUGAUCAAAGAUACGACGAGCACC<br>ACCAGGAUCUGACUCUCCUCAAGGCACUGGUCCGCCAACAGCUCCCGGAAAAGUACAAAGAGAUCUUCUUUGACCAAUCCAAAAAC<br>GGAUACGCUGGUUACAUAGACGGCGGAGCGUCACAAGAAGGUCACAAGUUCAUCAAGCCUAUCCUGGAAAAGAUGGACGGGAC<br>CGAGGAACUCCUGGUUAAGCUCAAUAGGGAGGAUCUGCUGCGCAAGCAACGCACGUUCGACAAUGGAAGCAUCCCCCAUCAGAUCC<br>ACCUGGGGGAGCUCCACGCGAUCCUGAGGCGCCAGGAAGAUUUCUACCCAUUUCUGAAGGACAAUAGAGAGAAAAUCGAAAAGAUC<br>CUGACUUUCCGAAUCCCGUACUACGUGGGCCCGCUCGCACGGGAAACUCACGGUUUGCCUGGAUGACUCGCAAAUCCGAAGAAAC<br>CAUUUACCCCCGGAAUUUCGAGGAGGUGGUCGAUAAAGGCGCCUCAGCCCAGUCGUUCAUCGAAAAGAAUGACCAACUUUGACAAGA<br>ACCUCCCAAAUGAGAAGGUGCUGCCAAAACAUAGCCUGCUGUACGAGUACUUUACUGUGUAUAACGAACUCACCAAGGUGAAAUAC<br>GUGACCGAGGGAAUGCGCAAGCCGGCAUUUCUGUCGGGCGAACAGAAGAAGGCAAUUGUGGACUUGCUGUUCAAAACCAACCGGAA<br>GGUGACCGUGAAACAGCUCAAGGAAGAUUACUUUAAGAAGAUCGAGUGUUUCGAUAGCGUCGAAAUUUCGGGGGUGGAAGAUCGCU<br>UCAAUGCAAGCCUUGGGACGUACCACGAUCUCGUUAAGACAUUAAGGACAAGGAUUUCCUUGACAACGAAGAGACGAGGAUAUU<br>CUCGAGGAUAUCGUCCUGACCCUGACUCUGUUUGAGGAUAGAGAAAUGAUCGAGGAGAGAUUGAAAACUUACGCACACCUCUUCGA<br>CGAUAAGGUGAUGAAACAGCUGAAAAGGCGUAGAUACACUGGUUGGGGAAGGCUGUCGAGAAAGCUGAUCAACGGAAUUAGGGACA<br>AGCAGUCCGGAAAAACCAUCCUGGAUUUCCUCAAGUCCGACGGUUUCGCCAACCGCAACUUCAUGCAGCUGAUCCACGAUGAUUCC<br>CUGACGUUCAAAGAGGAUAUCCAGAAGGCACAAGUGUCCGACCAAGGAGACUCACUCCACGAGCAUAUCGCUAAUCUCGCCGGAUC<br>GCCAGCUAUCAAGAAGGGAAUCUUGCAGACUGUCAAGGUGGUGGACGAACUGGUGAAAGUGAUGGGAAGGCAUAAGCCGGAGAAUA<br>UCGUGAUCGAGAUGGCGAGGGAAAACCAGACGACCCAGAAAGGACAGAAAAACAGCCGGGAACGCAUGAAGCGCAUCGAAGAGGGA<br>AUCAAAGAGCUUGGGAGCAAAUCCUCAAGAACACCCUGUGGAAAAUACCCAACUGCAGAAUGAGAAGCUUUACCUGUAUUACCU<br>CCAAAACGGGCGCGACAUGUACGUUGACCAGGAAUUGGACAUUAAUCGGCUUUCCGACUACGAUGUGGACGCUAUCGUCCCGCAGU<br>CCUUCCUGAAAGACGAUUCGAUCGACAAUAAGGUCCUGACACGAAGUACAACAGACAAGAACGGGAAAGUCAGACAACGUGCCUAGCGAA<br>GAGGUCGUUAAGAAGAUGAAGAAUUACUGGCGCCAGCUGCUGAACGCGAAGCUUAUCACUCAGCGCAAGUUCGACAACCUCACCAA<br>GGCAGAAAGAGGCGGAUUGUCGGAGCUCGACAAAGCUGGCUUCAUCAAGCGCCAGCUCGUCGAAAUCUGCCAGAUUACUAAGCAUG<br>UGGCGCAGAUCCUGGACAGCCGCAUGAAUACUAAGUAUGAUGAGAAUGACAAGCUCAUCCGGGAGGUGAAGGUCAUCACCCUGAAG<br>UCCAAGCUGGUGUCCGACUUCCGGAAGGACUUCCAAUUCUACAAGGUCAGAGAAAUCAACAAUUUACCACUCCGACGAUGCGCCUA<br>CUUGAAUGCAGUGGUGGGUACUGCCCUCAUCAAGAAAUACCCAAAGCUUGAAAGCGAGUUUGUCUACGGAGACUACAAGGUGUACG<br>ACGUCCGAGAUGAUCGCCAAAUCGGAACAGGAAAUUGGGAAGGCGACCGCUAAGUACUUCUUCUACUCGAAUAUCAUGAAUUUC<br>UUCAAGACCGAGAUCACGCUUGCAAAUGGCGAAAUCCGGAAGCGGCCCCUCAUCGAAACCAACGGAGAAACCGGAGAAAUCGUGUG<br>GGACAAGGGUCGCGAUUUUGCGACCGUCCGCAAAGGUUCUUAGCAUGCCUCAAGUGAACAUCGUCAAGAAAACGGAAGUGCAGACUG<br>GAGGCUUCAGCAAGGAGUCCAUUCUCCCGAAACGCAACUCCGACAAACUGAUCGCACGCAAGAAAGACUGGGACCCGAAGAAAUAC<br>GGAGGCUUCGAUUCGCCGACUGUGGCUUACUCGGUCCUGGUUGUGGCCAAGGUGGAAAAGGGAAAGUCCAAGAAGCUGAAGUCCGU<br>CAAGGAGCUCCUCGGAAUCACCAUCAUGGAACGGUCAAGCUUCGAGAAAAACCCAAUUGACUUCCUGGAGGCAAAGGGGUACAAGG<br>AGGUGAAGAAGGACUGAUCAUCAAACUGCCGAAGUACUCACUCUUUGAGCUCGAAAAUGGACGGCAAAAGGGAAAUCUCUCCGCC<br>GGAGAGCUGCAAAAGGGAAACGAGCUUGCCUUGCCUUCCAAGUACUGAACUUCCUGUACCUGGCAUCCCACUACGAAAAACUGAA<br>GGGAUCGCCGGAGGACAACGAACAGAAGCAGCUGUUGUGGAACAACACAAGCAUUAUCUGGAUGAAAUCAUCGAACAAAUCAGCG<br>AAUUCUCAAAAAGGGUGAUCUUGGCCGACGCCAACCUGGAUAAAGUGCUUUCCGCCUACAACAAACAUCGCGACAAGCCGAUCCGG<br>GAGCAGGCCGAAAACAUCAUUCACCUGUUUACCCUGACUAAUCUGGGUGCGCCCGCGGCUUUCAAAUACUUCGAUACCACGAUCGA<br>CCGGAAGAGAUACACCAGCACCAAAGAGGUGUUGGACGCGACCCUCAUCCACCAAUCUAUUACCGGCUCUAUGAAACUAGGAUCG<br>ACCUCAGCCAGCUGGGAGGCGAUGCCUACCCUUACGAUGUCCCGGACUACGCCUCGCUGGGAUCCGGAUCUCCGAAGAAGAAGCGG<br>AAGGUCGAGGACCCAAAGAAAAAGCGCAAAGUGGAUGGGAUCGGUAGCGGUUCCAACGGUUCCUCGGGUGGCGGCGGAGGCGGCAU<br>GGAUGCUAAGUCACUUACCGCCUGGUCCGGCGACGUGGACCUGAAUCUCAAAGAUGUGUUCGUGGAUUUCACCCGGGAAGAGUGGAAAU<br>UGCUGGACACUGCCCAACAGAUCGUCUACCGCAACGUCAUGCUUGAAAACUACAAAAACCUCGUGUCGCUGGGAUAUCAGCUGACC<br>AAGCCCGACGUGAUUCUGAGACUGGAGAAGGGCGAAGAACCUUGAUAAUAGGCUGGAGCCUCGGUGGCCAUGCUUCUUGCCCCUUG<br>GGCCUCCCCCCAGCCCCUCCUCCCCUUCCUGCACCCGUACCCCCAAACACCAUUGUCACACUCCAGUGGUCUUUGAAUAAAGUCU<br>GAGUGGGCGGC+A(140nt) tail | 53 |
| mRNA sequence of dCas9-VP64-miR122 | GGGAAAUAAGAGAGAAAAGAAGAGUAAGAAGAAAUAUAAGAGCCACCAUGGACAAGAAGUACUCAAUCGGACUCGCAAUCGGACC<br>AAUUCAGUCGGCUGGGCAGUCAUUACCGAUGAAUACAAGGUGCCGUCGAAGAAGUUCAAAGUCCUGGGUAACACUGACAGACAUUC<br>GAUCAAAAAGAACCUGAUCGGAGCCUUGCUGUUUGAUUCAGGCGAAACCGCCGAAGCUACCCGGUUGAAACGAACUGCUAGACGCC<br>GCUACACGCGCCGCAAGAACCGGAUCUGCUACCUCCAAGAAAUCUUCUCGAACGAAAUGGCUAAGGUGGACGACUCGUUCUUUCAC<br>CGGCUCGAGGGAGUCAUUCCUUGUGGAGGAAGAUAAGAAGCACGAAAGACACCCGAUCUUCGGCAACAUCGUGGACGAAGUCGCGUA<br>CCACGAAAAGUACCCGACUAUCUACCAUCUCCGGAAGAAGCUCGUGGAUAGCACCGAUAAGGCCGAUCUGCGACUGAUCUACCUCG<br>CGCUGGCCCAUAUGAUUAAGUUCCGCGGGCACUUCCUCAUCGAAGGGGACCUGAAUCCAGACAACUCGGACGUGGAUAAGCUGUUU<br>AUCCAGCUGGUGCAGACUUACAAUCAAUUGUUUGAAGAAAACCCUAUCAACGCGUCUGGGGUGGACGCAAAGGCCAUCCUGAGCGC<br>GCGGCUGUCAAAAUCCAGACGGCUGGAAAAUCUGAUAGCCCAACUGCCGGGCGAGAAGAAAAACGGCCUGUUUGGAAAUCUUAUCG<br>CCCUGUCCCUGGGACUGACCCCCAACUUCAAGUCGAACUUCGACUUGGCCGAGGAUGCGAAGCUCCAGCUCAGCAAAGACACCUAC<br>GACGAUGACCUCGAUAACCUGUUGGCCCAGAUCGGUGACCAGUAUGCUGAUCUCUUCUUGGCGGCCAAGAACCUGUCAGACGCAAU<br>UCUGCUCUCCGACAUCCUGCGGGUGAAUACUGAGAUCACUAAAGCCCCAUUGAGCGCGUCGAUGAUCAAAGAUACGACGAGCACC<br>ACCAGGAUCUGACUCUCCUCAAGGCACUGGUCCGCCAACAGCUCCCGGAAAAGUACAAAGAGAUCUUCUUUGACCAAUCCAAAAAC<br>GGAUACGCUGGUUACAUAGACGGCGGAGCGUCACAAGAAGGUCACAAGUUCAUCAAGCCUAUCCUGGAAAAGAUGGACGGGAC<br>CGAGGAACUCCUGGUUAAGCUCAAUAGGGAGGAUCUGCUGCGCAAGCAACGCACGUUCGACAAUGGAAGCAUCCCCCAUCAGAUCC<br>ACCUGGGGGAGCUCCACGCGAUCCUGAGGCGCCAGGAAGAUUUCUACCCAUUUCUGAAGGACAAUAGAGAGAAAAUCGAAAAGAUC<br>CUGACUUUCCGAAUCCCGUACUACGUGGGCCCGCUCGCACGGGAAACUCACGGUUUGCCUGGAUGACUCGCAAAUCCGAAGAAAC | 54 |

TABLE 10-continued

Synthetic polynucleotides encoding a CRISPR related protein and synthetic sgRNA

| Description | Sequence | SEQ ID NO |
|---|---|---|
| | CAUUACCCCCUGGAAUUUCGAGGAGGUGGUCGAUAAAGGCGCCUCAGCCCAGUCGUUCAUCGAAAGAAUGACCAACUUUGACAAGA ACCUCCCAAAUGAGAAGGUGCUGCCAAAACAUAGCCUGCUGUACGAGUACUUUACUGUGUAUAACGAACUCACCAAGGUGAAAUAC GUGACCGAGGGAAUGCGCAAGCCGGCAUUUCUGUCGGGCGAACAGAAGAAGGCAAUUGUGGACUUGCUGUUCAAAACCAACCGGAA GGUGACCGUGAAACAGCUCAAGGAAGAUUACUUUAAGAAGAUCGAGUGUUUCGAUAGCGUCGAAAUUUCGGGGGUGGAAGAUCGCU UCAAUGCAAGCCUUGGGACGUACCACGAUCUGCUUAAGAUCAUUAAGGACAAGGAUUUCCUUGACAACGAAGAGAACGAGGAUAUU CUCGAGGAUAUCGUCCUGACCUGUGUUUGAGGAUAGAGAAAUGAUCGAGGAGAGAUUGAAAACUUACGCACACCUCUUCGA CGAUAAGGUGAUGAAACAGCUGAAAAGGCGUAGAUACACUGGGUUGGGGAAGGCUGUCGAGAAAGCUGAUCAACGGAAUUAGGGACA AGCAGUCCGGAAAAACCAUCCUGGAUUUCCUCAAGUCCGACGGUUUCGCCAACCGCAACUUCAUGCAGCUGAUCCACGAUGAUUCC CUGACGUUCAAGAGGAUAUCCAGAAGGCACAAGUGUCCGGACAAGGAGACUCACUCCACGAGCAUAUCGCUAAUCUCGCCGGAUC GCCAGCUAUCAAGAAGGGAAUCUUGCAGACUGUCAAGGUGGUGGACGAACUGGUGAAAGUGAUGGGAAGGCAUAAGCCGGAGAAUA UCGUGAUCGAGAUGGCGAGGGAAAACCAGACGACCCAGAAAGGACAGAAGAACAGCCGGGAACGCAUGAAGCGCAUCGAAGAGGGA AUCAAAGAGCUUGGGAGCCAAAUCCUCAAAGAACACCCUGUGGAAAAUACCCAACUGCAGAAUGAGAAGCUUUACCUGUAUUACCU CCAAAACGGGCGCGACAUGUACGUGACCAGGAAUUGGACAUUAACCGGCUUUCCGACUACGAUGUGGACGCUAUCGUCCCGCAGU CCUUCCUGAAAGACGAUUCGAUCGACAAUAAGGUCCUGACUAGAUCAGACAAGAAUCGGGGAAAGUCAGACAACGUGCCUAGCGAA GAGGUCGUUAAGAAGAUGAAGAAUUACUGGCGCCACUCGCCGAAGCUUAUCACUCAGCGCAAGUUCGACAACCUCACCAA GGCAGAAAGAGGCGGAUUGUCGGAGCUCGACAAAGCUGGCUUCAUCAAGCGCCAGCUCGUCGAAACUCGCCAGAUUACUAAGCAUG UGGCGCAGAUCCUGGACAGCCGCAUGAAUACUAAGUAUGAUGAGAAUGACAAGCUCAUCCGGGAGGUGAAGGUCAUCACCCUGAAG UCCAAGCUGGUGUCCGACUUCCGGAAGGACUUCCAAUUCUACAAAGUCAGAGAAAUCAACAAUUACCAUCACGCGCAUGACGCCUA CUUGAAUGCAGUGGUGGGGUACUGCCCUCAUCAAGAAAUACCCAAAGCUUGAAAGCGAGUUUGUCUACGGAGACUACAAGGUGUACG ACGUCCGGAAGAUGAUCGCCAAAUCGGAACAGGAAUUGGAAGGCGACCGCUAAGUACUUCUUCUACUCGAAUAUCAUGAAUUUC UUCAAGACCGAGAUCACGCUUGCAAAUGGCGAAAUCCGGAAGCGGCCCCUCAUCGAAACCAACGGAGAAACCGGAGAAAUCGUGUG GGACAAGGGUCGCGAUUUUGCGACCGUCCGAAAGGUUCUUAGCAUGCCUCAAGUGAACAUCGUCAAGAAAACGGAAGUGCAGACUG GAGGCUUCAGCAAGGAGUCCAUUCUCCCGAAACGCAACUCCGACAAACUGAUCGCACGCAAGAAGGACUGGGACCCGAAGAAAUAU GGAGGCUUCGAUUCGCCGACUGUGGCUUACUCGGUCCUGGUUGUGGCCAAGGUGGAAAAGGGAAAGUCCAAGAAGCUGAAGUCCGU CAAGGAGCUCCUCGGAAUCACCAUCAUGGAACGGUCAAGCUUCGAGAAAAACCCAAUUGACUUCCUGGAGGCAAAGGGGUACAAGG AGGUGAAGAAGGAUCUGAUCAUCAAACUGCCGAAGUACAGCCUCUUUGAGCUCGAAAACGGACGCAAAAGGAUGCUGGCCUCCGCC GGAGAGCUGCAAAAGGGAAACGAGCUUGCCUUGCCUCUUCAAAGAUACGAUUUCUCGUUGUACCUGGCAUCCCACUACGAAAACCUGAA GGGAUCGCCGGAGGACAACGAACAGAAGCAGCUGUUUGUGGAACAACACAAGCAUUAUCUGGAUGAAAUCAUCGAACAAAUCAGCG AAUUCUCAAAAAGGGUGAUCUUGGCCGACGCCAACCUGGAUAAAGUGCUUUCCGCCUACAACAAAACAUCGCGACAAGCCGAUCCGG GAGCAGGCCGAAAACAUCAUUCACCUGUUUACCCUGACUAAUCUGGGUGCGCCCGCGGCUUUCAAAUACUUCGAUACCACGAUCGA CCGGAAGAGAUACACCAGCACCAAAGAGGUGUUGGACGCGACCCUCAUCCACCAAUCUAUUACCGGCCUCUAUGAAACUAGGAUCG ACCUCAGCCAGCUGGGAGGCGAUGGAUCCCCAAAGAAGAAGAGGAAAGUGUCCUCGACUACAAGGACCAUGAUGGACUAUAAA GAUCAUGAUAUUGAUUACAAGGACGACGACGACAAGGCCGCUGGAGGAGGAGGUUCCGGCGCGCCGAUGCUCUCGACGACUUCGA CCUCGACAUGCUGGGAUCCGACGCCCUGGACGACUUUGAUCUGGAUAUGCUGGGCUCGGACGCCCUUGAUGACUUCGAUCUGGACA UGCUGGGGUCGGAUGCACUGGACGACUUCGACCUUGAUAUGCUGUGAUAAUAGGCUGGAGCCUCGGUGGCCAUGCUUCUUGCCCCU UGGGCCUCCCCCAGCCCCUCCUCCCCUUCCUGCACCCGUACCCCCCAAACACCAUUGUCACACUCCAGUGGUCUUUGAAUAAAGU CUGAGUGGGCGGC+A(140nt) tail | |
| mRNA sequence of Cas9 (Mali) | GGGAAAUAAGAGAGAAAAGAAGAGUAAGAAGAAAUAUAAGAGCCACCAUGGACAAGAAAUACAGCAUCGGCCUGGAUAUUGGAACU AACAGCGUUGGAUGGGCAGUGAUCACCGACGAGUACAAGGUGCCGAGCAAGAAGUUCAAGGUGCUGGGGAACACUGACCGCCAUUC AAUUAAGAAAAACCUCAUUGGAGCACUGCUUUUUGACUCGGGGACUGCUGAAGCUACCAGGCUCAAACGCACCGCACGUAGAC GGUACACCCGCCGAAAGAAUCGCAUCUGCUAUCUGCAAGAGAUCUUUUCCAACGAGAUGGCAAGGUUGACGACAGCUUUUUCCAC CGGCUGGAAGAGAGCUUCCUCGUGGAAGAGGACAAAAAGCACGAAAGGCAUCCAACUUCGGUAACAUCGUGGACGAAGUGGCGUA UCACGAAAAGUACCCUACCAUCUACCAUCUGCGGAAGAAGCUGGUCGAUUCCACGGAUAAGGCAGACCUGAGGCUGAUCUACCUGG CUUUGGCCCAUAUGAUCAAAUUCCGCGGCCAUUUCCUGAUCGAGGGGGACCUUAACCCGGAUAAUCGGAUGUCGACAAGCUGUUC AUCCAGCUGGUCCAAACGUAUAACCAACUGUUUGAGGAAAAUCCCAUCAACGCUUCGGGGGUGGACGCCAAGCAAUCCUCUCCGC GCGCCUGAGCAAGUCACGGCGGCUCGAAAACCUGAUCGCGCAGCUGCCGGGAGAAAAGAAAAAUGGACUGUUUGGGAAUCUGAUCG CGCUGUCGCUCGGCCUGACUCCCAAACUUUAAGUCAAAUUUCGACCUGGCCGAAGAUGCCAAGCUGCAGCUGUCAAAGGACACUUAC GACGACGACCUGGACAACUUGCUGGCCCAGAUUGGGGACCAAUACGCAGACCUGUUUGGCGCGAAGAACCUGAGCGACGCCAU UCUUCUGUCCGAUAUUCUGAGAGUCAAUACCGAAAUCACUAAGGCUCCGCUGUCCGCUUCAUGAUCAAGCGCUACGAUGAACACACC ACCAGGAUCUCACUCUGCUCAAAGCCCUCGUGAGACAACAAUUGCCUGAAAAGUACAAGGAGAUCUUCUUCGACCAGAGCAAAAC GGCUACGCAGGCUACAUCGAUGGAGGAGCGUCAAGAAGAGUAAGAGUAAGUACAAGAGCAAGUACAAGAGCAAGGUGGACUC UGAAGAACUCCUUGUGAAGCUGAAUAGGGAGGAUUUGCUCAGAAAGCAGCGGACUUUUGACAACGGCUCGAUCCCUCAUCAGAUUC ACCUCGGUGAGCUGCAUGCCAUCCUUCGGCGCCAAGAGGAUUUUUACCCCCUUCCUGAAGGAUAAUCGCGAGAAAAUCGAAAAGAUC CUGACGUUCAGAAUUCCCUACUACGUGGGACCGCUGGCGCGCGGGUAACUCGCGGUUUGCAUGGAUGACUCGCAAGUCAGAGGAAAC UAUCACUCCUUGGAAUUUUGGAGGCUGUCGUCGUAAAGGGAGCCUCGCCCAGCAUCAUCGAACGCAUGACCAACUUCGACAAGA AUCUUCCGAACGAGGUCCUUCCAAAGCACUCCCUGUUGUACGAAUACUUCACCGUGUACAAUGAGCUGACAAAGGUUAAGUAU GUCACCGAGGGCAUGAGAAAGCCGGCCUUCCUCAGCGGCGAACAAAAGAAGGCCAUCGUCGACCUCCUCUUCAAGACCAACCGGAA GGUGACCGUCAAGCAACUCAAGGAGGACUACUUCAAGAAGAUCGAAUGCUUUGACUCGGUCGAAAUCAGCGGAGUGGAGGACCGGU UUAACGCGUCACUGGGACUACCAUGAUCUCCCUGAAAAUCAUCAAAGACAAGGACUUCCUGGACAACGAAGAAAACGAGGACAUC CUGGAAGAUAUUGUGUUGACCCUGACCCUGUUUGAGGACCGGGAAAUGAUCGAGGAAGCGCUUAAGACCUACGCACACCUCUUCGA UGACAAAGUGAUGAAGCAACUGAAGCGGCGGAGAUAUACUGGUGGGGAGGCUCUCCGGAAGCUCAUUAAUGGAAUCAGAGACA AACAGUCGGGUAAACUAUCCUCGACUUCCUCAAGUCGAUGGGUUCGCCAACCGGAACUUCAUGCAGCUGAUCCACGAUGAUUCC UUGACCUUCAAGGAAGAUAUCCAGAAGGCGCAAGUGAGCGGACAGGGAGAUUCGUUGCACGAACAUAUCGCUAAUCUCGCCGGAUC CCCAGCUAUCAAGAAGGGAAUCCUGCAGACCGUGAAGGUGGUGGAUGAACUGGUGAAAGUGAUGGGCCGCACAAACCGAGAGAAU CGUCAUUGAUGGCCCGCGAGAAUCAGACCACUCAGAAAGGACAAAGAACUCCAGAGAGCGAUGAAACGCAUCGAGGAAGGC AUCAAAGAGCUUGGUAGCCAAAUCCUGAAGGAACACCCCGGUCGAGAACACCCAGCUCCAGAACGAAAGCUUUACCUGUACUACCU CCAAAAUGGACGGGACAUGUACGUCGACCAGGAAUUGGACAUCAACAGACUCAGCGACUACGAUGUGGACCAUAUUGUGCCACAGU CCUUUCUUAAGGACGACAGCAUCGACAACAAGGUCCUGACUAGAUCAGACAAAAAUCGCGGGAAAUCAGACAAUGUGCCAUCGGAA GAGGUUGUCAAGAAGAUGAAAAACUACUGGAGACAGCUGCUCAAUGCCAAACUUAUCACCCAGCGGAAGUUCGACAACCUUACCAA GGCCGAGCGCGGAGGAUUGUCGGAACUCGACAAGGCCGGCUUCAUCAAAGGCAGCUGGUGGAAACCCGGCAGAUCACUAAACACG UGGCCCAGAUCCUGGAUUCGCGCAUGAACACUAAAUACGAUGAGAAUGACAAGCUGAUUAGGGAAGUCAAGGUCAUCACUCUGAAG UCGAAACUGGUGUCGGACUUUAGAAAGGAUUUCCAGUUCUACAAAGUCCGCGAGAUUAACAACUACCACCACGCUCAUGACGCCUA CCUGAAUGCAGUUGUGGGCACCGCGCUGAUCAAGAAGUAUCCGAAGCUGGAAUCCGAGUUCGUGUACGGAGAUUACAAAGUGUACG | 55 |

TABLE 10-continued

Synthetic polynucleotides encoding a CRISPR related protein and synthetic sgRNA

| Description | Sequence | SEQ ID NO |
|---|---|---|
| | ACGUGCGCAAGAUGAUCGCCAAGUCGGAACAGGAAAUCGGAAAGGCUACUGCAAAGUACUUCUUCUACUCAAACAUCAUGAACUUC UUCAAAACGGAGAUCACGCUCGCGAACGGCGAAAUCCGGAAAAGGCCGCUCAUUGAAACCAACGGAGAAACCGGGGAGAUCGUGUG GGACAAGGGAAGGGAUUUUGCGACUGUGAGGAAGGUGUUGUCCAUGCCGCAAGUCAAUAUUGUGAAAAAGACGGAAGUGCAAACCG GAGGAUUCAGCAAAGAAUCCAUCCUCCCAAAGCGCAACUCGGACAAACUCAUCGCGCGCAAGAAGGAUUGGGACCCCAAGAAAUAC GGUGGCUUUGACAGCCCUACUGUGGCUUACUCCGUCUCGUCGUGGCUAAAGUGGGAAAAGGGUAAAUCCAAAAAGCUCAAAUCGGU GAAGGAGCUCCUGGGAAUCACGAUCAUGGAGCGGCUCGAGCUUCGAAAAGAAUCCUAUUGAUUUCCUGGAGGCGAAGGGCUACAAGG AAGUCAAGAAAGACCUGAUCAUCAAGCUCCCGAAGUACAGCCUCUUCGAGCUCGAAAACGGCAGAAAGAGGAUGCUGGCAUCAGCG GGAGAAUUGCAGAAGGGAAACGAACUGGCACUGCCGUCCAAGUACGUGAAUUUUCUCUAUCUGGCUAGCCACUACGAAAAGCUGAA GGGAUCGCCCGAGGACAACGAGCAAAAACAACUGUUCGUGGAGCAGCACAAGCACUACCUGGAUGAGAUCAUCGAGCAGAUCUCCG AAUUCUCGAAACGCGUUGACCUUGCCGAUGCCAAUCUGGAUAAAGUGUUGGCUGGCUAUUACAACAAGCUGGGAUAAACCGAUCCGC GAACAGGCAGAAAACAUCAUUCAUCUGUUCACUUUUGACCAAUCUGGGAGCGCCUGCCGCGUUUAAGUACUUCGACACCACUAUUGA UAGAAAGCGCUACACCCUCGACCAAGGAAGUGCUGGACGCUACCCUGAUCCACCAGUCCAUCACCGGACUCUACGAAACUCGCAUUG ACCUGUCCCAGCUUGGAGGAGAUUCACGGGCCGAUCAAAGAAAAAGCGCAAGGUCUGAUAAUAGGCUGGAGCUCGGUGGCCAUG CUUCUUGCCCCUUGGGCCUCCCCCCAGCCCCUCCUCCCCUUCCUGCACCCGUACCCCCGUGGGUCUUUGAAUAAAGUCUGAGUGGGC GGC | |
| mRNA sequence of Cas9 (Cong) | GGGAAAUAAGAGAGAAAAGAAGAGUAAGAAGAAAUAUAAGAGCCACCAUGGACUACAAGGACCACGACGGAGACUACAAAGACCAU GACAUCGAUUACAAGGAUGACGAUGACAAAAUGGCACCGAAGAAGAAGAGAAAGGUCGAAUUCACGGGGUGCCGGCCGCGGACAA GAAGUACUCAAUCGGACUGGAUAUCGGCACGAACAGCGUGGGUUGGGCAGUGAUCACCGACGAAUACAAGGUGCCGAGCAAGAAGU UCAAAGUGCUGGGAAAUACCGAUCGCCAUUCGAUCAAGAAAAAUCUGAUUGGCGCGCUCCUGUUCGACUCGGGAGAGACUGCCGAG GCCACUAGACUGAAGAGGACCGCUAGGCGCCGCUACACGAGGCGCAAAAACCGCAUCUGCUAUCUUCAAGAAAUCUUCUCAAACGA GAUGGCCAAGGUGGACGACUCCUUUUUCCAUCGGCUGGAAGAAUCAUUCUUGGUGGAGGAGGACAAGAAGCACGAACGCCAUCCCA UUUUCGGCAACAUUGUCGACGAAGUGGCCUAUCAUGAGAAGUAUCCGACUAUCUACCACUUGAGAAGAAGCUGGUGGACUCCACU GACAAGGCAGAUCUGCGGUUGAUCUACCUCGCACUGGCCCAUAUGAUCAAAUUCCGGGGACACUUCCUCAUCGAGGGCGACCUUAA UCCCGACAAUUCCGAUGUGGAUAAAGCUUUUCAUCAGCUGGUCCAGACCUACAACCAACUGUUUGAAGAAAAUCCAAUCAAUGCGA GCGGUGUCGAUGCAAAGGCCAUCCUGAGCGCCCGCCUCUCGAAAAGCAGAAGGCUCGAAAACCUGAUCGCACAGUUGCCUGGAGAG AAGAAGAACGGCCUCUUCGGCAAUCUCAUCGCAUUGUCCCUGGGACUGACUCCAAACUUCAAAUCCAACUUCGACUUGGCCGAGGA CGCCAAACUGCAACUGAGCAAAGAUACCUACGAUGAUGACUUGGACAAUCUUUGGCUCAGAUCGGCGACCAGUACGCCGACCUGU UCCUUGCGGCUAAGAACCUGUCGGACGCCAUCCUGCUGUCCGACAUCCUGCGCGUCAAUACCGAAAUUACUAAAGCACCACUCUCG GCAUCCAUGAUCAAGAGAUACGAUGAACACCACCAGGAUCUCACCCUCCUGAAAGCACUGGUGCGGCAGCAGCUCCCUGAGAAAUA CAAGGAAAUCUUCUUUGACCAGUCCAAGAACGGAUACGCAGGCUACAUCGACGGCGGCGCCAGCAAGGAGAAUUCUACAAGUUCA UCAAGCCGAUCCUGGAAAAGAUGGAUGGCACGGAAGAACUCCUGGUCAAACUGAAUAGAGAGGAUCUGCUCCGCAAACAACGGACC UUCGAUAACGGAUCGAUCCCGCACCAGAUCCACCUCGGCGAACUGCAUGCCAUCCUGCGCCGGCAGGAGGACUUUUACCCGUUCCU CAAAGACAACAGAGAAAAGAUCGAGAAGAUCUUGACCUUUCGCAUCCCGUACUACGUGGGCCCGCUCGCGAGAGGUAACUCCCGCU UUGCUUGGAUGACUAGAAAGUCAGAGGGAAACGAUACACCCCAUGGAACUUCGAAGAGGUGGUUGACAAAGGAGCGAGCGCCCAAUCG UUCAUCGAACGGAUGACUAACUUCGAUAAGAAUCUGCCGAAUGAGAAGGUCCUGCCCAAGCACUCACUUCUGUAUGAAUACUUUAC UGUGUAUAACGAACUCACCAAAGUCAAAUACGUGACUGAGGGAAUGCGCAAGCCUGCGUUUUGUCCGGCGAGCAGAAAAAGGCCA UCGUGGACUUGCUGUUCAAAACCAACCGCAAGGUGACGUUAAGCAACUCAAAGAGGACUACUUUAAGAAGAUCGAAUGCUUUGAC UCGGUCGAGAUUUCCGGGGUUGAAGAUAGAUUCAACGCGUCGCUGGGAACCUACCAUGAUCUCCUCAAGAUUAUCAAGGACAAAGA CUUCCUGGAUAACGAGGAGAAUGAGGACAUCCUGGAAGAUAUUGUGCUUACCCUGACCCUUUUCGAAGAUCGCGAAAUGAUCGAAG AACGCCUGAAAACCUACGCGCUCACCUGUCGACGAUAAGGUGAUGAAACAGUUGAAACGCCGCCGGUACACGGGUUGGGGCCGGCUG UCGCGCAAGCUGAUCAACGGAAUUCGGGACAAACAGAGCGGAAAGACCAUCCUCGAUUUUCUGAAGUCCGAUGGUUUUGCCAACCG CAACUUCAUGCAGCUCAUCCAUGACGAUUCGCUUACCUUUAAGGAGGAUAUCCAGAAGGCACAAGUGUCGGGACAAGGGGAUUCGC UCCACGAACACAUCGCCAAUCUGGCGGGGUCGCCGGCAAUUAAGAAGGGAAUCCUCCAGACUGUUAAGGUGGUCGACGAGCUGGUG AAGGUGAUGGGGAGACAUAAGCCUGAAACAUUGUGAUCGAGAUGGCGAGAGAAAAUCAAACUACUCAGAAGGGACAGAAGAAUUC CCGGGAGCGGAUGAAGCGCAUCGAGGAGGGAAUCAAGGAACUGGGCUCCCAAAUCCUGAAGGAGCAUCCCGUGGAAAAUACUCAGC UGCAGAACGAGAAGCUUUACCUGUACUAUCUUCAAAAUGGCAGGGACAUGUACGUCGACCAAGAACUGGAUAUCAAUCGGCUCUCC GAUUACGACGUCGAUCACAUCGUCCCCCAAUCAUUCCUGAAGGAUGAUAGCAUCGAUAACAAGGUGCUCACUGAUCAGACAAAAA CCGGGGAAAGUCAGAUAACGUCCCCAGCGAAGAAGUCGUGAAGAAGAUGAAGAAUUACUGGAGGCAACUUCUGAACGCCAAACUCA UCACUCAGCGCAAGUUCGACAACCUGACCAAAGCAGAAAGGGGAGGACUCAGCGAGCUGGACAAGGCUGGUUUCAUCAAACGGCAG CUGGUGGAGACUCGCCAAAUCACGAAGCAUGUGGCCCAGAUUCUCGACUCGCGCAUGAAUACUAAGUACGACGAAAAUGAUAAGCU GAUCCGGGAGGUGAAGGUGAUCACCCUCAAGAGCAAGCUCGUGUCCGAUUUCCGGAAAGACUUCCAGUUCUACAAGGUGCGGGAGA UUAACAACUACCAUCACGCUCACGACGCUUACCUCAAUGCUGUGGUGGGACGGCGUUGAUUAAGAAGUACCCAAAACUGGAGUCC GAAUUCGUCUACGGAGAUUACAAGGUCUACGACGUGCGCAAGAUGAUUGCCAAGUCGGAGCAGGAAAUUGGGAAAGCGACUGCUAA GUACUUCUUCUACUCGAAUAUCAUGAACUUCUUCAAGACCGAAAUCACCCUGGCUAACGGCGAGAUCAGGAAACGGCCGCUGAUCG AAACUAAUGGUGAGACUGGUGAAAUCGUGUGGGAUAAGGGACGGGACUUCGCCACGGUCCGCAAGGUCCUCAGCAUGCCGCAAGUG AAUAUUGUAAAGAAAACCGAGGUCCAGACCGGGGUUUCCAGGAGAACAUCAUCCUGCCAAAGCGCAACUCUGAUAAGCUUAUUGC CCGCAAGAAGGAUUGGGACCCGAAAAAGUACGGUGGGUUCGACUCCCCUACCGUGGCGUACUCGGUGUUGGUGGUGCAAAGUGG AAAAGGGCAAAUCAAAGAAGCUCAAGAGCGUCAAGGAGCUGUGGGAAUCACCAUCAUGGAGAGGUCCAGCUUUGAGAAAACCCCG AUCGACUUCUUGGAAGCCAAGGGAUACAAAGAGGUGAAGAAAGACCUGAUCAUCAAAUUCCAAAGUACUCCCUGUUCGAACUCGA AAACGGGAGGAAGCGCAUGCUCGCCUCAGCCGGGAACUGCAAAAGGGCAACGAACUGGCCCUCCCGUCAAAAUACGUCAACUUCC UGUACUUGGCGUCACACUACGAGAAGCUGAAAGGAUCCCCAGAGGACAACGAGCAAAAGCAACUGUUCGUCGAGCAGCACAAGCAC UACCUGGACGAGAUCAUCGAACAGAUCUCGGAAUUCAGCAAGAGAGUGAUCUUGGCAGACGCUAACCUGAACAAGUCCUCUCGGC AUACAAUAAGCAUCGCGACAAGCCGAUCAGAGAACAGGCGGAGAACAUCAUCCACCUGUUCACUCUCACCAACCUGGGCGCGCCAG CGGCUUUUAAGUACUUUGAUACCACCAUUGACCGCAAGAGAUACACCUCAACUAAAGAAGUGCUGGACGCAACCCUGAUCCAUCAA AGCAUCACCGGACUUUAUGAAACUCGGAUCGAUCUCUCACAGCUCGGAGGAGACAAAAGACCGGCUGCCACCAAGAAGGCCGGACA GGCAAAGAAGAAGAAAUGAUAAUAGGCUGGAGCCUCGGUGGCCAUGCUUCUUGCCCCUUGGGCCUCCCCCCAGCCCCUCCUCCCCU UCCUGCACCCGUACCCCCGUGGGUCUUUGAAUAAAGUCUGAGUGGGCGGC | 56 |

TABLE 11

Synthetic sgRNA

| Description | Sequence | SEQ ID NO: |
|---|---|---|
| VEGF V1 sgRNA | GGGUGUGCAGACGGCAGUCACUAGGGUUUUAGAGCUAGAAAUAGCAAGUUAAAAUAAGGCUAGUCCGUUAUCAACUUGAAAAAGUGGCACCGAGUCGGUGC | 91 |
| VEGF V2 sgRNA | GGGUGAGUGAGUGUGUGCGUGUGGGUUUUAGAGCUAGAAAUAGCAAGUUAAAAUAAGGCUAGUCCGUUAUCAACUUGAAAAAGUGGCACCGAGUCGGUGC | 92 |
| VEGF V3 sgRNA | GGGUGAGUGAGUGUGUGCGUGUGGGUUUUAGAGCUAGAAAUAGCAAGUUAAAAUAAGGCUAGUCCGUUAUCAACUUGAAAAAGUGGCACCGAGUCGGUGC | 93 |
| VEGF V4 sgRNA | GGGUUGGAGCGGGGAGAAGGCCAGGGUUUUAGAGCUAGAAAUAGCAAGUUAAAAUAAGGCUAGUCCGUUAUCAACUUGAAAAAGUGGCACCGAGUCGGUGC | 94 |
| basic sgRNA template is based on Gilbert, Qi, Maeder, | GGGNNNNNNNNNNNNNNNNNNNNNNNNNNNGUUUUAGAGCUAGAAAUAGCAAGUUAAAAUAAGGCUAGUCCGUUAUCAACUUGAAAAAGUGGCACCGAGUCGGUGGUGC | 90 |

TABLE 12

Additional Sequences as deposited in Addgene database (plasmid repository, Cambridge, MA)

| Gene/Insert | Species | Plasmid Name | Mutation | Purpose |
|---|---|---|---|---|
| dCas9 (bacteria) | *S. pyogenes* | Plasmid 44249: pdCas9-bacteria | D10A H840A (catalytically inactive) | aTc-inducible expression of a catalytically inactive bacterial Cas9 (*S. pyogenes*) for bacterial gene knockdown |
| Cas9 | N/A | Plasmid 41815: hCas9 | human codon-optimized | Expresses human codon optimized Cas9 nuclease for genome engineering |
| Human codon optimized Cas9 | N/A | Plasmid 44758: pST1374-NLS-flag-linker-Cas9 | codon-optimized | Expresses human codon optimized Cas9 nuclease for genome engineering |
| Cas9_D10A | N/A | Plasmid 41816: hCas9_D10A | human codon-optimized, D10A nickase | Expresses human codon optimized Cas9 D10A mutant which functions as a nickase for genome engineering |
| dead Cas9 with 3X NLS | *H. sapiens* (human) | Plasmid 44246: pdCas9-humanized | D10A H840A (catalytically inactive) | Expression of a catalytically inactive, human codon-optimized Cas9 under the control of Murine Stem Cell retroVirus LTR promoter for mammalian gene knockdown |
| guide RNA (bacteria) | N/A | Plasmid 44251: pgRNA-bacteria | N/A | Expression of customizable guide RNA (gRNA) for bacterial gene knockdown |
| dCas9 fused to BFP | *H. sapiens* (human) | Plasmid 44247: pdCas9::BFP-humanized | D10A H840A | Expression of a catalytically inactive, human codon-optimized Cas9-BFP fusion under the |

TABLE 12-continued

| Additional Sequences as deposited in Addgene database (plasmid repository, Cambridge, MA) | | | | |
|---|---|---|---|---|
| Gene/Insert | Species | Plasmid Name | Mutation | Purpose |
| wild-type Cas9 | S. pyogenes | Plasmid 44250: pwtCas9-bacteria | N/A | control of Murine Stem Cell retroVirus LTR promoter for mammalian gene knockdown aTc-inducible expression of wild-type Cas9 (S. pyogenes) for bacterial gene knockdown |
| guide RNA | H. sapiens (human) | Plasmid 44248: pgRNA-humanized | N/A | Expression of customizable guide RNA (gRNA) under cotnrol of murine U6 promoter, also contains a CMV-puro-t2A-mCherry expression cassette for mammalian gene knockdown |
| Codon optimized Cas9 | N/A | Plasmid 45945: pHsp70-Cas9 | Silent change from C to A at bp 834 of insert | The codon-optimized Cas9 nuclease under the control of the Drosophila hsp70 promoter used in Gratz, et al. (2013). Plasmid is low copy number. |
| Csy4 | Pseudomonas aeruginosa | Plasmid 41091: pHMGWA-Pa14Csy4 | Wild type | |
| Csy4 | Pseudomonas aeruginosa | Plasmid 41092: pHMGWA-Pa14Csy4H29A | His29Ala mmutation to abolish ribonuclease activity | |
| mammalian codon-optimized Streptococcus pyogenes Cas9 - 3X Flag | Streptococcus pyogenes | Plasmid 43861: JDS246 | | Expresses mammalian codon optimized Cas9 nuclease with C-term 3X FLAG from CMV and T7 promoters |
| Streptococcus pyogenes Cas9 | Streptococcus pyogenes | Plasmid 42251: MLM3613 | | Expresses Cas9 nuclease (Streptococcus pyogenes) from CMV and T7 promoters |
| None | | Plasmid 43860: MLM3636 | | guide RNA (gRNA) expression vector used to create a gRNA to a specific sequence, uses U6 promoter |
| Streptococcus pyogenes Cas9-3X Flag | | Plasmid 42252: MLM3639 | | |
| Cas9 | Streptococcus thermophilus | Plasmid 39314: pMJ824 | | |
| Cas9 | Listeria innocua | Plasmid 39313: pMJ823 | | |
| Cas9 | Streptococcus pyogenes | Plasmid 39312: pMJ806 | | |
| Cas9 | Streptococcus pyogenes | Plasmid 39315: pMJ825 | | |
| Cas9 | Streptococcus pyogenes | Plasmid 39316: pMJ826 | | |
| Cas9 | Neisseria meningitidis | Plasmid 39317: pMJ839 | | |

TABLE 12-continued

Additional Sequences as deposited in Addgene database (plasmid repository, Cambridge, MA)

| Gene/Insert | Species | Plasmid Name | Mutation | Purpose |
|---|---|---|---|---|
| Cas9 | Streptococcus pyogenes | Plasmid 39318: pMJ841 | Aspartate 10 to Alanine (D10A) and Histidine 840 to Alanine (H840A) | |
| Cas9 | S. pyogenes | Plasmid 43945: p3s-Cas9HC | | |
| Human Optimized S. pyogenes Cas9 | H. sapiens (human), S. cerevisiae (budding yeast); S. pyogenes | Plasmid 43802: p414-TEF1p-Cas9-CYC1t | | |
| Human Optimized S. pyogenes Cas9 | H. sapiens (human), S. cerevisiae (budding yeast); S. pyogenes | Plasmid 43804: p415-GalL-Cas9-CYC1t | | |
| CAN1.y gRNA | S. cerevisiae (budding yeast) | Plasmid 43803: p426-SNR52p-gRNA.CAN1.Y-SUP4t | | |
| codon optimized Cas9 | | Plasmid 46294: pBS-Hsp70-Cas9 | Silent change from C to A at bp 834 of insert | A codon-optimized Cas9 nuclease under the control of the Drosophila hsp70 promoter. |
| tracr/Cas9 | | Plasmid 42876: pCas9 | | Bacterial expression of Cas9 nuclease, tracrRNA and crRNA guide |
| Cas9-2A-GFP | Synthetic | Plasmid 44719: pCas9_GFP | | Co-expression of human codon-optimized Cas9 nuclease and GFP, plasmid optimized for expression in human pluripotent stem cells |
| Cas9D10A-2A-GFP | Synthetic | Plasmid 44720: pCas9D10A_GFP | | Co-expression of human codon-optimized Cas9 (D10A) mutant nickase and GFP, plasmid optimized for expression in human pluripotent stem cells |
| dCas9 | S. Pyogenes | Plasmid 47106: pcDNA-dCas9 | D10A, H840A | Expresses inactivated S. pyogenes dCas9 (D10A, H840A) in mammalian cells |
| dCas9-VP64 | S. Pyogenes | Plasmid 47107: pcDNA-dCas9-VP64 | D10A, H840A | Expresses inactivated S. pyogenes dCas9 (D10A, H840A) fused to VP64 transactivator domain in mammalian cells |
| CRISPR-BsaI | | Plasmid 42875: pCRISPR | | A crRNA expression plasmid for targeting a specific sequence. |
| CRISPR::rpsL | | Plasmid 44505: pCRISPR::rpsL | | A crRNA expression plasmid specific to the rpsL allele. |

TABLE 12-continued

Additional Sequences as deposited in Addgene database (plasmid repository, Cambridge, MA)

| Gene/Insert | Species | Plasmid Name | Mutation | Purpose |
|---|---|---|---|---|
| nls-zcas9-nls | Synthetic | Plasmid 47929: pCS2-nCas9n | | expression of an optimized Cas9 for genome-editing in zebrafish |
| codon optimized Cas9_SV40 NLS with intron | Synthetic; S. pyogenes | Plasmid 46168: Peft-3::cas9-SV40_NLS::tbb-2 3'UTR | intron inserted at position 3113-3163, and SV40 NLS inserted from position 5192-5227 | |
| dCas9-BFP fusion | H. sapiens (human) | Plasmid 46910: pHR-SFFV-dCas9-BFP | | Human expression vector containing SFFV promoter, dCas9 that is fused to 2x NLS and tagBFP |
| dCas9-BFP-KRAB fusion | H. sapiens (human) | Plasmid 46911: pHR-SFFV-dCas9-BFP-KRAB | | Human expression vector containing SFFV promoter, dCas9 that is fused to 2x NLS, tagBFP and a KRAB domain |
| Cas9 | Synthetic; Streptococcus pyogenes | Plasmid 42234: pMJ920 | codon-optimized synthetic DNA sequence | |
| dCas9-p65AD-BFP fusion | H. sapiens (human) | Plasmid 46913: pMSCV-LTR-dCas9-p65AD-BFP | | Human expression vector containing MSCV LTR promoter, dCas9 that is fused to 2x NLS, p65 activation domain and tagBFP |
| dCas9-VP64-BFP fusion | H. sapiens (human) | Plasmid 46912: pMSCV-LTR-dCas9-VP64-BFP | | Human expression vector containing MSCV LTR promoter, dCas9 that is fused to 2x NLS, VP64 and tagBFP |
| SPgRNA | Synthetic | Plasmid 47108: pSPgRNA | | Expresses a S. pyogenes Cas9/dCas9 guide RNA in mammalian cells |
| Cas9 | Synthetic | Plasmid 46757: pT3TS-nCas9n | | |
| tyr Target | | Plasmid 46761: pT7tyrgRNA | | |
| dCas9 | | Plasmid 46920: pTDH3-dCas9 | | Yeast CEN/ARS vector (Leu2) that contains dCas9 fused to NLS controlled by TDH3 promoter |
| dCas9-Mxi1 | | Plasmid 46921: pTDH3-dCas9-Mxi1 | | Yeast CEN/ARS vector (Leu2) that contains dCas9 fused to NLS and Mxi1 domain controlled by TDH3 promoter |
| sgCD71-2 | | Plasmid 46918: pU6-sgCD71-2 | | Human pSico-based U6 vector containing murine U6 promoter and sgRNA targeting endogenous CD71 gene |

TABLE 12-continued

Additional Sequences as deposited in Addgene database (plasmid repository, Cambridge, MA)

| Gene/Insert | Species | Plasmid Name | Mutation | Purpose |
|---|---|---|---|---|
| sgCXCR4-2 | | Plasmid 46917: pU6-sgCXCR4-2 | | Human pSico-based U6 vector containing murine U6 promoter and sgRNA targeting endogenous CXCR4 gene |
| U6-SpTracrRNA-EF1a-hSpRNaseIII-mCherry | S. pyogenes | Plasmid 41863: pX097-U6-SpTracrRNA-EF1a-hSpRNaseIII-mCherry | | This plasmid is used to reconstitute the complete Type II CRISPR system from S. pyogenes and contains the host factor RNaseIII and tracrRNA. |
| Humanized S. pyogenes Cas9 | S. pyogenes | Plasmid 42229: pX260-U6-DR-BB-DR-Cbh-NLS-hSpCas9-NLS-H1-shorttracr-PGK-puro | | This plasmid separately encodes a human codon-optimized SpCas9, a tracrRNA and customizable crRNA. |
| humanized S. pyogenes Cas9 | S. pyogenes | Plasmid 42337: pX261-U6-DR-hEmx1-DR-Cbh-NLS-hSpCas9-NLS-H1-shorttracr-PGK-puro | Humanized | Dual expression plasmid of human codon-optimized SpCas9 and a gRNA to the human Emx1 locus, can be used to test SpCas9 cleavage in cell lines of choice. |
| humanized S. pyogenes Cas9 | S. pyogenes | Plasmid 42230: pX330-U6-Chimeric_BB-CBh-hSpCas9 | Humanized | A human codon-optimized SpCas9 and chimeric guide RNA expression plasmid. |
| humanized S. pyogenes Cas9 (D10A) nickase | S. pyogenes | Plasmid 42333: pX334-U6-DR-BB-DR-Cbh-NLS-hSpCas9n(D10A)-NLS-H1-shorttracr-PGK-puro | D10A nickase-converting mutation | This plasmid separately encodes a human codon-optimized SpCas9 nickase, a tracrRNA and customizable crRNA. |
| humanized S. pyogenes Cas9 (D10A) nickase | S. pyogenes | Plasmid 42335: pX335-U6-Chimeric_BB-CBh-hSpCas9n(D10A) | D10A nickase-converting mutation | A human codon-optimized SpCas9 nickase and chimeric guide RNA expression plasmid. |
| None | | Plasmid 41824: gRNA_Cloning Vector | | An empty gRNA expression vector, used to create a gRNA to a specific sequence. |
| gRNA_AAVS1-T1 | | Plasmid 41817: gRNA_AAVS1-T1 | | Expresses a guide RNA (gRNA) to target human AAVS1 (T1 target sequence) for genome engineering |
| gRNA_AAVS1-T2 | | Plasmid 41818: gRNA_AAVS1-T2 | | Expresses a guide RNA (gRNA) to target human AAVS1 (T2 target |

TABLE 12-continued

| Additional Sequences as deposited in Addgene database (plasmid repository, Cambridge, MA) | | | | |
|---|---|---|---|---|
| Gene/Insert | Species | Plasmid Name | Mutation | Purpose |
| gRNA_DNMT3a-T1 | | Plasmid 41821: gRNA_DNMT3a-T1 | | sequence) for genome engineering Expresses a guide RNA (gRNA) to target DNMT3a (T1 target sequence) for genome engineering |
| gRNA_DNMT3a-T2 | | Plasmid 41822: gRNA_DNMT3a-T2 | | Expresses a guide RNA (gRNA) to target DNMT3a (T2 target sequence) for genome engineering |
| gRNA_DNMT3b | | Plasmid 41823: gRNA_DNMT3b | | Expresses a guide RNA (gRNA) to target DNMT3b for genome engineering |

The invention claimed is:

1. A composition comprising
   (i) a plurality of lipid nanoparticles comprising a biodegradable cationic lipid, a non-cationic lipid, a sterol, and a PEG-lipid;
   (ii) mRNA comprising:
   (a) a first region of linked nucleosides consisting of nucleotides selected from 1-methyl-pseudouridine, cytidine, adenosine, and guanosine and encoding a protein comprising the sequence of SEQ ID NO: 7, 8, 9, 61, 62, 63, 64, or 65;
   (b) a 5'-untranslated region (UTR); and
   (c) a 3'-UTR comprising the sequence of SEQ ID NO: 81; and
   (iii) sgRNA comprising:
   (a) a first region of linked nucleosides complementary to either strand of a 5' UTR of a gene of interest;
   (b) a second region comprising a guide RNA scaffold sequence located at the 3' terminus of the first region; and
   (c) at least one phosphorothioate linkage and at least one nucleotide with a modification at the 2'-position of the sugar,
   wherein the plurality of lipid nanoparticles encapsulate the mRNA and/or the sgRNA.

2. A composition comprising
   (i) a plurality of lipid nanoparticles comprising a biodegradable cationic lipid, a non-cationic lipid, a sterol, and a PEG-lipid;
   (ii) mRNA comprising:
   (a) a first region of linked nucleosides consisting of nucleotides selected from 1-methyl-pseudouridine, cytidine, adenosine, and guanosine and encoding a protein comprising the sequence of SEQ ID NO: 7, 8, 9, 61, 62, 63, 64, or 65;
   (b) a 5'-UTR; and
   a 3'-UTR comprising the sequence of SEQ ID NO: 82; and
   (iii) sgRNA comprising:
   (a) a first region of linked nucleosides complementary to either strand of a 5' UTR of a gene of interest;
   (b) a second region comprising a guide RNA scaffold sequence located at the 3' terminus of the first region; and
   (c) at least one phosphorothioate linkage and at least one nucleotide with a modification at the 2'-position of the sugar,
   wherein the plurality of lipid nanoparticles encapsulate the mRNA and/or the sgRNA.

3. A composition comprising
   (i) a plurality of lipid nanoparticles comprising a biodegradable cationic lipid, a non-cationic lipid, a sterol, and a PEG-lipid;
   (ii) mRNA comprising:
   (a) a first region of linked nucleosides consisting of nucleotides selected from 1-methyl-pseudouridine, cytidine, adenosine, and guanosine and encoding a protein comprising the sequence of SEQ ID NO: 7, 8, 9, 61, 62, 63, 64, or 65;
   (b) a 5'-UTR; and
   (c) a 3'-UTR; and
   (iii) sgRNA comprising:
   (a) a first region of linked nucleosides complementary to either strand of a 5' UTR of a gene of interest;
   (b) a second region comprising a guide RNA scaffold sequence located at the 3' terminus of the first region; and
   (c) at least one phosphorothioate linkage and at least one nucleotide with a modification at the 2'-position of the sugar,
   wherein the modification at the 2'-position of the sugar is a 2'-methoxy modification, and wherein the plurality of lipid nanoparticles encapsulate the mRNA and/or the sgRNA.

* * * * *